United States Patent
Lanigan et al.

(10) Patent No.: US 10,987,505 B2
(45) Date of Patent: *Apr. 27, 2021

(54) INFUSION PUMP ASSEMBLY

(71) Applicant: DEKA Products Limited Partnership, Manchester, NH (US)

(72) Inventors: Richard J. Lanigan, Concord, NH (US); Gregory R. Lanier, Jr., Merrimack, NH (US); Kevin L. Grant, Litchfield, NH (US); Dean Kamen, Bedford, NH (US); Lisa A. Panneton, Manchester, NH (US); Bright C. K. Foo, Hollis, NH (US); Stephen L. Fichera, Salem, NH (US); Thomas F. Soldau, Bedford, NH (US); David D. B. Cannan, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 197 days.

This patent is subject to a terminal disclaimer.

(21) Appl. No.: 13/788,280

(22) Filed: Mar. 7, 2013

(65) Prior Publication Data
US 2014/0054883 A1 Feb. 27, 2014

Related U.S. Application Data

(60) Provisional application No. 61/607,863, filed on Mar. 7, 2012, provisional application No. 61/667,765, filed on
(Continued)

(51) Int. Cl.
*A61M 5/14* (2006.01)
*A61M 39/12* (2006.01)
(Continued)

(52) U.S. Cl.
CPC ........ *A61M 39/12* (2013.01); *A61M 5/14248* (2013.01); *A61M 39/1011* (2013.01); *A61M 5/14224* (2013.01); *A61M 5/1684* (2013.01); *A61M 39/08* (2013.01); *A61M 2005/14208* (2013.01); *A61M 2005/14268* (2013.01);
(Continued)

(58) Field of Classification Search
CPC .............. A61M 39/10; A61M 39/1011; A61M 2039/1061; A61M 39/12; A61M 2005/14268
See application file for complete search history.

(56) References Cited

U.S. PATENT DOCUMENTS 4,935,009 A * 6/1990 Caldwell ............. A61M 5/1424
604/218
5,066,278 A * 11/1991 Hirschberg ....... A61M 5/14276
604/246
(Continued)

*Primary Examiner* — Nathan R Price
*Assistant Examiner* — Courtney B Fredrickson
(74) *Attorney, Agent, or Firm* — Reid Cunningham

(57) ABSTRACT

A fluid connector assembly is disclosed. The fluid connector assembly includes a body portion, a plug portion located on the body portion, the plug portion comprising a fluid path, a tubing, a first end of the tubing fluidly connected to the plug fluid path, a catch feature located on a first end of the body portion and configured to interact with a reservoir, and a latching feature located on a second end of the body portion, the latching feature configured to interact and lock onto the reservoir.

10 Claims, 340 Drawing Sheets

Related U.S. Application Data on Jul. 3, 2012, provisional application No. 61/668,760, filed on Jul. 6, 2012, provisional application No. 61/736,358, filed on Dec. 12, 2012, provisional application No. 61/737,520, filed on Dec. 14, 2012.

(51) Int. Cl.
*A61M 39/10* (2006.01)
*A61M 5/142* (2006.01)
*A61M 39/08* (2006.01)
*A61M 39/02* (2006.01)
*A61M 39/00* (2006.01)
*A61M 5/168* (2006.01)

(52) U.S. Cl.
CPC ........... *A61M 2039/009* (2013.01); *A61M 2039/0244* (2013.01); *A61M 2205/0266* (2013.01); *A61M 2205/273* (2013.01); *A61M 2205/3334* (2013.01); *A61M 2205/3375* (2013.01); *A61M 2205/3389* (2013.01); *A61M 2205/3569* (2013.01); *A61M 2205/3592* (2013.01); *A61M 2205/8237* (2013.01); *A61M 2205/8262* (2013.01); *A61M 2209/01* (2013.01); *A61M 2209/086* (2013.01); *F04C 2270/041* (2013.01)

(56) References Cited

U.S. PATENT DOCUMENTS

| | | | | |
|---|---|---|---|---|
| 6,537,268 | B1* | 3/2003 | Gibson | A61M 5/14276 604/891.1 |
| 2005/0087715 | A1* | 4/2005 | Doyle | A61M 39/045 251/149.1 |
| 2005/0261664 | A1* | 11/2005 | Rome | A61M 25/0097 604/508 |
| 2005/0283118 | A1* | 12/2005 | Uth | A61M 39/0208 604/175 |
| 2008/0097328 | A1* | 4/2008 | Moberg | A61J 1/1406 604/155 |
| 2011/0144574 | A1* | 6/2011 | Kamen | A61M 5/14224 604/67 |

* cited by examiner

100

100

184

184

194

194

Send/Reply Data Flow Diagram

Each HW interface has its own Driver instance
Driver Interaction Data Flow Diagram

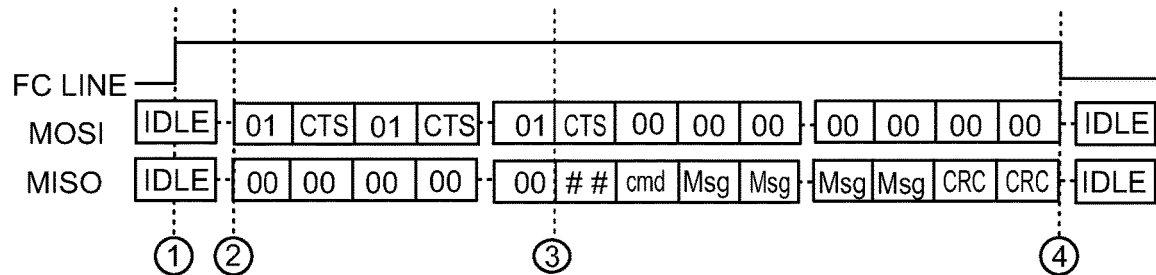

----- Indicates a time lapse

① Slave raises FlowControl line indicating a packet is pending
② Master begins sending 1 byte Clear To Send commands
③ Slave responds with the # of bytes being sent, Msg appended command & the Msg
④ The transaction is complete and the Slave lowers the FlowControl line

FIG.11Q

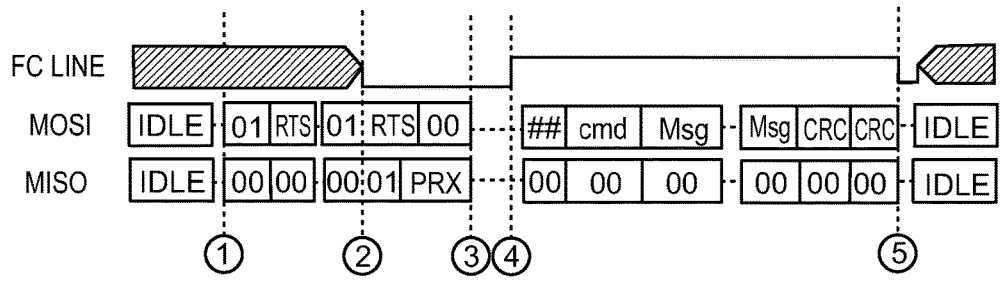

--- Indicates a time

① Master begins sending single byte RTS commands (state of Flow Control line is ignored
② Slave sends a Prepare for RX command indicating it is setting up dma to receive
③ Master stops clocking bytes and waits for the Flow Control Signal
④ Slave asserts the Flow Control line indicating the RX dma is ready to receive
⑤ The transaction is complete.

FIG.11R

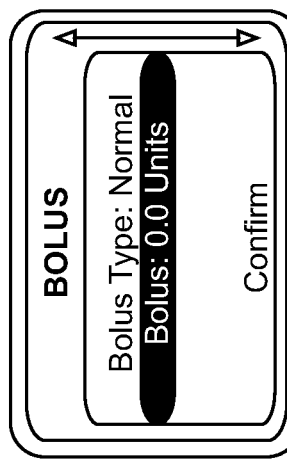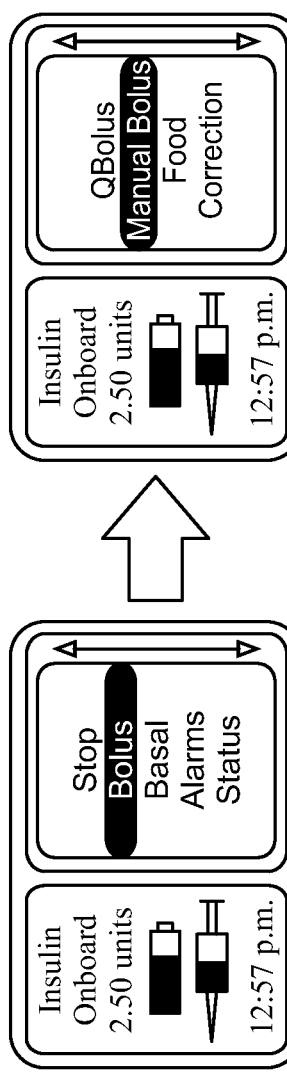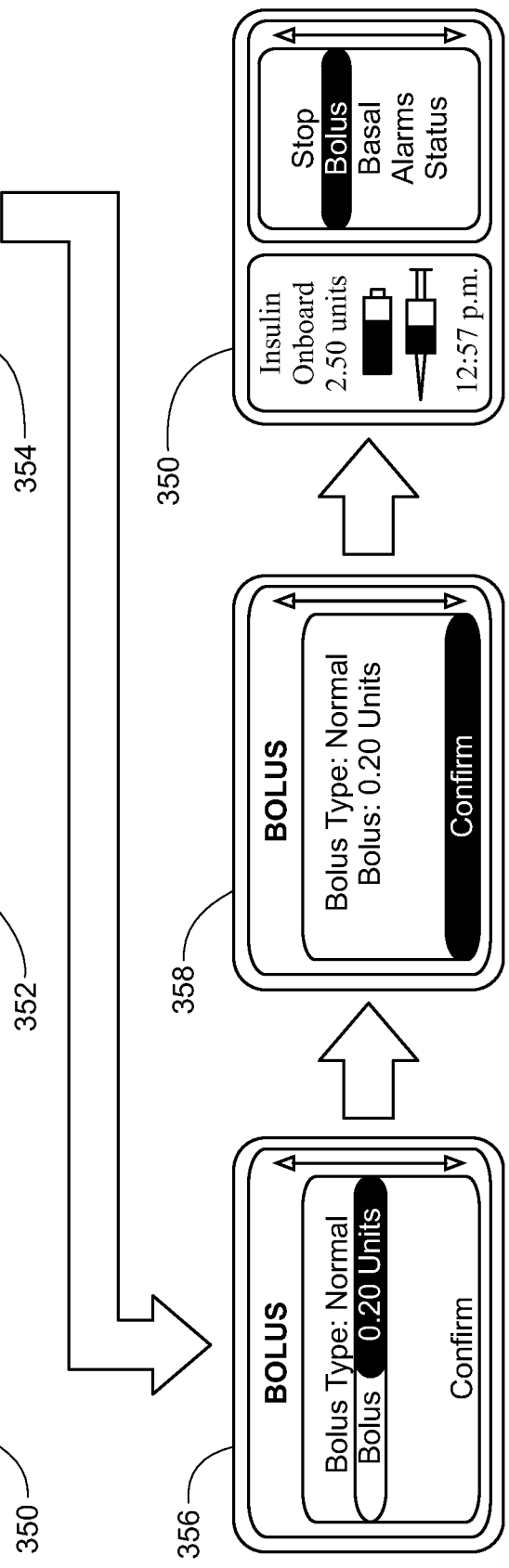
FIG. 12A FIG. 12B FIG. 12C FIG. 12D FIG. 12E FIG. 12F

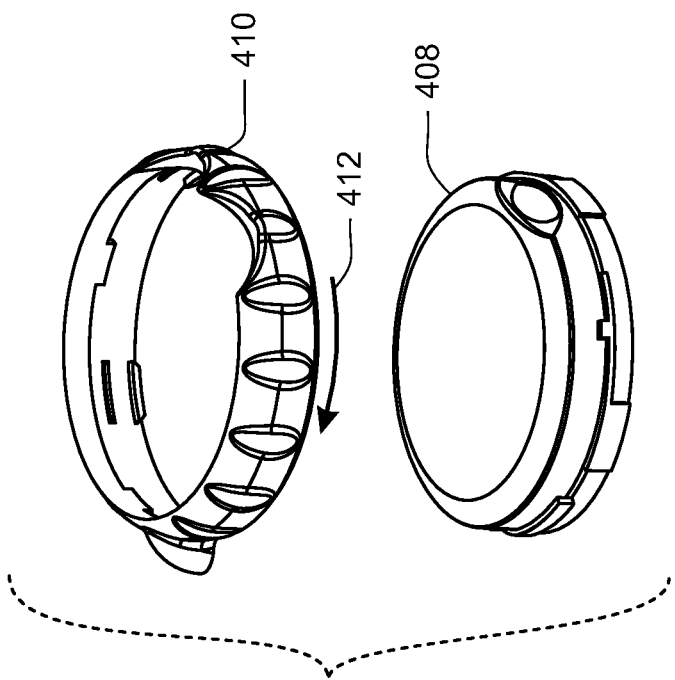
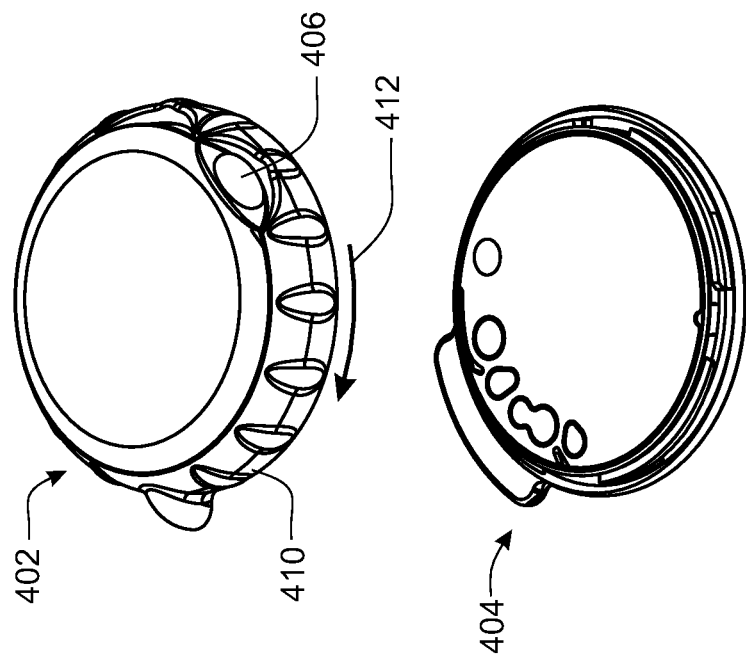
FIG. 13

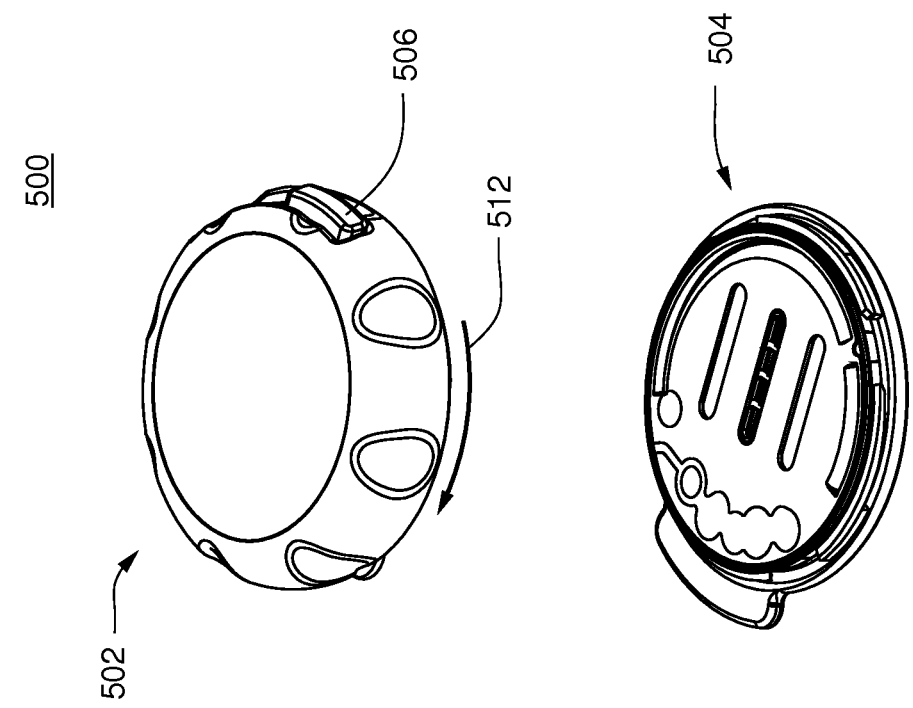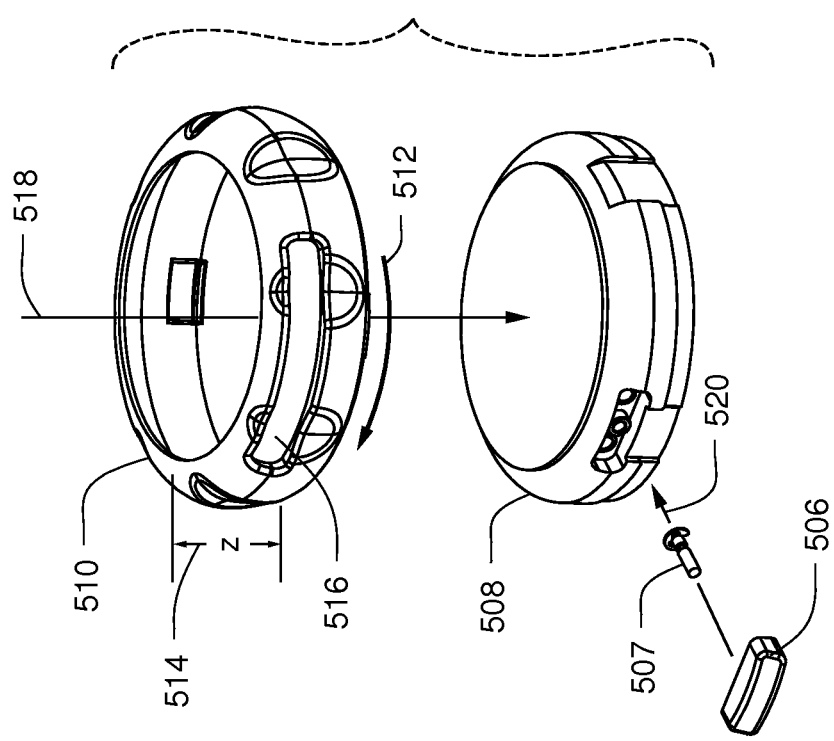
FIG. 16

818

818

818

818

818

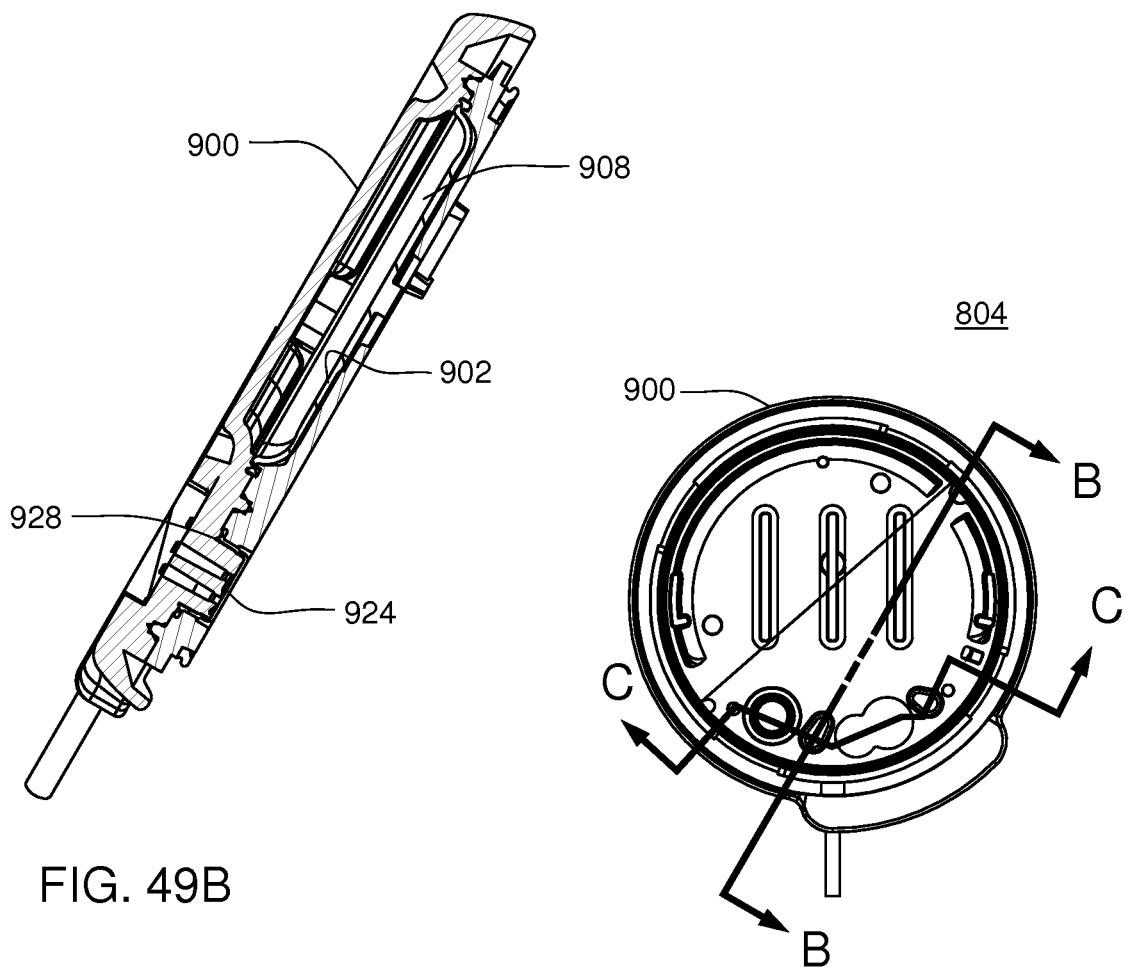
FIG. 49B
FIG. 49A
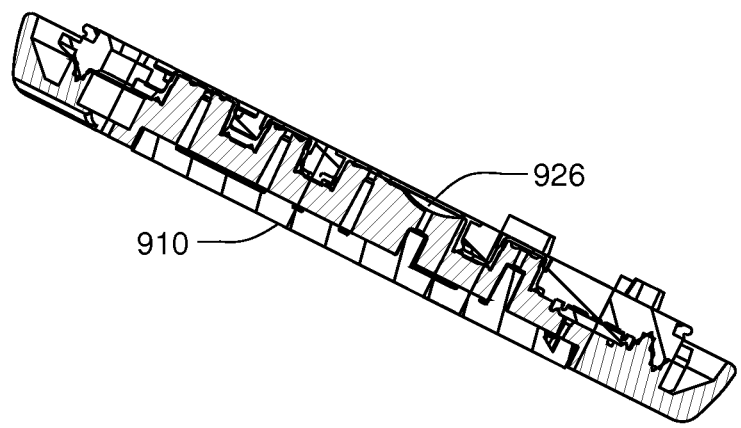
FIG. 49C

910

910

910

924

924

924

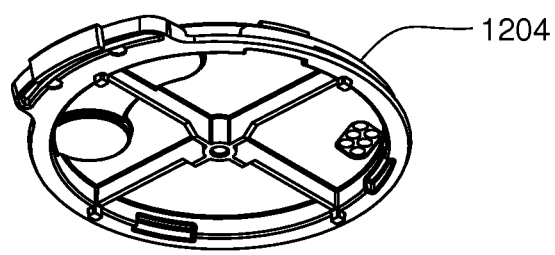
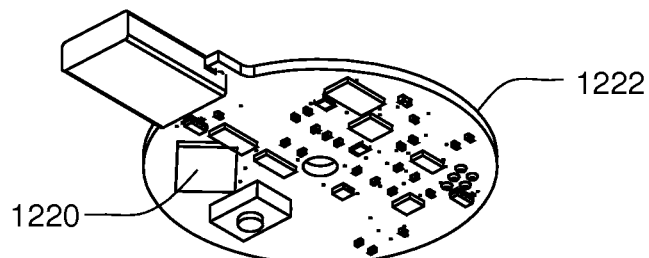
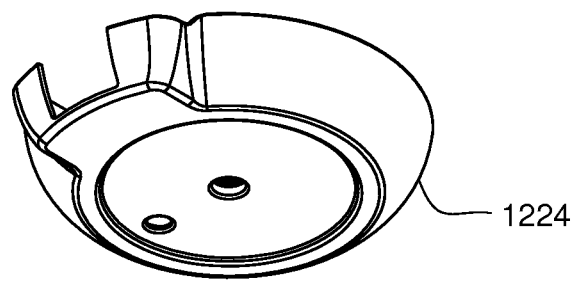
FIG. 79

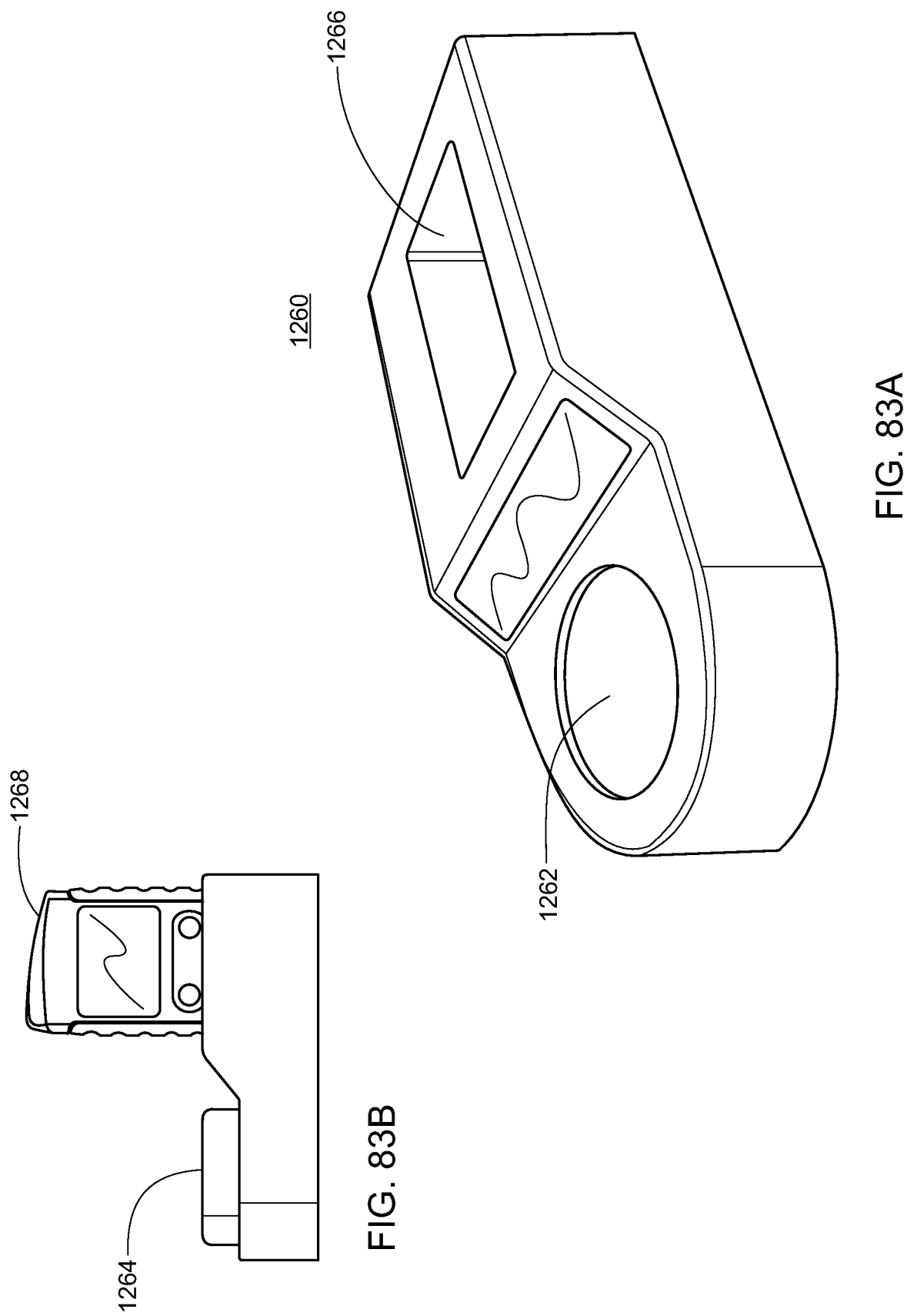

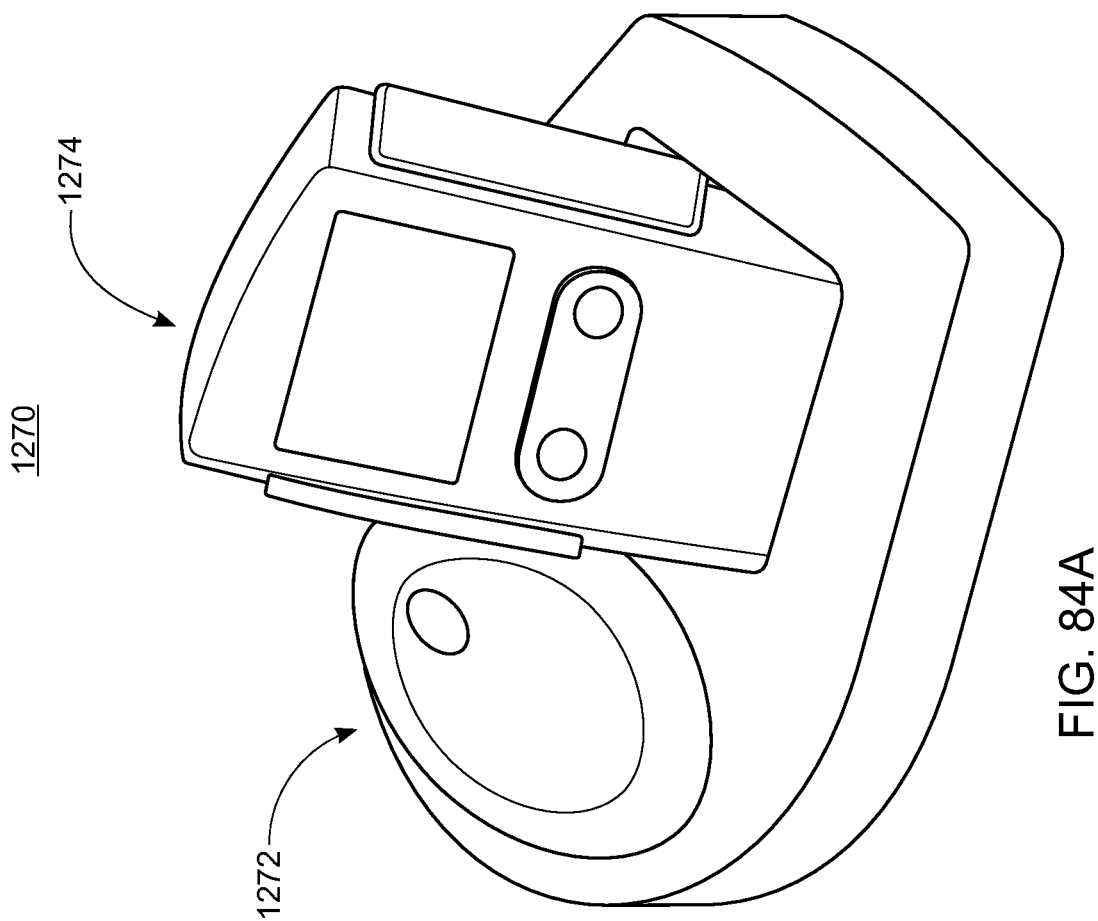
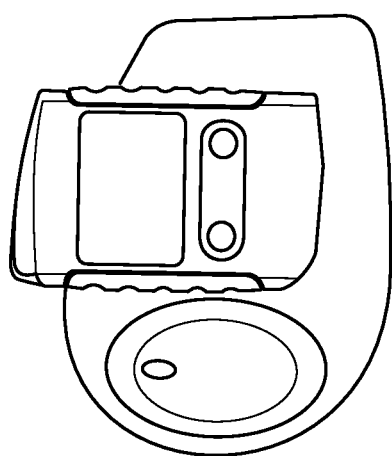
FIG. 84A
FIG. 84B

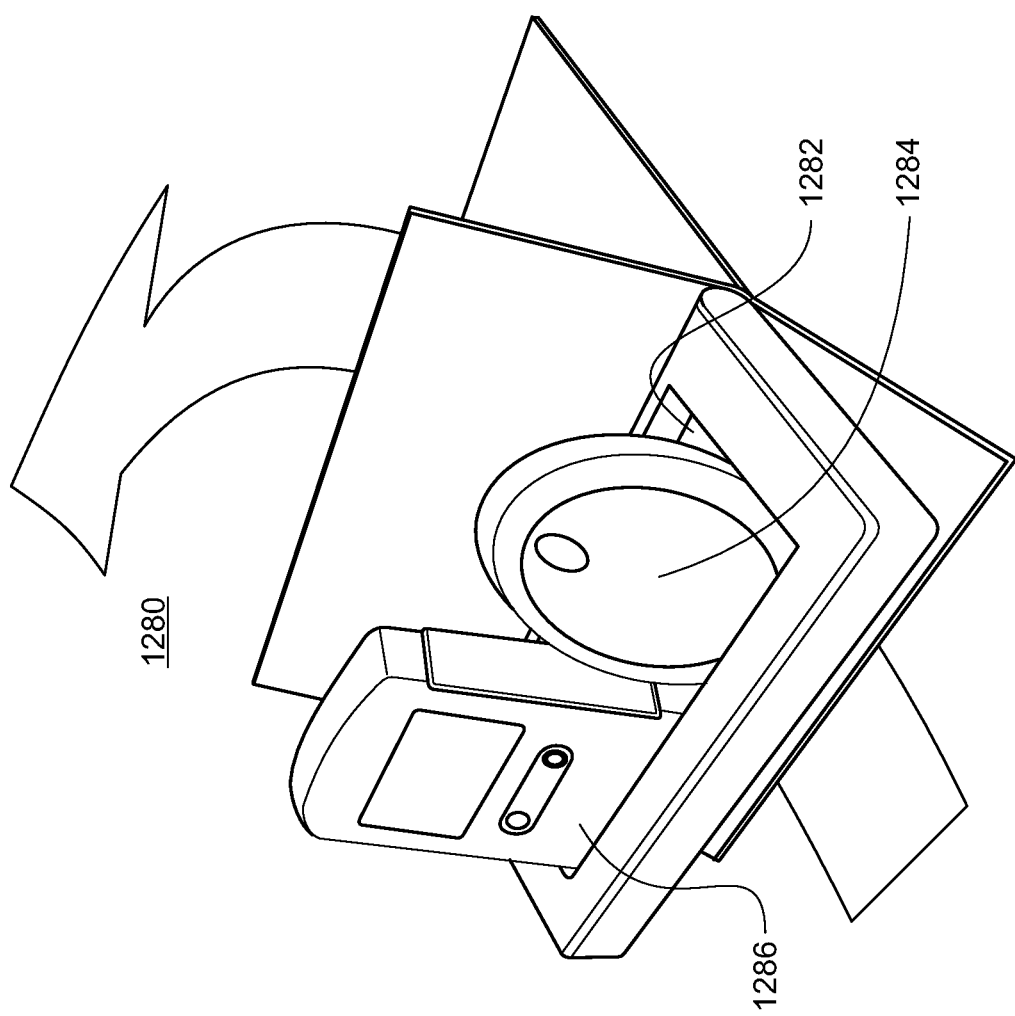
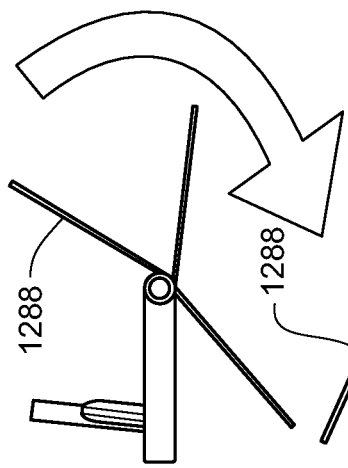
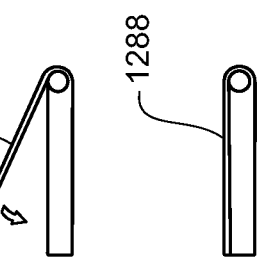
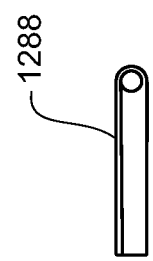
FIG. 85A
FIG. 85B
FIG. 85C
FIG. 85D

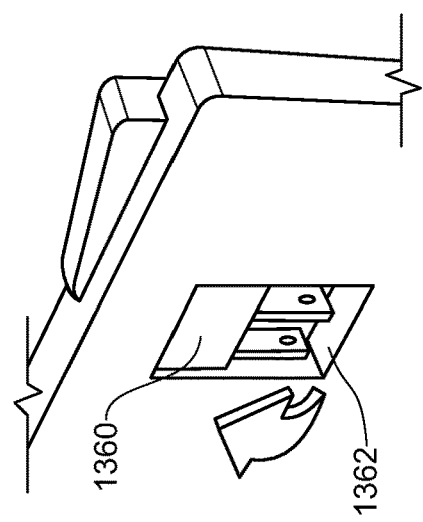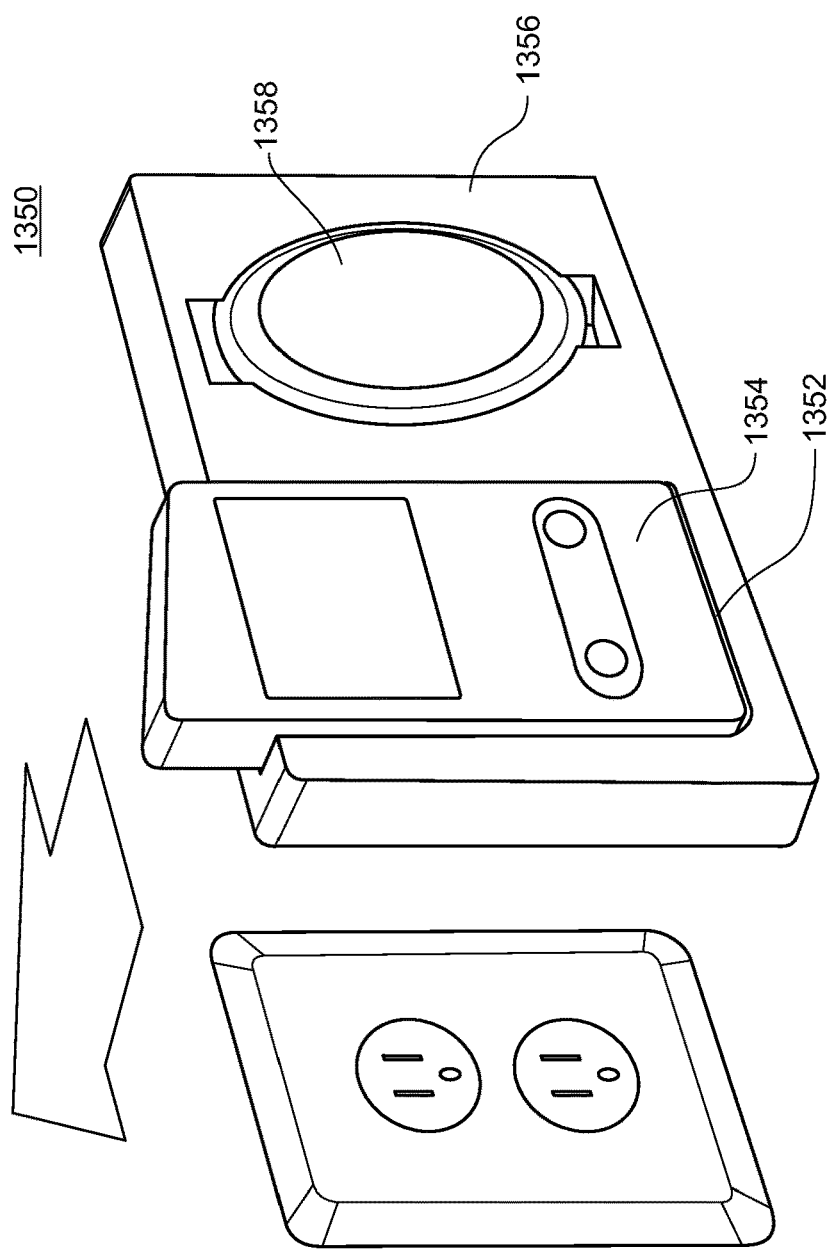

Section A-A

148

148

148

148

148

148

148

624

148

148

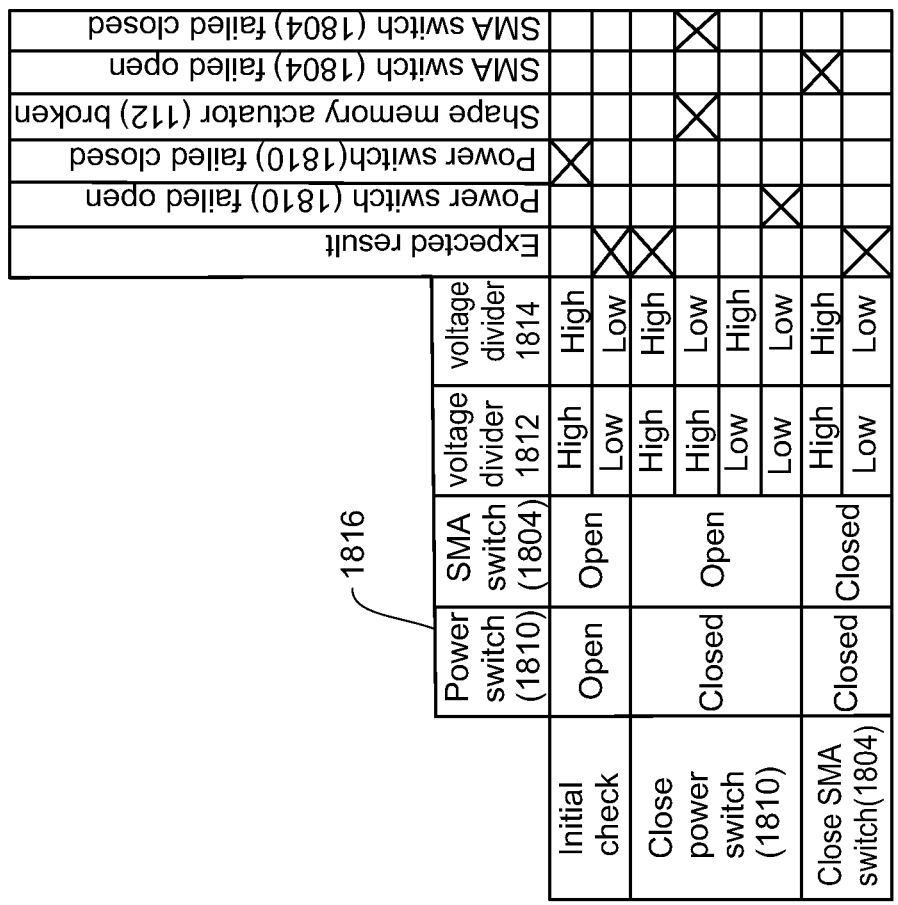
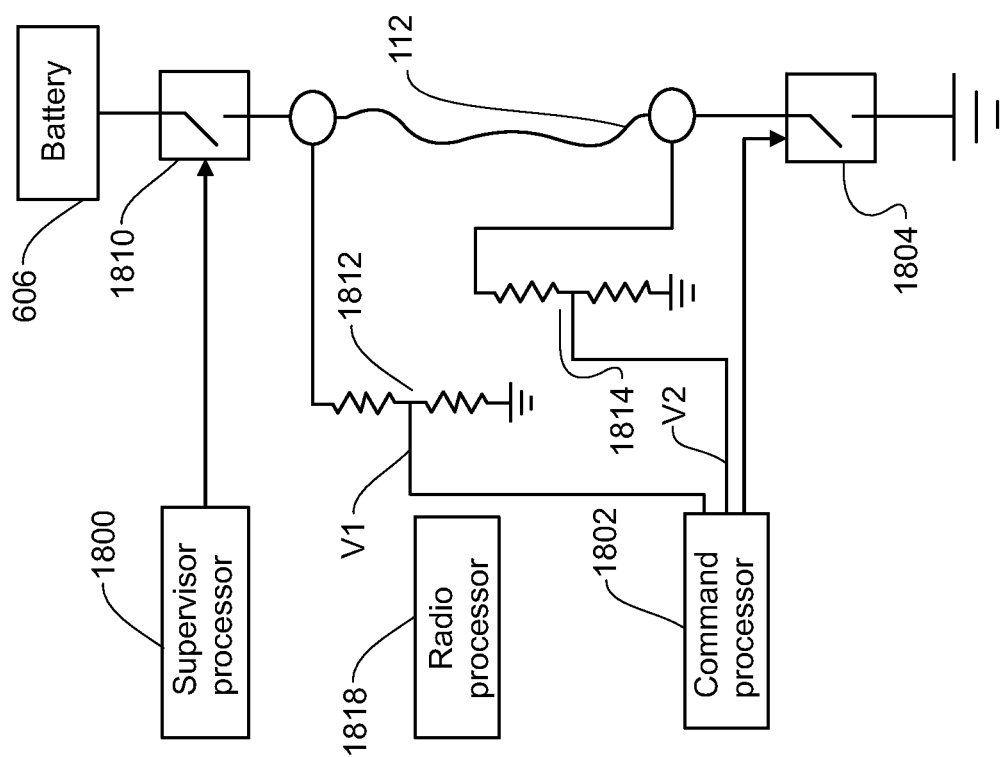
FIG. 116

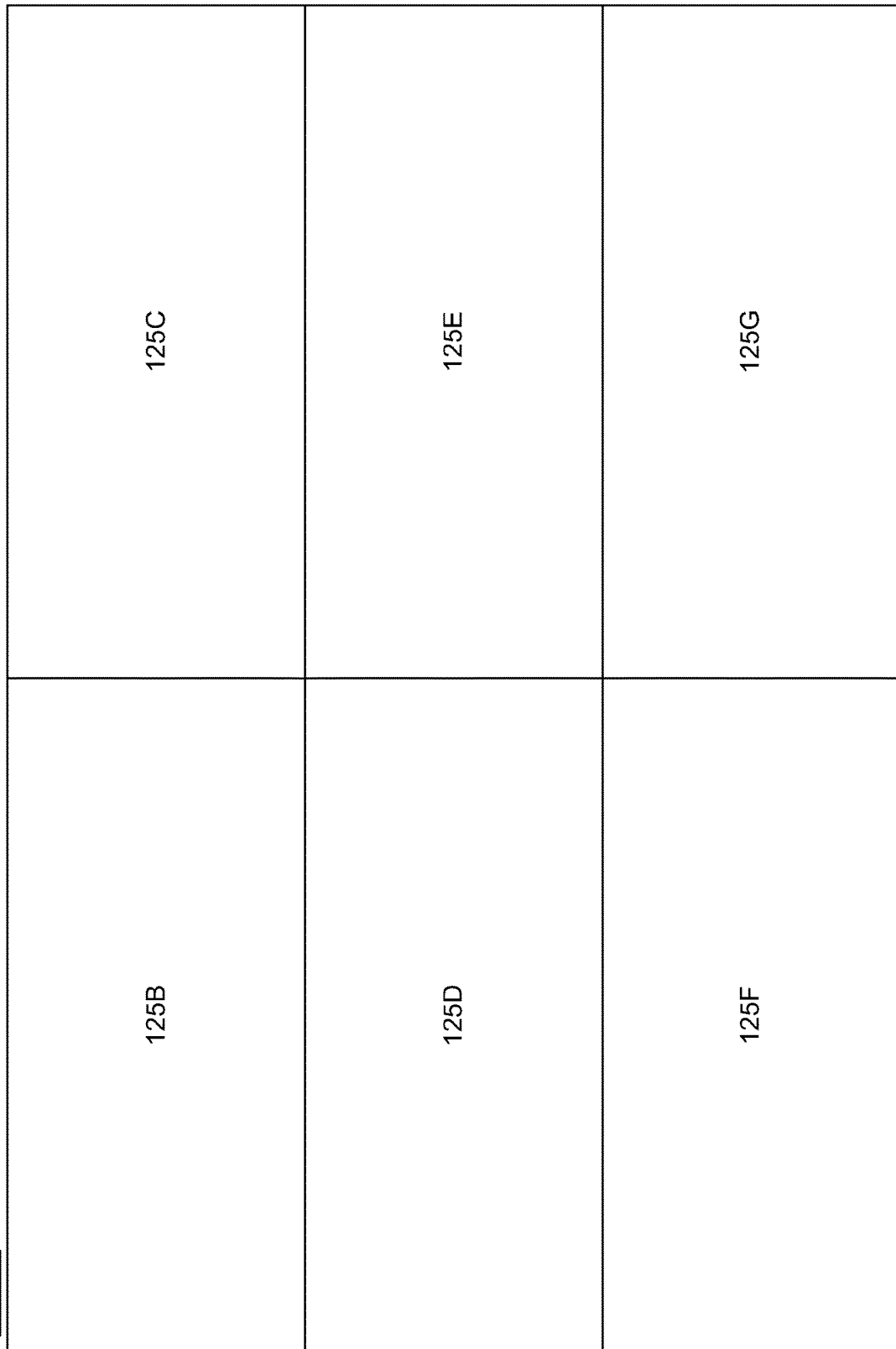

RIS event GetSingleVersionCommand |
RIS event GetAllVersionCommand |
RIS event ClearAlert |
RIS event LogCommand |
RIS event GetTotalRecordsLoggedCommand |
RIS event GetLogRecord |
RIS event ErasePumpLogs |
RIS event GetSerialNumberCommand |
RIS event IOBCommand |
RIS event UploadIOB |
RIS event DownloadIOB |
RIS event Airplane Mode/ Process RIS command

FIG. 126K

RIS event StartBasalCommand |
RIS event StopBasalCommand |
RIS event TempBasalModifyCommand |
RIS event TempBasalOverrideCommand |
RIS event BolusPrimeStatus
RIS event StopBasalCommand |
RIS event TempBasalModifyCommand |
RIS event TempBasalOverrideCommand |
RIS event NormalBolusCommand |
RIS event ExtendedBolusCommand |
RIS event DualBolusCommand |
RIS event AbortBolusCommand / NACK RIS command

FIG. 126L

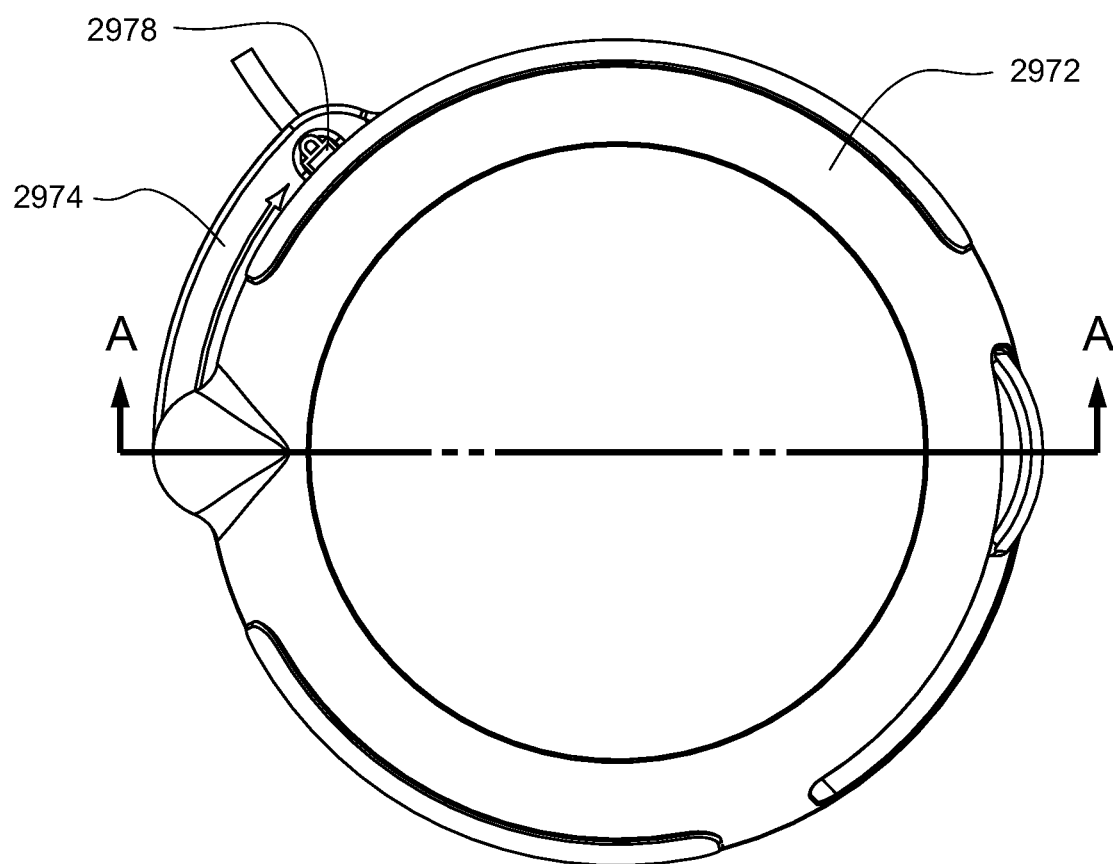
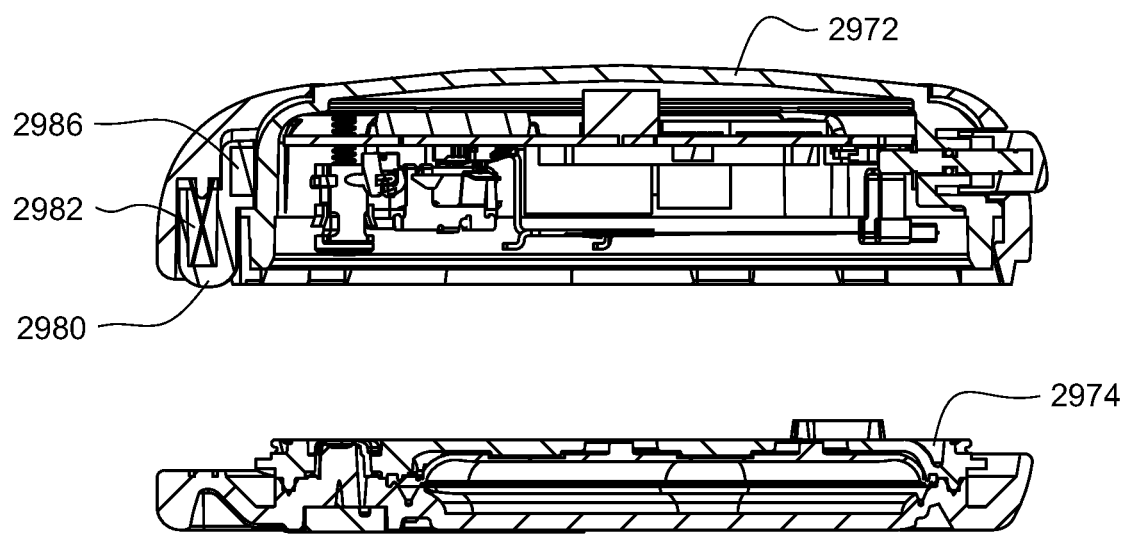
FIG. 137

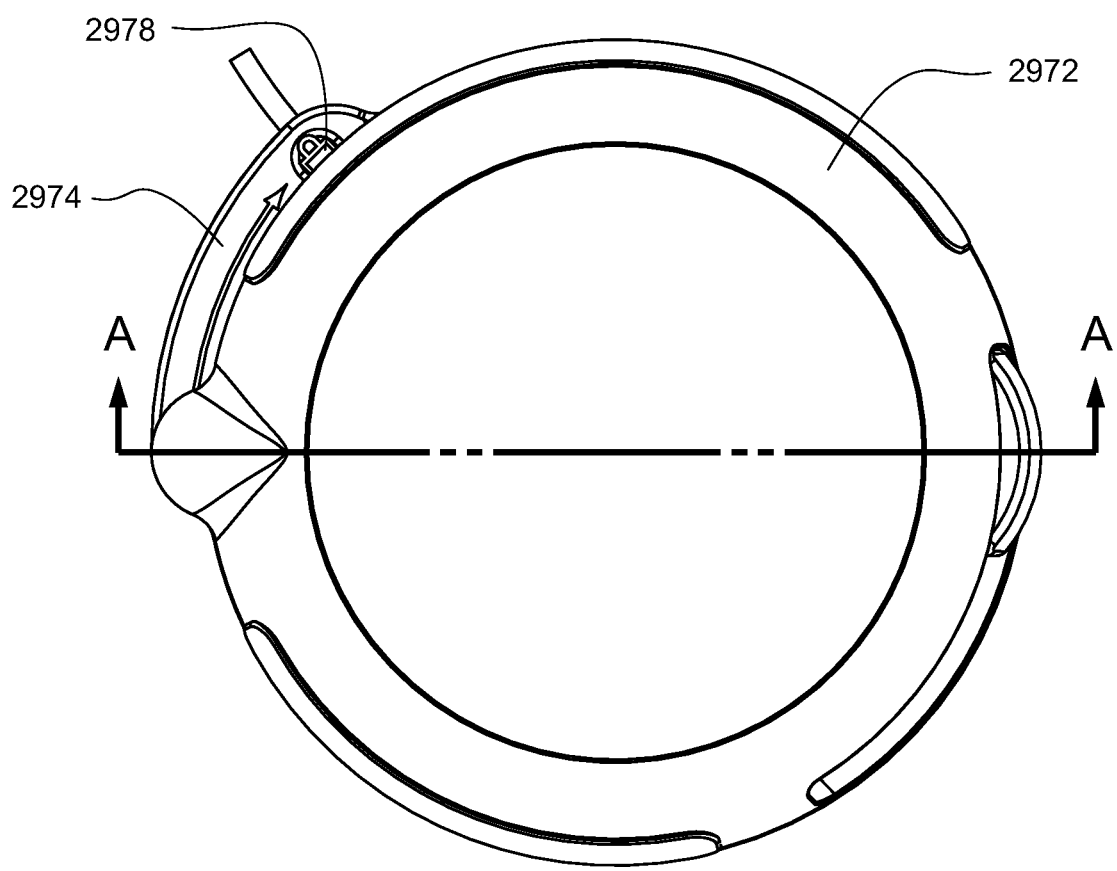
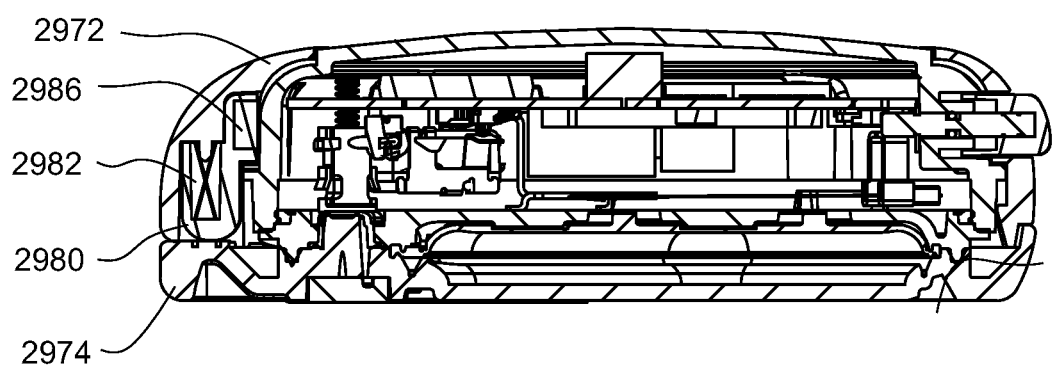
FIG. 138

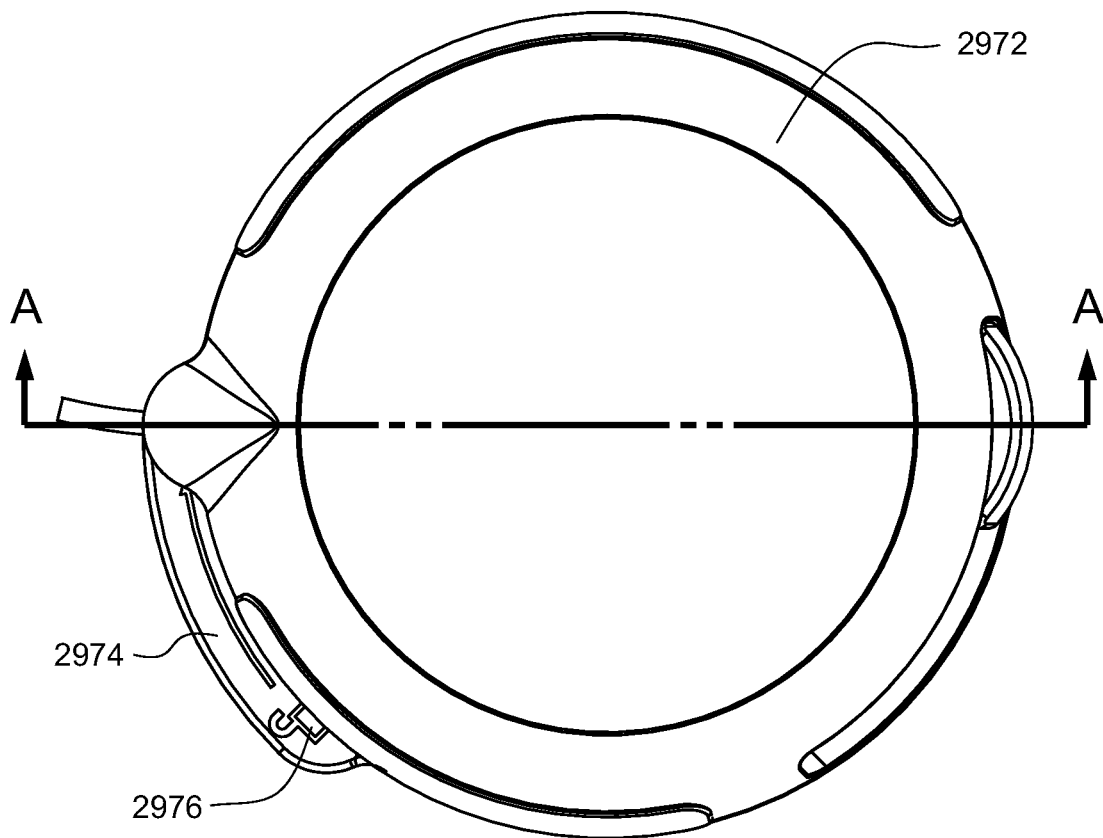
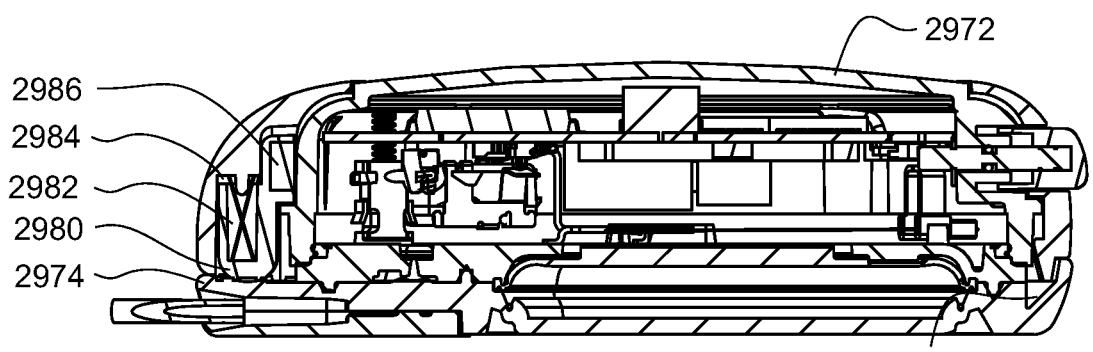
FIG. 139

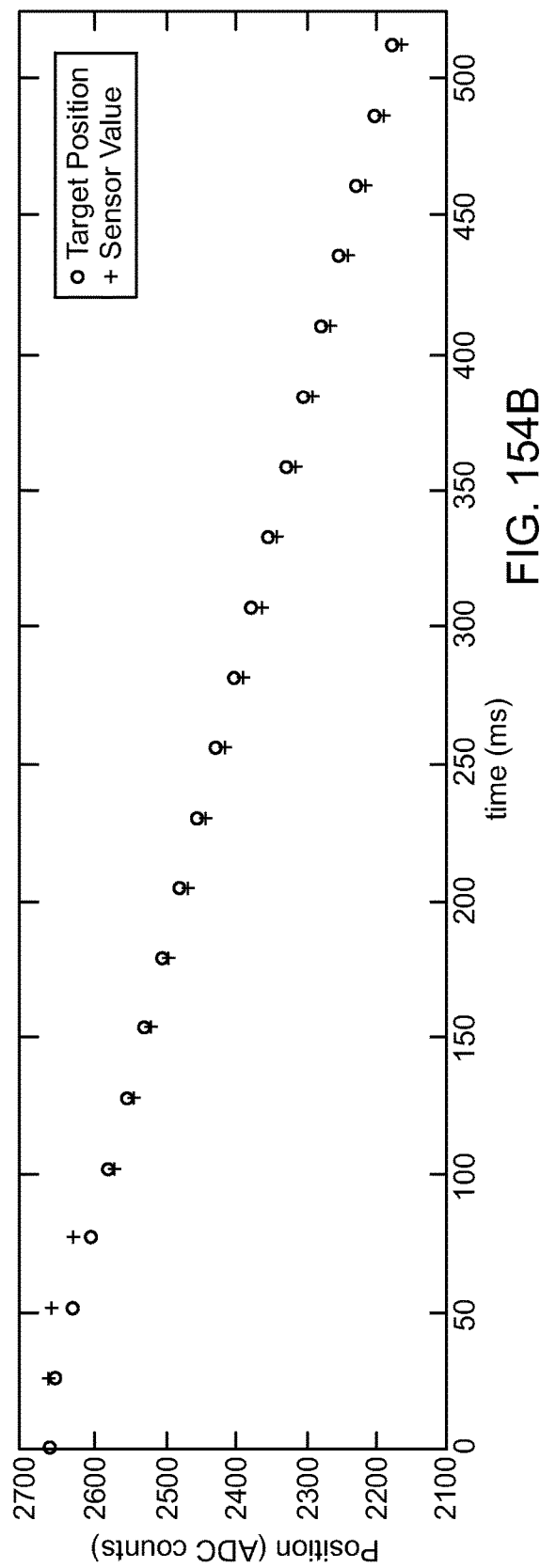
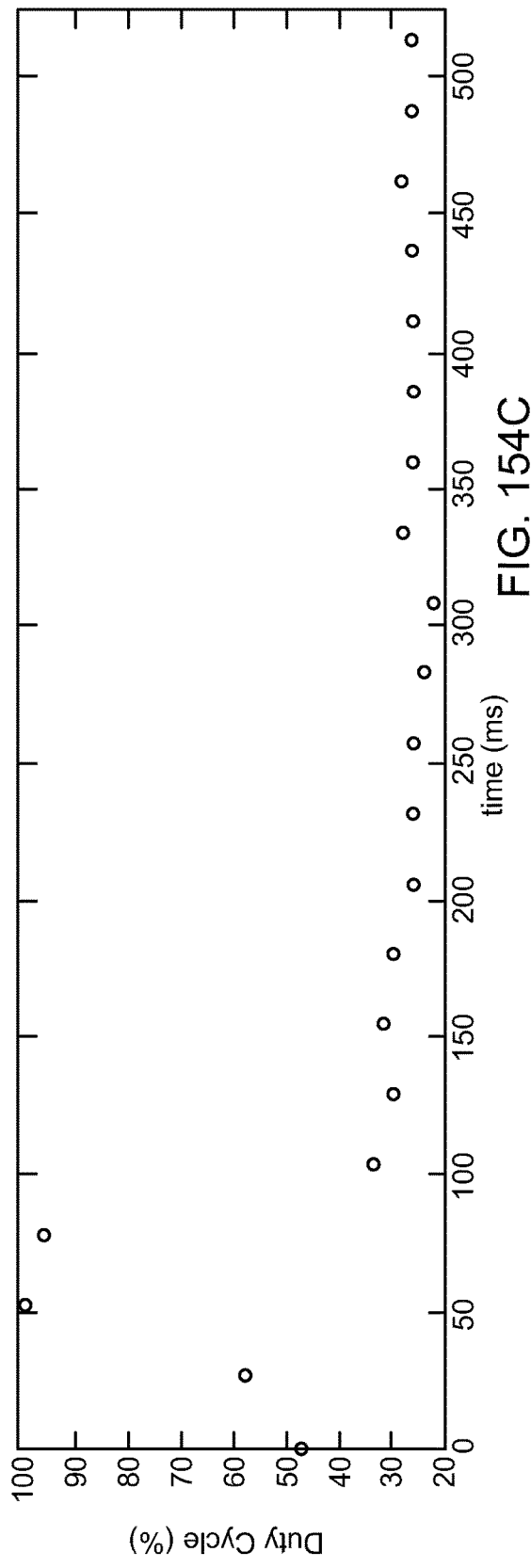
FIG. 154B
FIG. 154C

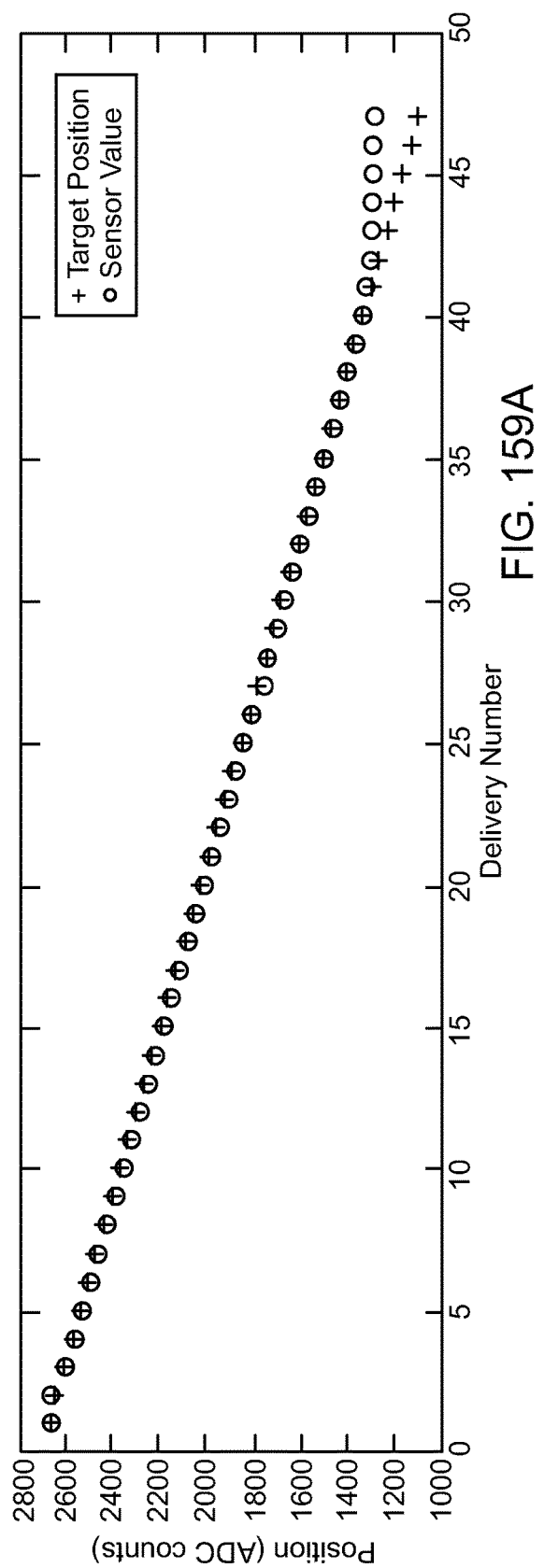
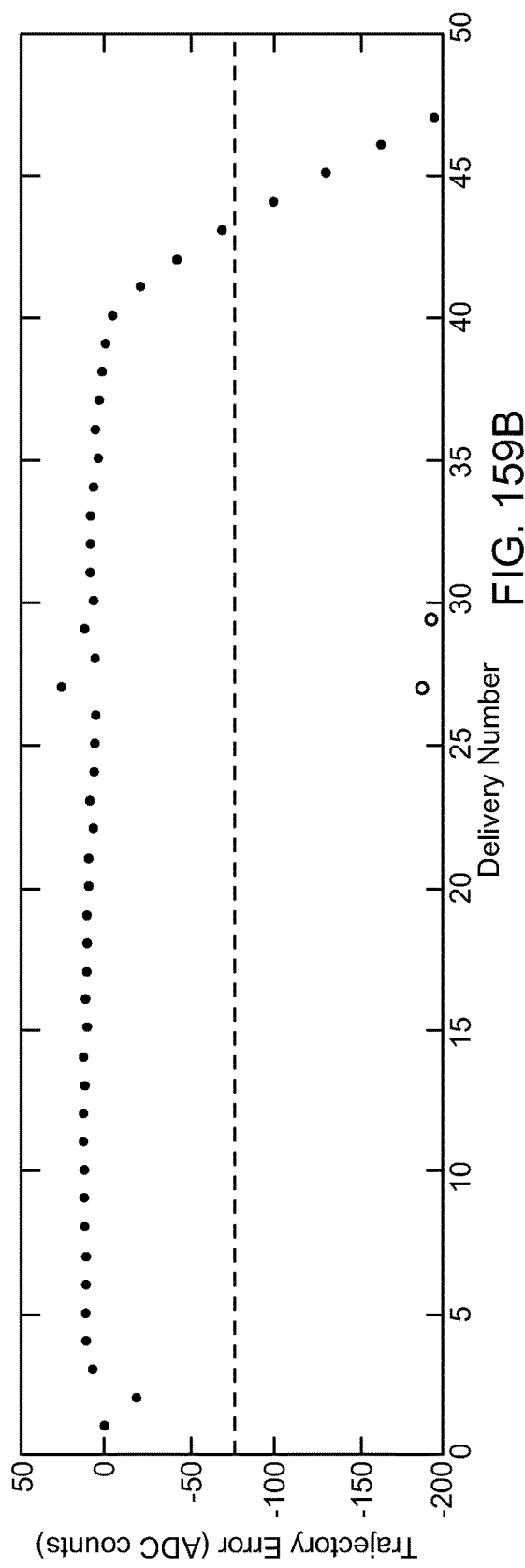
FIG. 159A
FIG. 159B

DETAIL A
SCALE 8 : 1

4090

Fill State - Pump Piston strokes up and the elastomer restoring force creates a negative fluid pressure that opens the Reservoir Valve to fill Pump Chamber.

Delivery State - Pump Piston strokes back down to resting state, developing a positive fluid pressure that closes the Reservoir Valve and opens the AVS Valve to move fluid into the AVS Chamber.

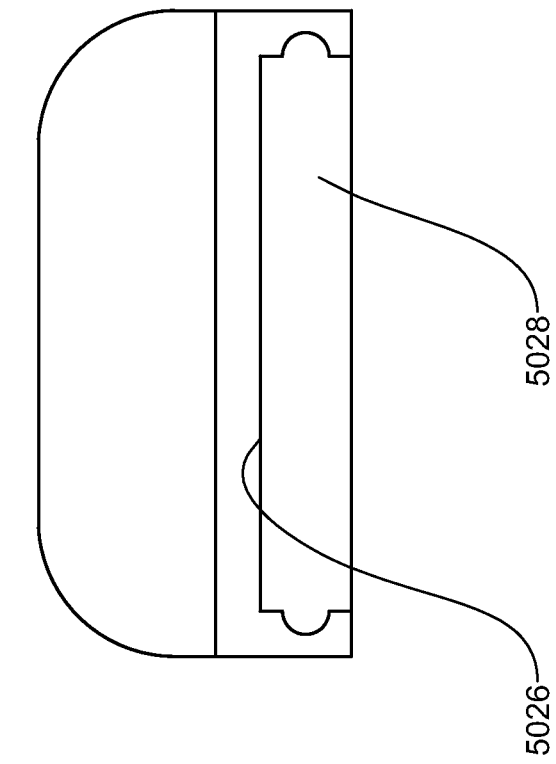
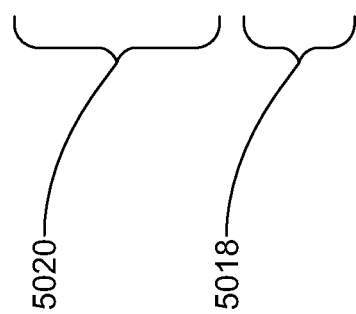
FIG. 196

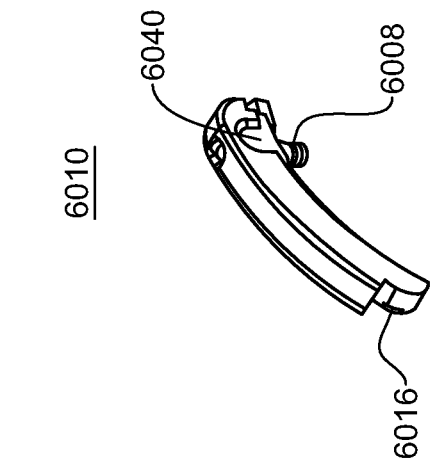
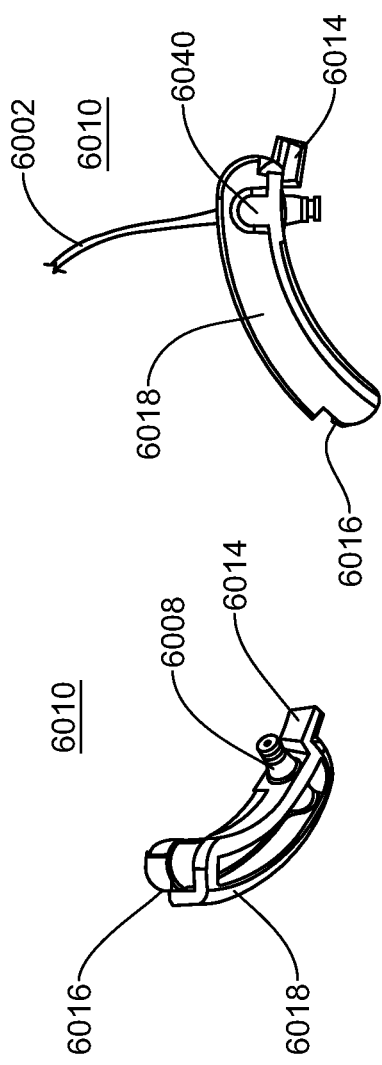
FIG. 235C
FIG. 235B
FIG. 235A

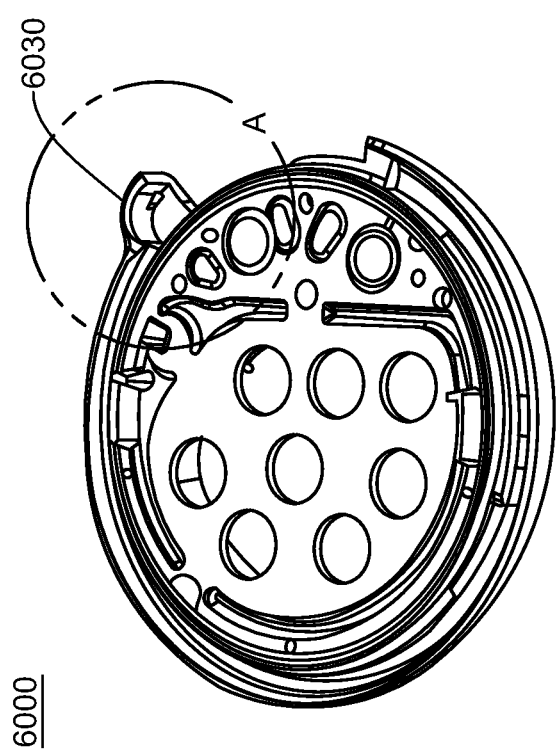
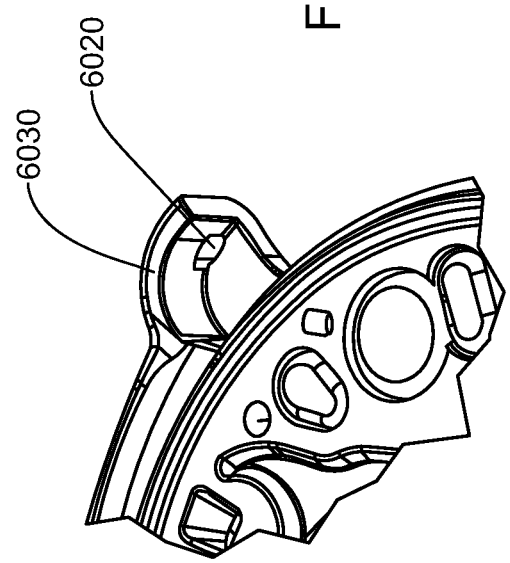
FIG. 235D
FIG. 235E

DETAIL G
SCALE 2:1
Speaker Mounting

INFUSION PUMP ASSEMBLY

CROSS REFERENCE TO RELATED APPLICATIONS

The present application is a Non-Provisional application which claims priority from:
U.S. Provisional Patent Application Ser. No. 61/607,863, filed Mar. 7, 2012 and entitled Infusion Pump Assembly;
U.S. Provisional Patent Application Ser. No. 61/667,765, filed Jul. 3, 2012 and entitled Infusion Pump Assembly;
U.S. Provisional Patent Application Ser. No. 61/668,760, filed Jul. 6, 2012 and entitled Infusion Pump Assembly;
U.S. Provisional Patent Application Ser. No. 61/736,358, filed Dec. 12, 2012 and entitled Infusion Pump Assembly; and
U.S. Provisional Patent Application Ser. No. 61/737,520, filed Dec. 14, 2012 and entitled Infusion Pump Assembly,
all of which are hereby incorporated herein by reference in their entireties.

FIELD OF THE INVENTION

This application relates generally to fluid delivery systems, and more particularly to infusion pump assemblies.

BACKGROUND

Many potentially valuable medicines or compounds, including biologicals, are not orally active due to poor absorption, hepatic metabolism or other pharmacokinetic factors. Additionally, some therapeutic compounds, although they can be orally absorbed, are sometimes required to be administered so often it is difficult for a patient to maintain the desired schedule. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compounds over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the malfunction rate. Reducing the size, weight and cost of these devices is also an ongoing challenge. Additionally, these devices often apply to the skin and pose the challenge of frequent re-location for application.

SUMMARY OF THE INVENTION

In accordance with one implementation, a fluid connector assembly is disclosed. The fluid connector assembly includes a body portion, a plug portion located on the body portion, the plug portion comprising a fluid path, a tubing, a first end of the tubing fluidly connected to the plug fluid path, a catch feature located on a first end of the body portion and configured to interact with a reservoir, and a latching feature located on a second end of the body portion, the latching feature configured to interact and lock onto the reservoir.

Some embodiments of this implementation may include one or more of the following features. Wherein the body portion further comprising an indent wherein the indent configured to interact with a reservoir. Wherein the catch feature comprising a ramp. Wherein the second end of the tubing connected to a cannula assembly. Wherein the body portion further comprising a tapered tubing opening, the first end of the tubing connecting to the tapered tubing opening. Wherein the underside of the body portion comprising a core. Wherein the core comprising an identification tag. Wherein the body portion comprising an identification tag. Wherein the identification tag is an RFID tag. Wherein the identification tag is a near-field communication readable RFID.

In accordance with one implementation a fluid reservoir system is disclosed. The fluid reservoir system includes a disposable housing assembly including a reservoir, a tab portion, the tab portion including a female latching feature, and an exit, the exit fluidly connected to the reservoir, and a fluid connector assembly which includes a body portion, a plug portion located on the body portion, the plug portion including a fluid path, a male latching feature located on a first end of the body portion, the male latching feature configured to interact with the female latching feature on the disposable housing assembly, and a tubing, a first end of the tubing fluidly connected to the plug fluid path, wherein the plug of the connector attaches to the exit of the disposable housing assembly and provides a fluid connection between the reservoir and the tubing.

Some embodiments of this implementation may include one or more of the following features. Wherein the fluid connector further includes a catch feature located on a second end of the body portion and configured to interact with the disposable housing assembly. Wherein the catch feature includes a ramp. Wherein a second end of the tubing is connected to a cannula assembly. Wherein the connector further includes wherein the body portion includes an indent wherein the indent configured to interact with a reusable portion of an infusion pump. Wherein the body portion further includes a tapered tubing opening, the first end of the tubing connecting to the tapered tubing opening. Wherein the body portion further including a core. Wherein the core further includes an identification tag. Wherein the body portion further including an identification tag. Wherein the identification tag is an RFID tag. Wherein the identification tag is a near-field communication readable RFID.

In accordance with one implementation, a connector. The connector includes a body portion, a plug, and a tubing in communication with the plug, wherein the plug is configured to attach to an exit in a disposable housing assembly.

In accordance with first implementation, a wearable infusion pump assembly is disclosed. The wearable infusion pump assembly includes a reservoir for receiving an infusible fluid and a fluid delivery system configured to deliver the infusible fluid from the reservoir to an external infusion set. The fluid delivery system includes a controller, a pump assembly for extracting a quantity of infusible fluid from the reservoir and providing the quantity of infusible fluid to the external infusion set, the pump assembly comprising a pump plunger, the pump plunger having distance of travel, the distance of travel having a starting position and an ending position, at least one optical sensor assembly for sensing the starting position and ending position of the pump plunger distance of travel and sending sensor output to the controller, and a first valve assembly configured to selectively isolate the pump assembly from the reservoir, wherein the controller receives the sensor output and determines the total displacement of the pump plunger.

Some embodiments of this implementation may include one or more of the following features. Wherein the wearable infusion pump assembly includes wherein the controller correlates the displacement of the pump plunger to a volume of fluid delivered. Wherein the wearable infusion pump assembly includes wherein the controller, based on the volume of fluid delivered, commands an actuator to actuate the pump plunger to a target position. Wherein the wearable infusion pump assembly further includes a second valve assembly configured to selectively isolate the pump assembly from the external infusion set. Wherein the wearable infusion pump assembly further includes at least one optical sensor assembly for sensing the position of the second valve assembly. Wherein the wearable infusion pump assembly further includes a disposable housing assembly including the reservoir and a first portion of the fluid delivery system, and a reusable housing assembly including a second portion of the fluid delivery system. Wherein the wearable infusion pump assembly includes wherein a first portion of the pump assembly is positioned within the disposable housing assembly, and a second portion of the pump assembly is positioned within the reusable housing assembly. Wherein the wearable infusion pump assembly includes wherein a first portion of the first valve assembly is positioned within the disposable housing assembly, and a second portion of the first valve assembly is positioned within the reusable housing assembly. Wherein the wearable infusion pump assembly includes wherein a first portion of the second valve assembly is positioned within the disposable housing assembly, and a second portion of the second valve assembly is positioned within the reusable housing assembly. Wherein the wearable infusion pump assembly includes wherein the external infusion set is a detachable external infusion set configured to releasably engage the fluid delivery system.

In accordance with first implementation, a disposable housing assembly for an infusion pump assembly is disclosed. The disposable housing assembly includes a reservoir portion fluidly connected to a fluid path, the reservoir portion including a bubble trap wherein the bubble trap prevents air from moving from the reservoir portion to the fluid path. The bubble trap further includes an outlet portion and a non-outlet portion, the non-outlet portion including a tapered portion that tapers to a bottom portion, the tapered portion of the non-outlet portion ending at the outlet portion. The bubble trap also includes wherein the outlet portion including the bottom portion in communication with an upward ramped portion in fluid communication with a reservoir outlet, wherein the bottom portion configured whereby fluid congregates in the bottom portion and the tapered portion configured whereby air bubbles congregate in the tapered portion.

Some embodiments of this implementation may include one or more of the following features. Wherein the disposable housing assembly further includes a membrane assembly, the membrane assembly connected to the reservoir wherein the membrane assembly forms a portion of the reservoir. Wherein the disposable housing assembly further includes a septum assembly, the septum assembly formed on the membrane assembly. Wherein the disposable housing assembly further includes a septum assembly, the septum assembly connected to the reservoir. Wherein the disposable housing assembly further includes a vent, wherein the vent further comprising a filter.

In accordance with one implementation, a fluid connector assembly is disclosed. The fluid connector assembly includes a body portion, a plug receiver portion located on the body portion, the plug receiver portion including a fluid path and configured to receive a plug on a reservoir, and a tubing, a first end of the tubing fluidly connected to the plug receiver portion fluid path.

Some embodiments of this implementation may include one or more of the following features. Wherein the body portion further includes an indent wherein the indent configured to interact with a reusable portion of an infusion pump. Wherein a second end of the tubing connected to a cannula assembly. Wherein the body portion further includes a tapered tubing opening, the first end of the tubing connecting to the tapered tubing opening. Wherein a first end of the body portion further comprising a locked icon. Wherein the underside of the body portion comprising a core. Wherein the core comprising an identification tag. Wherein the body portion comprising an identification tag. Wherein the identification tag is an RFID tag. Wherein the identification tag is a near-field communication readable RFID.

The details of one or more embodiments are set forth in the accompanying drawings and the description below. Other features and advantages will become apparent from the description, the drawings, and the claims.

BRIEF DESCRIPTION OF THE DRAWINGS

FIGS. 12A-12F is a plurality of display screens rendered by the remote control assembly of FIG. 11A;

FIG. 13 is an isometric view of an alternative embodiment of the infusion pump assembly of FIG. 1;

FIG. 16 is an isometric view of an alternative embodiment of the infusion pump assembly of FIG. 1;

FIG. 49A is a plan view of the disposable housing assembly of FIG. 48;

FIG. 49B is a sectional view of the disposable housing assembly of FIG. 49A taken along line B-B;

FIG. 49C is a sectional view of the disposable housing assembly of FIG. 49A taken along line C-C;

FIGS. 75-80 depict various views of an embodiment of a battery charger;

FIGS. 81-89B depict various embodiments of battery chargers/docking stations;

FIG. 116 is a diagrammatic view of a multi-processor control configuration that may be included within the infusion pump assembly of FIG. 1;

FIG. 125A-125G depicts a hierarchal state machine;

FIG. 126A-126M depicts a hierarchal state machine;

FIG. 137 shows a cross sectional view taken along "A" showing the reusable housing assembly orientated above the disposable housing assembly in an unlocked orientation;

FIG. 138 shows a cross sectional view taken along "A" showing the reusable housing assembly attached to the disposable housing assembly in an unlocked position;

FIG. 139 shows a cross sectional view taken along "A" showing the reusable housing assembly attached to the disposable housing assembly in a locked position;

FIG. 140A shows an isometric view of one embodiment of the reusable housing assembly and one embodiment of the dust cover;

FIG. 140B is a top view of one embodiment of the dust cover;

FIG. 140C is a cross sectional view taken at "C" as shown in FIG. 140B;

FIG. 140D is a cut-away cross-sectional view of section "D" as shown in FIG. 140C;

FIG. 141A is a view of one embodiment of a disposable housing assembly;

FIG. 141B is a magnified cut away view of FIG. 141A as indicated by "B";

FIG. 142A is a top view of one embodiments of a disposable housing assembly;

FIG. 142B is a magnified cut away view of FIG. 142A as indicated by "B";

FIG. 142C is a magnified cut away view of FIG. 142A as indicated by "C";

FIG. 143A is a top view of one embodiment of the disposable housing assembly;

FIG. 143B is a cross sectional view of one embodiment of the disposable housing assembly, taken at "B" as indicated on FIG. 143A;

Figure 144A:
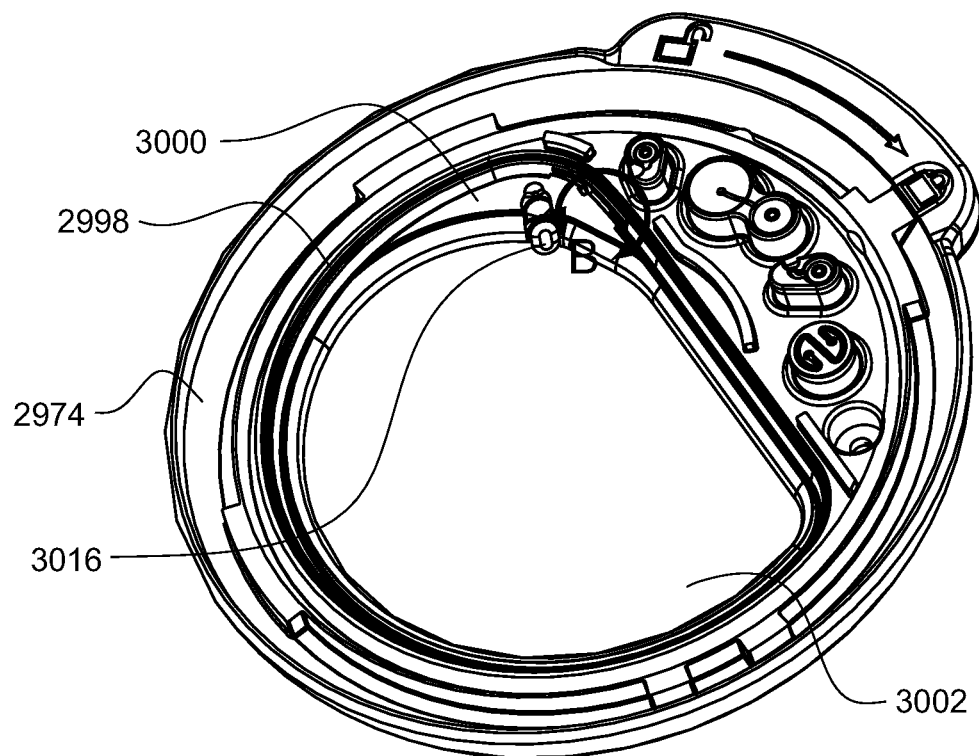
Figure 144B:
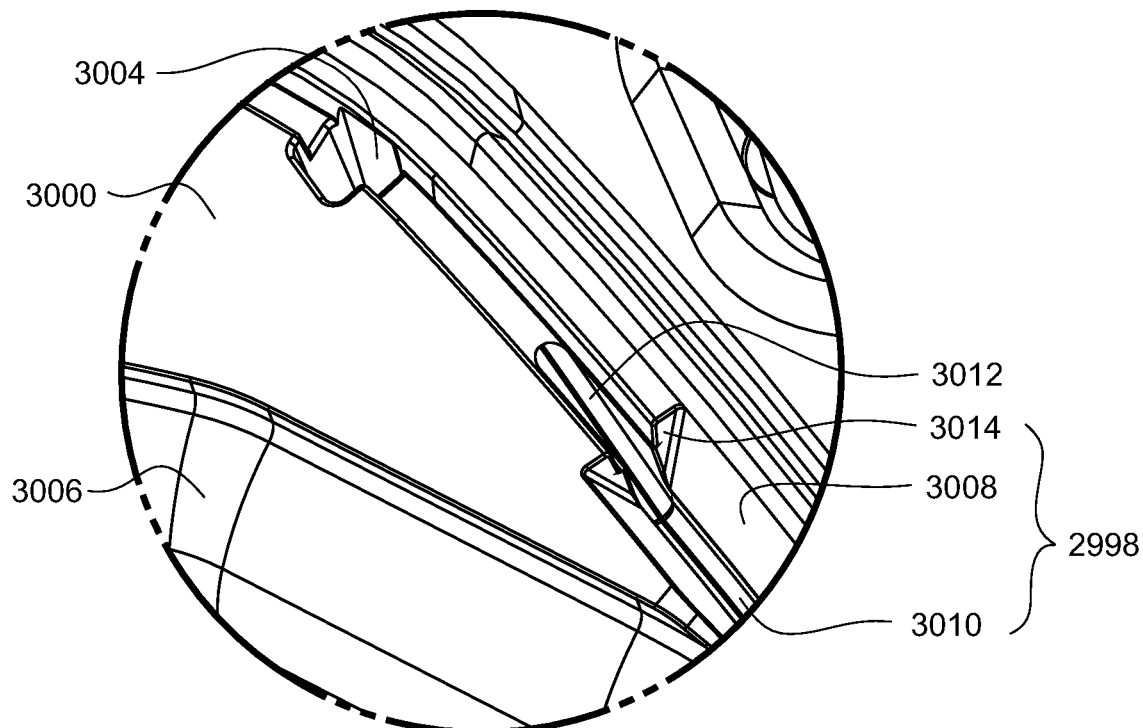
Figure 144C:
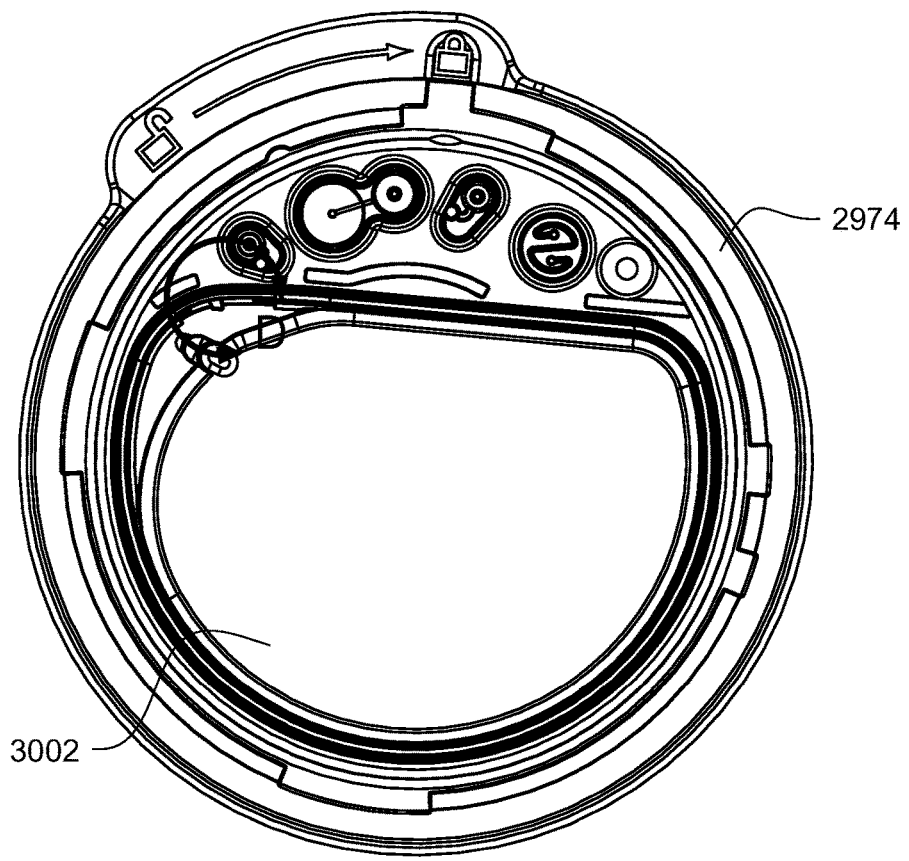
Figure 144D:
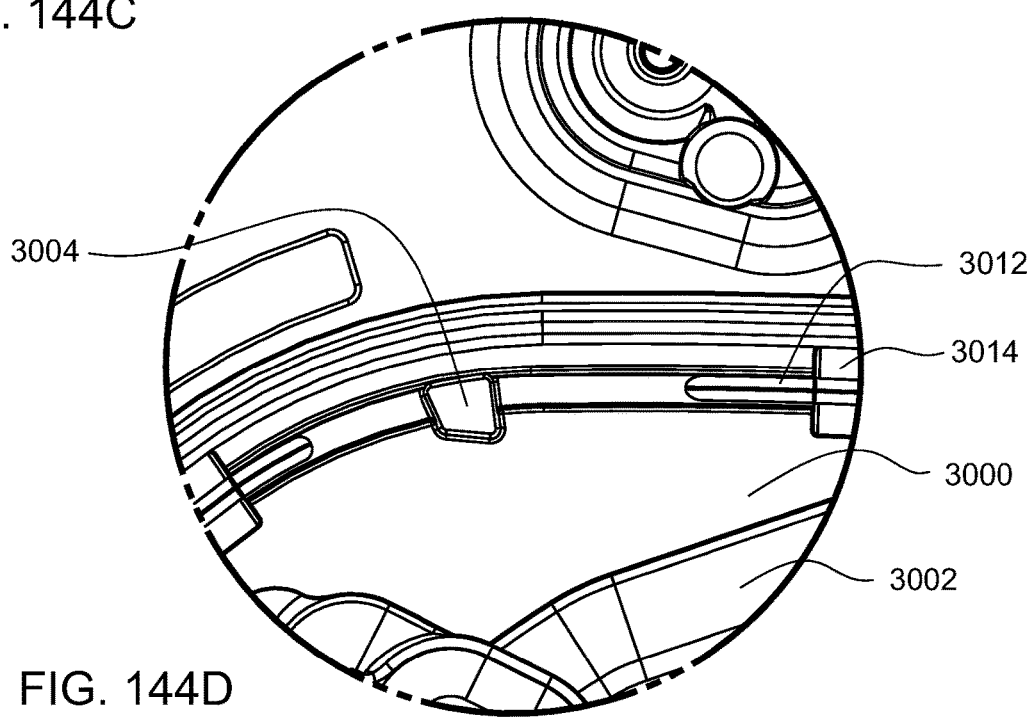
Figure 144E:
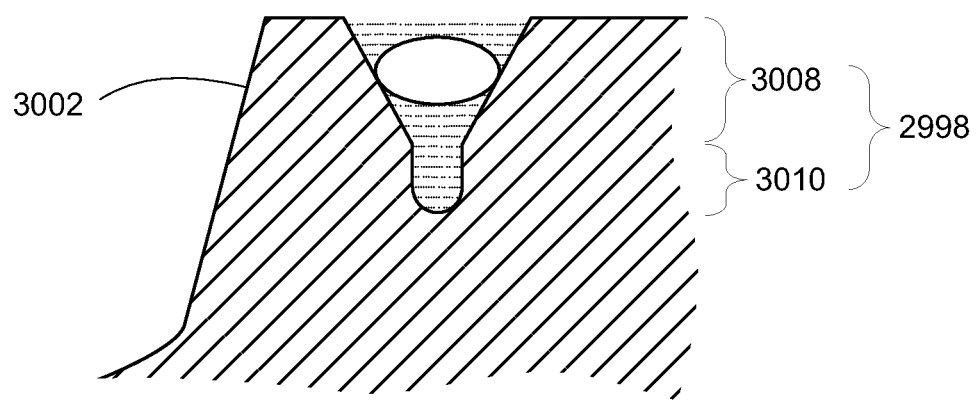
Figure 145:
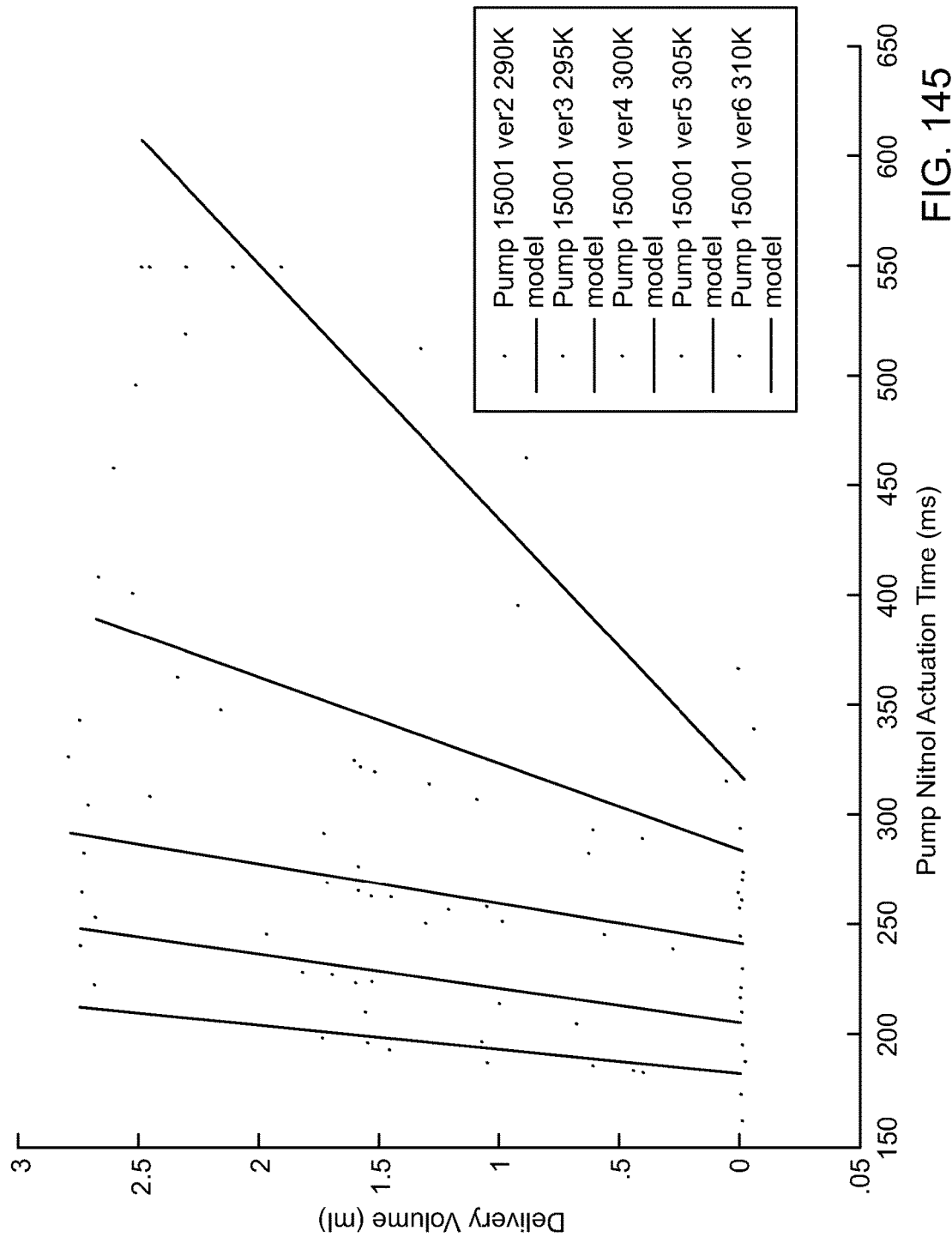
Figure 146:
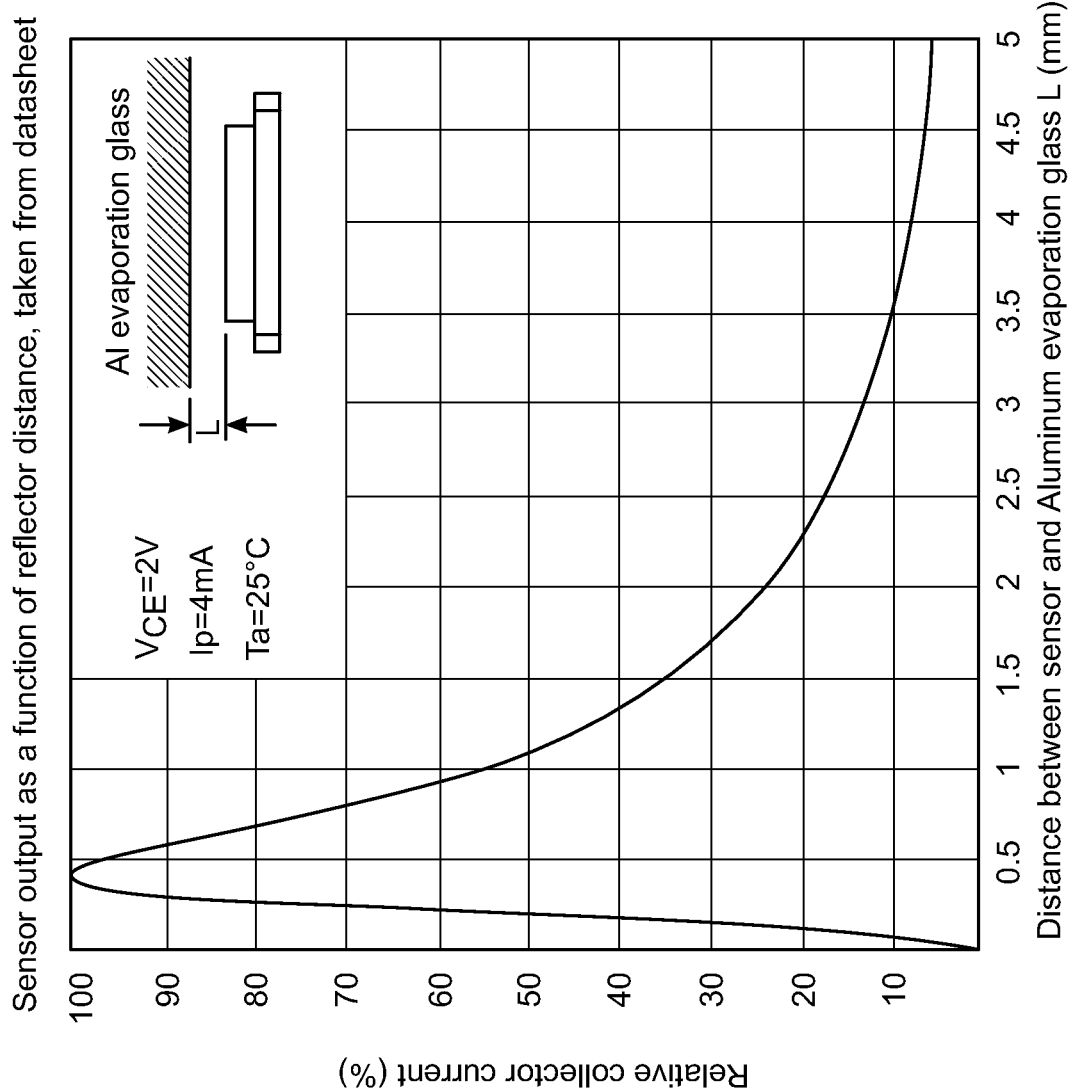
Figure 147:
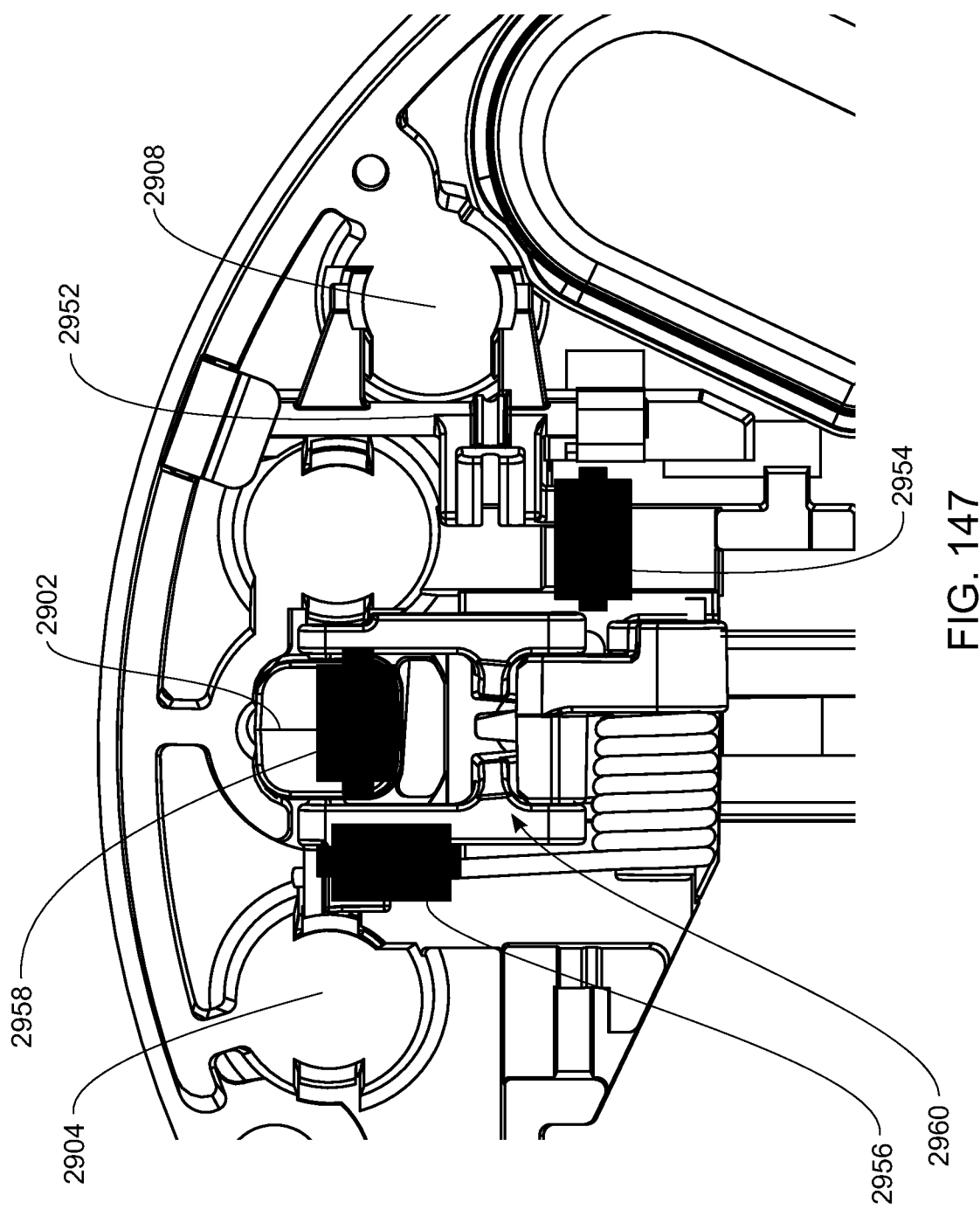
Figure 148A:
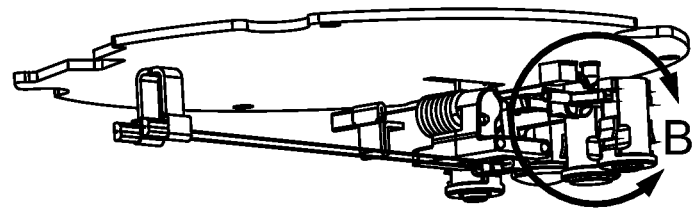
Figure 148B:
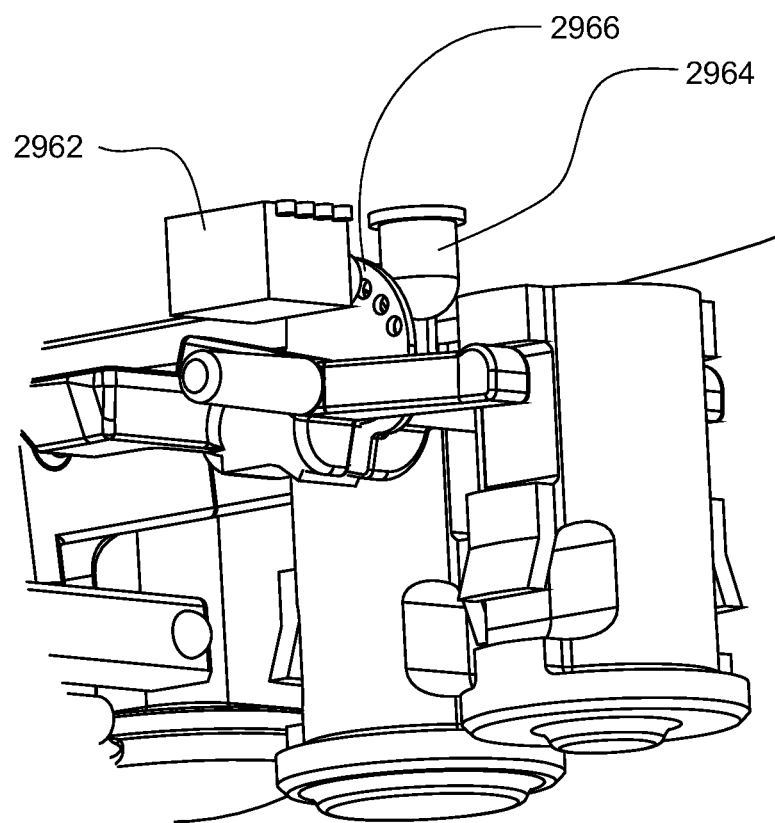
Figure 149A:
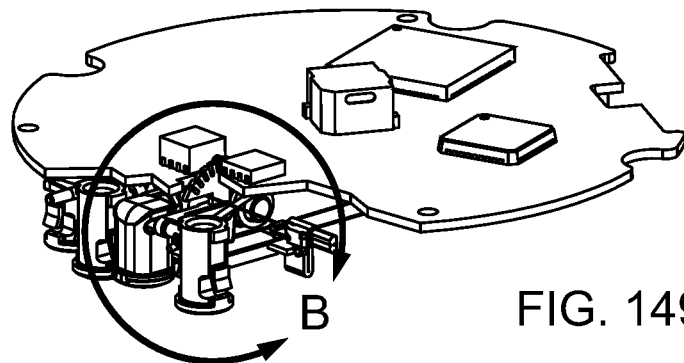
Figure 149B:
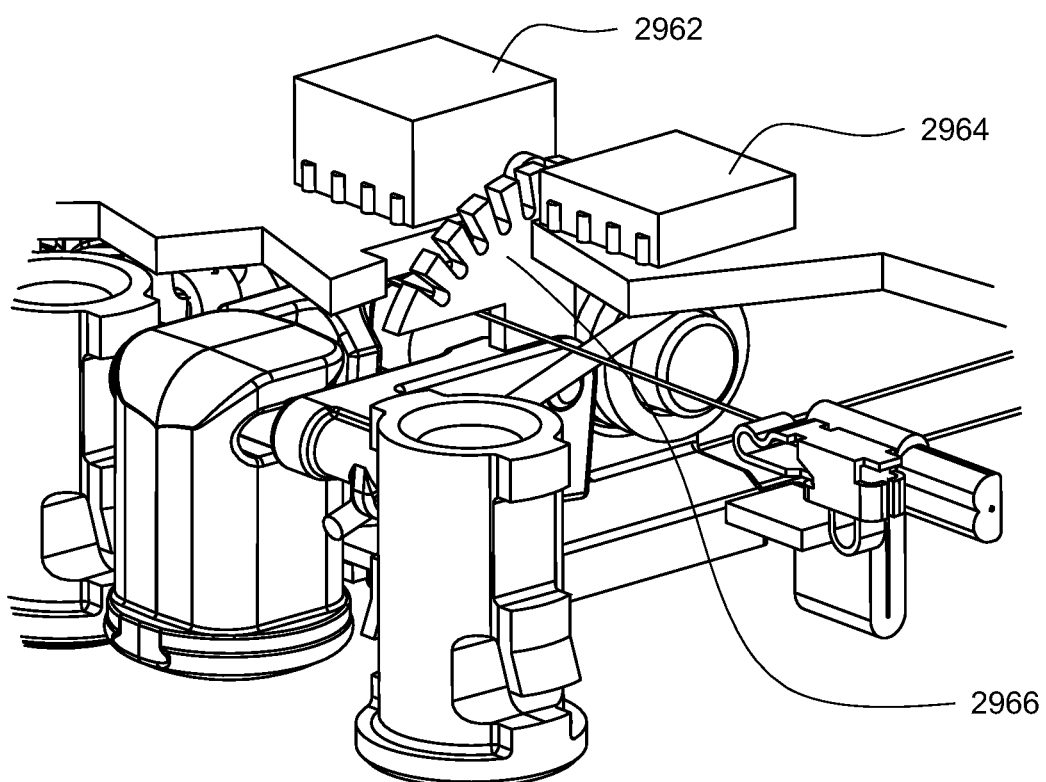
Figure 150:
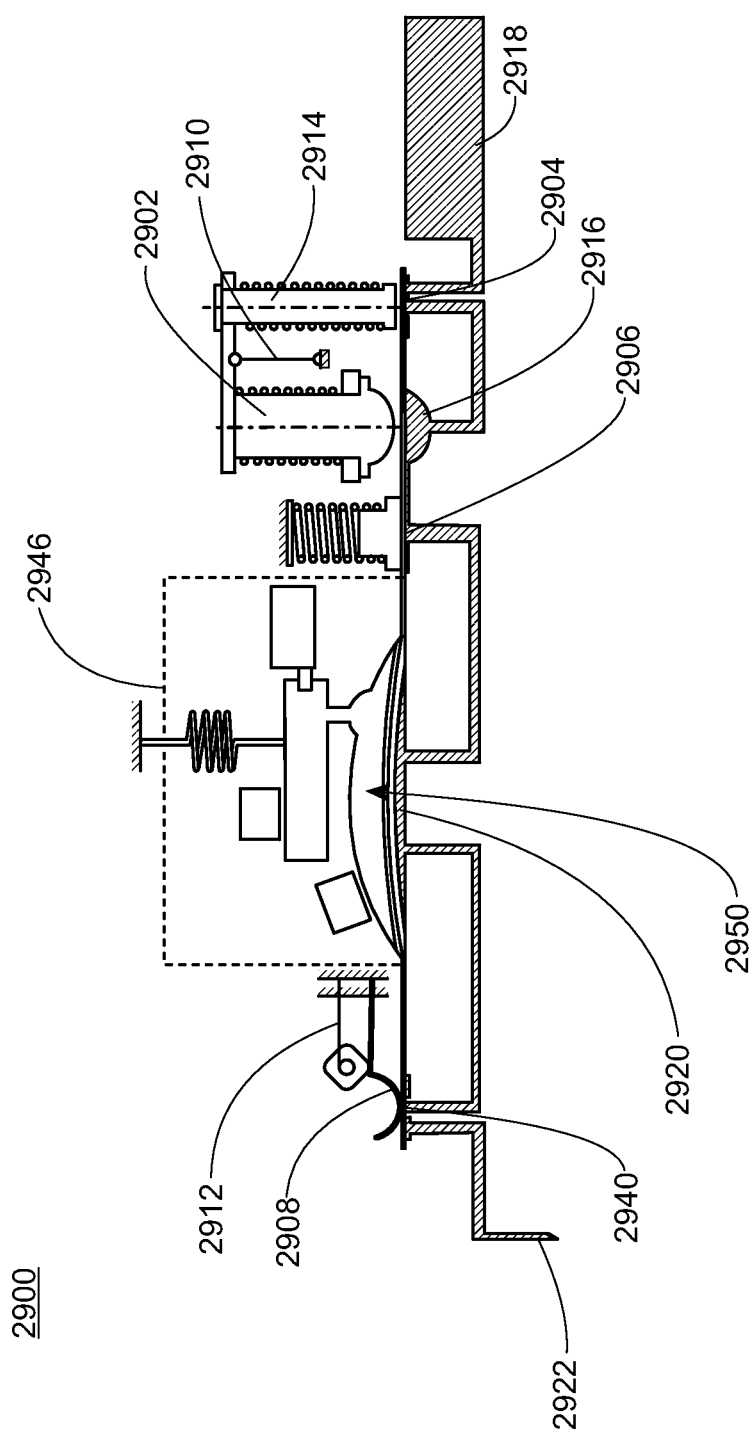
Figure 151:
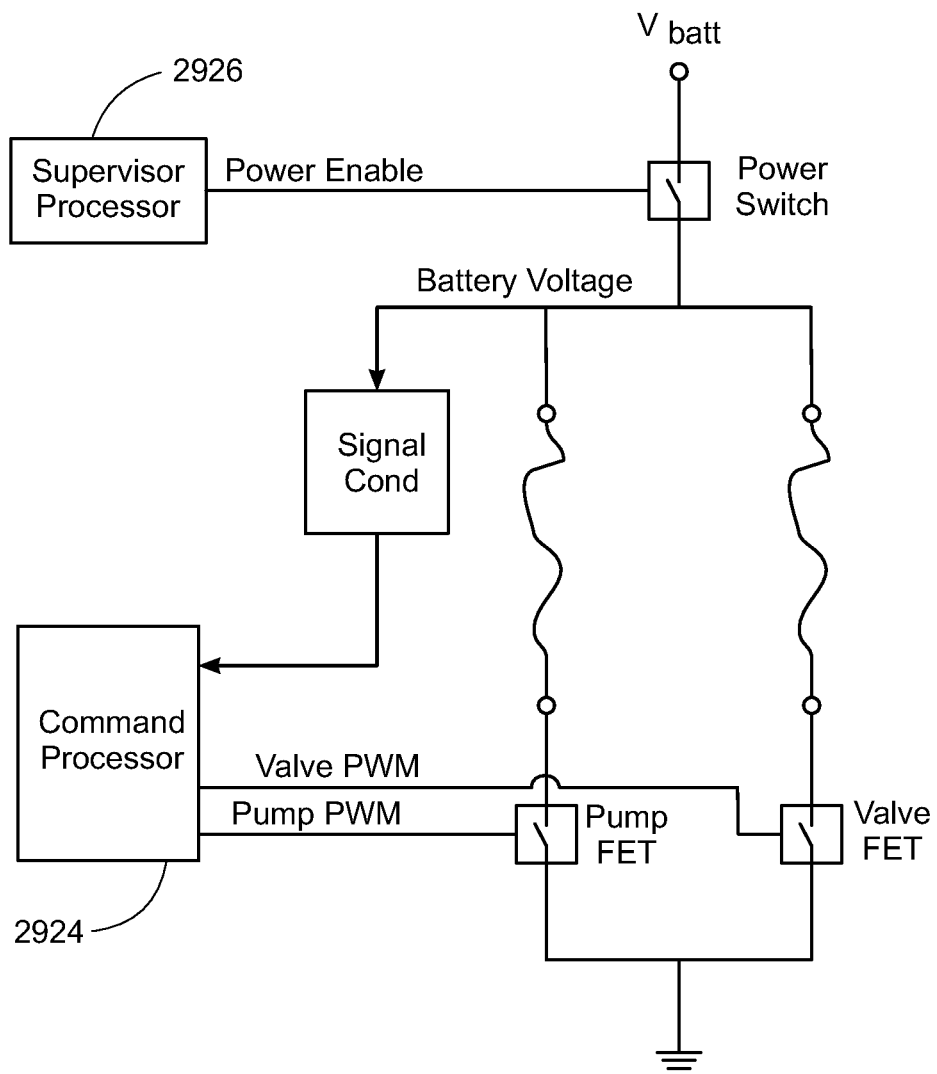
Figure 152:
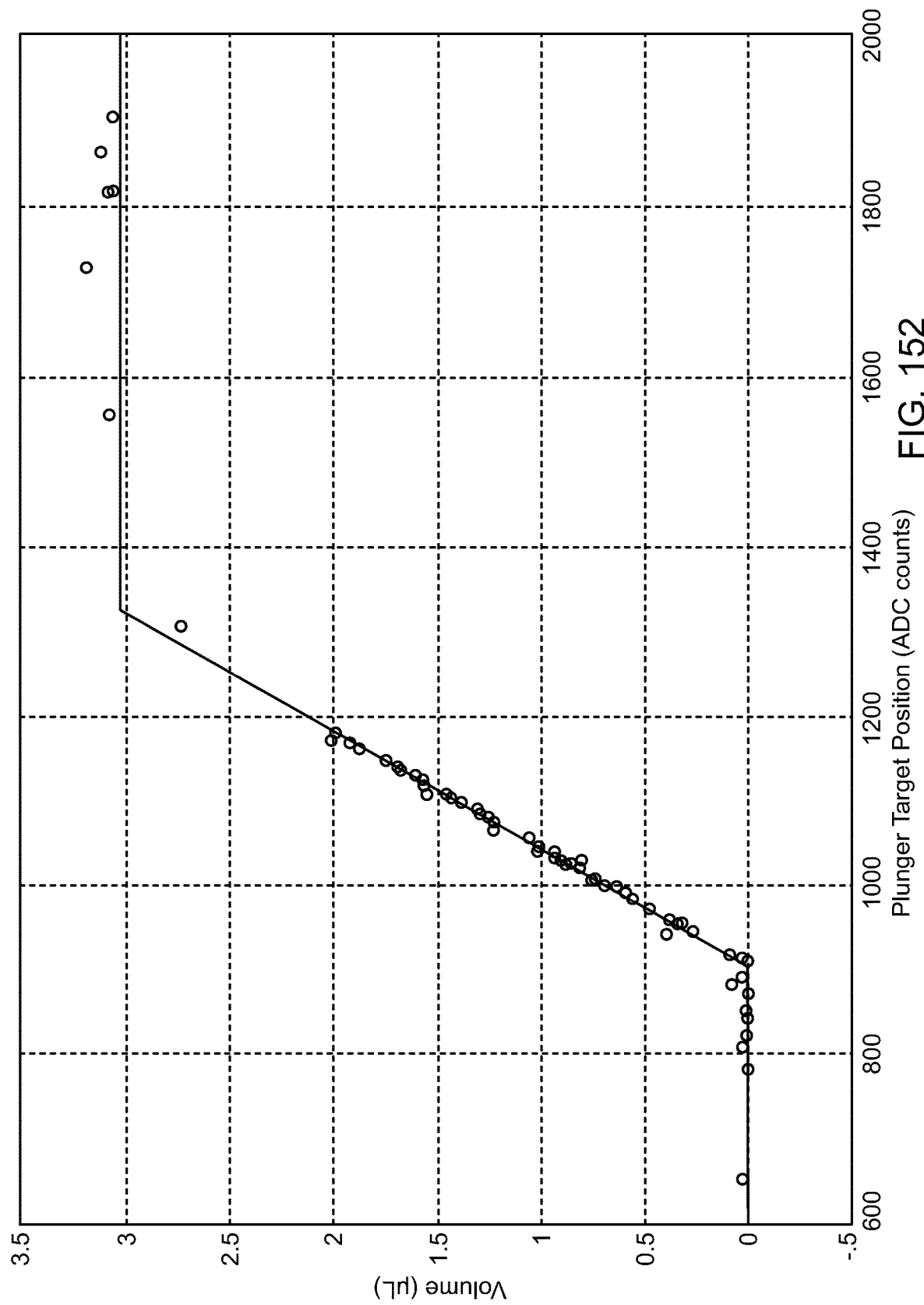
Figure 153:
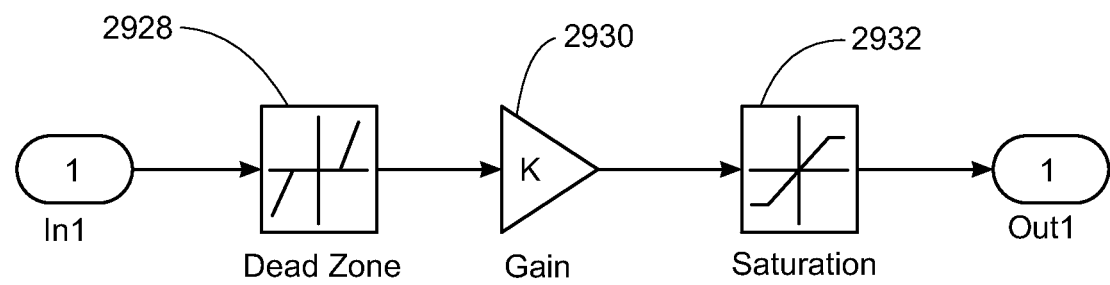
Figure 154A:
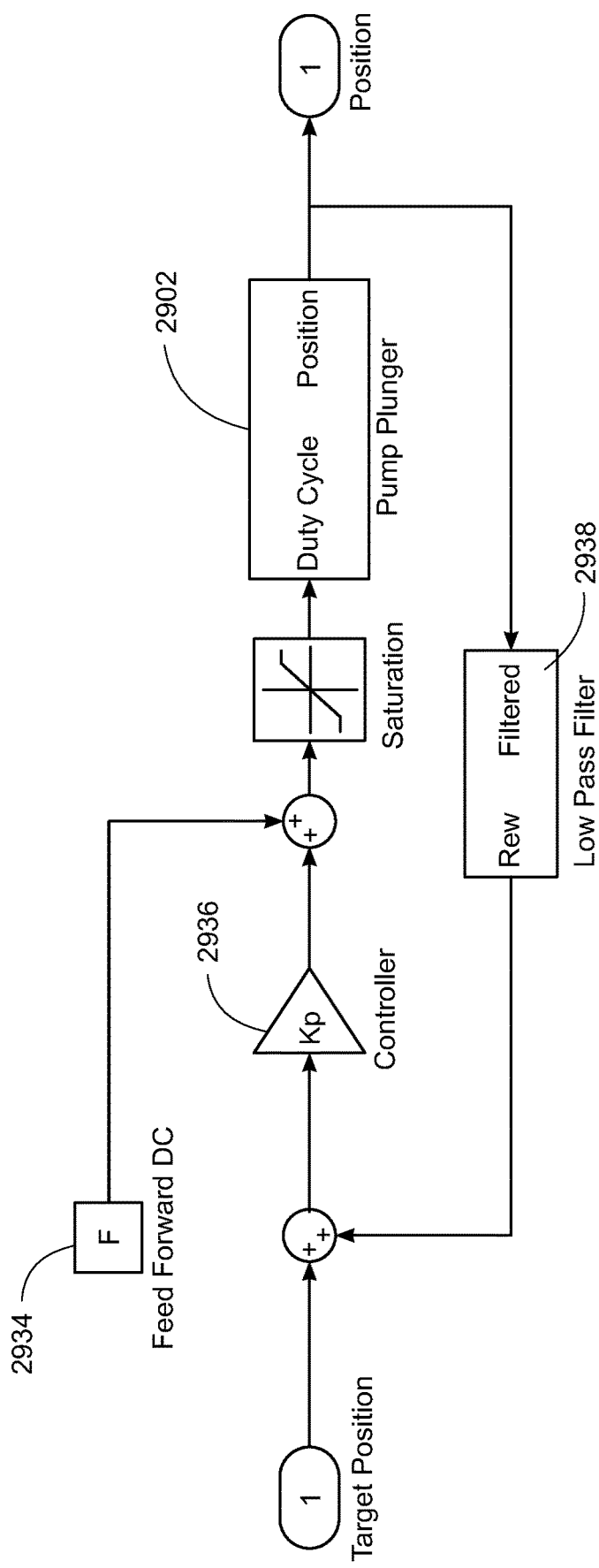
Figure 155:
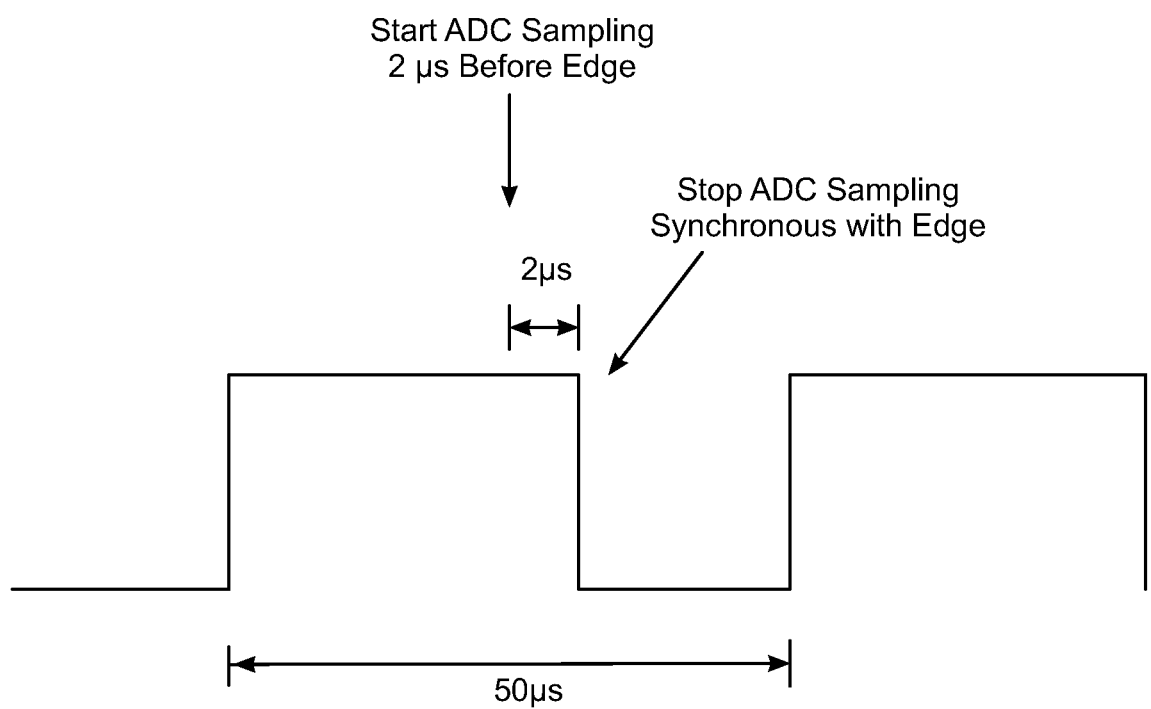
Figure 156:
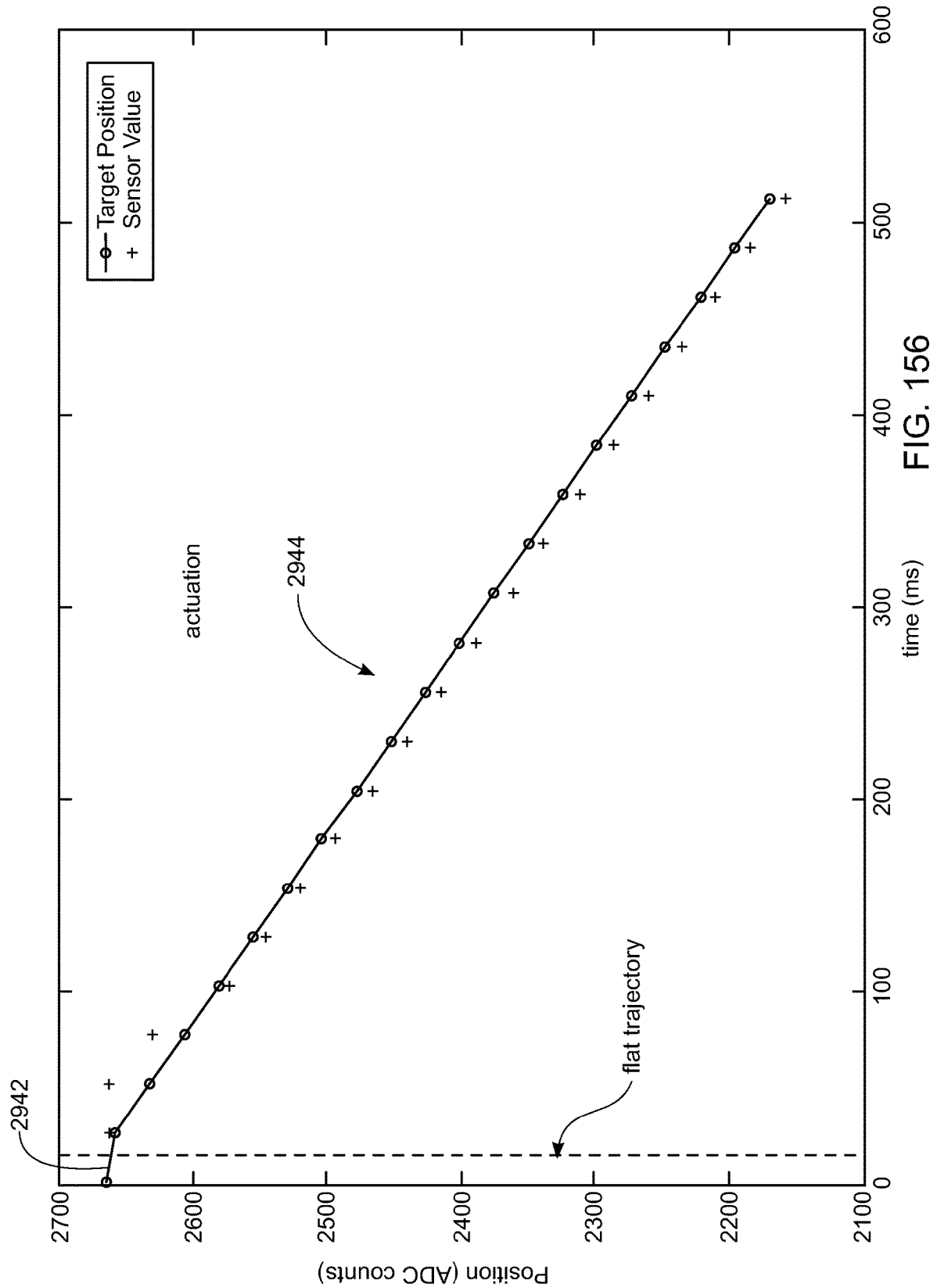
Figure 157:
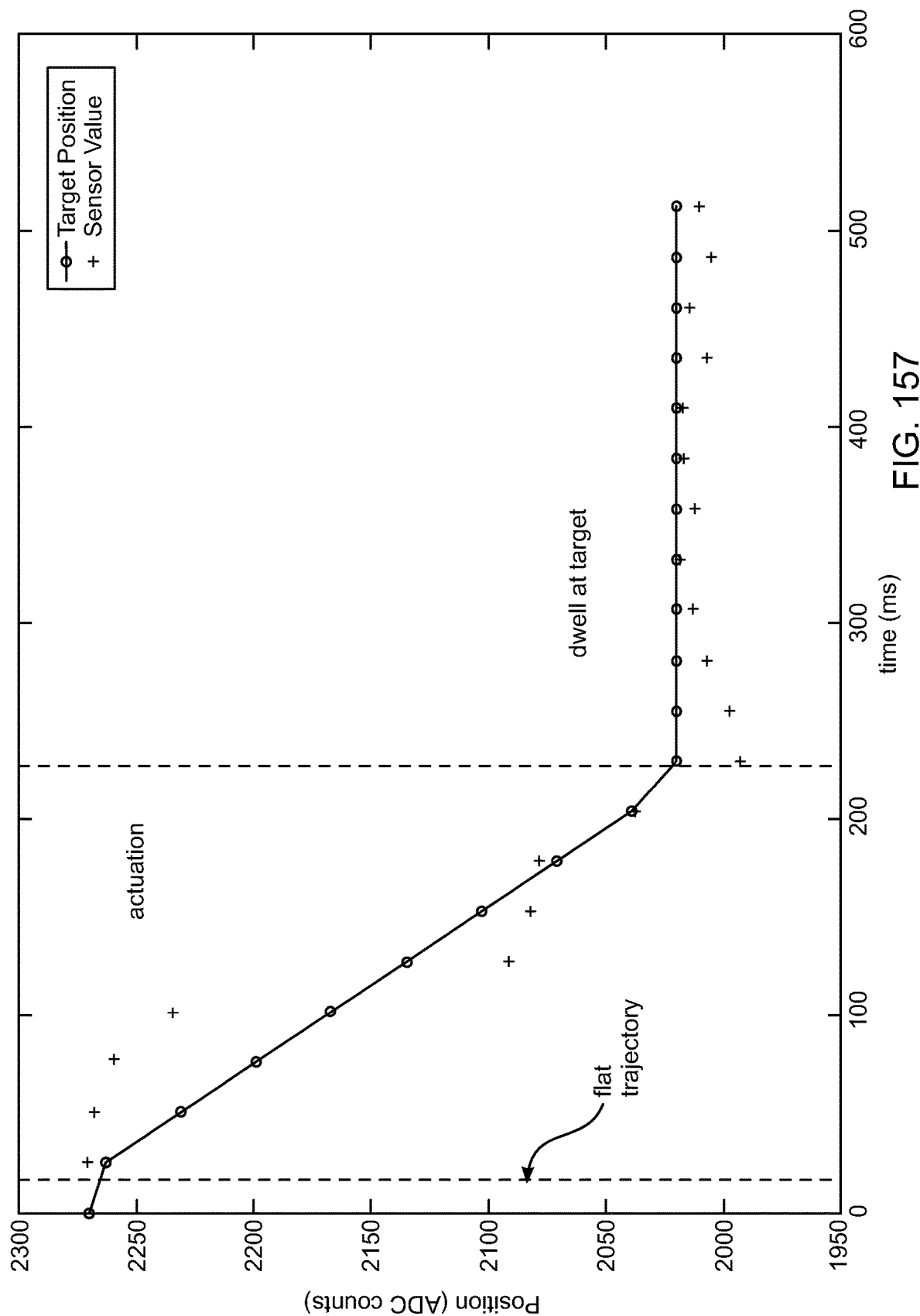
Figure 158:
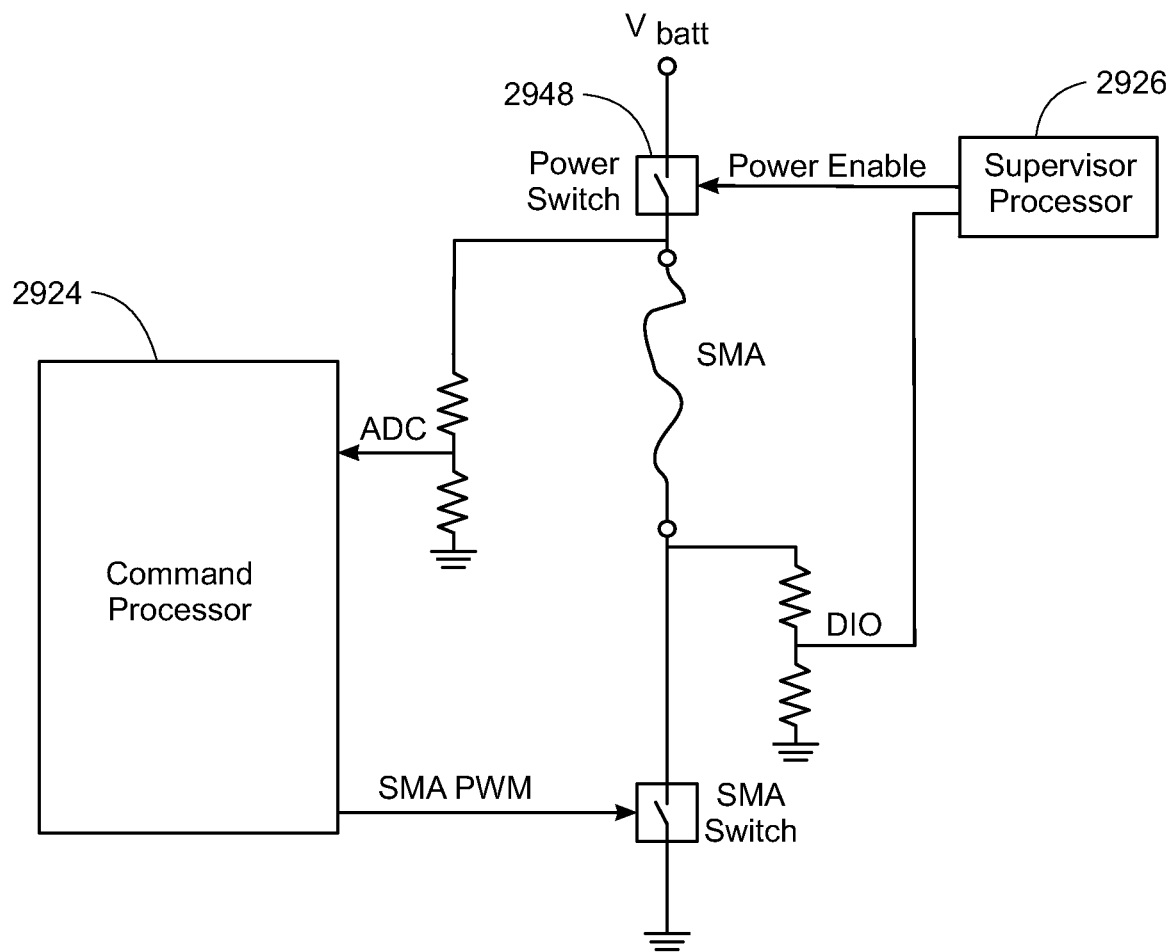
Figure 160:
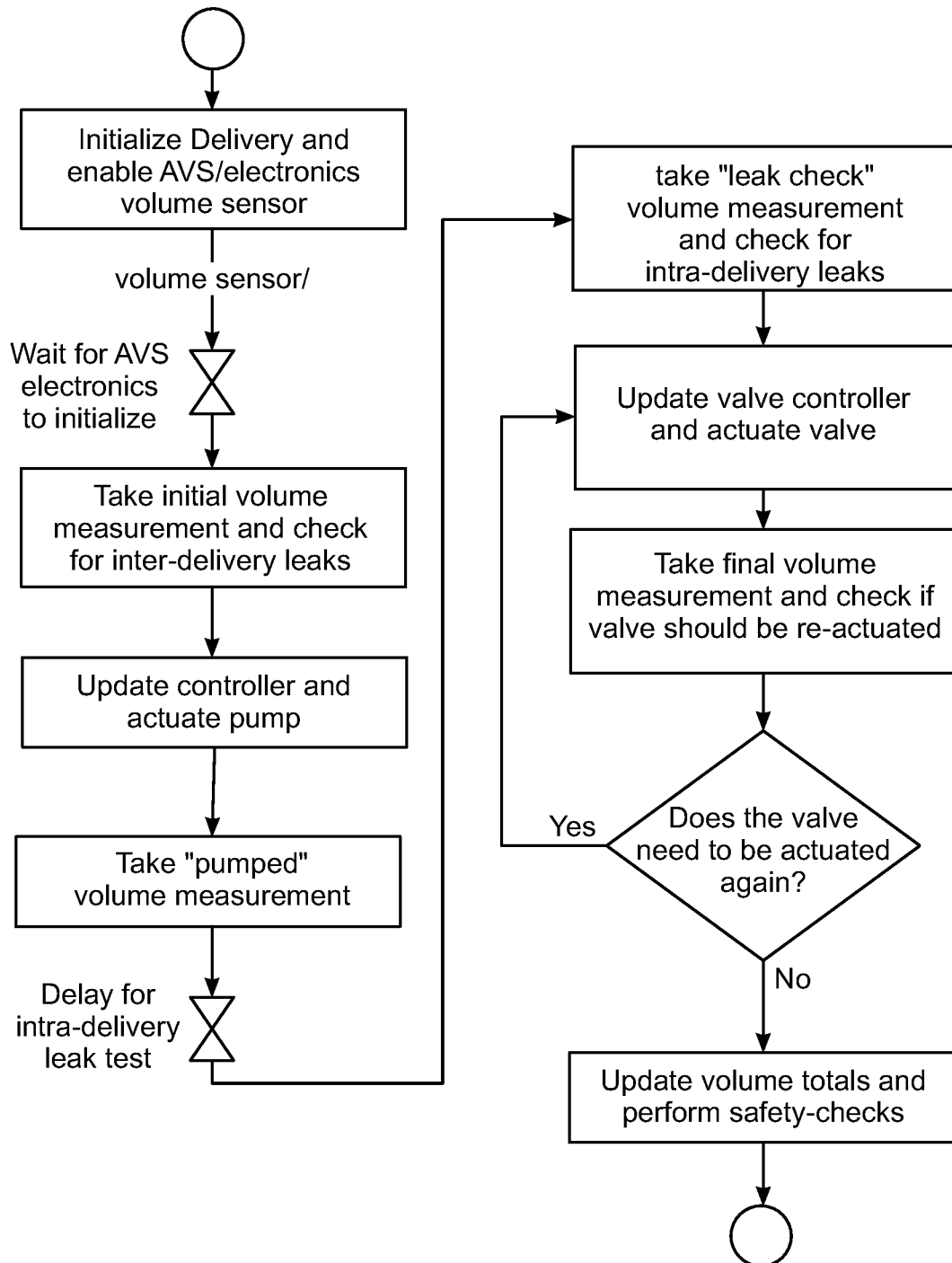
Figure 161:
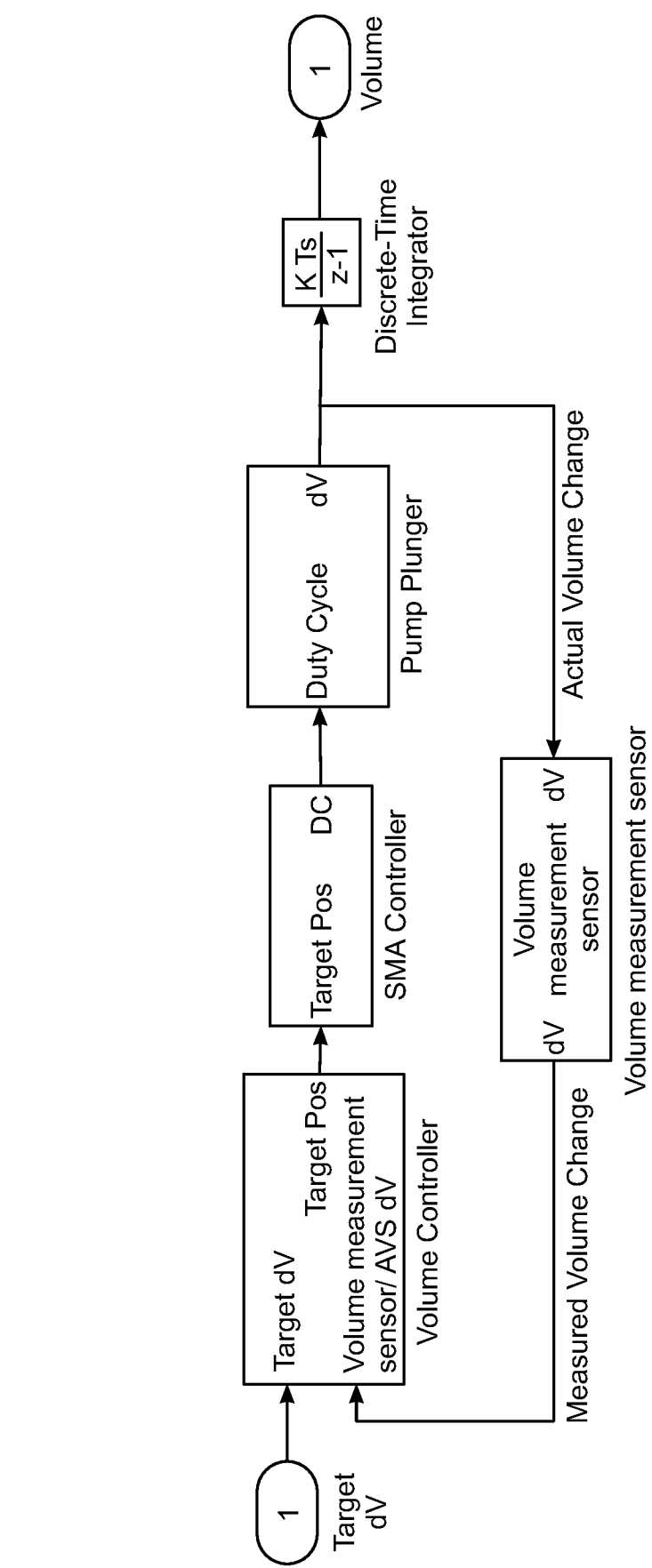
Figure 162:
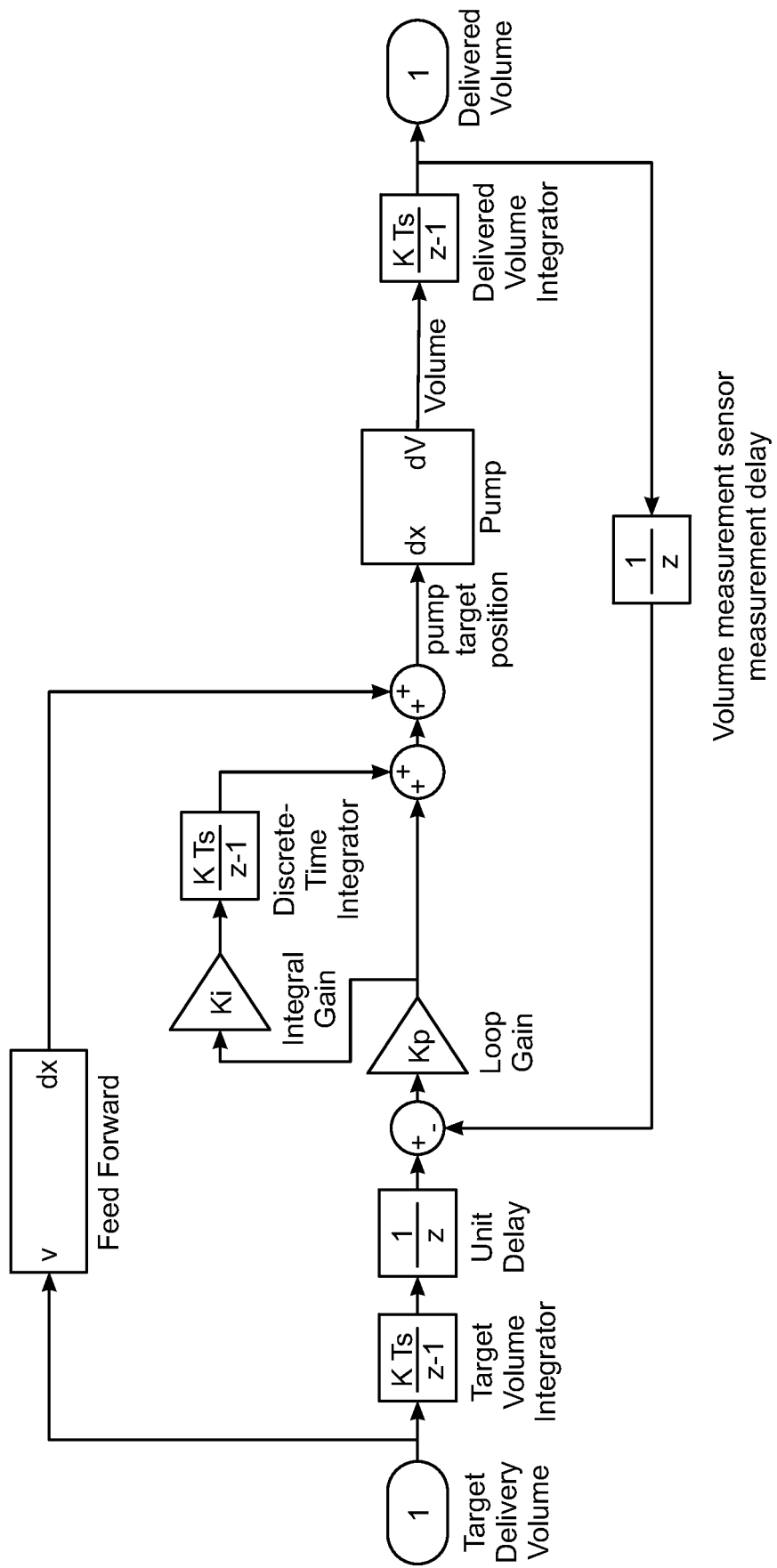
Figure 163:
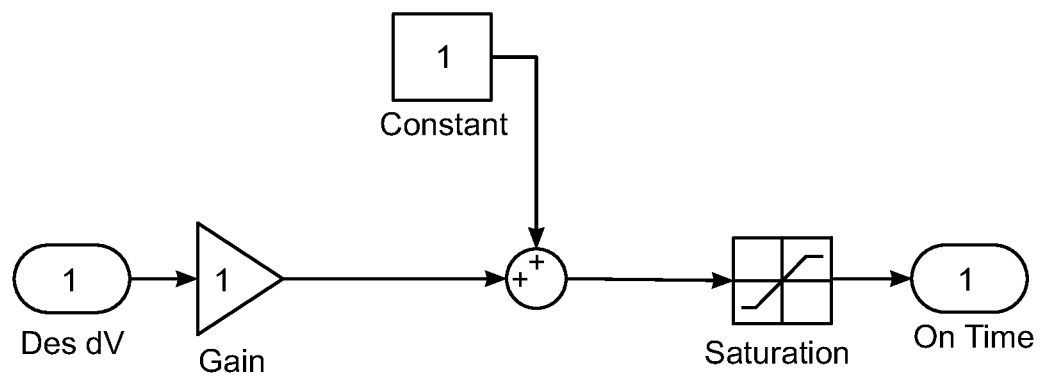
Figure 164:
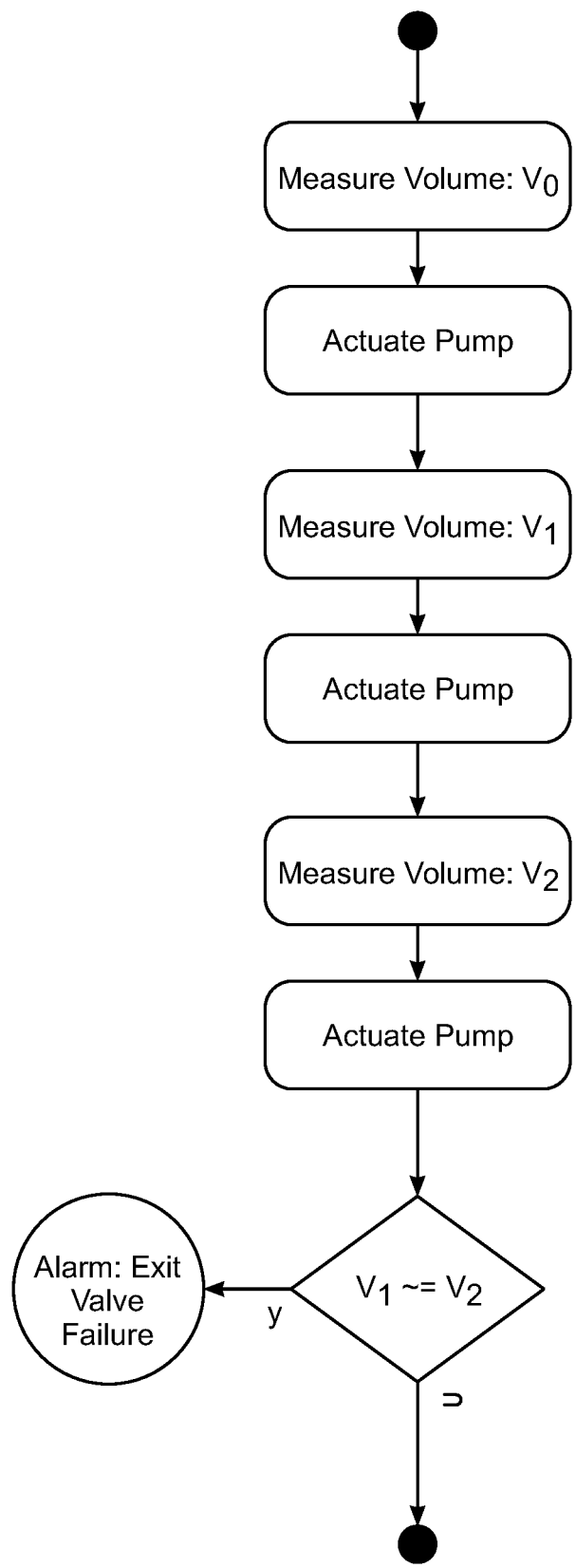
Figure 165:
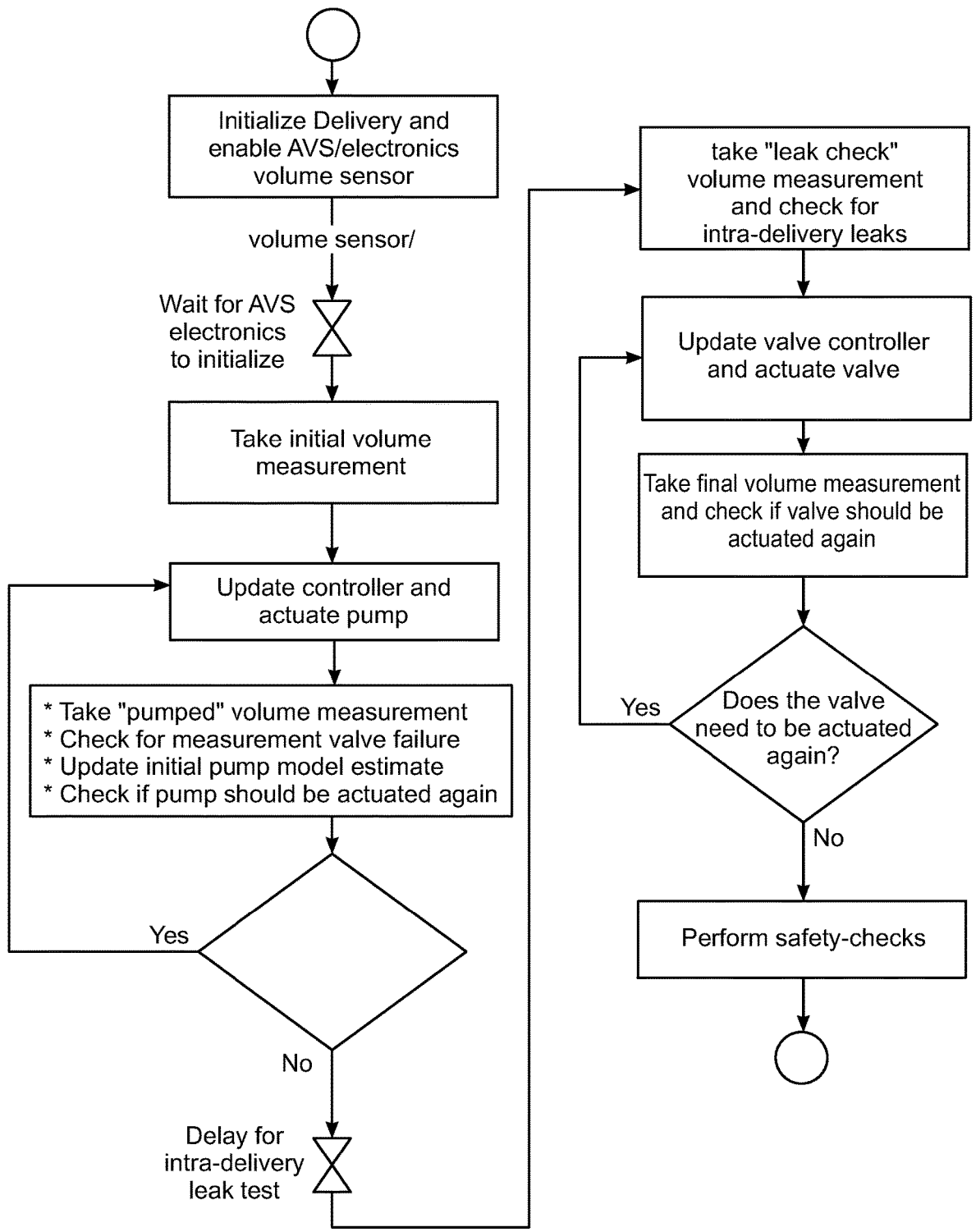
Figure 166:
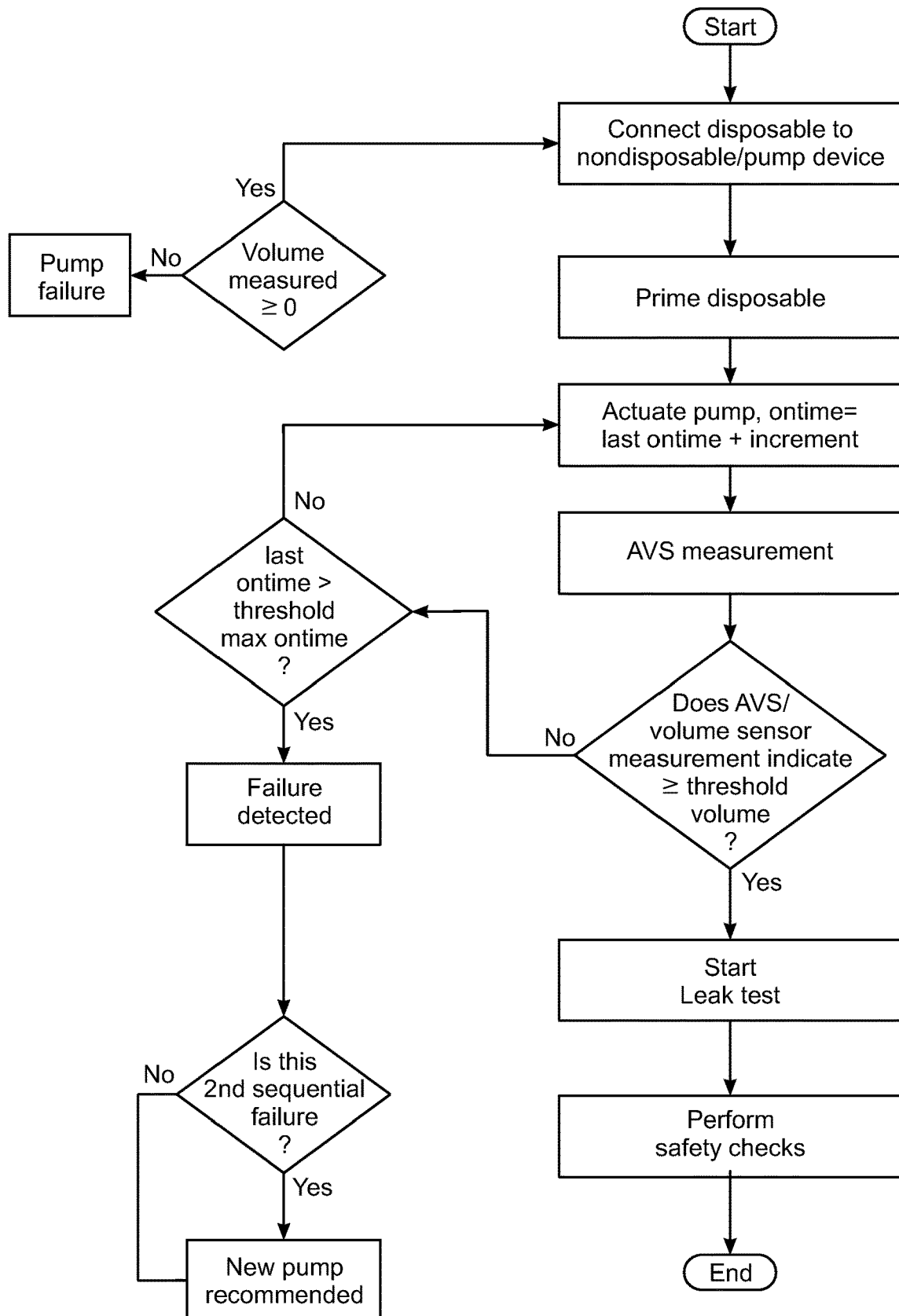
Figure 167:
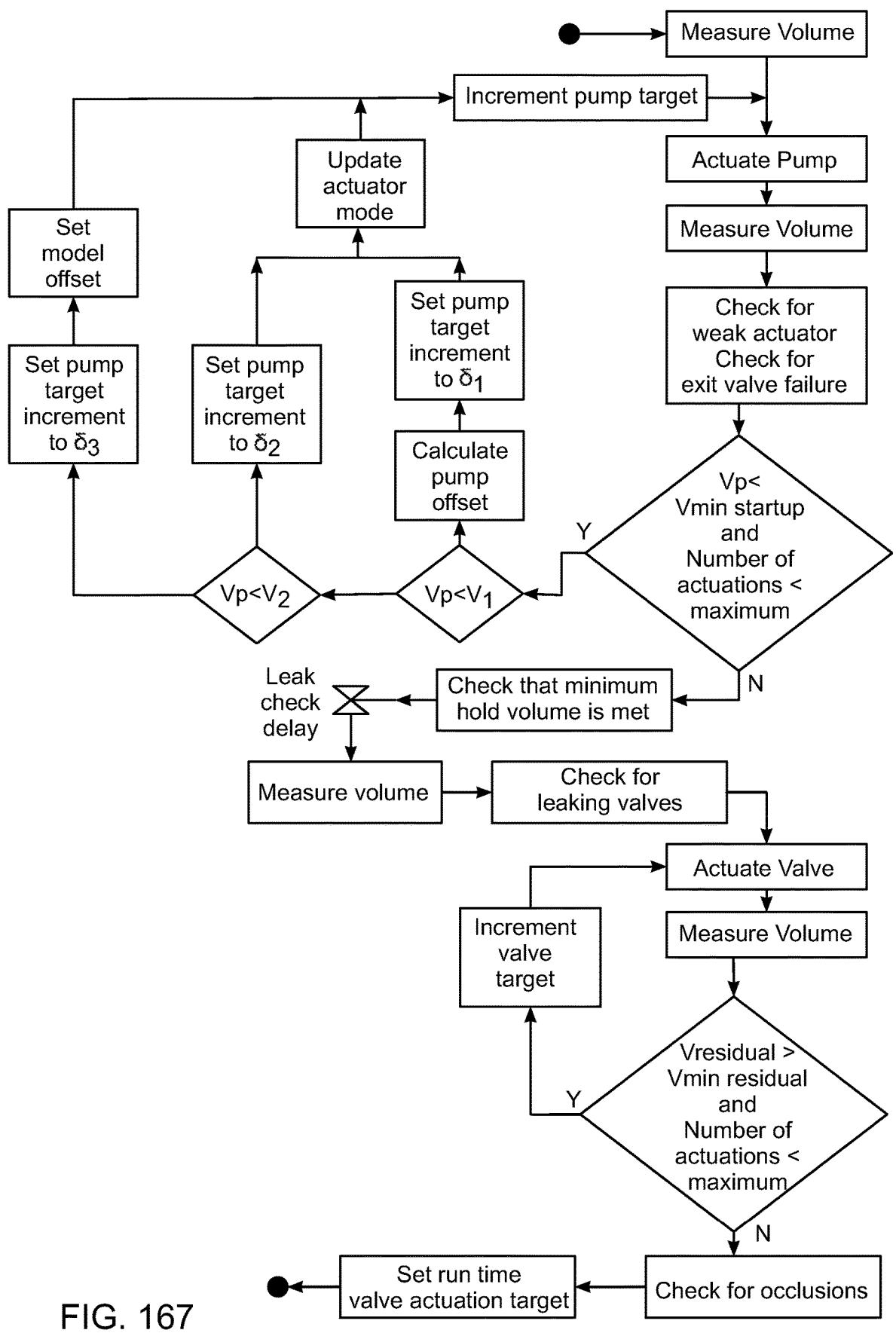
Figure 168:
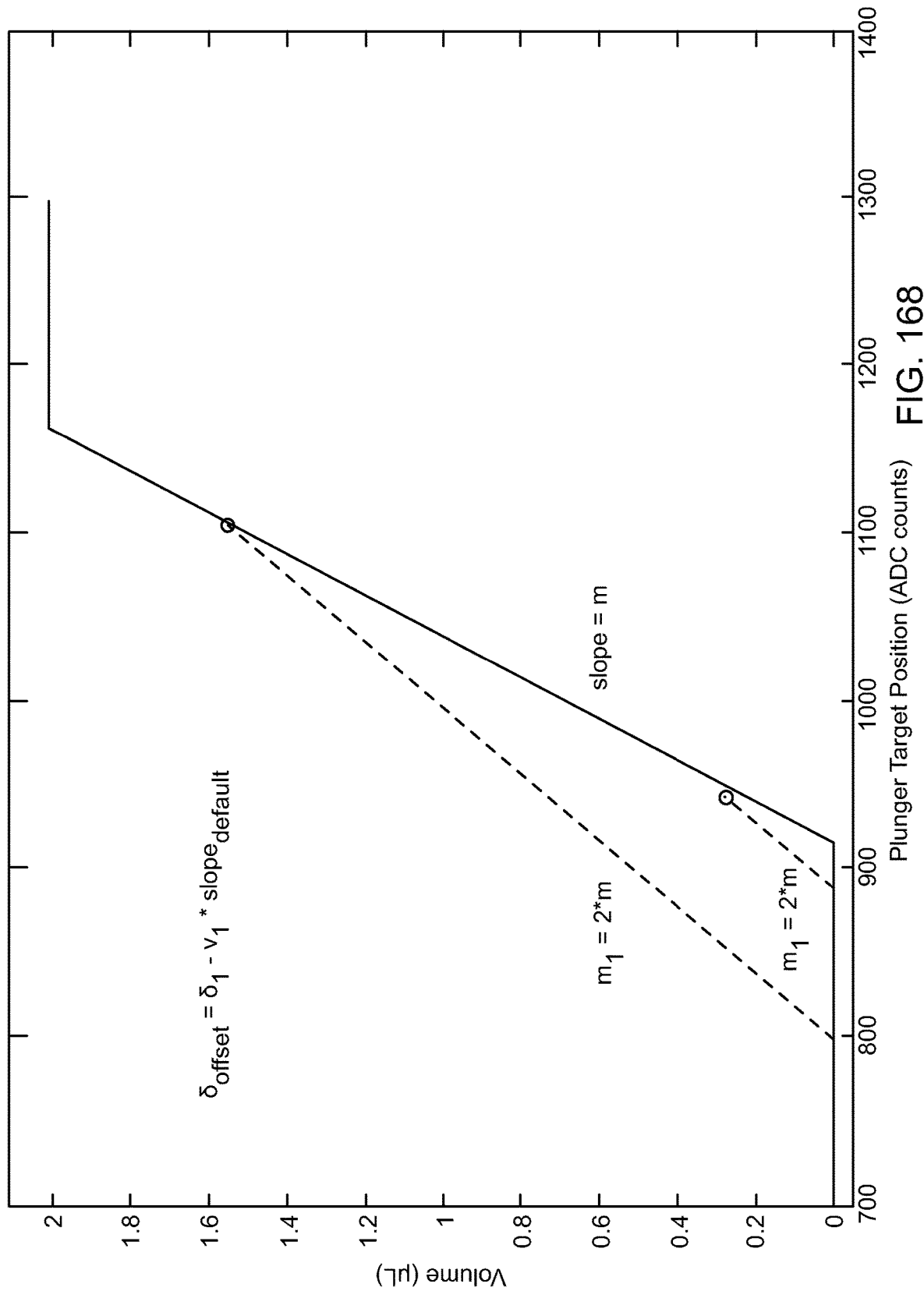
Figure 169:
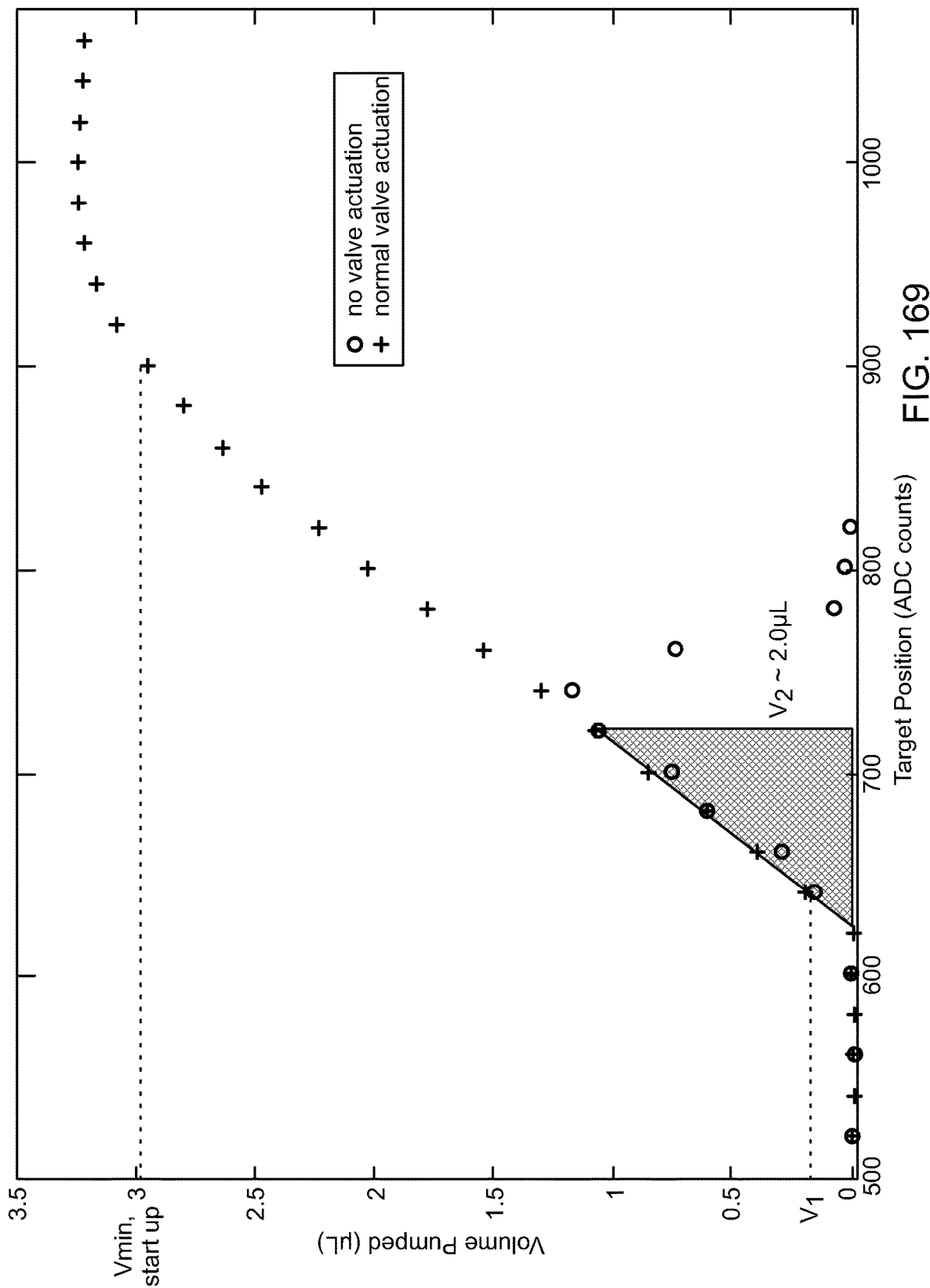
Figure 170:
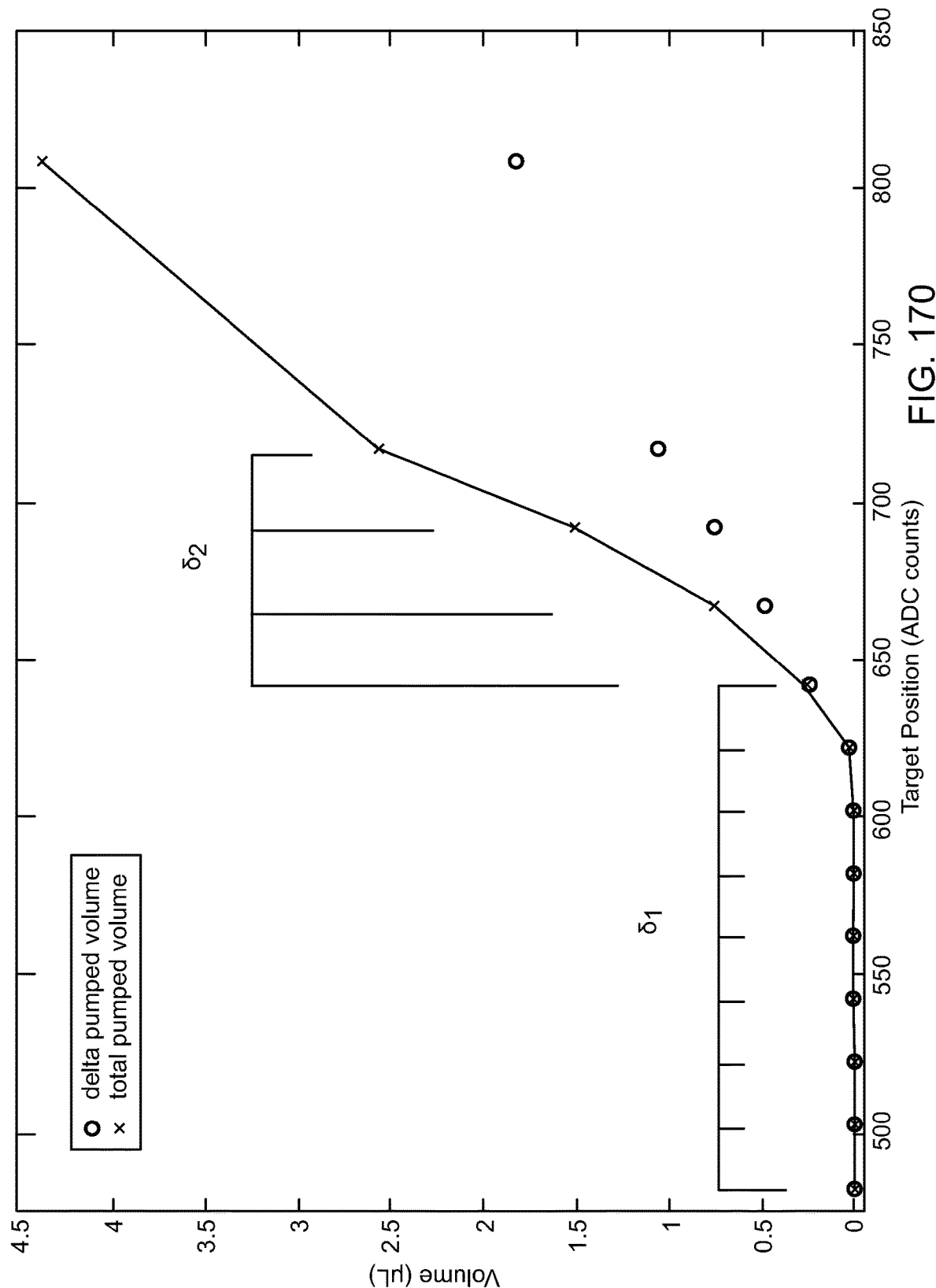
Figure 171:
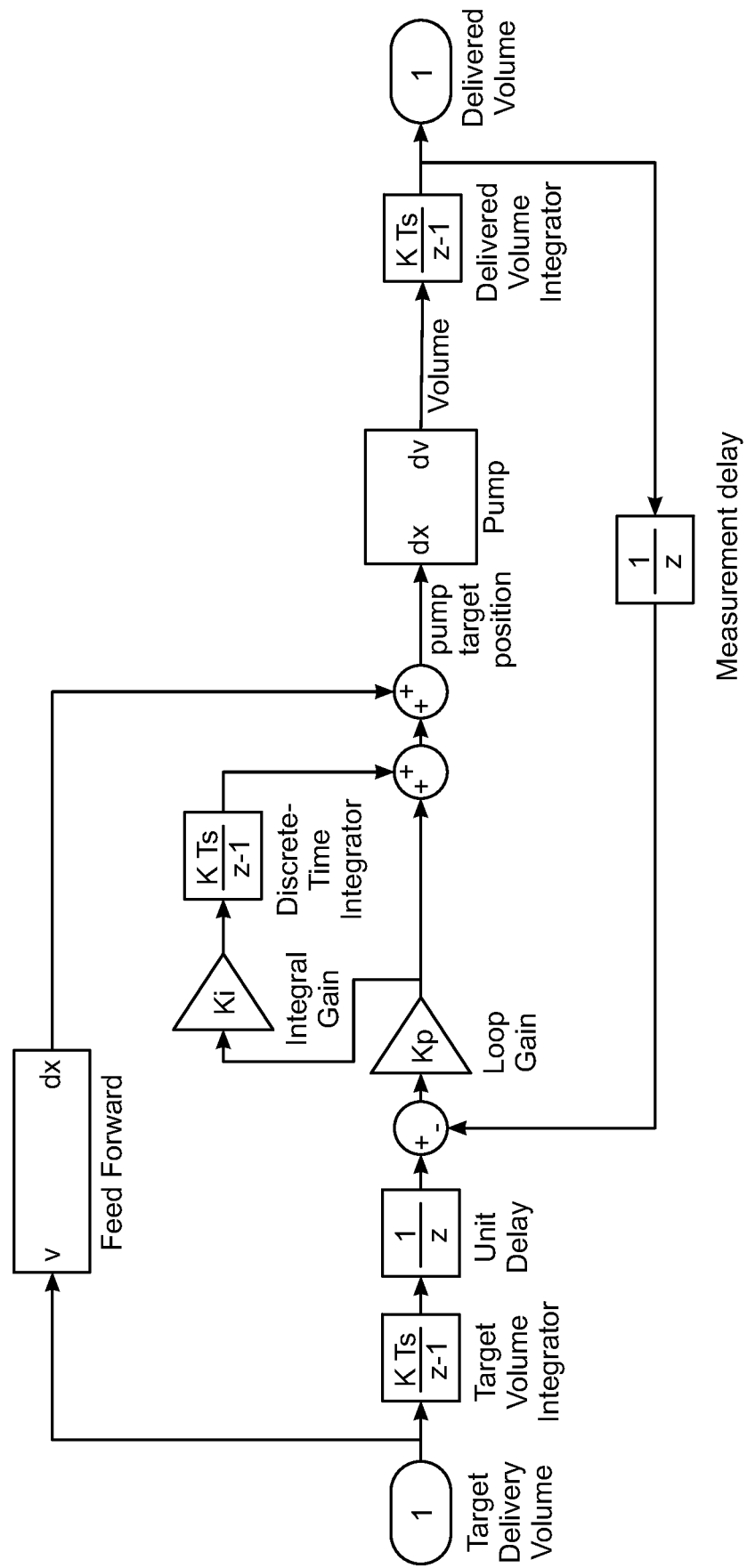
Figure 172:
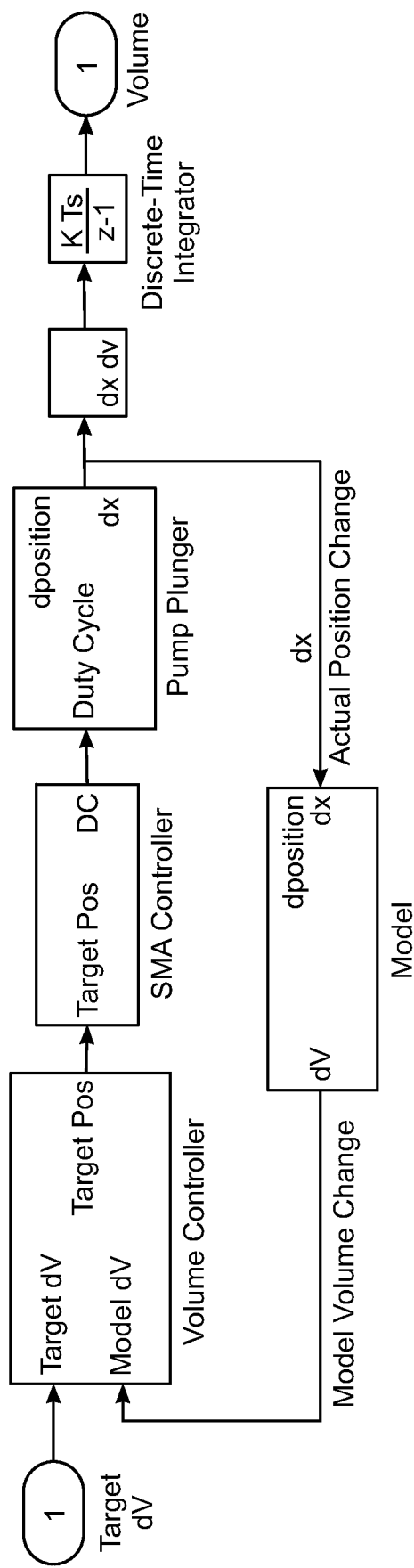
Figure 173A:
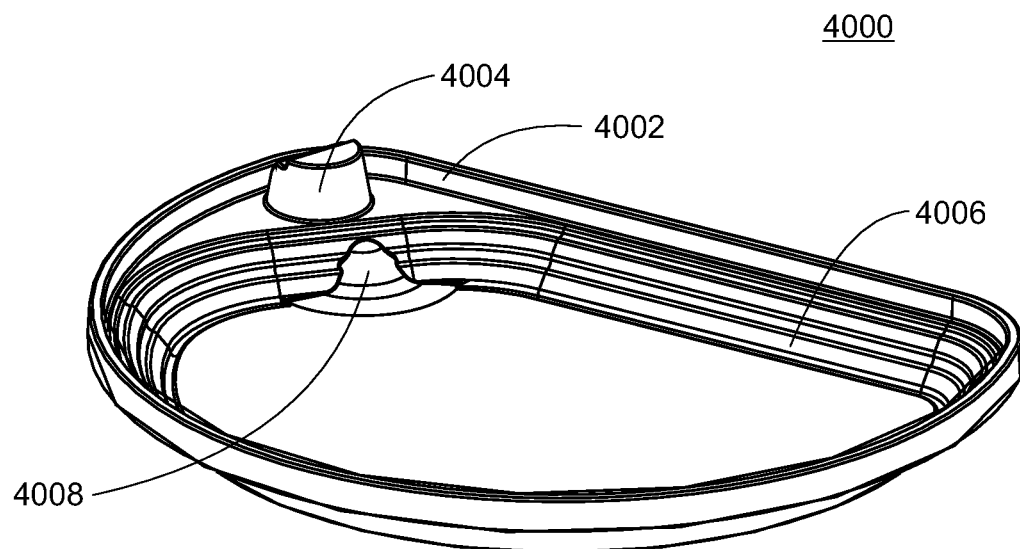
Figure 173B:
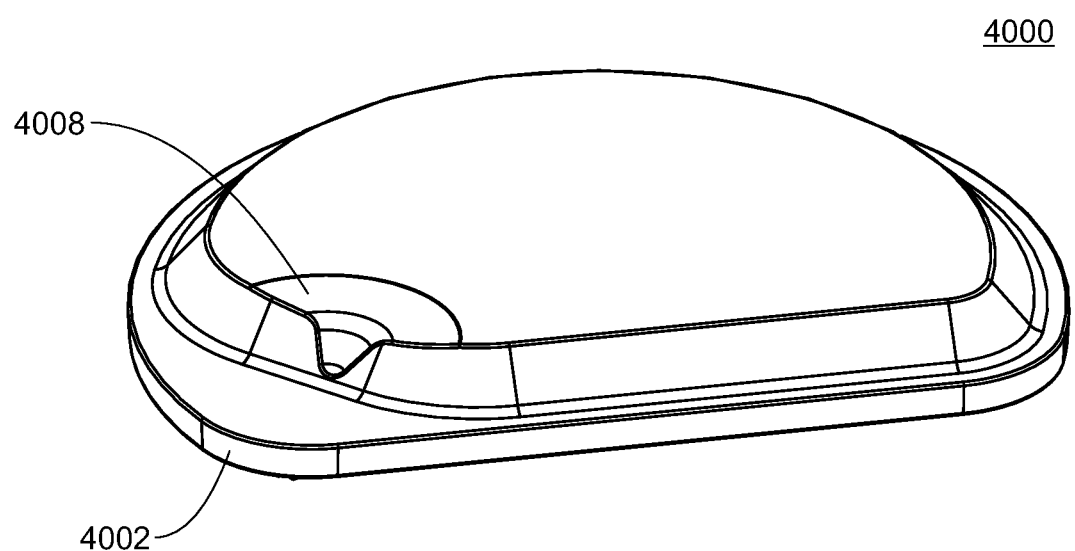
Figure 175:
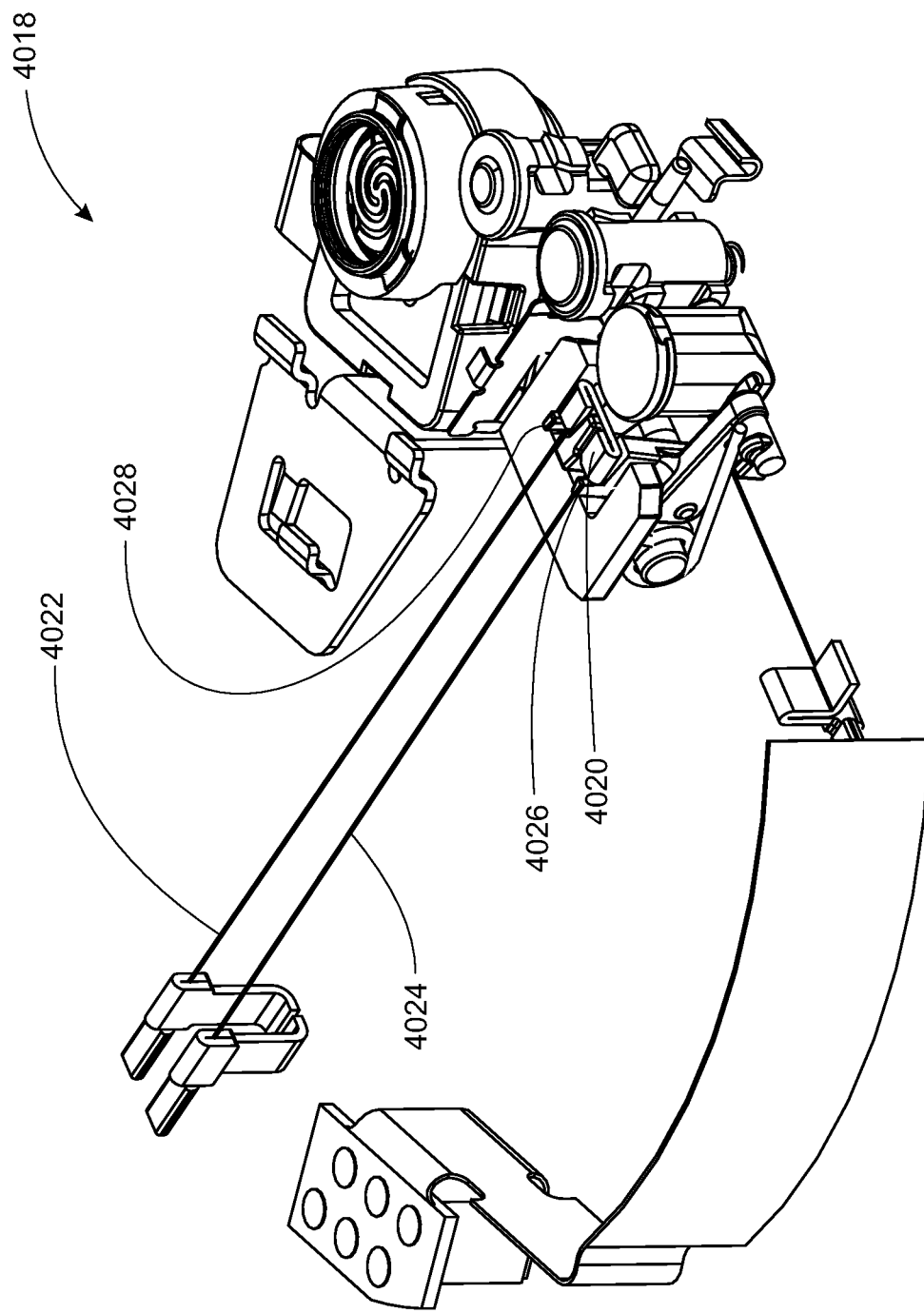
Figure 176A:
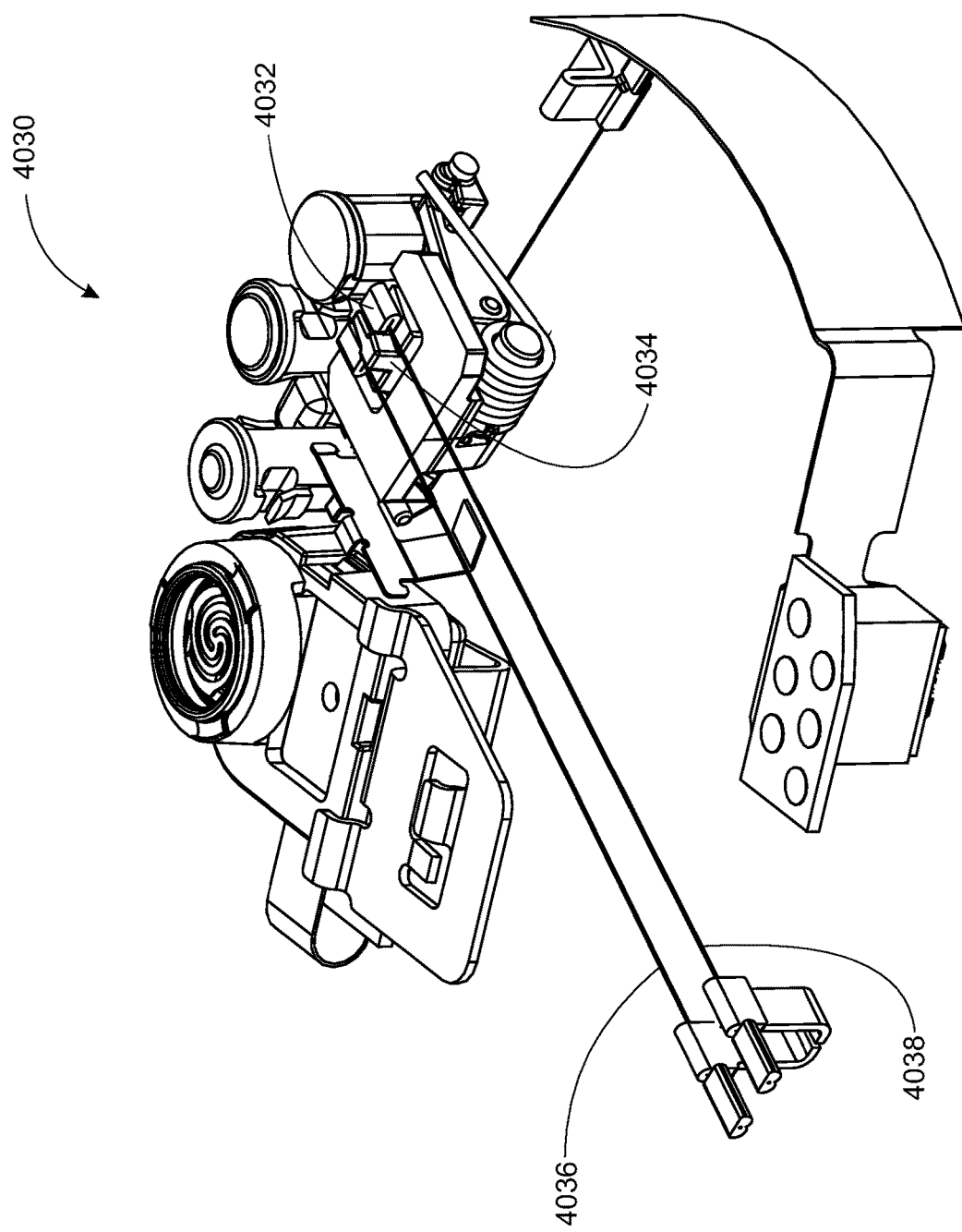
Figure 176B:
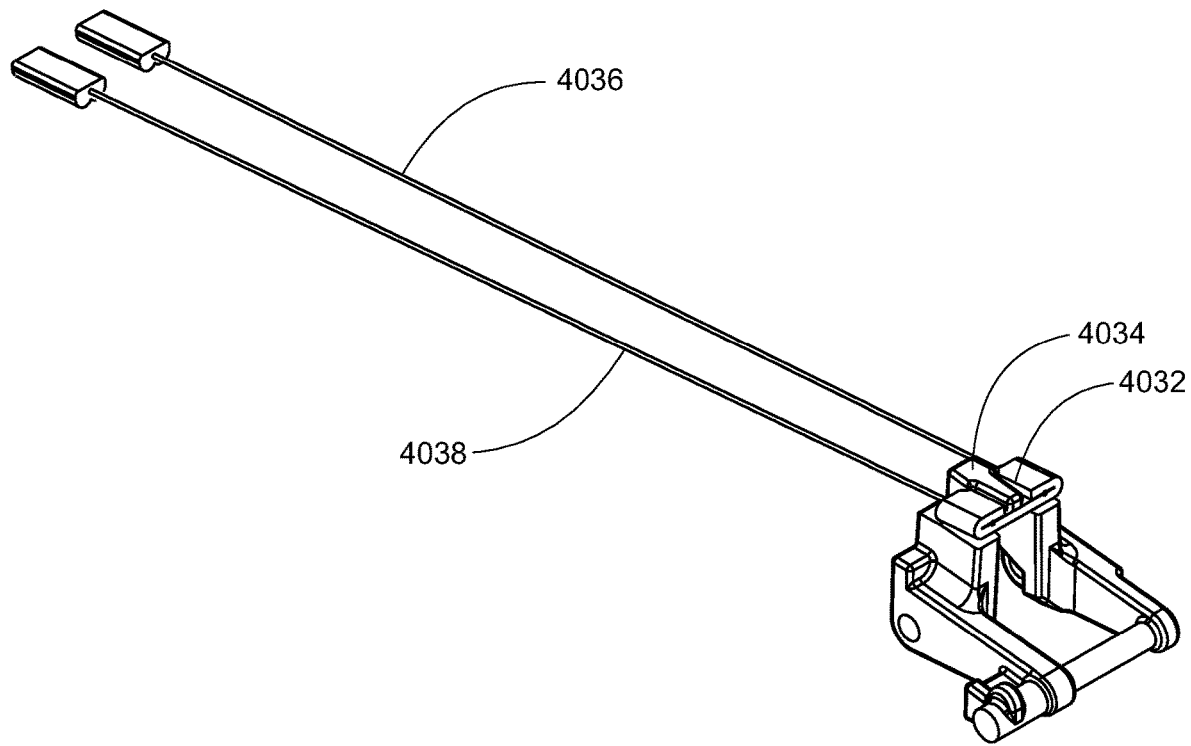
Figure 177A:
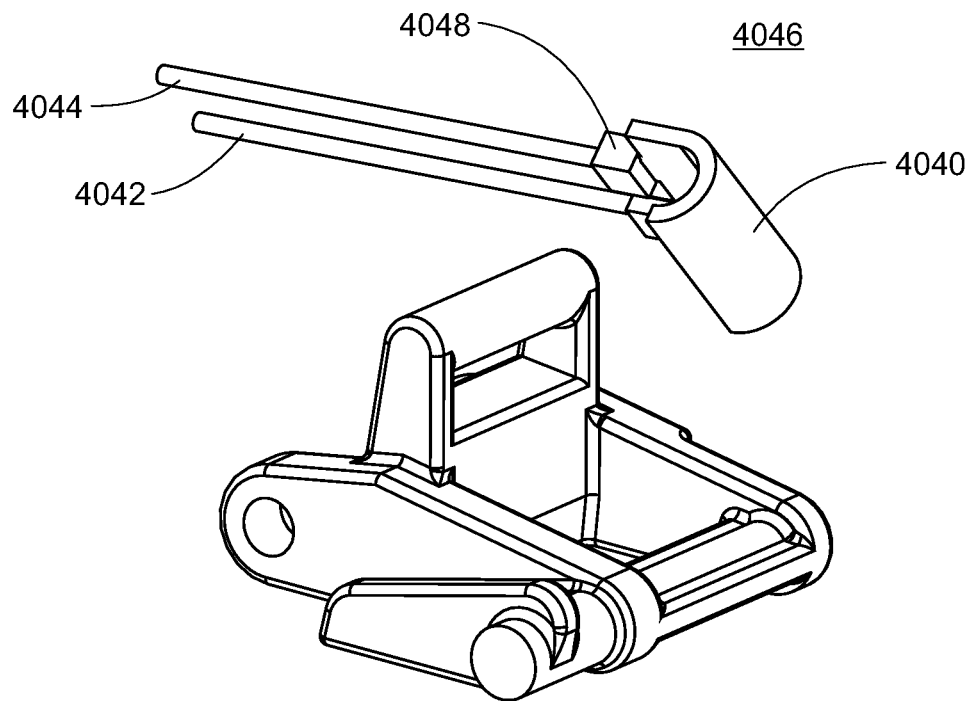
Figure 177B:
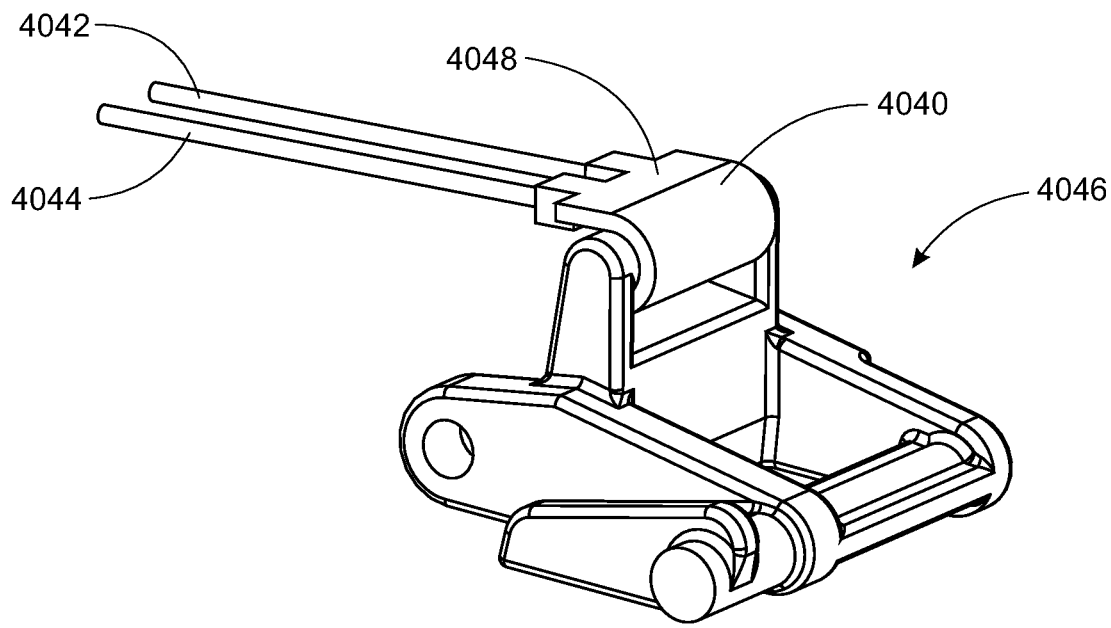
Figure 178A:
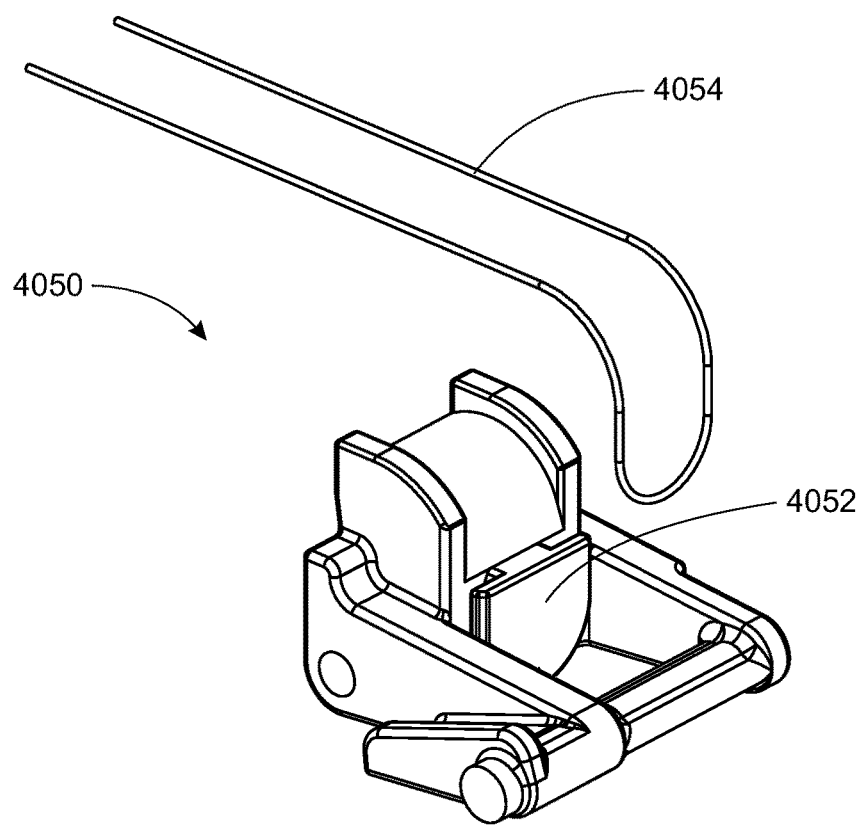
Figure 178B:
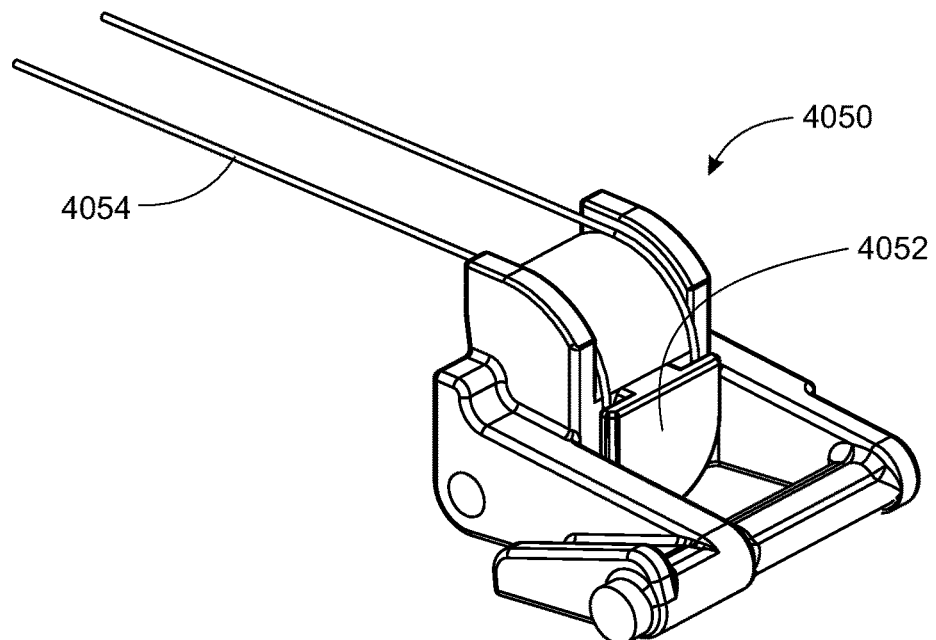
Figure 179A:
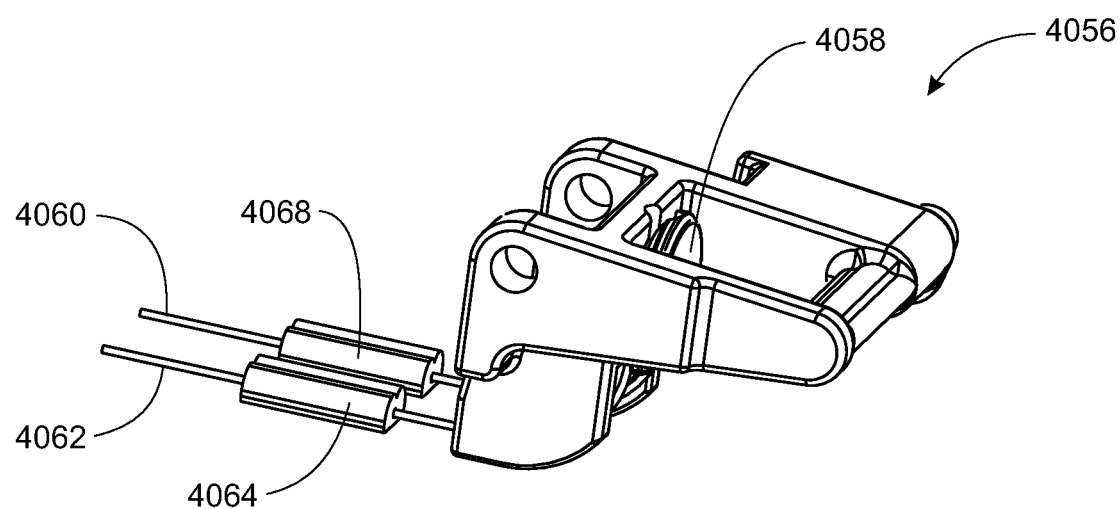
Figure 179B:
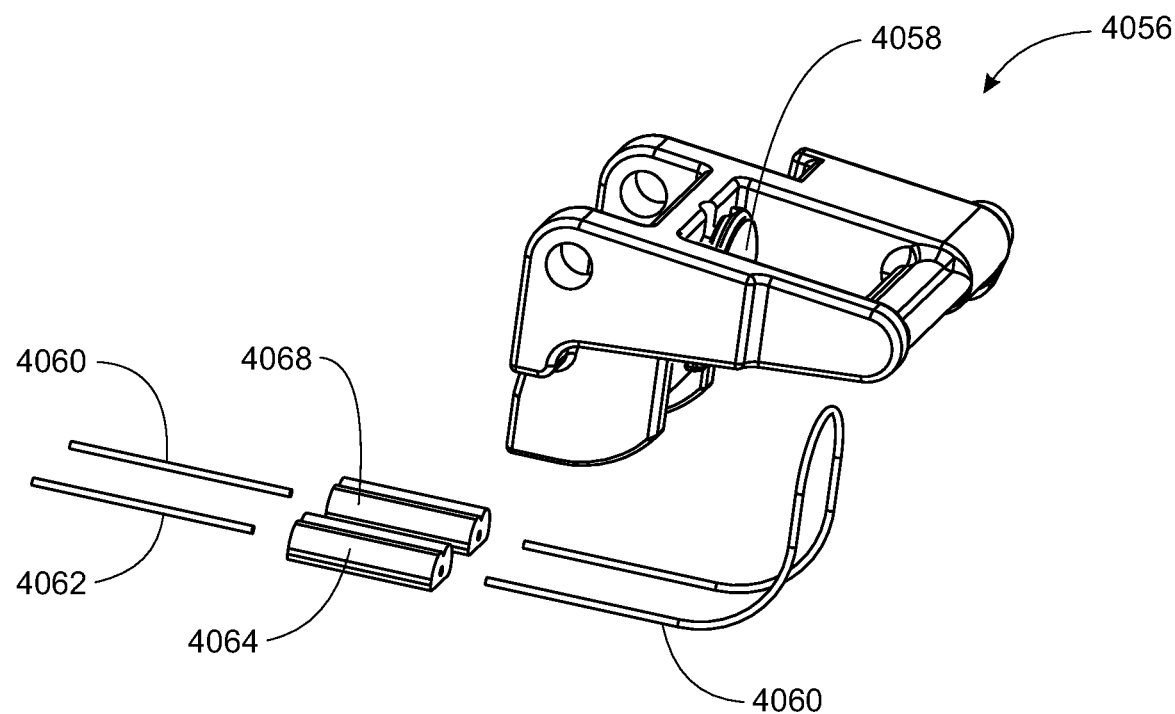
Figure 180:
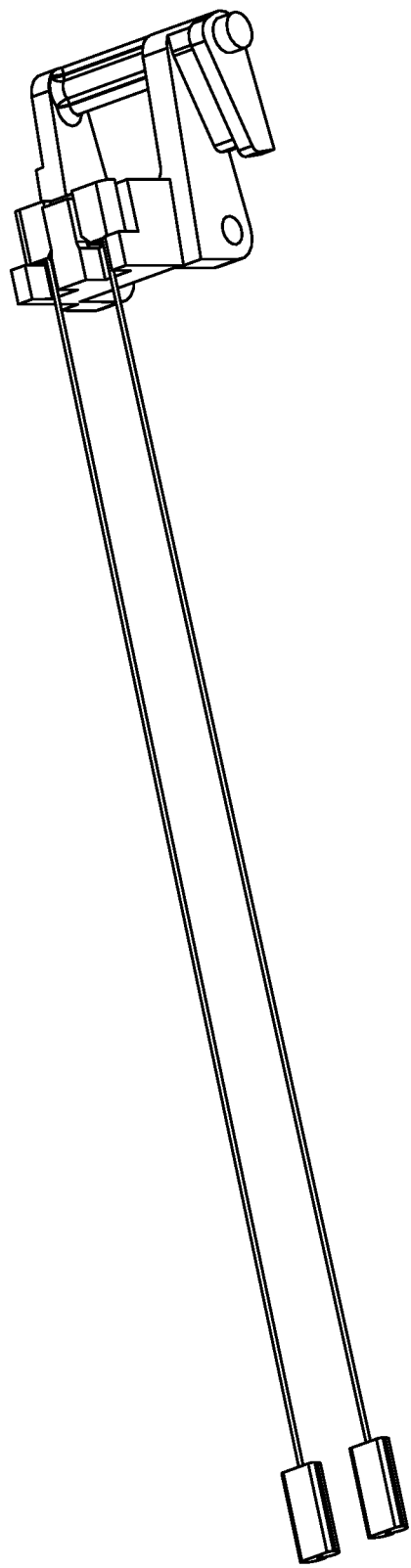
Figure 181:
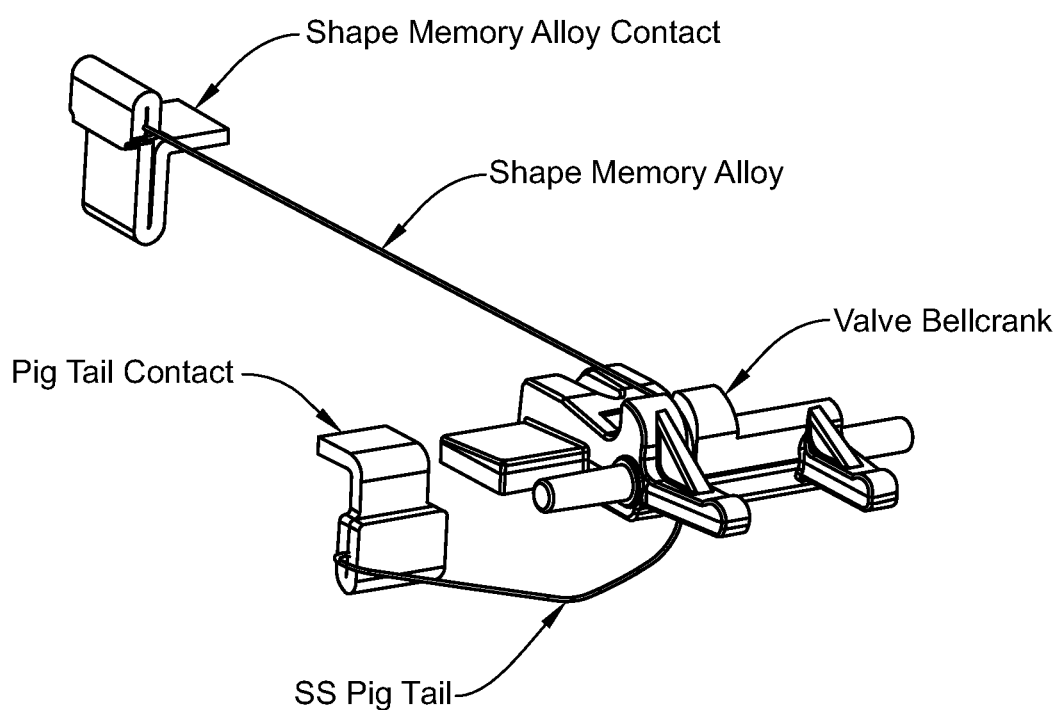
Figure 182A:
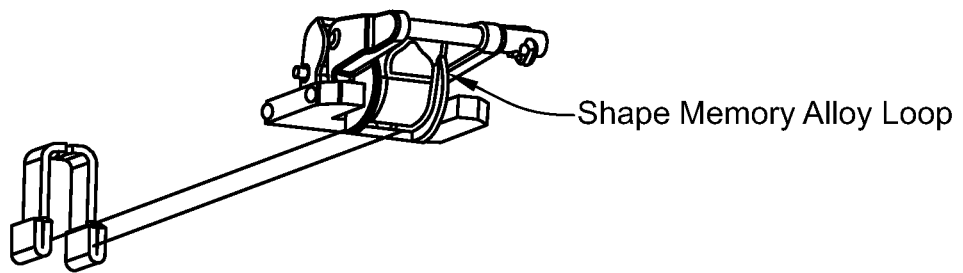
Figure 182B:
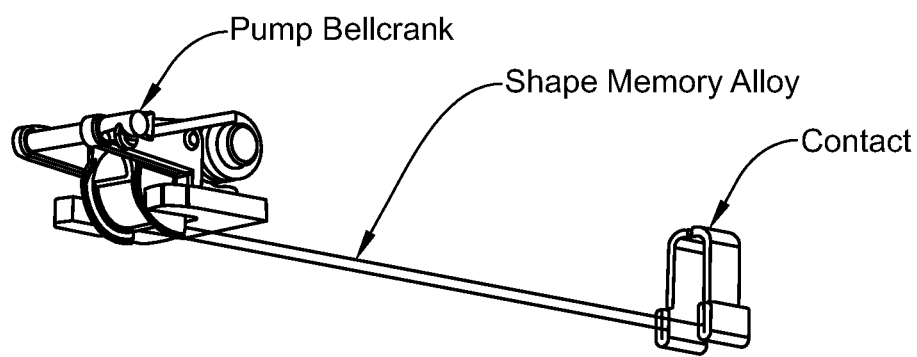
Figure 183A:
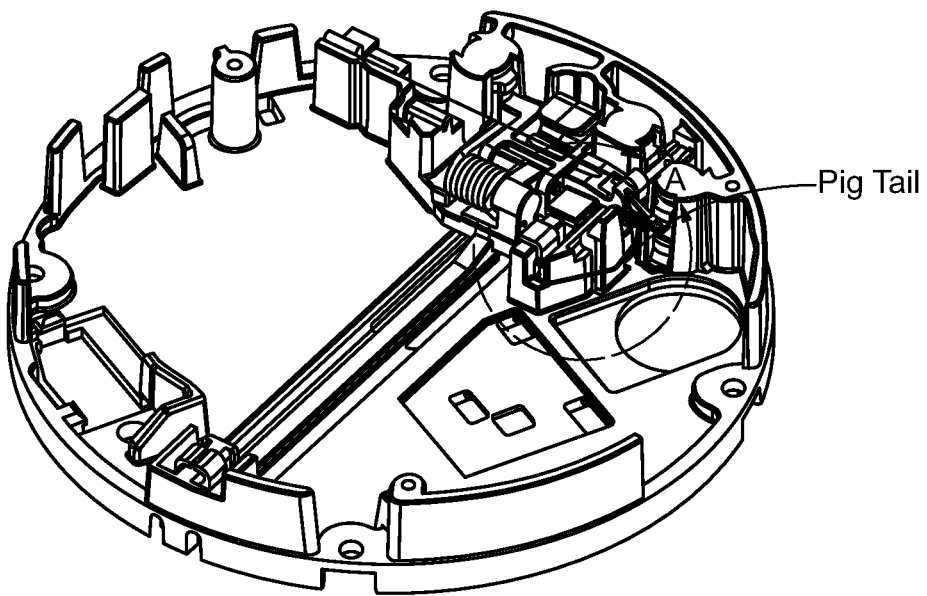
Figure 183B:
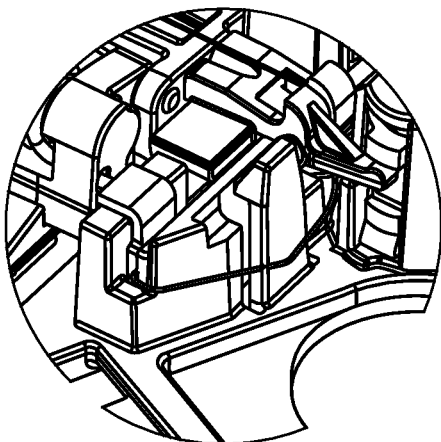
Figure 184:
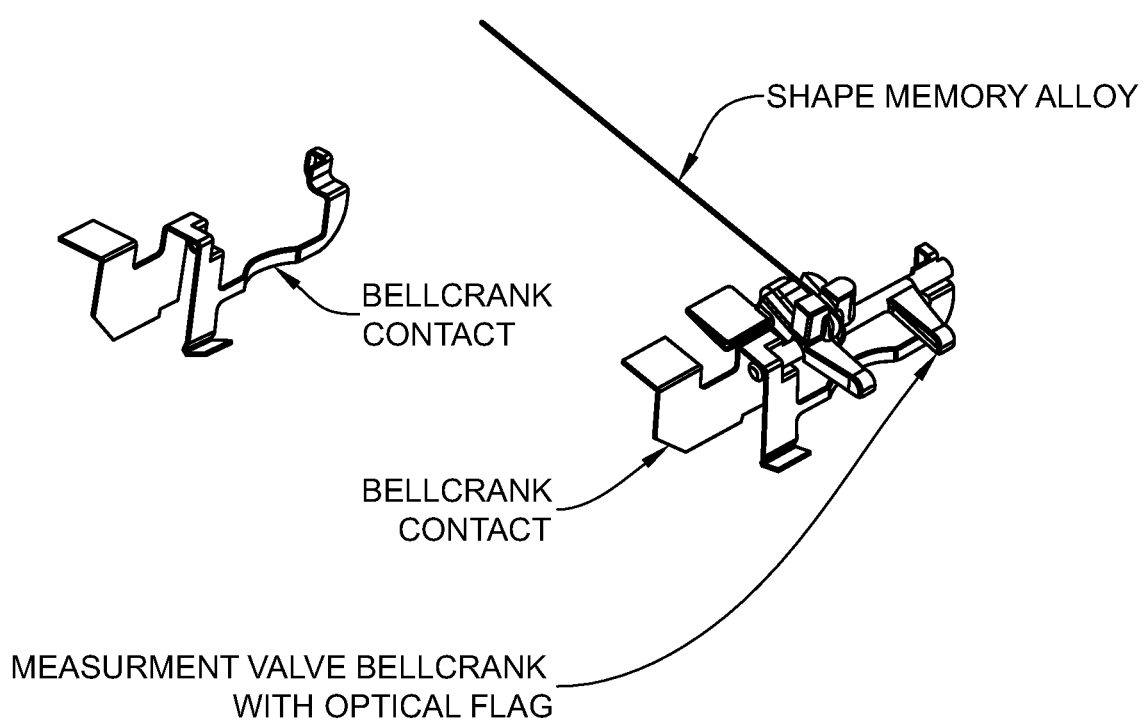
Figure 185A:
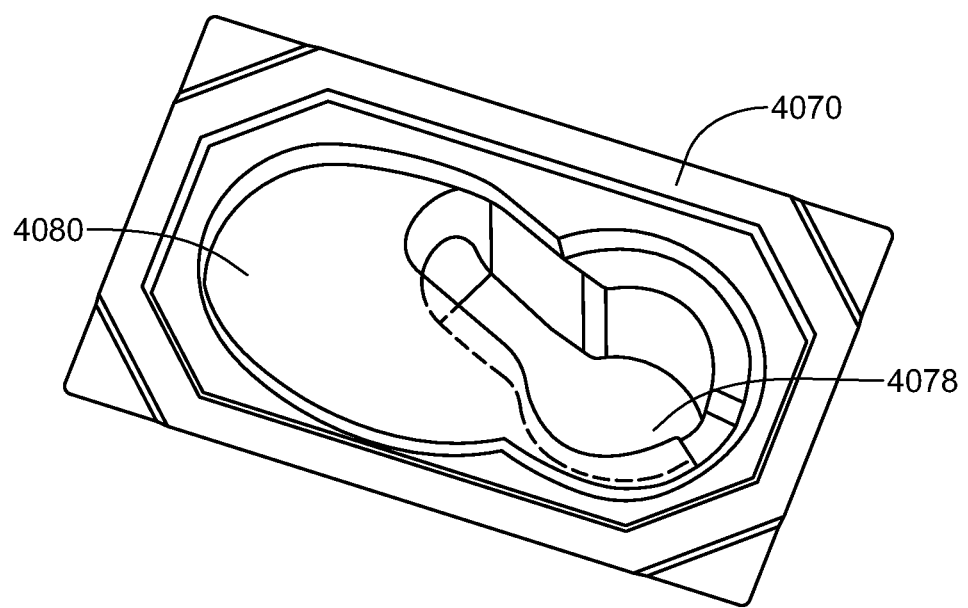
Figure 185B:
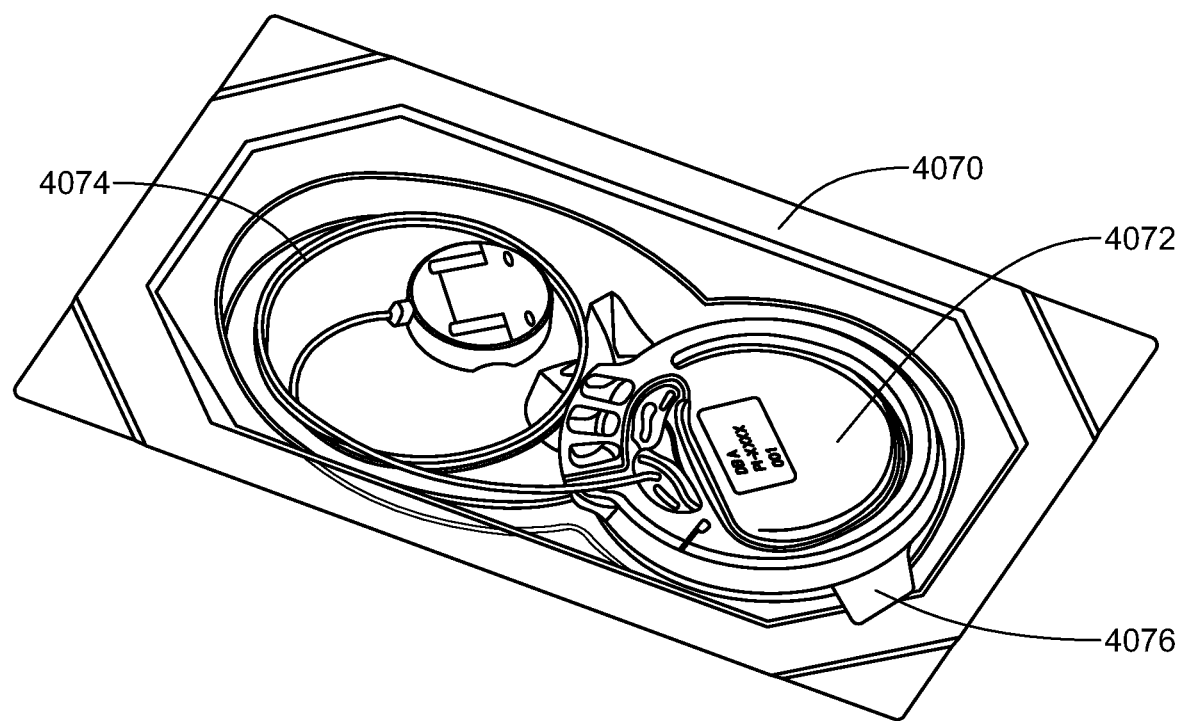
Figure 186A:
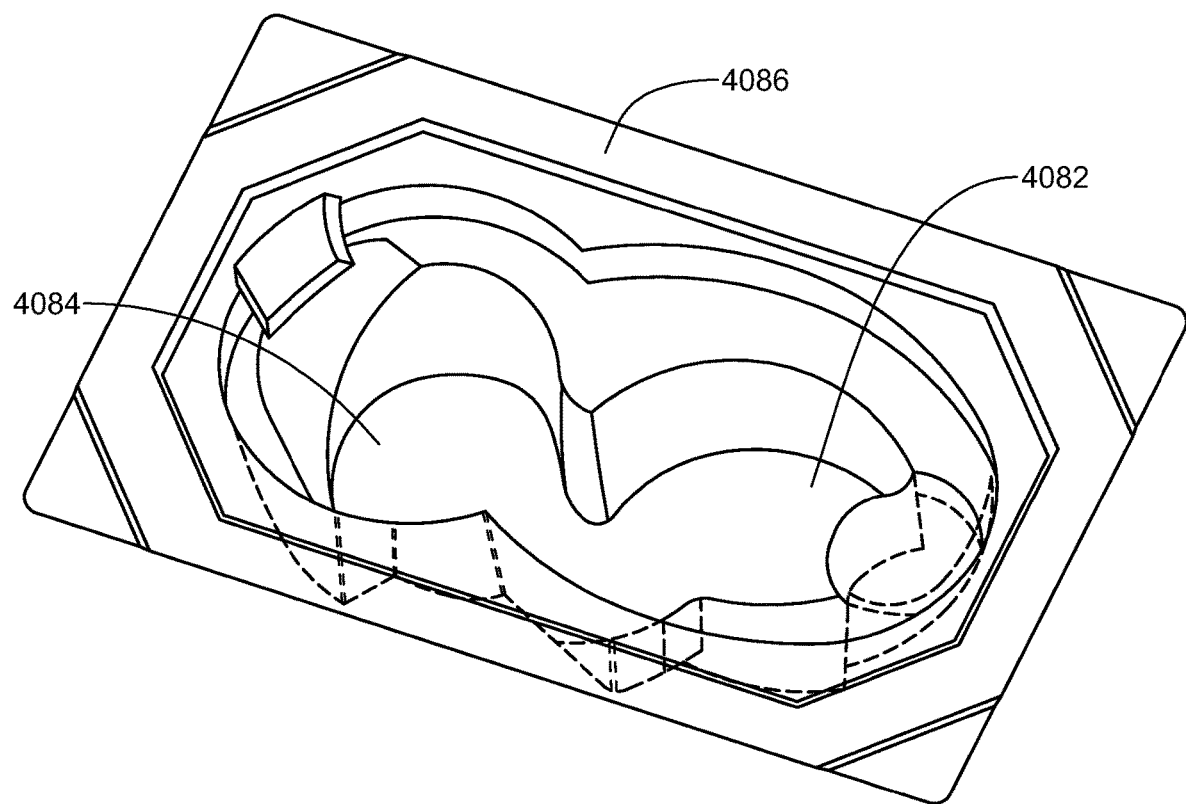
Figure 186B:
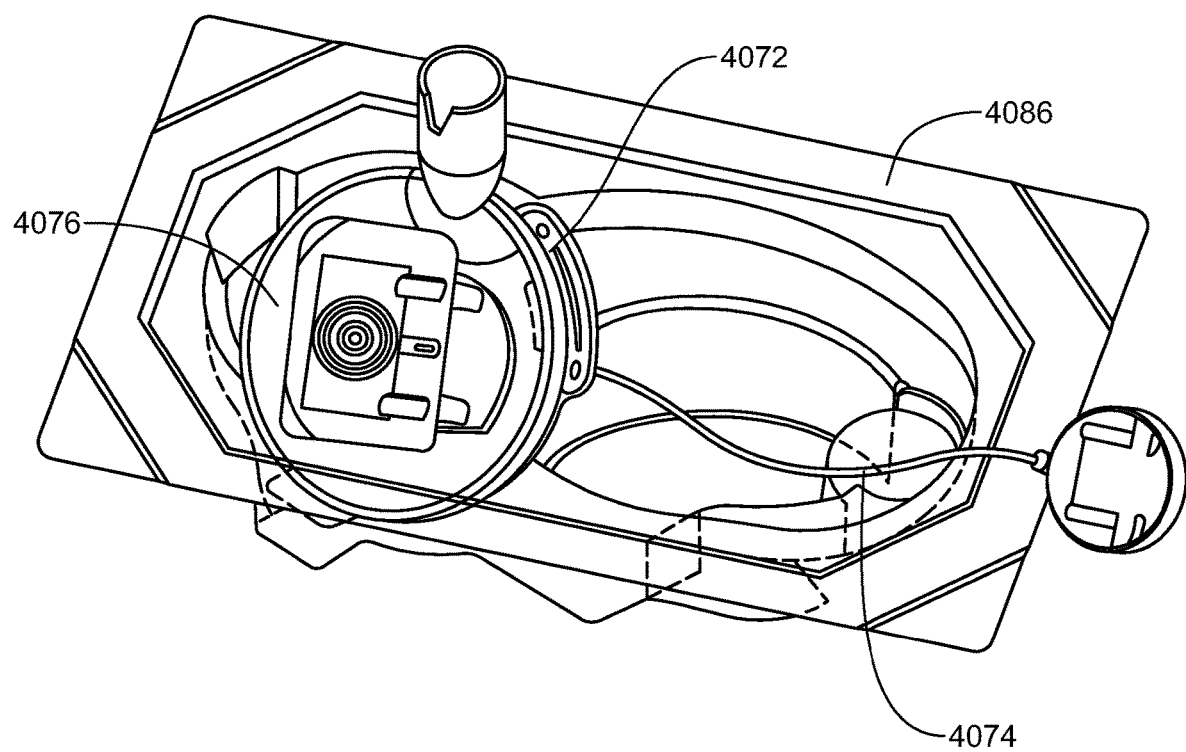
Figure 188:
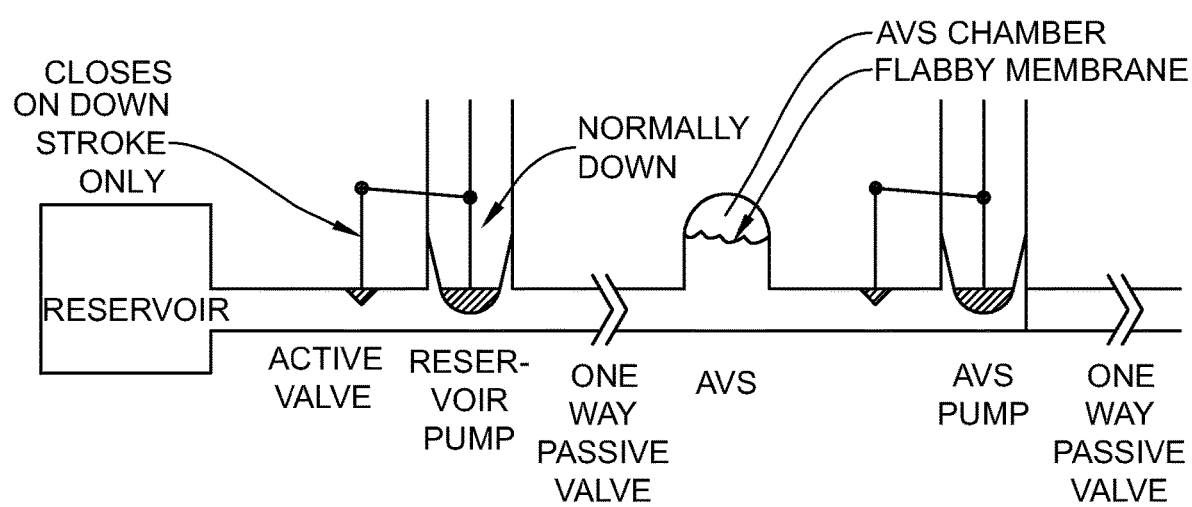
Figure 189A:
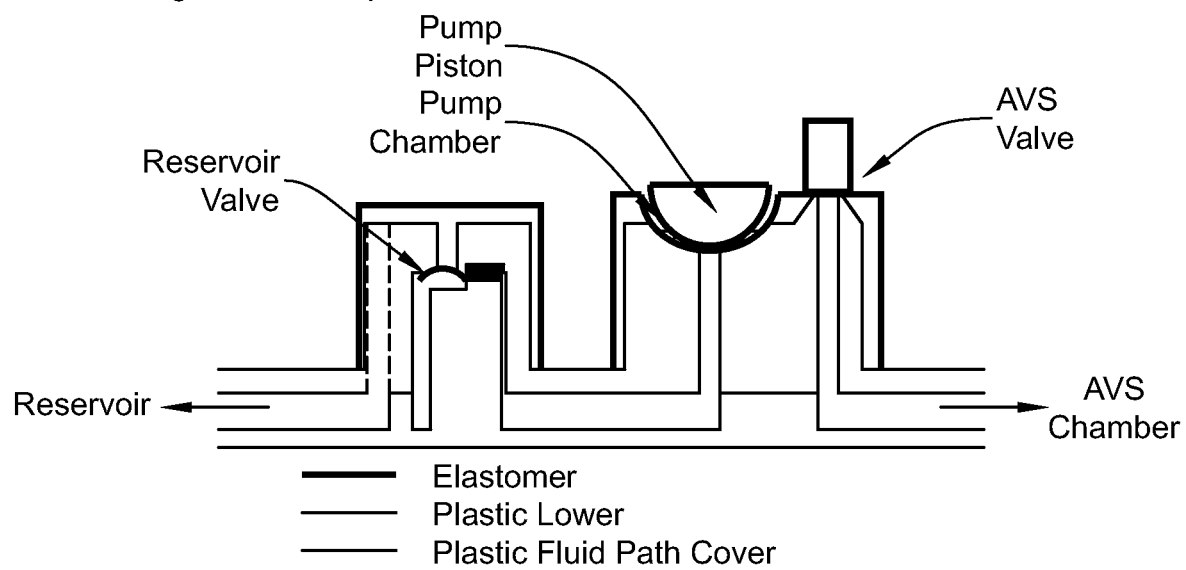
Figure 189B:
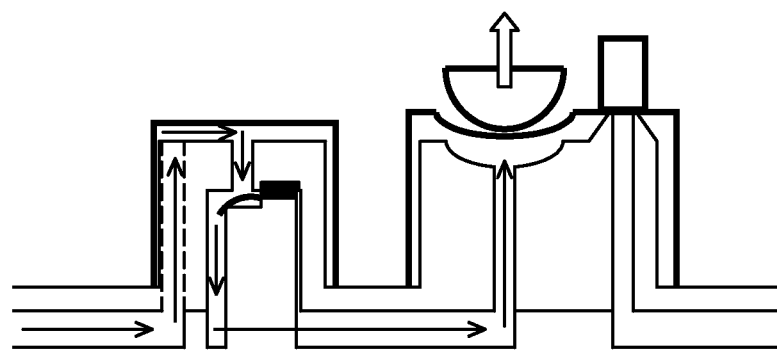
Figure 189C:
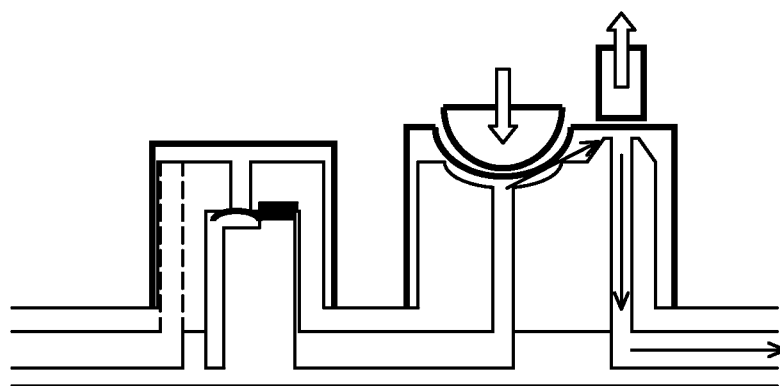
Figure 190:
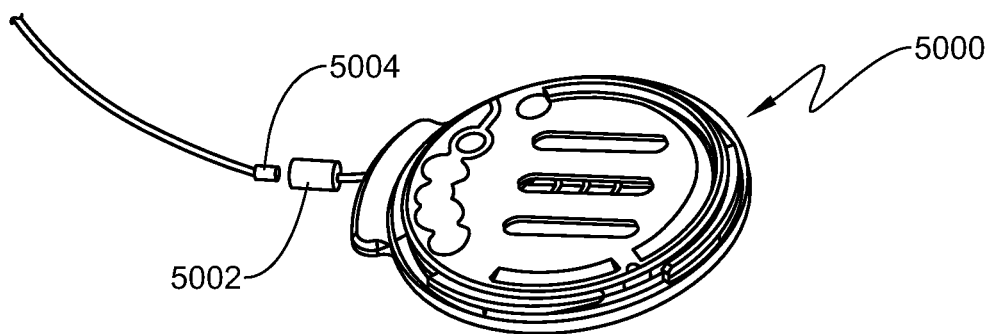
Figure 192:
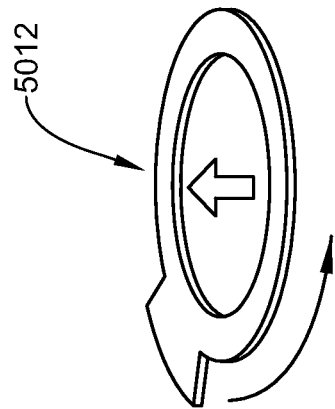
Figure 193B:
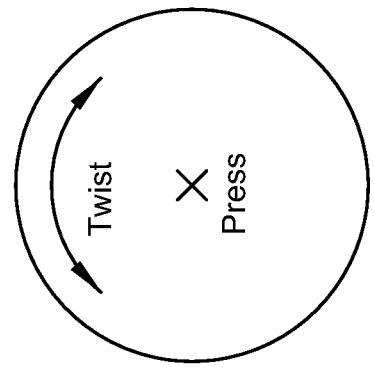
Figure 191:
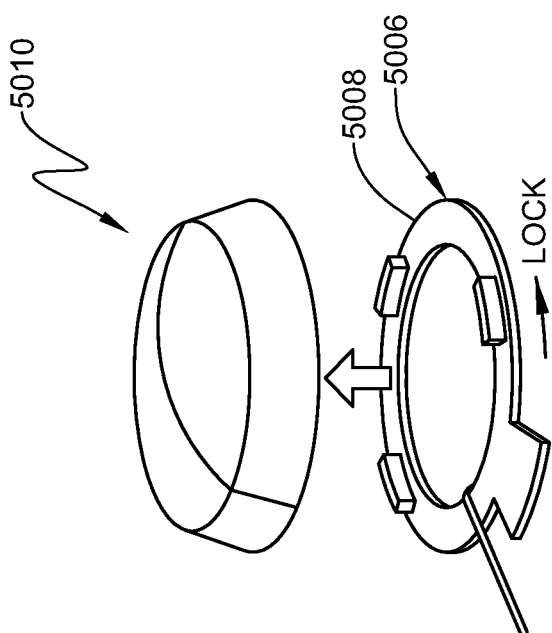
Figure 193A:
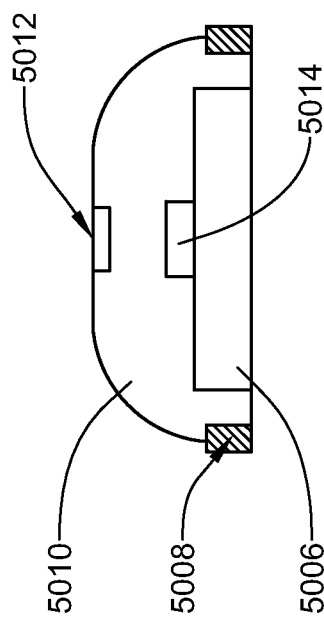
Figure 194:
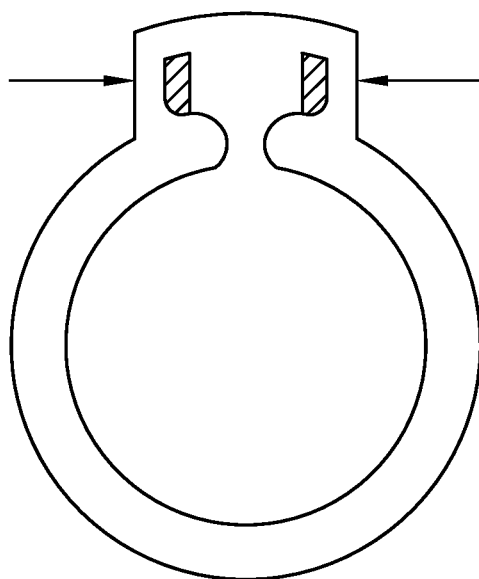
Figure 195:
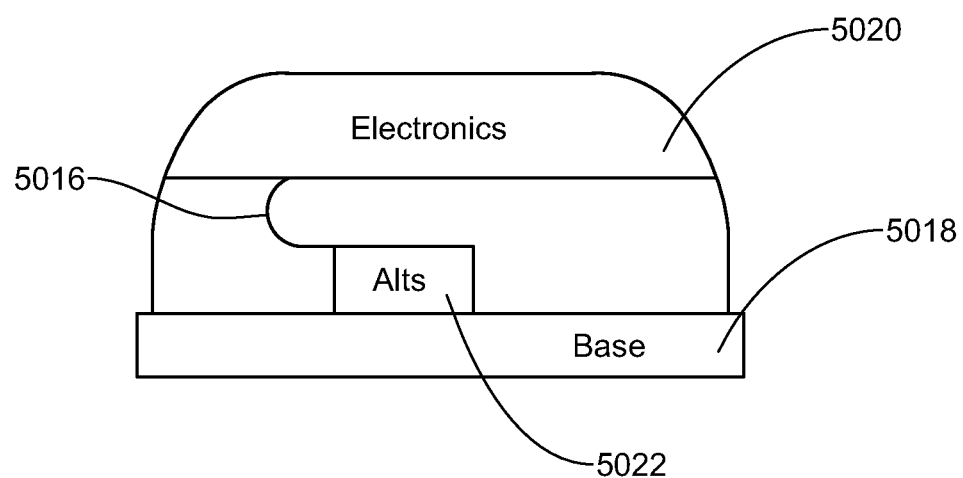
Figure 197:
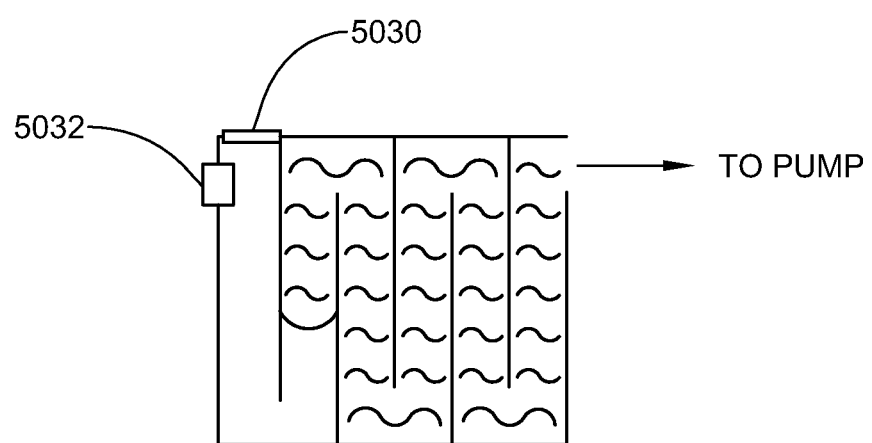
Figure 198:
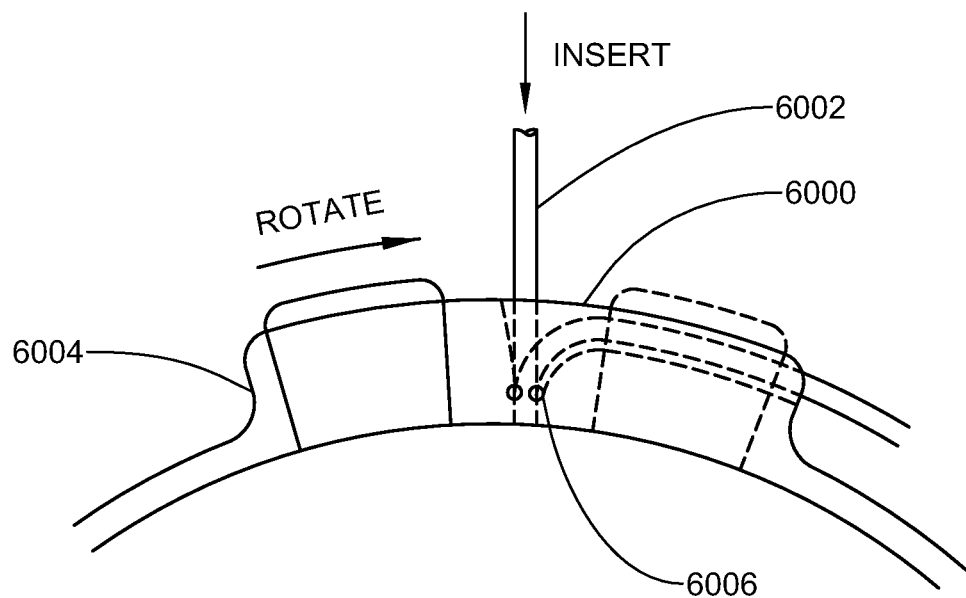
Figure 199:
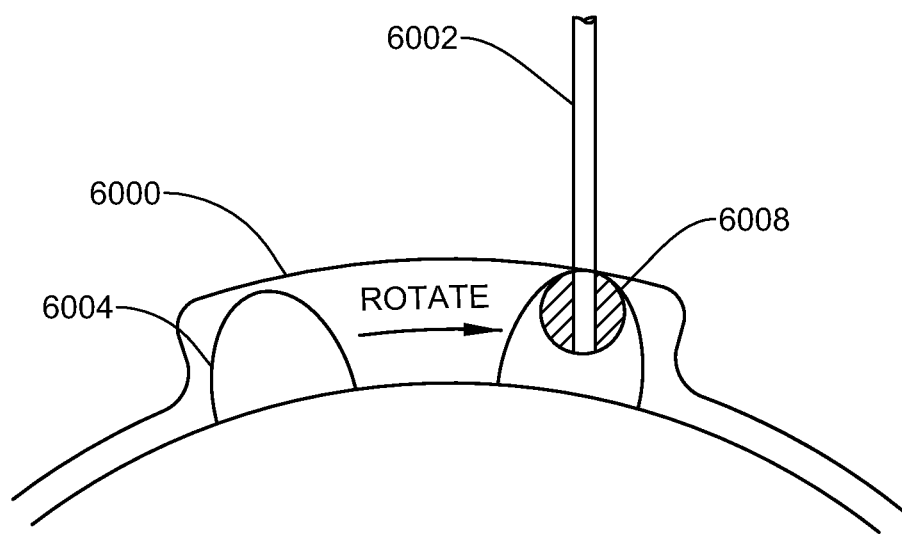
Figure 200A:
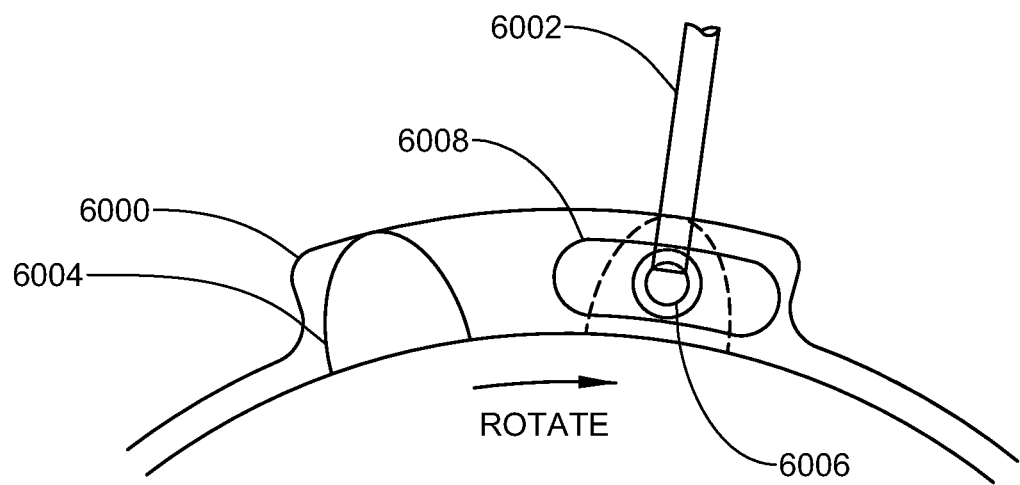
Figure 200B:
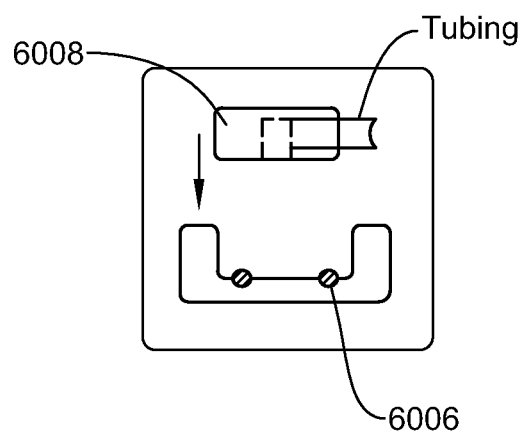
Figure 201A:
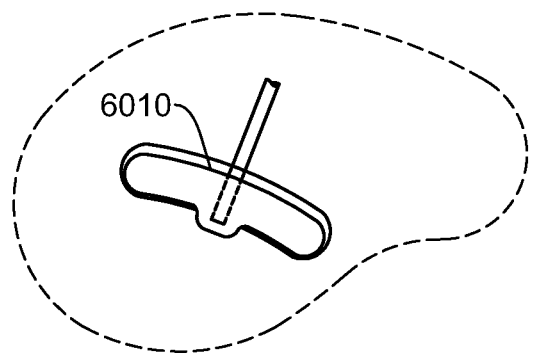
Figure 201B:
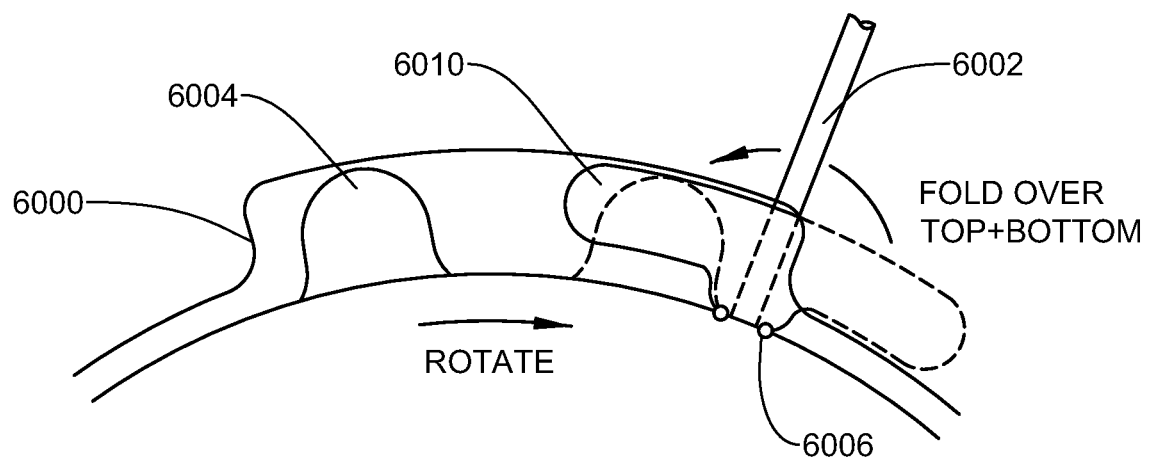
Figure 202:
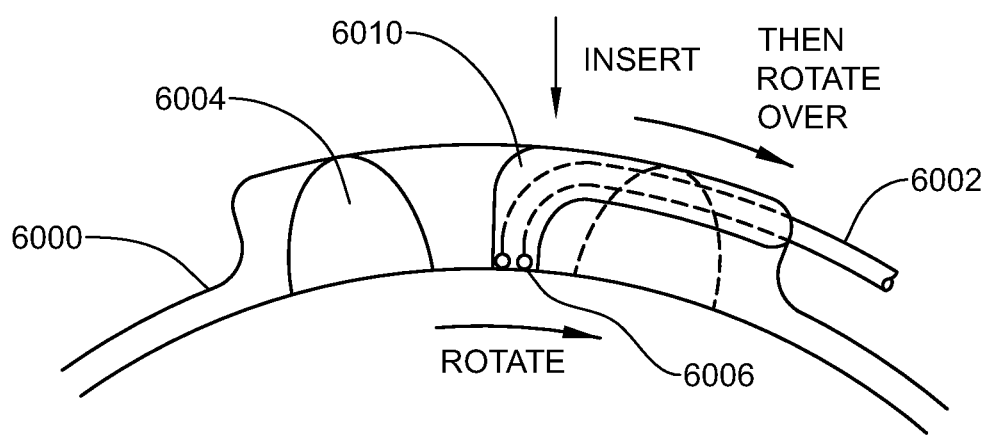
Figure 203A:
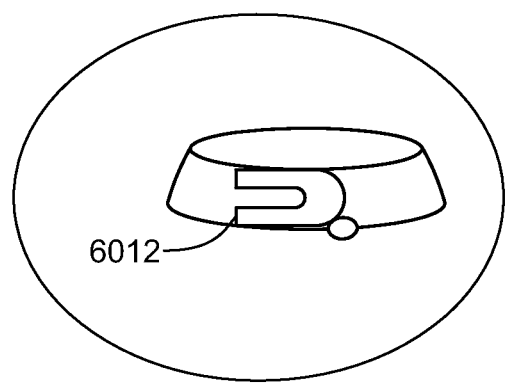
Figure 204A:
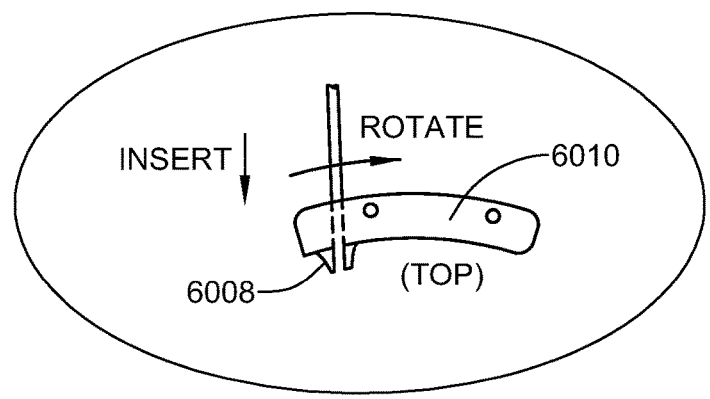
Figure 204B:
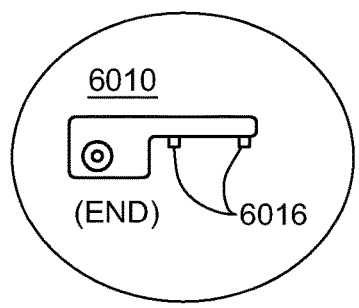
Figure 204C:
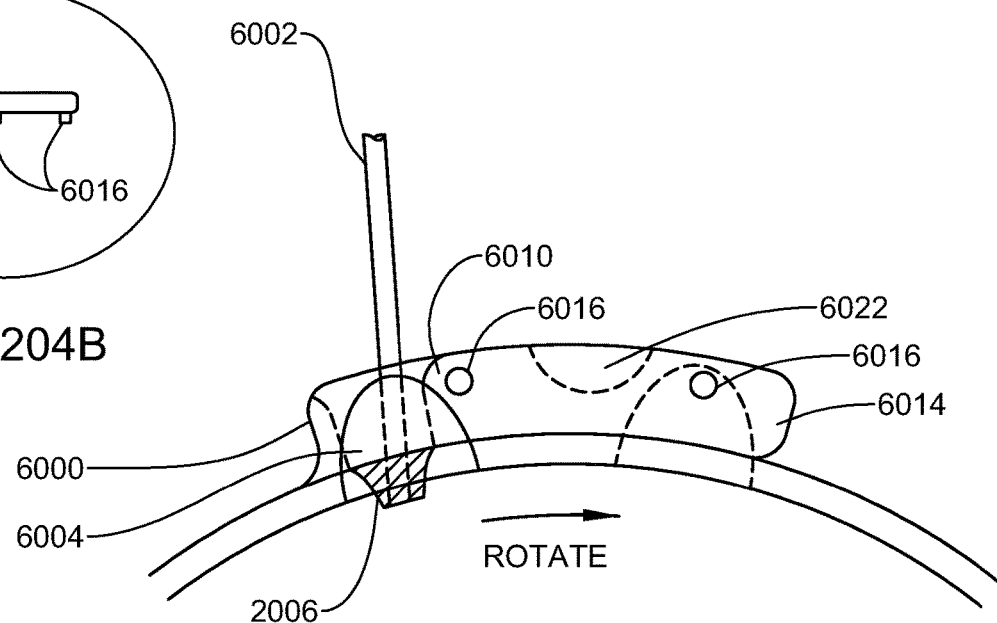
Figure 205:
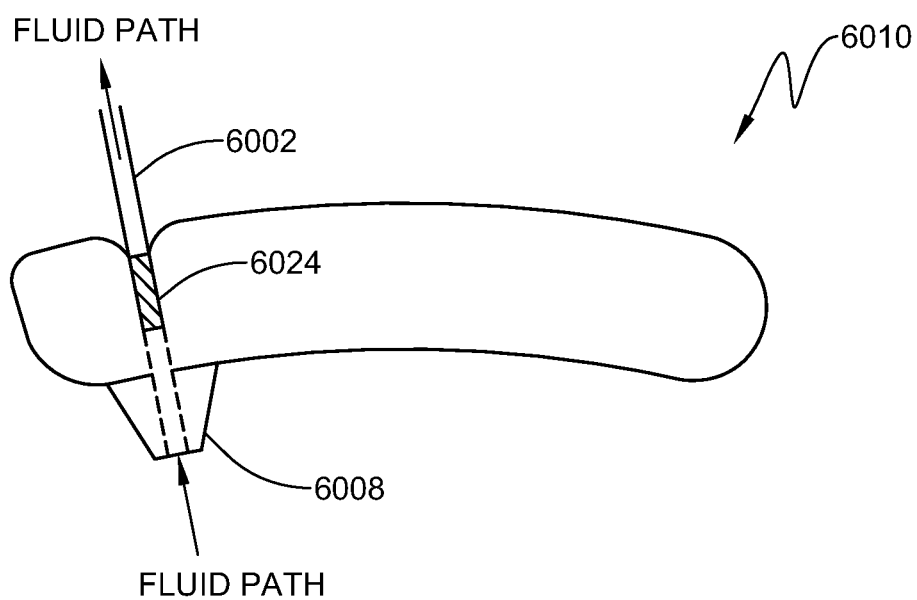
Figure 206:
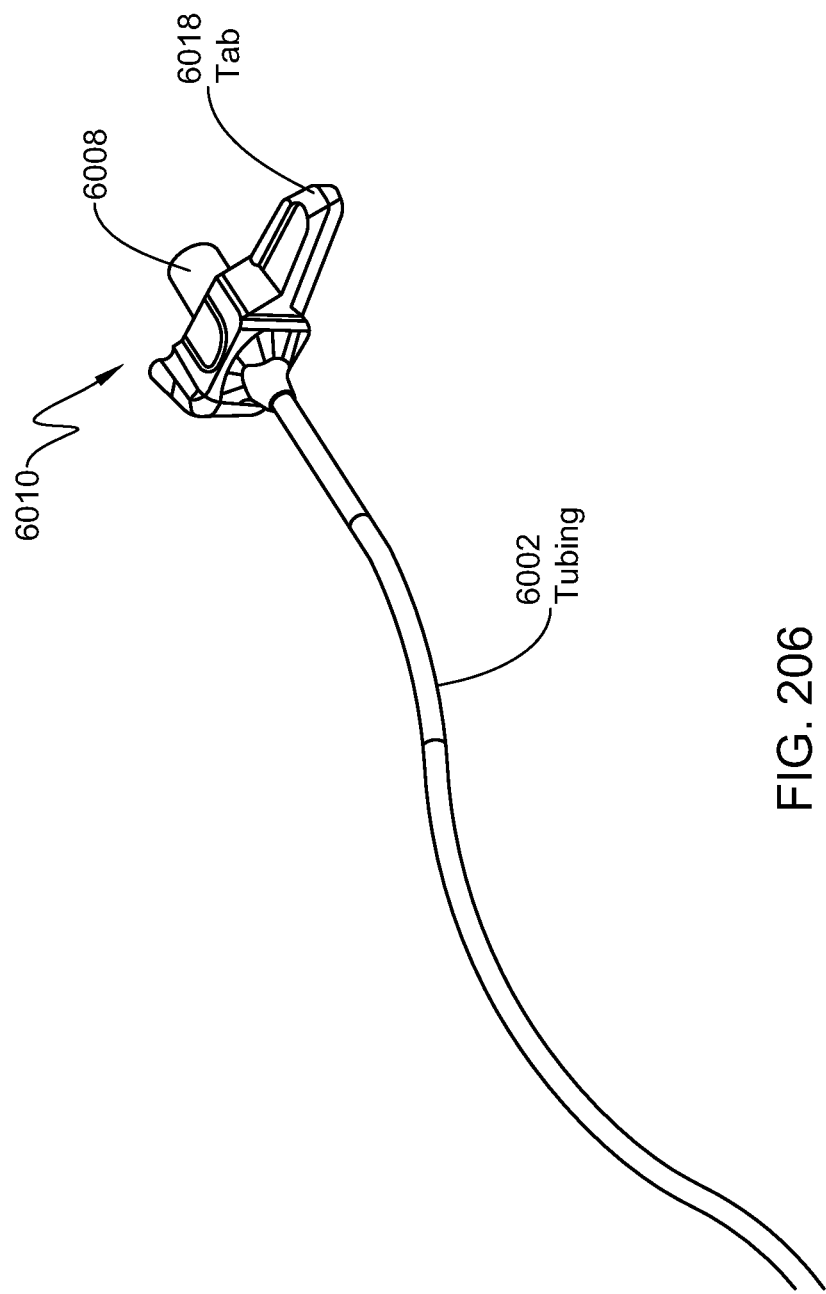
Figure 207:
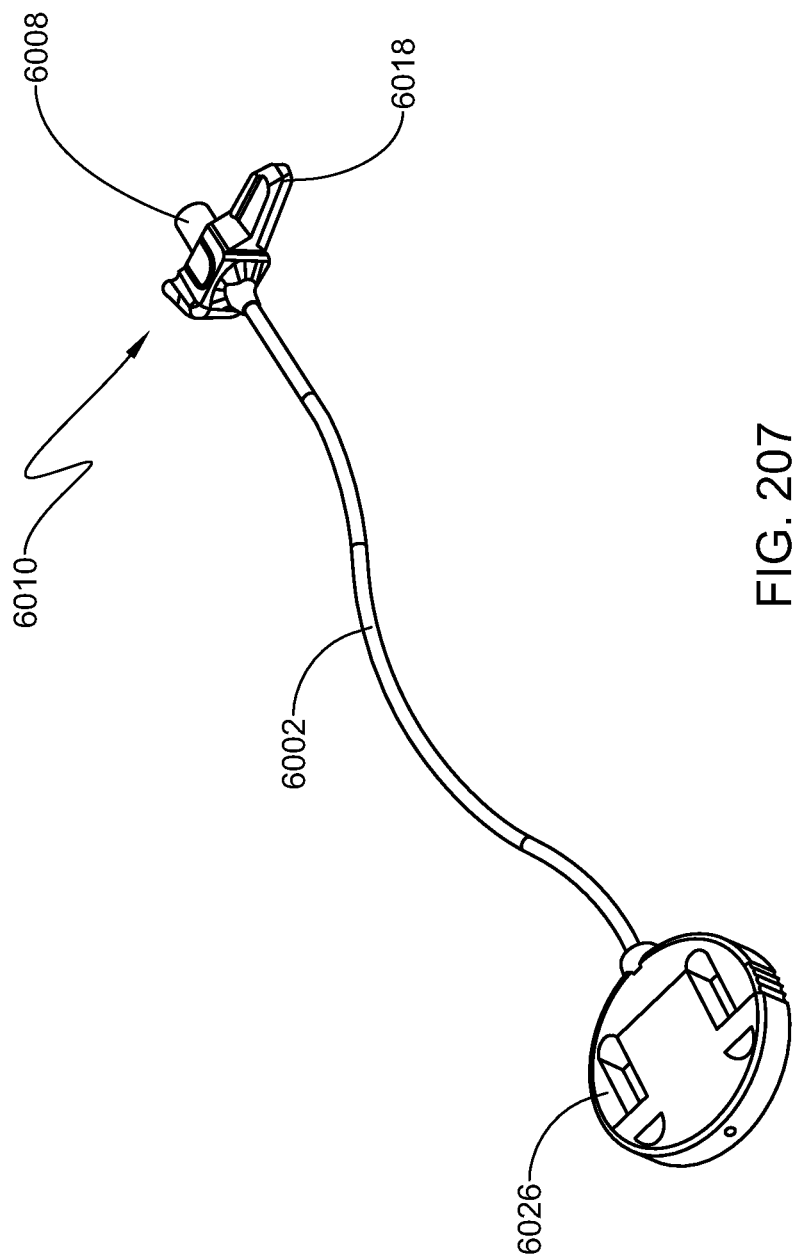
Figure 208:
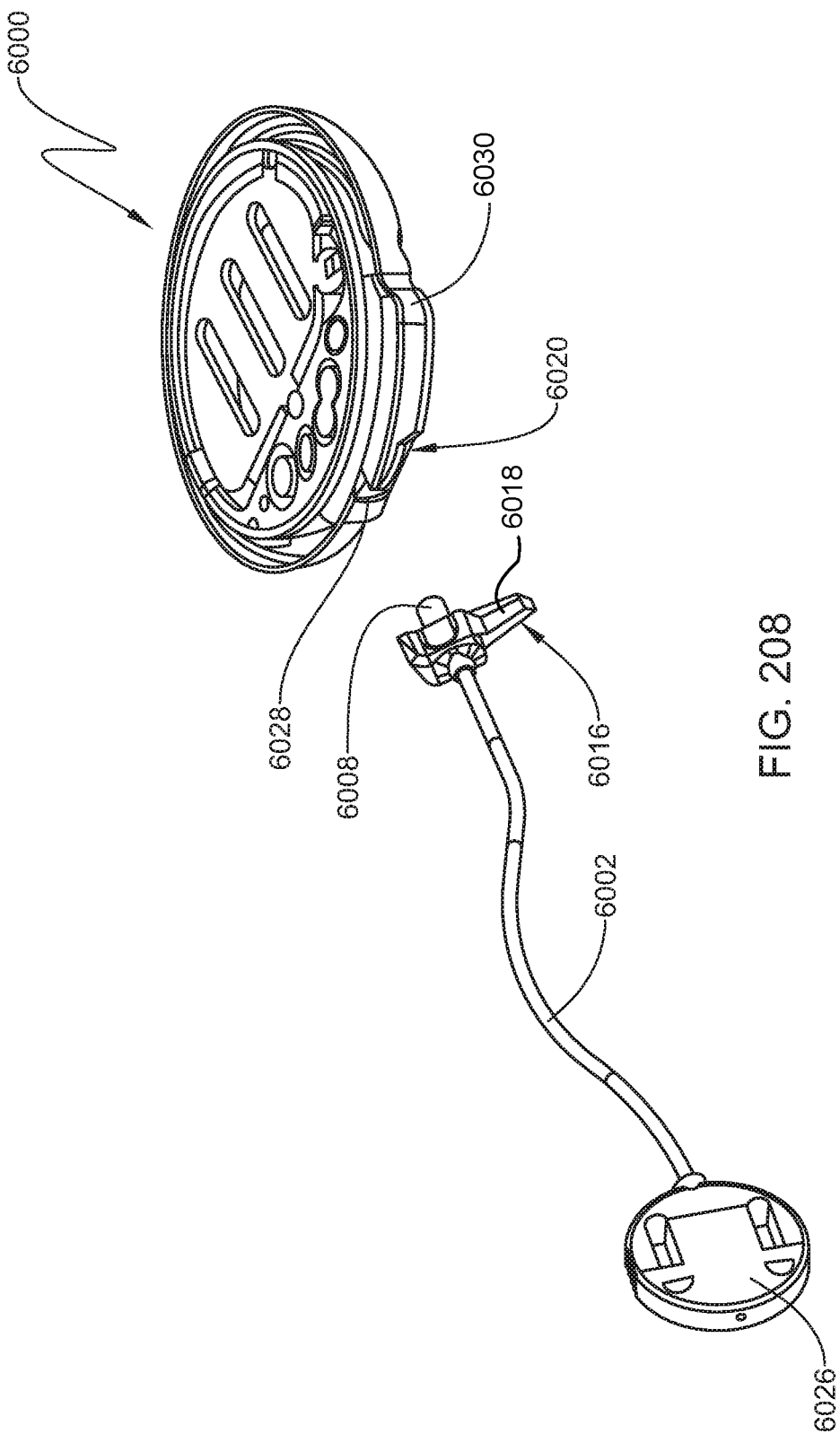
Figure 209:
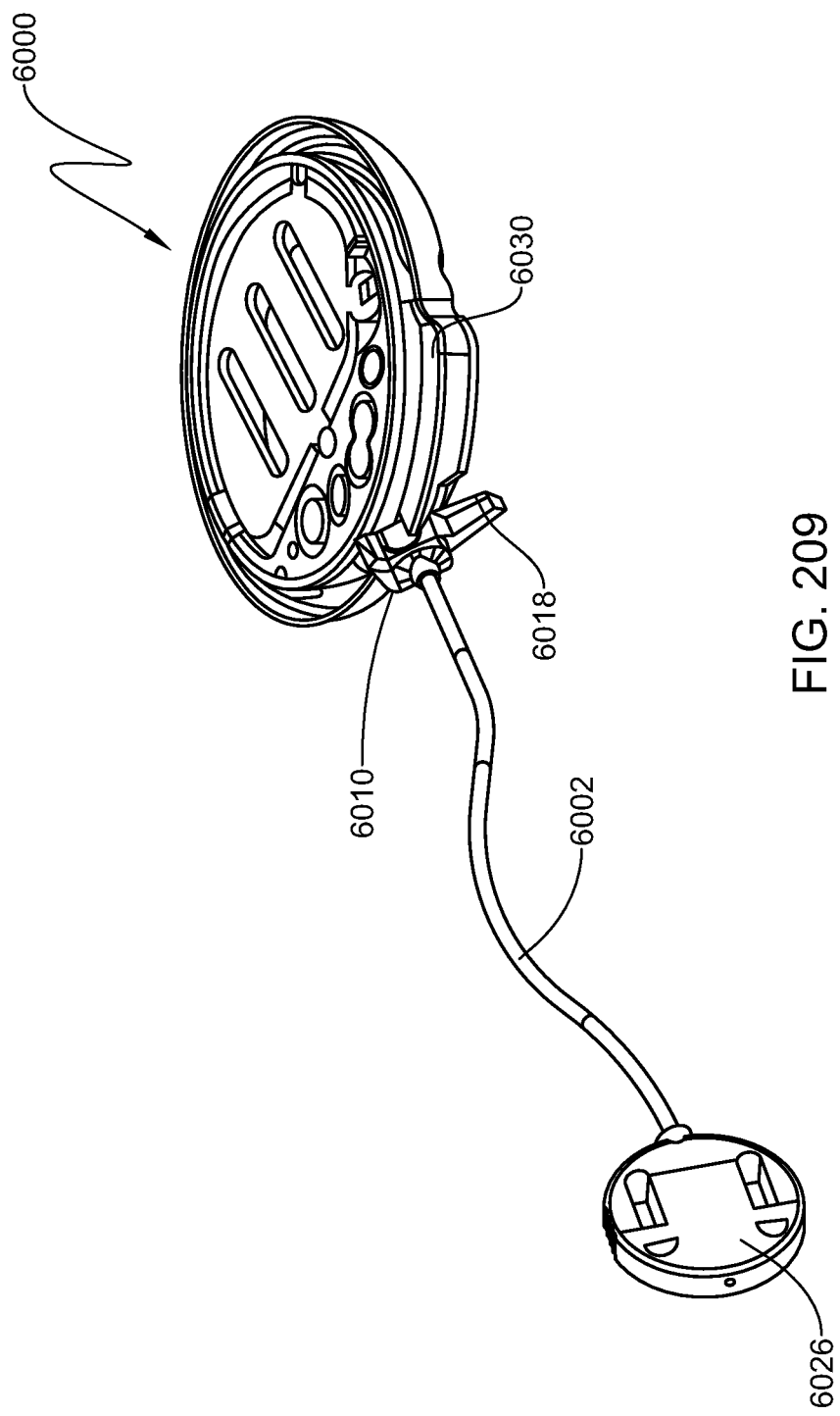
Figure 210:
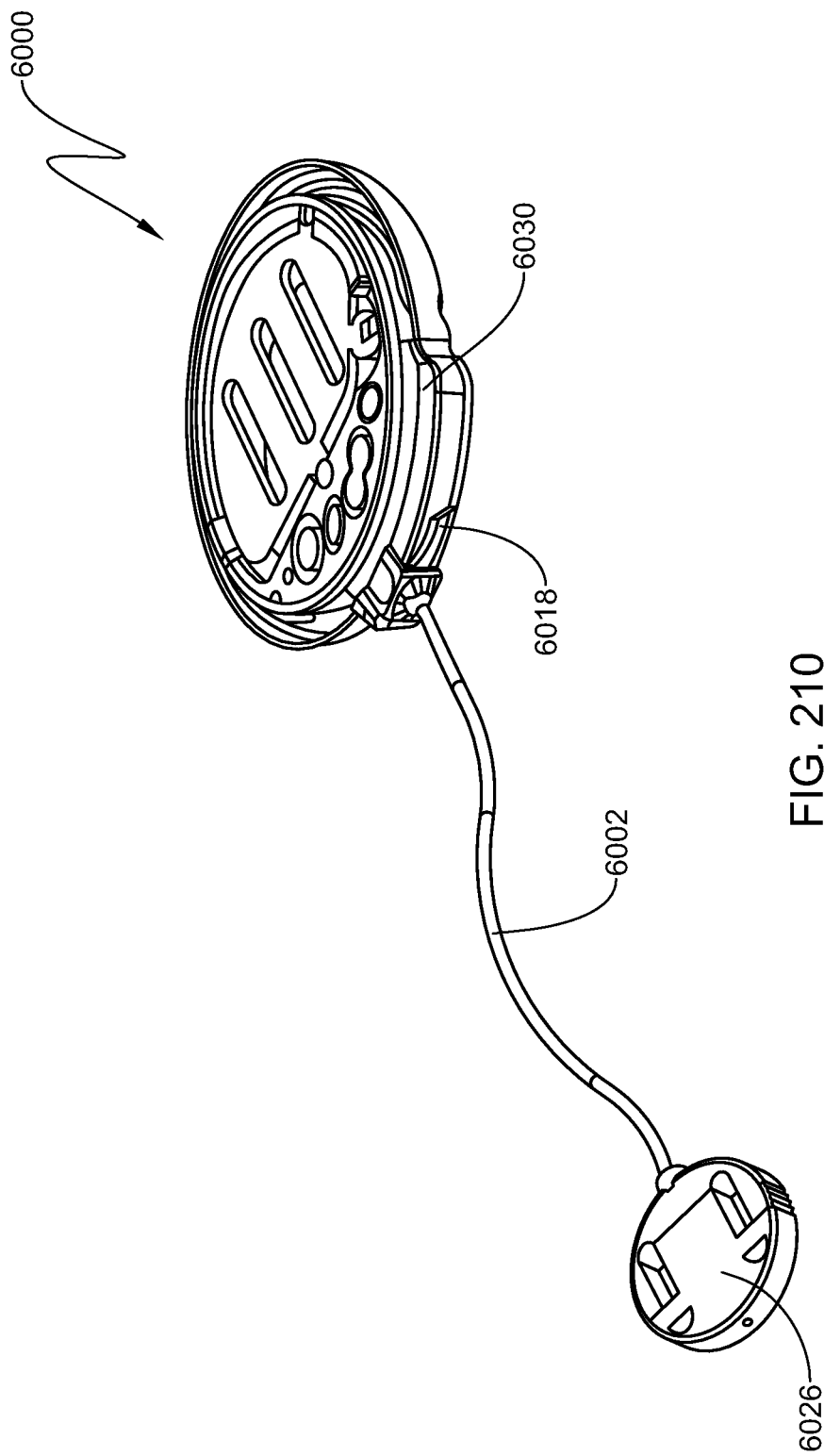
Figure 218A:
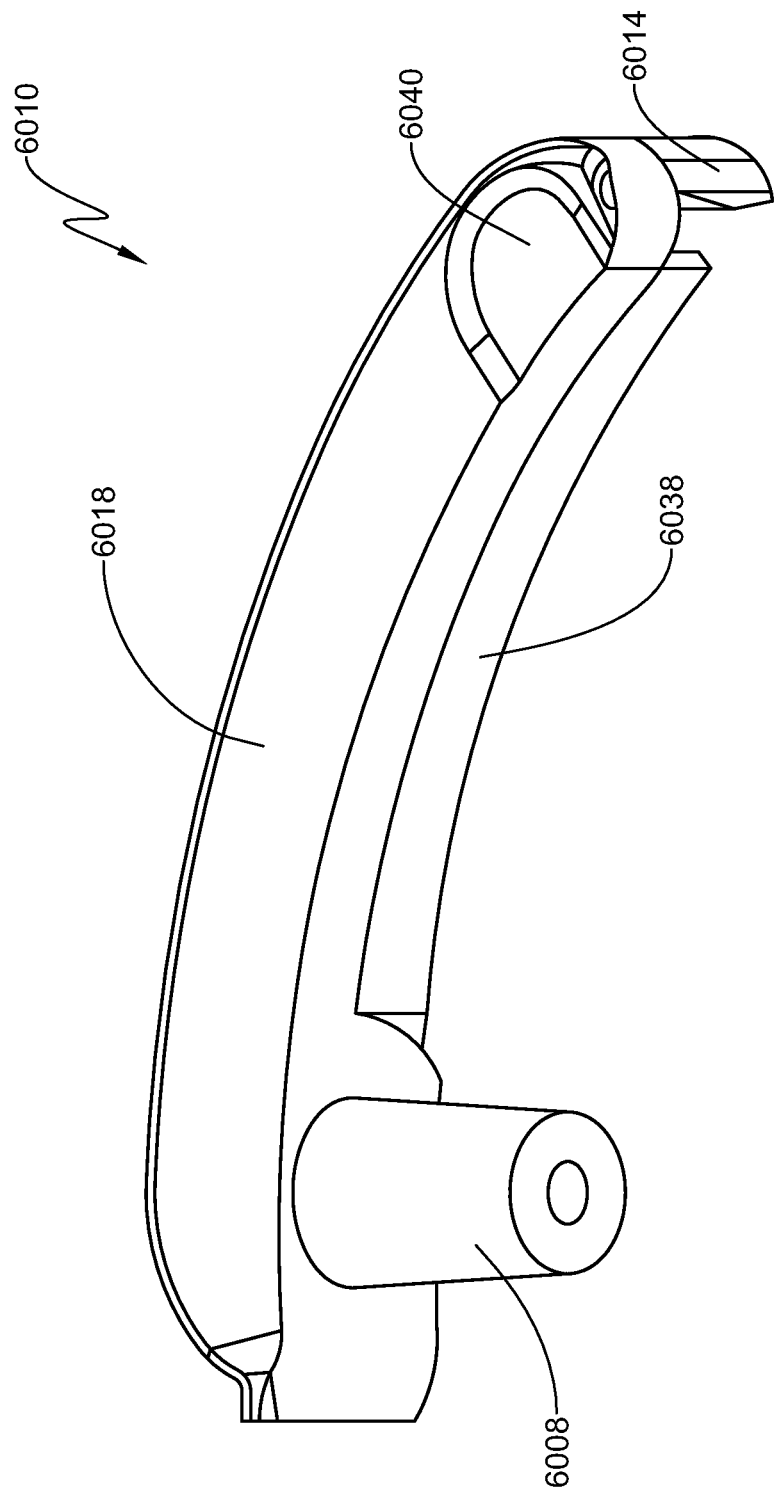
Figure 218B:
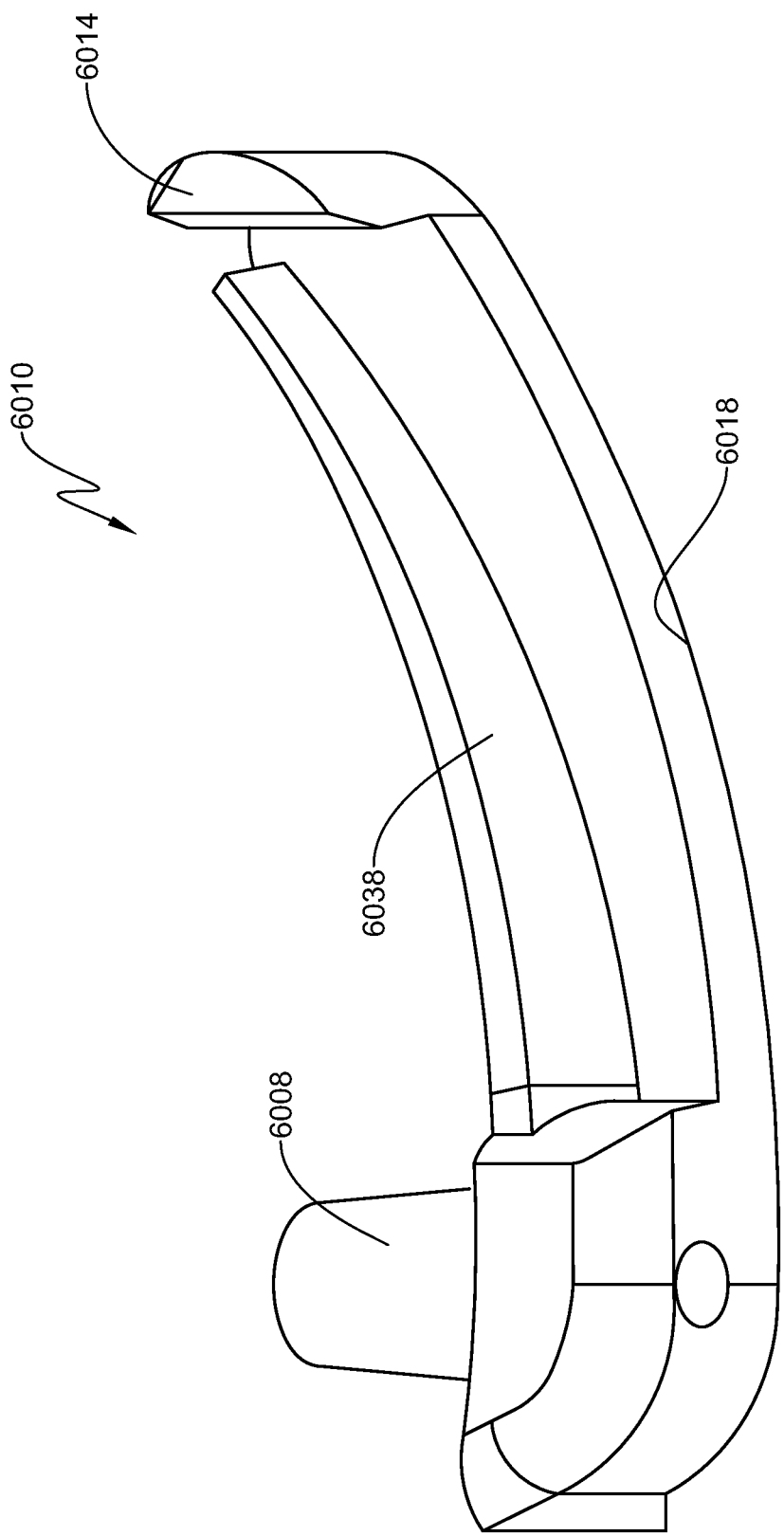
Figure 218C:
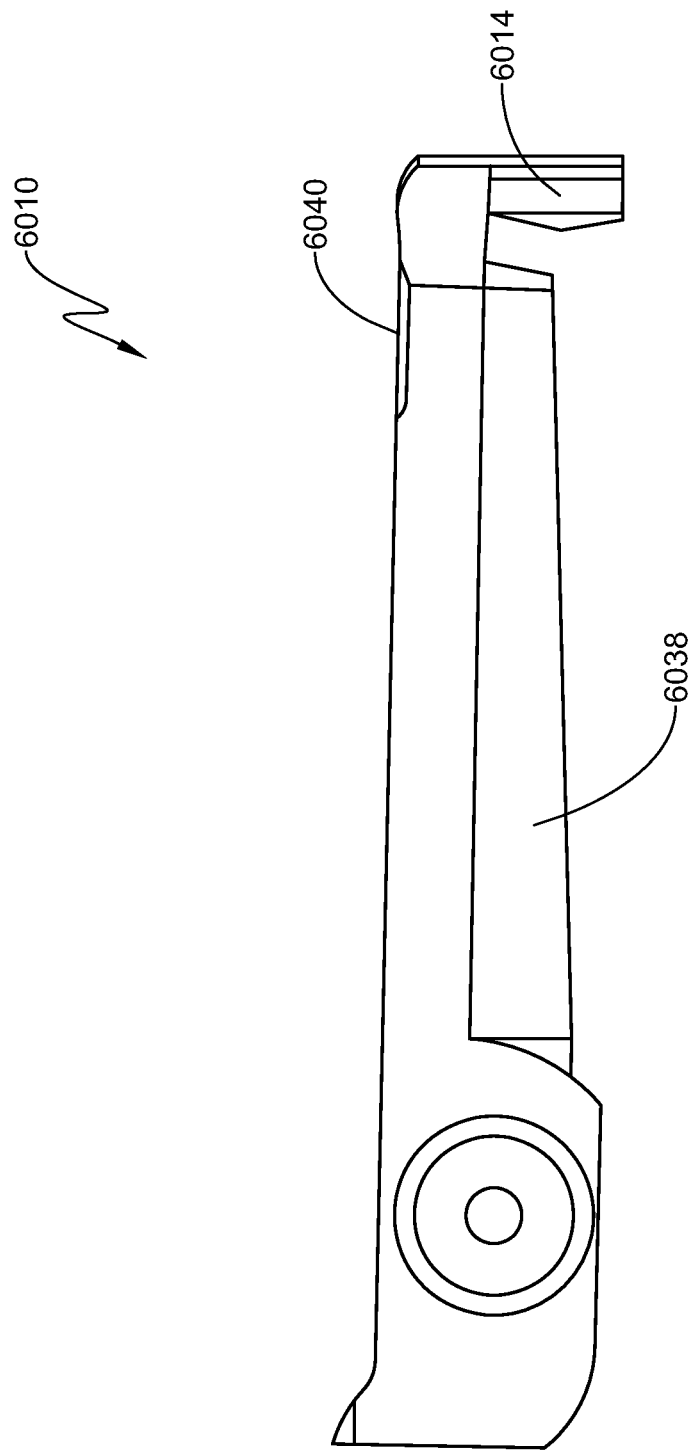
Figure 221:
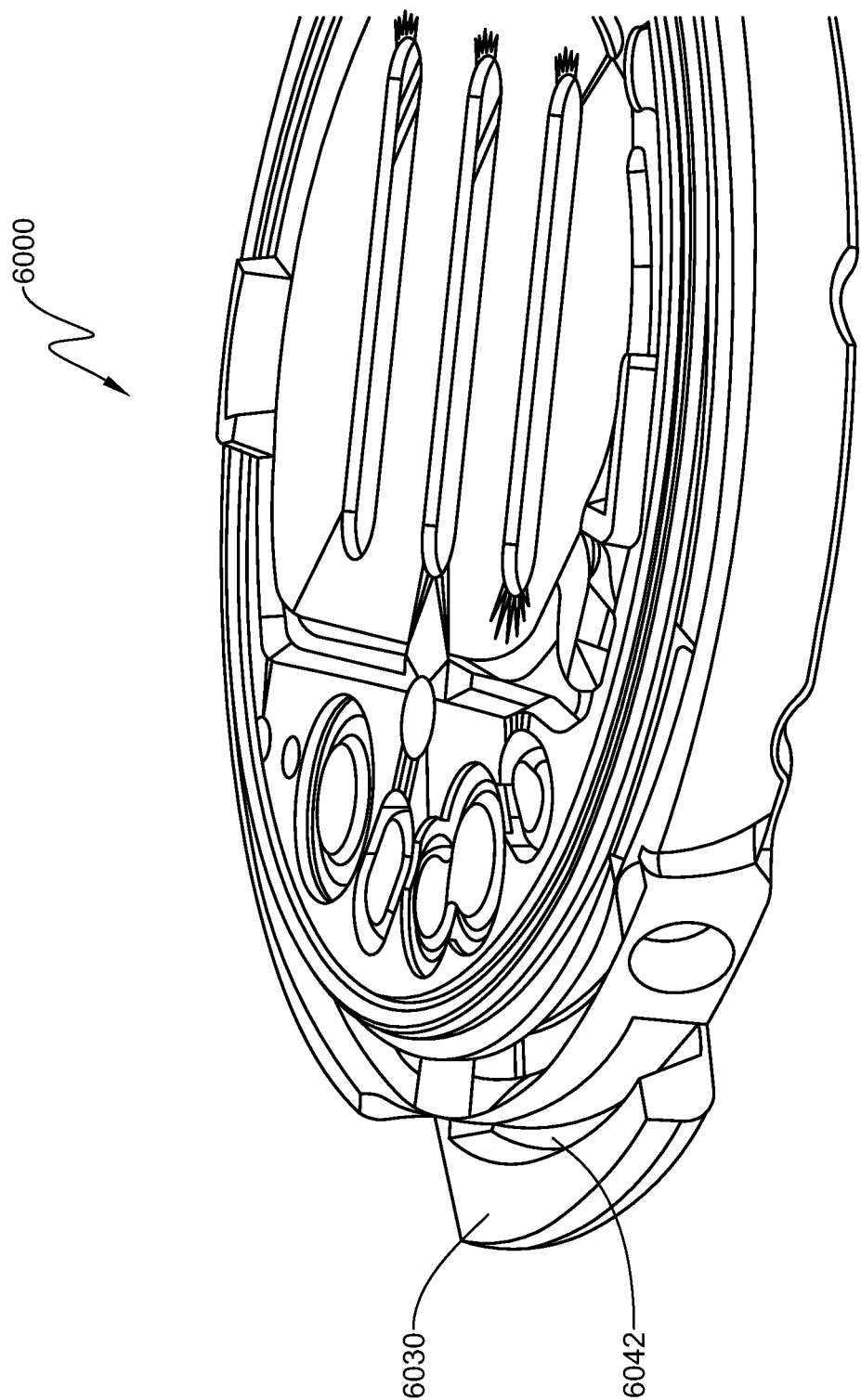
Figure 222:
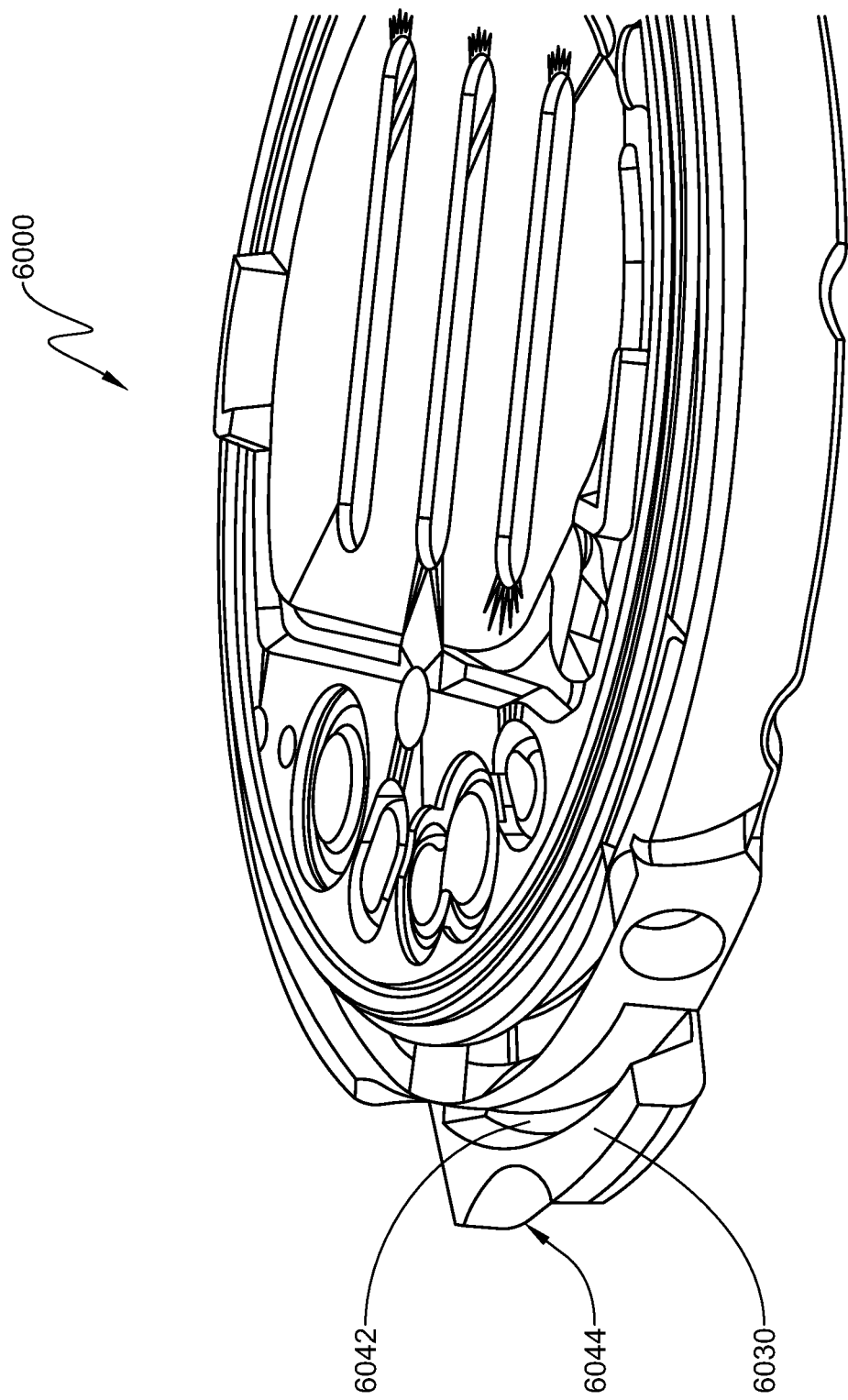
Figure 223A:
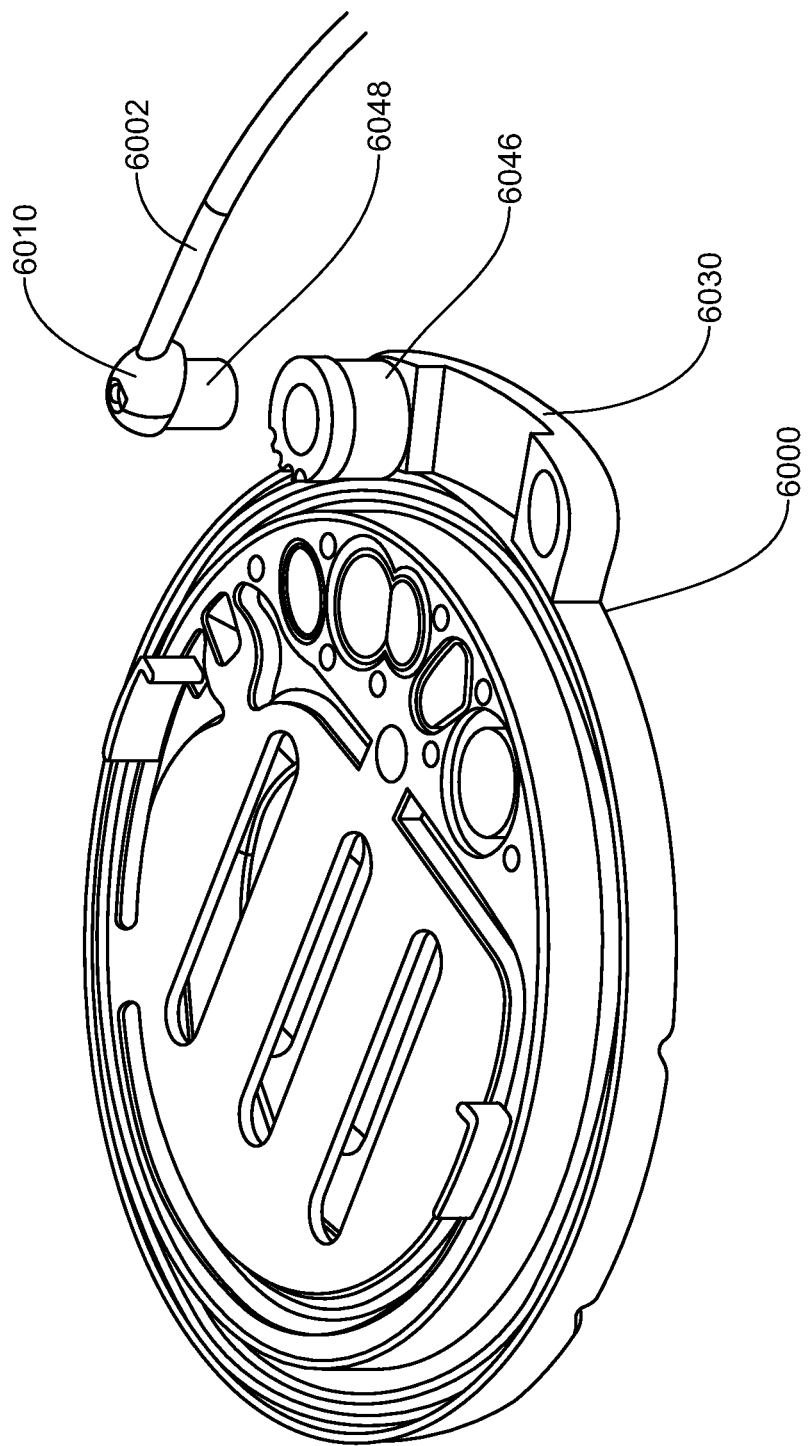
Figure 223B:
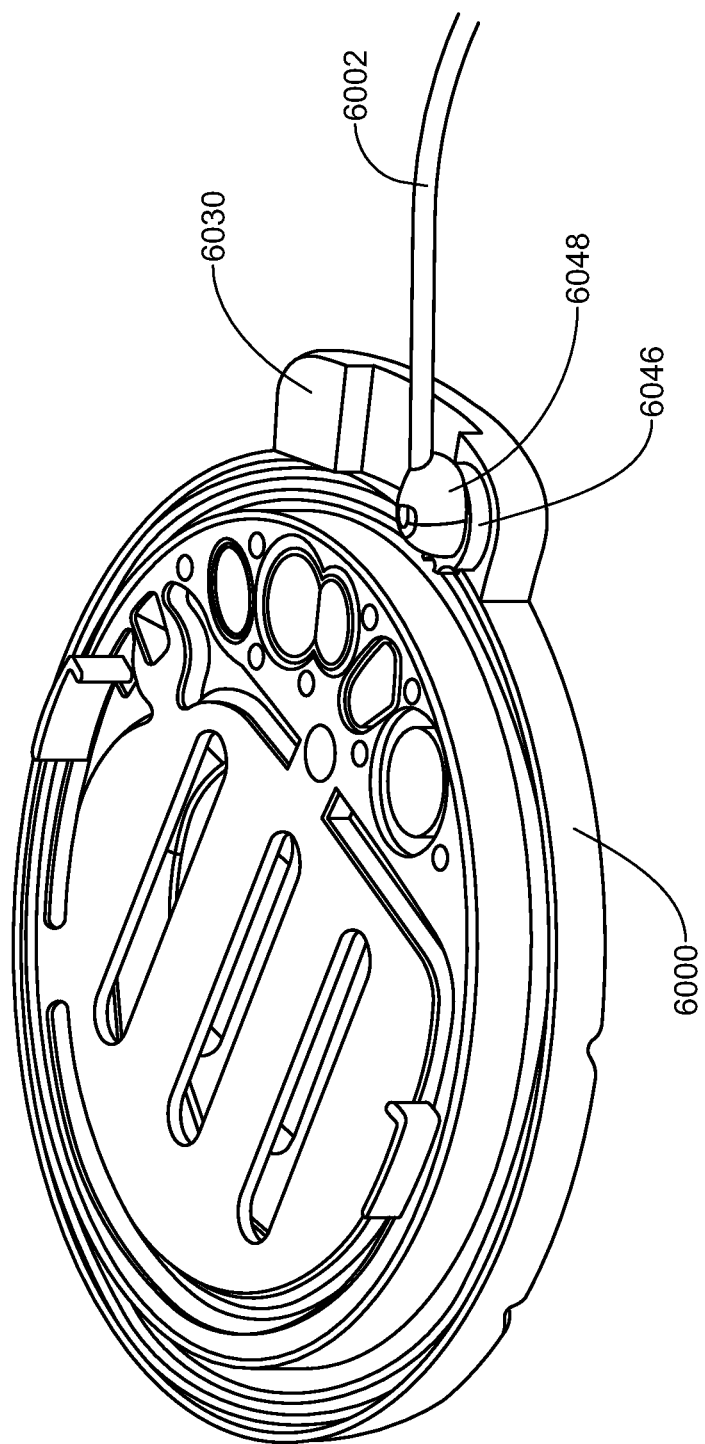
Figure 224:
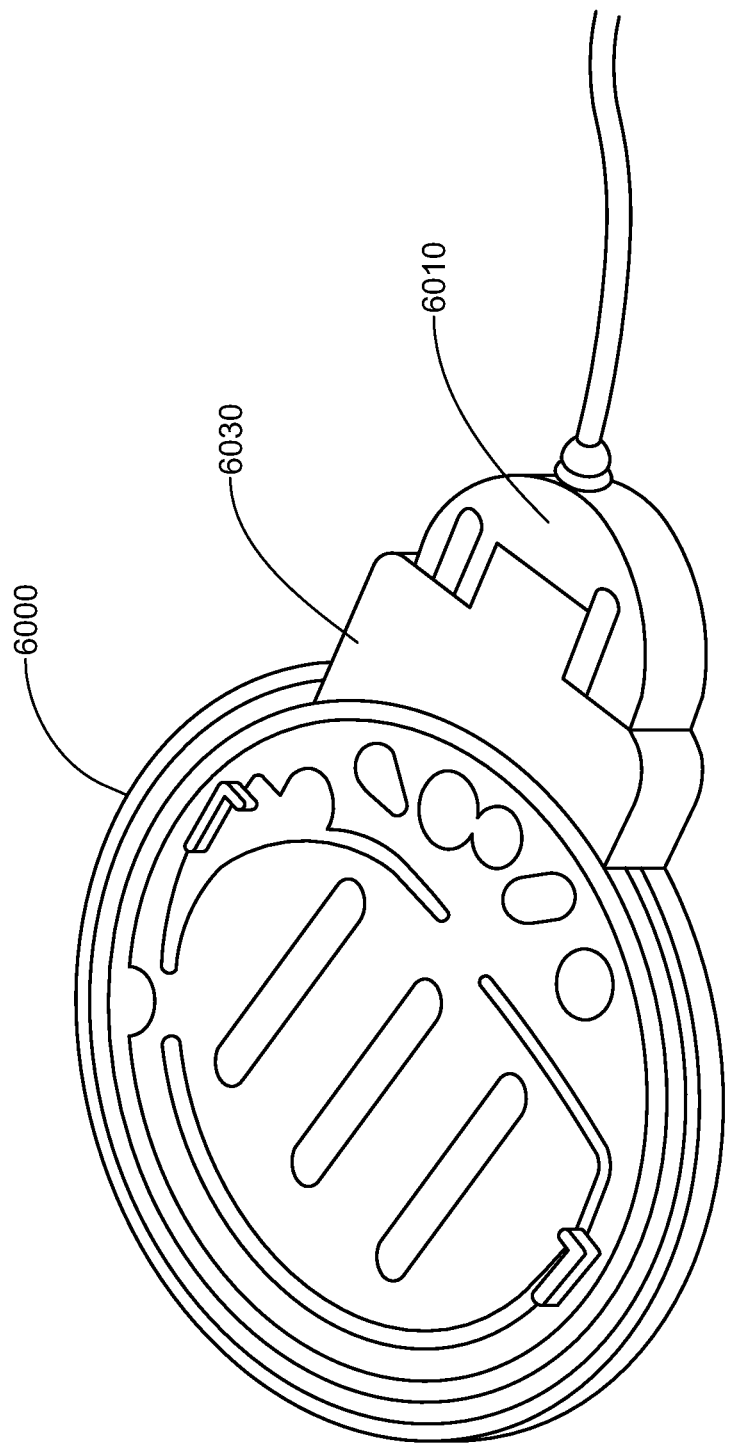
Figure 225A:
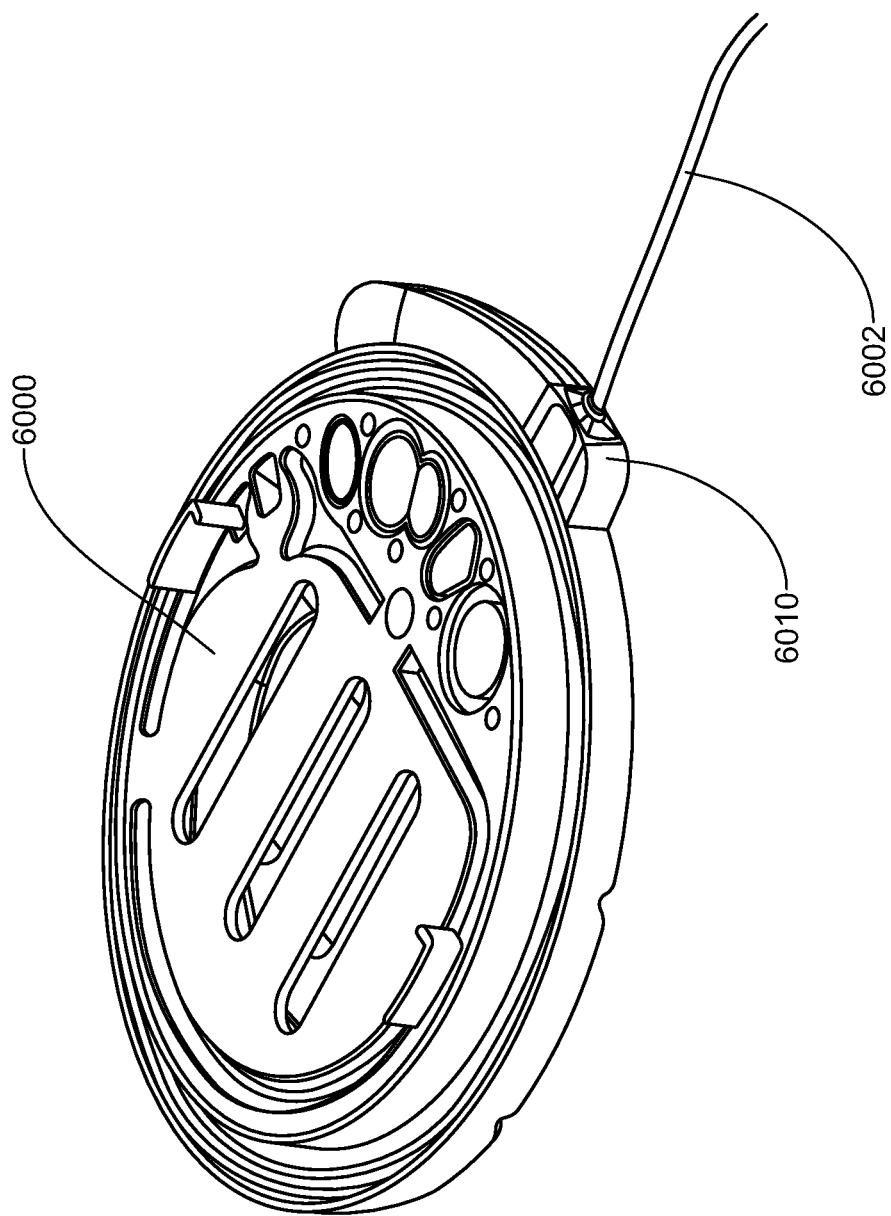
Figures 225B, 226:
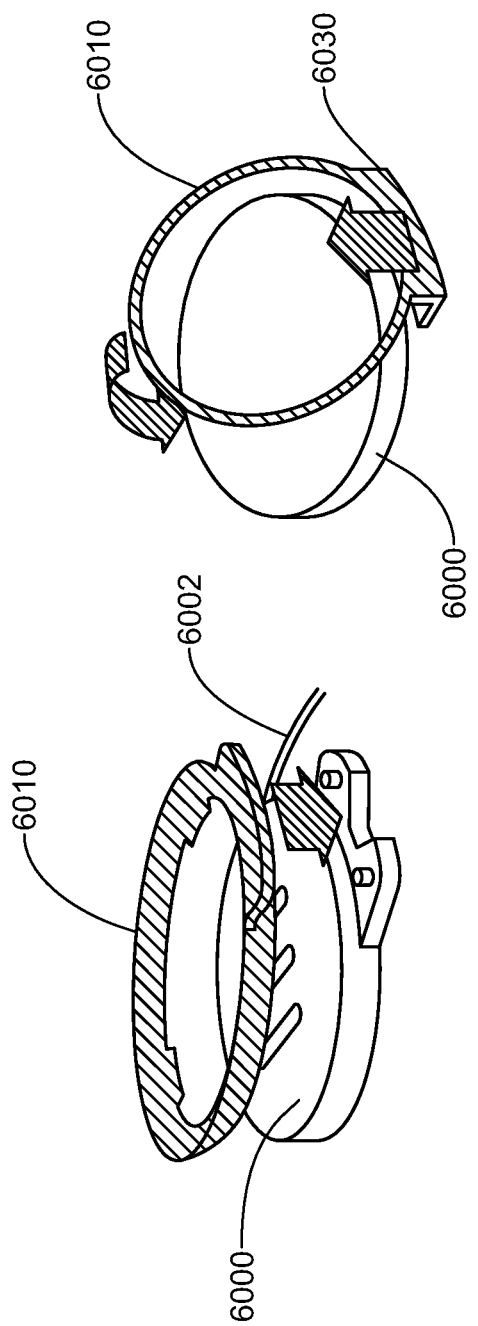
Figure 227A:
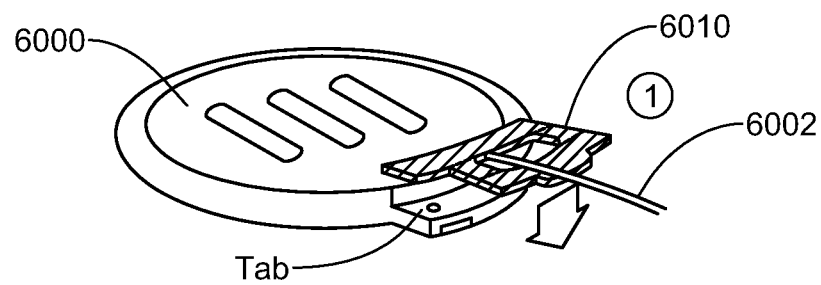
Figure 227B:
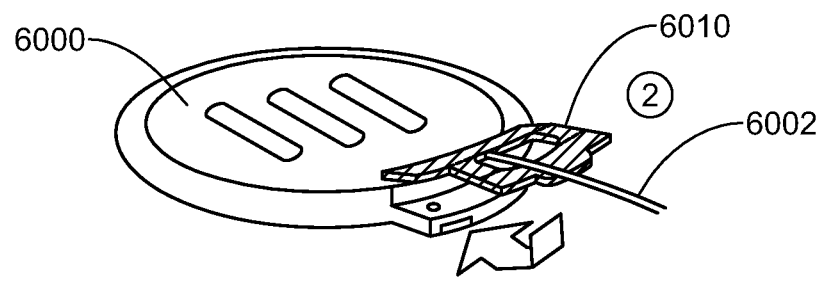
Figure 227C:
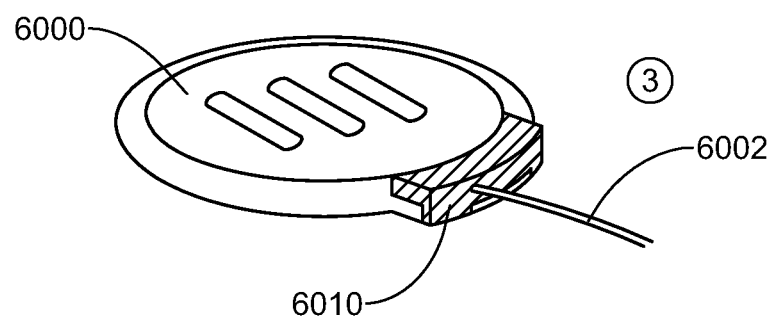
Figure 229:
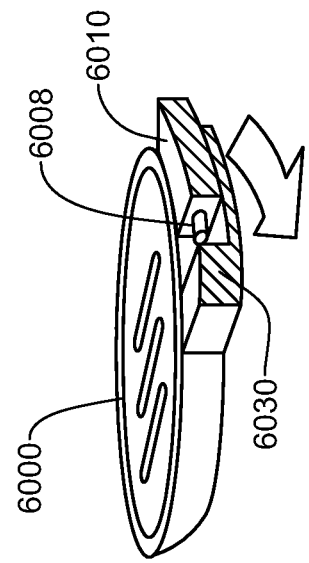
Figure 230:
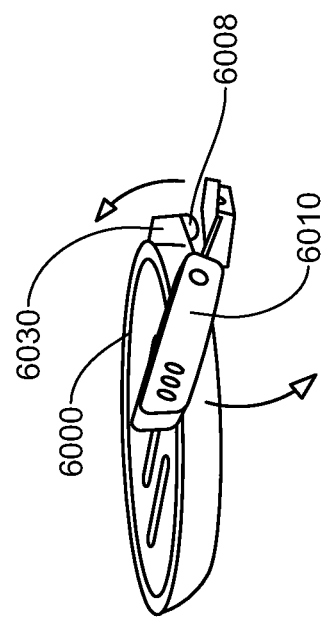
Figure 228A:
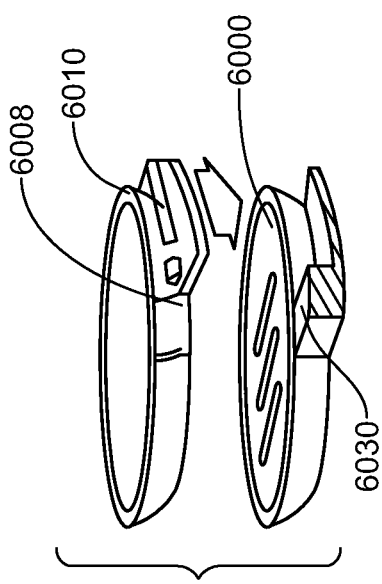
Figure 228B:
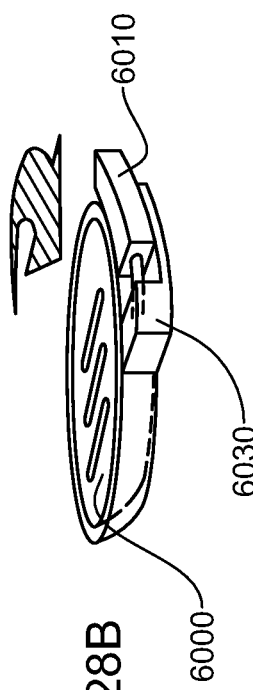
Figure 231A:
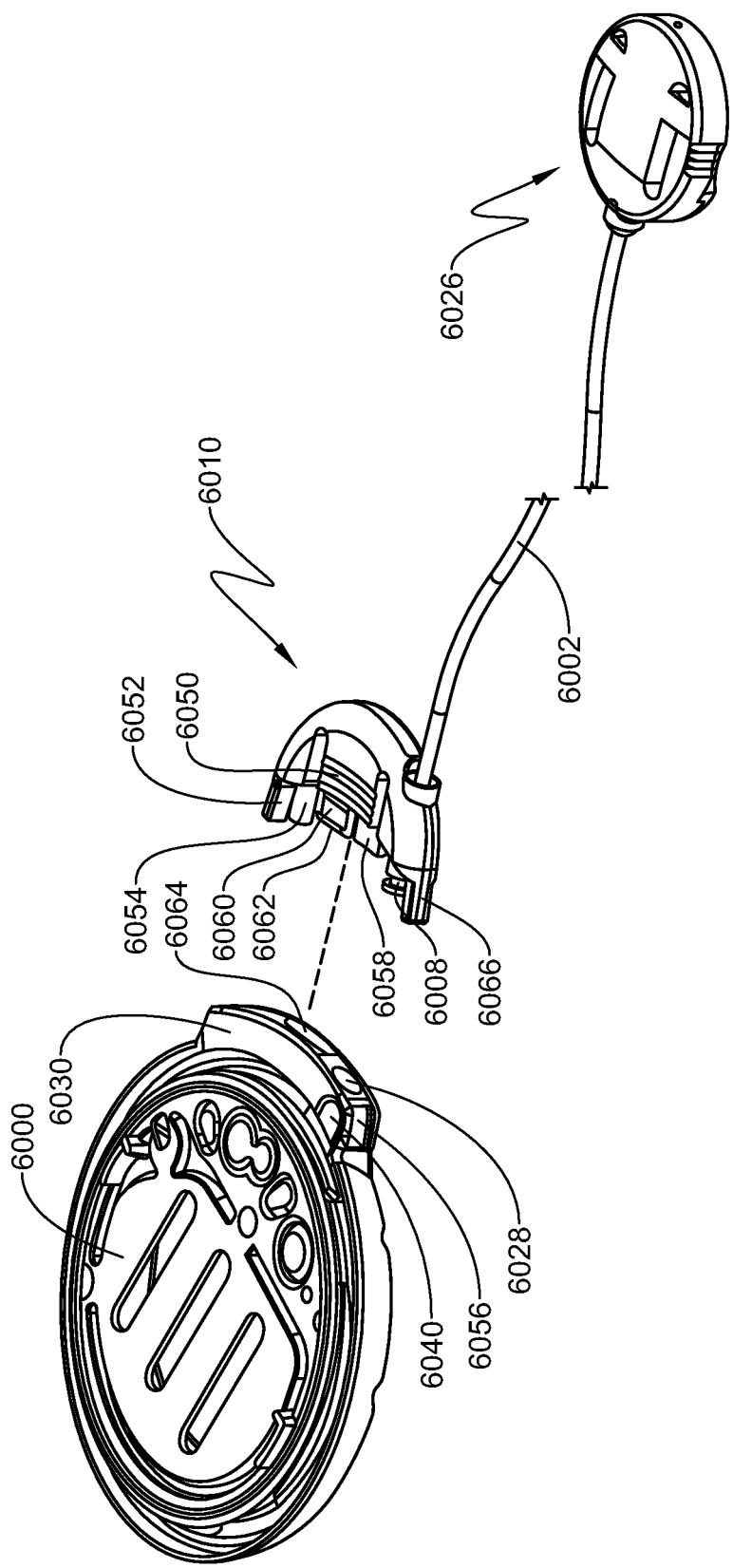
Figure 231B:
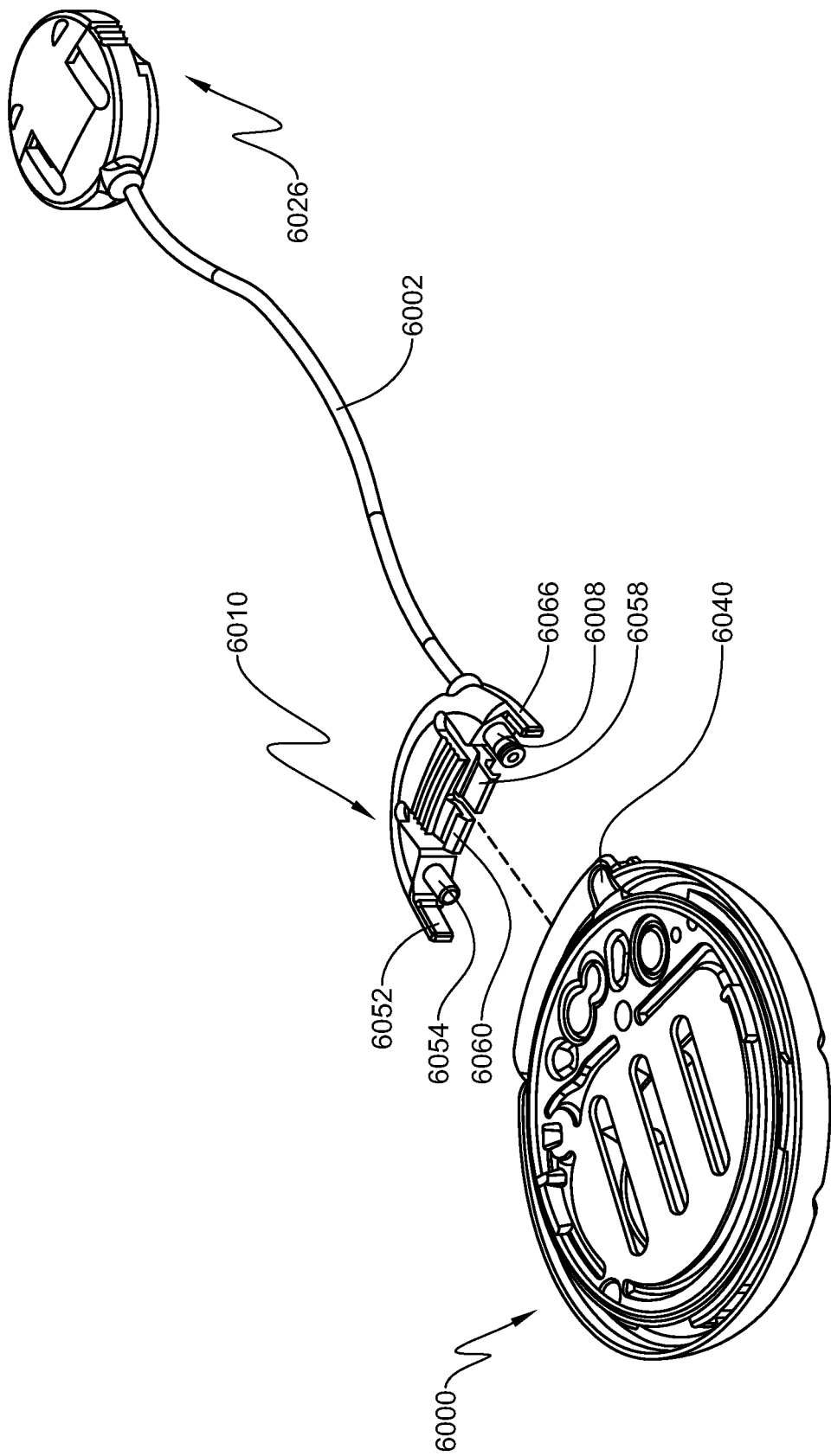
Figure 231C:
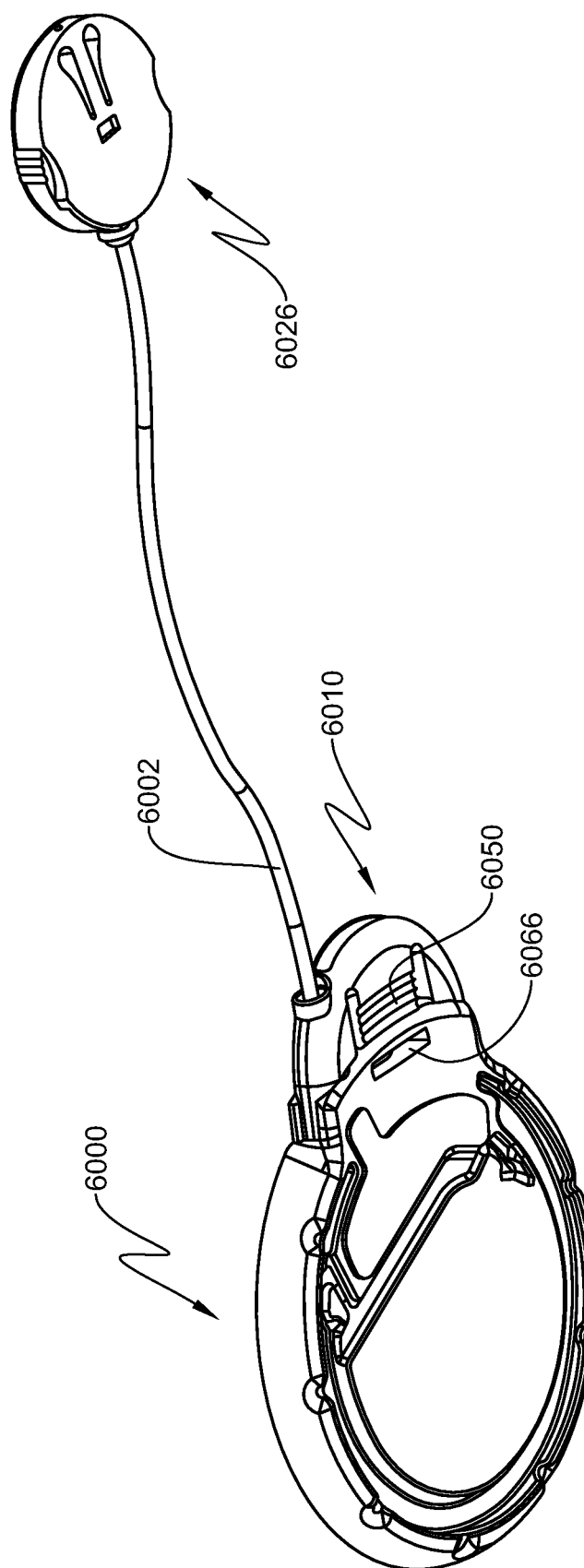
Figure 231D:
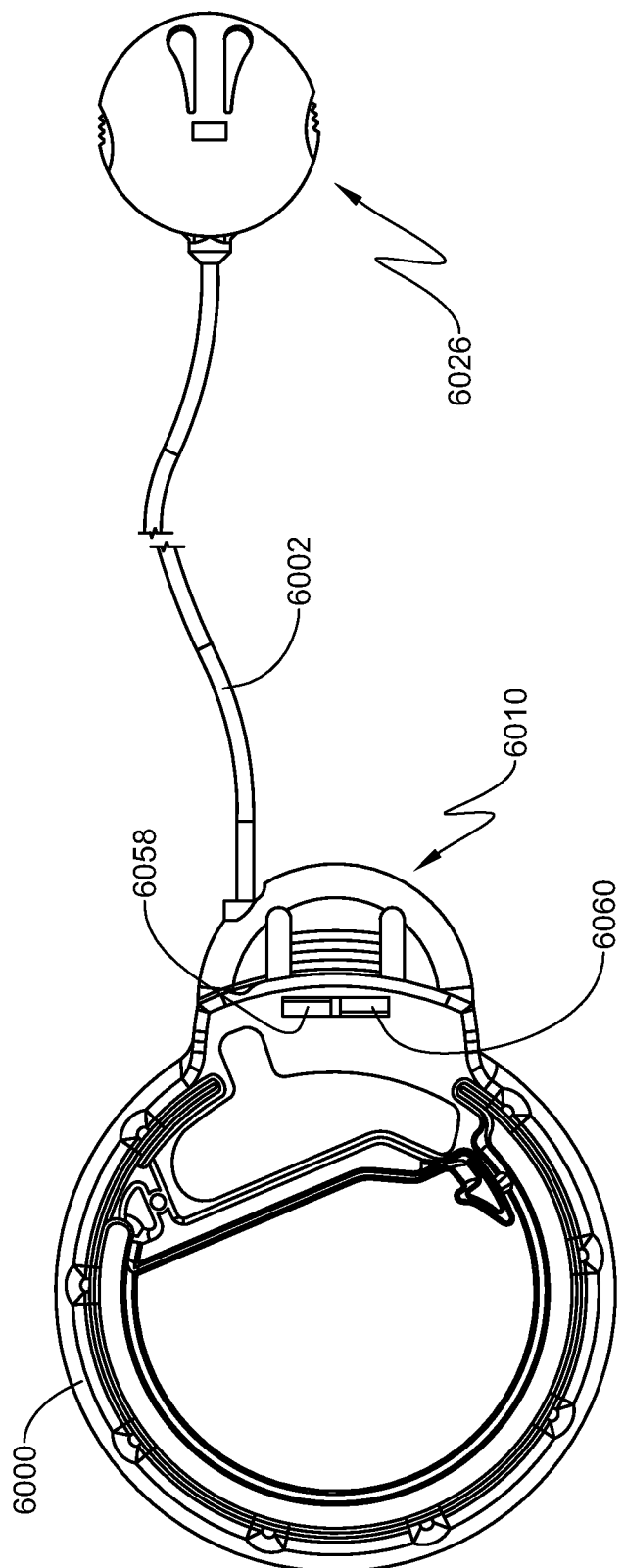
Figure 231E:
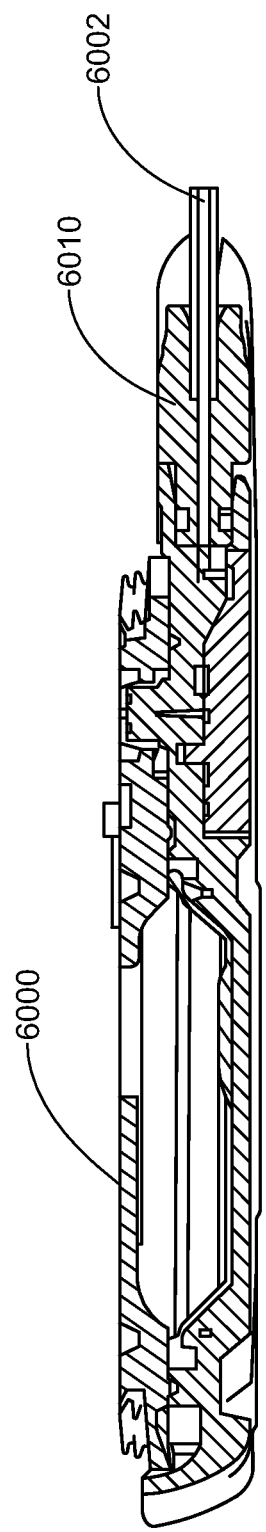
Figure 232A:
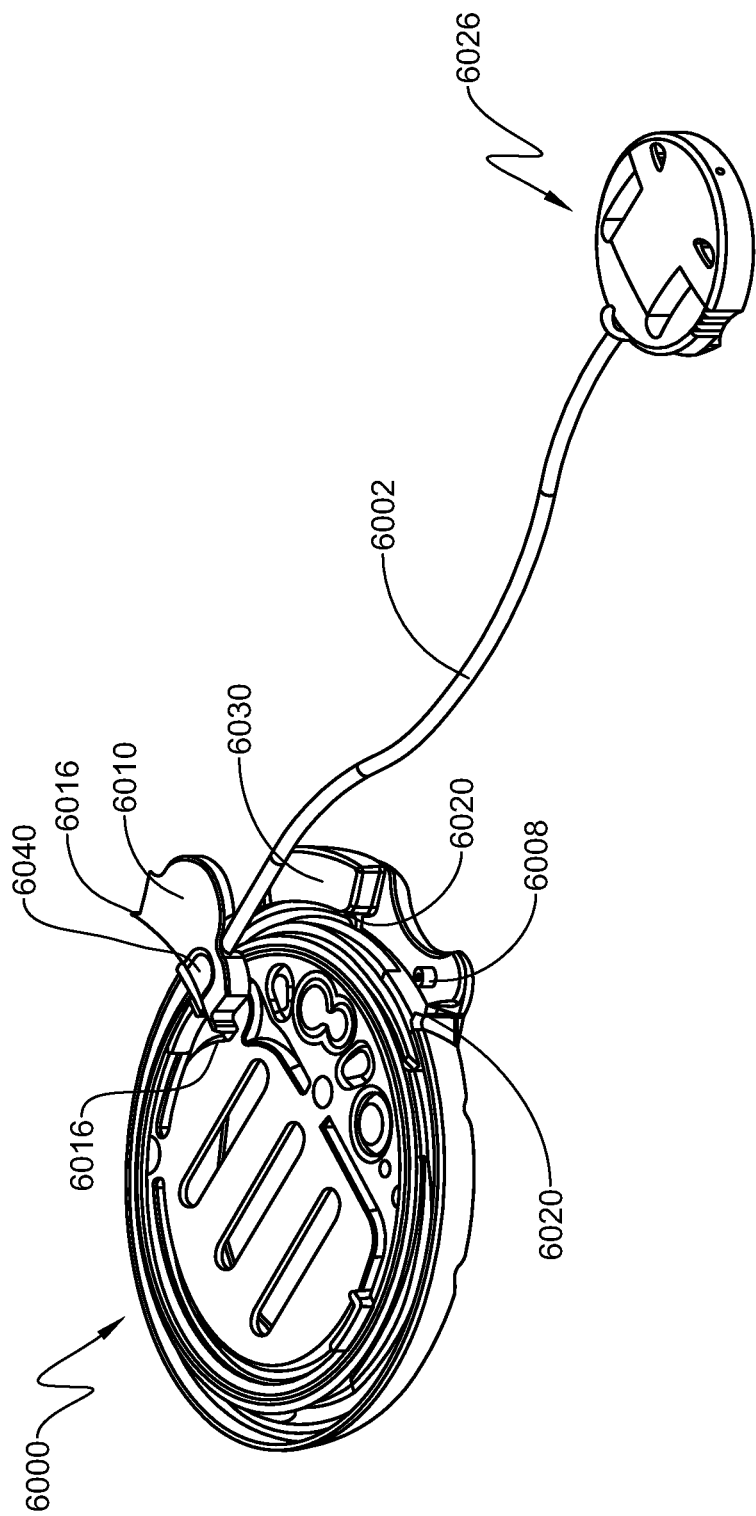
Figure 232B:
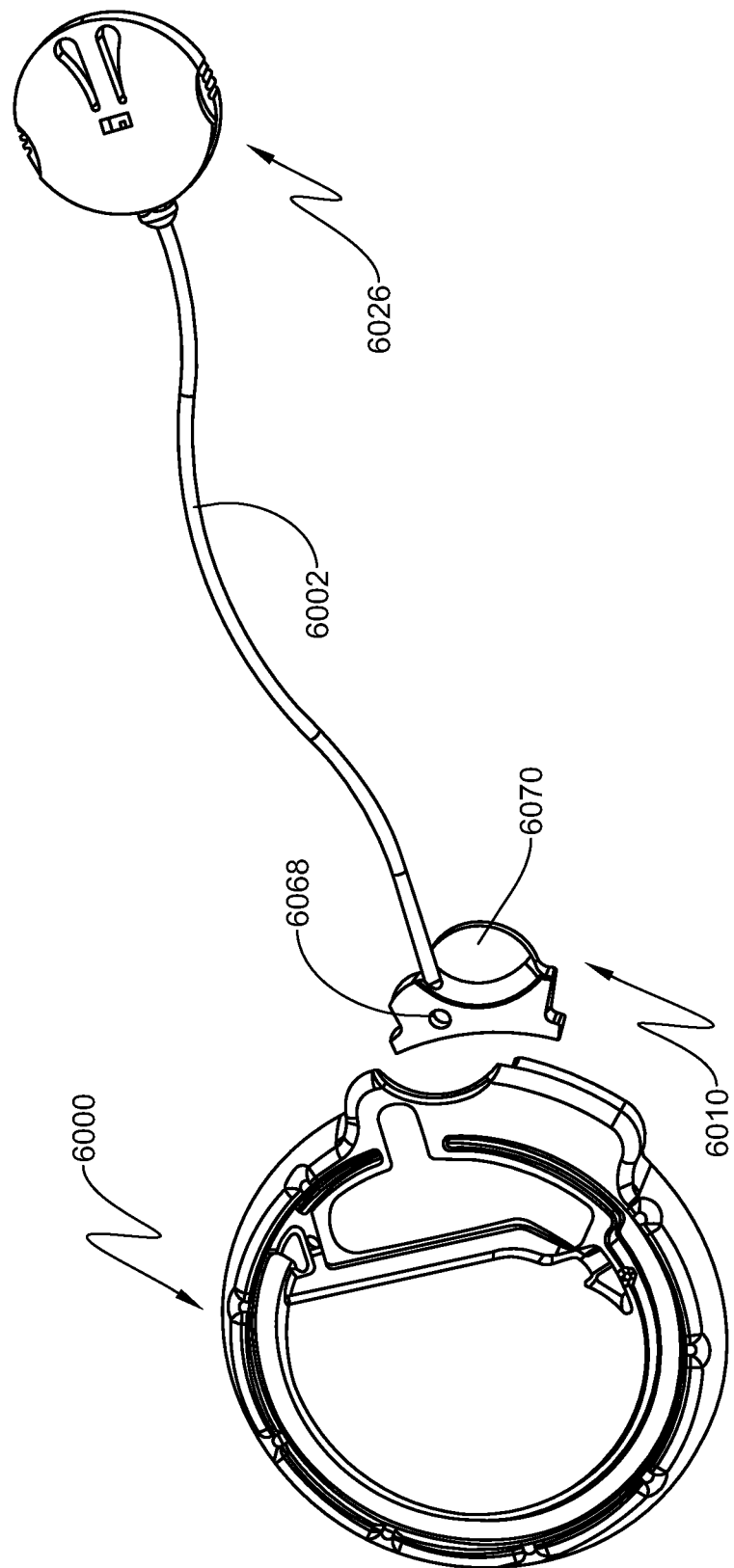
Figure 232C:
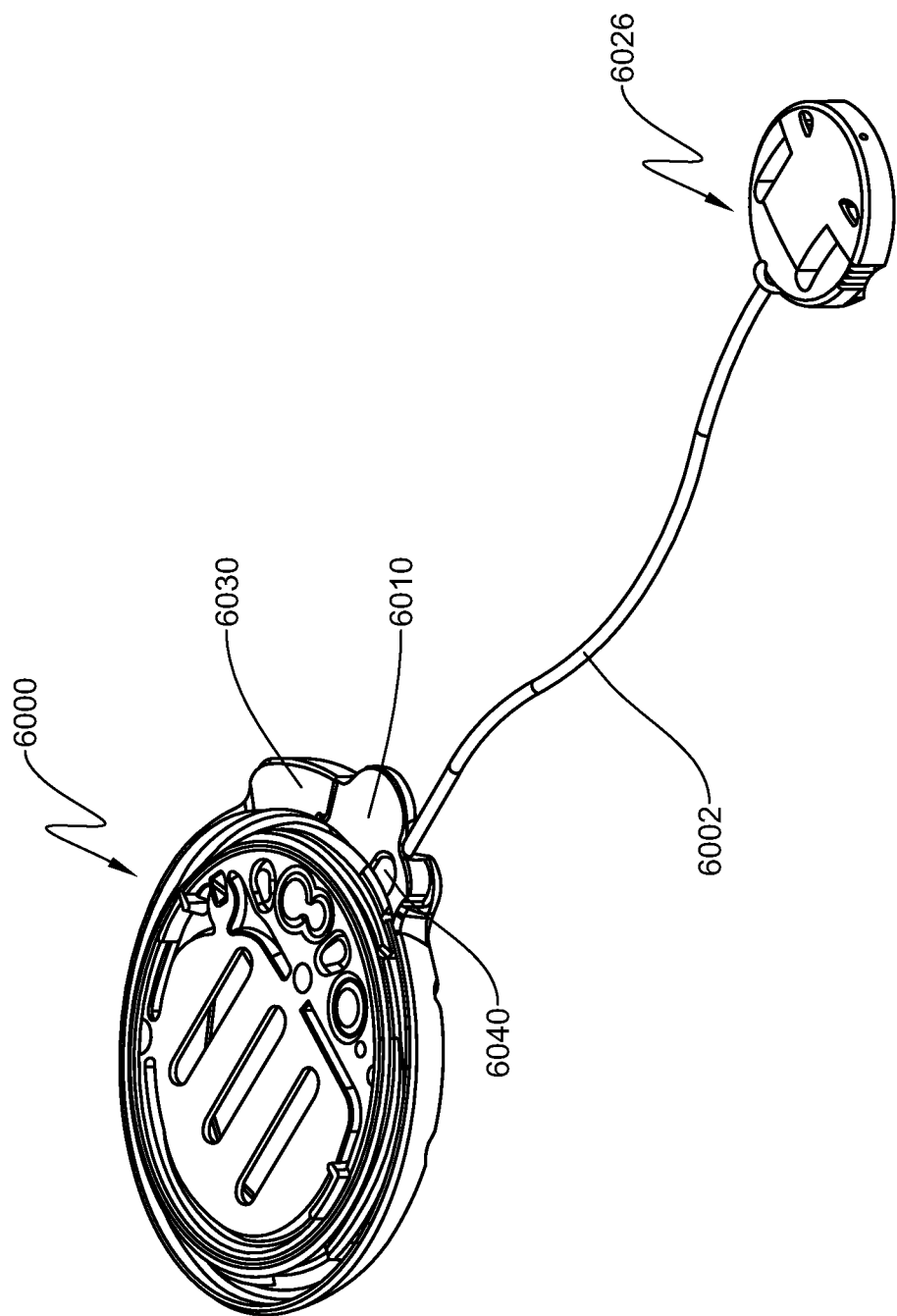
Figure 232D:
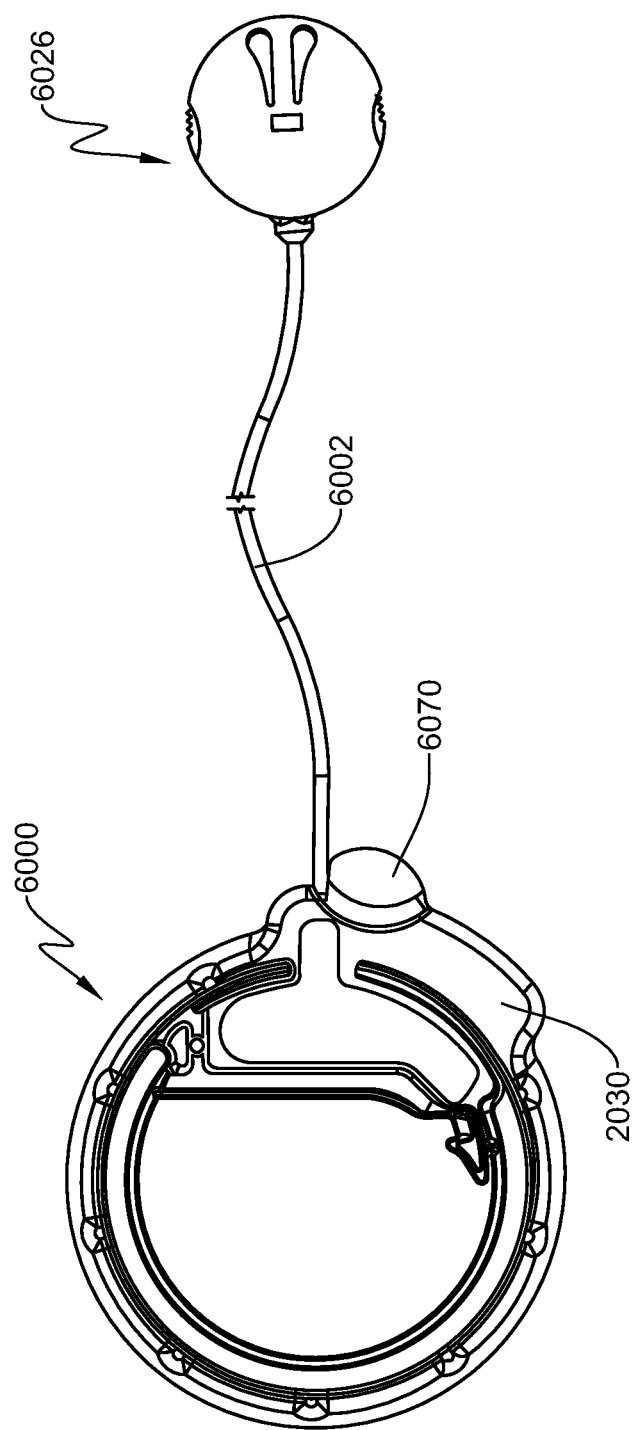
Figure 232:
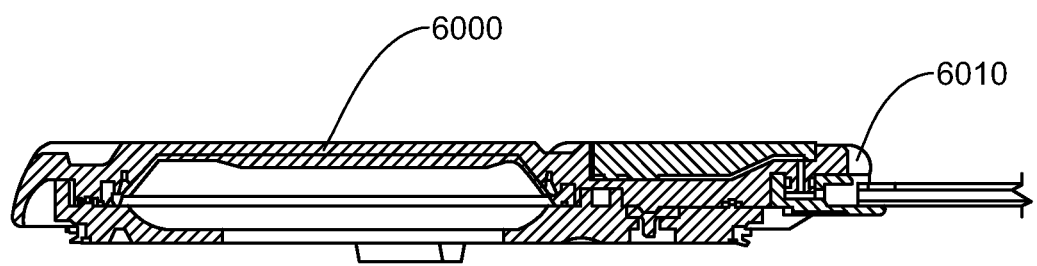
Figure 233A:
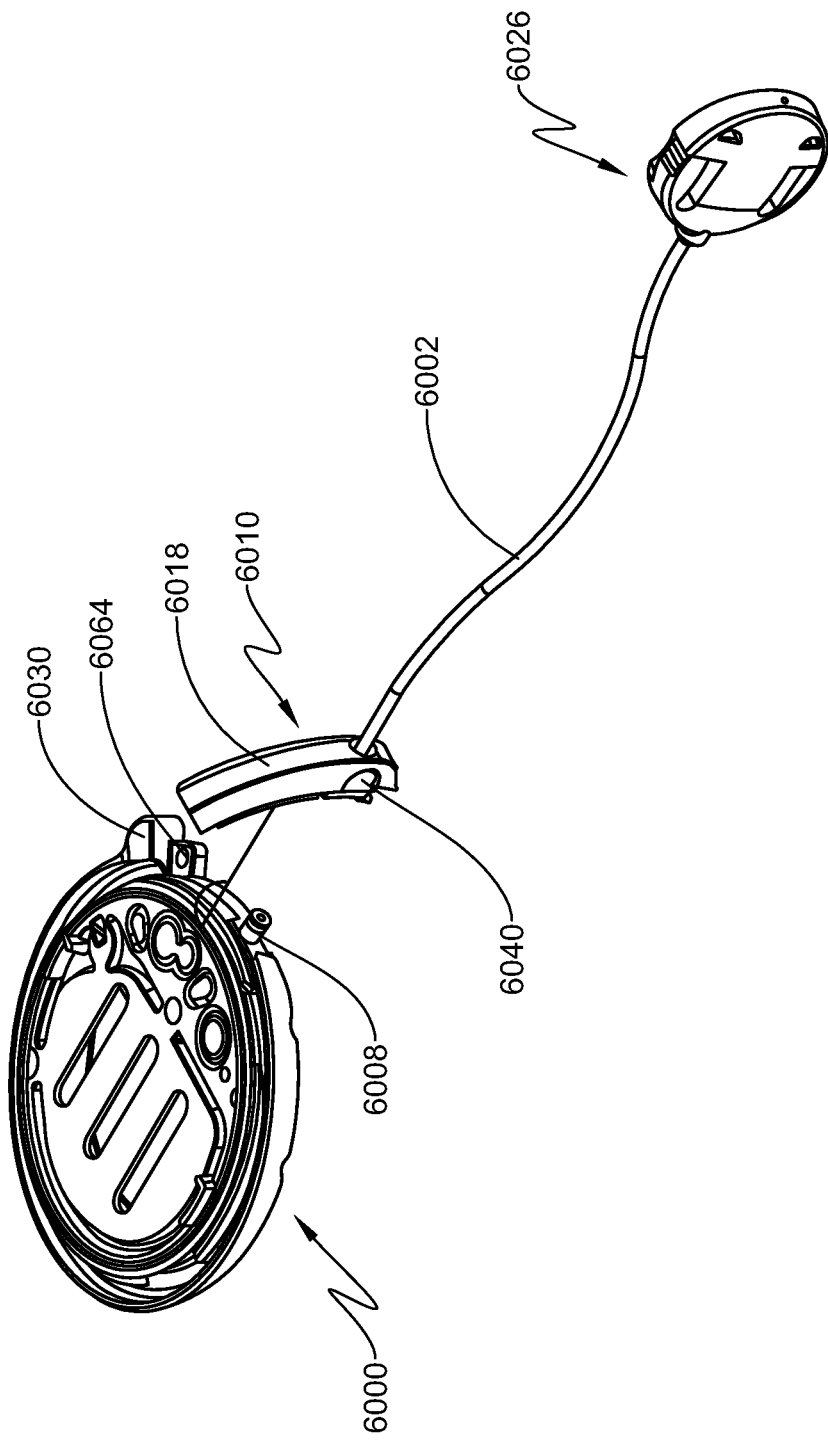
Figure 233B:
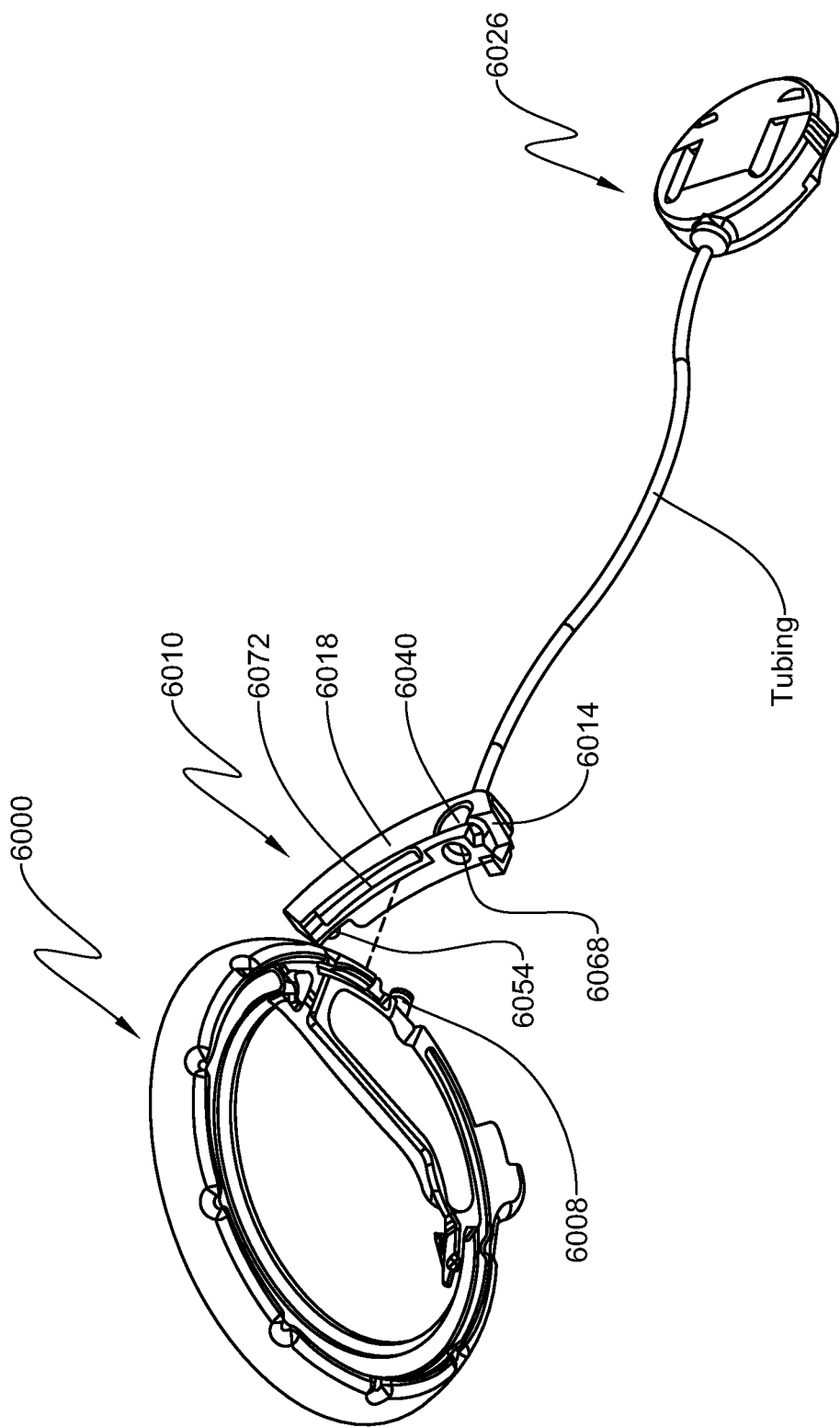
Figure 233C:
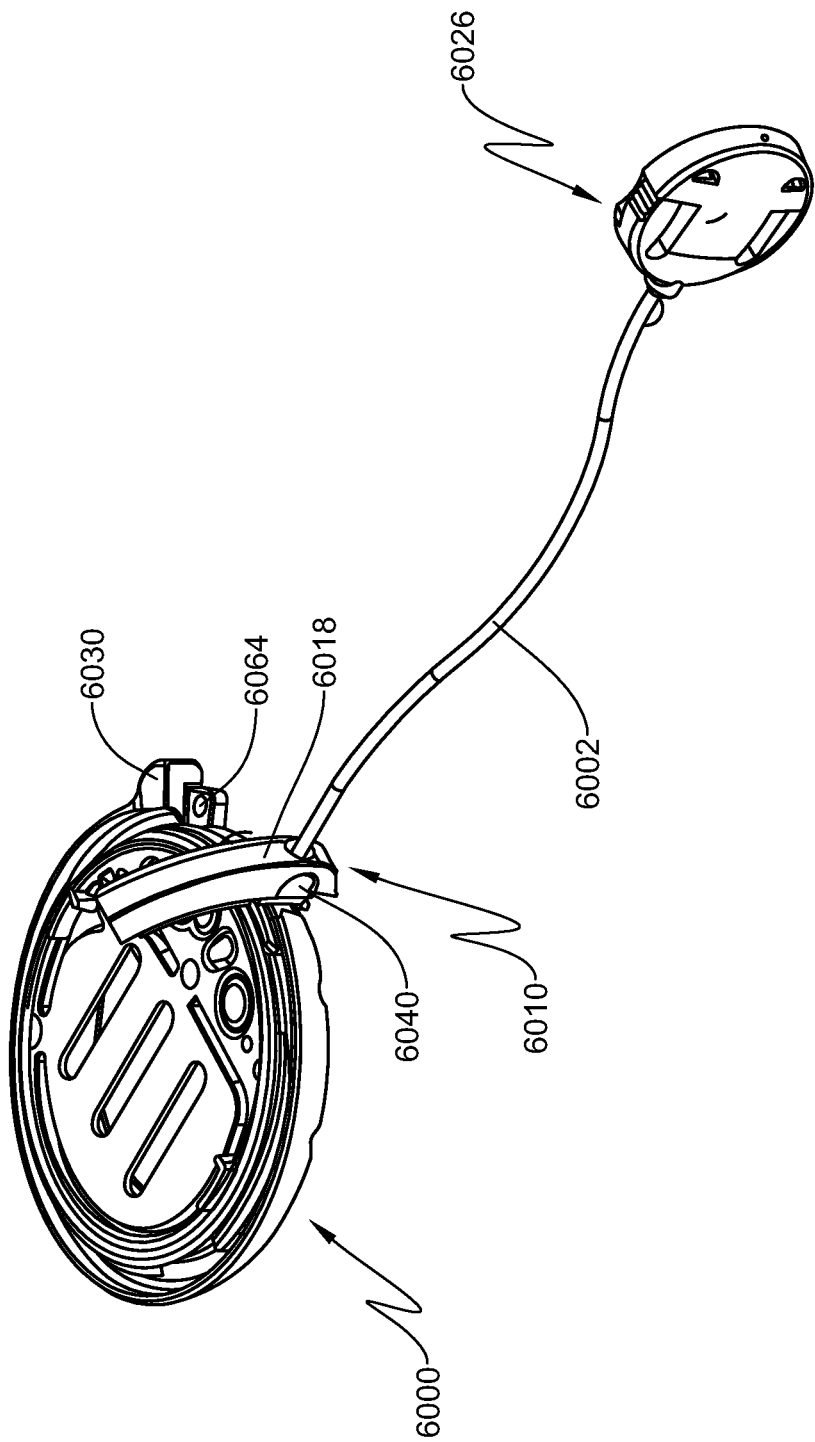
Figure 233D:
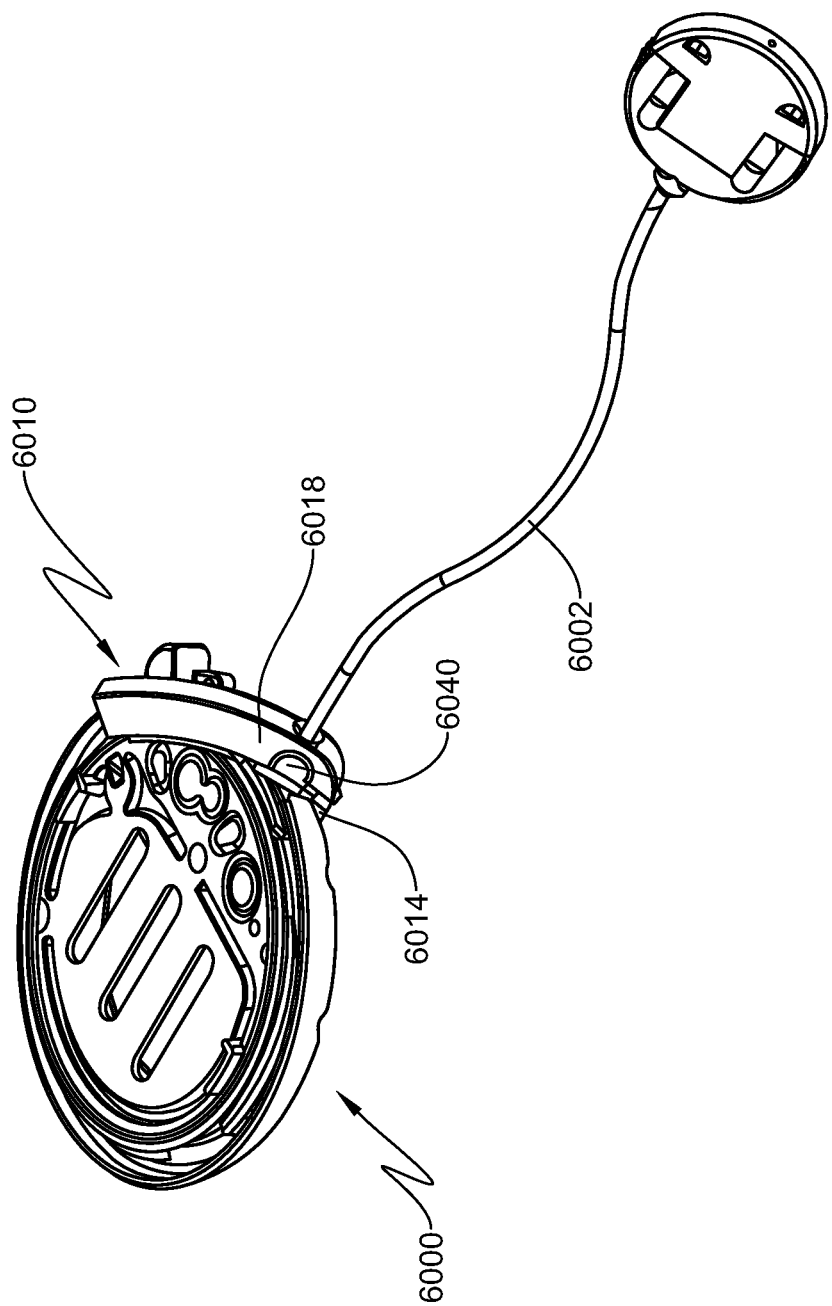
Figure 233E:
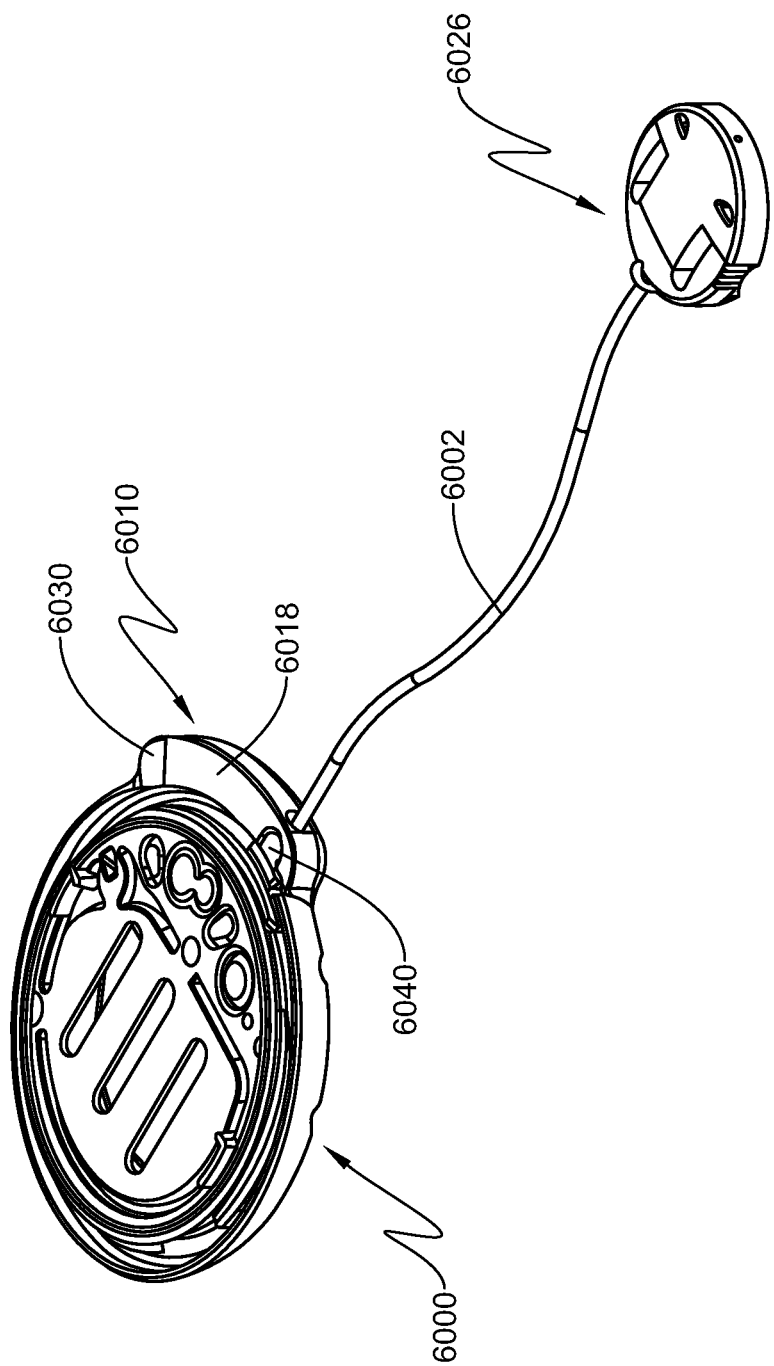
Figure 233F:
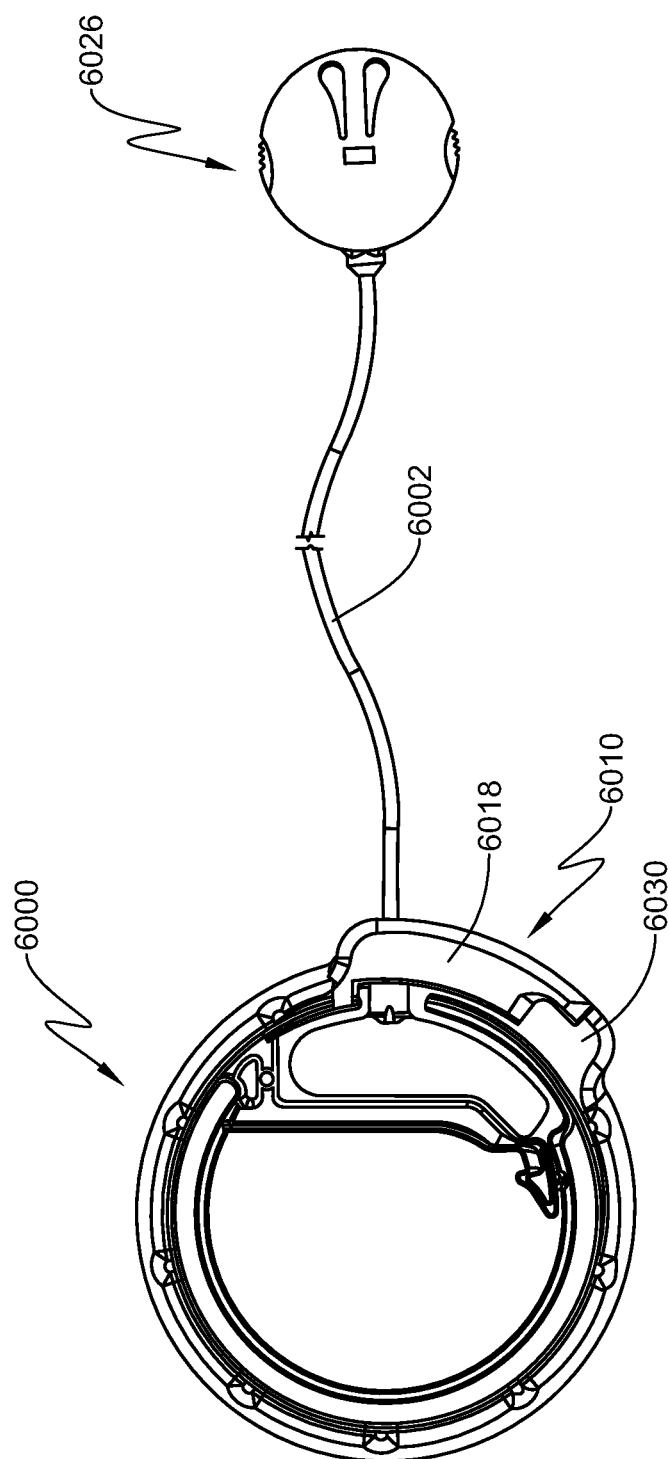
Figure 233G:
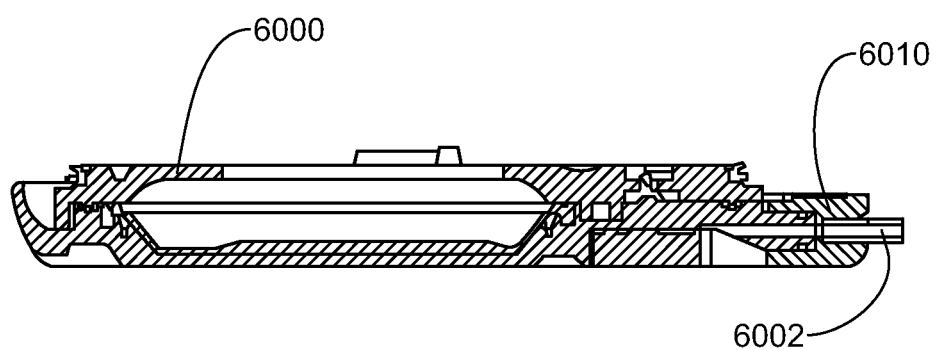
Figure 234A:
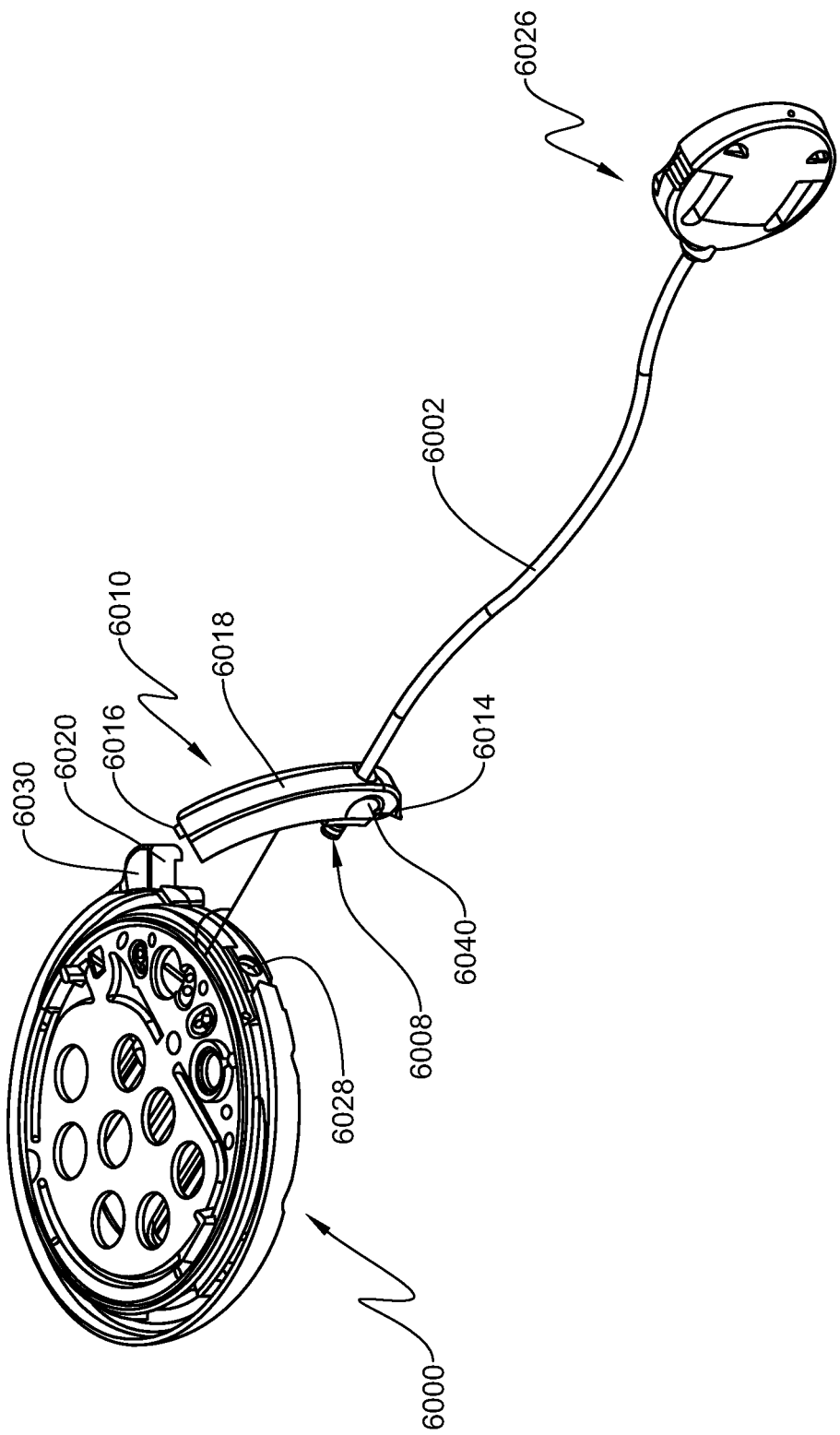
Figure 234B:
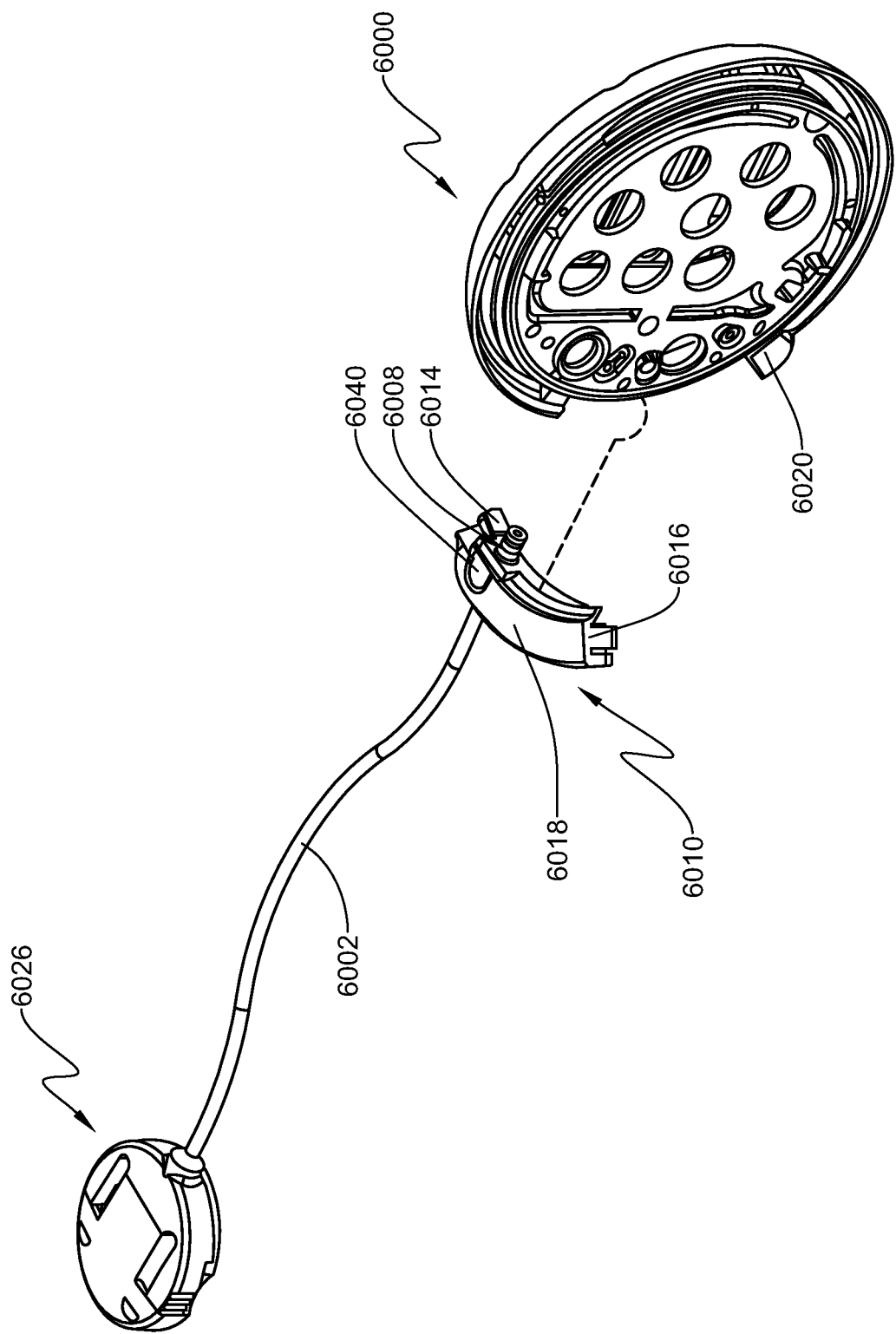
Figure 234C:
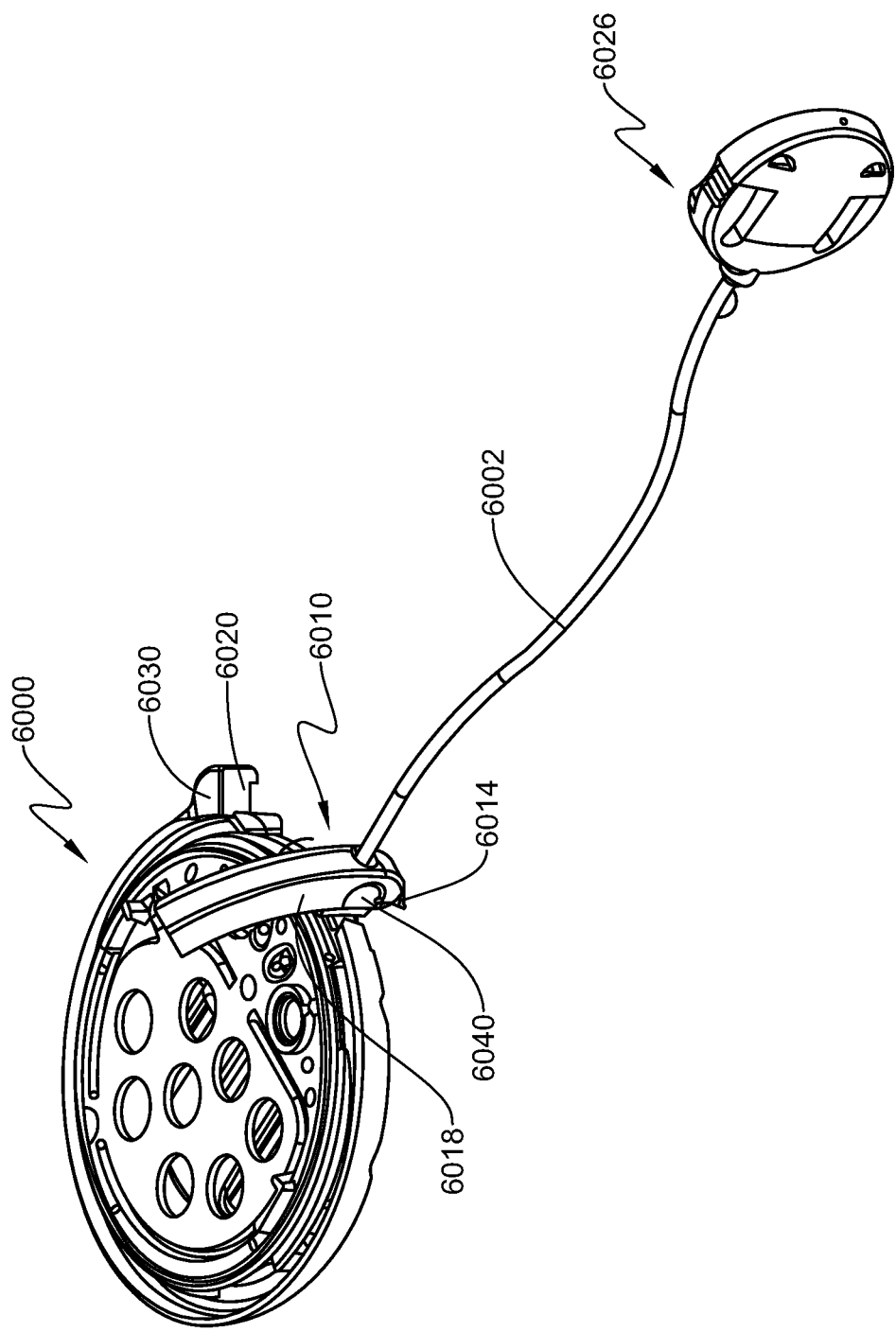
Figure 234D:
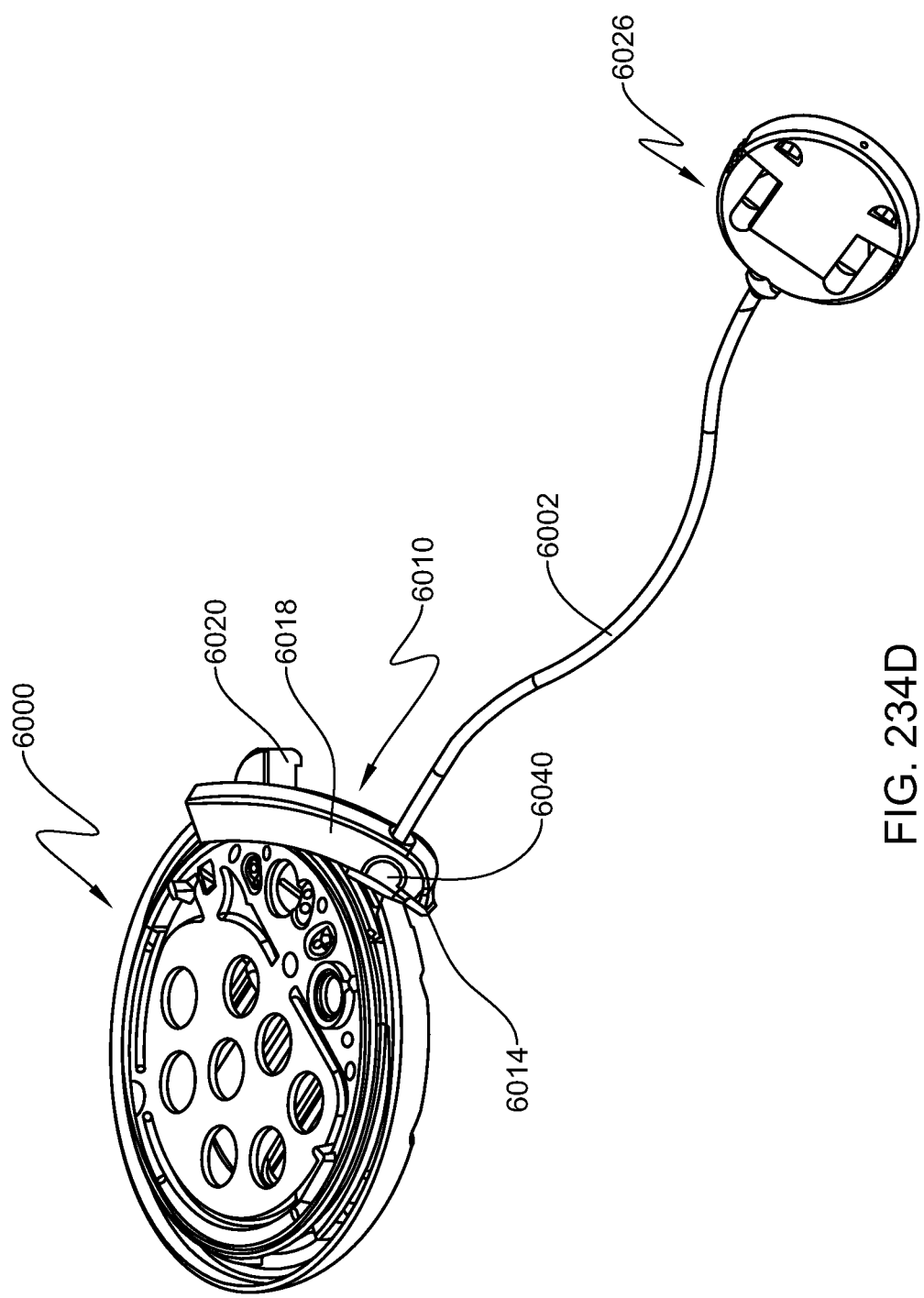
Figure 234E:
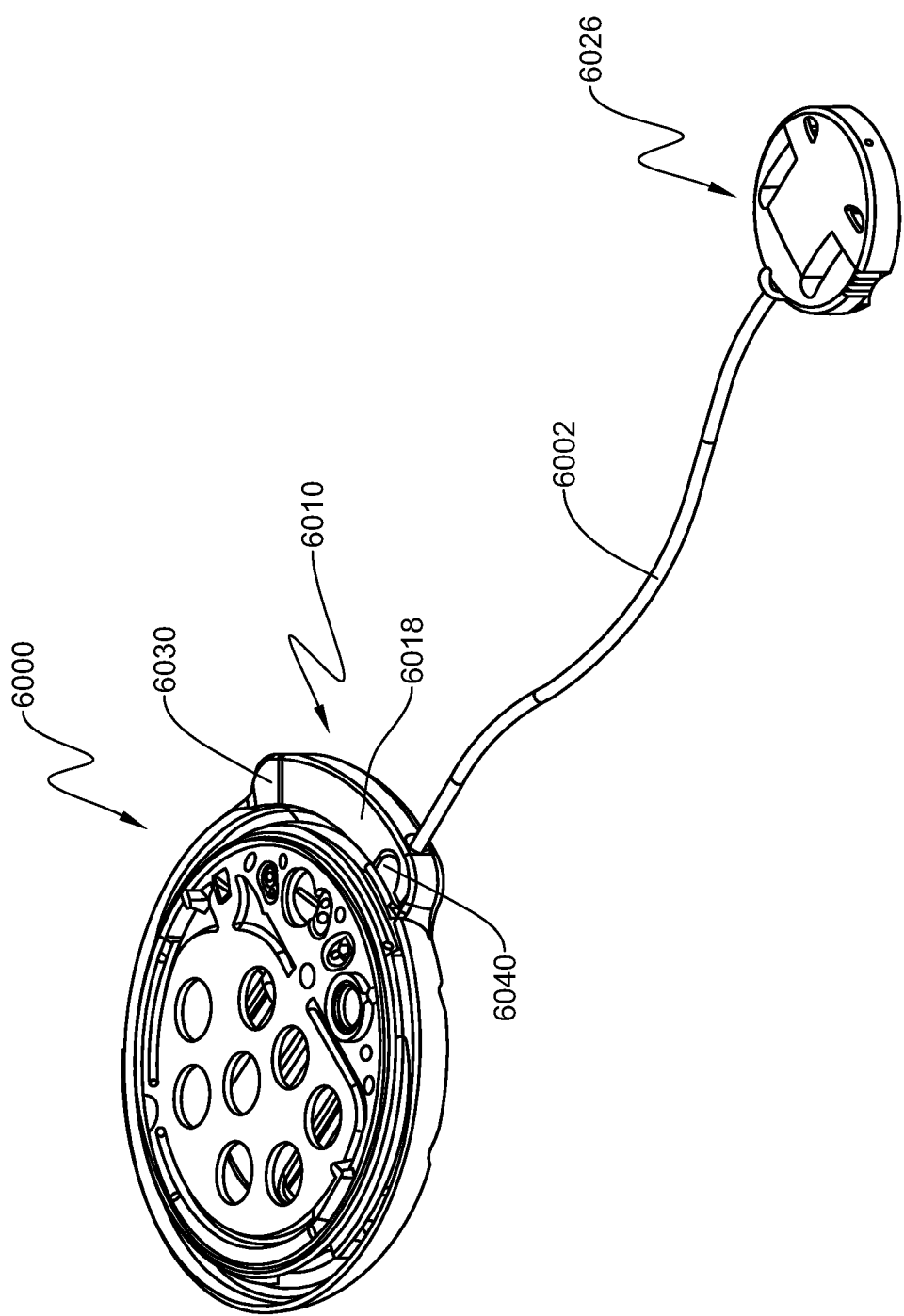
Figure 234F:
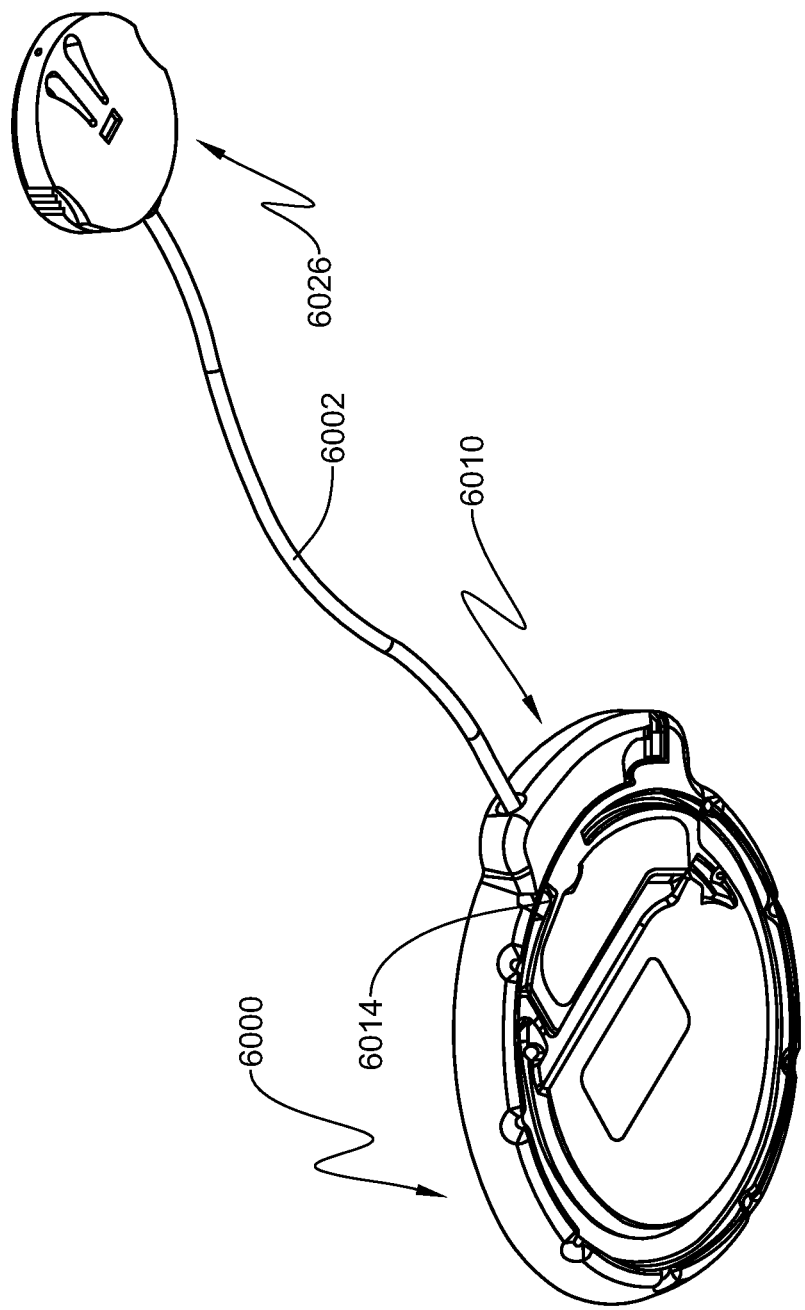
Figure 234G:
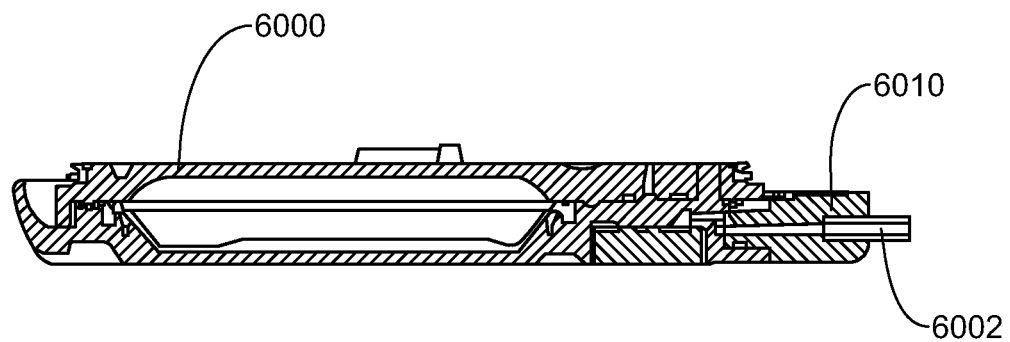
Figure 236A:
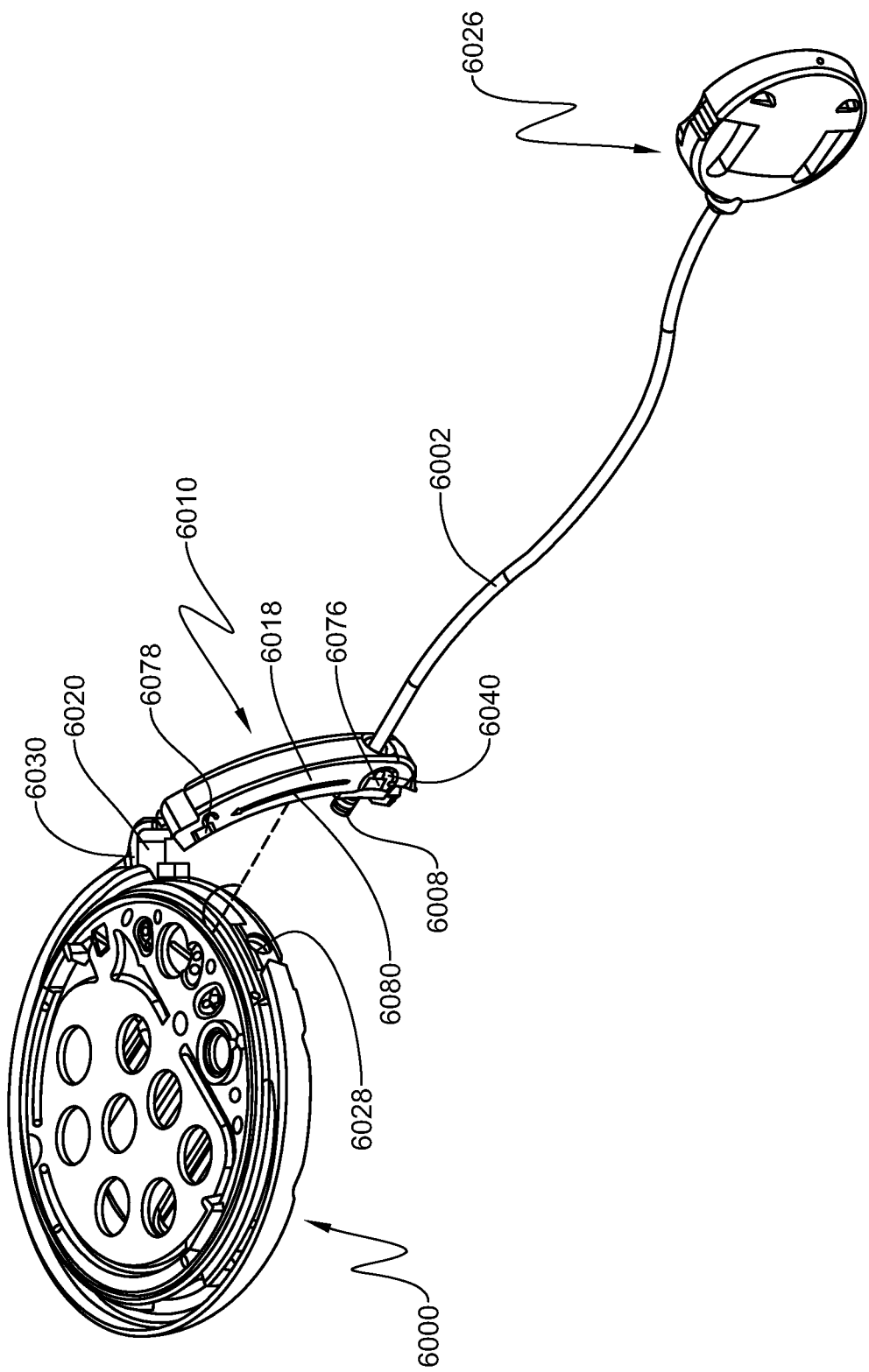
Figure 236B:
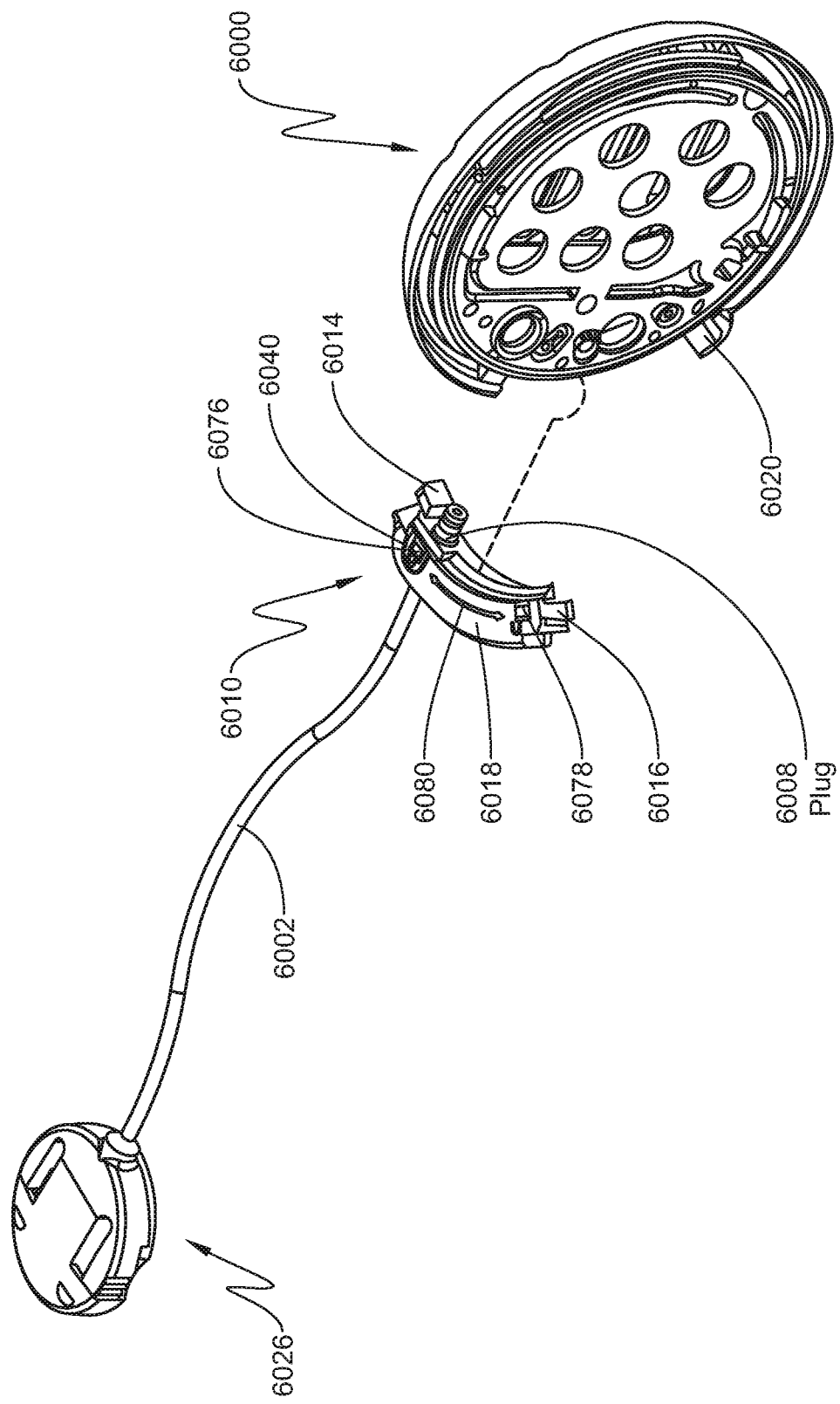
Figure 236C:
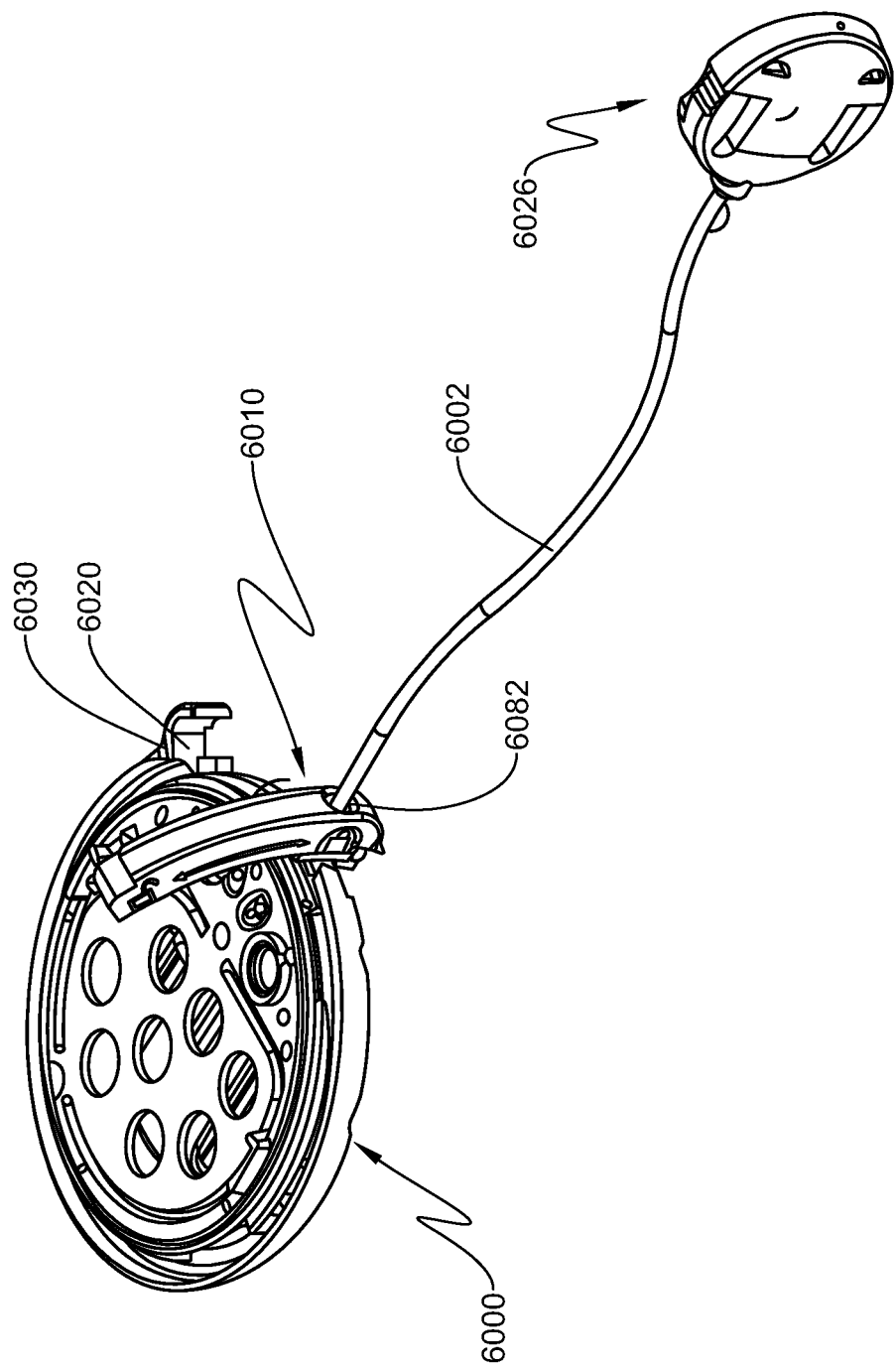
Figure 236D:
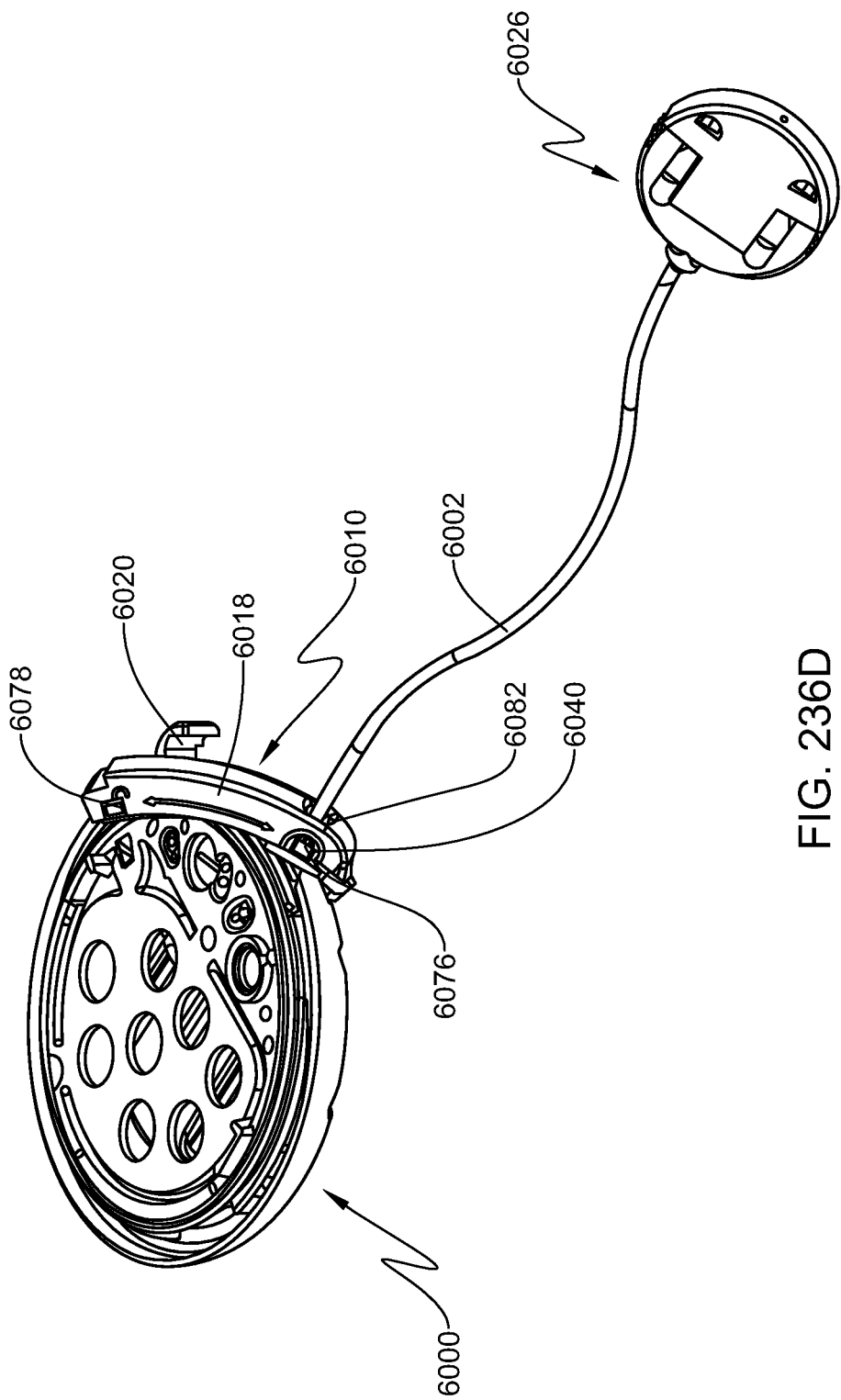
Figure 236E:
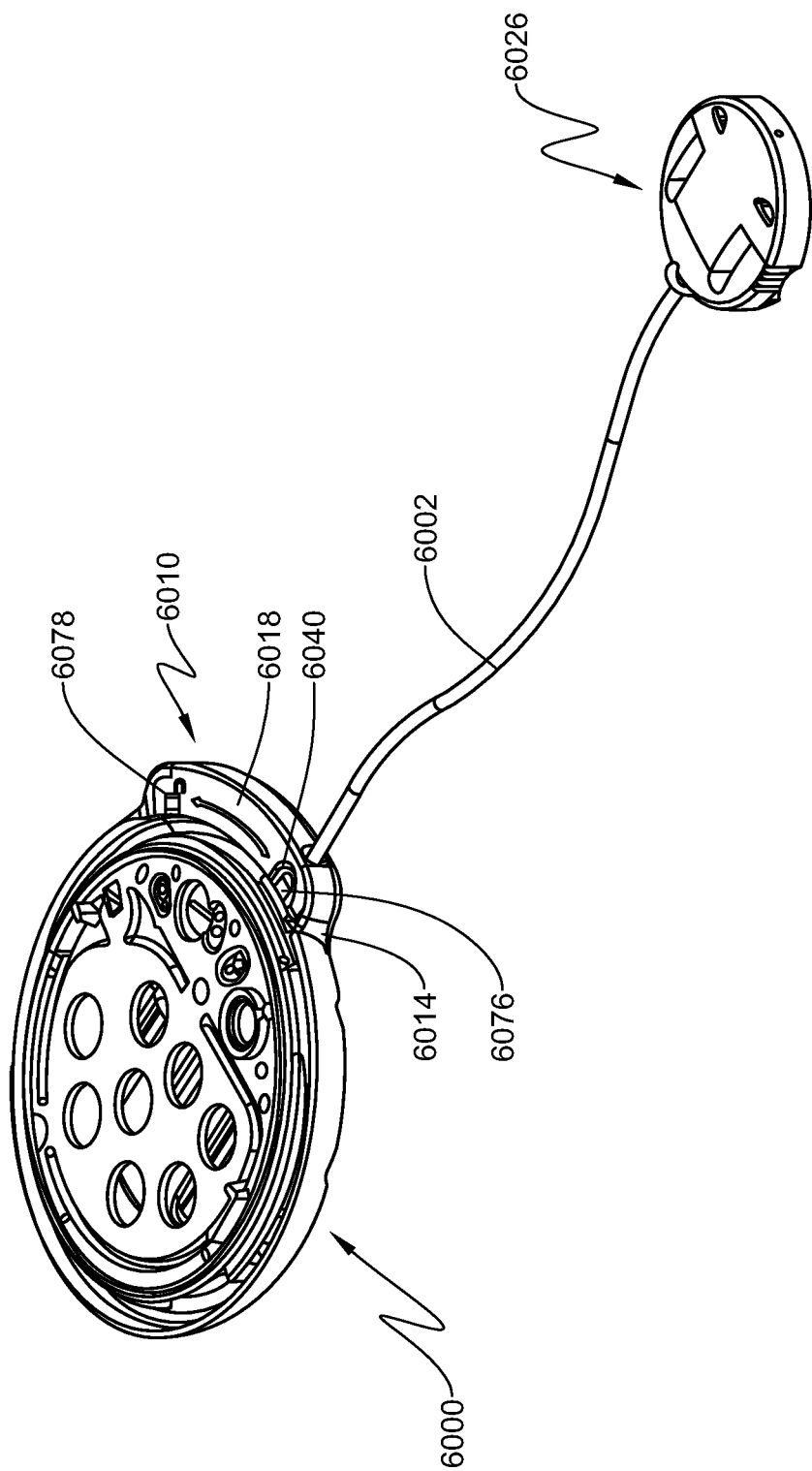
Figure 236F:
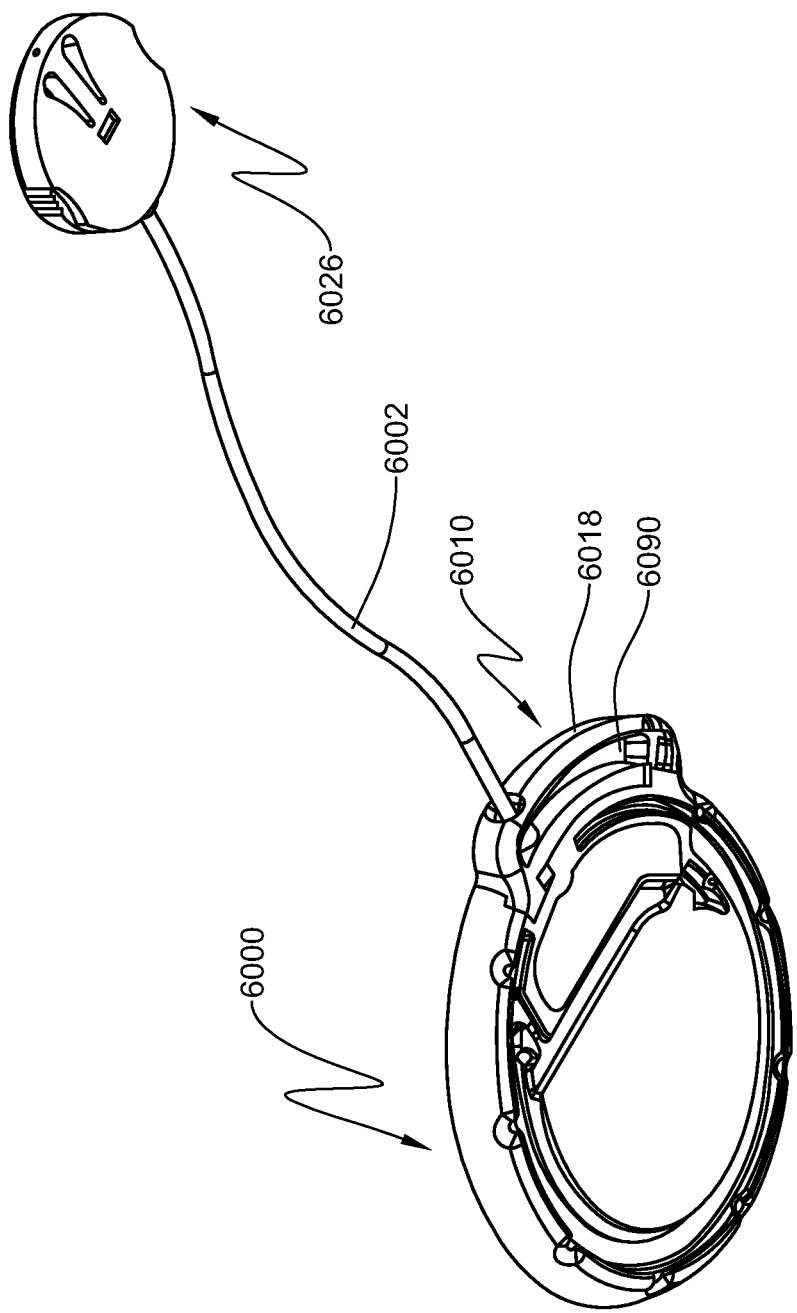
Figure 236G:
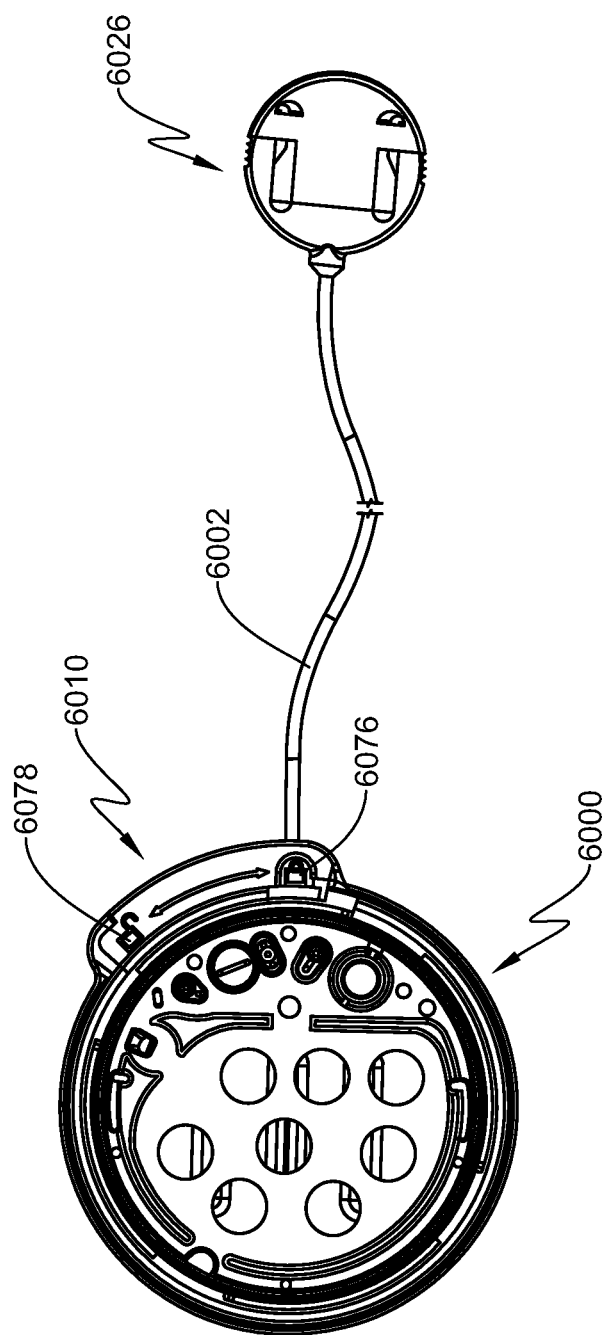
Figure 236H:
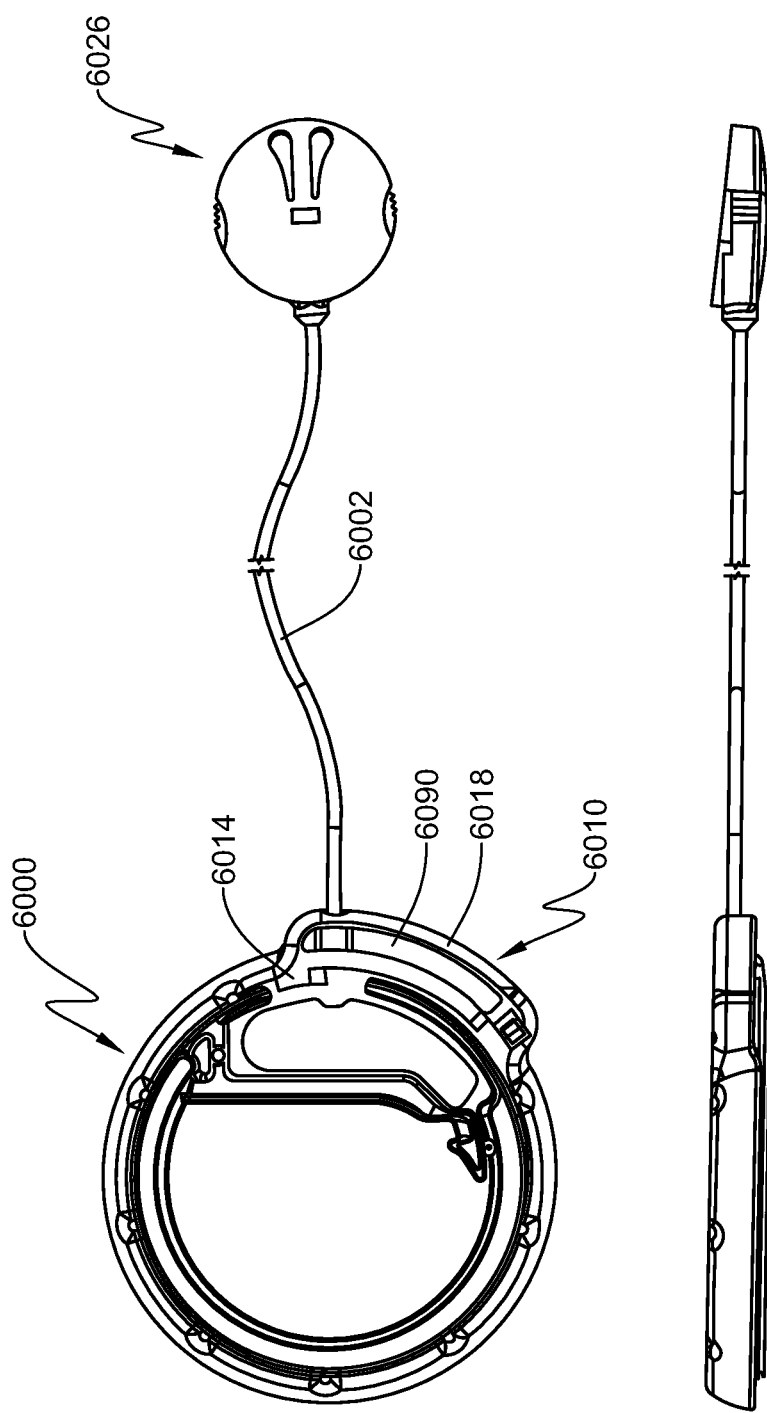
Figure 236L:
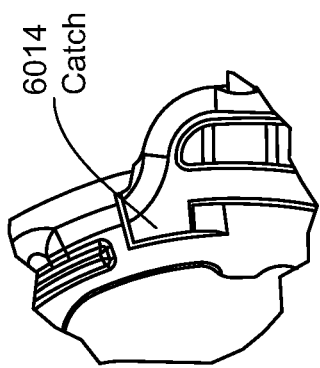
Figure 236J:
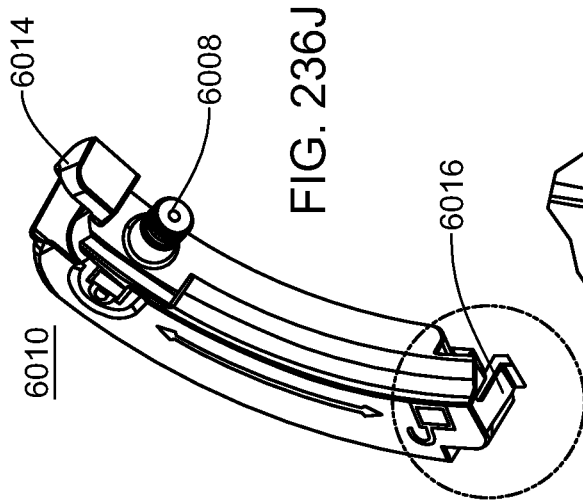
Figure 236K:
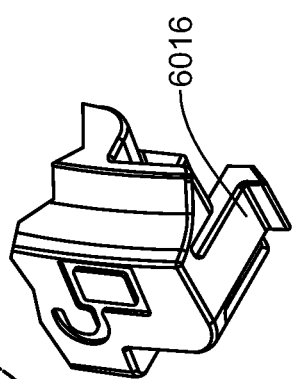
Figure 236I:
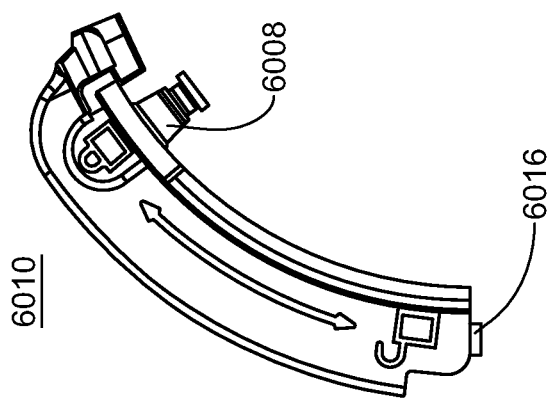
Figure 236O:
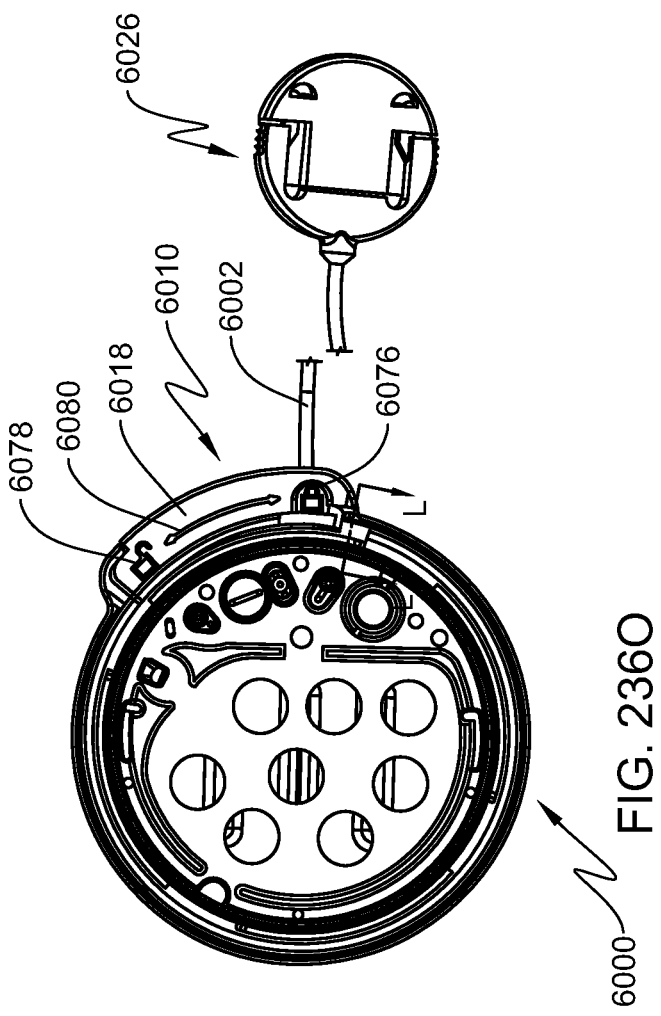
Figure 236P:
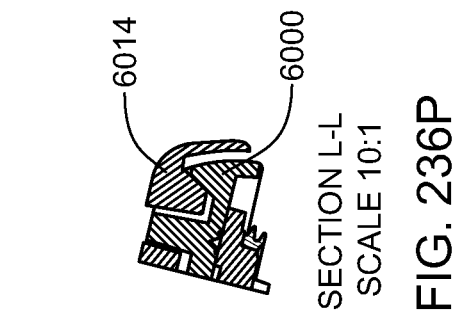
Figure 236M:
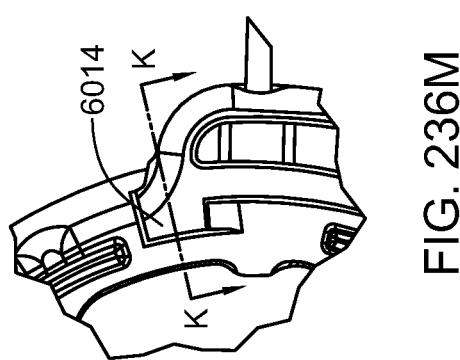
Figure 236N:
Figure 236Q:
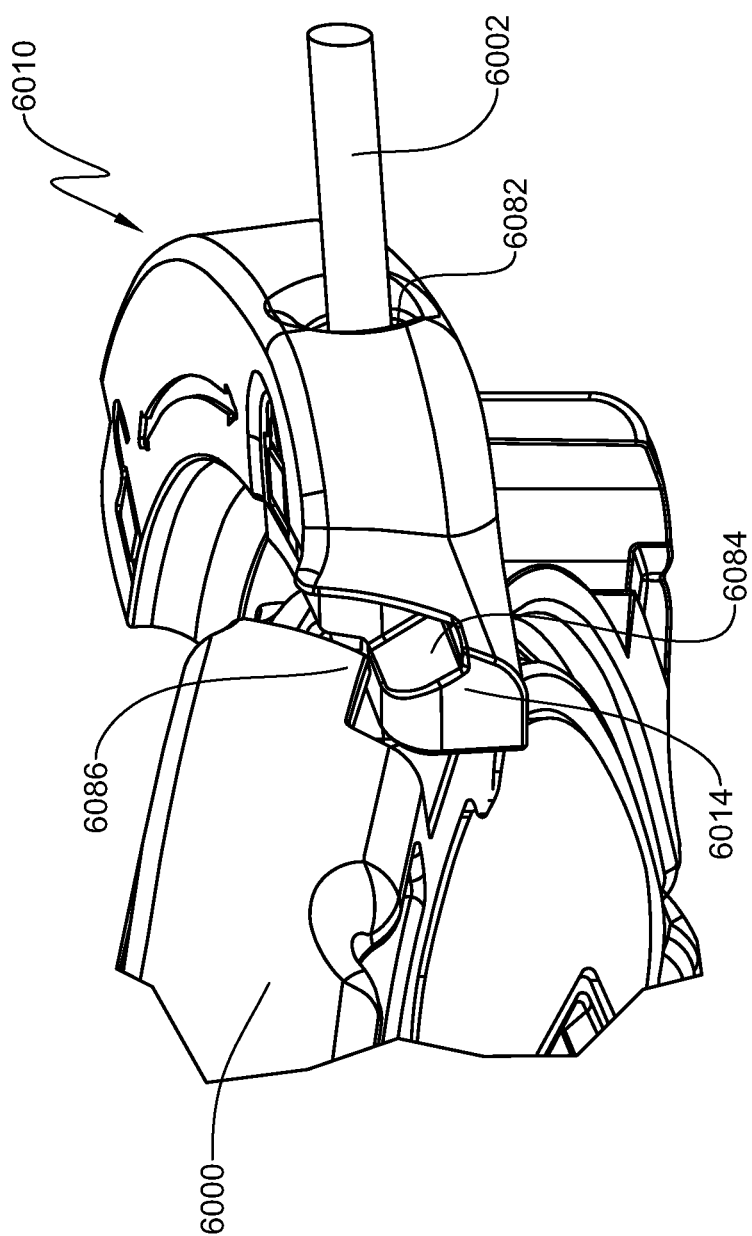
Figure 236R:
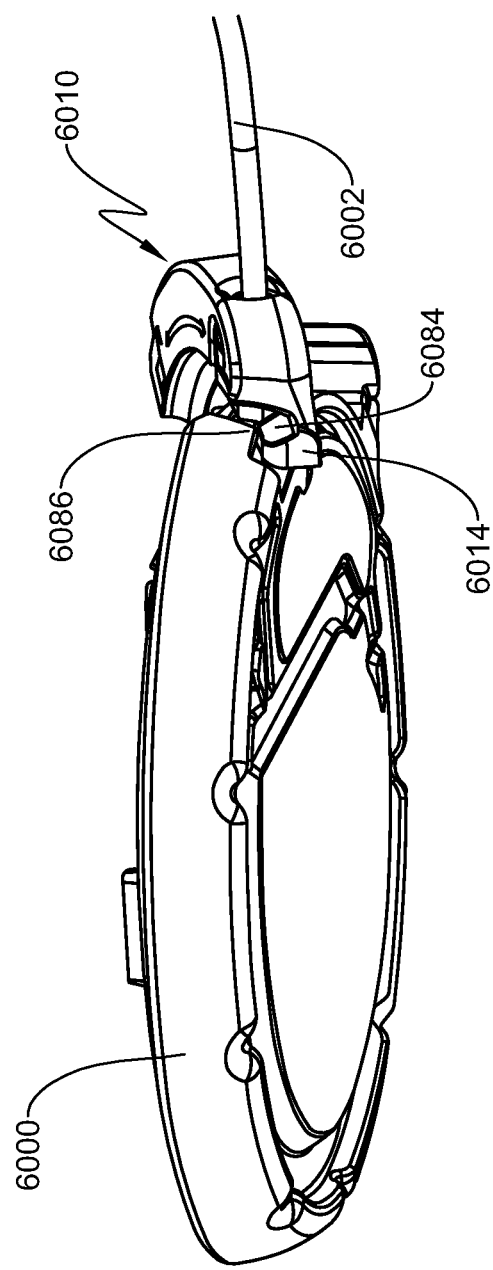
Figure 236S:
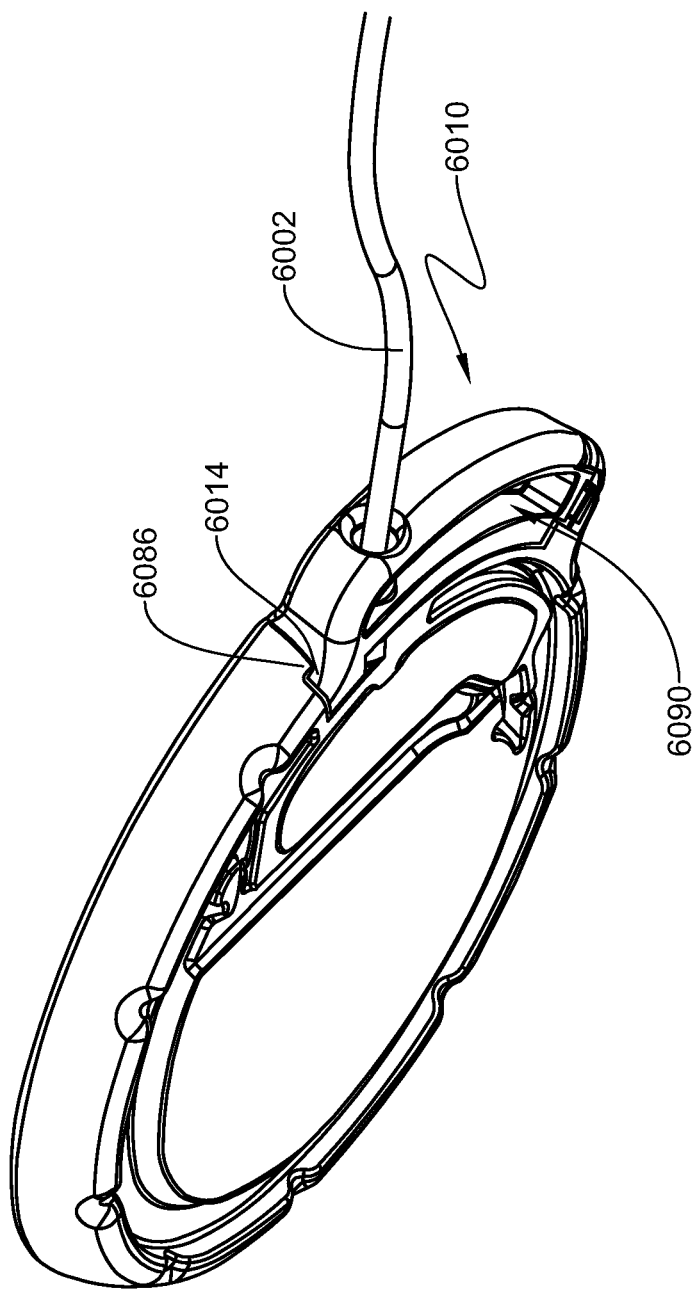
Figure 236T:
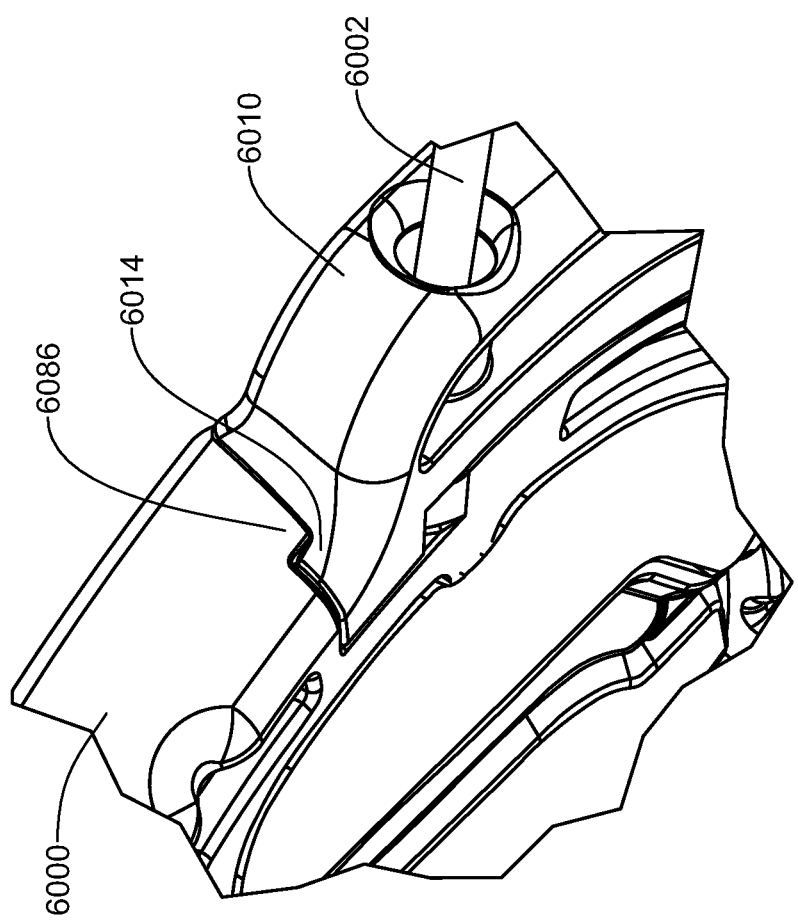
Figure 237:
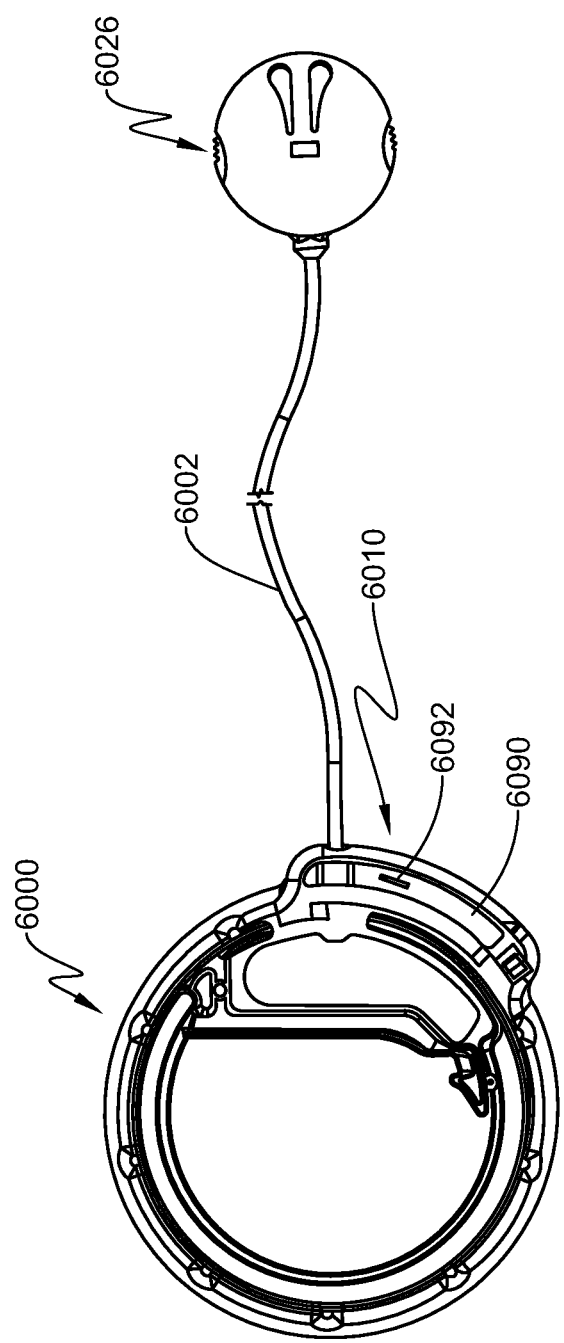
Figure 238:
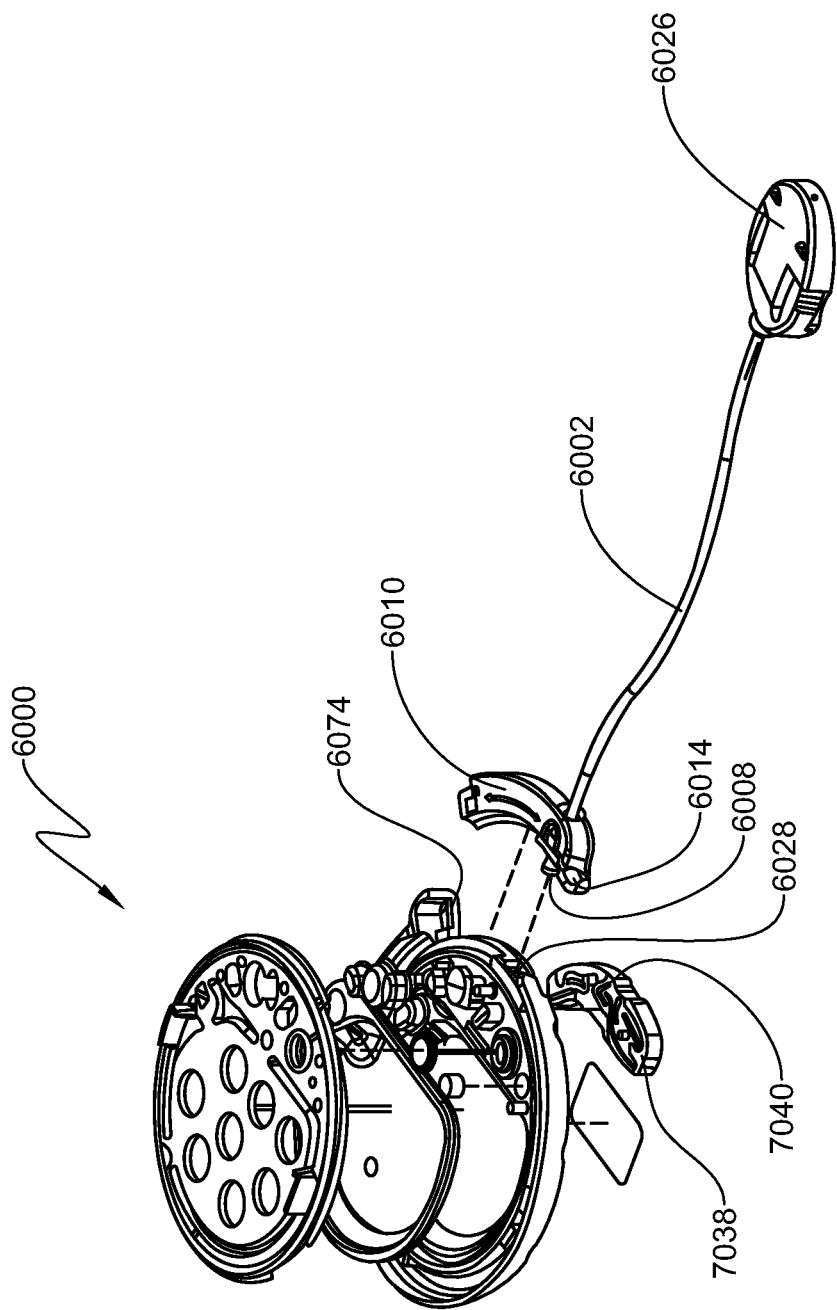
Figure 239:
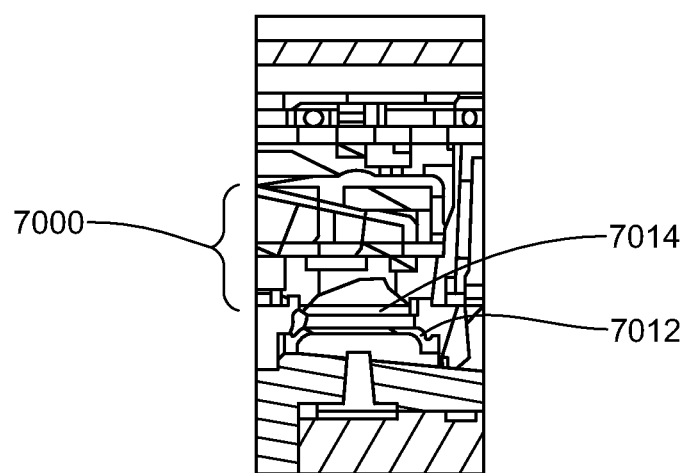
Figure 240:
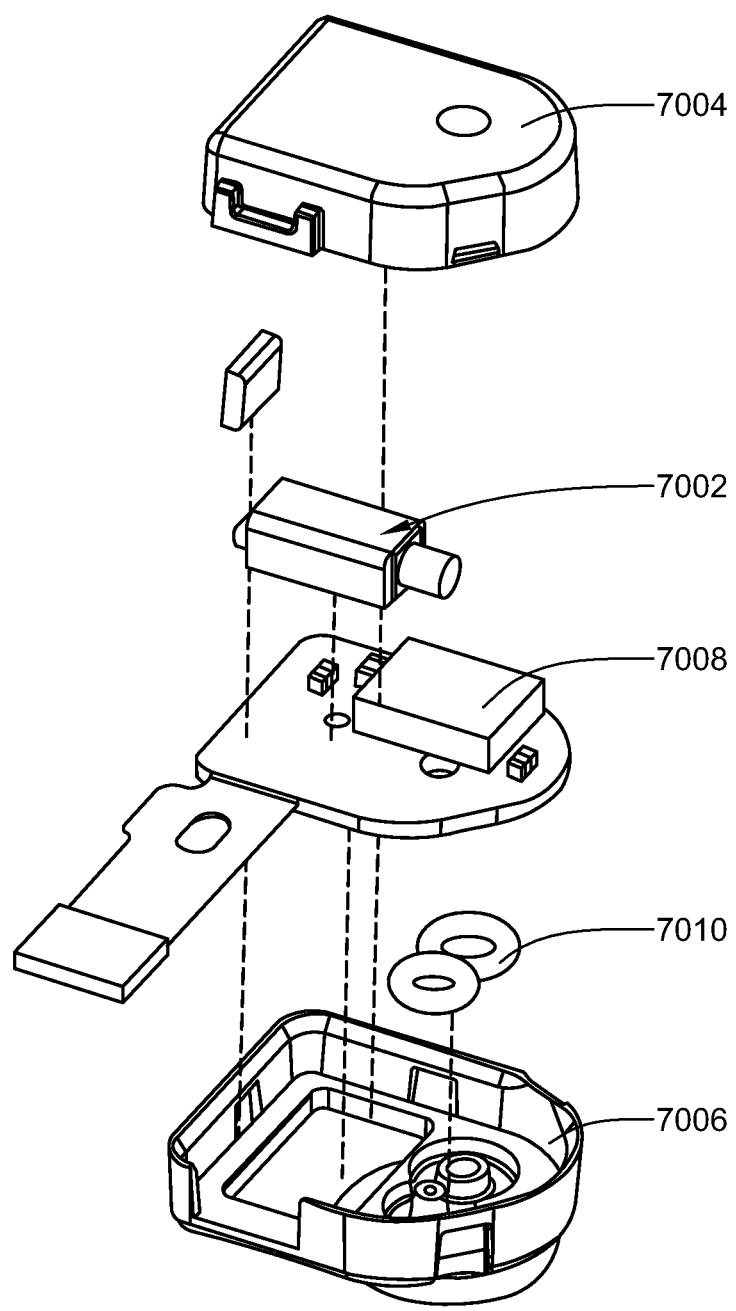
Figure 241A:
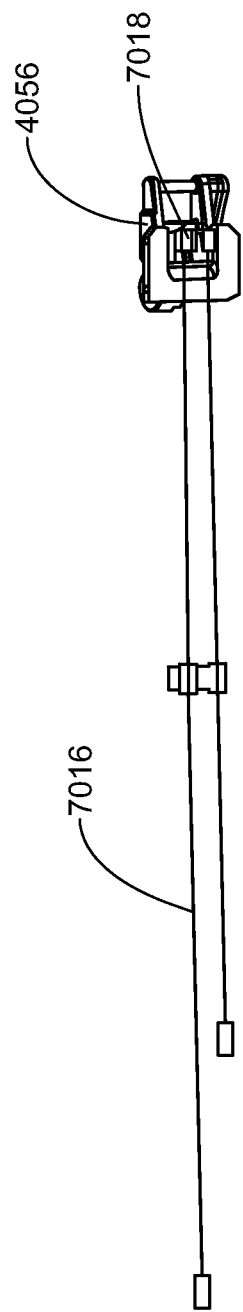
Figure 241B:
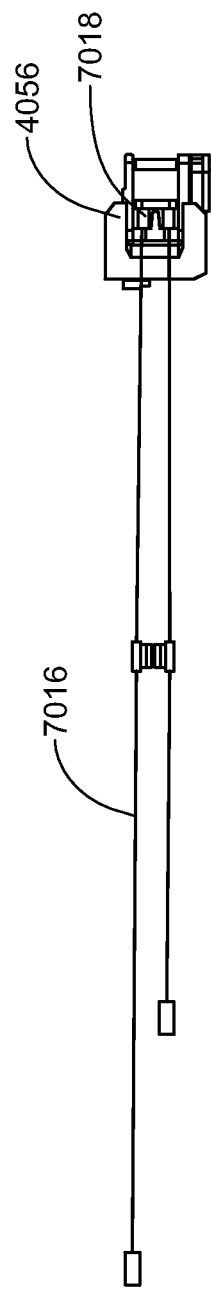
Figure 242:
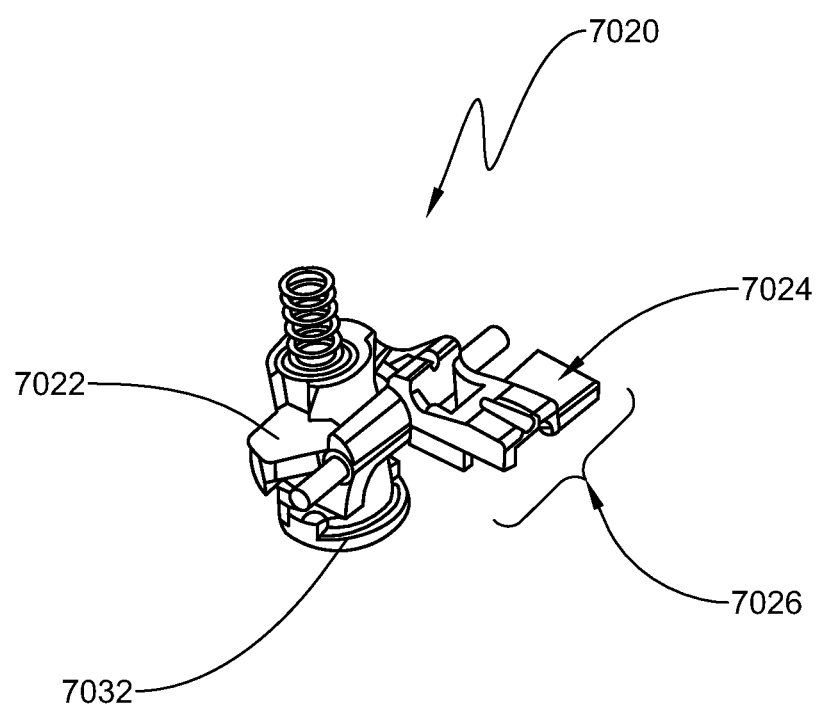
Figure 243:
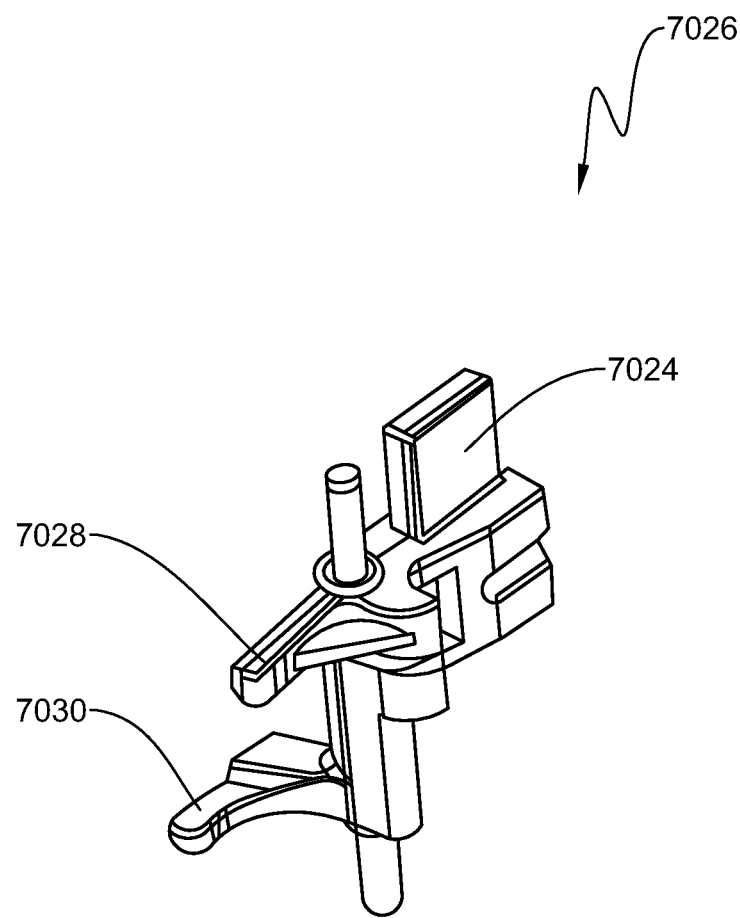
Figure 244A:
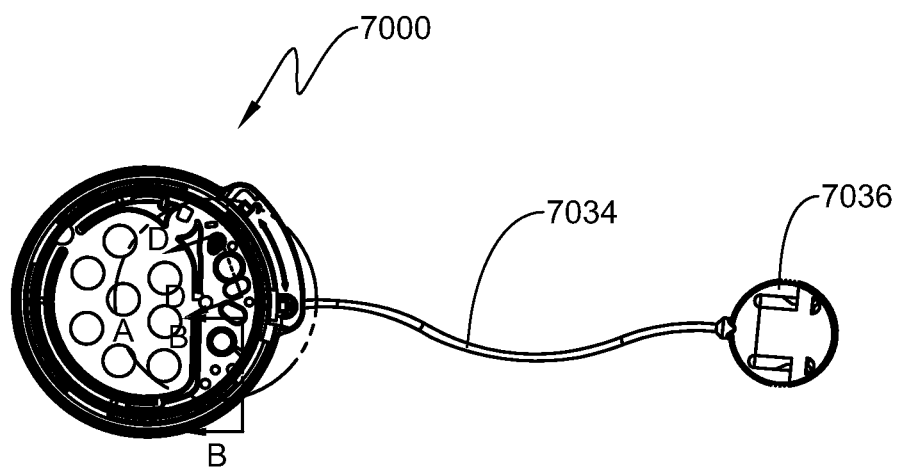
Figure 244B:
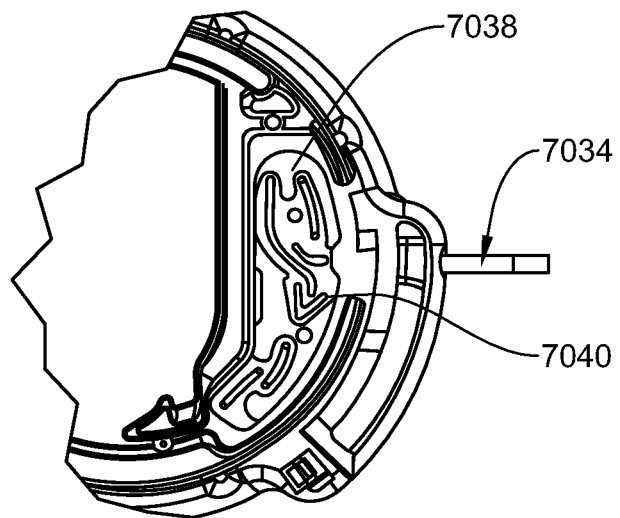
Figure 245A:
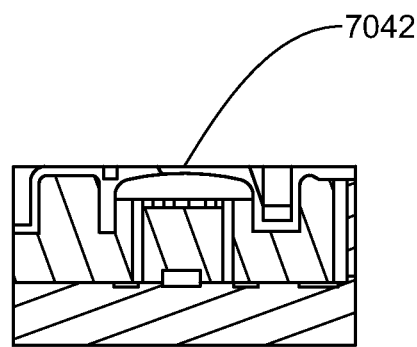
Figure 245B:
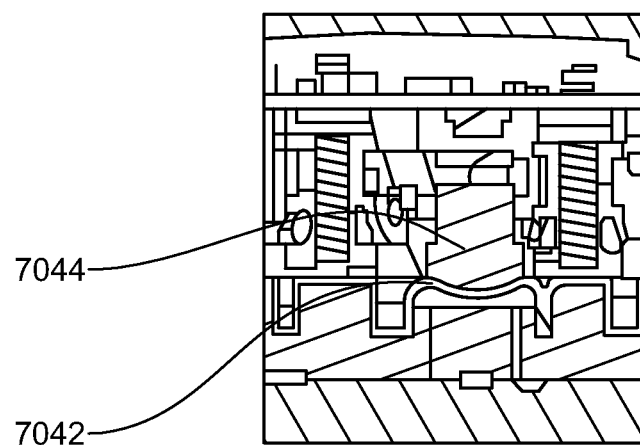
Figure 246A:
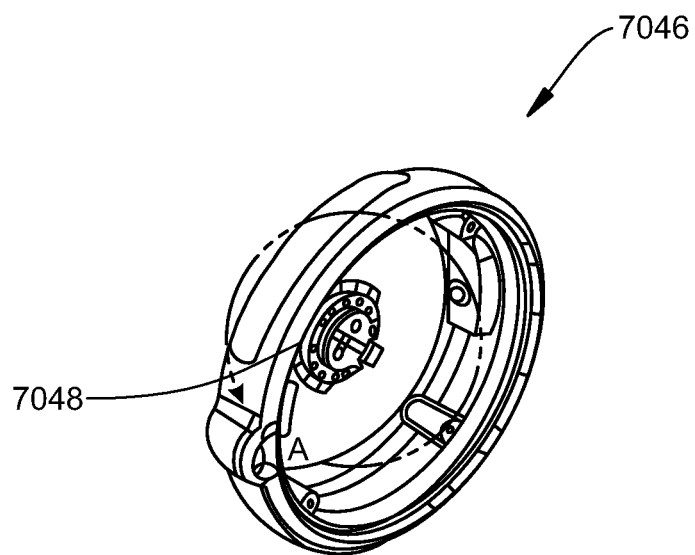
Figure 246B:
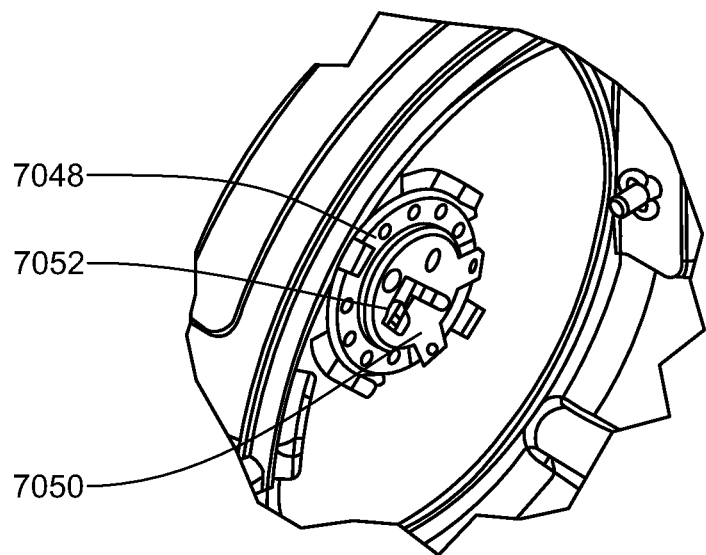

FIG. 144A is an isometric view of one embodiment of the disposable housing assembly;

FIG. 144B is a magnified cut away sectional view of section "B" as indicated in FIG. 144A;

FIG. 144C is a top view of one embodiment of the disposable housing assembly;

FIG. 144D is a magnified cut away sectional view of section "D" as indicated in FIG. 144C;

FIG. 144E is an illustrated view of a cross section of the bubble trap according to one embodiment;

FIG. 145 is a graph of delivery volume versus pump actuation time for an embodiment of the pump system;

FIG. 146 is a graph of one embodiment of the optical sensor output as a function of reflector distance;

FIG. 147 is an illustration of various locations of optical sensors in one embodiment of an infusion pump assembly;

FIG. 148A-148B is an embodiment of an optical sensor assembly where 148B is a magnified section view according to section "B" in FIG. 148A;

FIG. 149A-149B is an embodiment of an optical sensor assembly where 149B is a magnified section view according to section "B" in FIG. 149A;

FIG. 150 is a schematic of one embodiment of the pump system;

FIG. 151 is a schematic of the pump plunger drive electronics according to one embodiment;

FIG. 152 is a graph of pump plunger target position versus volume delivered according to one embodiment;

FIG. 153 is a schematic of a model of the pump plunger as a gain element with a dead band and saturation limit according to one embodiment;

FIG. 154A is a schematic of the SMA power controller according to one embodiment;

FIG. 154B is a graph of time versus pump plunger position according to one embodiment;

FIG. 154C is a graph of time versus duty cycle according to one embodiment;

FIG. 155 is a schematic representation of sampling time;

FIG. 156 is a graph of time versus pump plunger position according to one embodiment;

FIG. 157 is a graph of time versus measurement valve position according to one embodiment;

FIG. 158 is a schematic SMA switch monitoring according to one embodiment;

FIG. 159A is a graph of delivery number versus position according to one embodiment;

FIG. 159B is a graph of delivery number versus trajectory error according to one embodiment;

FIG. 160 is a flow chart of the delivery controller according to one embodiment;

FIG. 161 is a flow chart of the inner voltage and outer volume feedback controller according to one embodiment;

FIG. 162 is a flow chart of the volume controller architecture according to one embodiment;

FIG. 163 is a flow chart of one embodiment of the volume delivery controller feed-forward;

FIG. 164 is a flow chart of one embodiment of the discontinuous leak check;

FIG. 165 is a flow chart of one embodiment of at least a portion of a start-up integrity test;

FIG. 166 is a flow chart of one embodiment of at least a portion of a start-up integrity test;

FIG. 167 is a flow chart of one embodiment of at least a portion of a start-up integrity test;

FIG. 168 is a graph of the pump plunger target position versus the volume delivered according to one embodiment;

FIG. 169 is a graph of valve position versus the volume pumped according to one embodiment;

FIG. 170 is a graph of a pump plunger target position versus the volume delivered according to one embodiment;

FIG. 171 is a flow chart of the volume controller architecture according to one embodiment;

FIG. 172 is a flow chart of the inner voltage and outer volume feedback controller according to one embodiment;

FIGS. 173A-173B are views of a reservoir membrane according to one embodiment;

FIGS. 174A-174D are sections views of a reservoir membrane according to one embodiment;

FIG. 175 is a view of the actuator assembly according to one embodiment;

FIG. 176A is a view of the actuator assembly according to one embodiment;

FIG. 176B is a view of the actuator assembly according to one embodiment;

FIGS. 177A-177B are views of the actuator assembly according to one embodiment;

FIGS. 178A-178B are views of the actuator assembly according to one embodiment;

FIGS. 179A-179B are views of the actuator assembly according to one embodiment;

FIG. 180 is a view of the actuator assembly according to one embodiment;

FIGS. 181-184 show various views of various embodiments of the configuration of the measurement valve and the shape memory alloy configurations;

FIGS. 185A-185B show views of one embodiment of the disposable packaging according to one embodiment;

FIGS. 186A-186B show views of one embodiment of the disposable packaging according to one embodiment;

FIGS. 187A-187J show views of one embodiment of the disposable packaging according to one embodiment;

FIG. 188 is one embodiment of a two pump system;

FIG. 189A is an illustration of the resting state of one embodiment of a pump system;

FIG. 189B is an illustration of the fill state of one embodiment of a pump system;

FIG. 189C is an illustration of the delivery state of one embodiment of a pump system;

FIG. 190 shows one embodiments of a disposable housing assembly having a luer connector;

FIG. 191 shows one embodiment of a locking ring on a disposable housing assembly;

FIG. 192 shows one embodiment of a charger with charging pins;

FIG. 193A shows one embodiment of a pump assembly;

FIG. 193B shows an illustration of the embodiment shown in FIG. 193A;

FIG. 194 shows an illustration of one embodiment of a locking ring spring latch;

FIG. 195 shows an illustration of one embodiment of disposable detection system;

FIG. 196 is an illustrative view of one embodiment of a system to determine initial reservoir volume after fill;

FIG. 197 is an illustrative view of one embodiment of a reservoir;

FIG. 198 is an illustrative view of one embodiment of a tubing connection to the disposable housing assembly;

FIG. 199 is an illustrative view of one embodiment of a tubing connector to the disposable housing assembly;

FIGS. 200A-200B are illustrative views of one embodiment of a tubing connector to the disposable housing assembly;

FIGS. 201A-201B are illustrative views of one embodiment of a tubing connector to the disposable housing assembly;

FIG. 202 is an illustrative view of one embodiment of a tubing connector to the disposable housing assembly;

FIGS. 203A-203 B are illustrative views of one embodiment of a tubing connector to the disposable housing assembly;

FIGS. 204A-204C are illustrative views of one embodiment of a tubing connector to the disposable housing assembly;

FIG. 205 is an illustrative view of an embodiment of a tubing connection to a connector;

FIG. 206 is a view of one embodiment of a connector attached to a tubing;

FIG. 207 is a view of one embodiment of a connector attached to a tubing, which is attached to a cannula;

FIG. 208 is a view of one embodiment of a connector attached to a tubing, which is attached to a cannula, and a disposable housing assembly, according to one embodiment;

FIG. 209 is a view of one embodiment of the connector shown in FIGS. 206-208, connected to an embodiment of a disposable housing assembly;

FIG. 210 is a view of one embodiment of the connector shown in FIGS. 206-208, connected to an embodiment of a disposable housing assembly;

FIGS. 211-217 are illustrative views of various embodiments of plugs;

FIGS. 218A-218C are various views of an embodiment of a connector;

FIGS. 219A-219M are views of an embodiment of a connector in various stages of interacting with an embodiment of the disposable housing assembly such that the connector is attached to the disposable housing assembly;

FIGS. 220A-220J are views of an embodiment of the connector which is connected to a disposable housing assembly, and an embodiment of a reusable housing assembly in various stages of rotatably connecting to the disposable housing assembly;

FIG. 221 is a partial view of one embodiment of a disposable housing assembly;

FIG. 222 is a partial view of one embodiment of a disposable housing assembly including a finger cut-out;

FIG. 223A is a exploded view of the swivel connector and the stopcock style valve, according to one embodiment;

FIG. 223B is an assembled view of the swivel connector and the stopcock style valve, according to one embodiment;

FIG. 224 is a view of the latching connector attached to a disposable housing assembly according to one embodiment;

FIG. 225A is a view of one embodiment of a perimeter connector attached to a disposable housing assembly, according to one embodiment;

FIG. 225B is an illustrated exploded view of a perimeter connector and a disposable housing assembly, according to one embodiment;

FIG. 226 is an illustrated partially exploded view of a perimeter connector and a disposable housing assembly, according to one embodiment;

FIGS. 227A-227C are views of the assembly of one embodiment of a folding snap connector being attached to one embodiments of the disposable housing assembly;

FIG. 228A is an exploded view of one embodiment of a perimeter connector and one embodiment of a disposable housing assembly;

FIG. 228B is a view of one embodiments of the perimeter connector shown in FIG. 228A attaching to the disposable housing assembly shown in FIG. 228A;

FIG. 229 shows one embodiment of a connected being attached to an embodiment of a disposable housing assembly;

FIG. 230 shows one embodiment of a connected being attached to an embodiment of a disposable housing assembly;

FIG. 231A-231D are various views of an embodiment of a pinch connector, tubing set and a disposable housing assembly, according to one embodiment;

FIG. 231E is a cross sectional view of one embodiment of a pinch connector connected to an embodiment of the disposable housing assembly;

FIG. 232A-232D are various views of an embodiment of a top down connector, tubing set and a disposable housing assembly, according to one embodiment;

FIG. 232E is a cross sectional view of one embodiment of a top down connector connected to an embodiment of the disposable housing assembly;

FIG. 233A-233F are various views of an embodiment of a connector, tubing set and a disposable housing assembly, according to one embodiment;

FIG. 233G is a cross sectional view of one embodiment of a connector connected to an embodiment of the disposable housing assembly;

FIG. 234A-234F are various views of an embodiment of a connector, tubing set and a disposable housing assembly, according to one embodiment;

FIG. 234G is a cross sectional view of one embodiment of a connector connected to an embodiment of the disposable housing assembly;

FIGS. 235A-235C are views of an embodiment of a connector;

FIG. 235D is a view of an embodiment of a disposable housing assembly;

FIG. 235E is a sectional view of section "A" from FIG. 235D;

FIGS. 236A-236H are various views of an embodiment of a connector, tubing set and a disposable housing assembly, according to one embodiment;

FIGS. 236I-236K are various views of an embodiment of a connector;

FIG. 236L is a cut-away views of a connector connected to a disposable housing assembly according to one embodiment;

FIGS. 236M-236P are various views of a connector connected to a disposable housing assembly according to one embodiment;

FIGS. 236Q-236R are views of a connector partially connected to a disposable housing assembly according to one embodiment;

FIGS. 236S-236T are views of a connector connected to a disposable housing assembly according to one embodiment;

FIG. 237 is a bottom view of one embodiment of a connector connected to one embodiment of a disposable housing assembly, the connector including an RFID tag;

FIG. 238 is an exploded view of an embodiment of a disposable housing assembly and an embodiment of connector, tubing and cannula assembly;

FIG. 239 is a cross sectional view of one section of the reusable housing assembly connected with the disposable housing assembly, according to one embodiment;

FIG. 240 is an exploded view of one embodiment of the volume measurement sensor;

FIGS. 241A and 241B are views of the actuator assembly according to one embodiment;

FIGS. 242 and 243 are views of the measurement valve assembly according to one embodiment;

FIG. 244A is a top view of one embodiment of the disposable housing assembly;

FIG. 244B is a sectional view, taken from section "B" shown on FIG. 244A, of one embodiment of the disposable housing assembly;

FIG. 245A is a partial cross sectional view of the disposable housing assembly according to one embodiment;

FIG. 245B is a partial cross section view of the disposable housing assembly and reusable housing assembly engaged, according to one embodiment;

FIG. 246A is a view of the inside of the reusable housing assembly cover according to one embodiment; and FIG. 246B is a section view of section "A" of FIG. 246A.

Like reference symbols in the various drawings indicate like elements.

DETAILED DESCRIPTION

Figure 1:
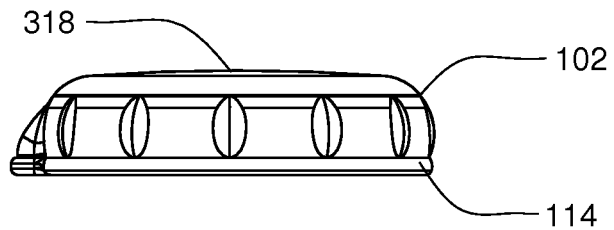
FIG. 1 is a side view of an infusion pump assembly.
Figure 2:
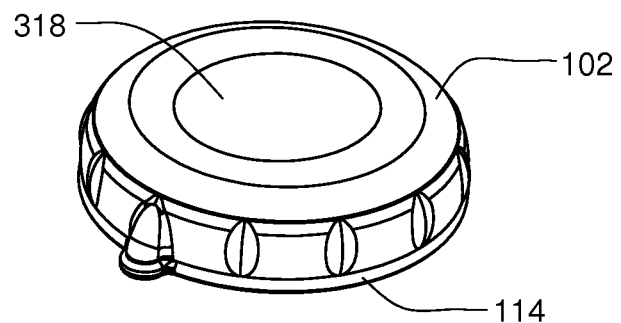
FIG. 2 is a perspective view of the infusion pump assembly of FIG. 1.
Figure 3:
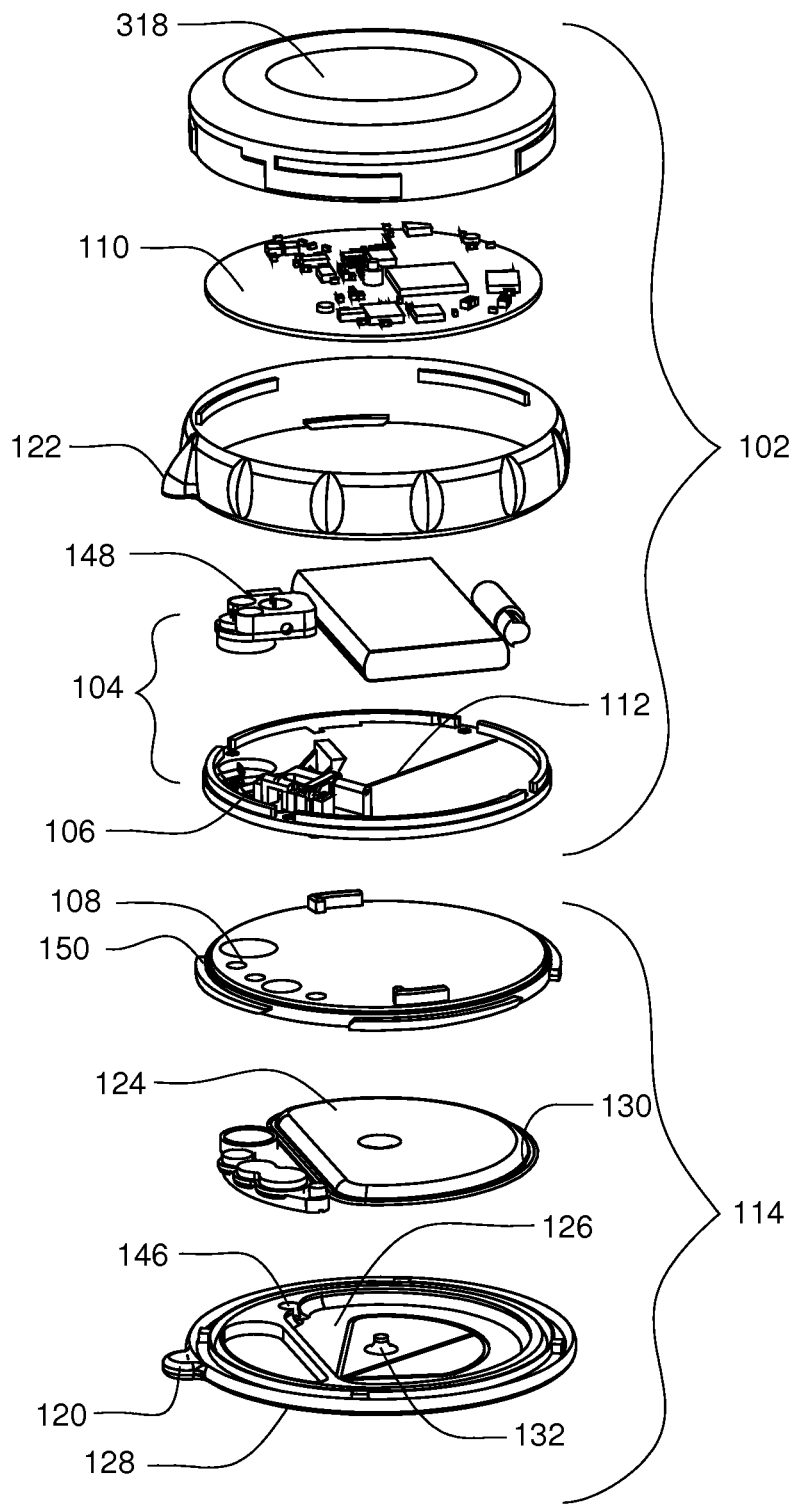
FIG. 3 is an exploded view of various components of the infusion pump assembly of FIG. 1.

Referring to FIGS. 1-3, an infusion pump assembly 100 may include a reusable housing assembly 102. Reusable housing assembly 102 may be constructed from any suitable material, such as a hard or rigid plastic, that will resist compression. For example, use of durable materials and parts may improve quality and reduce costs by providing a reusable portion that lasts longer and is more durable, providing greater protection to components disposed therein.

Reusable housing assembly 102 may include mechanical control assembly 104 having a pump assembly 106 and at least one valve assembly 108. Reusable housing assembly 102 may also include electrical control assembly 110 configured to provide one or more control signals to mechanical control assembly 104 and effectuate the basal and/or bolus delivery of an infusible fluid to a user. Disposable housing assembly 114 may include valve assembly 108 which may be configured to control the flow of the infusible fluid through a fluid path. Reusable housing assembly 102 may also include pump assembly 106 which may be configured to pump the infusible fluid from the fluid path to the user.

Electrical control assembly 110 may monitor and control the amount of infusible fluid that has been and/or is being pumped. For example, electrical control assembly 110 may receive signals from volume sensor assembly 148 and calculate the amount of infusible fluid that has just been dispensed and determine, based upon the dosage required by the user, whether enough infusible fluid has been dispensed. If enough infusible fluid has not been dispensed, electrical control assembly 110 may determine that more infusible fluid should be pumped. Electrical control assembly 110 may provide the appropriate signal to mechanical control assembly 104 so that any additional necessary dosage may be pumped or electrical control assembly 110 may provide the appropriate signal to mechanical control assembly 104 so that the additional dosage may be dispensed with the next dosage. Alternatively, if too much infusible fluid has been dispensed, electrical control assembly 110 may provide the appropriate signal to mechanical control assembly 104 so that less infusible fluid may be dispensed in the next dosage.

Mechanical control assembly 104 may include at least one shape-memory actuator 112. Pump assembly 106 and/or valve assembly 108 of mechanical control assembly 104 may be actuated by at least one shape-memory actuator, e.g., shape-memory actuator 112, which may be a shape-memory wire in wire or spring configuration. Shape memory actuator 112 may be operably connected to and activated by electrical control assembly 110, which may control the timing and the amount of heat and/or electrical energy used to actuate mechanical control assembly 104. Shape memory actuator 112 may be, for example, a conductive shape-memory alloy wire that changes shape with temperature. The temperature of shape-memory actuator 112 may be changed with a heater, or more conveniently, by application of electrical energy. Shape memory actuator 112 may be a shape memory wire constructed of nickel/titanium alloy, such as NITINOL™ or FLEXINOL®.

Infusion pump assembly 100 may include a volume sensor assembly 148 configured to monitor the amount of fluid infused by infusion pump assembly 100. For example, volume sensor assembly 148 may employ, for example, acoustic volume sensing. Acoustic volume measurement technology is the subject of U.S. Pat. Nos. 5,575,310 and 5,755,683 assigned to DEKA Products Limited Partnership, as well as U.S. patent application Publication Nos. US 2007/0228071 A1, US 2007/0219496 A1, US 2007/0219480 A1, US 2007/0219597 A1, the entire disclosures of all of which are incorporated herein by reference. Other alternative techniques for measuring fluid flow may also be used; for example, Doppler-based methods; the use of Hall-effect sensors in combination with a vane or flapper valve; the use of a strain beam (for example, related to a flexible member over a fluid reservoir to sense deflection of the flexible member); the use of capacitive sensing with plates; or thermal time of flight methods. One such alternative technique is disclosed in U.S. patent application Ser. No. 11/704,899 filed Feb. 9, 2007, now U.S. Publication No. US-2007-0228071-A1 published Oct. 4, 2007 and entitled Fluid Delivery Systems and Methods, the entire disclosure of which is incorporated herein by reference. Infusion pump assembly 100 may be configured so that the volume measurements produced by volume sensor assembly 148 may be used to control, through a feedback loop, the amount of infusible fluid that is infused into the user.

Infusion pump assembly 100 may further include a disposable housing assembly 114. For example, disposable housing assembly 114 may be configured for a single use or for use for a specified period of time, e.g., three days or any other amount of time. Disposable housing assembly 114 may be configured such that any components in infusion pump assembly 100 that come in contact with the infusible fluid are disposed on and/or within disposable housing assembly 114. For example, a fluid path or channel including a reservoir, may be positioned within disposable housing assembly 114 and may be configured for a single use or for a specified number of uses before disposal. The disposable nature of disposable housing assembly 114 may improve sanitation of infusion pump assembly 100.

Figure 4:
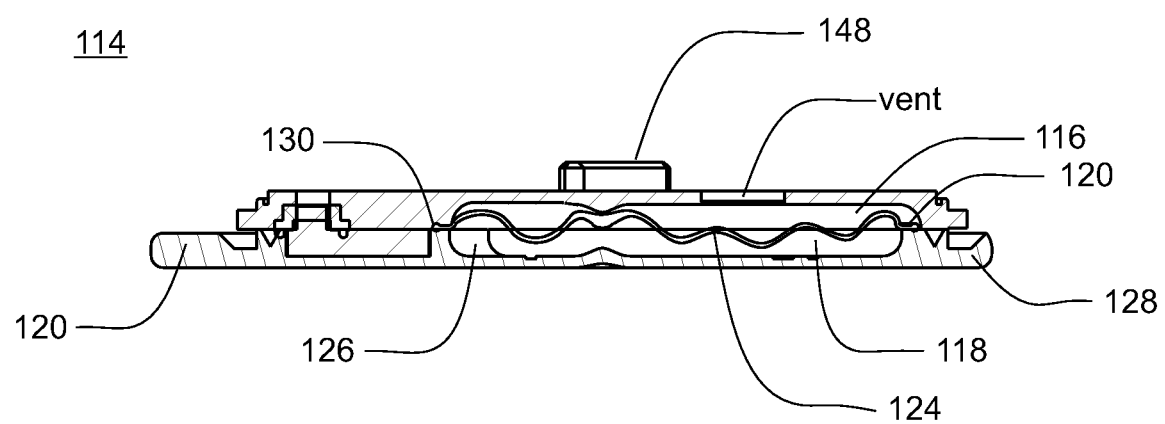
FIG. 4 is a cross-sectional view of the disposable housing assembly of the infusion pump assembly of FIG. 1.

Referring also to FIG. 4, disposable housing assembly 114 may be configured to releasably engage reusable housing assembly 102, and includes a cavity 116 that has a reservoir 118 for receiving an infusible fluid (not shown), e.g., insulin. Such releasable engagement may be accomplished by a screw-on, a twist-lock or a compression fit configuration, for example. Disposable housing assembly 114 and/or reusable housing assembly 102 may include an alignment assembly configured to assist in aligning disposable housing assembly 114 and reusable housing assembly 102 for engagement in a specific orientation. Similarly, base nub 120 and top nub 122 may be used as indicators of alignment and complete engagement.

Cavity 116 may be at least partially formed by and integral to disposable housing assembly 114. Cavity 116 may include a membrane assembly 124 for at least partially defining reservoir 118. Reservoir 118 may be further defined by disposable housing assembly 114, e.g., by a recess 126 formed in base portion 128 of disposable housing assembly 114. For example, membrane assembly 124 may be disposed over recess 126 and attached to base portion 128, thereby forming reservoir 118. Membrane assembly 124 may be attached to base portion 128 by conventional means, such as gluing, heat sealing, and/or compression fitting, such that a seal 130 is formed between membrane assembly 124 and base portion 128. Membrane assembly 124 may be flexible and the space formed between membrane assembly 124 and recess 126 in base portion 128 may define reservoir 118. Reservoir 118 may be non-pressurized and in fluid communication with a fluid path (not shown). Membrane assembly 124 may be at least partially collapsible and cavity 116 may include a vent assembly, thereby advantageously preventing the buildup of a vacuum in reservoir 118 as the infusible fluid is delivered from reservoir 118 to the fluid path. In a preferred embodiment, membrane assembly 124 is fully collapsible, thus allowing for the complete delivery of the infusible fluid. Cavity 116 may be configured to provide sufficient space to ensure there is always some air space even when reservoir 118 is filled with infusible fluid.

The membranes and reservoirs described herein may be made from materials including but not limited to silicone, NITRILE, butyl rubber, SANTOPRENE, thermal plastic elastomers (TPE), styrene ethylene butylene styrene (SEBS) and/or any other material having desired resilience and properties for functioning as described herein. Additionally, other structures could serve the same purpose.

The use of a partially collapsible non pressurized reservoir may advantageously prevent the buildup of air in the reservoir as the fluid in the reservoir is depleted. Air buildup in a vented reservoir could prevent fluid egress from the reservoir, especially if the system is tilted so that an air pocket intervenes between the fluid contained in the reservoir and the septum of the reservoir. Tilting of the system is expected during normal operation as a wearable device.

Reservoir 118 may be conveniently sized to hold an insulin supply sufficient for delivery over one or more days. For example, reservoir 118 may hold about 1.00 to 3.00 ml of insulin. A 3.00 ml insulin reservoir may correspond to approximately a three day supply for about 90% of potential users. In other embodiments, reservoir 118 may be any size or shape and may be adapted to hold any amount of insulin or other infusible fluid. In some embodiments, the size and shape of cavity 116 and reservoir 118 is related to the type of infusible fluid that cavity 116 and reservoir 118 are adapted to hold.

Disposable housing assembly 114 may include a support member 132 (FIG. 3) configured to prevent accidental compression of reservoir 118. Compression of reservoir 118 may result in an unintentional dosage of infusible fluid being forced through the fluid path to the user. In a preferred embodiment, reusable housing assembly 102 and disposable housing assembly 114 may be constructed of a rigid material that is not easily compressible. However, as an added precaution, support member 132 may be included within disposable housing assembly 114 to prevent compression of infusion pump assembly 100 and cavity 116 therein. Support member 132 may be a rigid projection from base portion 128. For example, support member 132 may be disposed within cavity 116 and may prevent compression of reservoir 118.

As discussed above, cavity 116 may be configured to provide sufficient space to ensure there is always some air space even when reservoir 118 is filled with infusible fluid. Accordingly, in the event that infusion pump assembly 100 is accidentally compressed, the infusible fluid may not be forced through cannula assembly 136 (e.g., shown in FIG. 9).

Cavity 116 may include a septum assembly 146 (FIG. 3) configured to allow reservoir 118 to be filled with the infusible fluid. Septum assembly 146 may be a conventional septum made from rubber or plastic and have a one-way fluid valve configured to allow a user to fill reservoir 118 from a syringe or other filling device. In some embodiments, septum 146 may be located on the top of membrane assembly 124. In these embodiments, cavity 116 may include a support structure (e.g., support member 132 in FIG. 3) for supporting the area about the back side of the septum so as to maintain the integrity of the septum seal when a needle is introducing infusible fluid into cavity 116. The support structure may be configured to support the septum while still allowing the introduction of the needle for introducing infusible fluid into cavity 116.

Figure 134A:
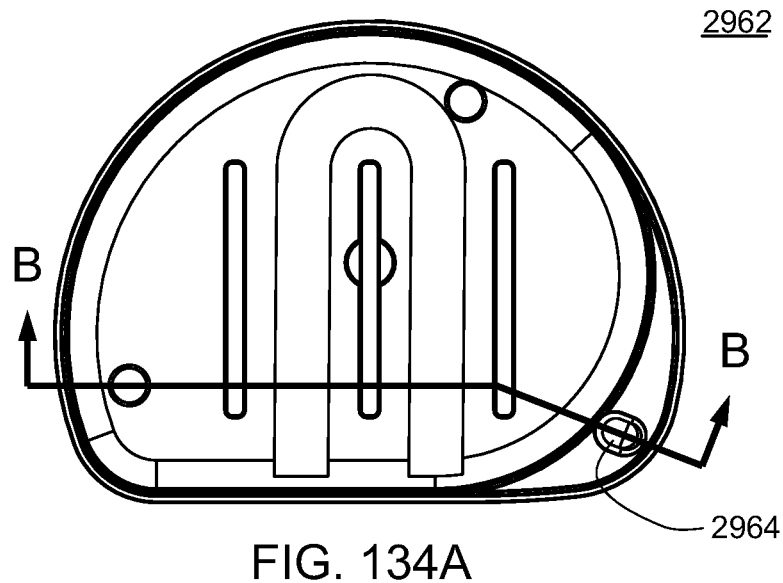
FIGS. 134A-134C shows a top, cross sectional, taken at cross section "B", and isometric view of one embodiment of a top portion of a disposable housing assembly.
Figure 134B:
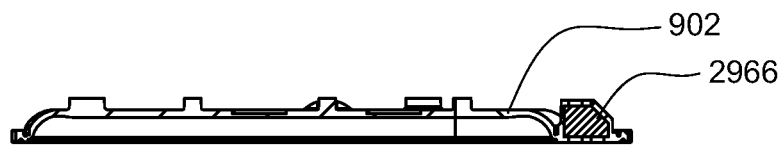
Figure 134C:
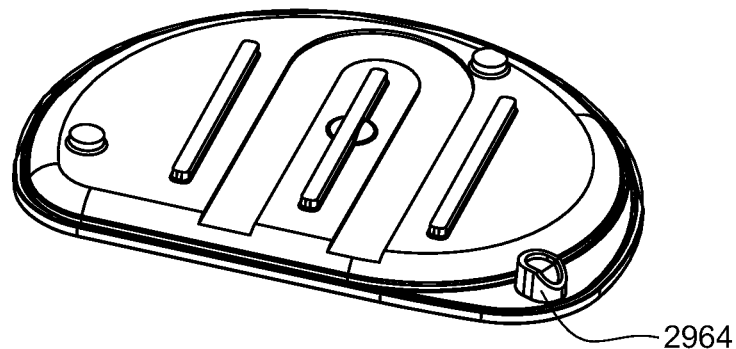

Referring also to FIGS. 134A-135B, embodiments of a top portion 2962 of the disposable housing assembly are shown. Top portion 2962 is shown in FIG. 134A, with the cross sectional view, taken at "B", shown in FIG. 134B. Septum assembly 2964 is shown. In some embodiments, the septum assembly 2964 includes a tunnel feature which may, in some embodiments, serves as a feature to press a needle (e.g., filling needle) against while not pressing full force directly onto the septum 2966. In some embodiments, as shown in FIGS. 134A-134C, the septum 2966 may be a separately molded part attached to the disposable housing assembly portion 2962, but separate from the membrane assembly 902.

Figure 135A:
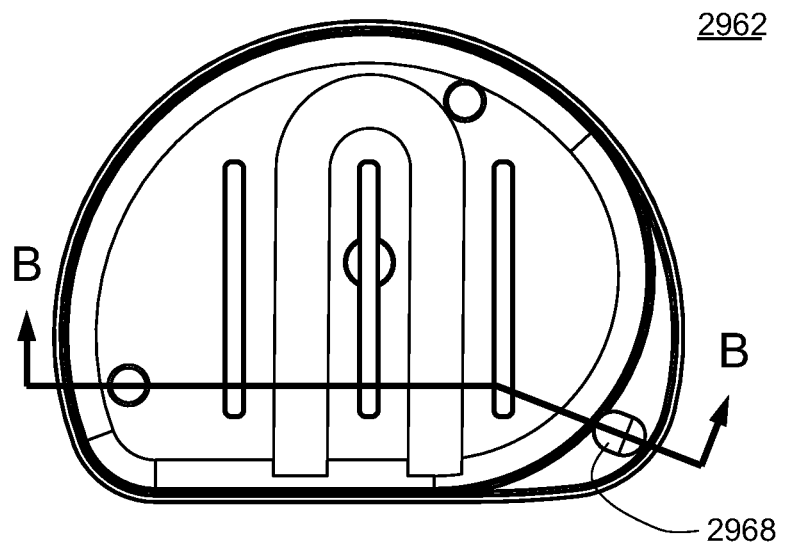
FIGS. 135A-135B shows top and cross sectional views, taken at cross section "B", of one embodiment of a top portion of a disposable housing assembly.
Figure 135B:
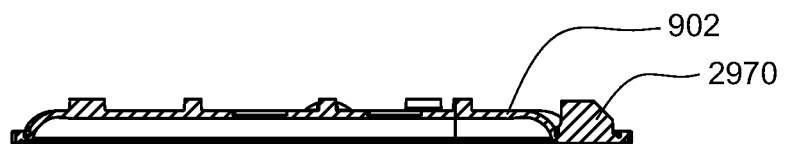

Referring now to FIGS. 135A-135B, another embodiment of a septum assembly 2968, part of a top portion 2962 of the disposable housing assembly is shown. In this embodiment, the septum 2970 may be molded into the membrane assembly 902.

In some embodiments of the various embodiments of the septum assembly 2964, 2968, the septum 2970, 2976 may be at a forty-five degree angle relative to the top portion 2962. In some embodiments, the septum 2970, 2976 may be made from the same material as the membrane assembly 902.

Infusion pump assembly 100 may include an overfill prevention assembly (not shown) that may e.g., protrude into cavity 116 and may e.g., prevent the overfilling of reservoir 118.

In some embodiments, reservoir 118 may be configured to be filled a plurality of times. For example, reservoir 118 may be refillable through septum assembly 146. As infusible fluid may be dispensed to a user, electronic control assembly 110 may monitor the fluid level of the infusible fluid in reservoir 118. When the fluid level reaches a low point, electronic control assembly 110 may provide a signal, such as a light or a vibration, to the user that reservoir 118 needs to be refilled. A syringe, or other filling device, may be used to fill reservoir 118 through septum 146.

Reservoir 118 may be configured to be filled a single time. For example, a refill prevention assembly (not shown) may be utilized to prevent the refilling of reservoir 118, such that disposable housing assembly 114 may only be used once. The refill prevention assembly (not shown) may be a mechanical device or an electro-mechanical device. For example, insertion of a syringe into septum assembly 146 for filling reservoir 118 may trigger a shutter to close over septum 146 after a single filling, thus preventing future access to septum 146. Similarly, a sensor may indicate to electronic control assembly 110 that reservoir 118 has been filled once and may trigger a shutter to close over septum 146 after a single filling, thus preventing future access to septum 146. Other means of preventing refilling may be utilized and are considered to be within the scope of this disclosure.

As discussed above, disposable housing assembly 114 may include septum assembly 146 that may be configured to allow reservoir 118 to be filled with the infusible fluid. Septum assembly 146 may be a conventional septum made from rubber or any other material that may function as a septum, or, in other embodiments, septum assembly 146 may be, but is not limited to, a plastic, or other material, one-way fluid valve. In various embodiments, including the exemplary embodiment, septum assembly 146 is configured to allow a user to fill reservoir 118 from a syringe or other filling device. Disposable housing assembly 114 may include a septum access assembly that may be configured to limit the number of times that the user may refill reservoir 118.

Figure 5A:
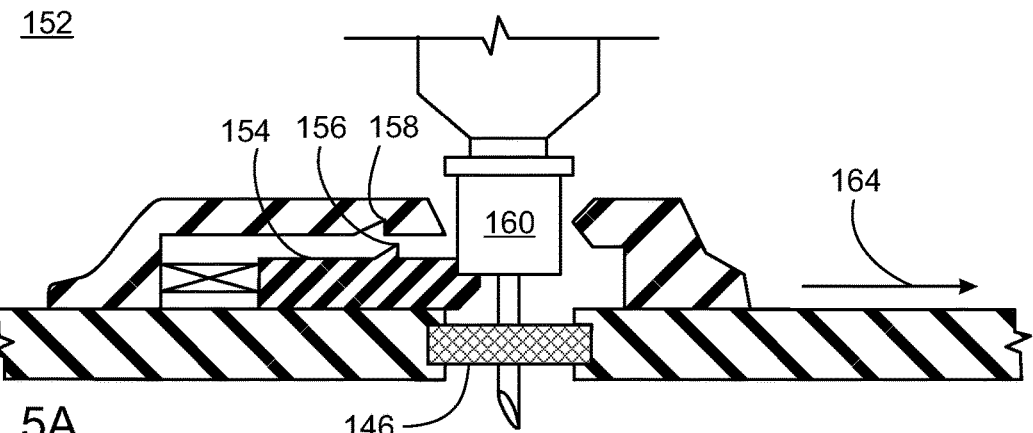
FIGS. 5A-5C are cross-sectional views of an embodiment of a septum access assembly.
Figure 5B:
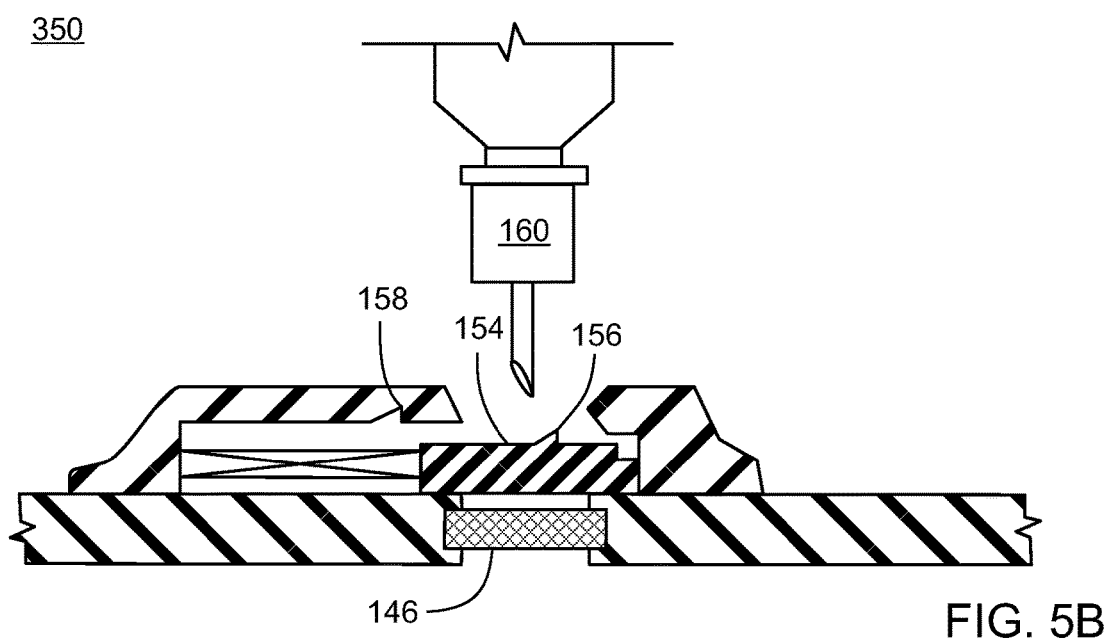
Figure 5C:
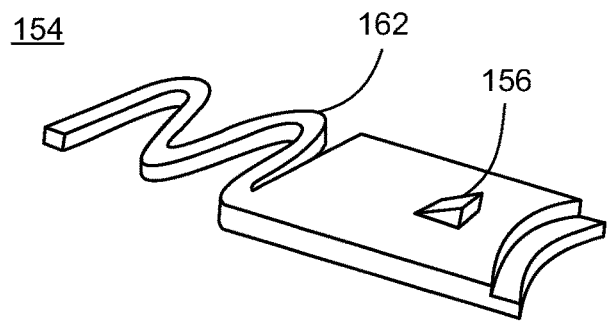

For example and referring also to FIGS. 5A-5C, septum access assembly 152 may include shutter assembly 154 that may be held in an "open" position by a tab assembly 156 that is configured to fit within a slot assembly 158. Upon penetrating septum 146 with filling syringe 160, shutter assembly 154 may be displaced downward, resulting in tab assembly 156 disengaging from slot assembly 158. Once disengaged, spring assembly 162 may displace shutter assembly 154 in the direction of arrow 164, resulting in septum 146 no longer being accessible to the user.

Figure 6A:
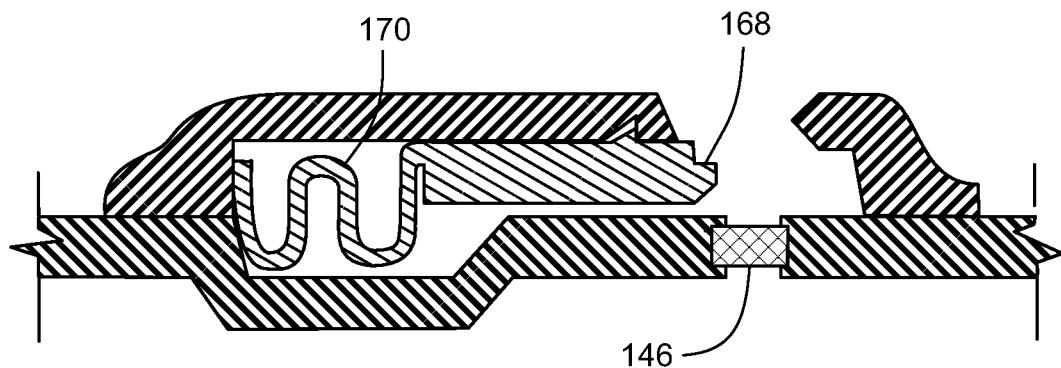
FIGS. 6A-6B are cross-sectional views of another embodiment of a septum access assembly.

Referring also to FIG. 6A, an alternative-embodiment septum access assembly 166 is shown in the "open" position. In a fashion similar to that of septum access assembly 152, septum access assembly 166 includes shutter assembly 168 and spring assembly 170.

Figure 6B:
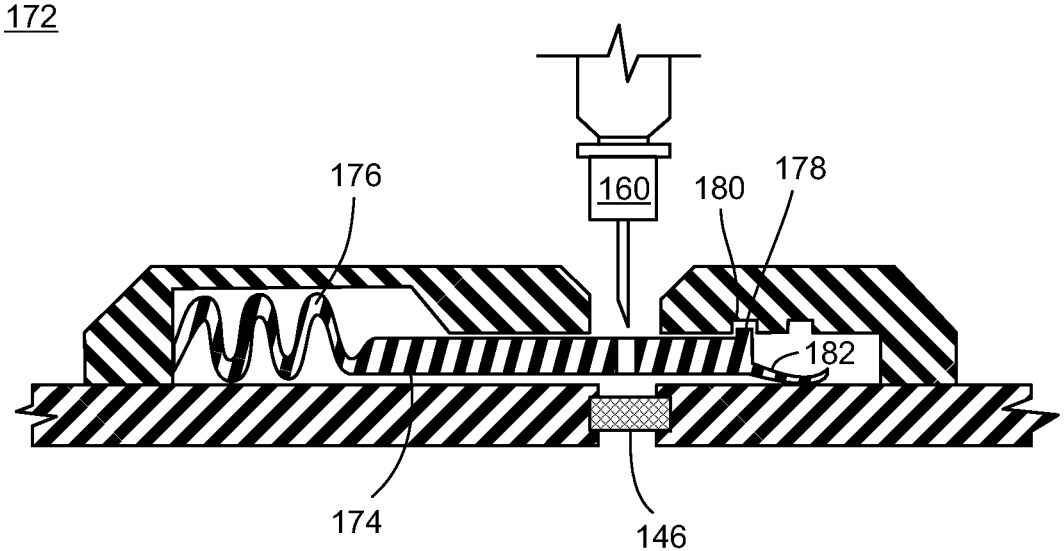

Referring also to FIG. 6B, an alternative-embodiment of septum access assembly 172 is shown in the "open" position where tab 178 may engage slot 180. In a fashion similar to that of septum access assembly 166, septum access assembly 172 may include shutter assembly 174 and spring assembly 176. Once shutter assembly 172 moves to the "closed" position (e.g., which may prevent further access of septum 146 by the user), tab 178 may at least partially engage slot 180a. Engagement between tab 178 and slot 180a may lock shutter assembly 172 in the "closed" position to inhibit tampering and reopening of shutter assembly 172. Spring tab 182 of shutter assembly 172 may bias tab 178 into engagement with slot 180a.

Figure 7A:
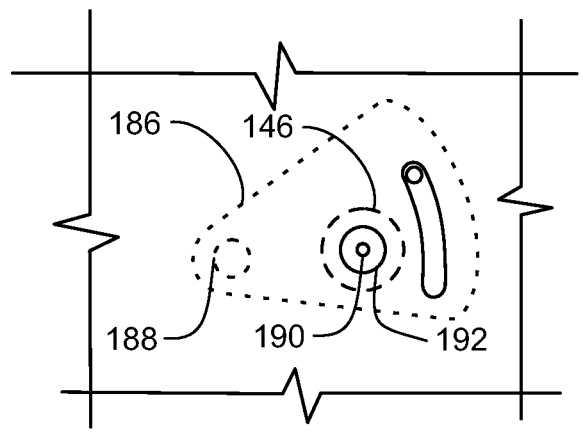
FIGS. 7A-7B are partial top views of another embodiment of a septum access assembly.
Figure 7B:
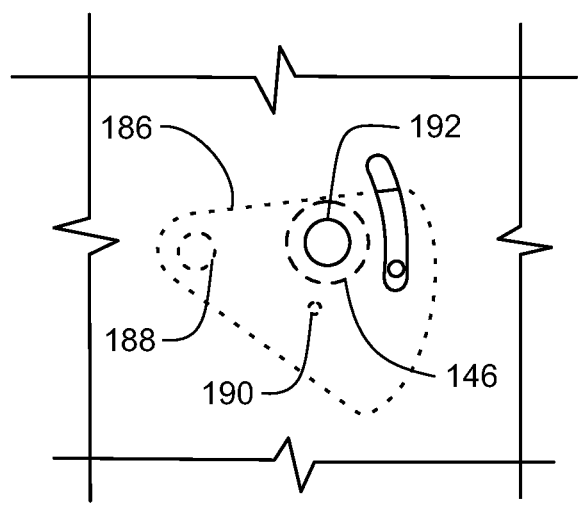

However, in various embodiments, septum access assemblies may not be actuated linearly. For example and referring also to FIGS. 7A-7B, there is shown alternative embodiment septum access assembly 184 that includes shutter assembly 186 that is configured to pivot about axis 188. When positioned in the open position (as shown in FIG. 7A), septum 146 may be accessible due to passage 190 (in shutter assembly 186) being aligned with passage 192 in e.g., a surface of disposable housing assembly 114. However, in a fashion similar to septum access assemblies 166, 172, upon penetrating septum 146 with filling syringe 160 (See FIG. 6B), shutter assembly 186 may be displaced in a clockwise fashion, resulting in passage 190 (in shutter assembly 186) no longer being aligned with passage 192 in e.g., a surface of disposable housing assembly 114, thus preventing access to septum 146.

Figure 8A:
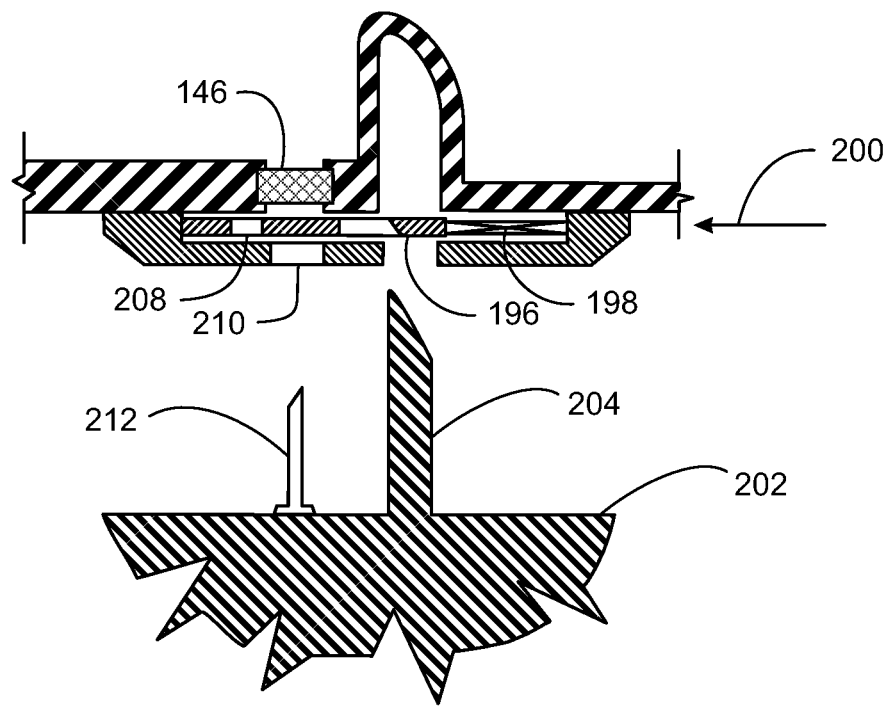
FIGS. 8A-8B are cross-sectional views of another embodiment of a septum access assembly.
Figure 8B:
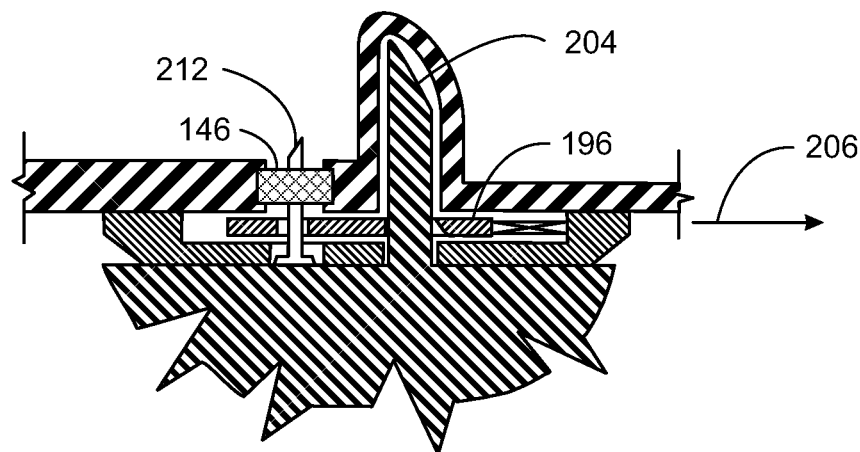

Referring also to FIGS. 8A-8B, an alternative-embodiment septum access assembly 194 is shown. In a fashion similar to that of septum access assemblies 166, 172, septum access assembly 194 includes shutter assembly 196 and spring assembly 198 that is configured to bias shutter assembly 196 in the direction of arrow 200. Filling assembly 202 may be used to fill reservoir 118. Filling assembly 202 may include shutter displacement assembly 204 that may be configured to displace shutter assembly 196 in the direction of arrow 206, which in turn aligns shutter assembly 196 with septum 146 and passage 210 in septum access assembly 194, thus allowing filling syringe assembly 212 to penetrate septum 146 and fill reservoir 118.

Infusion pump assembly 100 may include a sealing assembly 150 (FIG. 3) configured to provide a seal between reusable housing assembly 102 and disposable housing assembly 114. For example, when reusable housing assembly 102 and disposable housing assembly 114 are engaged by e.g. rotational screw-on engagement, twist-lock engagement or compression engagement, reusable housing assembly 102 and disposable housing assembly 114 may fit together snuggly, thus forming a seal. In some embodiments, it may be desirable for the seal to be more secure. Accordingly, sealing assembly 150 may include an o-ring assembly (not shown). Alternatively, sealing assembly 150 may include an over molded seal assembly (not shown). The use of an o-ring assembly or an over molded seal assembly may make the seal more secure by providing a compressible rubber or plastic layer between reusable housing assembly 102 and disposable housing assembly 114 when engaged thus preventing penetration by outside fluids. In some instances, the o-ring assembly may prevent inadvertent disengagement. For example, sealing assembly 150 may be a watertight seal assembly and, thus, enable a user to wear infusion pump assembly 100 while swimming, bathing or exercising.

Figure 9:
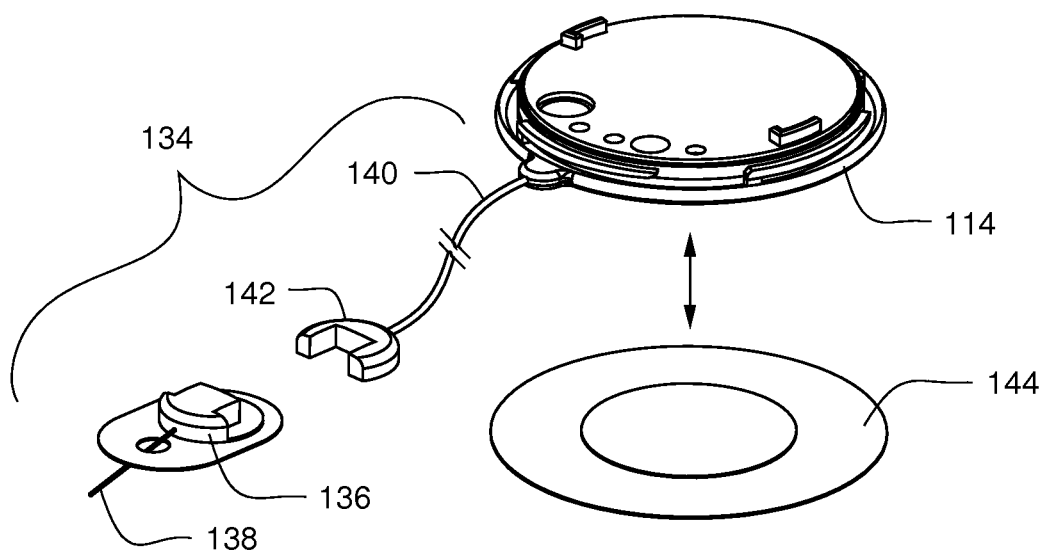
FIG. 9 is a perspective view of the infusion pump assembly of FIG. 1 showing an external infusion set.

Referring also to FIG. 9, infusion pump assembly 100 may include an external infusion set 134 configured to deliver the infusible fluid to a user. External infusion set 134 may be in fluid communication with cavity 118, e.g. by way of the fluid path. External infusion set 134 may be disposed adjacent to infusion pump assembly 100. Alternatively, external infusion set 134 may be configured for application remote from infusion pump assembly 100, as discussed in greater detail below. External infusion set 134 may include a cannula assembly 136, which may include a needle or a disposable cannula 138, and tubing assembly 140. Tubing assembly 140 may be in fluid communication with reservoir 118, for example, by way of the fluid path, and with cannula assembly 138 for example, either directly or by way of a cannula interface 142.

External infusion set 134 may be a tethered infusion set, as discussed above regarding application remote from infusion pump assembly 100. For example, external infusion set 134 may be in fluid communication with infusion pump assembly 100 through tubing assembly 140, which may be of any length desired by the user (e.g., 3-18 inches). Though infusion pump assembly 100 may be worn on the skin of a user with the use of adhesive patch 144, the length of tubing assembly 140 may enable the user to alternatively wear infusion pump assembly 100 in a pocket. This may be beneficial to users whose skin is easily irritated by application of adhesive patch 144. Similarly, wearing and/or securing infusion pump assembly 100 in a pocket may be preferable for users engaged in physical activity.

In addition to/as an alternative to adhesive patch 144, a hook and loop fastener system (e.g. such as hook and loop fastener systems offered by Velcro USA Inc. of Manchester, N.H.) may be utilized to allow for easy attachment/removal of an infusion pump assembly (e.g., infusion pump assembly 100) from the user. Accordingly, adhesive patch 144 may be attached to the skin of the user and may include an outward facing hook or loop surface. Additionally, the lower surface of disposable housing assembly 114 may include a complementary hook or loop surface. Depending upon the separation resistance of the particular type of hook and loop fastener system employed, it may be possible for the strength of the hook and loop connection to be stronger than the strength of the adhesive to skin connection. Accordingly, various hook and loop surface patterns may be utilized to regulate the strength of the hook and loop connection.

Figure 10A:
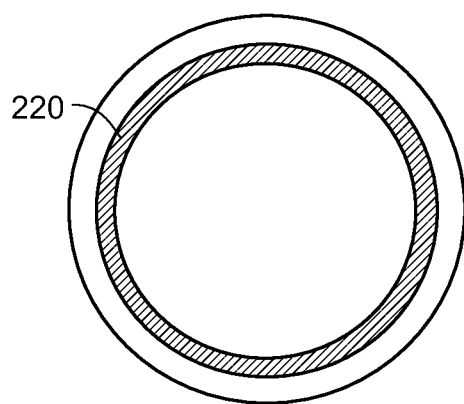
FIGS. 10A-10E depict a plurality of hook-and-loop fastener configurations.
Figure 10B:
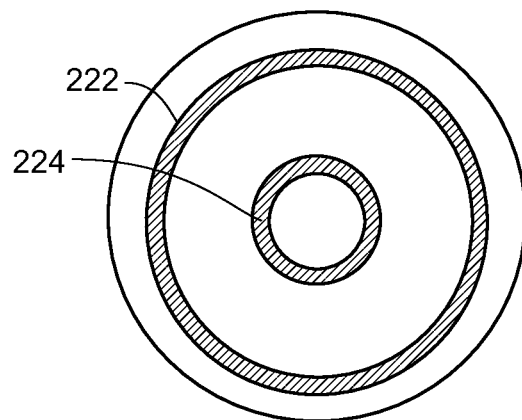
Figure 10C:
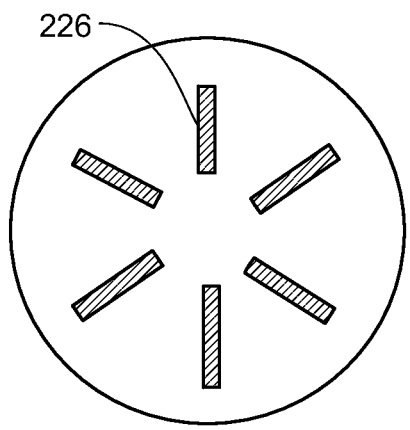
Figure 10D:
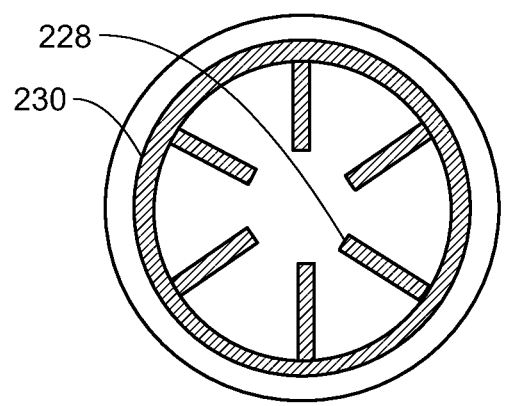
Figure 10E:
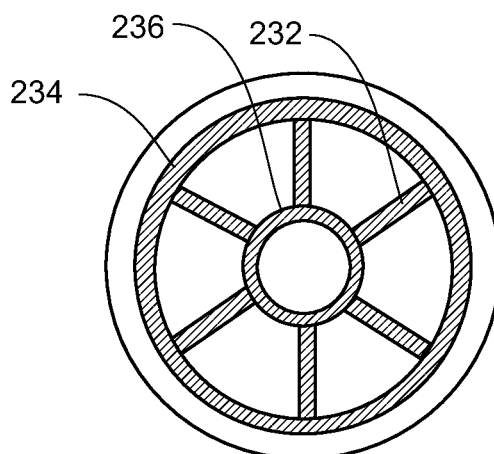

Referring also to FIGS. 10A-10E, five examples of such hook and loop surface patterns are shown. Assume for illustrative purposes that the entire lower surface of disposable housing assembly 114 is covered in a "loop" material. Accordingly, the strength of the hook and loop connection may be regulated by varying the pattern (i.e., amount) of the "hook" material present on the surface of adhesive patch 144. Examples of such patterns may include but are not limited to: a singular outer circle 220 of "hook" material (as shown in FIG. 10A); a plurality of concentric circles 222, 224 of "hook" material (as shown in FIG. 10B); a plurality of radial spokes 226 of "hook" material (as shown in FIG. 10C); a plurality of radial spokes 228 of "hook" material in combination with a single outer circle 230 of "hook" material (as shown in FIG. 10D); and a plurality of radial spokes 232 of "hook" material in combination with a plurality of concentric circles 234, 236 of "hook" material (as shown in FIG. 10E).

Figure 11A:
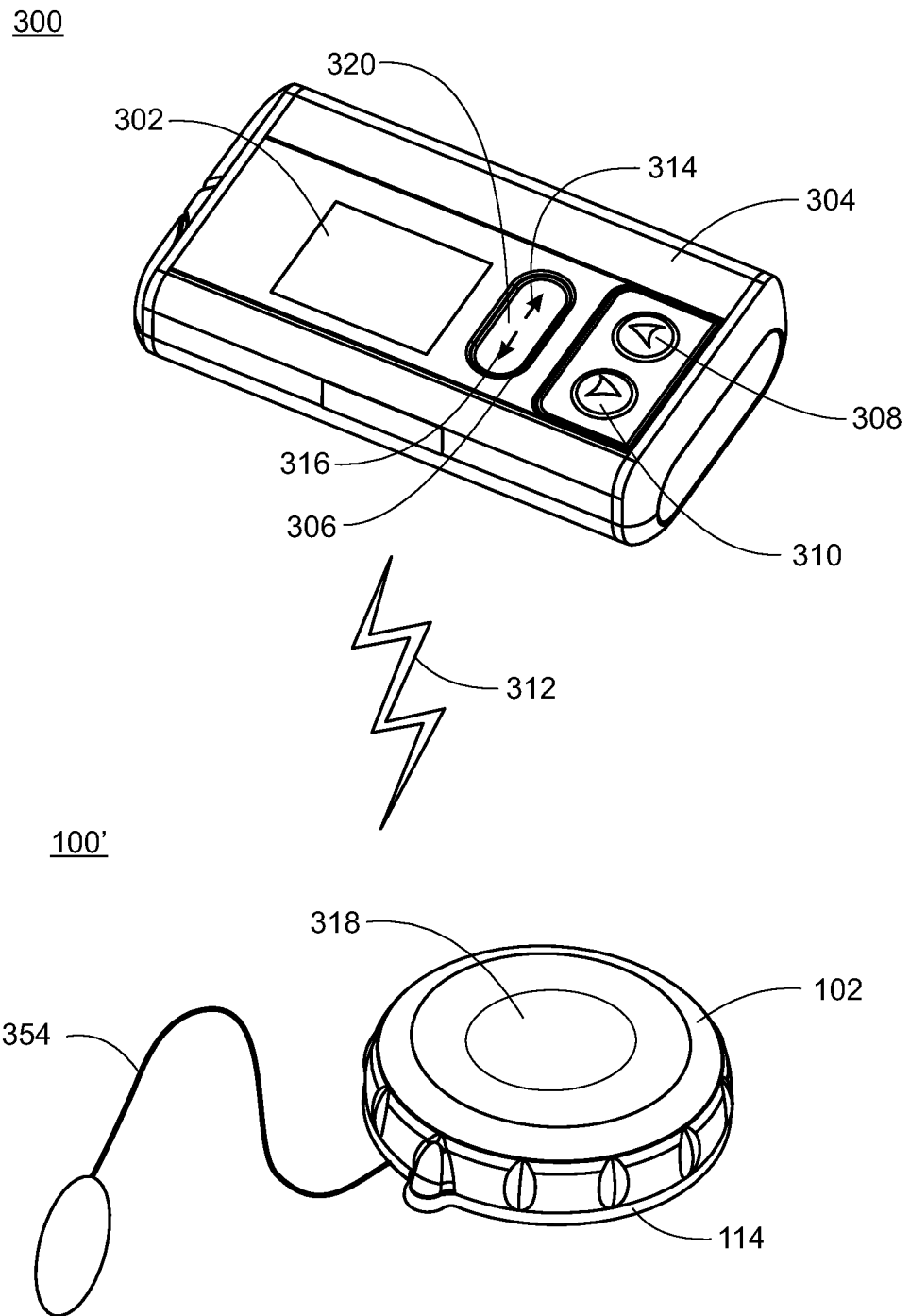
FIG. 11A is an isometric view of a remote control assembly and an alternative embodiment of the infusion pump assembly of FIG. 1.

Additionally and referring also to FIG. 11A, in one exemplary embodiment of the above-described infusion pump assembly, infusion pump assembly 100' may be configured via a remote control assembly 300. In this particular embodiment, infusion pump assembly 100' may include telemetry circuitry (not shown) that allows for communication (e.g., wired or wireless) between infusion pump assembly 100' and e.g., remote control assembly 300, thus allowing remote control assembly 300 to remotely control infusion pump assembly 100'. Remote control assembly 300 (which may also include telemetry circuitry (not shown) and may be capable of communicating with infusion pump assembly 100') may include display assembly 302 and input assembly 304. Input assembly 304 may include slider assembly 306 and switch assemblies 308, 310. In other embodiments, the input assembly may include a jog wheel, a plurality of switch assemblies, or the like.

Remote control assembly 300 may include the ability to pre-program basal rates, bolus alarms, delivery limitations, and allow the user to view history and to establish user preferences. Remote control assembly 300 may also include a glucose strip reader.

During use, remote control assembly 300 may provide instructions to infusion pump assembly 100' via wireless communication channel 312 established between remote control assembly 300 and infusion pump assembly 100'. Accordingly, the user may use remote control assembly 300 to program/configure infusion pump assembly 100'. Some or all of the communication between remote control assembly 300 and infusion pump assembly 100' may be encrypted to provide an enhanced level of security.

Figure 11B:
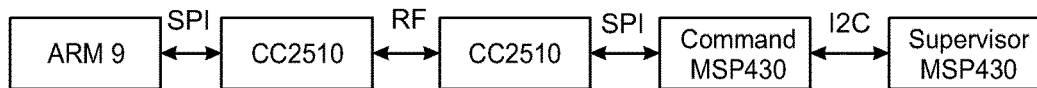
FIGS. 11B-11R depicts various views of high level schematics and flow charts of the infusion pump assembly of FIG. 1.

Communication between remote control assembly 300 and infusion pump assembly 100' may be accomplished utilizing a standardized communication protocol. Further, communication between the various components included within infusion pump assembly 100, 100' may be accomplished using the same protocol. One example of such a communication protocol is the Packet Communication Gateway Protocol (PCGP) developed by DEKA Research & Development of Manchester, N.H. As discussed above, infusion pump assembly 100, 100' may include electrical control assembly 110 that may include one or more electrical components. For example, electrical control assembly 110 may include a plurality of data processors (e.g. a supervisor processor and a command processor) and a radio processor for allowing infusion pump assembly 100, 100' to communicate with remote control assembly 300. Further, remote control assembly 300 may include one or more electrical components, examples of which may include but are not limited to a command processor and a radio processor for allowing remote control assembly 300 to communicate with infusion pump assembly 100, 100'. A high-level diagrammatic view of one example of such a system is shown in FIG. 11B.

Each of these electrical components may be manufactured from a different component provider and, therefore, may utilize native (i.e. unique) communication commands. Accordingly, through the use of a standardized communication protocol, efficient communication between such disparate components may be accomplished.

Figure 11C:
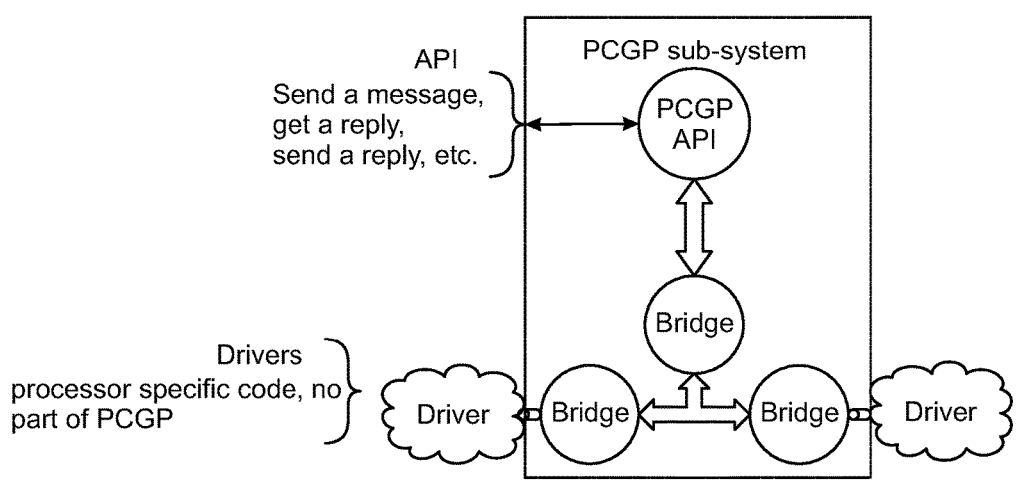

PCGP may be a flexible extendable software module that may be used on the processors within infusion pump assembly 100, 100' and remote control assembly 300 to build and route packets. PCGP may abstract the various interfaces and may provide a unified application programming interface (API) to the various applications being executed on each processor. PCGP may also provide an adaptable interface to the various drivers. For illustrative purposes only, PCGP may have the conceptual structure illustrated in FIG. 11C for any given processor.

PCGP may ensure data integrity by utilizing cyclic redundancy checks (CRCs). PCGP may also provide guaranteed delivery status. For example, all new messages should have a reply. If such a reply isn't sent back in time, the message may time out and PCGP may generate a negative acknowledge reply message for the application (i.e., a NACK). Accordingly, the message-reply protocol may let the application know whether the application should retry sending a message.

PCGP may also limit the number of messages in-flight from a given node, and may be coupled with a flow-control mechanism at the driver level to provide a deterministic approach to message delivery and may let individual nodes have different quantities of buffers without dropping packets. As a node runs out of buffers, drivers may provide back pressure to other nodes and prevent sending of new messages.

PCGP may use a shared buffer pool strategy to minimize data copies, and may avoid mutual exclusions, which may have a small affect on the API used to send/receive messages to the application, and a larger affect on the drivers. PCGP may use a "Bridge" base class that provides routing and buffer ownership. The main PCGP class may be sub-classed from the bridge base class. Drivers may either be derived from a bridge class, or talk to or own a derived bridge class.

Figure 11D:
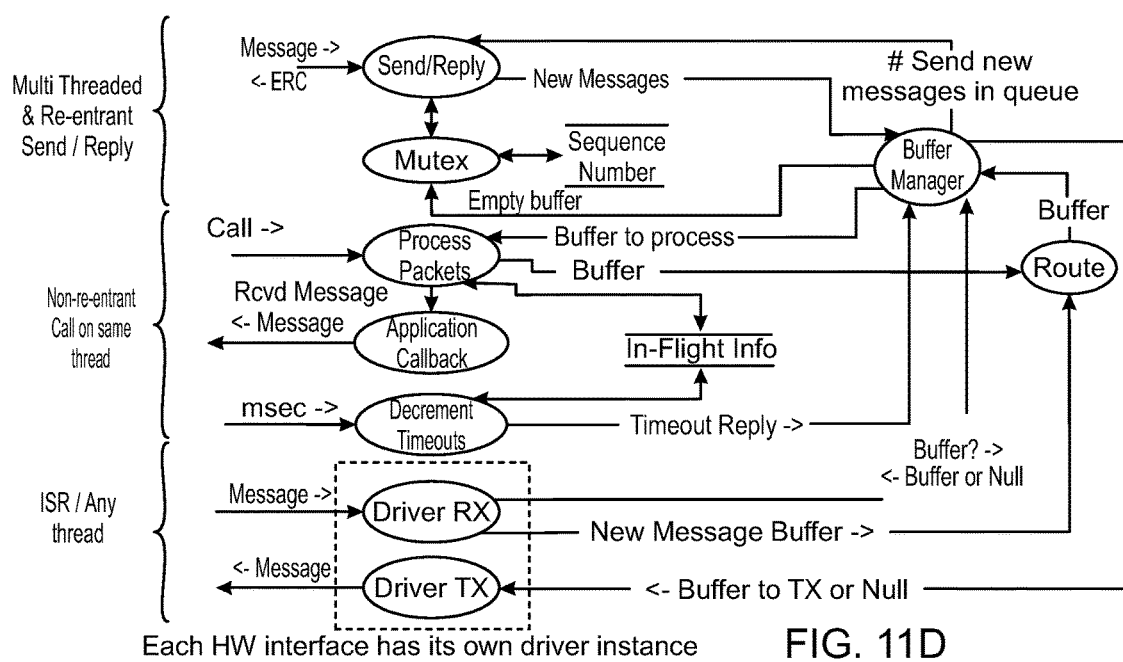

PCGP may be designed to work in an embedded environment with or without an operating system by using a semaphore to protect shared data such that some calls can be re-entrant and run on a multiple threads. One illustrative example of such an implementation is shown in FIG. 11D. PCGP may operate the same way in both environments, but there may be versions of the call for specific processor types (e.g., the ARM 9/OS version). So while the functionality may be the same, there may be an operating system abstraction layer with slightly different calls tailored for e.g., the ARM 9 Nucleus OS environment.

Figure 11E:
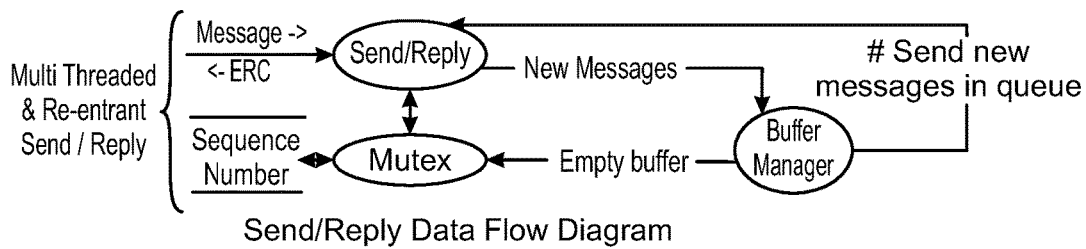

Referring also to FIG. 11E, PCGP may:
allow multiple Send/Reply calls to occur (on Pilot's ARM 9 on multiple tasks re-entrant);
have multiple drivers running asynchronously for RX and TX on different interfaces; and
provide packet ordering for send/receive, and deterministic timeout on message send.

Each software object may ask the buffer manager for the next buffer to use, and may then give that buffer to another object. Buffers may pass from one exclusive owner to another autonomicly, and queues may occur automatically by ordering buffers by sequence number. When a buffer is no longer in use, the buffer may be recycled (e.g., object attempts to give the buffer to itself, or frees it for the buffer manager to re-allocate later). Accordingly, data generally doesn't need to be copied, and routing simply writes over the buffer ownership byte.

Such an implementation of PCGP may provide various benefits, examples of which may include but are not limited to:
dropping a message due to lack of buffers may be impossible, as once a message is put into a buffer, the message may live there until it is transferred or received by the application;
data may not need to be copied, as offsets are used to access driver, PCGP and payload sections of a buffer;
drivers may exchange ownership of message data by writing over one byte (i.e., the buffer ownership byte);
there may be no need for multiple exclusions except for re-entrant calls, as a mutual exclusion may be needed only when a single buffer owner could simultaneously want to use a buffer or get a new sequence number;
there may be fewer rules for application writers to follow to implement a reliable system;
drivers may use ISR/push/pull and polled data models, as there are a set of calls provided to push/pull data out of the buffer management system from the drivers;
drivers may not do much work beyond TX and RX, as drivers may not copy, CRC or check anything but the destination byte and CRC and other checks may be done off of the ISR hot path later;
as the buffer manager may order access by sequence number, queue ordering may automatically occur; and
a small code/variable foot print may be utilized; hot path code may be small and overhead may be low.

Figure 11F:
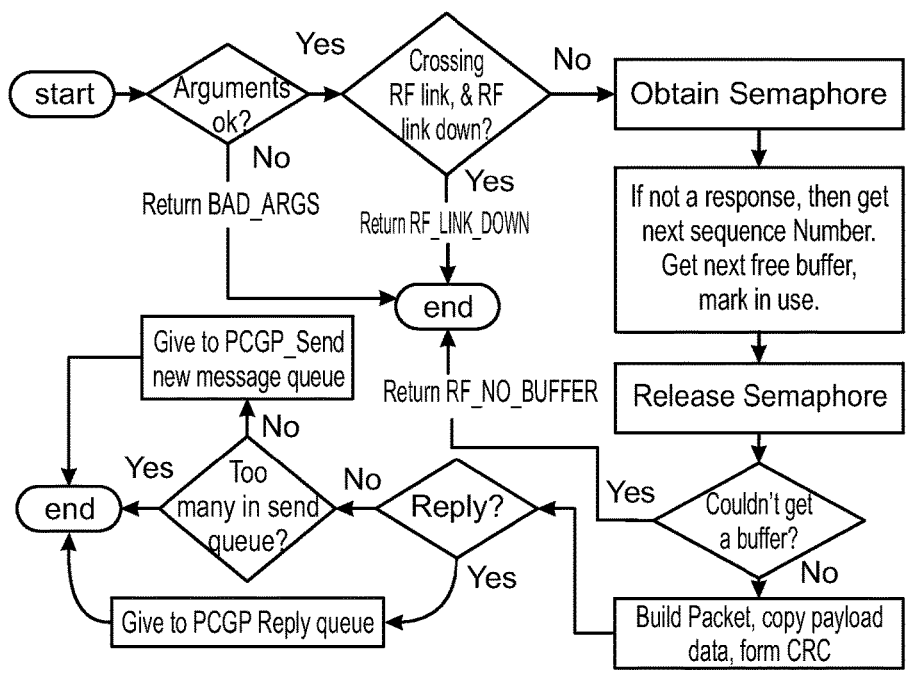

As shown in FIG. 11F, when a message needs to be sent, the PCGP may build the packet quickly and may insert it into the buffer management system. Once in the buffer management system, a call to "packetProcessor" may apply protocol rules and may give the messages to the drivers/application.
To send a new message or send a reply, PCGP may:
check the call arguments to e.g., make sure the packet length is legal, destination is ok, etc.;
avoid trying to send a message across a link that is down unless the down link is the radio node, which may allow PCGP to be used by the radio processors to establish a link, pair, etc. and may notify the application when PCGP is trying to talk across a link that is not functional (instead of timing out);
obtain a sequence number for a new message or utilize an existing sequence number for an existing message;
build the packet, copy the payload data and write in the CRC, wherein (from this point forward) the packet integrity may be protected by the CRC; and
either give the message to the buffer manager as a reply or as a new message, and check to see if putting this buffer into the buffer manager would exceed the maximum number of en-queued send messages.

Figure 11G:
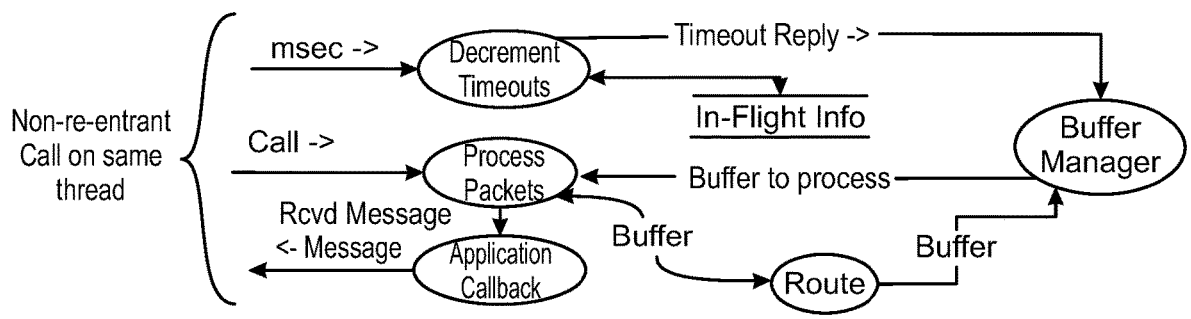
Figure 11H:
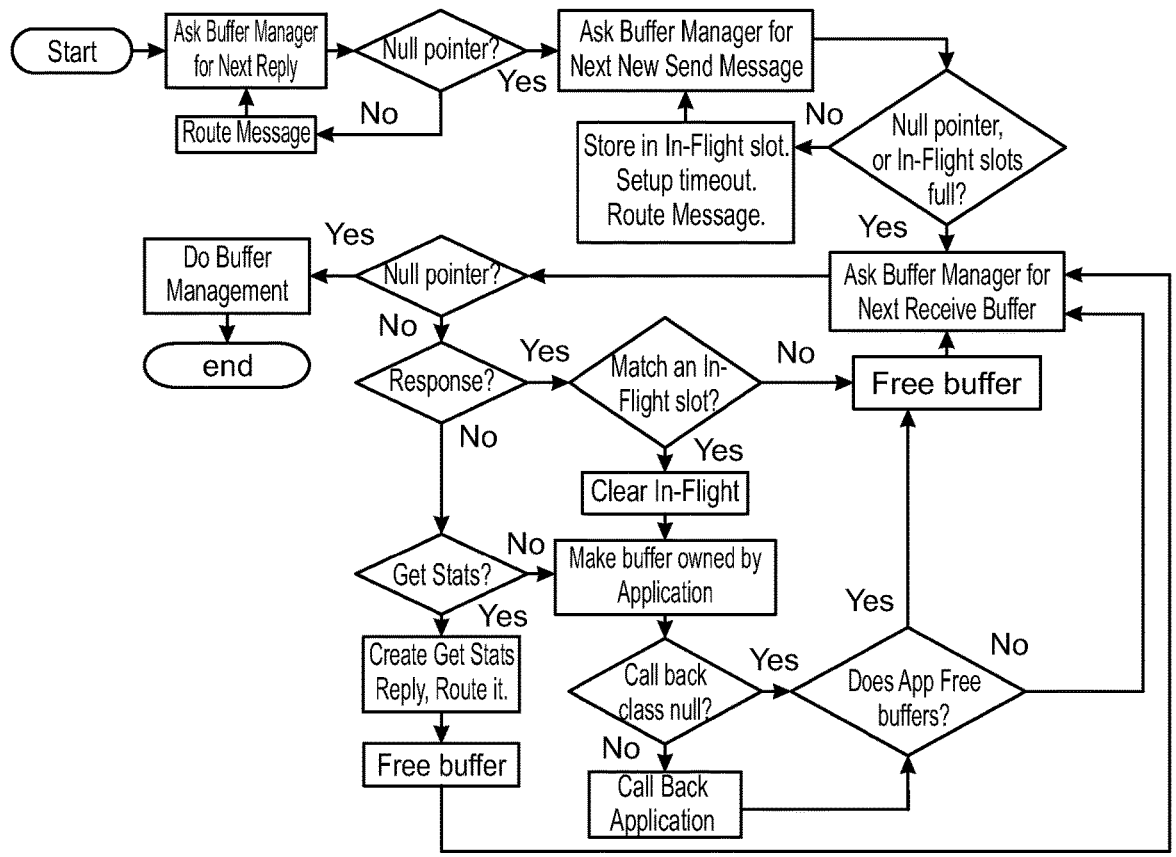

Referring also to FIGS. 11G-11H, PCGP may work by doing all of the main work on one thread to avoid mutual exclusions, and to avoid doing considerable work on the send/reply or driver calls. The "packetProcessor" call may have to apply protocol rules to replies, new sent messages, and received messages. Reply messages may simply get routed, but new messages and received messages may have rules for routing the messages. In each case, the software may loop while a message of the right type is available to apply protocol rules until it cannot process the packets.

Sending a new message may conform to the following rules:
only two messages may be allowed "in-flight" on the network; and
enough data about an in-flight message may be stored to match the response and handle timeout.

Receiving a message may conform to the following rules:
responses that match may clear out the "in-flight" information slot so a new packet can be sent;
responses that do not match may be dropped;
new messages may be for the protocol (e.g., getting/clearing network statistics for this node);
to receive a message, the buffer may be given up to the application and may use a call back; and
the buffer may be freed or left owned by the application.

Accordingly, PCGP may be configured such that:
the call back function may copy the payload data out or may use it completely before returning;
the call back function owns the buffer and may reference the buffer and the buffer's payload by the payload address, wherein the message may be processed later;
applications may poll the PCGP system for received messages; and
applications may use the call back to set an event and then poll for received messages.

The communication system may have a limited number of buffers. When PCGP runs out of buffers, drivers may stop receiving new packets and the application may be told that the application cannot send new packets. To avoid this and maintain optimal performance, the application may try to perform one or more procedures, examples of which may include but are not limited to:
a) The application should keep PCGP up to date with radio status: Specifically, if the link goes down and PCGP doesn't know, PCGP may accept and queue new messages to send (or not timeout messages optimally), which may jam the send queue and delay the application from using the link optimally.
b) The application should call "decrement timeouts" regularly: Optimally, every 20-100 milliseconds unless the processor is asleep. In general, a message moves fast (milliseconds) slow (seconds) or not at all. Timeouts are an attempt to remove "in-flight" messages that should be dropped to free up buffers and bandwidth. Doing this less often may delay when a new message gets sent, or when the application can queue a new message.
c) The application should ask PCGP if it has work to do that is pending before going to sleep: If PCGP has nothing to do, driver activity may wake up the system and thus PCGP, and then PCGP won't need a call to "packetProcessor" or "decrement timeouts" until new packets enter the system. Failure to do this may cause messages that could have been sent/forwarded/received successfully to be dropped due to a timeout condition.

d) The application should not hold onto received messages indefinitely: The message system relies on prompt replies. If the application is sharing PCGP buffers, then holding onto a message means holding onto a PCGP buffer. The receiving node doesn't know if the sending node has timeout configured for slow or fast radio. This means when a node receives a message it should assume the network's fast timeout speed.

e) The application should call the "packetProcessor" often: The call may cause new messages queued by the application to get sent and may handle receipt of new messages. The call may also cause buffers to re-allocate and calling it infrequently may delay message traffic.

Figure 11I:
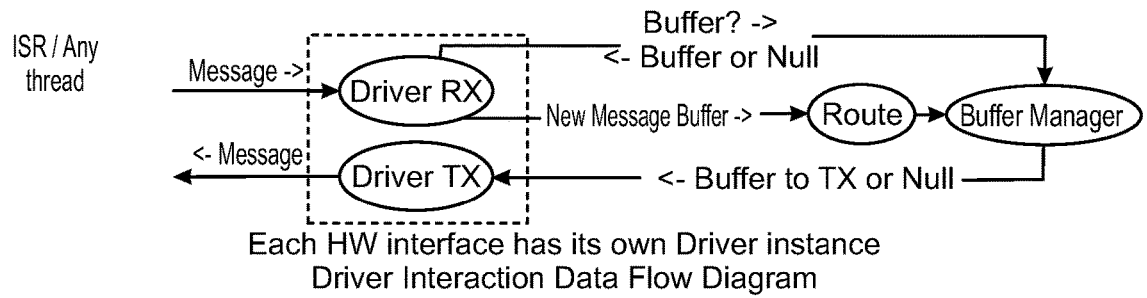

As shown in FIG. 11I, at some point the RX driver may be asked to receive a message from the other side of the interface. To ensure a message does not get dropped, the RX driver may ask the buffer manager if there is an available buffer for storing a new message. The driver may then ask for a buffer pointer and may start filling the buffer with received data. When a complete message is received, the RX driver may call a function to route the packet. The route function may examine the destination byte in the packet header and may change the owner to either the other driver, or the application, or may detect that the packet is bad and may drop the packet by freeing the buffer.

PCGP RX overhead may consist of asking for the next available buffer and calling the route function. An example of code that performs such a function is as follows:

```
@ Receive request
uint8 i=0, *p;
if (Bridge::canReceiveFlowControl( ) )
{
  p = Bridge::nextBufferRX( );
  while (not done)  {  p[i] = the next byte; }
  Bridge::route(p);
}
```

A driver may perform a TX by asking the buffer manager for the pointer to the next buffer to send. The TX driver may then ask the other side of the interface if it can accept a packet. If the other side denies the packet, the TX driver may do nothing to the buffer, as its status has not changed. Otherwise, the driver may send the packet and may recycle/free the buffer. An example of code that performs such a function is as follows:

```
uint8 *p = Bridge::nextBufferTX( );
if (p != (uint8 *)0)
{
  send the buffer p;
  Bridge::recycle(p);
}
```

To avoid forwarding packets that are past the maximum message system timeout time, asking for the nextBuffer may call the BufferManager::first(uint8 owner) function that may scan for buffers to free. Accordingly, full TX buffers with no hope of making a timeout may be freed on the thread that owns the buffer. A bridge that is doing TX (i.e., while looking for the next TX buffer) may free all of the TX buffers that are expired before receiving the next TX buffer for processing.

Figure 11J:
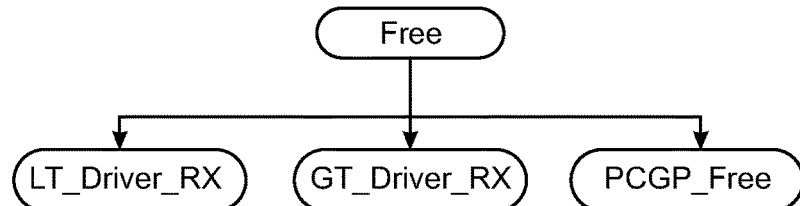
Figure 11K:
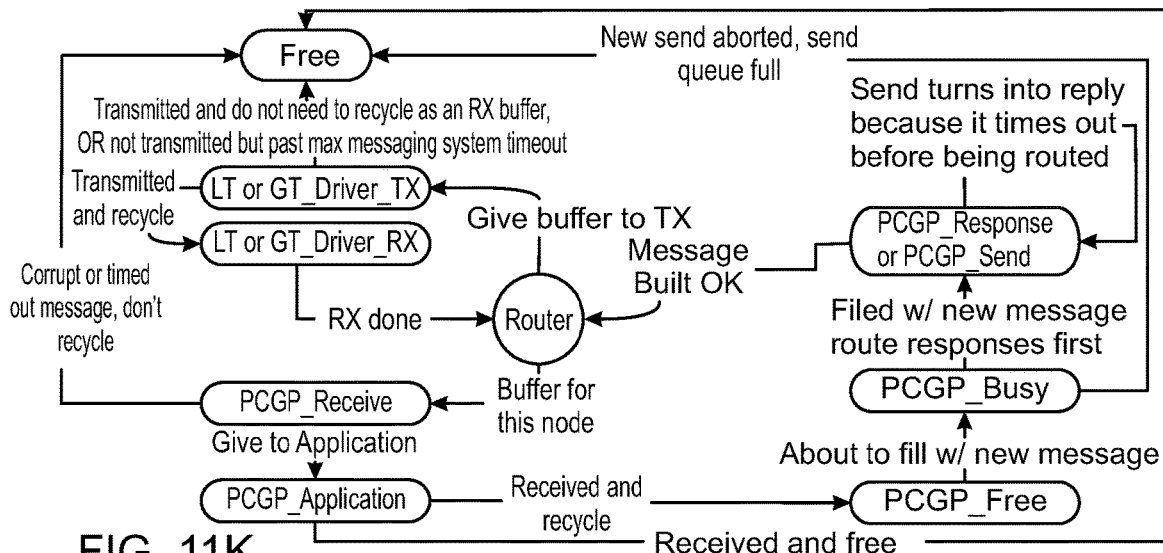
Figure 11L:
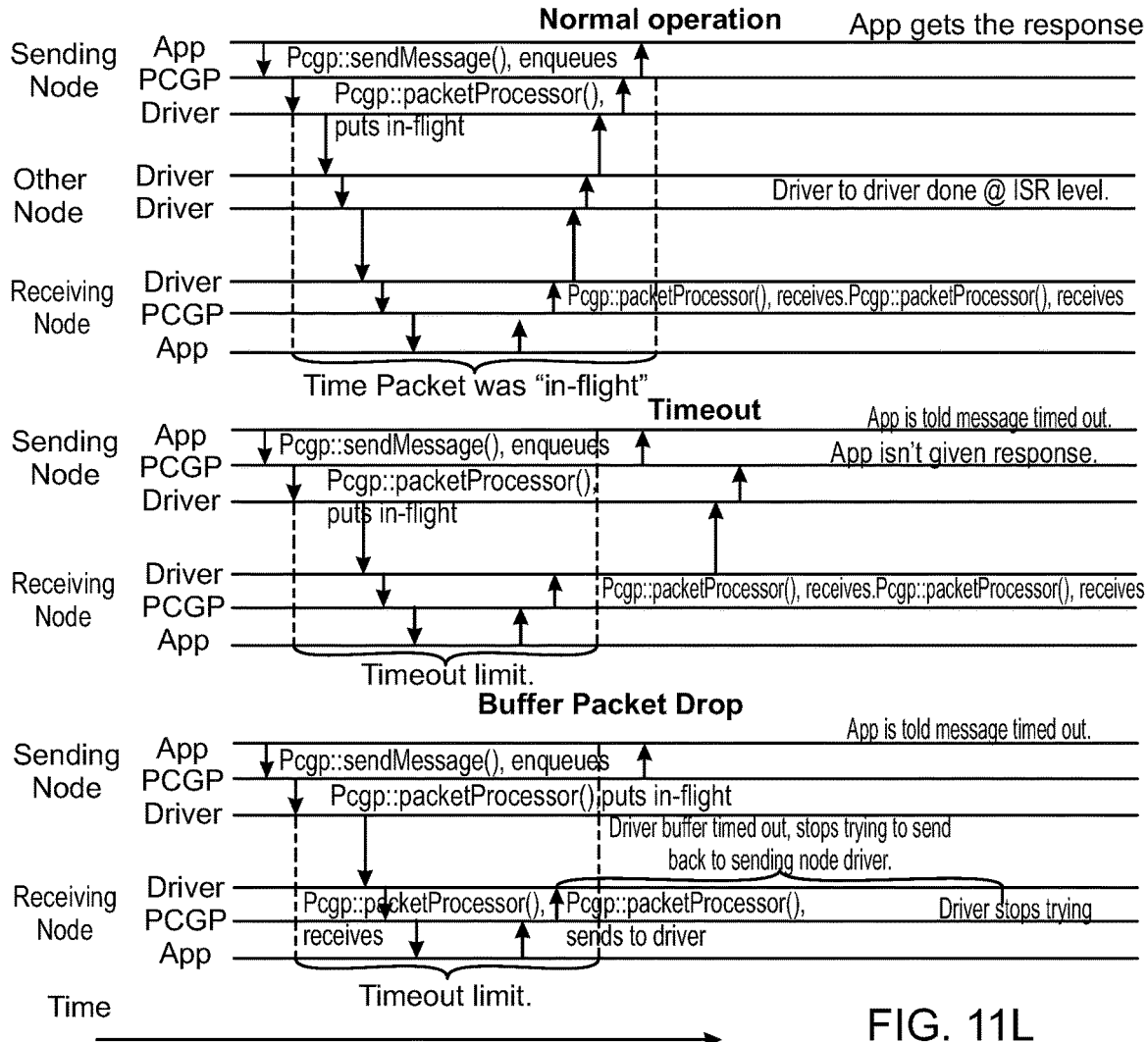

As shown in FIG. 11J-11L, during the buffer allocation process, buffers marked free may be transferred to the drivers to receive new packets, or to PCGP to receive new payloads for TX. Allocation from "free" may be done by the "packetProcessor" function. The number of sends and receives between "packetProcessor" calls may dictate how many LT_Driver_RX, GT_Driver_RX and PCGP_Free buffers need to be allocated. LT_Driver may represent drivers that handle addresses that are less than the node address. GT_Driver may represent drivers that handle addresses that are greater than the node address.

When a driver receives a packet, the driver may put the data into an RX buffer that gets handed to the router. The router may then reassign the buffer to PCGP_Receive or to the other driver's TX (not shown). If the buffer contains obviously invalid data, the buffer may transition to free.

After a router marks a buffer for TX, the driver may discover the buffer is TX and may send the message. After sending the message, the buffer may immediately become an RX buffer if the driver was low in RX buffers, or the buffer may be freed for re-allocation.

During the "packetProcessor" call, PCGP may process all buffers that the router marked as PCGP_Receive. At this point, data may be acted upon, so the CRC and other data items may be checked. If the data is corrupted, a statistic may be incremented and the buffer may be freed. Otherwise, the buffer may be marked as owned by the application. Buffers marked as owned by the application may be either recycled for the use of PCGP or freed for reallocation by the buffer manager.

When the application wants to send a new message, it may be done in a re-entrant friendly/mutual exclusion manner. If the buffer may be allocated, PCGP may mark the buffer as busy. Once marked busy, no other thread calling the send or reply functions may grab this buffer, as it is owned by this function call's invocation. The remainder of the process of error checking and building the message may be done outside the isolated race condition mutual exclusion guarded code. The buffer may either transition to free or may become a valid filled CRC-checked buffer and passed to the router. These buffers may not be routed immediately and may be queued so that messages can be sent later (assuming that protocol rules allow). Reply messages may be marked differently than new send messages because reply messages may be routed with a higher priority than regular send messages and reply messages may have no rules limiting how many/when they can be sent.

PCGP was designed to work with flow control, and flow control may negotiate the transfer of messages from one node to another node so that a buffer is never dropped because the other side of an interface lacks a buffer (which may cause back pressure on the sending node).

Flow control may be apart of the shared buffer format. The first two bytes may be reserved for the driver so that the driver never needs to shift the packet bytes. Two bytes may be used so that one byte is the DMA length−1, and the second byte is to control the flow of messages. These same two bytes may be synchronizing bytes if a PCGP message is transmitted over RS232.

When a packet is "in-flight", the packet may be in the process of being sent by a driver on the way to its destination, being processed by the destination, or being sent back as a response.

Typical delays are as follows:

| Interface/Delay cause | Delay (seconds) | Notes |
|---|---|---|
| SPI | <3 | Roughly 400 kbps |
| I2C | <1 | |

-continued

| Interface/Delay cause | Delay (seconds) | Notes |
|---|---|---|
| Waking a CC2510 | <6 ? | Clock calibration, min. sleep time. |
| Flow control | <0.2 | |
| RF link | 20 to 2000 | |
| Interference/ separation | Minutes, never | |

Accordingly, messages tend to complete the round trip either: quickly (e.g., <50 ms); slowly (e.g., one or more seconds); or not at all.

PCGP may use two different times (set at initialization) for all timeouts, one for when the RF link is in fast heartbeat mode, and another for when the RF link is in slow mode. If a message is in-flight and the link status changes from fast to slow, the timeout may be adjusted and the difference between fast and slow may be added to the time-to-live counter for the packet. No additional transitions back and forth may affect the time-to-live time for the message.

There is a second timeout that may be twice as long as the slow timeout that is used to monitor buffer allocation inside PCGP. Accordingly, if a message is "stuck" inside a driver and hasn't been sent due to e.g., flow control or hardware damage, the buffer may be freed by the buffer manager, resulting in the buffer being dropped. For a "new" message, this may mean that the packet already timed out and the application was already given a reply saying the message wasn't delivered, resulting in the buffer being freed. Since the driver polls the buffer manager for buffers that need to be sent, the buffer is freed up so that a message that could be sent is handed to the driver the next time that it unblocks. For a reply message, the reply may simply get dropped and the sending node may time out.

The PCGP messaging system may pass messages that contain header information and payload. Outside of PCGP, the header may be a set of data items in a call signature. However, internal to PCGP, there may be a consistent, driver friendly byte layout. Drivers may insert bytes either into the PCGP packet or before the PCGP packet such:

DE, CA: Synch bytes for use with RS232, nominal value of 0xDE, 0xCA or 0x5A, 0xA5.
LD: Driver DMA length byte, equals amount driver is pushing in this DMA transfer, which is the total size, not including the size byte or synch bytes.
Cmd: Driver command and control byte used for flow control.
LP: PCGP packet length, always the total header+payload size in bytes+CRC size. LD=LP+1.
Dst: Destination address.
Src: Source address.
Cmd: Command byte
Scd: Sub command byte
AT: Application Tag is defined by the application and has no significance to PCGP. It allows the application to attach more information to a message e.g., the thread from which the message originated.
SeqNum: thirty-two bit sequence number is incremented by PCGP for a new message sent, guarantees the number will not wrap, acts as a token, endianess isn't relevant.
CRC16: A sixteen bit CRC of the PCGP header and payload.

An example of a message with no payload, cmd=1, subcmd=2 is as follows:

0xDE, 0xCA, 0xC, 0x5, 0x14, 1, 2, 0, 0, 0, 0, 0x1, crchigh, crclow.
0x0D, cmd, 0xC, 0x5, 0x14, 1, 2, 0, 0, 0, 0, 0x1, crchigh, crclow.

There may be several advantages to this methodology, examples of which may include but are not limited to:

Most of our hardware DMA engines may use the first byte to define how many additional bytes to move, so in this methodology, drivers and PCGP may share buffers.
A byte may be provided right after the DMA length to pass flow control information between drivers.
Driver length and "Cmd" byte may be outside the CRC region so they may be altered by the driver, may be owned by the driver transport mechanism, and the driver may guard for invalid lengths.
There may be a separate PGCP packet length byte that is CRC protected. Accordingly, the application may trust the that payload length is correct.
The endianness of the sequence number may not be relevant, as it is just a byte pattern that may be matched that happens to also be a thirty-two bit integer.
The sequence number may be four bytes aligned to the edge of the shared buffer pool length.
There may be optional RS232 synchronizing bytes so that users may move cables around while debugging a message stream and both sides of the interface may resynchronize.
The application, driver and PCGP may share buffers and may release them by pointer.

Figure 11M:
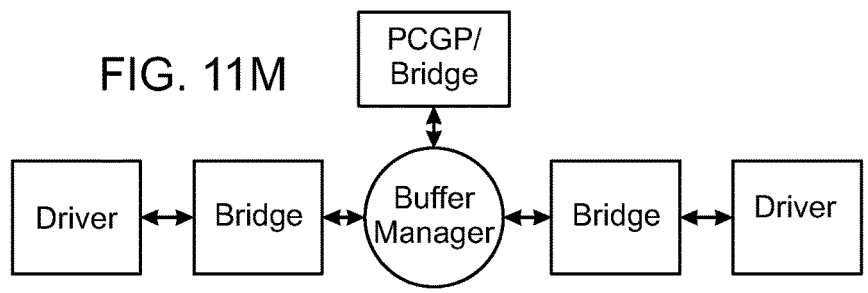
Figure 11N:
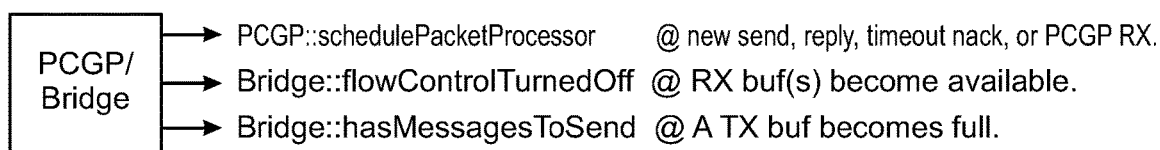

PCGP may not be an event driven software design, but may be used in event driven architectures by how the sub-classes are written. Data may be exchanged between the classes conceptually (as shown in FIG. 11M-11N).

Some event model in the driver may wake the driver, may receive a message and may pass the message through the bridge into the buffer manager that routes the message to new owner of the new message (through a bridge to either a driver or PCGP).

The following summarizes some exemplary events:

| Event: | Possible use: | Where this occurs: |
|---|---|---|
| When a new send or reply is queued, or decTimeouts generates a timeout reply. | Decide to run packetProcessor. | Inside PCGP::sendInternal |
| When a messages is received for PCGP. | Decide to run packetProcessor. | BufferManager::give |
| When a driver has something new to send. | Wake driver for TX. | BufferManager::give |
| When a Driver RX buffer becomes available. | Turn off flow control. | BufferManager::give |

The following illustrative example shows how the PCGP event model may work with Nucleus to wakeup the PCGP task after every message send, reply, or decTimeout that generated a NACK:

```
class PcgpOS : public Pcgp
{
  virtual void schedulePacketProcessor(void)
  {
    OS_EventGrp_Set(g_RCVEvGrps[EVG_RF_TASK].pEvgHandle,
              RfRadioTxEvent, OS_EV_OR_NO_CLEAR);
  }
}
```

The following is a pseudo code driver that is event based, illustrating how driver events work. The Driver subclasses Bridge and overrides hasMessagesToSend and flowControlTurnedOff to schedule the TX and RX functions to run if they aren't already running.

```
class SPI_Driver : public Bridge
{
  virtual void hasMessagesToSend( )
  {
    Trigger_ISR(TX_ISR, this);
  }
  virtual void flowControlTurnedOff( )
  {
    Trigger_ISR(RX_ISR, this);
  }
  static void TX_RetryTimer( )
  {
    Trigger_ISR(TX_ISR, this);
  }
  static void TX_ISR(Bridge *b)
  {
    DisableISRs( );
    do
    {
      uint8 *p = b->nextBufferTX( );
      if (p == null) break;
      if (b->_bufferManager->bufferTimedOut(p)==false)
      {
        if (OtherSideSPI_FlowControl( ) == false)
        {
          Trigger TX_RetryTimer in 20 msec.
          break;
        }
        send(p);
      }
      free(p);
    } while (true) ;
    EnableISRs( );
  }
  static void RX_ISR(Bridge *b)
  {
    DisableISRs( );
    do
    {
      uint8* p = b->nextBufferRX( );
      if (p == null) break;
      uint i;
      while (not done receiving)
        p[i++] = getChar( );
      b->route(p);
    } while (true) ;
    EnableISRs( );
  }
}
```

The following statistics may be supported by PCGP:
Number of packets sent;
Number of packets received;
CRC errors;
Timeouts; and
Buffer unavailable (ran out of buffers)

PCGP may be designed to run in multiple processing environments. Most parameters may be run time configured because it facilitates testing, and any run time fine tuning for performance. Other parameters may be compile time e.g., anything that alters memory allocation must be done statically at compile time.

The following may be compile time configuration #defines that may vary where PCGP is implemented:
  # driver bytes: may be two bytes reserved in the common buffer scheme for the driver, but this may be a compile time option to accommodate other drivers such as RF protocol.
  # RX driver buffers: may be tuned to how many buffers would be good for that processor/traffic flow, etc.
  # PCGP RX buffers: may be tuned to how many buffers would be good for that processor/traffic flow, etc.
  Total # of buffers: may be tuned to how many buffers should be at that processor.

The CRC may be used to ensure data integrity. If a CRC is invalid, it may not be delivered to the application and the CRC error may be tracked. The message may eventually timeout and may be retried by the originator.

Likewise, if the messaging system informs the application that a message was delivered when it was not, this may be a hazard to the system. The Stop Bolus Command is an example of such a command. This may be mitigated by the Request/Action sequence of messages which may be required by the application to change therapy. The Controller may receive a matching command from the Pump application to consider the message delivered.

Figure 11O:
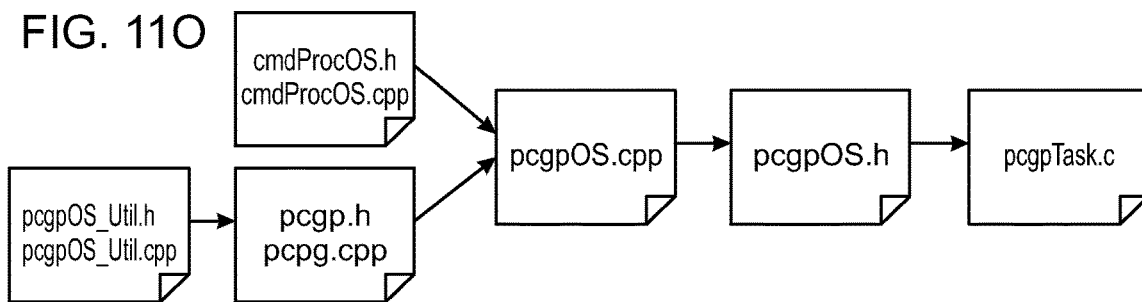

DEKA may provide a reference way of interfacing PCGP into the Nucleus OS system on the ARM 9 (as shown in FIG. 11O).

Figure 11P:
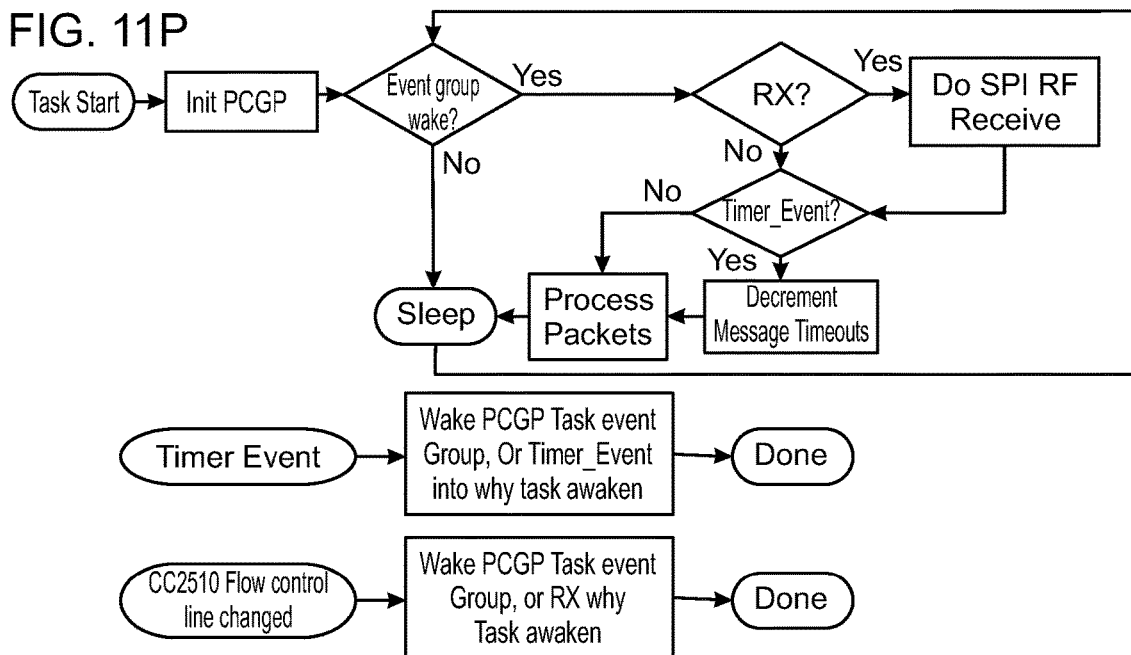

As shown in FIG. 11P, the pcgpOS.cpp file may instantiate a PCGP node instance (Pcgp, a Bridge, etc.) and may provide through pcgpOS.h a 'C' linkable set of function calls that provide a 'C' language interface to the C++ code. This may simplify the 'C' code as the objects acted upon are implicit.

The following general rules may be applied:
  PCGP may run on all nodes: any driver may support a generic driver interface.
  Race conditions may not be permitted.
  May support half duplex on the SPI port between slave processor and master processor.
  Data transfer may not be attempted; as it either succeeds or returns fail/false.
  May require low overhead (time, processing, bandwidth wasted).
  May support CC2510 operating at DMA (fast) SPI clock rates.

SPI flow control may prevent data from being sent if the receiving side does not currently have an empty buffer to place the packet. This may be accomplished by asking for permission to send and waiting for a response indicating that you have been cleared to do so. There may also be a way to tell the other side that there are currently no free buffers and the transfer should be attempted at a later time.

All transmission may begin with a length byte that indicates the number of bytes to be sent, not including the length byte itself. Following the length may be a single byte indicating the command being sent.

The actual transmission of a packet may be the length of packet plus one for the command byte, followed by the command byte for a message appended and finally the packet itself.

In addition to the command bytes that will be sent, an additional hardware line called the FlowControl line may be added to the traditional four SPI signals. The purpose of this line is to allow the protocol to run as quickly as possible without a need for preset delays. It also allows the slave processor to tell the master processor that it has a packet waiting to be sent, thus eliminating the need for the master processor to poll the slave processor for status.

The following exemplary command values may be used:
Commands to be Sent by the Master Processor:

| Command | Value | Description |
| --- | --- | --- |
| M_RTS | 0xC1 | Master is requesting to send a packet |
| M_MSG_APPENDED | 0xC2 | Master is sending a packet |

-continued

| Command | Value | Description |
| --- | --- | --- |
| M_CTS | 0xC3 | Master is tell slave it is Cleared to Send |
| M_ERROR | 0xC4 | An Error condition has been encountered |

Commands to be Sent by the Slave Processor:

| Command | Value | Description |
| --- | --- | --- |
| S_PREPARING_FOR_RX | 0xA1 | Slave is prepare the dma to receive a packet |
| S_RX_BUFF_FULL | 0xA2 | Slave is currently out of RX buffers, retry later |
| S_MSG_APPENDED | 0xA3 | Slave is sending a packet |
| S_ERROR | 0xA4 | An Error condition has been encountered |

As illustrated in FIG. 11Q, when the slave processor has a packet to send to the master processor, the slave processor may notify the master processor (by asserting the FlowControl line) that it has a pending packet that is waiting to be sent. Doing so may result in an IRQ on the master processor at which time the master processor may decide when to go retrieve the message from the slave processor. Retrieving the packet may be delayed at the discretion of the master processor, and the master processor may even decide to attempt to send a packet to the slave processor before retrieving from the slave processor.

The master processor may begin the retrieval by sending the slave processor M_CTS commands; this shall be repeated until the slave processor responds by sending the S_MSG_APPENDED command along with the packet itself. The FlowControl line may be cleared after the packet has been sent. If a M_CTS command is received by the slave processor when one is not expected, the M_CTS command may be ignored.

As illustrated in FIG. 11R, when the master processor has a packet to send to the slave processor, the master processor may initiate the transfer by sending a M_RTS command. Upon receiving the M_RTS command, if the slave processor currently has a send packet pending, the slave processor will lower the FlowControl line so that it may be re-used as a Cleared To Send signal. The slave processor may then tell the master processor that it is in the process of preparing the SPI DMA to receive the packet, during which time the master processor may stop clocking bytes onto the bus and may allow the slave processor to finish preparing for the receive.

The slave processor may then indicate it is ready to receive the full packet by raising the FlowControl line (which is now used as the CTS signal). Upon receiving the CTS signal, the master processor may proceed to send the M_MSG_APPENDED command along with the packet itself.

After the completion of the transfer, the slave processor may lower the FlowControl line. If a packet was pending at the start of the transfer, or a send occurred on the slave processor when the packet was being received, the slave processor may reassert the FlowControl line now indicating that it has a pending packet.

Referring again to FIG. 11A, infusion pump assembly 100, 100' may include switch assembly 318 coupled to electrical control assembly 110 (FIG. 3) that may allow a user (not shown) to perform at least one, and in some embodiments, a plurality of tasks. One illustrative example of such a task is the administration of a bolus dose of the infusible fluid (e.g., insulin) without the use of a display assembly. Remote control assembly 300 may allow the user to enable/disable/configure infusion pump assembly 100, 100' to administer the bolus dose of insulin.

Referring also to FIG. 12A, slider assembly 306 may be configured, at least in part, to enable the user to manipulate the menu-based information rendered on display assembly 302. An example of slider assembly 306 may include a capacitive slider assembly, which may be implemented using a CY8C21434-24LFXI PSOC offered by Cypress Semiconductor of San Jose, Calif., the design an operation of which are described within the "CSD User Module" published by Cypress Semiconductor. For example, via slider assembly 306, the user may slide their finger in the direction of arrow 314, resulting in the highlighted portion of the information included within main menu 350 (shown in FIG. 12A) rendered on display assembly 302 scrolling upward. Alternatively, the user may slide their finger in the direction of arrow 316, resulting in the highlighted portion of the information included within main menu 350 rendered on display assembly 302 scrolling downward.

Slider assembly 306 may be configured so that the rate at which e.g. the highlighted portion of main menu 350 scrolls "upward" or "downward" varies depending upon the displacement of the finger of the user with respect to point of origin 320. Therefore, if the user wishes to quickly scroll "upward", the user may position their finger near the top of slider assembly 306. Likewise, if the user wishes to quickly scroll "downward", the user may position their finger near the bottom of slider assembly 306. Additionally, if the user wishes to slowly scroll "upward", the user may position their finger slightly "upward" with respect to point of origin 320. Further, if the user wishes to slowly scroll "downward", the user may position their finger slightly "downward" with respect to point of origin 320. Once the appropriate menu item is highlighted, the user may select the highlighted menu item via one or more switch assemblies 308, 310.

Referring also to FIGS. 12B-12F, assume for illustrative purposes that infusion pump assembly 100, 100' is an insulin pump and the user wishes to configure infusion pump assembly 100, 100' so that when switch assembly 318 is depressed by the user, a 0.20 unit bolus dose of insulin is administered. Accordingly, the user may use slider assembly 306 to highlight "Bolus" within main menu 350 rendered on display assembly 302. The user may then use switch assembly 308 to select "Bolus". Once selected, processing logic (not shown) within remote control assembly 300 may then render submenu 352 on display assembly 302 (as shown in FIG. 12B).

The user may then use slider assembly 306 to highlight "Manual Bolus" within submenu 352, which may be selected using switch assembly 308. Processing logic (not shown) within remote control assembly 300 may then render submenu 354 on display assembly 302 (as shown in FIG. 12C).

The user may then use slider assembly 306 to highlight "Bolus: 0.0 Units" within submenu 354, which may be selected using switch assembly 308. Processing logic (not shown) within remote control assembly 300 may then render submenu 356 on display assembly 302 (as shown in FIG. 12D).

The user may then use slider assembly 306 to adjust the "Bolus" insulin amount to "0.20 units", which may be selected using switch assembly 308. Processing logic (not shown) within remote control assembly 300 may then render submenu 358 on display assembly 302 (as shown in FIG. 12E).

The user 14 may then use slider assembly 306 to highlight "Confirm", which may be selected using switch assembly 308. Processing logic (not shown) within remote control assembly 300 may then generate the appropriate signals that may be sent to the above-described telemetry circuitry (not shown) included within remote control assembly 300. The telemetry circuitry (not shown) included within the remote control assembly may then transmit, via wireless communication channel 312 established between remote control assembly 300 and infusion pump assembly 100', the appropriate configuration commands to configure infusion pump assembly 100' so that whenever switch assembly 318 is depressed by the user, a 0.20 unit bolus dose of insulin is administered.

Once the appropriate commands are successfully transmitted, processing logic (not shown) within remote control assembly 300 may once again render submenu 350 on display assembly 302 (as shown in FIG. 12F).

Specifically and once programmed via remote control assembly 300, the user may depress switch assembly 318 of infusion pump assembly 100' to administer the above-described 0.20 unit bolus dose of insulin. Via the above-described menuing system included within remote control assembly 300, the user may define a quantity of insulin to be administered each time that the user depresses switch assembly 318. While this particular example specifies that a single depression of switch assembly 318 is equivalent to 0.20 units of insulin, this is for illustrative purposes only and is not intended to be a limitation of this disclosure, as other values (e.g. 1.00 units of insulin per depression) are equally applicable.

Assume for illustrative purposes that the user wishes to administer a 2.00 unit bolus dose of insulin. To activate the above-describe bolus dose administration system, the user may be required to press and hold switch assembly 318 for a defined period of time (e.g. five seconds), at which point infusion pump assembly 100, 100' may generate an audible signal indicating to the user that infusion pump assembly 100, 100' is ready to administer a bolus does of insulin via switch assembly 318. Accordingly, the user may depress switch assembly 318 ten times (i.e., 2.00 units is ten 0.20 unit doses). After each time that switch assembly 318 is depressed, infusion pump assembly 100, 100' may provide on audible response to the user via an internal speaker/sound generation device (not shown). Accordingly, the user may depress switch assembly 318 the first time and infusion pump assembly 100, 100' may generate a confirmation beep in response, thus indicating to the user that infusion pump assembly 100, 100' received the command for (in this particular example) 0.20 units of insulin. As the desired bolus dose is 2.00 units of insulin, the user may repeat this procedure nine more times in order to effectuate a bolus dose of 2.00 units, wherein infusion pump assembly 100, 100' generates a confirmation beep after each depression of switch assembly 318.

While in this particular example, infusion pump assemblies 100, 100' are described as providing one beep after each time the user depresses switch assembly 318, this is for illustrative purposes only and is not intended to be a limitation of this disclosure. Specifically, infusion pump assembly 100, 100' may be configured to provide a single beep for each defined quantity of insulin. As discussed above, a single depression of switch assembly 318 may be equivalent to 0.20 units of insulin. Accordingly, infusion pump assembly 100, 100' may be configured to provide a single beep for each 0.10 units of insulin. Accordingly, if infusion pump assembly 100, 100' is configured such that a single depression of switch assembly 318 is equivalent to 0.20 units of insulin, each time switch assembly 318 is depressed, infusion pump assembly 100, 100' may provide the user with two beeps (i.e. one for each 0.10 units of insulin).

Once the user has depressed switch assembly 318 on infusion pump assembly 100' a total of ten times, the user may simply wait for infusion pump assembly 100, 100' to acknowledge receipt of the instructions to administer a 2.00 unit bolus dose of insulin (as opposed to the confirmation beep received at each depression of switch assembly 318). Once a defined period of time (e.g., two seconds) passes, infusion pump assembly 100, 100' may provide an audible confirmation to the user concerning the quantity of units to be administered via the bolus insulin dose that the user just requested. For example, as (in this example) infusion pump assembly 100, 100' was programmed by the user so that a single depression of switch assembly 318 is equivalent to 0.20 units of insulin, infusion pump assembly 100, 100' may beep ten times (i.e., 2.00 units is ten 0.20 unit doses).

When providing feedback to the user concerning the quantity of units to be administered via the bolus insulin dose, infusion pump assembly 100, 100' may provide a multifrequency audible confirmation. For example and continuing with the above-stated example in which ten beeps are to be provided to the user, infusion pump assembly 100, 100' may group the beeps into groups of five (to facilitate easier counting by the user) and the beeps within each group of five may be rendered by infusion pump assembly 100, 100' so that each subsequent beep has a higher frequency than the preceding beep (in a manner similar to a musical scale). Accordingly and continuing with the above-stated example, infusion pump assembly 100, 100' may render a 1,000 Hz beep, followed by an 1,100 Hz beep, followed by a 1,200 Hz beep, followed by a 1,300 Hz beep, followed by a 1,400 Hz beep (thus completing a group of five beeps), followed by a short pause, and then a 1,000 Hz beep, followed by an 1,100 Hz beep, followed by a 1,200 Hz beep, followed by a 1,300 Hz beep, followed by a 1,400 Hz beep (thus completing the second group of five beeps). According to various additional/alternative embodiments the multifrequency audible confirmation may utilize various numbers of tones incrementing in frequency. For example, an embodiment may utilize twenty different tones incrementing in frequency. However, the number of tones should not be construed as a limitation of the present disclosure as number of tones may vary according to design criteria and user need.

Once infusion pump assembly 100, 100' completes the rendering of the multifrequency audible confirmation (i.e. the ten beeps described above), the user may, within a defined period of time (e.g. two seconds), depress switch assembly 318 to provide a confirmation signal to infusion pump assembly 100, 100', indicating that the multifrequency audible confirmation was accurate and indicative of the size of the bolus dose of insulin to be administered (i.e. 2.00 units). Upon receiving this confirmation signal, infusion pump assembly 100, 100' may render a "confirmation received" audible tone and effectuate the delivery of (in this particular example) the 2.00 unit bolus dose of insulin. In the event that infusion pump assembly 100, 100' fails to receive the above-described confirmation signal, infusion pump assembly 100, 100' may render a "confirmation failed" audible tone and will not effectuate the delivery of the bolus dose of insulin. Accordingly, if the multifrequency audible confirmation was not accurate/indicative of the size of the bolus dose of insulin to be administered, the user may simply not provide the above-described confirmation signal, thereby canceling the delivery of the bolus dose of insulin.

As discussed above, in one exemplary embodiment of the above-described infusion pump assembly, infusion pump assembly 100' may be used to communicate with a remote control assembly 300. When such a remote control assembly 300 is utilized, infusion pump assembly 100' and remote control assembly 300 may routinely contact each other to ensure that the two devices are still in communication with each other. For example, infusion pump assembly 100' may "ping" remote control assembly 300 to ensure that remote control assembly 300 is present and active. Further, remote control assembly 300 may "ping" infusion pump assembly 100' to ensure that infusion pump assembly 100' is still present and active. In the event that one of infusion pump assembly 100' and remote control assembly 300 fails to establish communication with the other assembly, the assembly that is unable to establish communication may sound a "separation" alarm. For example, assume that remote control assembly 300 is left in the car of the user, while infusion pump assembly 100' is in the pocket of the user. Accordingly and after a defined period of time, infusion pump assembly 100' may begin sounding the "separation" alarm, indicating that communication with remote control assembly 300 cannot be established. Using switch assembly 318, the user may acknowledge/silence this "separation" alarm.

As the user may define and administer a bolus insulin dose via switch assembly 318 of infusion pump assembly 100' while remote control assembly 300 is not in communication with infusion pump assembly 100', infusion pump assembly 100' may store information concerning the administered bolus insulin dose within a log file (not shown) stored within infusion pump assembly 100'. This log file (not shown) may be stored within nonvolatile memory (not shown) included within infusion pump assembly 100'. Upon communication being reestablished between infusion pump assembly 100' and remote control assembly 300, infusion pump assembly 100' may provide the information concerning the administered bolus insulin dose stored within the log file (not shown) of infusion pump assembly 100' to remote control assembly 300.

Further, if the user anticipates separating remote control assembly 300 from infusion pump assembly 100', the user (via the above-described menuing system) may configure infusion pump assembly 100' and remote control assembly 300 to be in "separation" mode, thus eliminating the occurrence of the above-described "separation" alarms. However, the devices may continue to "ping" each other so that when they come back into communication with each other, infusion pump assembly 100' and remote control assembly 300 may automatically exit "separation" mode.

Further, if the user anticipates traveling in an airplane, the user (via the above-described menuing system of remote control assembly 300) may configure infusion pump assembly 100' and remote control assembly 300 to be in "airplane" mode, in which each of infusion pump assembly 100' and remote control assembly 300 suspend any and all data transmissions. While in "airplane" mode, infusion pump assembly 100' and remote control assembly 300 may or may not continue to receive data.

Switch assembly 318 may be used to perform additional functions, such as: checking the battery life of reusable housing assembly 102; pairing reusable housing assembly 102 with remote control assembly 300; and aborting the administration of a bolus does of infusible fluid.

Checking Battery Life:

Reusable housing assembly 102 may include a rechargeable battery assembly that may be capable of powering infusion pump assembly 100, 100' for approximately three days (when fully charged). Such a rechargeable battery assembly may have a usable life of a predetermined number of usable hours, for example, or years, or other predetermined length of usage. However, the predetermined life may depend on many factors, including but not limited to, one or more of the following: climate, daily usage, and number of recharges. Whenever reusable housing assembly 102 is disconnected from disposable housing assembly 114, infusion pump assembly 100, 100' may perform a battery check on the above-described rechargeable battery assembly whenever switch assembly 318 is depressed for a defined period of time (e.g. in excess of two seconds). In the event that the above-described rechargeable battery assembly is determined to be charged above a desired threshold, infusion pump assembly 100, 100' may render a "battery pass" tone. Alternatively, in the event that the above-described rechargeable battery assembly is determined to be charged below a desired threshold, infusion pump assembly 100, 100' may render a "battery fail" tone. Infusion pump assembly 100, 100' may include components and/or circuitry to determine whether reusable housing assembly 102 is disconnected from disposable housing assembly 114.

Pairing:

As discussed above and in one exemplary embodiment of the above-described infusion pump assembly, infusion pump assembly 100' may be used to communicate with remote control assembly 300. In order to effectuate communication between infusion pump assembly 100' and remote control assembly 300, a paring process may be performed. During such a pairing process, one or more infusion pump assemblies (e.g. infusion pump assembly 100') may be configured to communicate with remote control assembly 300 and (conversely) remote control assembly 300 may be configured to communicate with one or more infusion pump assemblies (e.g. infusion pump assembly 100'). Specifically, the serial numbers of the infusion pump assemblies (e.g. infusion pump assembly 100') may be recorded within a pairing file (not shown) included within remote control assembly 300 and the serial number of remote control assembly 300 may be recorded within a pairing file (not shown) included within the infusion pump assemblies (e.g. infusion pump assembly 100').

According to an embodiment, in order to effectuate such a pairing procedure, the user may simultaneously hold down one or more switch assemblies on both remote control assembly 300 and infusion pump assembly 100'. For example, the user may simultaneously hold down switch assembly 310 included within remote control assembly 300 and switch assembly 318 included within infusion pump assembly 100' for a defined period exceeding e.g. five seconds. Once this defined period is reached, one or more of remote control assembly 300 and infusion pump assembly 100' may generate an audible signal indicating that the above-described pairing procedure has been effectuated.

According to another embodiment, prior to performing the pairing process, the user may uncouple reusable housing assembly 102 from disposable housing assembly 114. By requiring this initial step, further assurance is provided that an infusion pump assembly being worn by a user may not be surreptitiously paired with a remote control assembly.

Once uncoupled, the user may enter pairing mode via input assembly 304 of remote control assembly 300. For example, the user may enter pairing mode on remote control assembly 300 via the above-described menuing system in combination with e.g., switch assembly 310. The user may be prompted on display assembly 302 of remote control assembly 300 to depress and hold switch assembly 318 on infusion pump assembly 100'. Additionally, remote control assembly 304 may switch to a low power mode to e.g., avoid trying to pair with distant infusion pump assemblies. The user may then depress and hold switch assembly 318 on infusion pump assembly 100' so that infusion pump assembly 100' enters a receive mode and waits for a pairing command from remote control assembly 300.

Remote control assembly 300 may then transmit a pairing request to infusion pump assembly 100', which may be acknowledged by infusion pump assembly 100'. Infusion pump assembly 100' may perform a security check on the pairing request received from remote control assembly 300 and (if the security check passes) infusion pump assembly 100' may activate a pump pairing signal (i.e., enter active pairing mode). Remote control assembly 300 may perform a security check on the acknowledgment received from infusion pump assembly 100'.

The acknowledgment received from infusion pump assembly 100' may define the serial number of infusion pump assembly 100' and remote control assembly 300 may display that serial number on display assembly 302 of remote control assembly 300. The user may be asked if they wish to pair with the pump found. If the user declines, the pairing process may be aborted. If the user agrees to the pairing process, remote control assembly 300 may prompt the user (via display assembly 302) to depress and hold switch assembly 318 on infusion pump assembly 100'.

The user may then depress and hold switch assembly 318 on infusion pump assembly 100' and depress and hold e.g. switch assembly 310 on remote control assembly 300.

Remote control assembly 300 may confirm that remote switch assembly 310 was held (which may be reported to infusion pump assembly 100'). Infusion pump assembly 100' may perform a security check on the confirmation received from remote control assembly 300 to confirm the integrity of same. If the integrity of the confirmation received is not verified, the pairing process is aborted. If the integrity of the confirmation received is verified, any existing remote pair configuration file is overwritten to reflect newly-paired remote control assembly 300, the pump pairing completed signal is activated, and the pairing process is completed.

Additionally, infusion pump assembly 100' may confirm that switch assembly 318 was held (which may be reported to remote control assembly 300). Remote control assembly 300 may perform a security check on the confirmation received from infusion pump assembly 100' to confirm the integrity of same. If the integrity of the confirmation received is not verified, the pairing process is aborted. If the integrity of the confirmation received is verified, a pair list file within remote control assembly 300 may be modified to add infusion pump assembly 100'. Typically, remote control assembly 300 may be capable of pairing with multiple infusion pump assemblies, while infusion pump assembly 100' may be capable of only pairing with a single remote control assembly. The pairing completed signal may be activated and the pairing process may be completed.

When the pairing process is completed, one or more of remote control assembly 300 and infusion pump assembly 100' may generate an audible signal indicating that the above-described pairing procedure has been successfully effectuated.

Aborting Bolus Dose:

in the event that the user wishes to cancel a bolus dose of e.g. insulin being administered by infusion pump assembly 100', the user may depress switch assembly 318 (e.g., shown in FIGS. 1 & 2) for a defined period exceeding e.g. five seconds. Once this defined period is reached, infusion pump assembly 100' may render an audible signal indicating that the above-described cancellation procedure has been effectuated.

While switch assembly 318 is shown as being positioned on the top of infusion pump assembly 100, 100', this is for illustrative purposes only and is not intended to be a limitation of this disclosure, as other configurations are possible. For example, switch assembly 318 may be positioned about the periphery of infusion pump assembly 100, 100'.

Figure 14:
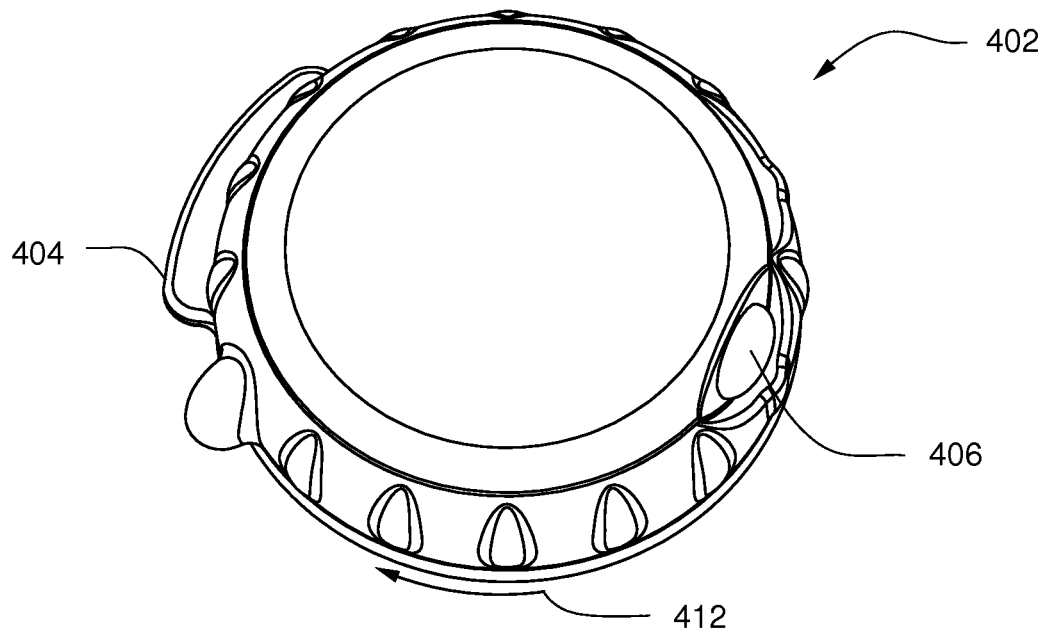
FIG. 14 is an isometric view of the infusion pump assembly of FIG. 13.
Figure 15:
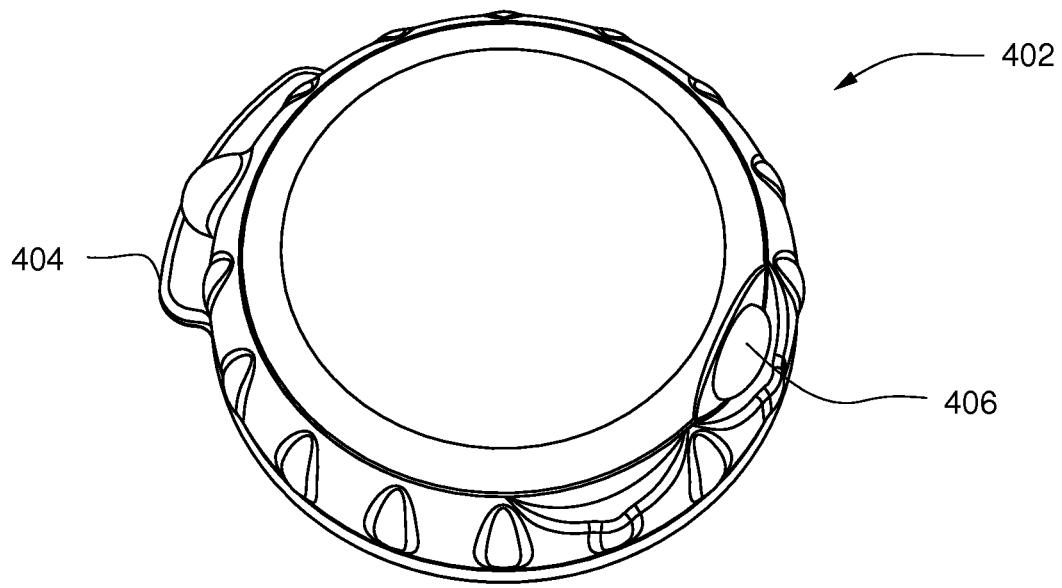
FIG. 15 is an isometric view of the infusion pump assembly of FIG. 13.

Referring also to FIGS. 13-15, there is shown an alternative-embodiment infusion pump assembly 400. As with pump assembly 100, 100', infusion pump assembly 400 may include reusable housing assembly 402 and disposable housing assembly 404.

In a fashion similar to reusable housing assembly 102, reusable housing assembly 402 may include a mechanical control assembly (that includes at least one pump assembly and at least one valve assembly). Reusable housing assembly 402 may also include an electrical control assembly that is configured to provide control signals to the mechanical control assembly and effectuate the delivery of an infusible fluid to a user. The valve assembly may be configured to control the flow of the infusible fluid through a fluid path and the pump assembly may be configured to pump the infusible fluid from the fluid path to the user In a fashion similar to disposable housing assembly 114, disposable housing assembly 404 may be configured for a single use or for use for a specified period of time, e.g., e.g., three days or any other amount of time. Disposable housing assembly 404 may be configured such that any components in infusion pump assembly 400 that come in contact with the infusible fluid are disposed on and/or within disposable housing assembly 404.

In this particular embodiment of the infusion pump assembly, infusion pump assembly 400 may include switch assembly 406 positioned about the periphery of infusion pump assembly 400. For example, switch assembly 406 may be positioned along a radial edge of infusion pump assembly 400, which may allow for easier use by a user. Switch assembly 406 may be covered with a waterproof membrane configured to prevent the infiltration of water into infusion pump assembly 400. Reusable housing assembly 402 may include main body portion 408 (housing the above-described mechanical and electrical control assemblies) and locking ring assembly 410 that may be configured to rotate about main body portion 408 (in the direction of arrow 412).

In a fashion similar to reusable housing assembly 102 and disposable housing assembly 114, reusable housing assembly 402 may be configured to releasably engage disposable housing assembly 404. Such releasable engagement may be accomplished by a screw-on, a twist-lock or a compression fit configuration, for example. In an embodiment in which a twist-lock configuration is utilized, the user of infusion pump assembly 400 may first properly position reusable housing assembly 402 with respect to disposable housing assembly 404 and may then rotate locking ring assembly 410 (in the direction of arrow 412) to releasably engage reusable housing assembly 402 with disposable housing assembly 404.

Through the use of locking ring assembly 410, reusable housing assembly 402 may be properly positioned with respect to disposable housing assembly 404 and then releasably engaged by rotating locking ring assembly 410, thus eliminating the need to rotate reusable housing assembly 402 with respect to disposable housing assembly 404. Accordingly, reusable housing assembly 402 may be properly aligned with disposable housing assembly 404 prior to engagement, and such alignment may not be disturbed during the engagement process. Locking ring assembly 410 may include a latching mechanism (not shown) that may prevent the rotation of locking ring assembly 410 until reusable housing assembly 402 and disposable housing assembly 404 are properly positioned with respect to each other.

Figure 17:
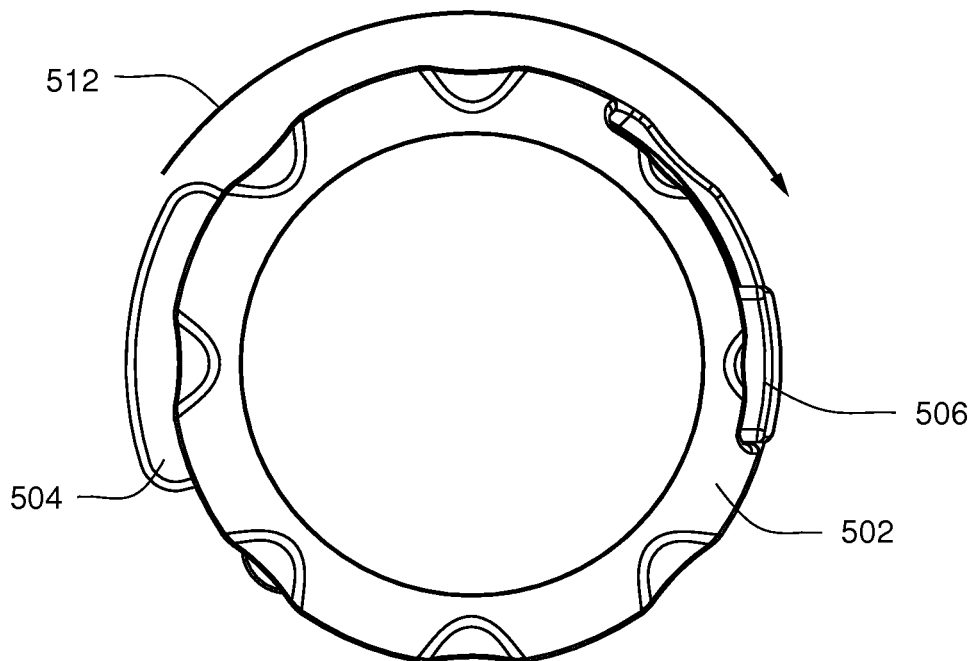
FIG. 17 is an plan view of the infusion pump assembly of FIG. 16.
Figure 18:
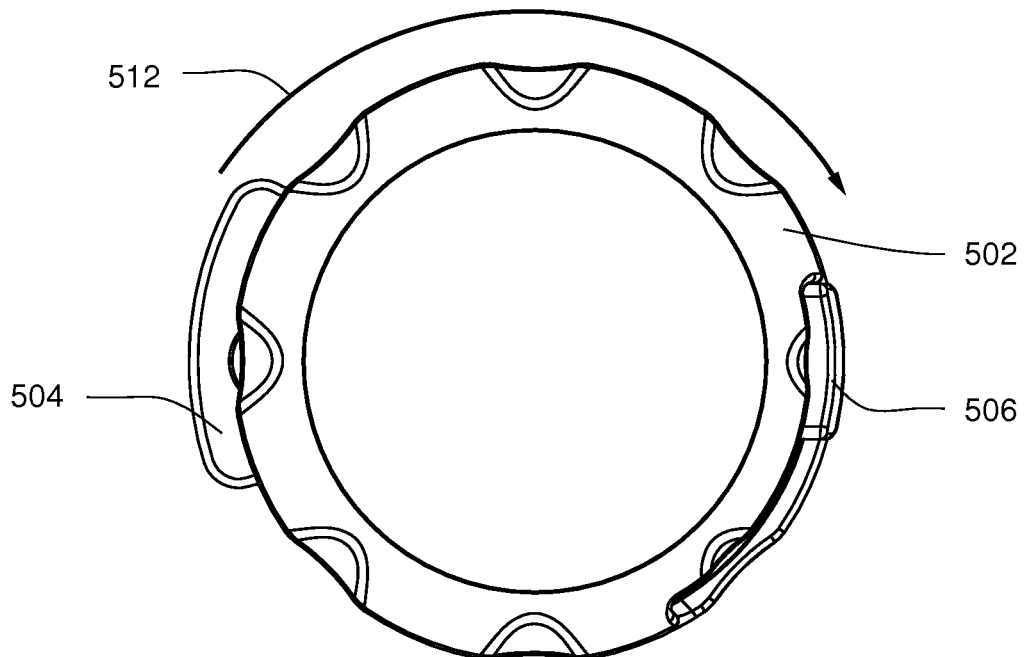
FIG. 18 is a plan view of the infusion pump assembly of FIG. 16.
Figure 19:
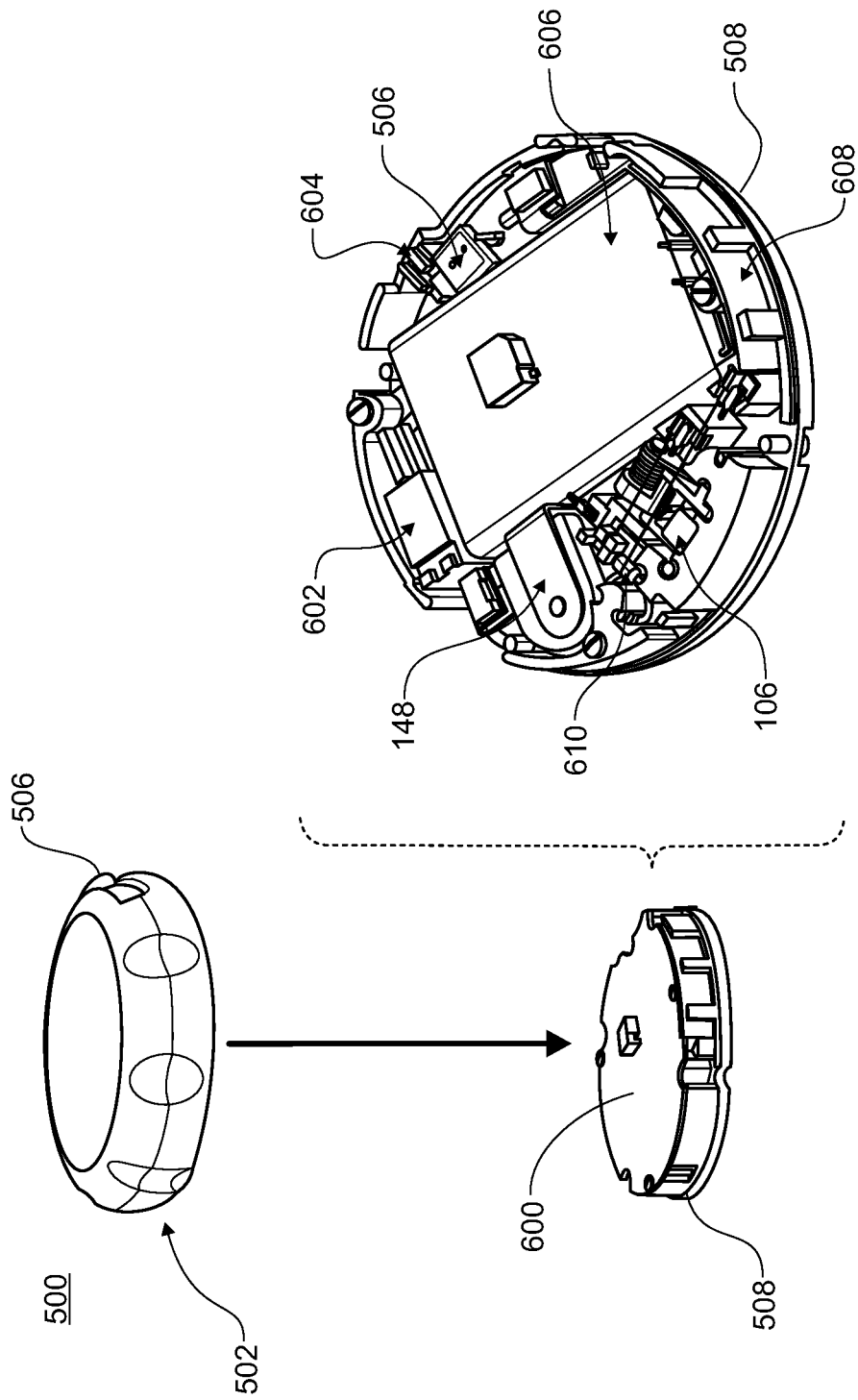
FIG. 19A is an exploded view of various components of the infusion pump assembly of FIG. 16.
FIG. 19B is an isometric view of a portion of the infusion pump assembly of FIG. 16.
Figure 20:
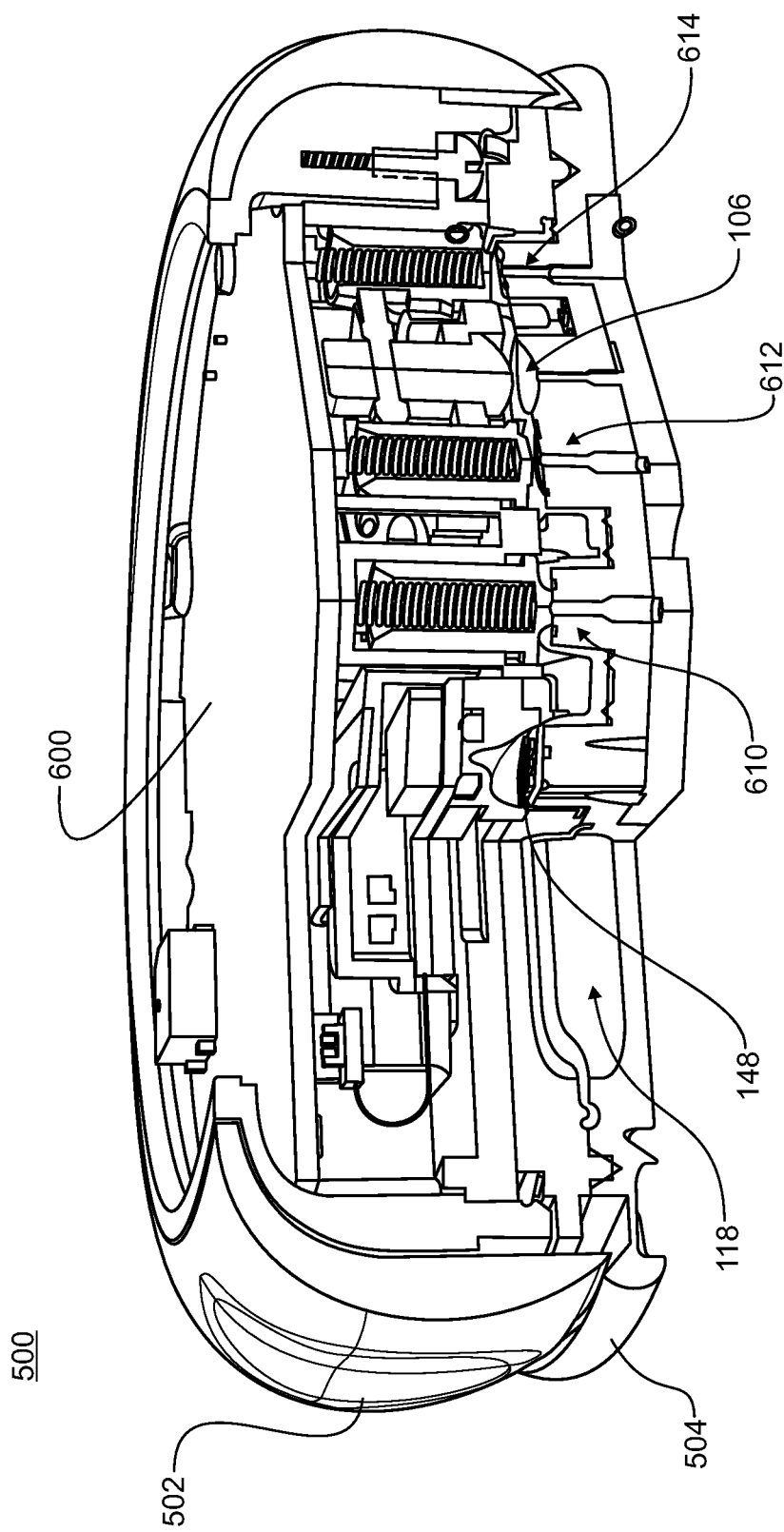
FIG. 20 is a cross-sectional view of the disposable housing assembly of the infusion pump assembly of FIG. 16.
Figure 21:
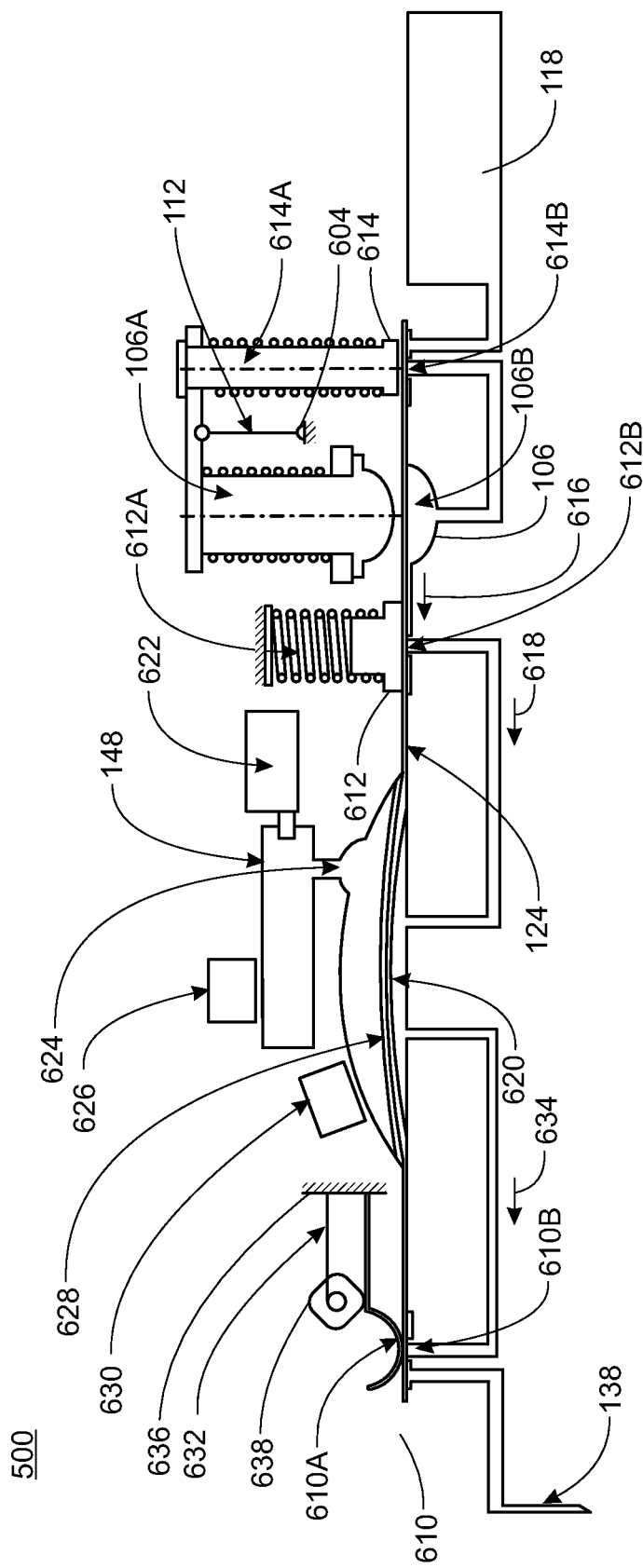
FIG. 21 is a diagrammatic view of a fluid path within the infusion pump assembly of FIG. 16.

Referring also to FIGS. 16-18, there is shown an alternative-embodiment infusion pump assembly 500. As with pump assembly 100, 100', infusion pump assembly 500 may include reusable housing assembly 502 and disposable housing assembly 504.

In a fashion similar to reusable housing assembly 402, reusable housing assembly 502 may include a mechanical control assembly (that includes at least one pump assembly and at least one valve assembly). Reusable housing assembly 502 may also include an electrical control assembly that is configured to provide control signals to the mechanical control assembly and effectuate the delivery of an infusible fluid to a user. The valve assembly may be configured to control the flow of the infusible fluid through a fluid path and the pump assembly may be configured to pump the infusible fluid from the fluid path to the user In a fashion similar to disposable housing assembly 404, disposable housing assembly 504 may be configured for a single use or for use for a specified period of time, e.g., e.g., three days or any other amount of time. Disposable housing assembly 504 may be configured such that any components in infusion pump assembly 500 that come in contact with the infusible fluid are disposed on and/or within disposable housing assembly 504.

In this particular embodiment of the infusion pump assembly, infusion pump assembly 500 may include switch assembly 506 positioned about the periphery of infusion pump assembly 500. For example, switch assembly 506 may be positioned along a radial edge of infusion pump assembly 500, which may allow for easier use by a user. Switch assembly 506 may be covered with a waterproof membrane and/or an o-ring or other sealing mechanism may be included on the stem 507 of the switch assembly 506 configured to prevent the infiltration of water into infusion pump assembly 500. However, in some embodiments, switch assembly 506 may include an overmolded rubber button, thus providing functionality as a waterproof seal without the use of a waterproof membrane or an o-ring. However, in still other embodiments, the overmolded rubber button may additionally be covered by a waterproof membrane and/or include an o-ring. Reusable housing assembly 502 may include main body portion 508 (housing the above-described mechanical and electrical control assemblies) and locking ring assembly 510 that may be configured to rotate about main body portion 508 (in the direction of arrow 512).

In a fashion similar to reusable housing assembly 402 and disposable housing assembly 404, reusable housing assembly 502 may be configured to releasably engage disposable housing assembly 504. Such releasable engagement may be accomplished by a screw-on, a twist-lock or a compression fit configuration, for example. In an embodiment in which a twist-lock configuration is utilized, the user of infusion pump assembly 500 may first properly position reusable housing assembly 502 with respect to disposable housing assembly 504 and may then rotate locking ring assembly 510 (in the direction of arrow 512) to releasably engage reusable housing assembly 502 with disposable housing assembly 404.

As locking ring assembly 510 included within infusion pump assembly 500 may be taller (i.e., as indicated by arrow 514) than locking ring assembly 410, locking ring assembly 510 may include a passage 516 through which button 506 may pass. Accordingly, when assembling reusable housing assembly 502, locking ring assembly 510 may be installed onto main body portion 508 (in the direction of arrow 518). Once locking ring assembly 510 is installed onto main body portion 508, one or more locking tabs (not shown) may prevent locking ring assembly 510 from being removed from main body portion 508. The portion of switch assembly 506 that protrudes through passage 516 may then be pressed into main body portion 508 (in the direction of arrow 520), thus completing the installation of switch assembly 506.

Although button 506 is shown in various locations on infusion pump assembly 500, button 506, in other embodiments, may be located anywhere desirable on infusion pump assembly 500.

Through the use of locking ring assembly 510, reusable housing assembly 502 may be properly positioned with respect to disposable housing assembly 504 and then releasably engaged by rotating locking ring assembly 510, thus eliminating the need to rotate reusable housing assembly 502 with respect to disposable housing assembly 504. Accordingly, reusable housing assembly 502 may be properly aligned with disposable housing assembly 504 prior to engagement, and such alignment may not be disturbed during the engagement process. Locking ring assembly 510 may include a latching mechanism (not shown) that prevents the rotation of locking ring assembly 510 until reusable housing assembly 502 and disposable housing assembly 504 are properly positioned with respect to each other. Passage 516 may be elongated to allow for the movement of locking ring 510 about switch assembly 506.

Referring also to FIGS. 19A-19B & 20-21, there are shown various views of infusion pump assembly 500, which is shown to include reusable housing assembly 502, switch assembly 506, and main body portion 508. As discussed above, main body portion 508 may include a plurality of components, examples of which may include but are not limited to volume sensor assembly 148, printed circuit board 600, vibration motor assembly 602, shape memory actuator anchor 604, switch assembly 506, battery 606, antenna assembly 608, pump assembly 106, measurement valve assembly 610, volume sensor valve assembly 612 and reservoir valve assembly 614. To enhance clarity, printed circuit board 600 has been removed from FIG. 19B to allow for viewing of the various components positioned beneath printed circuit board 600.

The various electrical components that may be electrically coupled with printed circuit board 600 may utilize spring-biased terminals that allow for electrical coupling without the need for soldering the connections. For example, vibration motor assembly 602 may utilize a pair of spring-biased terminals (one positive terminal and one negative terminal) that are configured to press against corresponding conductive pads on printed circuit board 600 when vibration motor assembly 602 is positioned on printed circuit board 600. However, in the exemplary embodiment, vibration motor assembly 602 is soldered directly to the printed circuit board.

As discussed above, volume sensor assembly 148 may be configured to monitor the amount of fluid infused by infusion pump assembly 500. For example, volume sensor assembly 148 may employ acoustic volume sensing, which is the subject of U.S. Pat. Nos. 5,575,310 and 5,755,683 assigned to DEKA Products Limited Partnership, as well as the U.S. Patent Application Publication Nos. US 2007/0228071 A1, US 2007/0219496 A1, US 2007/0219480 A1, US 2007/0219597 A1, the entire disclosures of all of which are incorporated herein by reference.

Vibration motor assembly 602 may be configured to provide a vibration-based signal to the user of infusion pump assembly 500. For example, in the event that the voltage of battery 606 (which powers infusion pump assembly 500) is below the minimum acceptable voltage, vibration motor assembly 602 may vibrate infusion pump assembly 500 to provide a vibration-based signal to the user of infusion pump assembly 500. Shape memory actuator anchor 604 may provide a mounting point for the above-described shape memory actuator (e.g. shape memory actuator 112). As discussed above, shape memory actuator 112 may be, for example, a conductive shape-memory alloy wire that changes shape with temperature. The temperature of shape-memory actuator 112 may be changed with a heater, or more conveniently, by application of electrical energy. Accordingly, one end of shape memory actuator 112 may be rigidly affixed (i.e., anchored) to shape memory actuator anchor 604 and the other end of shape memory actuator 112 may be applied to e.g. a valve assembly and/or a pump actuator. Therefore, by applying electrical energy to shape memory actuator 112, the length of shape memory actuator 112 may be controlled and, therefore, the valve assembly and/or the pump actuator to which it is attached may be manipulated.

Antenna assembly 608 may be configured to allow for wireless communication between e.g. infusion pump assembly 500 and remote control assembly 300 (FIG. 11). As discussed above, remote control assembly 300 may allow the user to program infusion pump assembly 500 and e.g. configure bolus infusion events. As discussed above, infusion pump assembly 500 may include one or more valve assemblies configured to control the flow of the infusible fluid through a fluid path (within infusion pump assembly 500) and pump assembly 106 may be configured to pump the infusible fluid from the fluid path to the user. In this particular embodiment of infusion pump assembly 500, infusion pump assembly 500 is shown to include three valve assemblies, namely measurement valve assembly 610, volume sensor valve assembly 612, and reservoir valve assembly 614.

Figure 22A:
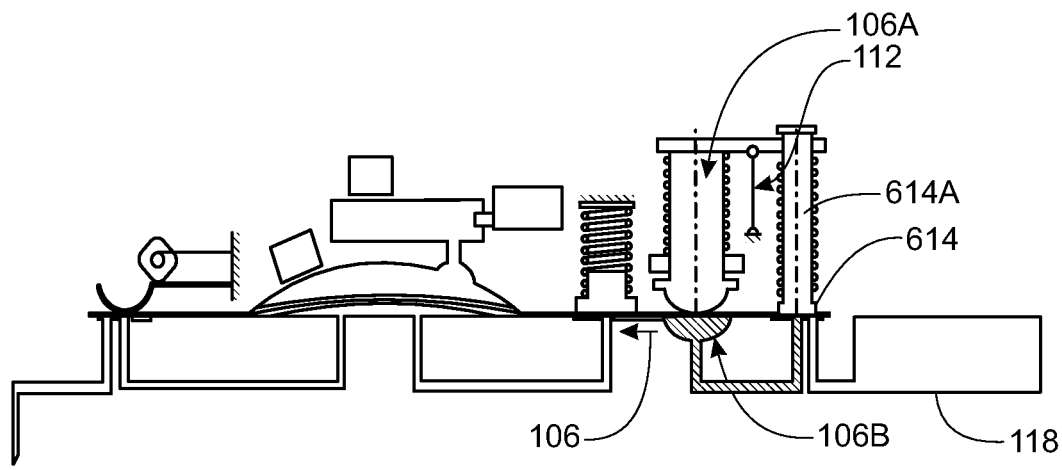
FIGS. 22A-22C are diagrammatic views of a fluid path within the infusion pump assembly of FIG. 16.

As discussed above and referring also to FIG. 21, the infusible fluid may be stored within reservoir 118. In order to effectuate the delivery of the infusible fluid to the user, the processing logic (not shown) included within infusion pump assembly 500 may energize shape memory actuator 112, which may be anchored on one end using shape memory actuator anchor 604. Referring also to FIG. 22A, shape memory actuator 112 may result in the activation of pump assembly 106 and reservoir valve assembly 614. Reservoir valve assembly 614 may include reservoir valve actuator 614A and reservoir valve 614B, and the activation of reservoir valve assembly 614 may result in the downward displacement of reservoir valve actuator 614A and the closing of reservoir valve 614B, resulting in the effective isolation of reservoir 118. Further, pump assembly 106 may include pump plunger 106A and pump chamber 106B and the activation of pump assembly 106 may result in pump plunger 106A being displaced in a downward fashion into pump chamber 106B and the displacement of the infusible fluid (in the direction of arrow 616).

Figure 22B:
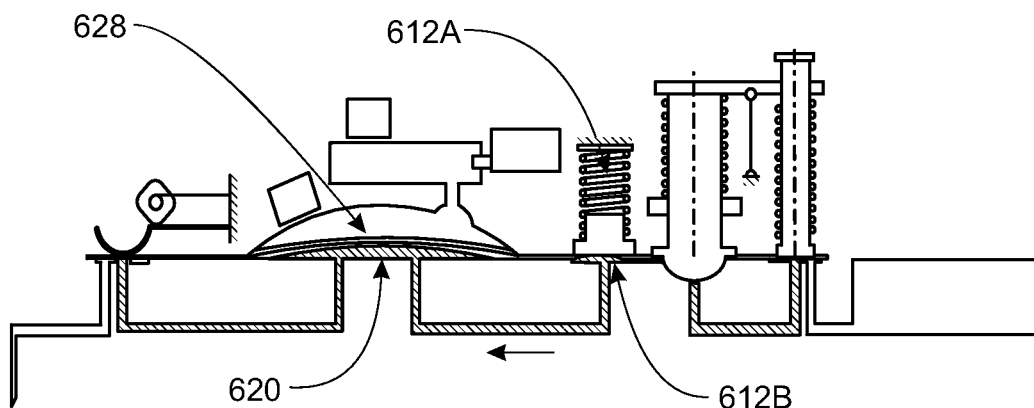

Volume sensor valve assembly 612 may include volume sensor valve actuator 612A and volume sensor valve 612B. Referring also to FIG. 22B, volume sensor valve actuator 612A may be closed via a spring assembly that provides mechanical force to seal volume sensor valve 612B. However, when pump assembly 106 is activated, if the displaced infusible fluid is of sufficient pressure to overcome the mechanical sealing force of volume sensor valve assembly 612, the displacement of the infusible fluid occurs in the direction of arrow 618. This may result in the filling of volume sensor chamber 620 included within volume sensor assembly 148. Through the use of speaker assembly 622, port assembly 624, reference microphone 626, spring diaphragm 628, invariable volume microphone 630, volume sensor assembly 148 may determine the volume of infusible fluid included within volume sensor chamber 620.

Figure 22C:
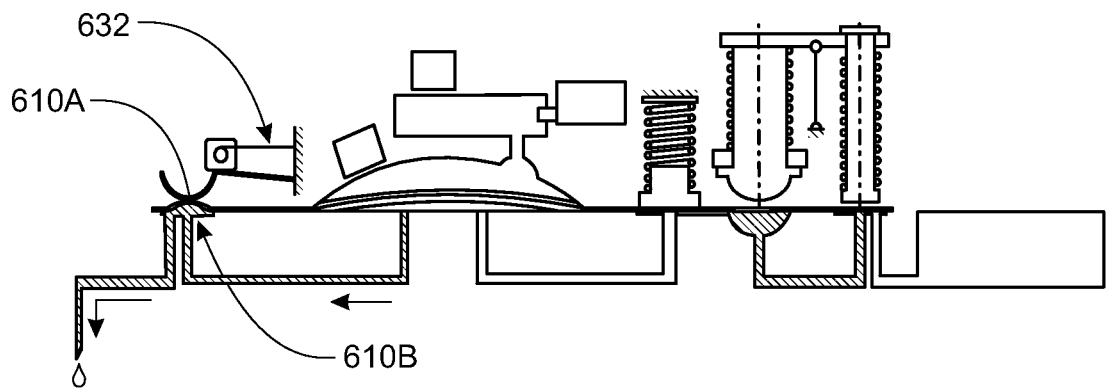

Referring also to FIG. 22C, once the volume of infusible fluid included within volume sensor chamber 620 is calculated, shape memory actuator 632 may be energized, resulting in the activation of measurement valve assembly 610, which may include measurement valve actuator 610A and measurement valve 610B. Once activated and due to the mechanical energy asserted on the infusible fluid within volume sensor chamber 620 by spring diaphragm 628, the infusible fluid within volume sensor chamber 620 may be displaced (in the direction of arrow 634) through disposable cannula 138 and into the body of the user.

Figure 23:
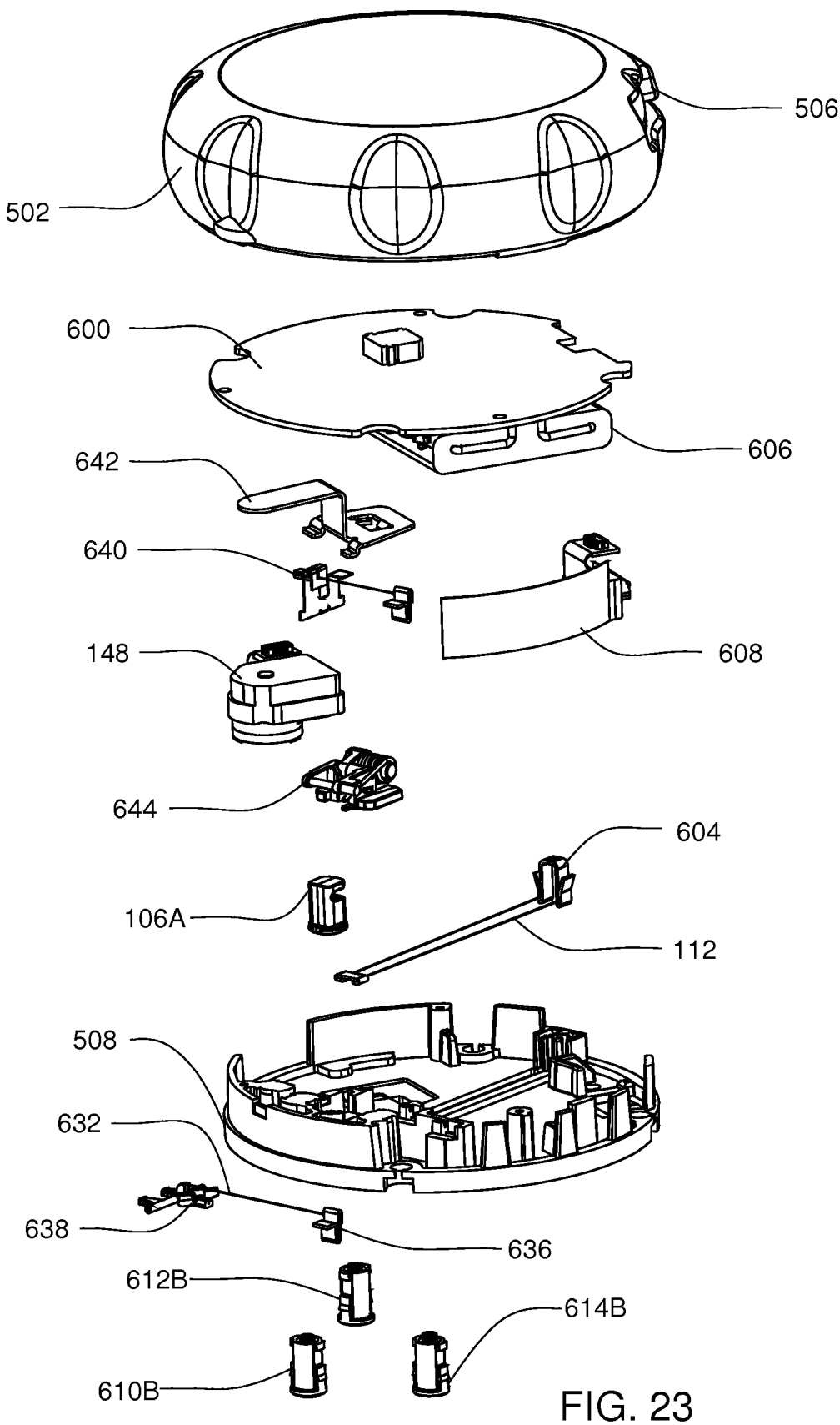
FIG. 23 is an exploded view of various components of the infusion pump assembly of FIG. 16.
Figure 24:
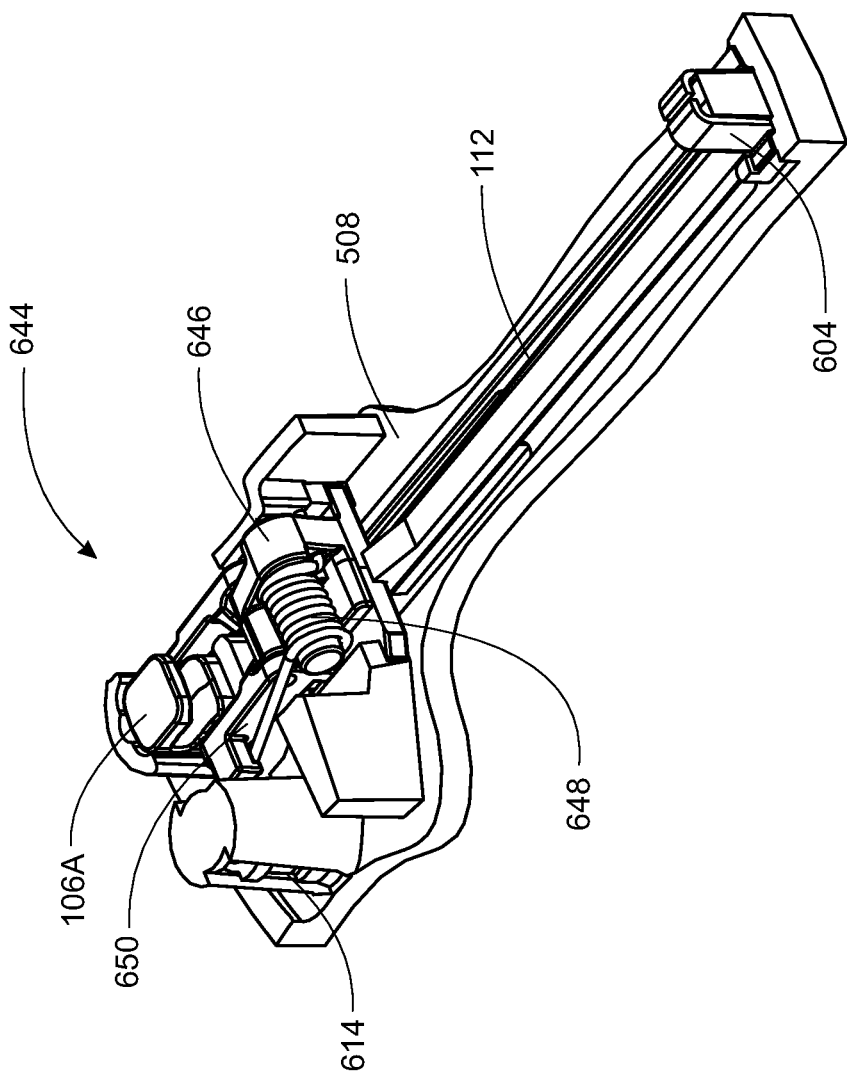
FIG. 24 is a cutaway isometric view of a pump assembly of the infusion pump assembly of FIG. 16.
Figure 25A:
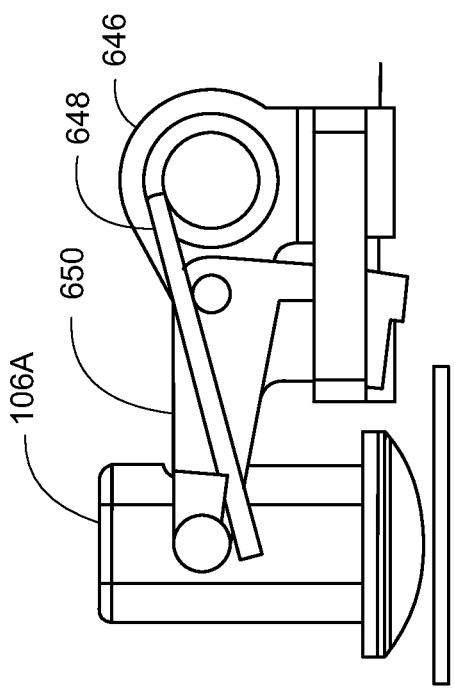
FIGS. 25A-25D are other isometric views of the pump assembly of FIG. 24.
Figure 25B:
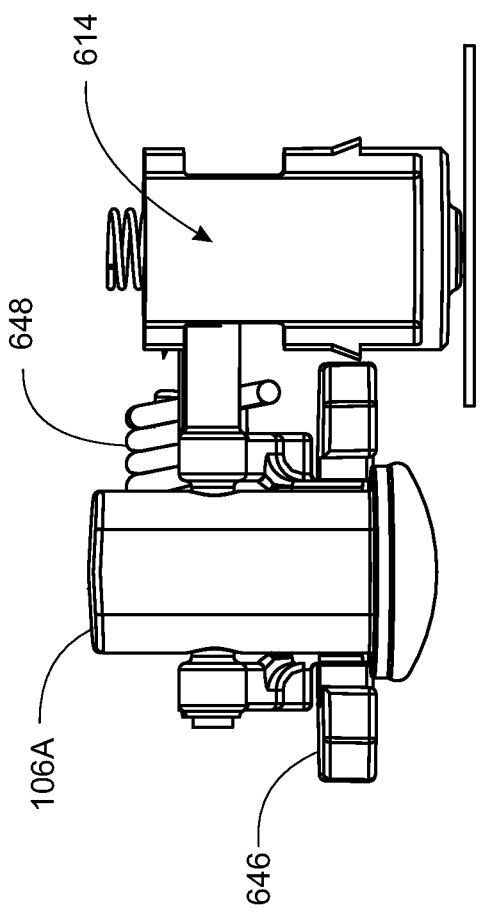
Figure 25C:
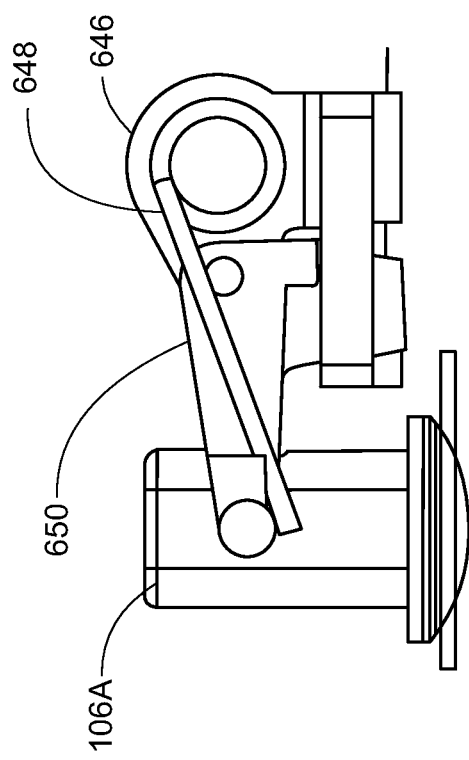
Figure 25D:
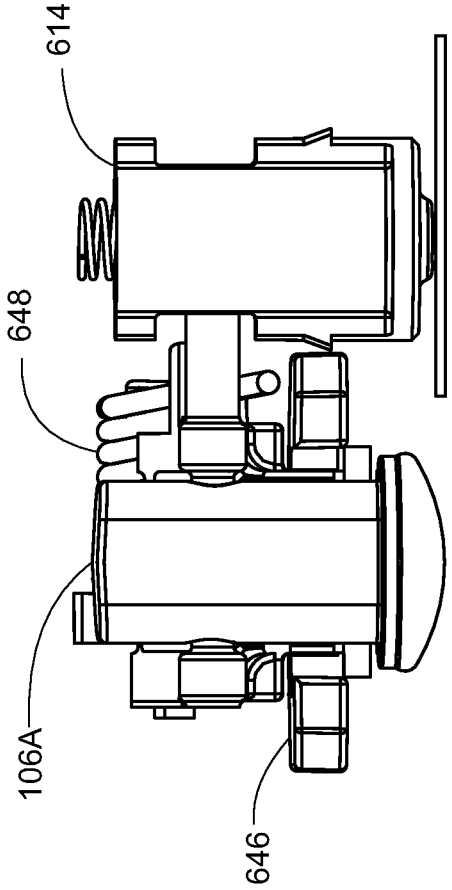
Figure 26B:
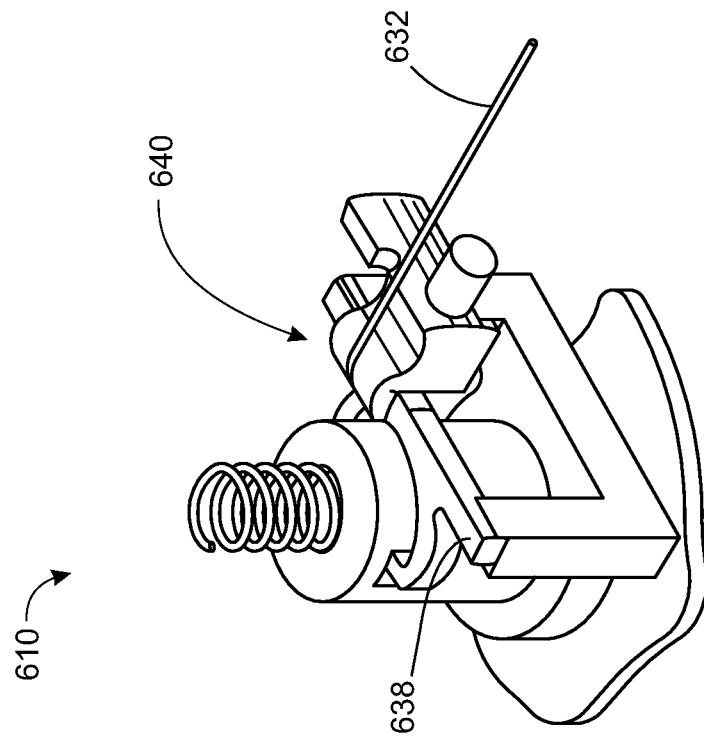
FIG. 26A-26B are isometric views of a measurement valve assembly of the infusion pump assembly of FIG. 16.
Figure 26A:
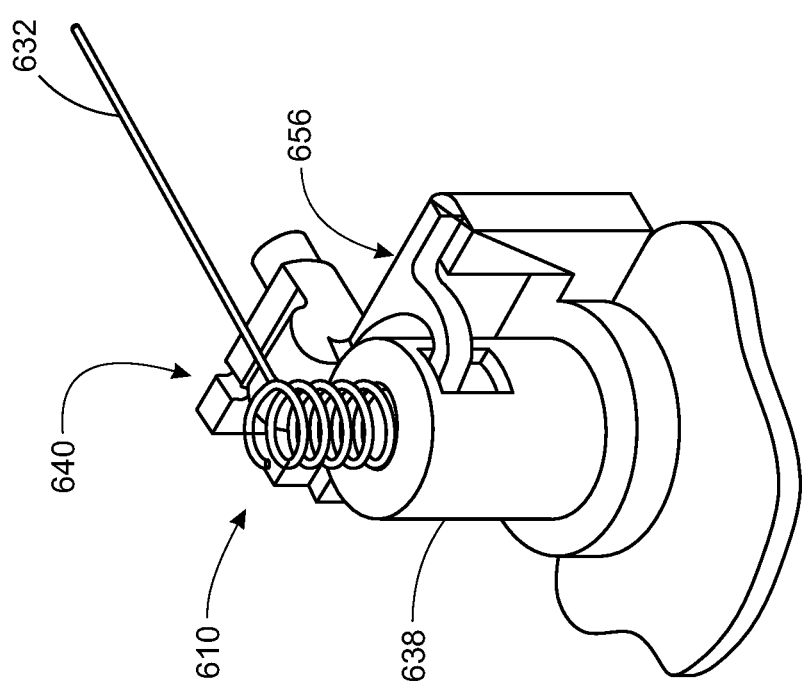
Figure 27B:
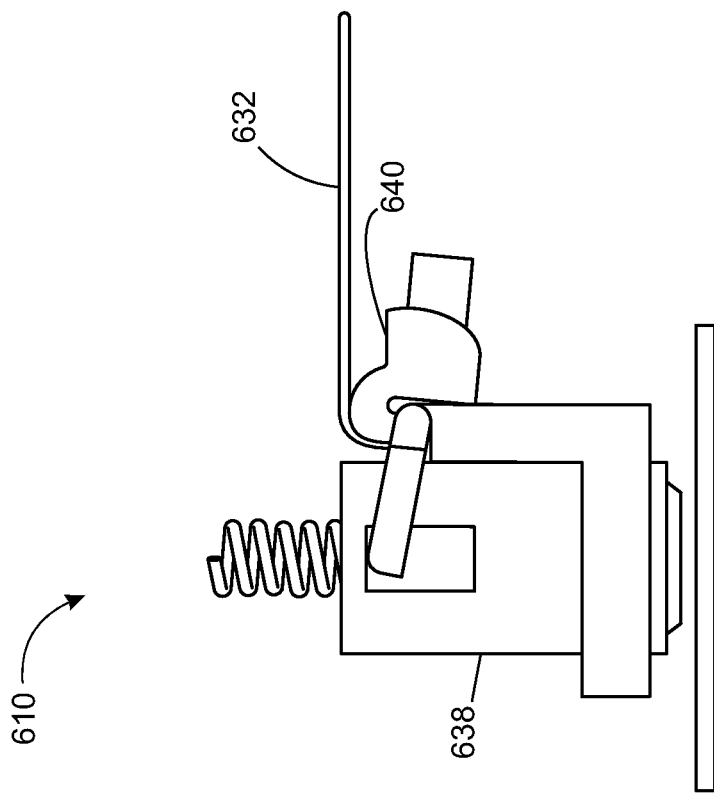
FIG. 27A-27B are side views of the measurement valve assembly of FIGS. 26A-26B.
Figure 27A:
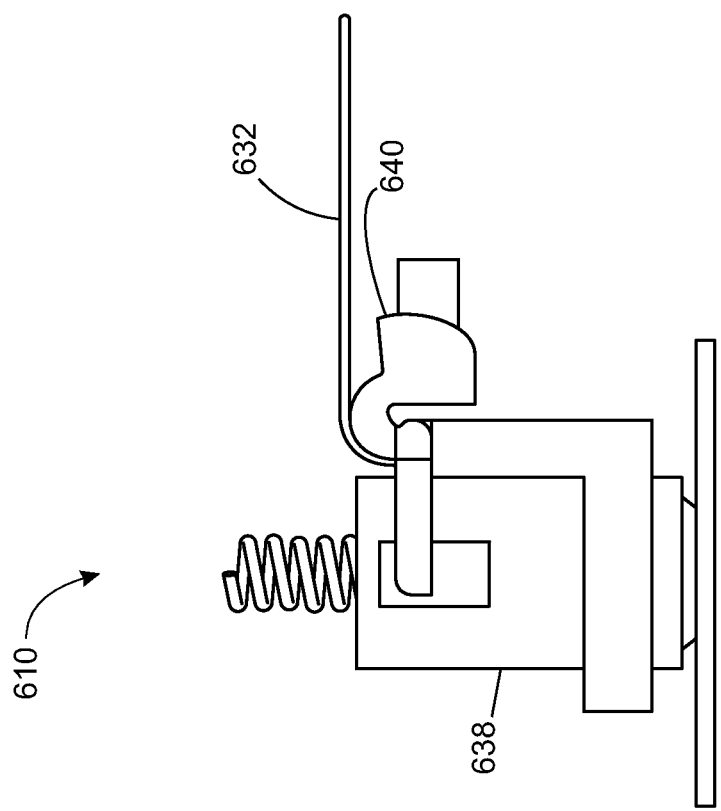
Figure 28A:
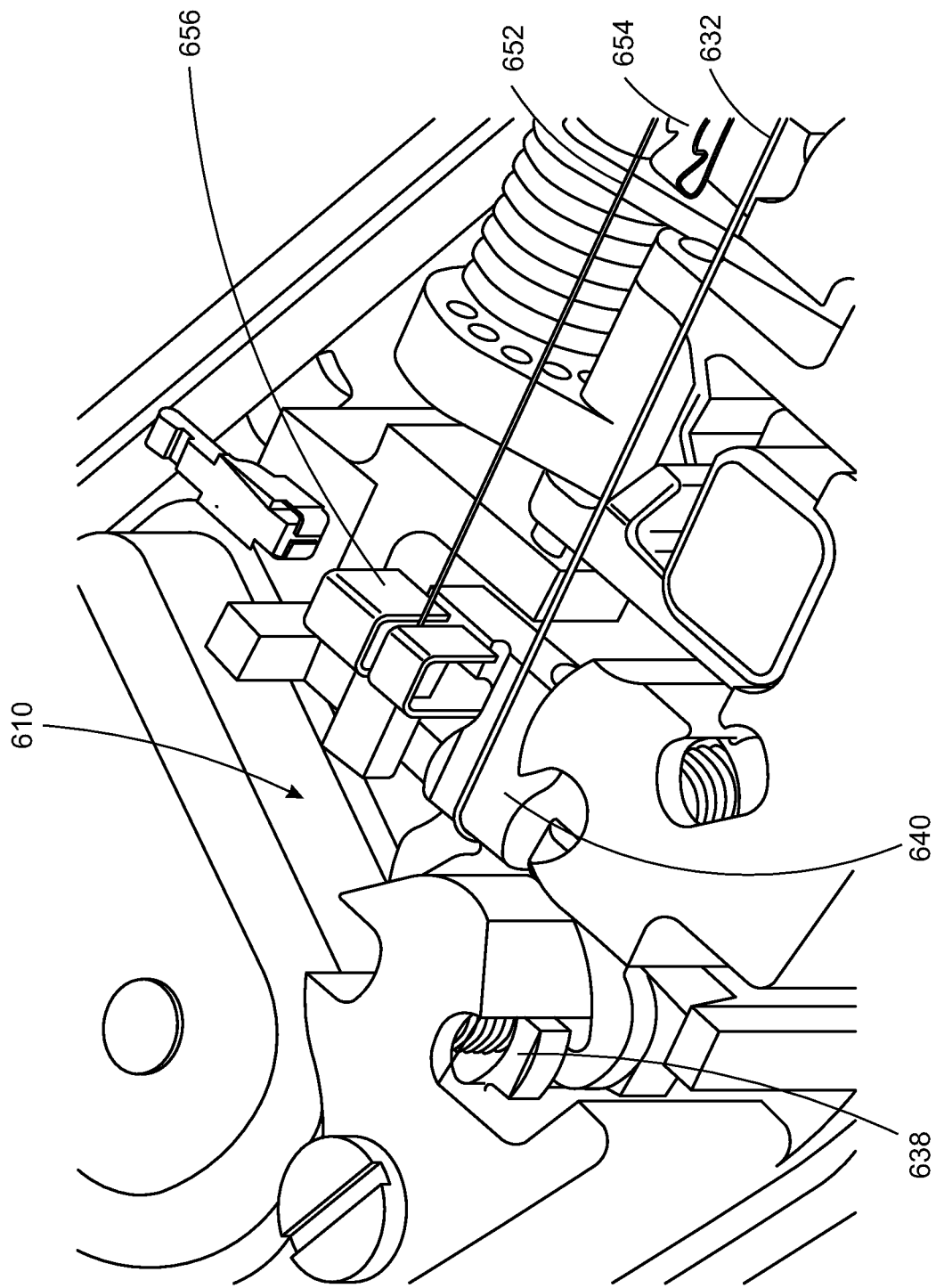
FIGS. 28A-28D are views of a measurement valve assembly of the infusion pump assembly of FIG. 16.
Figure 28B:
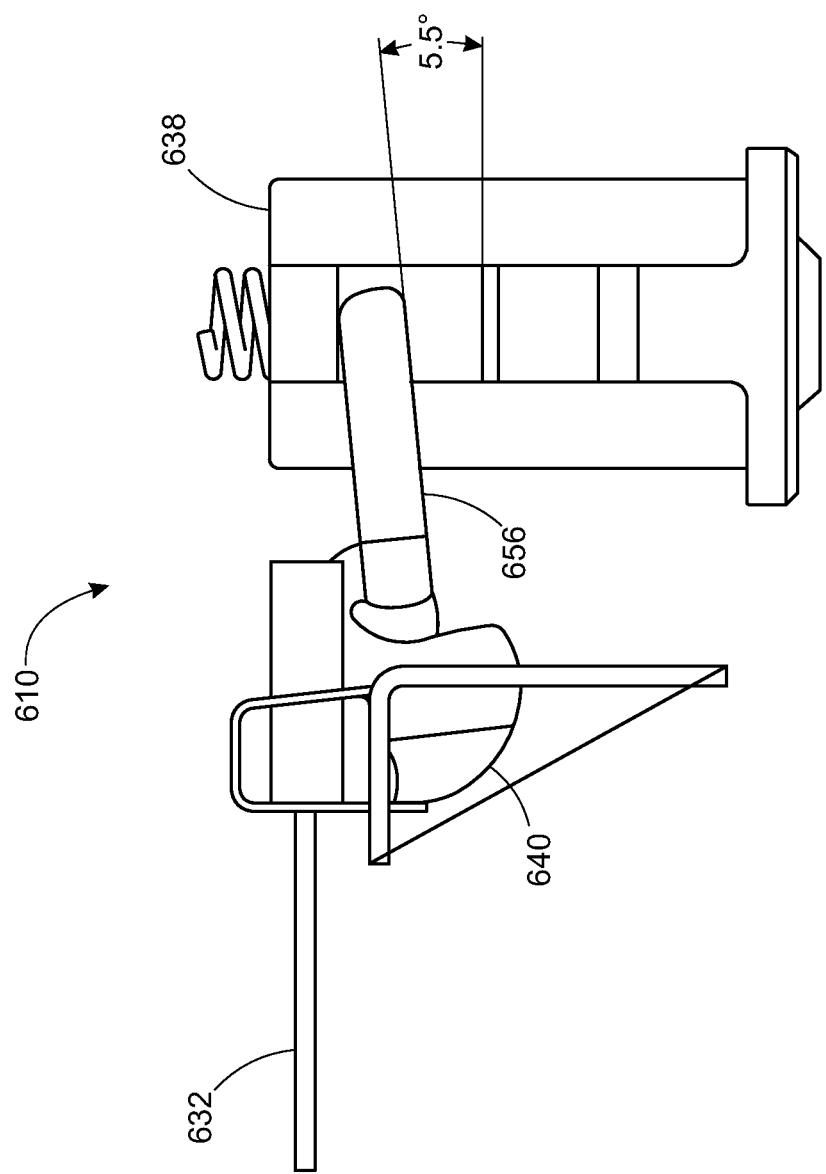
Figure 28C:
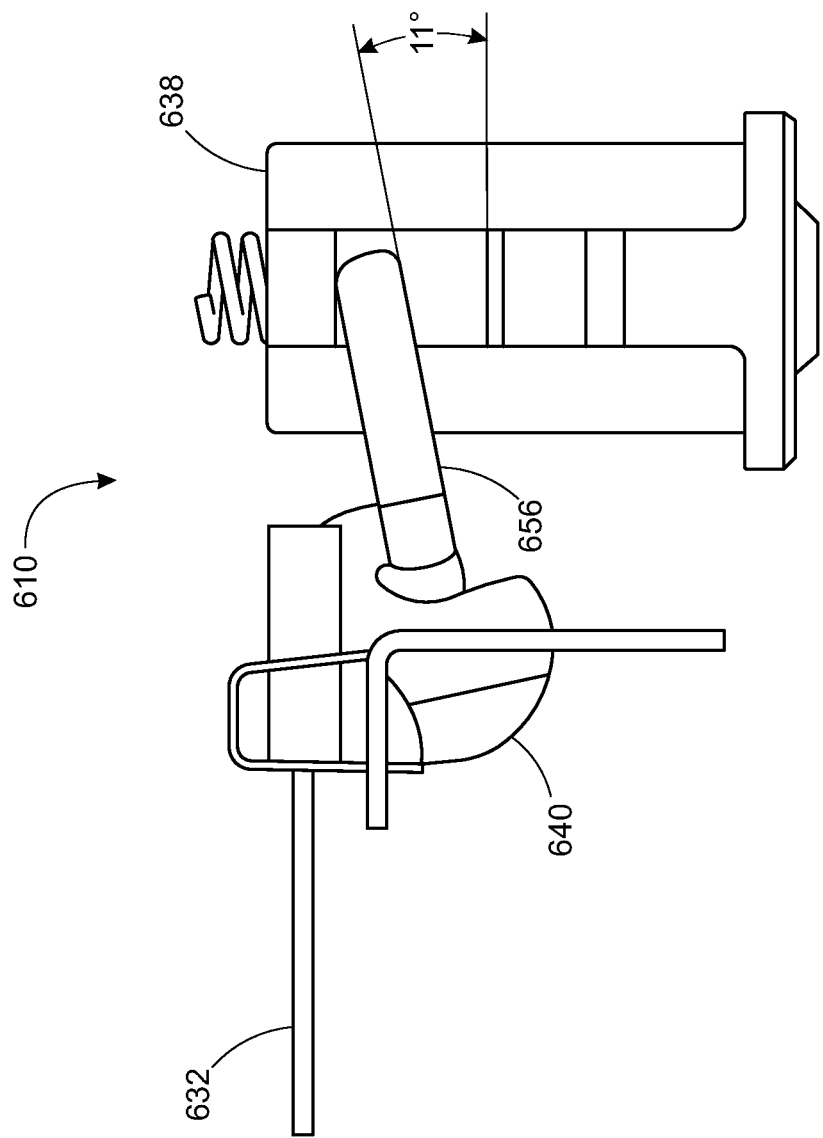
Figure 28D:
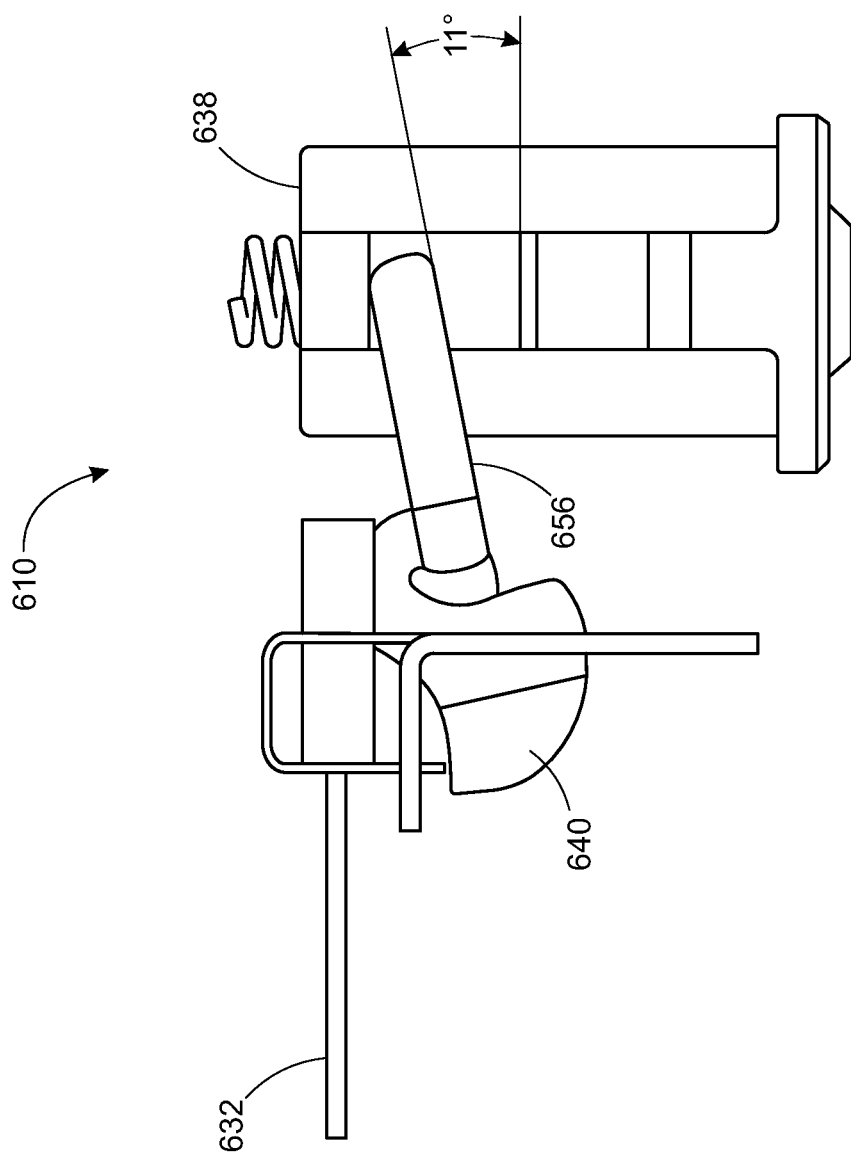

Referring also to FIG. 23, there is shown an exploded view of infusion pump assembly 500. Shape memory actuator 632 may be anchored (on a first end) to shape memory actuator anchor 636. Additionally, the other end of shape memory actuator 632 may be used to provide mechanical energy to valve assembly 638, which may activate measurement valve assembly 610. Volume sensor assembly spring retainer 642 may properly position volume sensor assembly 148 with respect to the various other components of infusion pump assembly 500. Valve assembly 638 may be used in conjunction with shape memory actuator 112 to activate pump plunger 106A. Measurement valve 610B, volume sensor valve 612B and/or reservoir valve 614B may be self-contained valves that are configured to allow for installation during assembly of infusion pump assembly 500 by pressing the valves upward into the lower surface of main body portion 508.

Referring also to FIG. 24 & FIGS. 25A-25D, there is shown a more-detailed view of pump assembly 106. Pump actuator assembly 644 may include pump actuator support structure 646, bias spring 648, and lever assembly 650.

Referring also to FIGS. 26A-26B & FIGS. 27A-27B, there is shown a more-detailed view of measurement valve assembly 610. As discussed above, valve assembly 638 may activate measurement valve assembly 610.

Referring also to FIGS. 28A-28D, infusion pump assembly 500 may include measurement valve assembly 610. As discussed above, valve assembly 638 may be activated via shape memory actuator 632 and actuator assembly 640. Accordingly, to infuse the quantity of infusible fluid stored within volume sensor chamber 620, shape memory actuator 632 may need to activate valve assembly 638 for a considerable period of time (e.g. one minute or more). As this would consume a considerable amount of power from battery 606, measurement valve assembly 610 may allow for the temporary activation of valve assembly 638, at which point measurement valve latch 656 may prevent valve assembly 638 from returning to its non-activated position. Shape memory actuator 652 may be anchored on a first end using electrical contact 654. The other end of shape memory actuator 652 may be connected to a valve latch 656. When shape memory actuator 652 is activated, shape memory actuator 652 may pull valve latch 656 forward and release valve assembly 638. As such, measurement valve assembly 610 may be activated via shape memory actuator 632. Once measurement valve assembly 610 has been activated, valve latch 656 may automatically latch valve assembly 638 in the activated position. Actuating shape memory actuator 652 may pull valve latch 656 forward and release valve assembly 638. Assuming shape memory actuator 632 is no longer activated, measurement valve assembly 610 may move to a de-activated state once valve latch 656 has released valve assembly 638. Accordingly, through the use of measurement valve assembly 610, shape memory actuator 632 does not need to be activated during the entire time that it takes to infuse the quantity of infusible fluid stored within volume sensor chamber 620.

As discussed above, the above-described infusion pump assemblies (e.g., infusion pumps assemblies 100, 100', 400, 500) may include an external infusion set 134 configured to deliver the infusible fluid to a user. External infusion set 134 may include a cannula assembly 136, which may include a needle or a disposable cannula 138, and tubing assembly 140 which may be also referred to as a tubing set. Tubing assembly 140 may be in fluid communication with reservoir 118, for example, by way of the fluid path, and with cannula assembly 138 for example, either directly or by way of a cannula interface 142.

Figure 29:
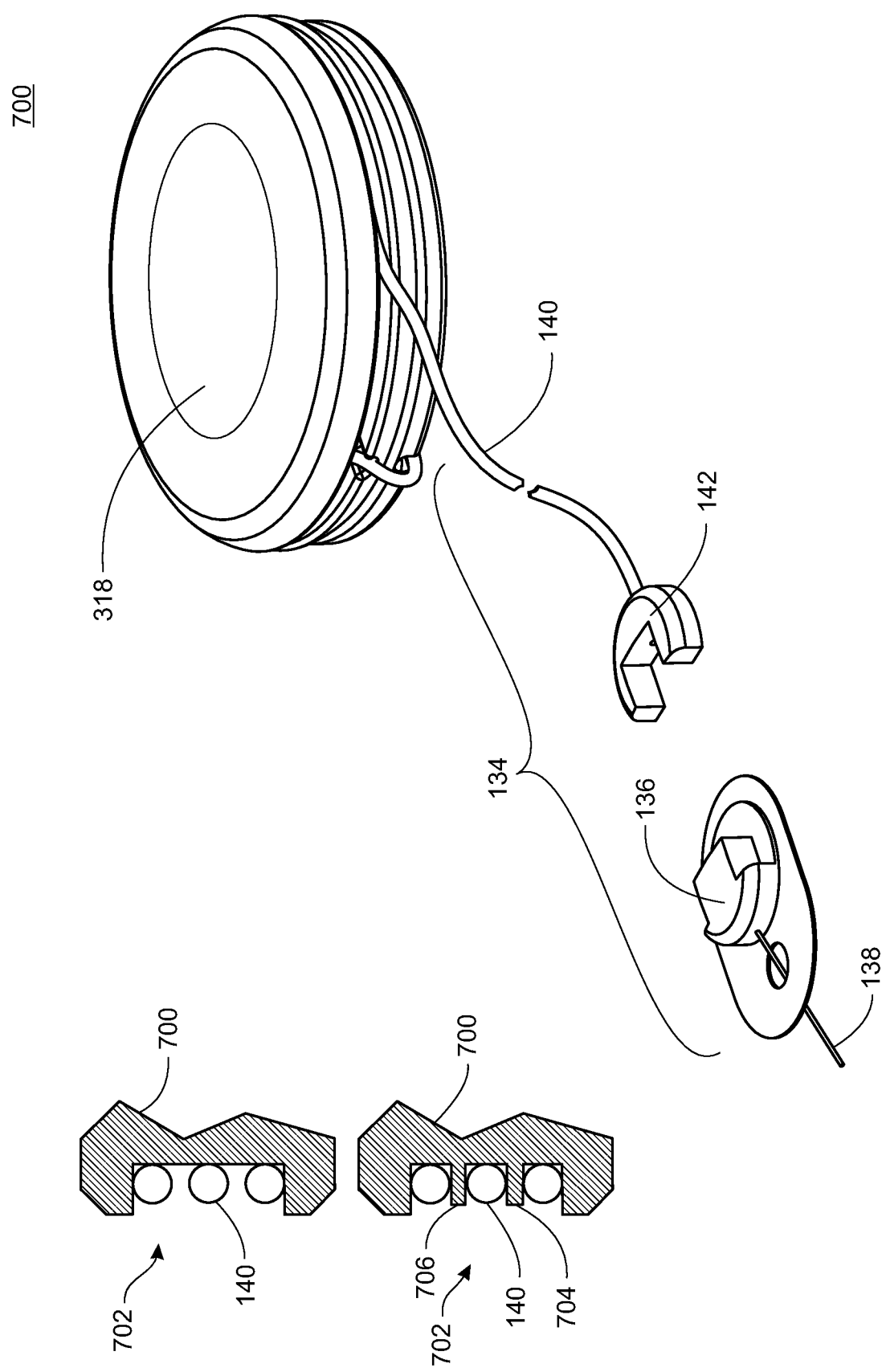
FIG. 29 is an isometric view of an alternative embodiment of the infusion pump assembly of FIG. 1.

Referring also to FIG. 29, there is shown an alternative embodiment infusion pump assembly 700 that is configured to store a portion of tubing assembly 140. Specifically, infusion pump assembly 700 may include peripheral tubing storage assembly 702 that is configured to allow the user to wind a portion of tubing assembly 140 about the periphery of infusion pump assembly 700 (in a manner similar to that of a yoyo). Peripheral tubing storage assembly 702 may be positioned about the periphery of infusion pump assembly 700. Peripheral tubing storage assembly 702 may be configured as an open trough into which a portion of tubing assembly 140 may be wound. Alternatively, peripheral tubing storage assembly 702 may include one or more divider portions 704, 706 that form a plurality of narrower troughs that may be sized to generate an interference fit between the walls of the narrower trough and the exterior surface of the portion of tubing 140. When peripheral tubing storage assembly 705 includes plurality of divider portions 704, 706, the resulting narrower troughs may be wound in a spiral fashion about the periphery of infusion pump assembly 700 (in a manner similar to the thread of a screw).

Figure 30:
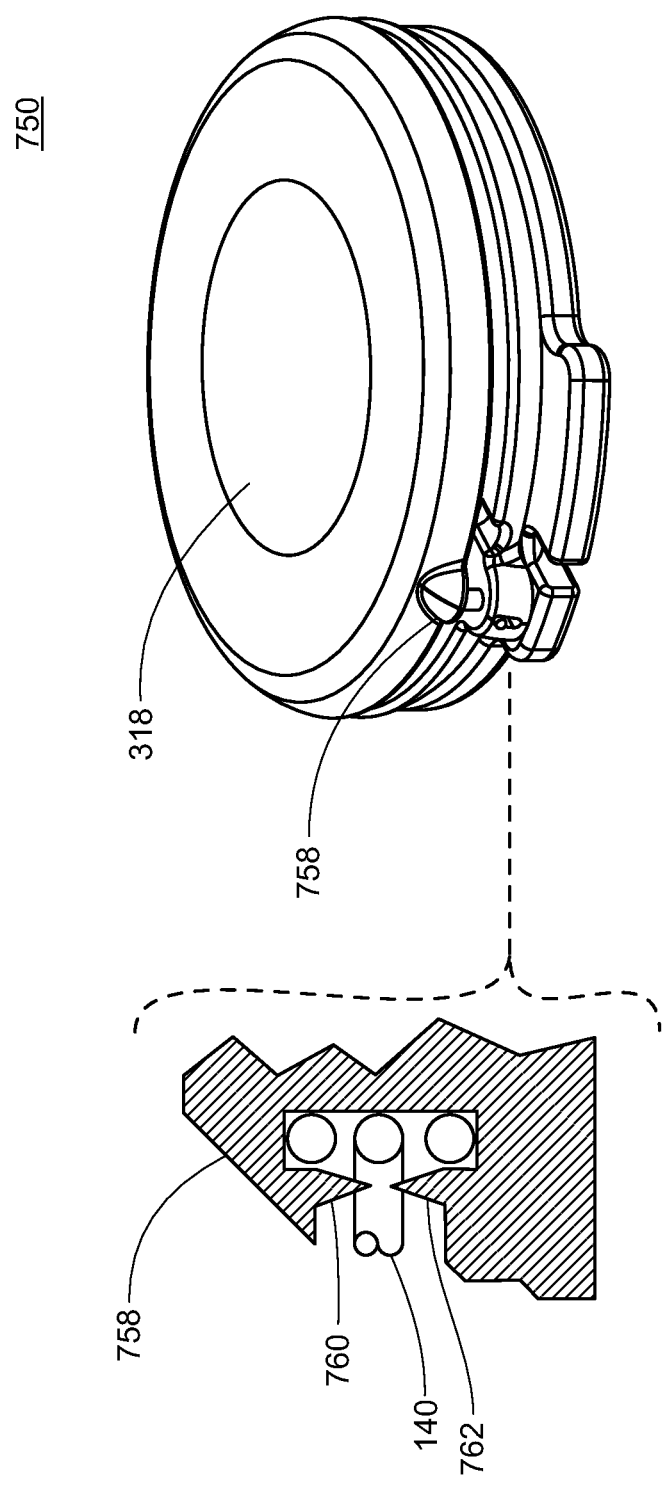
FIG. 30 is an isometric view of an alternative embodiment of the infusion pump assembly of FIG. 1.
Figure 31:
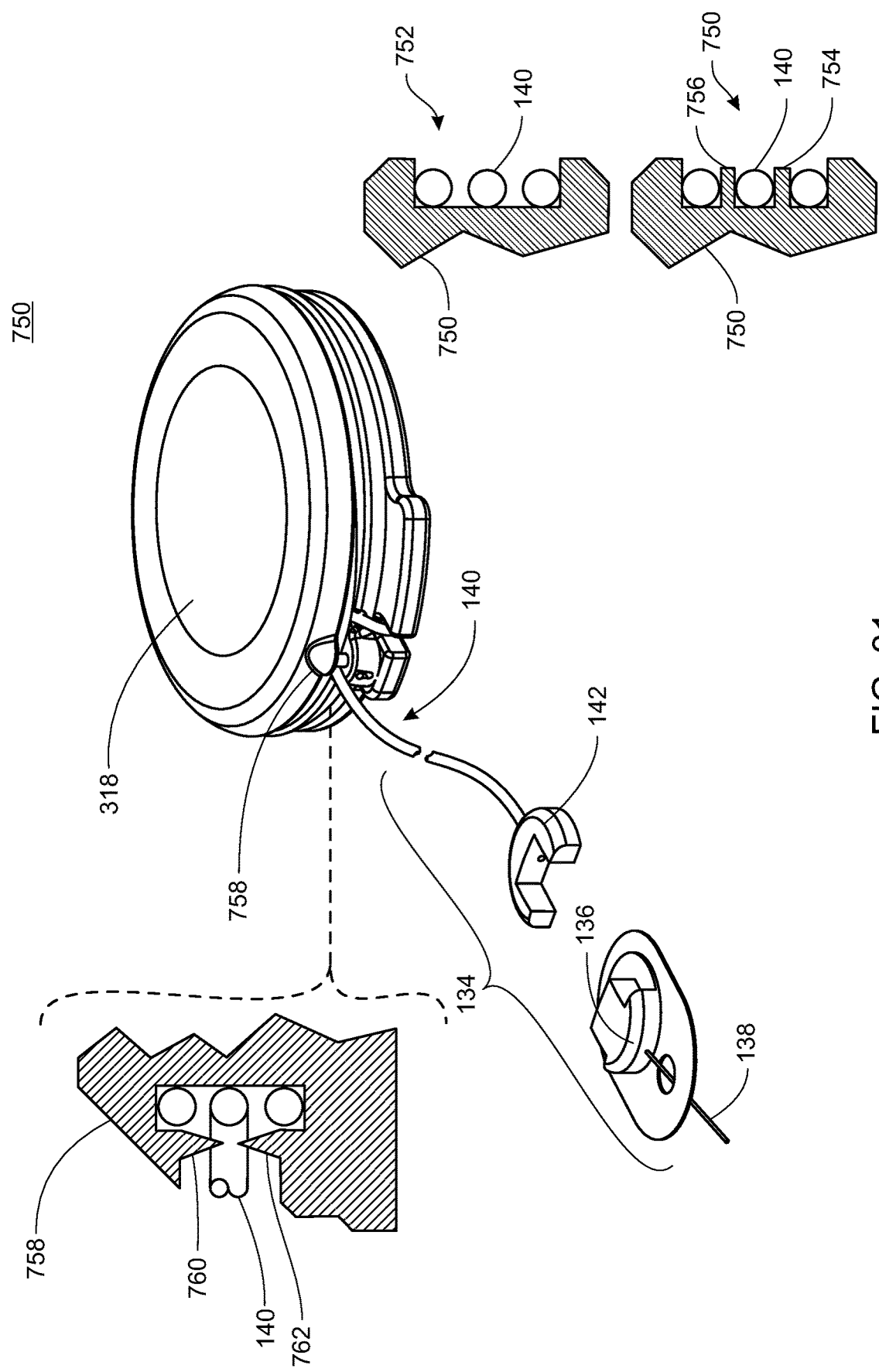
FIG. 31 is another view of the alternative embodiment infusion pump assembly of FIG. 9.

Referring also to FIGS. 30-31, there is shown an alternative embodiment infusion pump assembly 750 that is configured to store a portion of tubing assembly 140. Specifically, infusion pump assembly 750 may include peripheral tubing storage assembly 752 that is configured to allow the user to wind a portion of tubing assembly 140 about the periphery of infusion pump assembly 750 (again, in a manner similar to that of a yoyo). Peripheral tubing storage assembly 752 may be positioned about the periphery of infusion pump assembly 750. Peripheral tubing storage assembly 752 may be configured as an open trough into which a portion of tubing assembly 140 is wound. Alternatively, peripheral tubing storage assembly 752 may include one or more divider portions 754, 756 that form a plurality of narrower troughs that may be sized to generate an interference fit between the walls of the narrower trough and the exterior surface of the portion of tubing 140. When peripheral tubing storage assembly 752 includes plurality of divider portions 754, 756, the resulting narrower trough may be wound in a spiral fashion about the periphery of infusion pump assembly 750 (again, in a manner similar to the thread of a screw).

Infusion pump assembly 750 may include tubing retainer assembly 758. Tubing retainer assembly 758 may be configured to releasably secure tubing assembly 140 so as to prevent tubing assembly 140 from unraveling from around infusion pump assembly 750. In one embodiment of tubing retainer assembly 758, tubing retainer assembly 758 may include downward facing pin assembly 760 positioned above upward facing pin assembly 762. The combination of pin assemblies 760, 762 may define a "pinch point" through which tubing assembly 140 may be pushed. Accordingly, the user may wrap tubing assembly 140 around the periphery of infusion pump assembly 750, wherein each loop of tubing assembly 140 is secured within peripheral tubing storage assembly 752 via tubing retainer assembly 758. In the event that the user wishes to lengthen the unsecured portion of tubing assembly 140, the user may release one loop of tubing assembly 140 from tubing retainer assembly 758. Conversely, in the event that the user wishes to shorten the unsecured portion of tubing assembly 140, the user may secure one additional loop of tubing assembly 140 within tubing retainer assembly 758.

Figure 33:
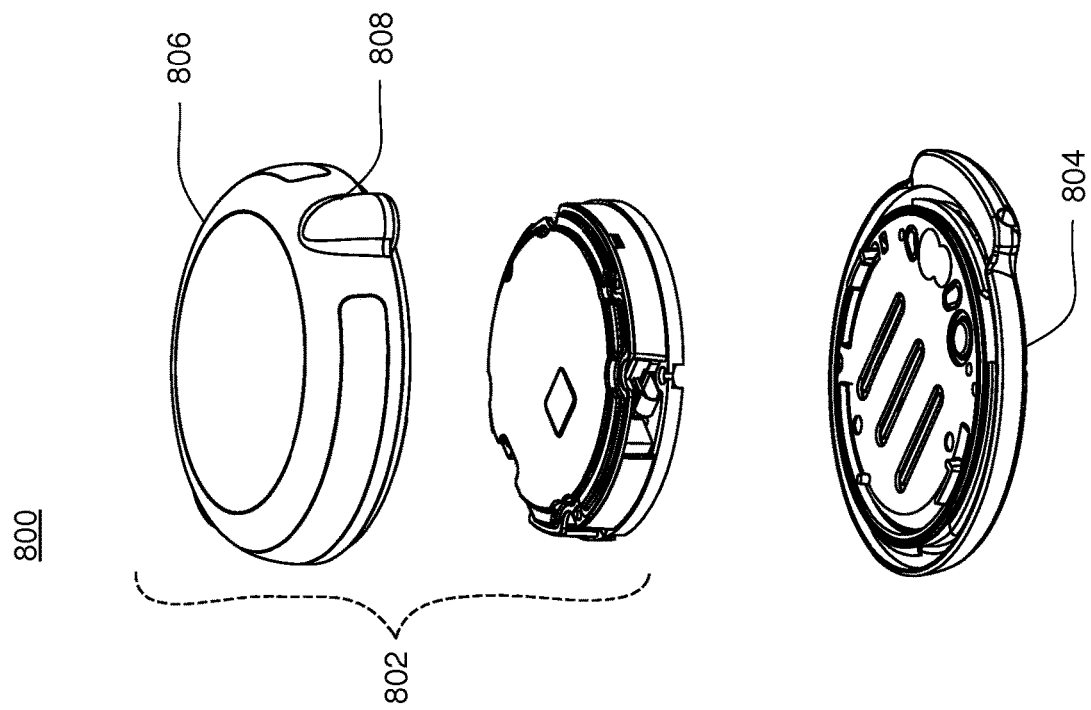
FIG. 33 is another exploded view of the infusion pump assembly of FIG. 32.
Figure 32:
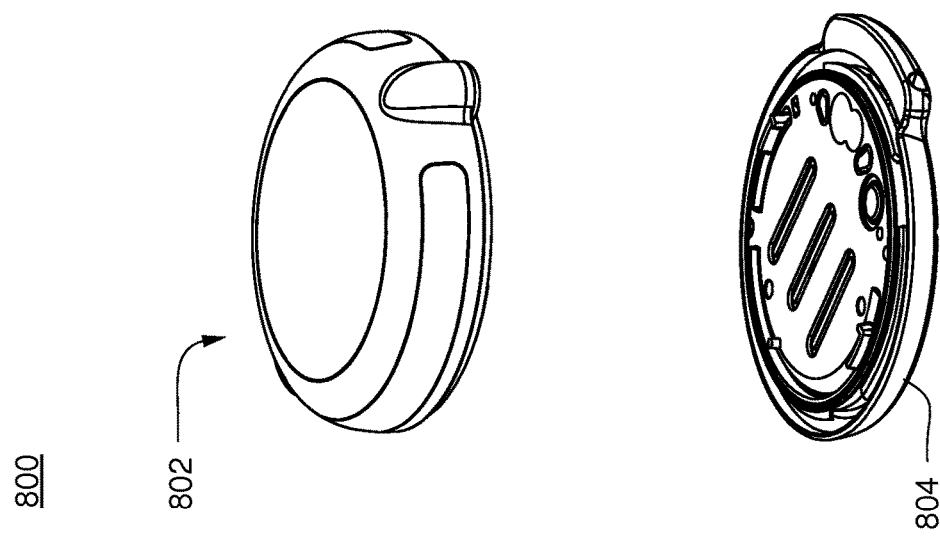
FIG. 32 is an exploded view of another embodiment of an infusion pump assembly.

Referring also to FIGS. 32-33, there is shown an exemplary embodiment of infusion pump assembly 800. As with infusion pump assemblies 100, 100', 400, and 500, infusion pump assembly 800 may include reusable housing assembly 802 and disposable housing assembly 804.

Figure 34A:
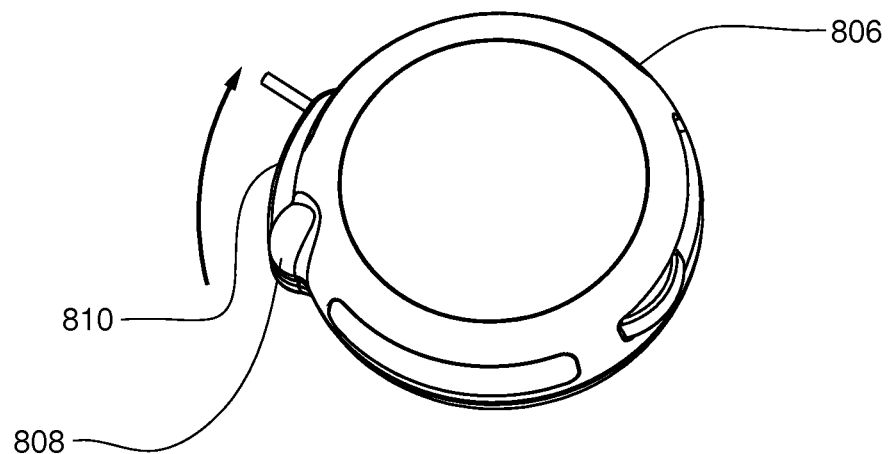
FIGS. 34A-34B depict another embodiment of an infusion pump assembly.
Figure 34B:
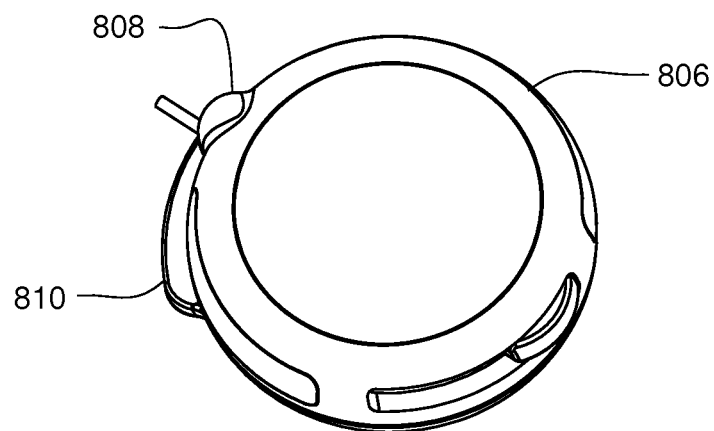

With reference also to FIGS. 34A-34B, in a fashion similar to infusion pump assembly 100, reusable housing assembly 802 may be configured to releasably engage disposable housing assembly 804. Such releasable engagement may be effectuated by a screw-on, twist-lock, or compression fit configuration, for example. Infusion pump assembly 800 may include locking ring assembly 806. For example, reusable housing assembly 802 may be properly positioned relative to disposable housing assembly, and locking ring assembly 806 may be rotated to releasable engage reusable housing assembly 802 and disposable housing assembly 804.

Locking ring assembly 806 may include nub 808, having a spring actuated tab 2980, that may facilitate rotation of locking ring assembly 806. Additionally, the position of nub 808, e.g., relative to tab 810 of disposable housing assembly 804, may provide verification that reusable housing assembly 802 is fully engaged with disposable housing assembly 804. For example, as shown in FIG. 34A, when reusable housing assembly 802 is properly aligned with disposable housing assembly 804, nub 808 may be aligned in a first position relative to tab 810. Upon achieving a fully engaged condition, by rotation locking ring assembly 806, nub 808 may be aligned in a second position relative to tab 810, as shown in FIG. 34B.

Figure 35A:
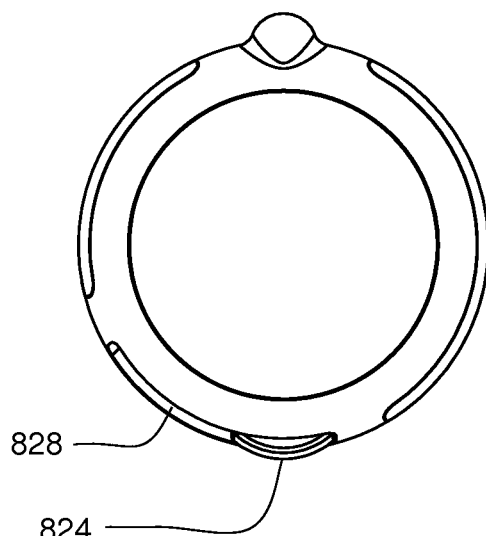
FIGS. 35A-35C are a top view, side view, and bottom view of a reusable housing assembly of the infusion pump assembly of FIG. 32.
Figure 35B:
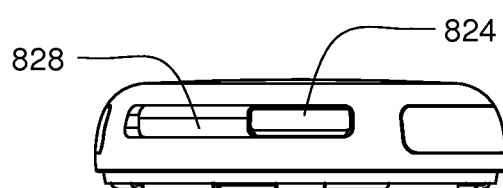
Figure 35C:
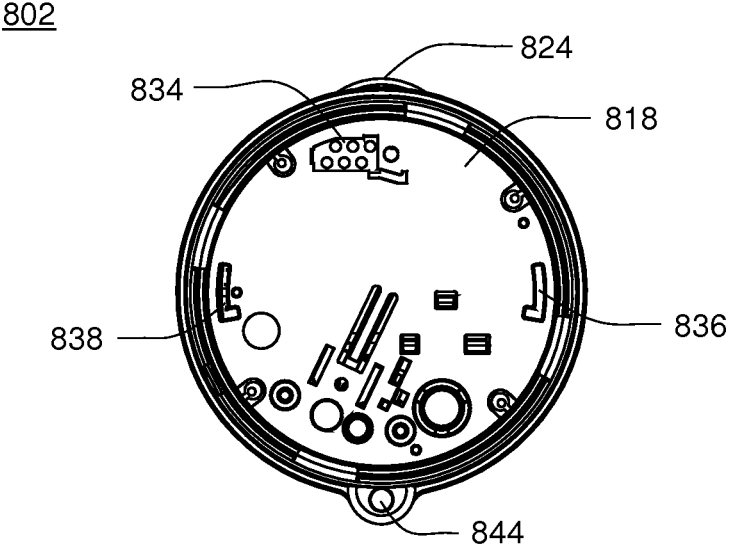
Figure 36:
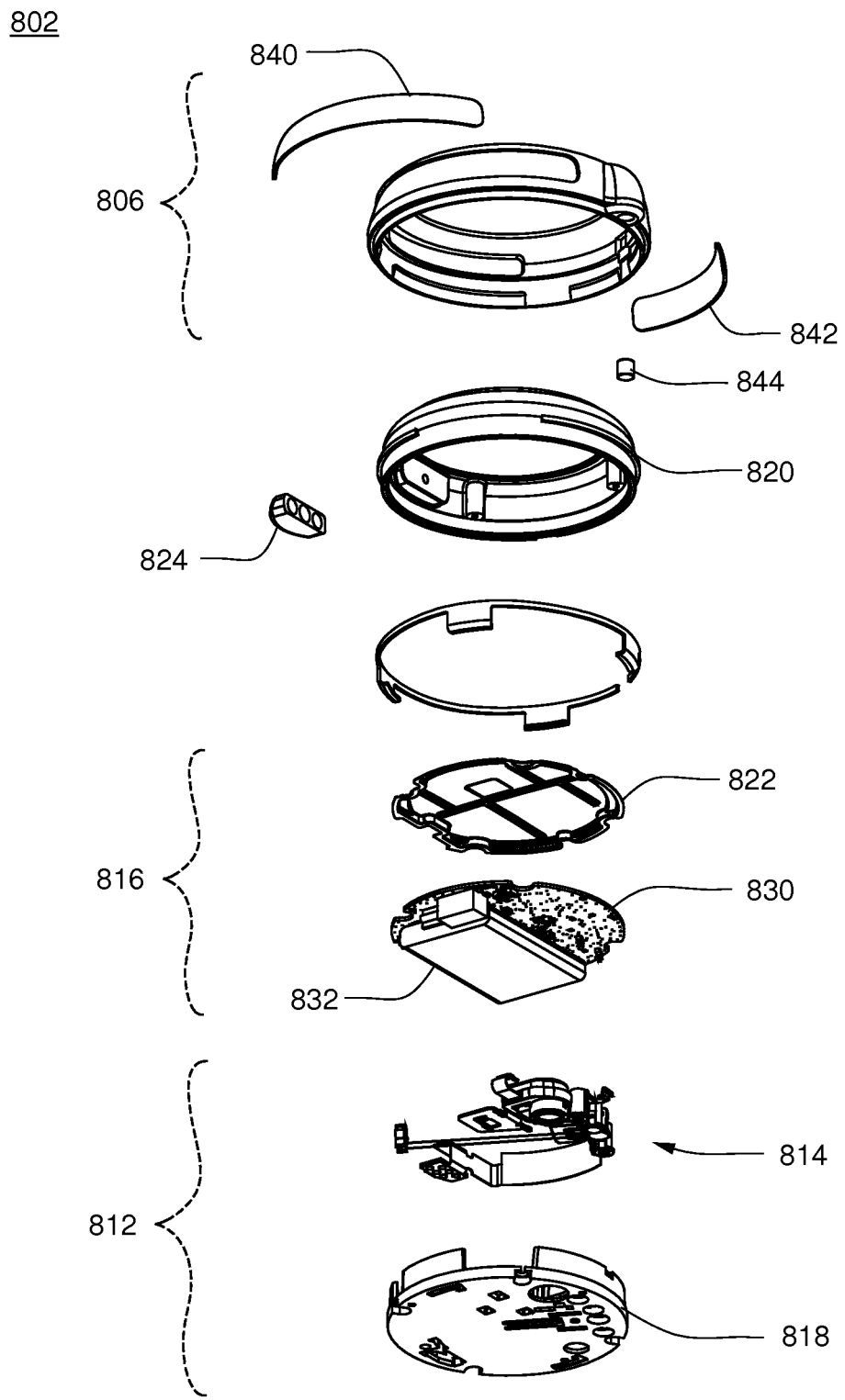
FIG. 36 is an exploded view of the reusable housing assembly of FIGS. 35A-35C.

Referring also to FIGS. 35A-35C and FIGS. 36-38A, in a fashion similar to reusable housing assembly 102, reusable housing assembly 802 may include mechanical control assembly 812 (e.g., which may include valve assembly 814, shown in FIG. 36, including one or more valves and one or more pumps for pumping and controlling the flow of the infusible fluid). Reusable housing assembly 802 may also include an electrical control assembly 816 that may be configured to provide control signals to the mechanical control assembly 812 to effectuate the delivery of an infusible fluid to the user. Valve assembly 814 may be configured to control the flow of the infusible fluid through a fluid path and the pump assembly may be configured to pump the infusible fluid from the fluid path to the user.

Figure 37:
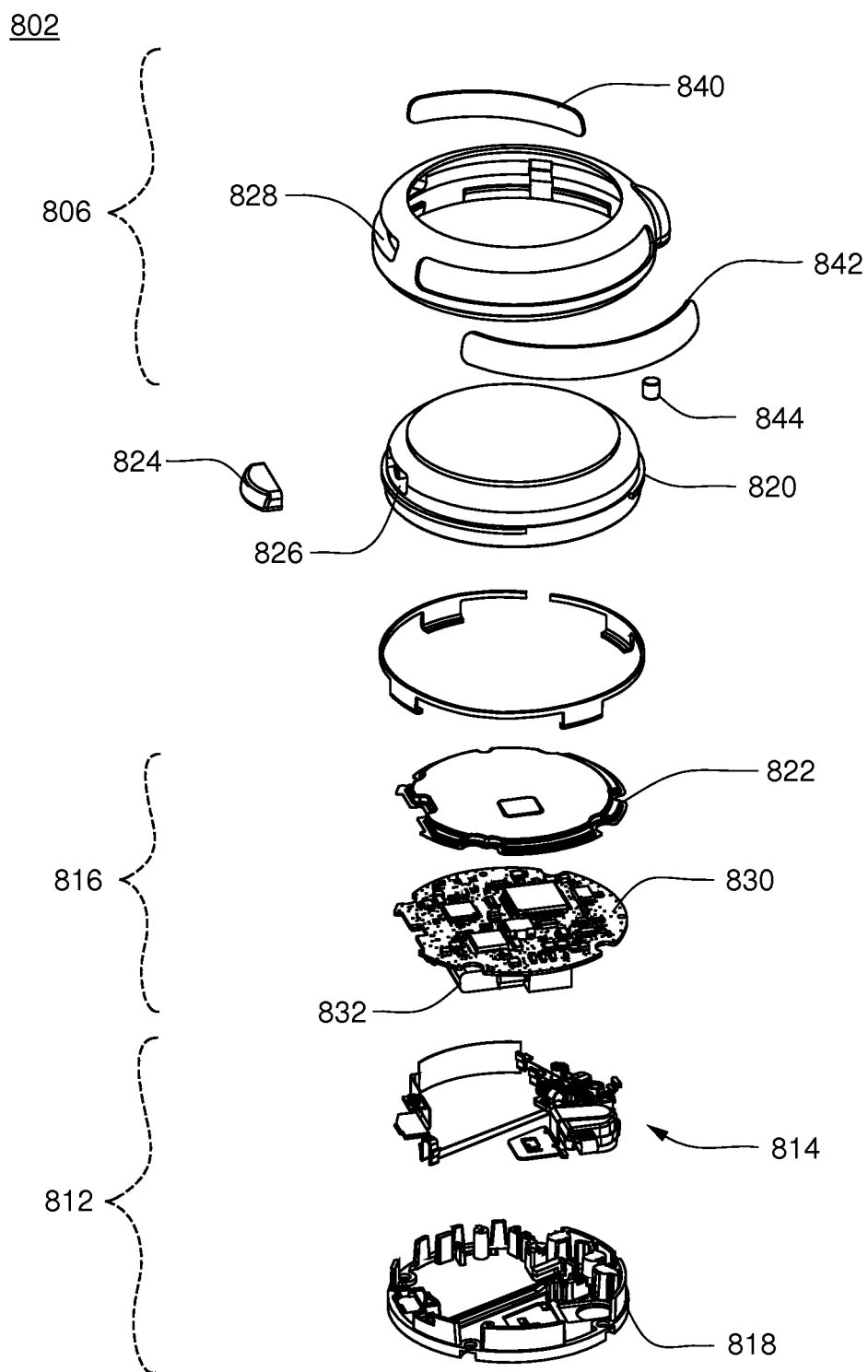
FIG. 37 is an exploded view of the reusable housing assembly of FIGS. 35A-35C.

Mechanical control assembly 812 and electrical control assembly 816 may be contained within a housing defined by base plate 818, body 820. In some embodiments one or more of base plate 818 and body 820 may provide electromagnetic shielding. In such an embodiment, the electromagnetic shielding may prevent and/or reduce electromagnetic interference received by electrical control assembly 816 and/or created by electrical control assembly 816. Additionally/alternatively, EMI shield 822 may be included, as shown in FIG. 36 and FIG. 37. EMI shield 822 may provide shielding against generated and/or received electromagnetic interference.

Reusable housing assembly 802 may include a switch assembly that may be configured to receive user commands (e.g., for bolus delivery, pairing with a remote control assembly, or the like). The switch assembly may include button 824 that may be disposed in opening 826 of body 820. As shown, e.g., in FIG. 35B, locking ring assembly 806 may include radial slot 828 that may be configured to allow locking ring assembly 806 to be rotated relative to body 820 while still providing facile access to button 824.

Figure 39A:
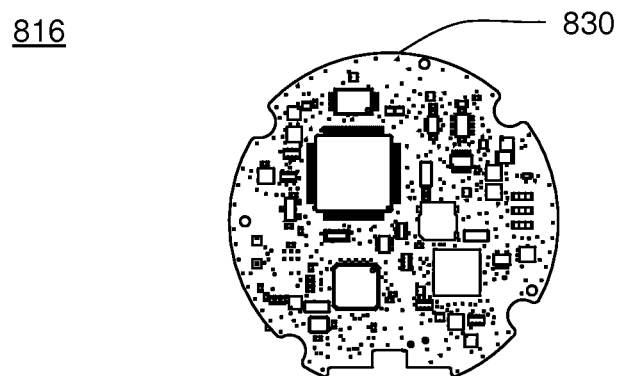
FIGS. 39A-39C are a top view, side view, and bottom view of an electrical control assembly of the reusable housing assembly of FIGS. 35A-35C.
Figure 39B:
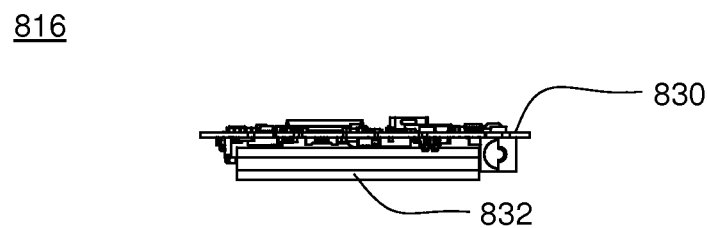
Figure 39C:
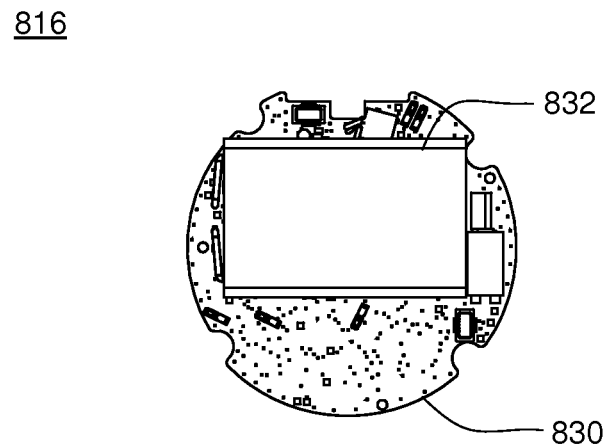
Figure 40A:
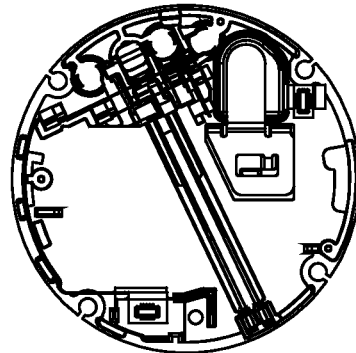
FIGS. 40A-40C are a top view, side view, and bottom view of a base plate of the reusable housing assembly of FIGS. 35A-35C.
Figure 40B:
Figure 40C:
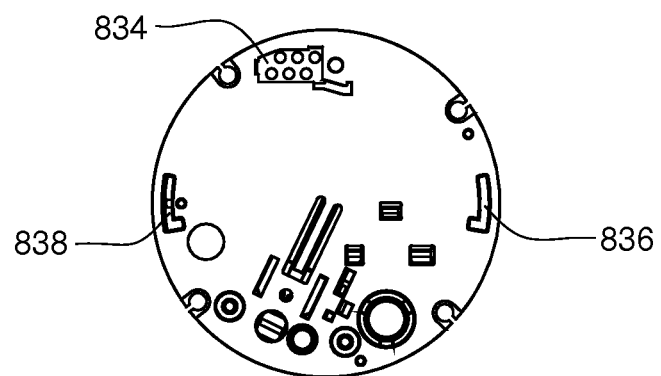
Figure 41A:
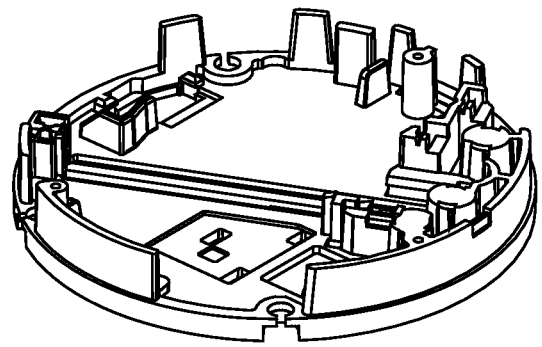
FIGS. 41A-41B are a perspective top view and a perspective bottom view of the base plate of FIGS. 40A-40C.
Figure 41B:
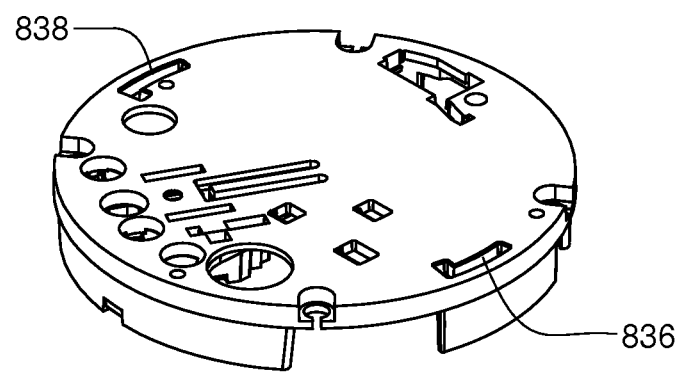
Figure 42A:
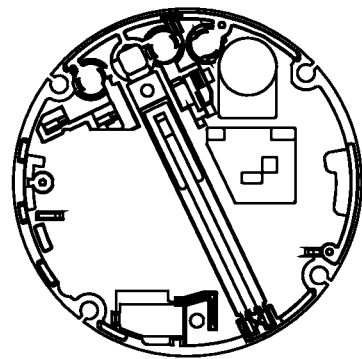
FIGS. 42A-42C are a top view, side view, and bottom view of a base plate of the reusable housing assembly of FIGS. 35A-35C.
Figure 42B:
Figure 42C:
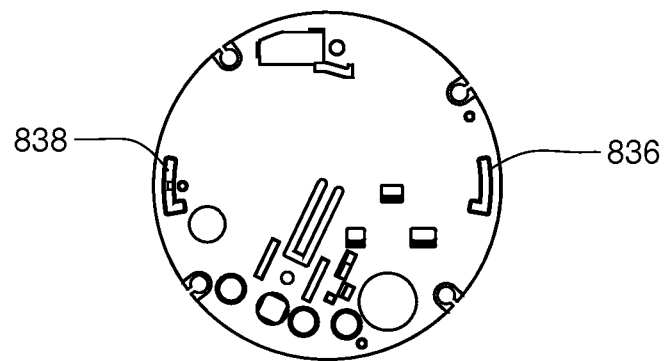
Figure 43A:
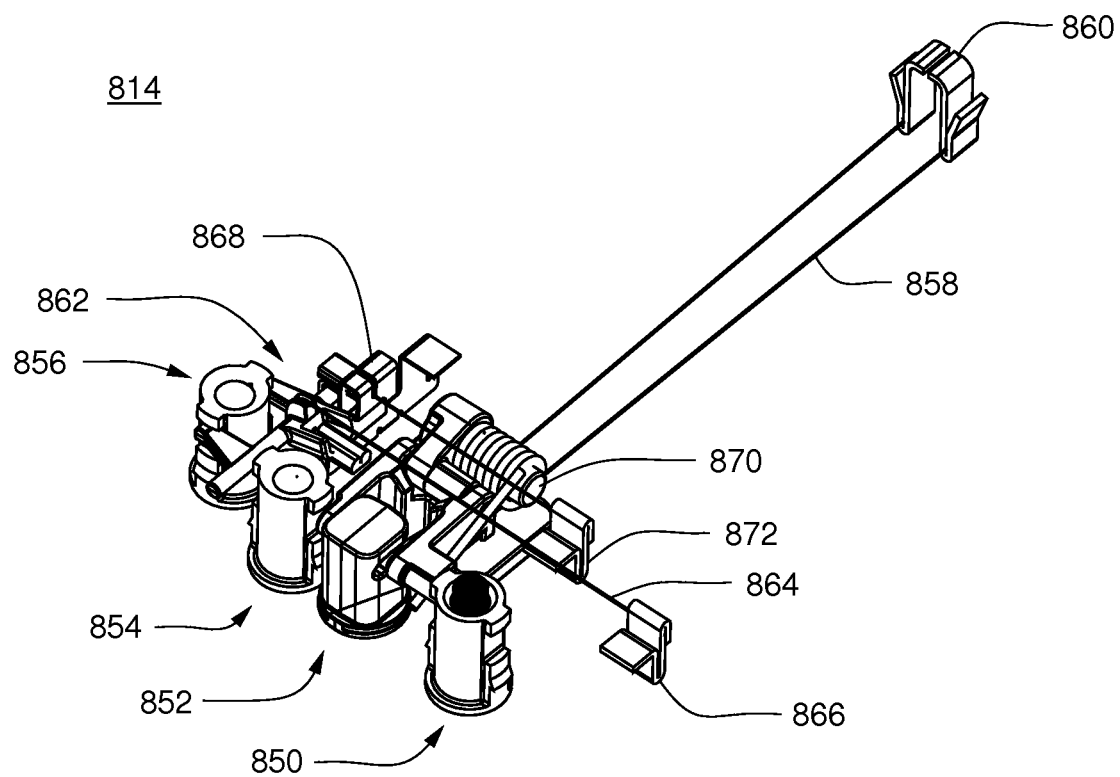
FIGS. 43A-43B depict a mechanical control assembly of the reusable housing assembly of FIGS. 35A-35C.
Figure 43B:
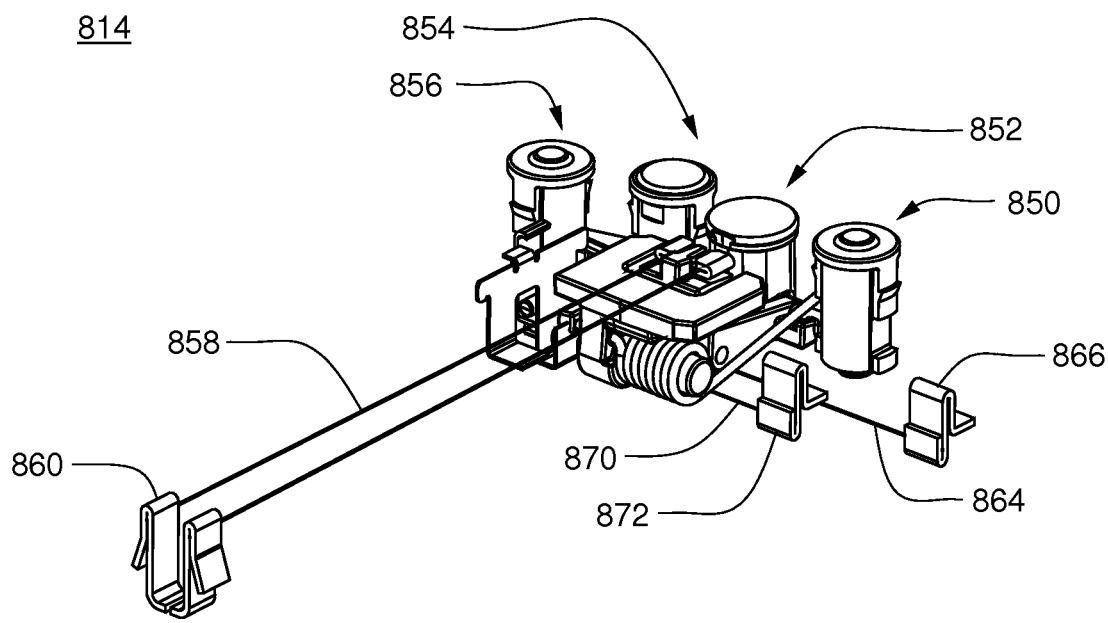
Figure 44A:
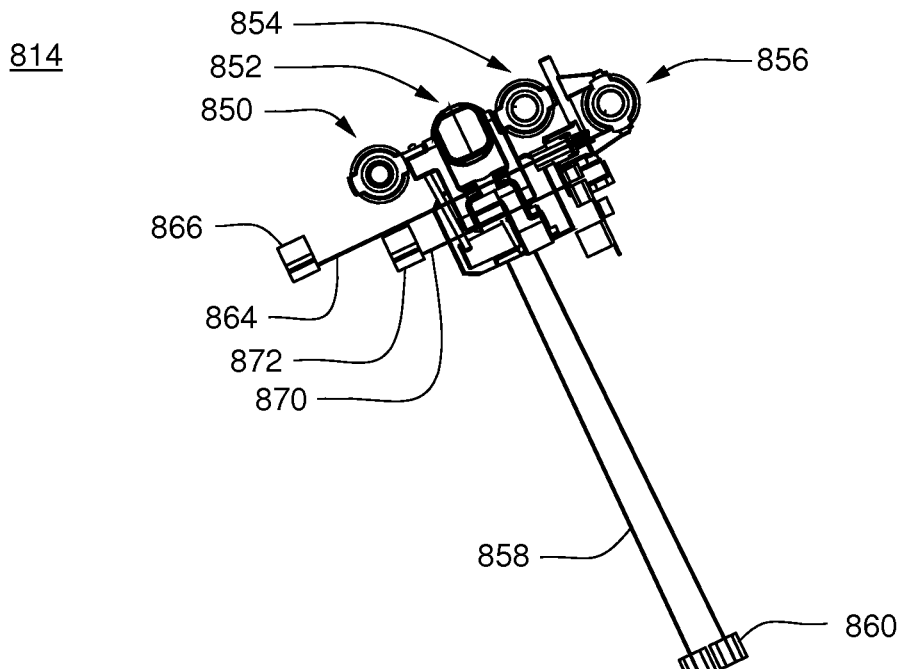
FIGS. 44A-44C depict the mechanical control assembly of the reusable housing assembly of FIGS. 35A-35C.
Figure 44B:
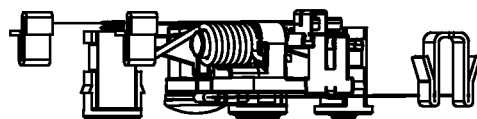
Figure 44C:
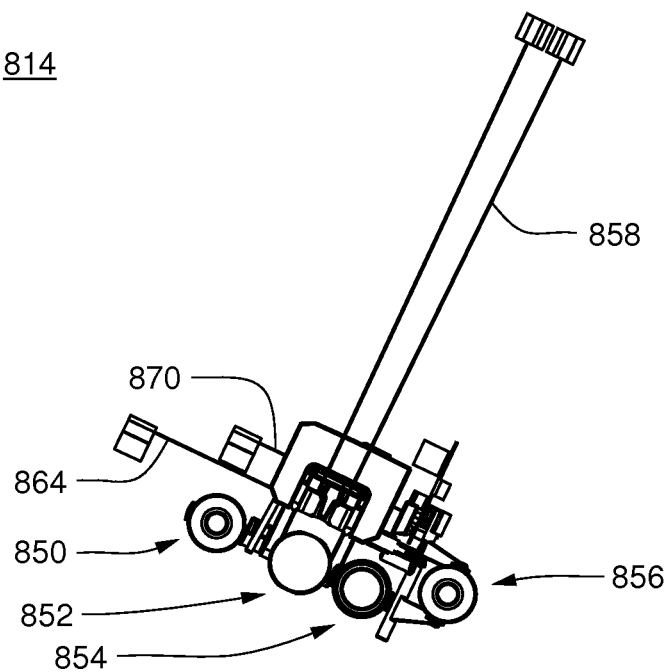
Figure 45A:
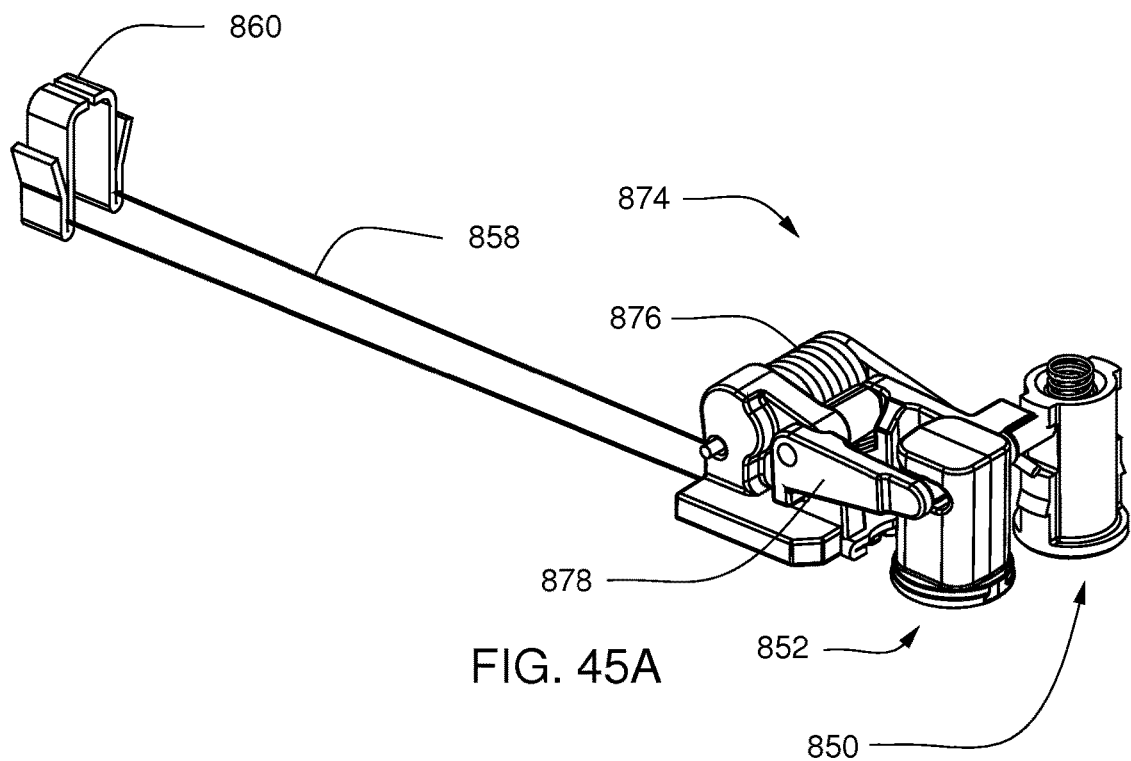
FIGS. 45A-45B depict the pump plunger and reservoir valve of the mechanical control assembly of the reusable housing assembly of FIGS. 35A-35C.
Figure 45B:
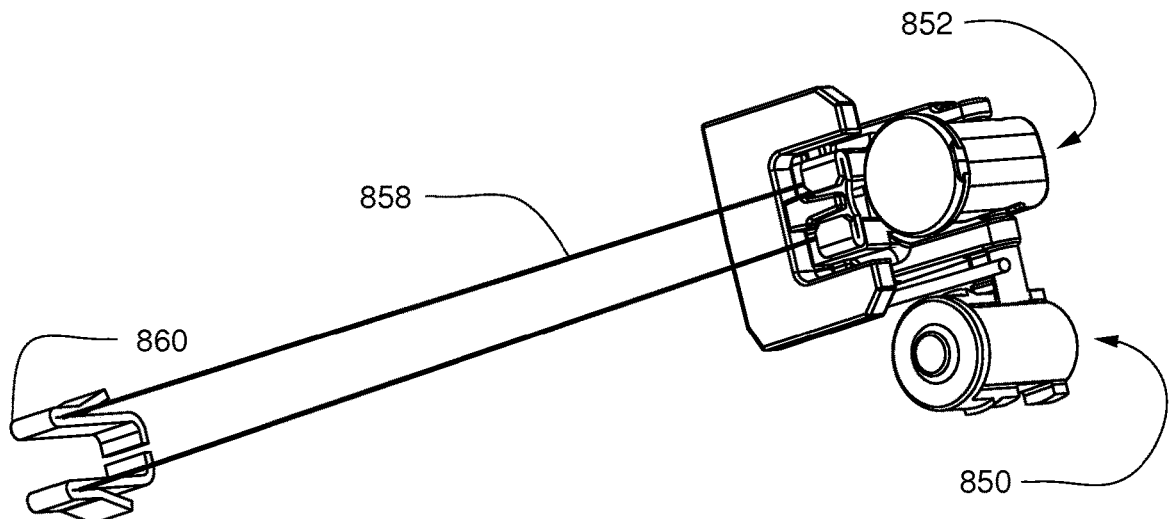
Figure 46A:
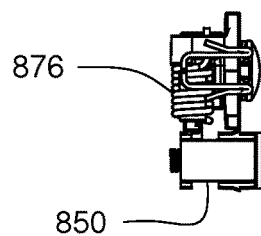
FIGS. 46A-46E depict various views of the plunger pump and reservoir valve of the mechanical control assembly of the reusable housing assembly of FIGS. 35A-35C.
Figure 46B:
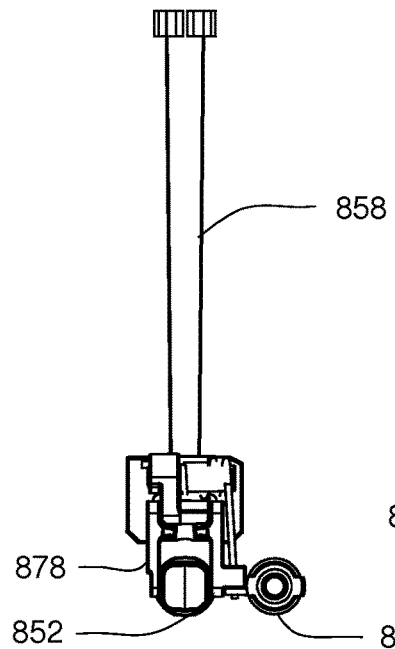
Figure 46C:
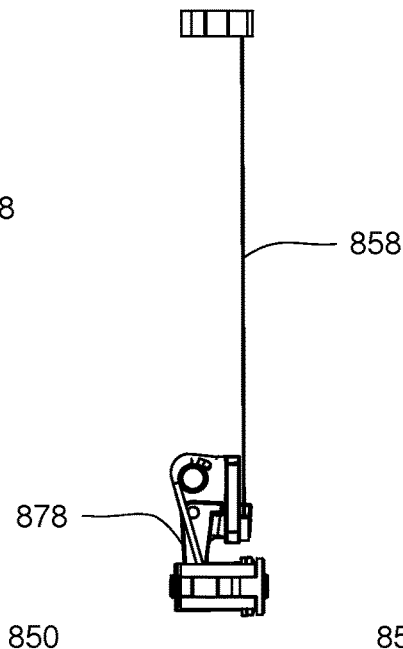
Figure 46D:
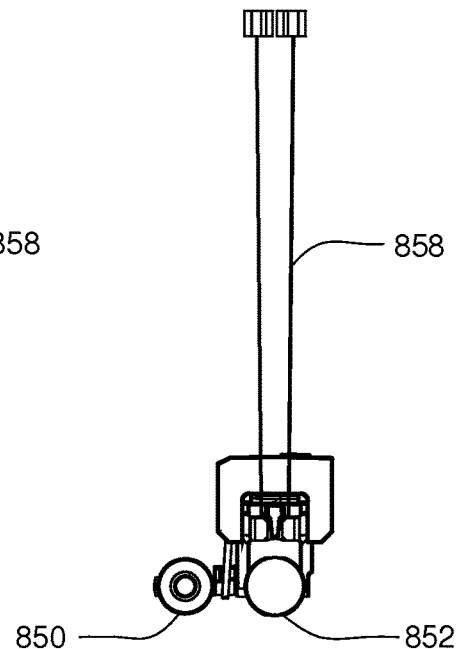
Figure 46E:
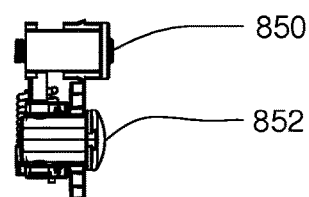

Referring also to FIGS. 39A-39C, electrical control assembly 816 may include printed circuit board 830 as well as battery 832. Printed circuit board 830 may include the various control electronics for monitoring and controlling the amount of infusible fluid that has been and/or is being pumped. For example, electrical control assembly 816 may measure the amount of infusible fluid that has just been dispensed, and determine, based upon the dosage required by the user, whether enough infusible fluid has been dispensed. If not enough infusible fluid has been dispensed, electrical control assembly 816 may determine that more infusible fluid should be pumped. Electrical control assembly 816 may provide the appropriate signal to mechanical control assembly 812 so that any additional necessary dosage may be pumped or electrical control assembly 816 may provide the appropriate signal to mechanical control assembly 812 so that the additional dosage may be dispensed with the next dosage. Alternatively, if too much infusible fluid has been dispensed, electrical control assembly 816 may provide the appropriate signal to mechanical control assembly 812 so that less infusible fluid may be dispensed in the next dosage. Electrical control assembly 816 may include one or more microprocessors. In an exemplary embodiment, electrical control assembly 816 may include three microprocessors. One processor (e.g., which may include, but is not limited to a CC2510 microcontroller/RF transceiver, available from Chipcon AS, of Oslo, Norway) may be dedicated to radio communication, e.g., for communicating with a remote control assembly. Two additional microprocessors (example of which may include, but is not limited to an MSP430 microcontroller, available from Texas Instruments Inc. of Dallas, Tex.) may be dedicated to issuing and carrying out commands (e.g., to dispense a dosage of infusible fluid, process feedback signals from a volume measurement device, and the like).

As shown in FIG. 35C, base plate 818 may provide access to electrical contacts 834, e.g., which may be electrically coupled to electrical control assembly 816 for recharging battery 832. Base plate 818 may include one or more features (e.g., openings 836, 838) which may be configured to facilitate proper alignment with disposable housing assembly 804 by way of cooperating features (e.g., tabs) of disposable housing assembly 804. Additionally, as shown in FIGS. 40A-40C, 41A-41B, and 42A-42C, base plate 818 may include various features for mounting valve assembly 814 and electrical control assembly 816, as well as providing access to disposable housing assembly 804 by valve assembly 814.

Locking ring assembly 806 may include grip inserts 840, 842, e.g., which may include an elastomeric or textured material that may facilitate gripping and twisting locking ring assembly 806, e.g., for engaging/disengaging reusable housing assembly 802 and disposable housing assembly 804. Additionally, locking ring assembly 806 may include a sensing component (e.g., magnet 844) that may interact with a component of reusable housing assembly 802 (e.g., a Hall Effect sensor), e.g., to provide an indication of the nature of a mating component (e.g., which in some embodiments may include, but is not limited to, one or more of disposable housing assembly 804, a charging station, or a filling station) and/or of whether reusable housing assembly 802 is properly engaged with the mating component. In the exemplary embodiment, a Hall Effect sensor (not shown) may be located on the pump printed circuit board. The Hall Effect sensor may detect when the locking ring has been rotated to a closed position. Thus, the Hall Effect sensor together with magnet 844 may provide a system for determining whether the locking ring has been rotated to a closed position.

The sensing component (magnet) 844 together with the reusable housing assembly components, i.e., in the exemplary embodiment, the Hall Effect sensor, may work to provide for a determination of whether the reusable housing assembly is properly attached to the intended component or device. Locking ring assembly 806 may not turn without being attached to a component, i.e., disposable housing assembly 804, a dust cover or a charger. Thus, the sensing component together with the reusable housing assembly component may function to provide many advantageous safety features to the infusion pump system. These features may include, but are not limited to, one or more of the following. Where the system does not detect being attached to a disposable assembly, a dust cover or a charger, the system may notify, alert or alarm the user as the reusable portion, e.g., the valves and pumping components, may be vulnerable to contamination or destruction which may compromise the integrity of the reusable assembly. Thus, the system may provide for an integrity alarm to alert the user of potential reusable integrity threats. Also, where the system senses the reusable assembly is attached to a dust cover, the system may power off or reduce power to conserve power. This may provide for more efficient use of power where the reusable assembly is not connecting to a component in which it needs to interact.

Referring also now to FIGS. 136-139, in some embodiments, in addition to the sensing component, a mechanical audible, or "click", indication may indicate that the reusable housing assembly 2972 is fully attached to the disposable housing assembly 2976. In some embodiments, the latching mechanism shown and described above, for example, with respect to FIG. 38A, may include a spring 2982 actuated tab 2980 assembly. In some embodiments, the tab 2980 includes the sensing component, which, in some embodiments, may be a magnetic 2986. Referring now also to FIG. 137, a cross section view at "A" is shown of the reusable housing assembly 2972 above the disposable housing assembly 2974 in the "unlocked" position. In some embodiments, the "locked" and "unlocked" position may also be visually indicated to a user/patient using icons 2976, 2978 that may be molded, etched and/or printed on the disposable housing assembly 2974, indicating whether the reusable housing assembly 2972, or, in some embodiments, a fill adapter, is in a locked or unlocked relationship with the disposable housing assembly 2974 (or, in some embodiments, the same or similar icons may appear on the dust cover). In various embodiments, the icons 2976, 2978 may be any form that may indicate "locked" and "unlocked", or a similar indication, to aid in the user/patient's understanding of the orientation/position between the reusable housing assembly 2972 and the disposable housing assembly 2974 (or the dust cover). As shown, the reusable housing assembly 2972 is aligned about the disposable housing assembly 2974 in an unlocked orientation. Referring now also to FIG. 138, a cross section view at "A" is shown of the reusable housing assembly 2972 attached to the disposable housing assembly 2974 in the unlocked orientation/position is shown. The tab 2080 is in the unlocked position. Referring now to FIG. 139, a cross section view at "A" is shown of the reusable housing assembly 2972 attached to the disposable housing assembly 2974 in the locked orientation/position is shown. As may be seen, the tab 2980 has moved towards the disposable housing assembly 2974, leaving a space 2984 above the tab 2980 in the reusable housing assembly 2972. When the tab 2980 moves from the unlocked position (shown in FIG. 138) to the locked position (shown in FIG. 139) in some embodiments, an audible "click" sound, and tactile "click", may be detected by the user/patient. This may be beneficial for many reasons including that the user/patient may only hear the audible "click" sound if the reusable housing assembly 2972 and the disposable housing assembly 2974 (or, the dust cover or charger in various embodiments) are in the correct orientation and fully locked arrangement. This may ensure the user/patient that the infusion pump assembly is in the correct and fully locked position. Thus, in various embodiments where an audible "click" may be heard upon the disposable housing assembly 2974 and reusable housing assembly 2972 being attached, the infusion pump assembly will include two safety checks that they are fully locked: 1) the sensing component described and discussed above; and 2) the audible "click" mechanical component. In various embodiments the disposable housing assembly 2974 may include a ramp feature that the tab 2980 assembly rides on as the reusable housing assembly 2972 is rotated from an unlocked to a locked position with respect to the disposable housing assembly 2974. At the end of the ramp, in some embodiments, an indentation or relief in the disposable housing assembly 2974 allows the tab 2980, actuated by the spring 2982, to "click" into the indentation/relief. Other embodiments allowing for an audible and or tactile indication to the user/patient may be used in various embodiments.

Figure 38A:
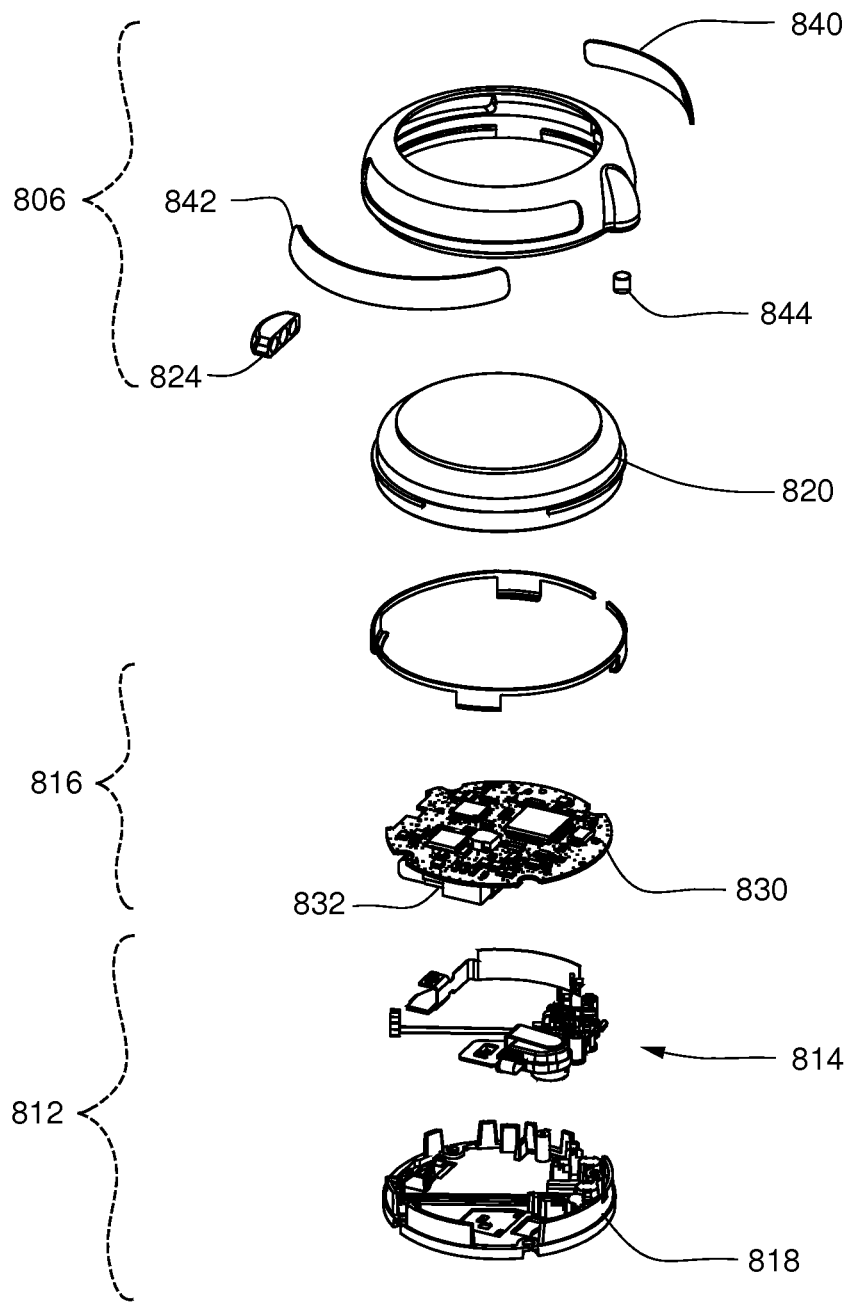
FIG. 38A is an exploded view of the reusable housing assembly of FIGS. 35A-35C.
Figure 38D:
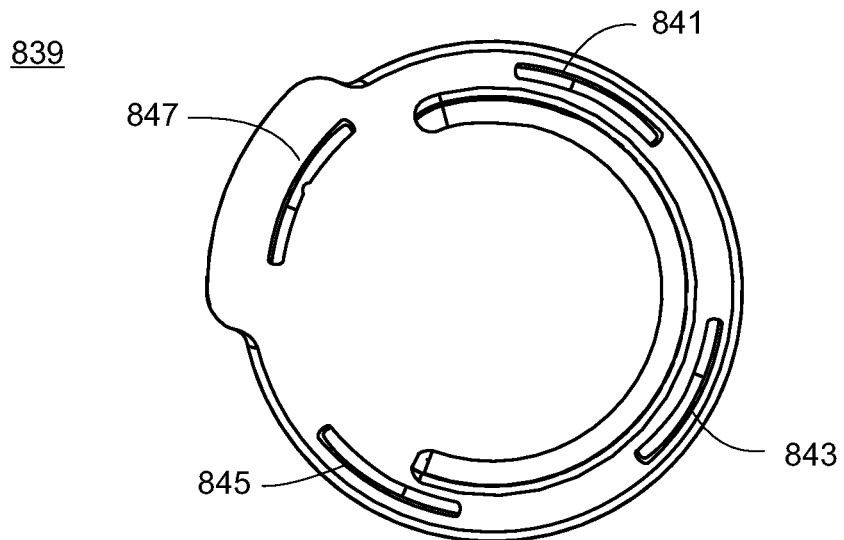
FIG. 38B-38D are top, side and bottom views of one embodiment of a dust cover.
Figure 38C:
Figure 38B:
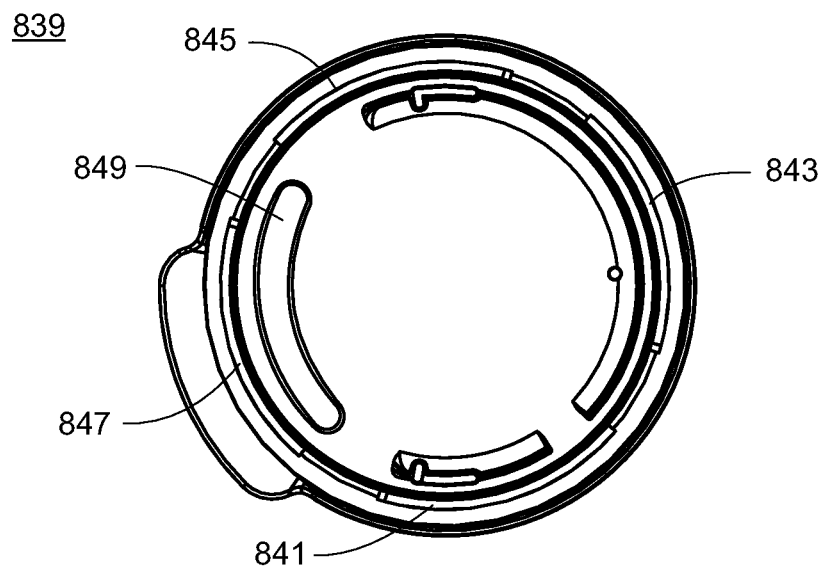
Figure 140A:
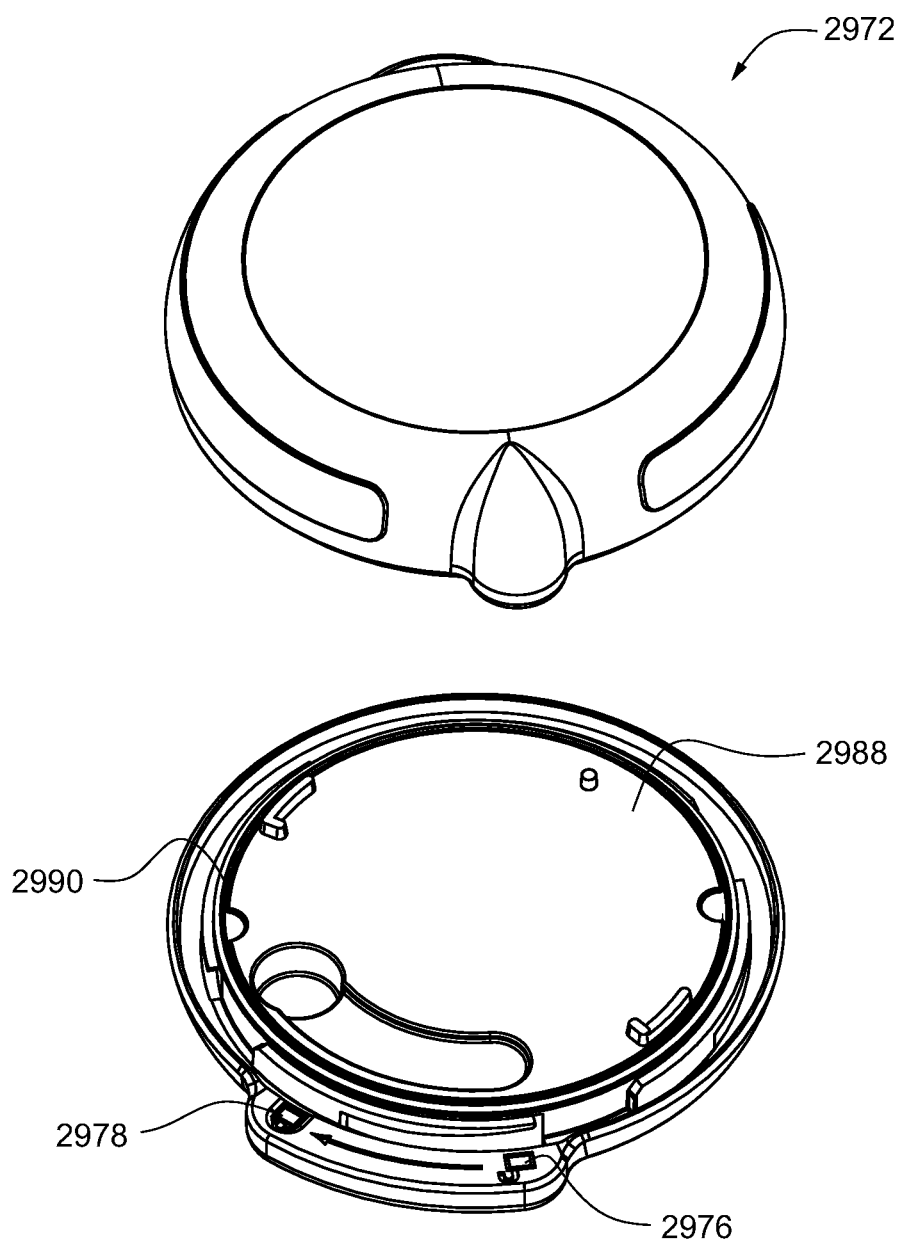
Figure 140B:
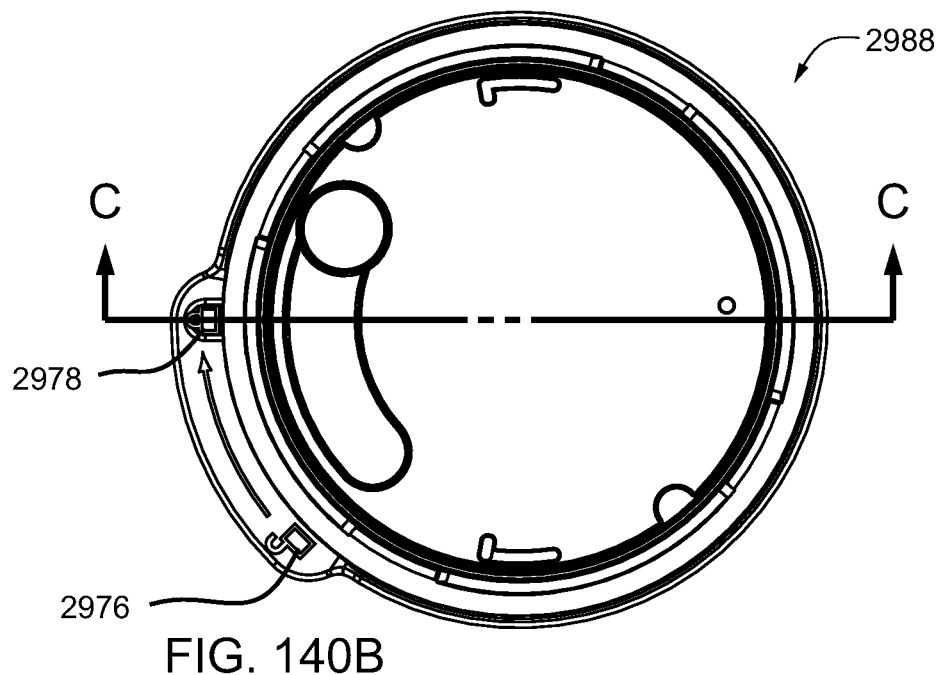
Figure 140C:
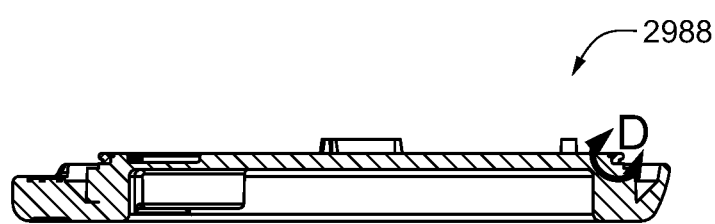
Figure 140D:
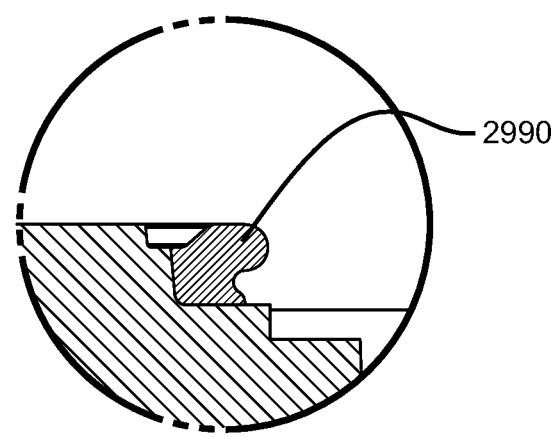

Reusable housing assembly 802 may attach to a number of different components, including but not limited to, a disposable housing assembly, a dust cover or a battery charger/battery charging station. In each case, the Hall Effect sensor may detect that the locking ring is in the closed position, and therefore, that reusable housing assembly 802 is releasably engaged to a disposable housing assembly, a dust cover, or a battery charger/battery charging station (or, another component). The infusion pump system may determine the component to which it is attached by using the AVS system (which may also be referred to as the volume measurement sensor) described in more detail below or by an electronic contact. Referring now also to FIGS. 38B-38D, one embodiment of a dust cover (e.g., dust cover 839) is shown. In the exemplary embodiment, dust cover 839 may include features 841, 843, 845, 847 such that the locking ring of reusable housing assembly 802 may releasably engage dust cover 839. In addition, dust cover 839 may further include recess region 849 for accommodating the valving and pumping features of reusable housing assembly 804. Referring also to FIGS. 140A-140D, in some embodiments, various embodiments of the dust cover 839, 2988 may include a sealing assembly 2990 that may be over molded to provide for a complete seal of the dust cover 839, 2988 to the reusable housing assembly 2972. As shown in FIG. 140D, where a cut-away cross-sectional view of section D in FIG. 140C, the sealing assembly 2990 is over molded. Additionally, as may be seen in FIGS. 140A and 140B, in some embodiments of the dust cover 2988, the dust cover 2988 may include icons 2976, 2978. As discussed above, the icons 2976, 2978, may be molded, etched and/or printed onto the dust cover 2988 and may be any form that may indicate "locked" and "unlocked", or a similar indication, to aid in the user/patient's understanding of the orientation/position between the reusable housing assembly 2972 and the dust cover 2988 and/or indicating whether the reusable housing assembly 2972 is in a locked or unlocked position with respect to the dust cover 2988. For example, with respect to the dust cover, the AVS system may determine that a dust cover, and not a disposable housing assembly, is connected to the reusable housing assembly. The AVS system may distinguish using a look-up table or other comparative data and comparing the measurement data with characteristic dust cover or empty disposable housing assembly data. With respect to the battery charger, the battery charger, in the exemplary embodiments, may include electric contacts. When the reusable housing assembly is attached to the battery charger, the infusion pump assembly electronic system may sense that the contacts have been made, and will thus indicate that the reusable housing assembly is attached to a battery charger.

Referring also to FIGS. 43A-45B and FIGS. 44A-44C an embodiment of valve assembly 814, which may include one or more valves and one or more pumps, is shown. As with infusion pump assemblies 100, 100', 400, and 500, valve assembly 814 may generally include reservoir valve 850, plunger pump 852, volume sensor valve 854, and measurement valve 856. Similar to the previous description, reservoir valve 850 and plunger pump 852 may be actuated by shape memory actuator 858, which may be anchored (on a first end) to shape memory actuator anchor 860. Additionally, measurement valve 856 may be actuated, via valve actuator 862, by shape memory actuator 864, which may be anchored (on a first end) to shape memory actuator anchor 866. In a similar manner as discussed above, measurement valve may be maintained in an open position via measurement valve latch assembly 868. Measurement valve 856 may be released via actuation of shape memory actuator 870, which may be anchored (on a first end) by shape memory actuator anchor 872. In some embodiments, shape memory actuator anchor 860 may be potted onto the reusable housing assembly. Using this process during manufacture ensures shape memory length actuator 858 is installed and maintains the desired length and tension/strain.

Referring also to FIGS. 45A-45B and FIGS. 46A-46E, shape memory actuator 858 (e.g., which may include one or more shape memory wires) may actuate plunger pump 852 via actuator assembly 874. Actuator assembly 874 may include bias spring 876 and lever assembly 878. Actuator assembly 874 may actuate both plunger pump 852 and measurement valve 850.

Figure 47A:
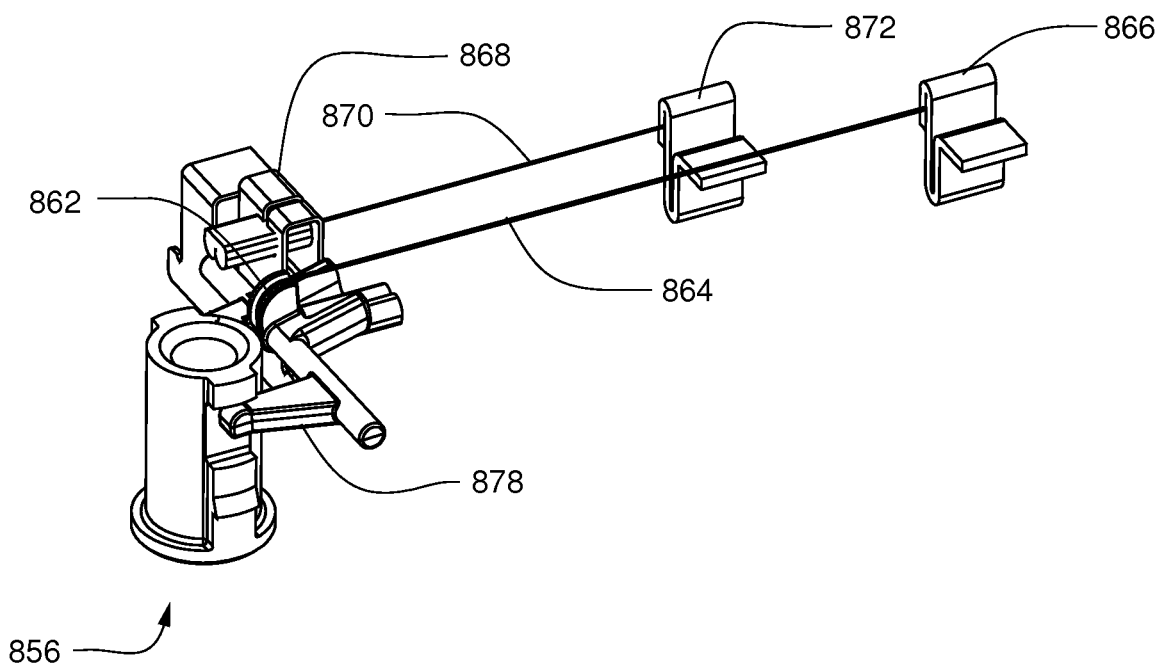
FIGS. 47A-47B depict the measurement valve of the mechanical control assembly of the reusable housing assembly of FIGS. 35A-35C.
Figure 47B:
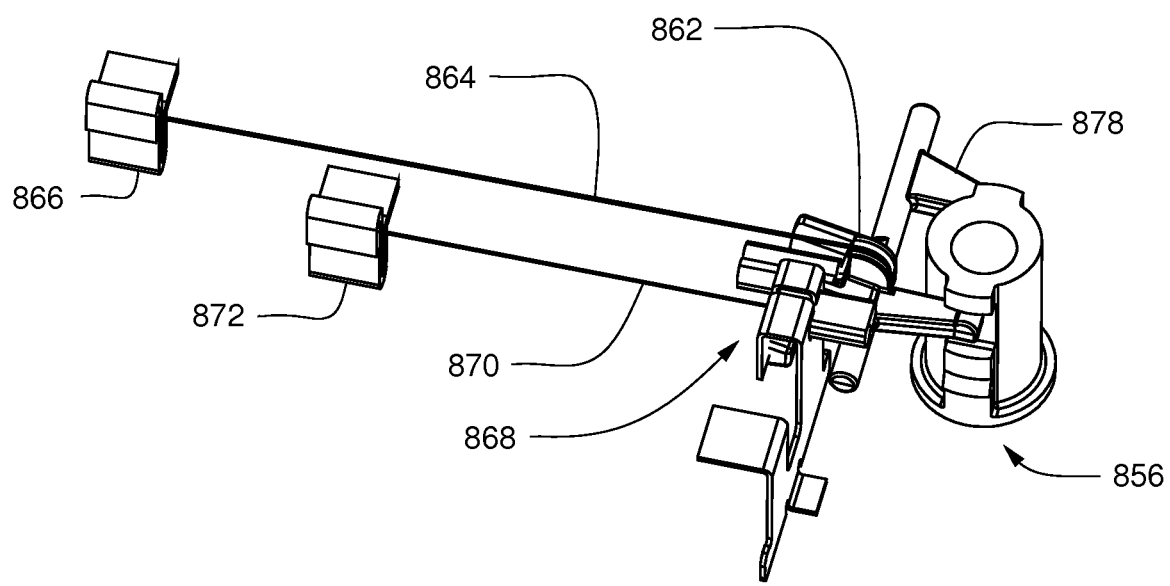

Referring also to FIGS. 47A-47B, measurement valve 856 may be actuated by shape memory actuator 864, via valve actuator 862 and lever assembly 878. Once actuated, measurement valve latch assembly 868 may maintain measurement valve 856 in an open position. Measurement valve latch assembly 868 actuated by shape memory actuator 870 to release measurement valve 856, allowing it to return to a closed position.

Disposable housing assembly 804 may be configured for a single use or for use for a specified period of time, e.g., e.g., three days or any other amount of time. Disposable housing assembly 804 may be configured such that any of the component of infusion pump assembly 800 that come in contact with the infusible fluid may be disposed on and/or within disposable housing assembly 804. As such, the risk of contaminating the infusible fluid may be reduced.

Figure 50A:
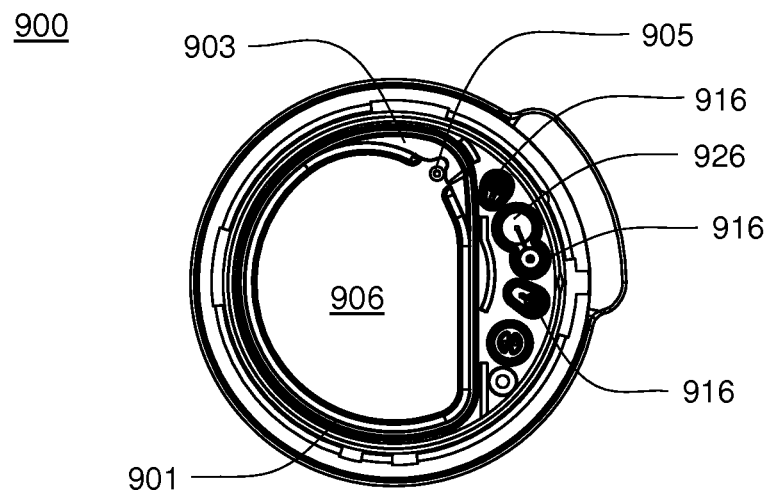
FIGS. 50A-50C depict the base portion of the disposable housing assembly of FIG. 48.
Figure 50B:
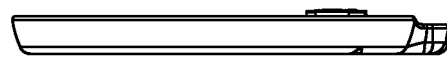
Figure 50C:
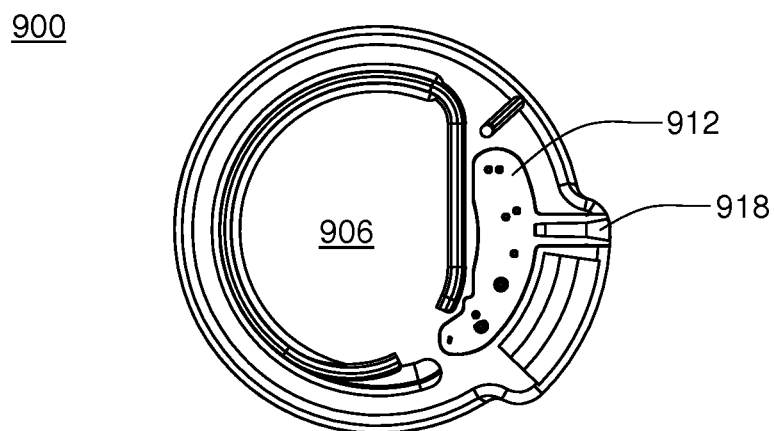

Referring also to FIG. 48 and FIGS. 49A-49C, disposable housing assembly 804 may include base portion 900, membrane assembly 902, and top portion 904. Base portion 900 may include recess 906 that together with membrane assembly 902 defines reservoir 908 for receiving an infusible fluid (not shown), e.g., insulin. Referring also to FIGS. 50A-50C, recess 906 may be at least partially formed by and integral with base portion 900. Membrane assembly 902 may be sealingly engaged with base portion 900, e.g., by being compressively pinched between base portion 900 and top portion 904. Top portion 904 may be attached to base portion 900 by conventional means, such as gluing, heat sealing, ultrasonic welding, and compression fitting. Additionally/alternatively, membrane assembly 902 may be attached to base portion 900, e.g., via gluing, ultrasonic welding, heat sealing, and the like, to provide a seal between membrane assembly 902 and base portion 900.

Figure 141A:
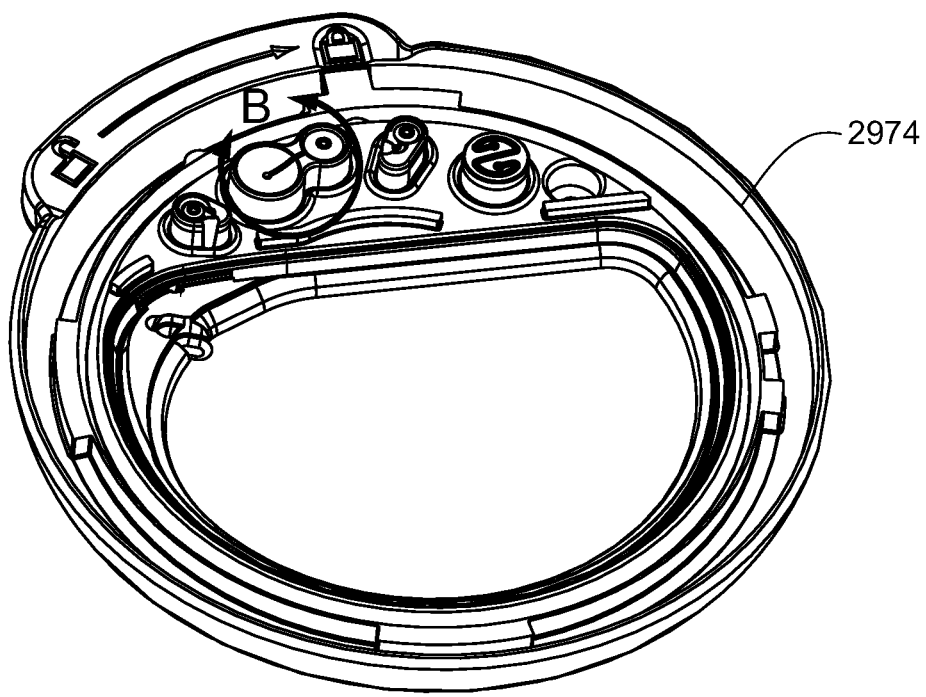
Figure 141B:
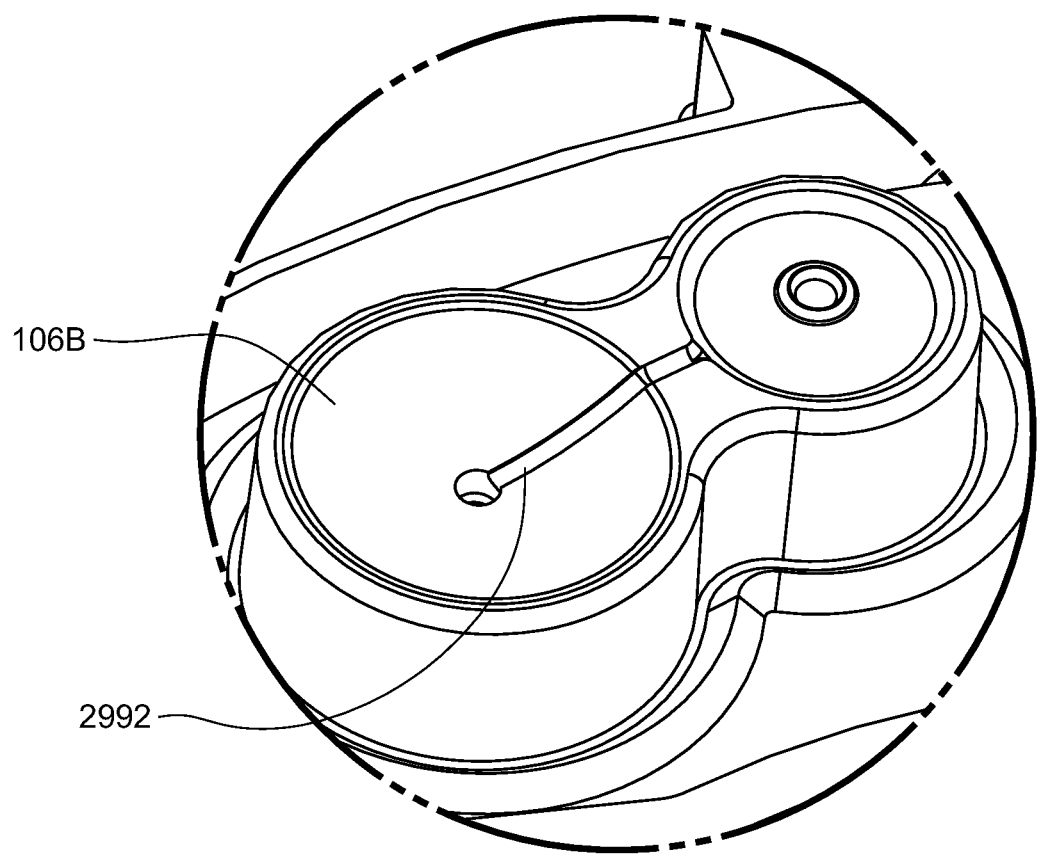
Figure 142A:
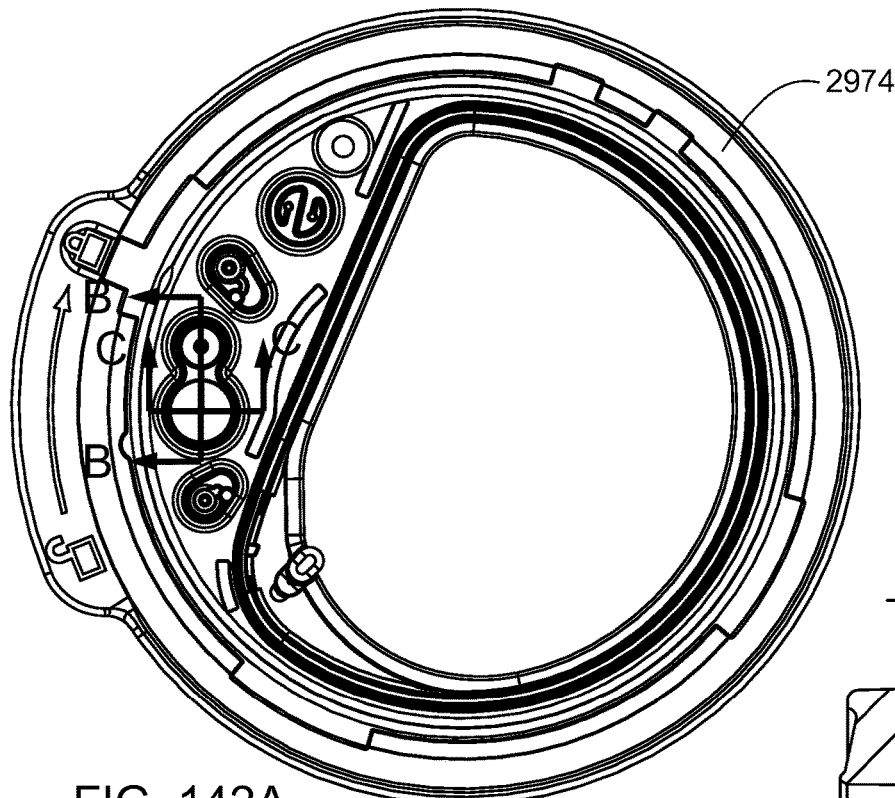
Figure 142B:
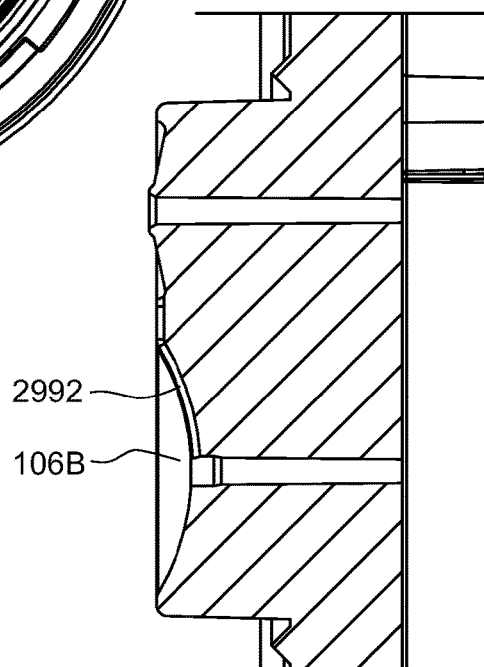
Figure 142C:
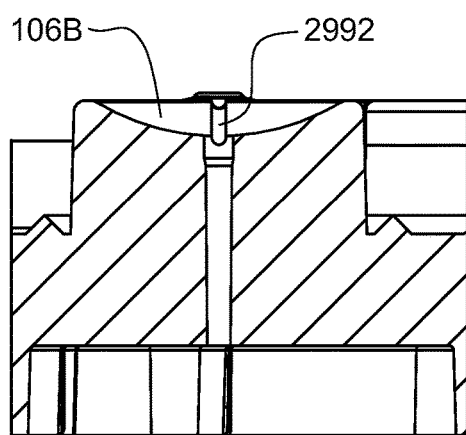

Referring also to FIGS. 141A-141B, an embodiment of the disposable housing assembly 2974 is shown without the top portion or membrane assembly. Referring to FIG. 141B, a magnified cut away view of the pump chamber 106B as indicated by "B" in FIG. 141A is shown. In some embodiments, a groove 2992 is included on the wall of the pump chamber. In some embodiments, the groove may allow fluid to flow while the pump plunger 106A is fully actuated, thus, preventing the pump plunger 106A from sealing flow out of the pump chamber 106B. FIGS. 142B and 142C are cross sectional views of FIG. 142A taken at section "B" and "C" respectively. The groove 2992 may be seen in the pump chamber 106B.

Figure 143B:
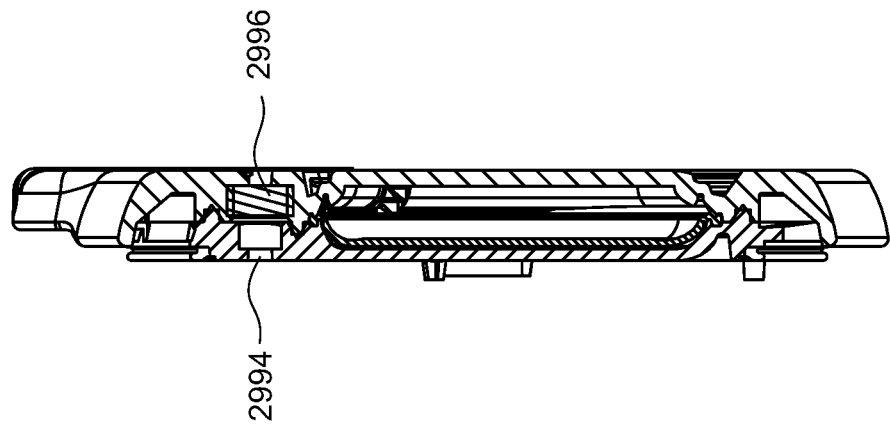
Figure 143A:
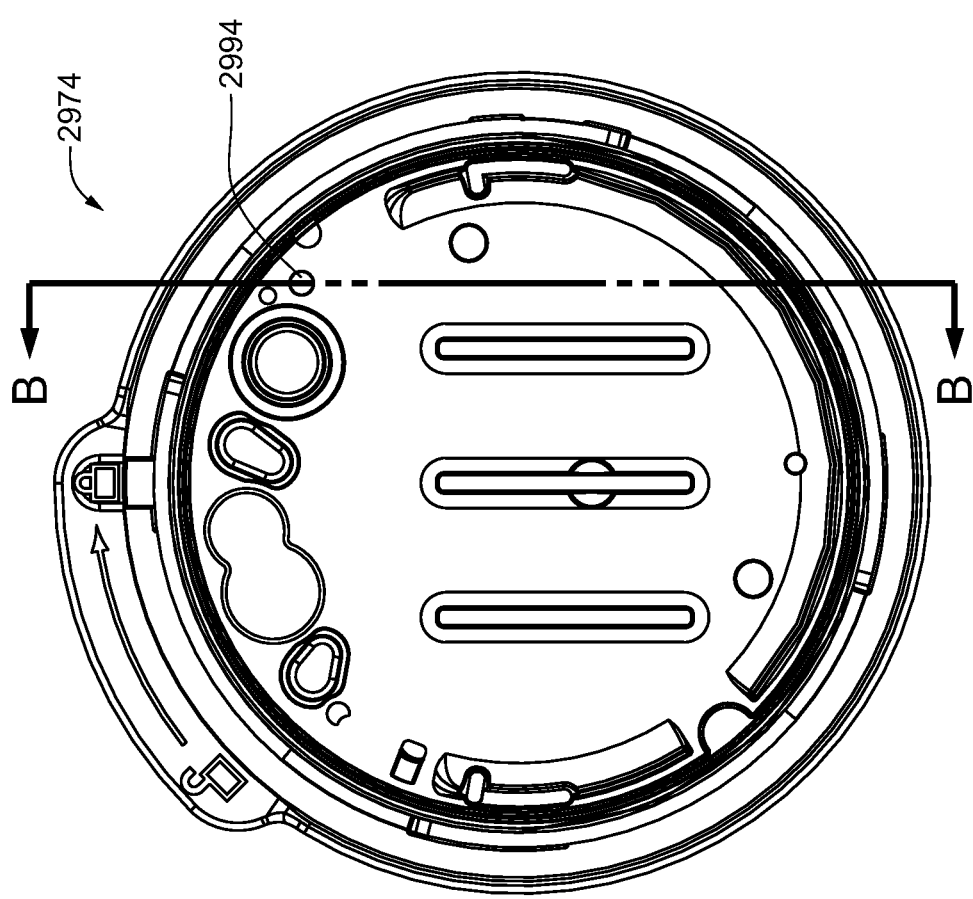

Referring also to FIGS. 143A-143B, in some embodiments of the disposable housing assembly 2974, the disposable housing assembly 2974 may include at least one vent 2994 which, in some embodiments, may include a filter 2996, which may, in some embodiments, be a hydrophobic filter, which may be, in some embodiments, be a 10 micron filter made from POREX PM 1020 MUPOR micro porous PTFE membrane, however, in other embodiments may be a different sized or type of filter for example, a 5 micron, 15 microns, filter and/or a GORTEX filter.

Figure 48:
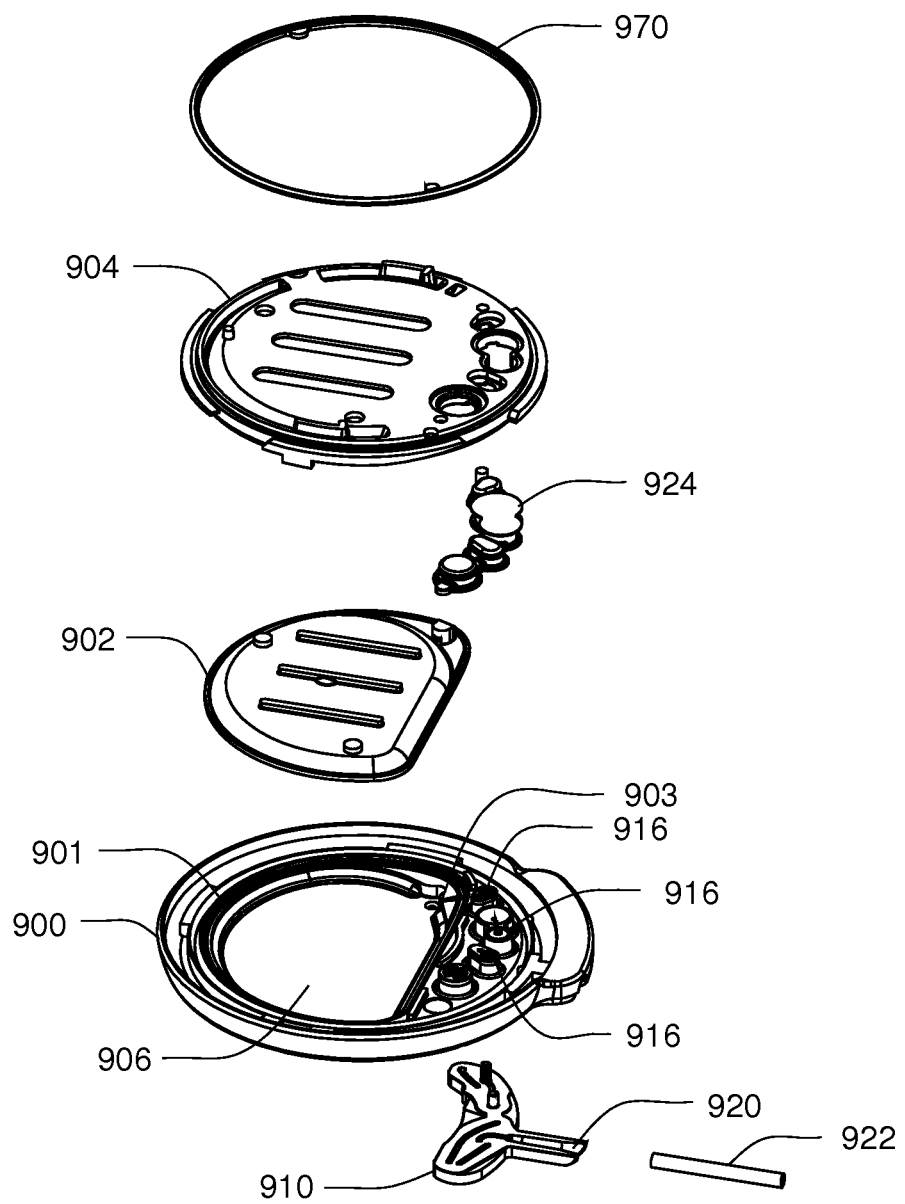
FIG. 48 is an exploded view of the disposable housing assembly of the infusion pump assembly of FIG. 32.

Still referring to FIGS. 48 and 50A, recess 906, in the exemplary embodiment, includes raised portion 901 which includes area 903 about fluid openings 905 leading to the fluid line. Raised portion 901, in the exemplary embodiment, extends about the perimeter of recess 906. However, in other embodiments, raised portion 901 may not extend the entire perimeter, but may be partially about the perimeter. Area 903 about fluid openings 905 may be shaped as shown in the exemplary embodiment, including an angled portion, which in some embodiments, includes 45 degree angles, however in other embodiments, the angle may be greater or lesser. In some embodiments, the pump may not generate a sufficient enough vacuum to collapse the reservoir so as to eliminate the entire volume of fluid that may be stored in the reservoir. Raised portion 901 may act to minimize wasted fluid.

Fluid openings 905, which, in the exemplary embodiment, may include three openings, however, in other embodiments may include more openings or fewer openings, may be surrounded by area 903 of the raised portion. In the exemplary embodiment, fluid openings 905 may be narrow in the center, thus creating a surface tension that may prevent the air from being drawn into the opening. In the exemplary embodiment, this area may be designed to encourage any air that is present in the reservoir to be drawn above one of fluid openings 905 rather than be pulled through fluid openings 905 and into the fluid line. Additionally, because there may be more than one fluid opening 905, where an air bubble is caught above one, the air may not prevent fluid from flowing through the other two openings.

Referring also to FIGS. 144A-144E, another embodiment of the disposable housing assembly 2974 is shown. In these embodiments, and as may be seen in FIG. 144B, showing a magnified sectional view of section "B" as indicated in FIG. 144A, and as may be seen in FIG. 144D, showing a magnified sectional view of section "D" as indicated in FIG. 144C, and FIG. 144E is an illustration of the bubble trap, a bubble trap 2998 and raised area 3000, as well as a radius 3006 and a relief for the septum 3016 are included in the reservoir 3002. In this embodiment, the bubble trap 2998 is located about the perimeter of the reservoir 3002 wall and the radius 3006. However, in the area of the raised area 3000, the bubble trap 2998 includes an outlet section. In the non-outlet section of the perimeter of the reservoir 3002, the bubble trap 2998 includes essentially two portions, a taper portion 3008, which tapers to a bottom portion 3010. In the outlet section, the taper portion 3008 ends, shown as the end of the taper portion 3014, and the bottom portion 3010 continues in an upward ramp portion 3012 to the reservoir outlet 3004. The reservoir 3002 includes a membrane (not shown) which forms, together with the raised area 3000 and the upward ramp portion 3012, essentially a "tunnel" between the membrane and the fluid outlet.

As the fluid in the reservoir is pumped out of the reservoir, the membrane (not shown) moves towards the reservoir wall 3002. In the embodiments shown in FIGS. 144A-144D, the fluid tends to congregate in bottom portion 3010 of the bubble trap 2998 and air bubbles do not. Rather, to the extent air is present, air bubbles tend to congregate in taper portion 3008 of the bubble trap 2998. At the raised area 3000, where the taper portion 3008 of the bubble trap 2998 ends at the end of the taper portion 3014, bubbles, to the extent present, will not likely enter into the upward ramp portion 3012, and thus, will not likely be pumped through the exit of the reservoir 3004.

Thus, as the fluid is pumped through the exit of the reservoir 3004, air is not pulled through the exit of the reservoir 3004. The embodiments shown in FIGS. 144A-144D may be beneficial for many reasons, including but not limited to, decreasing air that is pumped from the reservoir 3002 and into the fluid path in the disposable housing assembly 2974. As air bubbles have a greater surface tension than fluid, the bubbles will not tend to congregate in the bottom portion 3010 of the bubble trap 2998, and further, will not tend to flow passed the end of the taper portion 3014 and onto the upward ramp portion 3012 and through the exit of the reservoir 3004.

Figure 51A:
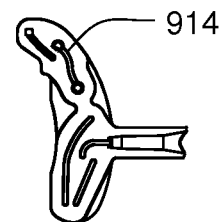
FIGS. 51A-51C depict the fluid pathway cover of the disposable housing assembly of FIG. 48.
Figure 51B:
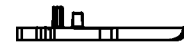
Figure 51C:
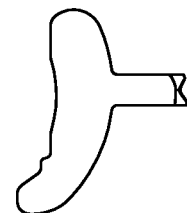

Referring also to FIGS. 51A-51C, disposable housing assembly 804 may also include fluid pathway cover 910. Fluid pathway cover 910 may be received in cavity 912 formed on/within base portion 900. Fluid pathway cover 910 may, in some embodiments, include at least a portion of one or more channels (e.g., channel 914). The channels included in fluid pathway cover 910 may fluidly couple one or more volcano valve features (e.g. volcano valves 916) included on base portion 900. Volcano valves 916 may include a protrusion having an opening extending through it. Additionally, fluid pathway cover 910 and base portion 900 may each define a portion of recess (e.g., recess portions 918, 920 included in base portion 900 and fluid pathway cover 910 respectively) for fluidly coupling to an infusion set (e.g., including cannula 922). Cannula 922 may be coupled to disposable housing assembly 804 by conventional means (e.g., gluing, heat sealing, compression fit, or the like). The fluid pathways defined by fluid pathway cover 910 and the volcano valves (e.g., volcano valves 916) of base portion 900 may define a fluid pathway between reservoir 908 and cannula 922 for the delivery of the infusible fluid to the user via the infusion set. However, in some embodiments, fluid path cover 910 may include at least a portion of the fluid path, and in some embodiments, fluid path cover 910 may not include at least a portion of the fluid path. In the exemplary embodiment, fluid pathway cover 910 may be laser welded to base portion 900. However, in other embodiments, fluid pathway cover 910 may also be connected to base portion 900 by conventional means (e.g., gluing, heat sealing, ultrasonic welding, compression fit, or the like) to achieve a generally fluid tight seal between fluid pathway cover 910 and base portion 900.

Figure 54A:
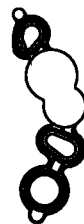
FIGS. 54A-54C depict the valve membrane insert of the disposable housing assembly of FIG. 48.
Figure 54B:
Figure 54C:
Figure 55A:
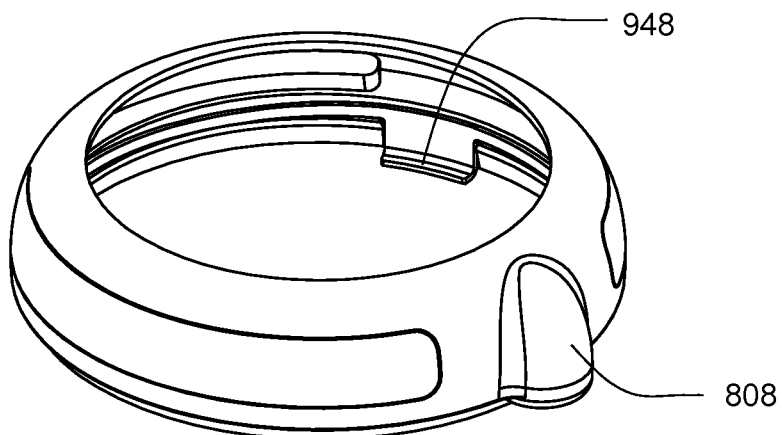
FIGS. 55A-55B depict the locking ring assembly of the infusion pump assembly of FIG. 32.
Figure 55B:
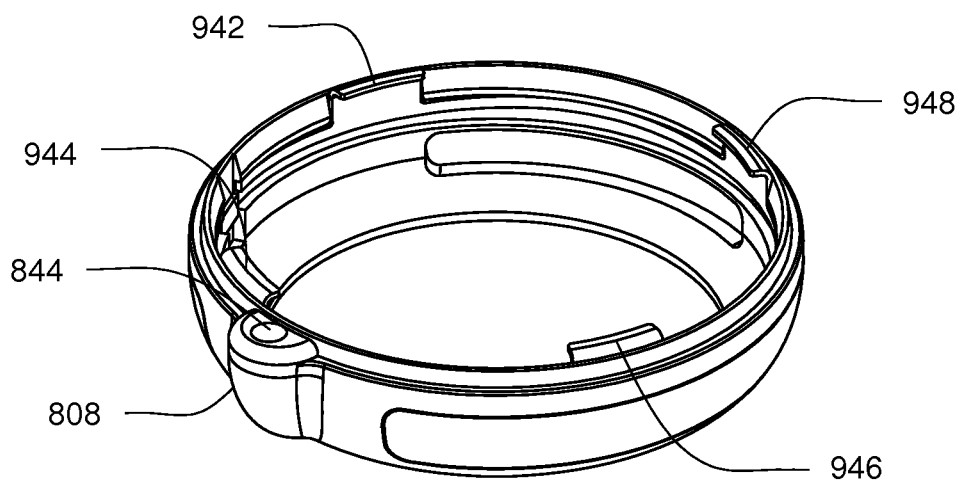
Figure 56A:
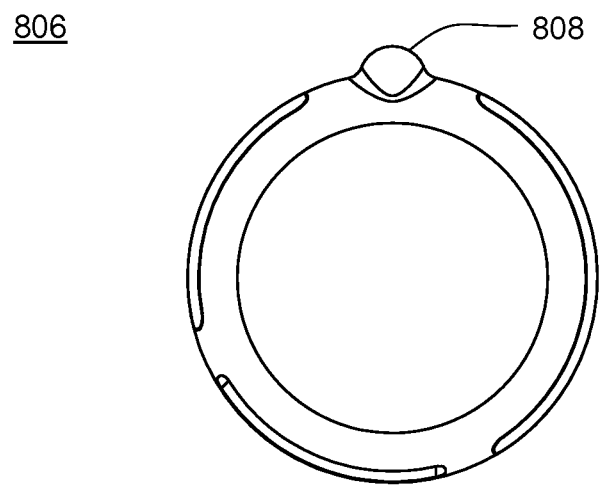
FIG. 56A-56C depict the locking ring assembly of the infusion pump assembly of FIG. 32.
Figure 56B:
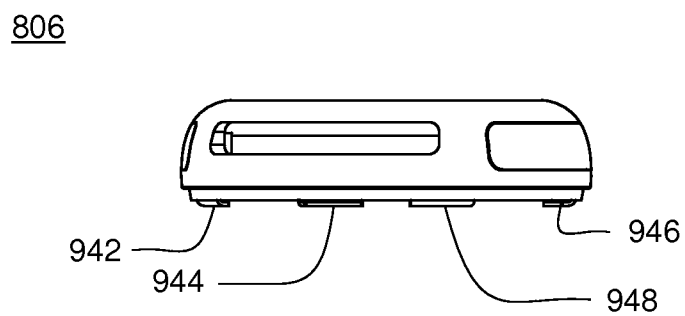
Figure 56C:
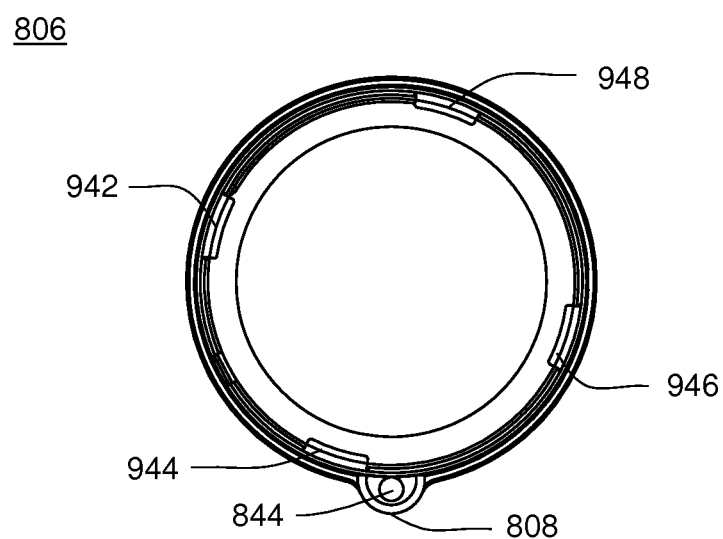
Figure 57:
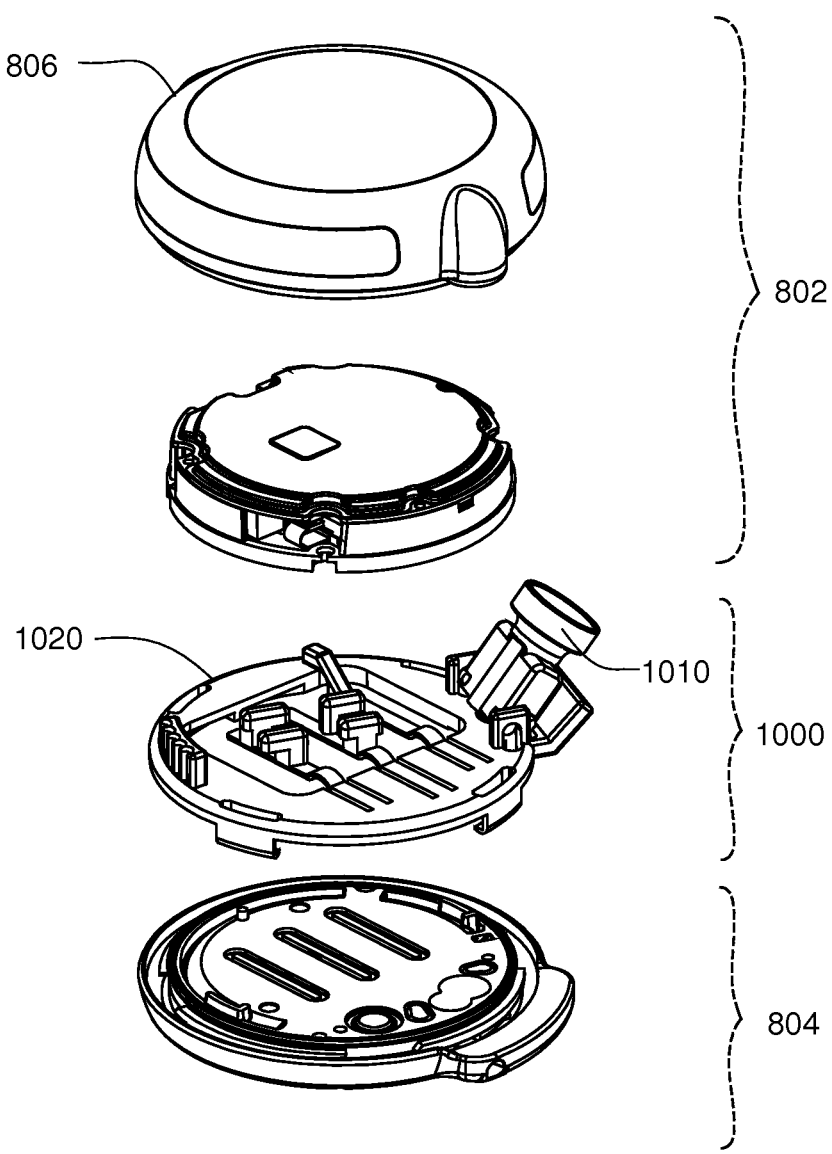
FIGS. 57-58 is an isometric view of an infusion pump assembly and a fill adapter.
Figure 58:
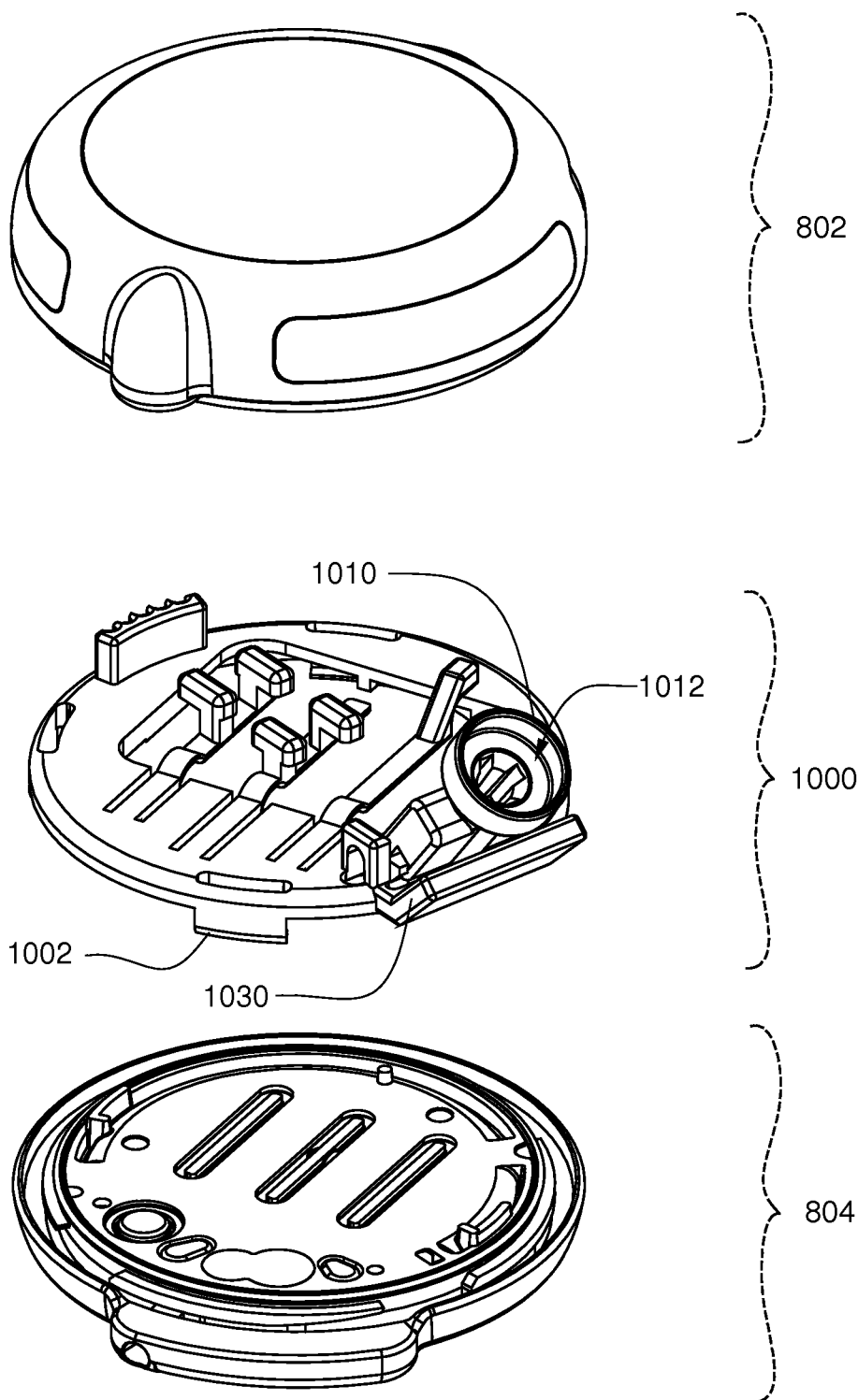
Figure 59:
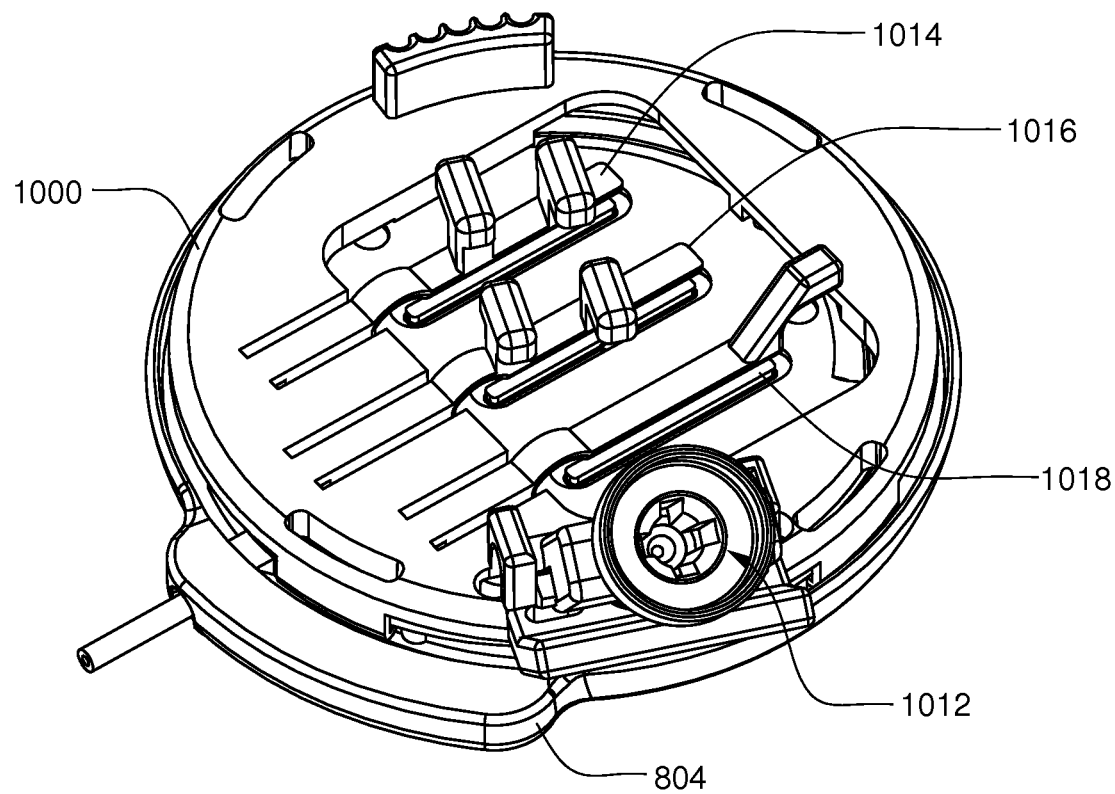
FIGS. 59-64 are various views of the fill adapter of FIG. 57.
Figure 60:
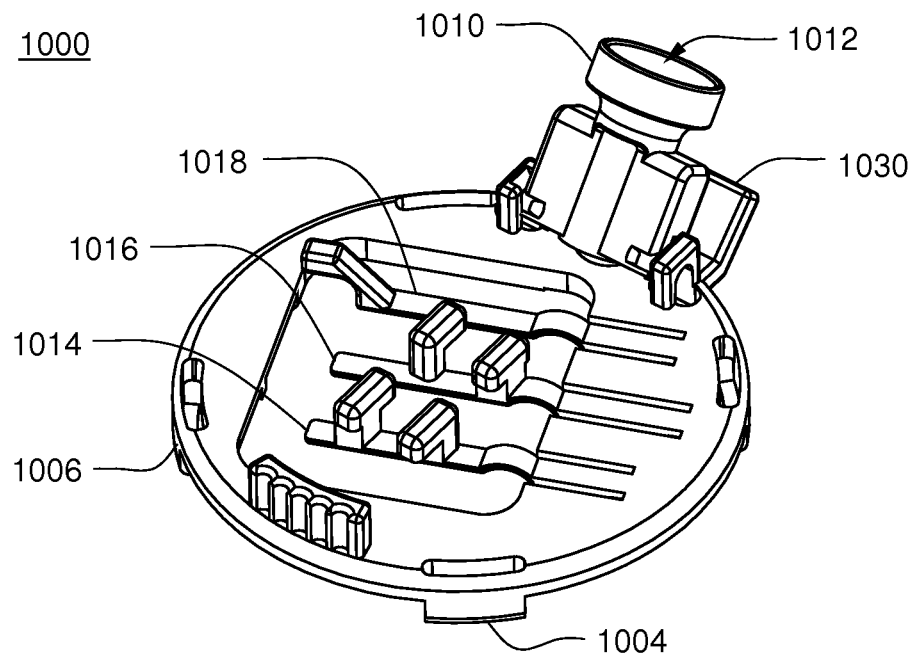
Figure 61:
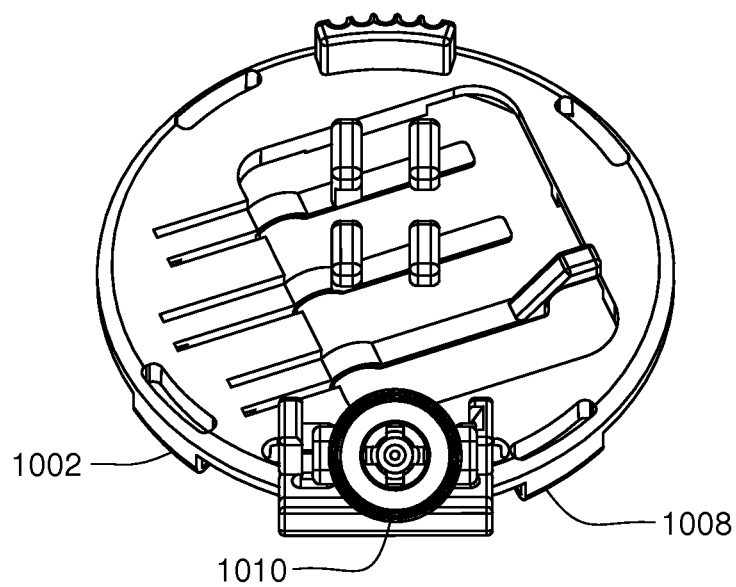

With reference also to FIGS. 54A-54C, disposable housing assembly 804 may further include valve membrane cover 924. Valve membrane cover 924 may be at least partially disposed over the volcano valves (e.g., volcano valve 916) and pumping recess 926 included on/within base portion 900. Valve membrane cover 924 may include a flexible material, e.g., which may be selectively engaged against the volcano valves by reservoir valve 850, volume sensor valve 854, and measurement valve 856 of reusable housing assembly 802, e.g., for controlling the flow of the infusible fluid. Additionally, valve membrane cover 924 may be resiliently deformed into pumping recess 926 by plunger pump 852 to effectuate pumping of the infusible fluid. Valve membrane cover 924 may be engaged between base portion 900 and top portion 904 of disposable housing assembly 804 to form seal 928 between valve membrane cover 924 and base portion 900. For example, in the exemplary embodiment, valve membrane cover 924 may be overmolded onto base portion 900. In other embodiment, valve membrane cover 924 may be compressively pinched between base portion 900 and top portion 904 to form seal 928. Additionally/alternatively, valve membrane insert may be connected to one or more of base portion 900 and top portion 904, e.g., by gluing, heat sealing, or the like.

Figure 53A:
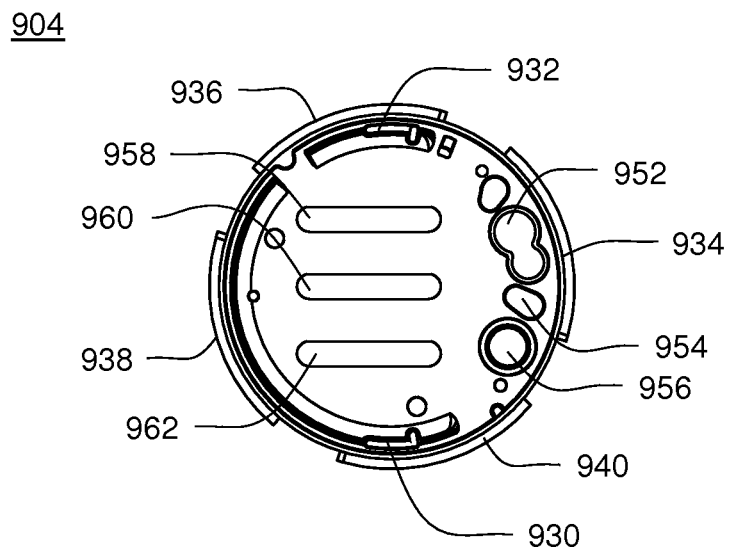
FIGS. 53A-53C depict the top portion of the disposable housing assembly of FIG. 48.
Figure 53B:
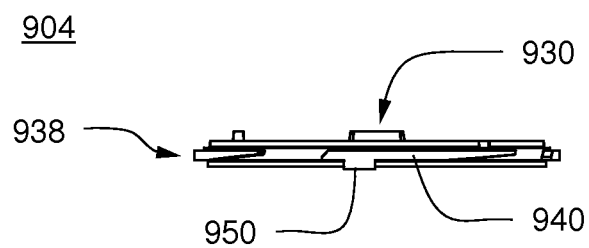
Figure 53C:
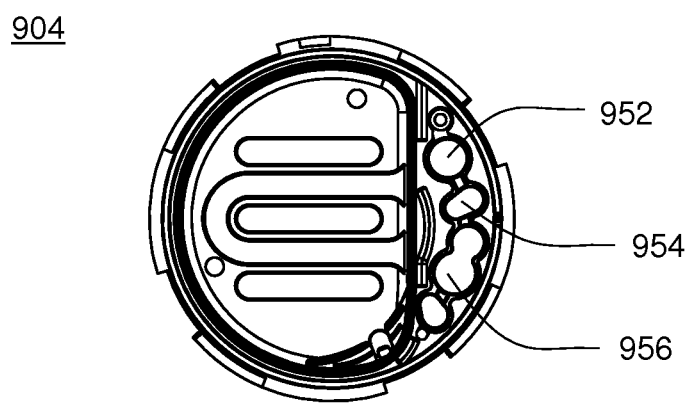

Referring also to FIGS. 53A-C, top portion 904 may include alignment tabs 930, 932 that may be configured to be at least partially received in openings 836, 838 of base plate 818 of reusable housing assembly 802 to ensure proper alignment between reusable housing assembly 802 and disposable housing assembly 804. Additionally, top portion 904 may include one or more radial tabs 934, 936, 938, 940 configured to be engaged by cooperating tabs 942, 944, 946, 948 of locking ring assembly 806. The one or more radial tabs (e.g., radial tab 940) may include stops (e.g., alignment tab stop 950, which may be used for welding, it's the tab that fits in the recess to locate and ultrasonically weld), e.g., which may prevent further rotation of locking ring assembly 806 once reusable housing assembly 802 and disposable housing assembly 804 are fully engaged.

Figure 52A:
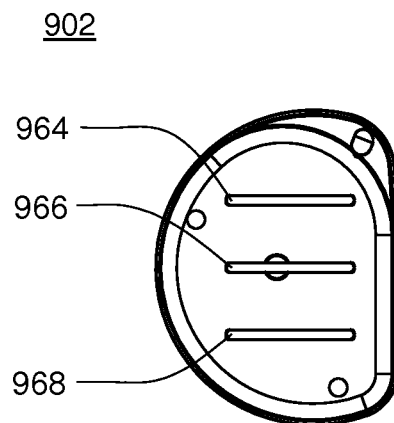
FIGS. 52A-52C depict the membrane assembly of the disposable housing assembly of FIG. 48.
Figure 52B:
Figure 52C:
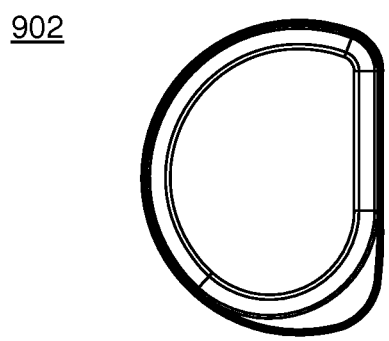

As discussed above, valve membrane insert 924 may allow for pumping and flow of the infusible fluid by reservoir valve 850, plunger pump 852, volume sensor valve 854, and measurement valve 856. Accordingly, top portion 904 may include one or more openings (e.g., openings 952, 954, 956) that may expose at least a portion of valve membrane insert 924 for actuation by reservoir valve 850, plunger pump 852, volume sensor valve 854, and measurement valve 856. Additionally, top portion 904 may include one or more openings 958, 960, 962 which may be configured to allow the fill volume to be controlled during filling of reservoir 908, as will be discussed in greater detail below. Reservoir assembly 902 may include ribs 964, 966, 968 (e.g., as shown in FIG. 52A), which may be at least partially received in respective openings 958, 960, 962. As will be described in greater detail below, a force may be applied to one or more of ribs 964, 966, 968 to, at least temporarily, reduce the volume of reservoir 908.

In some embodiments, it may be desirable to provide a seal between reusable housing assembly 802 and disposable housing assembly 804. Accordingly, disposable housing assembly 804 may include sealing assembly 970. Sealing assembly 970 may include, for example, an elastomeric member that may provide a compressible rubber or plastic layer between reusable housing assembly 802 and disposable housing assembly 804 when engaged, thus preventing inadvertent disengagement and penetration by outside fluids. For example, sealing assembly 970 may be a watertight seal assembly and, thus, enable a user to wear infusion pump assembly 800 while swimming, bathing or exercising.

In a fashion similar to, e.g., disposable housing assembly 114, disposable housing assembly 802 may, in some embodiments, be configured to have reservoir 908 filled a plurality of times. However, in some embodiments, disposable housing assembly 114 may be configured such that reservoir 908 may not be refilled. Referring also to FIGS. 57-64, fill adapter 1000 may be configured to be coupled to disposable housing assembly 804 for refilling reservoir 908 using a syringe (not shown). Fill adapter 1000 may include locking tabs 1002, 1004, 1006, 1008 that may be configured to engage radial tabs 934, 936, 938, 940 of disposable housing assembly 804 in a manner generally similar to tabs 942, 944, 946, 948 of locking ring assembly 806. Accordingly, fill adapter 1000 may be releasably engaged with disposable housing assembly 804 by aligning fill adapter 1000 with disposable housing assembly 804 and rotating fill adapter 1000 and disposable housing assembly 804 relative to one another to releasably engage locking tabs 1002, 1004, 1006, 1008 with radial tabs 934, 936, 938, 940.

Fill adapter 1000 may further include filling aid 1010, which may include guide passage 1012, e.g., which may be configured to guide a needle of a syringe (not shown) to a septum of disposable housing assembly 804 to allow reservoir 908 of disposable housing assembly 804 to be filled by the syringe. In some embodiments, guide passage 1012 may be an angled bevel or other gradual angled bevel to further guide a syringe to a septum. Fill adapter 1000 may facilitate filling reservoir 908 by providing a relatively large insertion area, e.g., at the distal opening of guide passage 1012. Guide passage 1012 may generally taper to a smaller proximal opening that may be properly aligned with the septum of disposable housing assembly 804, when fill adapter 1000 is engaged with disposable housing assembly 804. Accordingly, fill adapter 1000 may reduce the dexterity and aim necessary to properly insert a needle through the septum of disposable housing assembly 804 for the purpose of filling reservoir 908.

As discussed above, disposable housing assembly 804 may configured to facilitate controlling the quantity of infusible fluid delivered to reservoir 908 during filling. For example, membrane assembly 902 of disposable housing assembly 804 may include ribs 964, 966, 968 that may be depressed and at least partially displaced into reservoir 908, thereby reducing the volume of reservoir 908. Accordingly, when infusible fluid is delivered to reservoir 908, the volume of fluid that may be accommodated by reservoir 908 may be correspondingly reduced. Ribs 964, 966, 968 may be accessible via openings 958, 960, 962 in top portion 904 of disposable housing assembly 804.

Fill adapter 1000 may include one or more button assemblies (e.g., button assemblies 1014, 1016, 1018) corresponding to ribs 964, 966, 968. That is, when fill adapter 1000 is releasably engaged with disposable housing assembly 804, buttons 1014, 1016, 1018 may be aligned with ribs 964, 966, 968. Button assemblies 1014, 1016, 1018 may be, for example, cantilever members capable of being depressed. When fill adapter 1000 is releasably engaged with disposable housing assembly 804, one or more of button assemblies 1014, 1016, 1018 may be depressed, and may correspondingly displace a respective one of ribs 964, 966, 698 into reservoir 908, causing an attendant reduction in the volume of reservoir 908.

For example, assume for illustrative purposes that reservoir 908 has a maximum capacity of 3.00 mL. Further, assume that button assembly 1014 is configured to displace rib 964 into disposable housing assembly 804, resulting in a 0.5 mL reduction in the 3.00 mL capacity of disposable housing assembly 804. Further, assume that button assembly 1016 is configured to displace rib 966 into disposable housing assembly 804, also resulting in a 0.5 mL reduction in the 3.00 mL capacity of disposable housing assembly 804. Further, assume that button assembly 1018 is configured to displace slot assembly 968 into disposable housing assembly 804, also resulting in a 0.5 mL reduction in the 3.00 mL capacity of disposable housing assembly 804. Therefore, if the user wishes to fill reservoir 908 within disposable housing assembly 804 with 2.00 mL of infusible fluid, in some embodiments, the user may first fill the reservoir to the 3.00 mL capacity and then depresses button assemblies 1016 and 1014 (resulting in the displacement of rib 966 into disposable housing assembly 804), effectively reducing the 3.00 mL capacity of reservoir 908 within disposable housing assembly 804 to 2.00 mL. In some embodiments, the user may first depress a respective number of button assemblies, effectively reducing the capacity of reservoir 908, and then fill reservoir 908. Although a particular number of button assemblies are shown, representing the exemplary embodiment, in other embodiments, the number of button assemblies may vary from a minimum of 1 to as many as is desired.

Additionally, although for descriptive purposes, and in the exemplary embodiment, each button assembly may displace 0.5 mL, in other embodiments, the volume of displacement per button may vary. Additionally, the reservoir may be, in various embodiments, include a larger or smaller volume than described in the exemplary embodiment. According to the above-described configuration, the button assemblies (e.g., button assemblies 1014, 1016, 108) may employed, at least in part, to control the fill volume of reservoir 908. By not depressing any of the button assemblies, the greatest fill volume of reservoir 908 may be achieved. Depressing one button assembly (e.g., button assembly 1014) may allow the second greatest fill volume to be achieved. Depressing two button assemblies (e.g., button assemblies 1014, 1016) may achieve the third greatest fill volume. Depressing all three button assemblies (e.g., button assemblies 1014, 1016, 1018) may allow the smallest fill volume to be achieve.

Further, in an embodiment button assemblies 1014, 1016, 1018 may be utilized, at least in part, to facilitate filling of reservoir 908. For example, once a filling needle (e.g., which may be fluidly coupled to a vial of infusible fluid) has been inserted into reservoir 908, button assemblies 1014, 1016, 1018 may be depressed to pump at least a portion of any air that may be contained within reservoir into the vial of infusible fluid. Button assemblies 1014, 1016, 1018 may subsequently be released to allow infusible fluid to flow from the vial into reservoir 908. Once reservoir 908 has been filled with the infusible fluid, one or more button assemblies (e.g., one or more of button assemblies 1014, 1016, 1018) may be depressed, thereby squeezing at least a portion of the infusible fluid from reservoir 908 (e.g., via a needle used to fill reservoir 908 and back into the vial of infusible fluid). As discussed above, the volume of infusible fluid contained within reservoir 908 may be controlled, e.g., depending upon how many button assemblies are depressed (e.g., which may control how much infusible fluid is squeezed back into the vial of infusible fluid).

Figure 62:
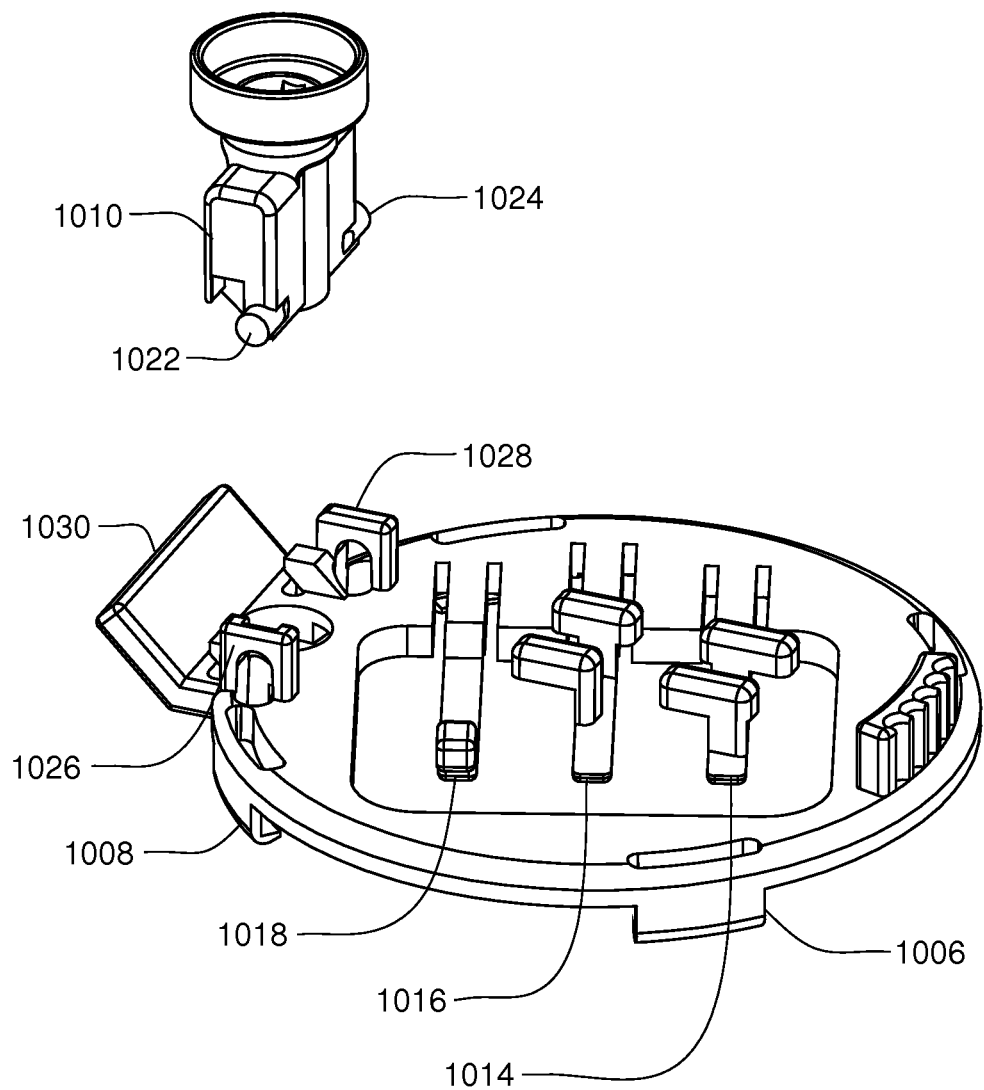
Figure 63:
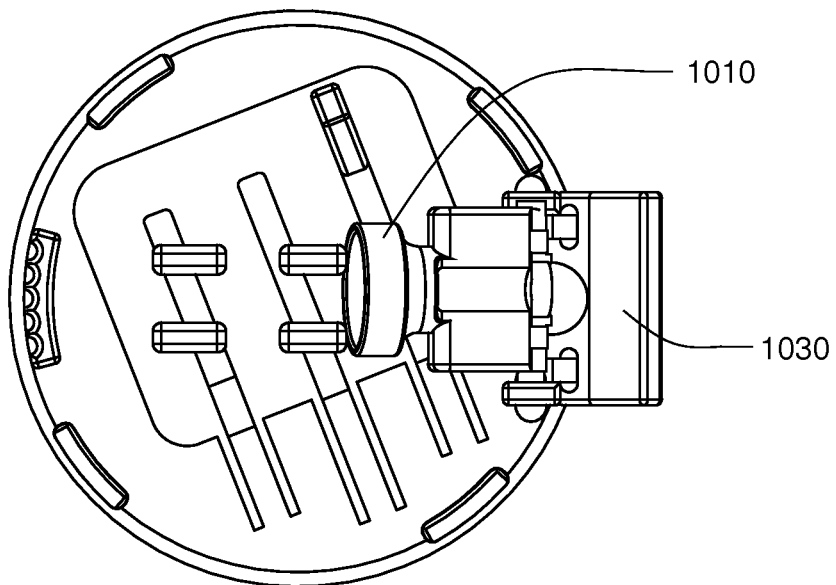
Figure 64:
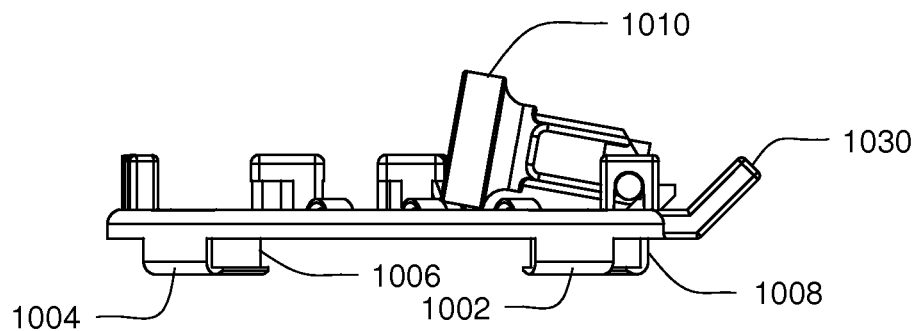

With particular reference to FIGS. 62-64, filling aid 1010 may be pivotally coupled to fill adapter base plate 1020. For example, filling aid 1010 may include pivot members 1022, 1024 that may be configured to be received in pivot supports 1026, 1028, thereby allowing filling aid to pivot between an open position (e.g., as shown in FIGS. 57-61) and a closed position (e.g., as shown in FIGS. 63-64). The closed position may be suitable, e.g., for packaging fill adapter 1000, storage of fill adapter 1000, or the like. In order to ensure that filling aid 1010 is properly oriented for filling reservoir 908, fill adapter 1000 may include support member 1030. To properly orient filling aid 1010, a user may pivot filling aid 1010 to a fully open position, wherein filling aid 1010 may contact support member 1030.

Figure 65:
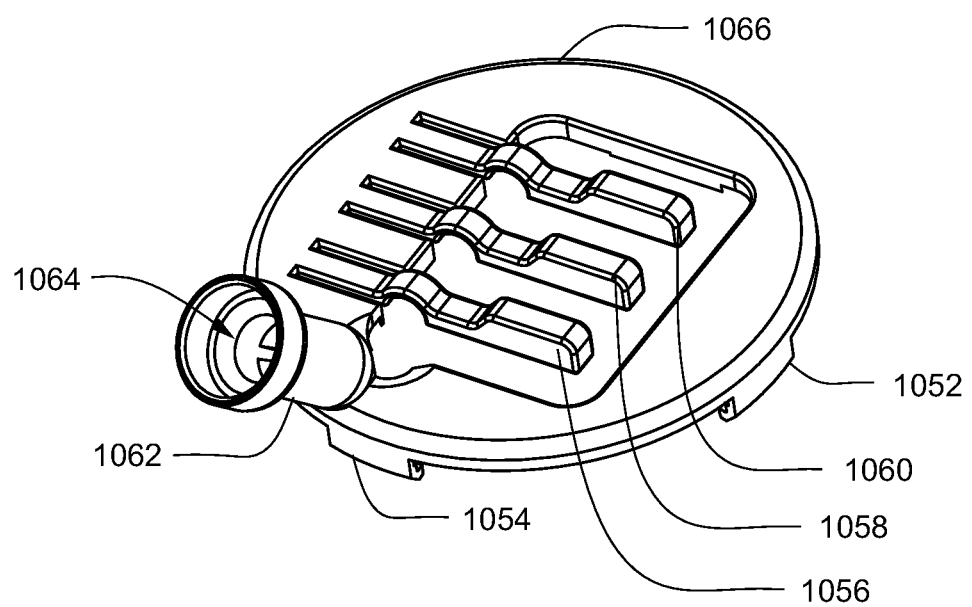
FIG. 65 is an isometric view of another embodiment of a fill adapter.
Figure 66:
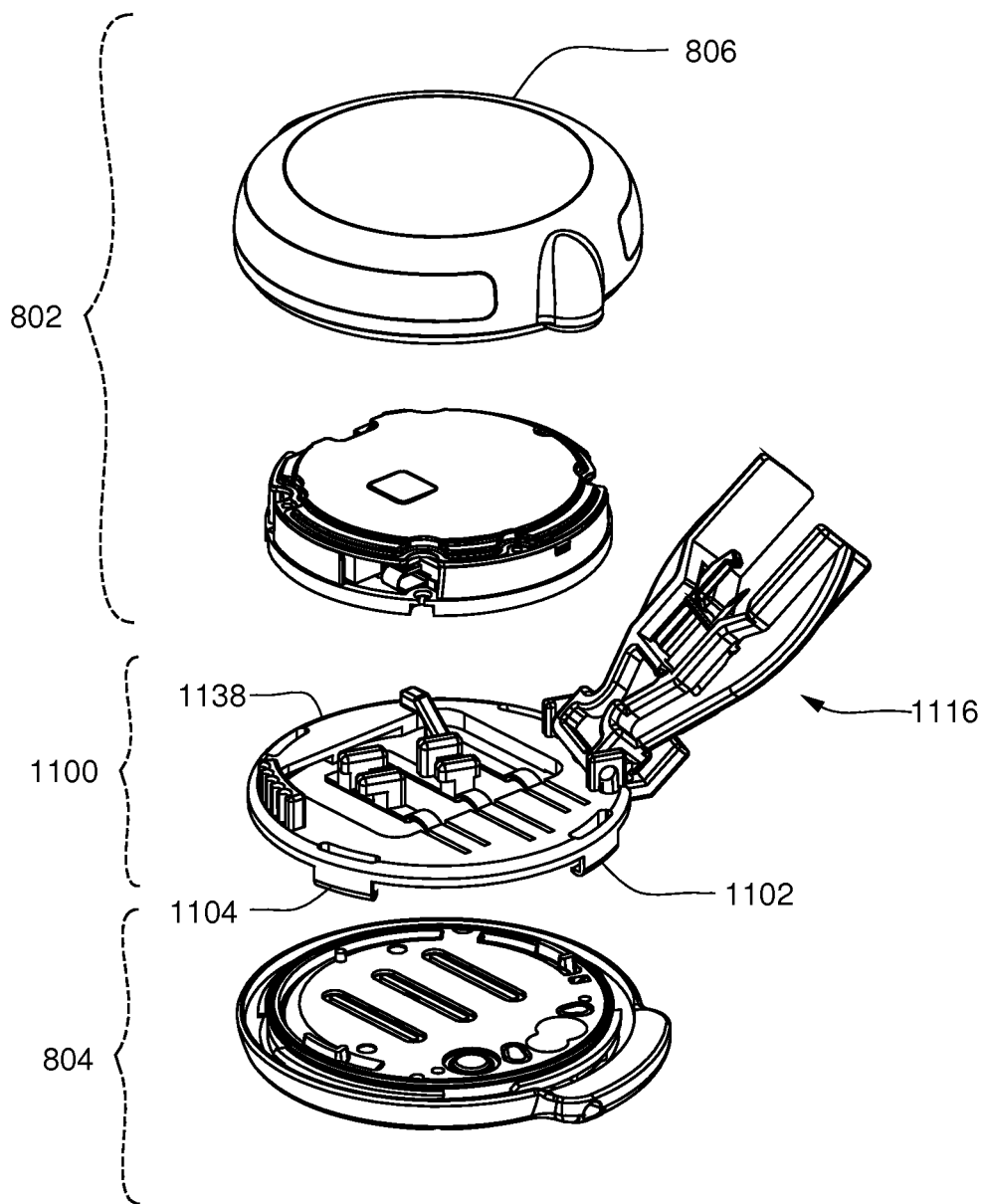
FIGS. 66-67 depict an infusion pump assembly and another embodiment of a fill adapter.
Figure 67:
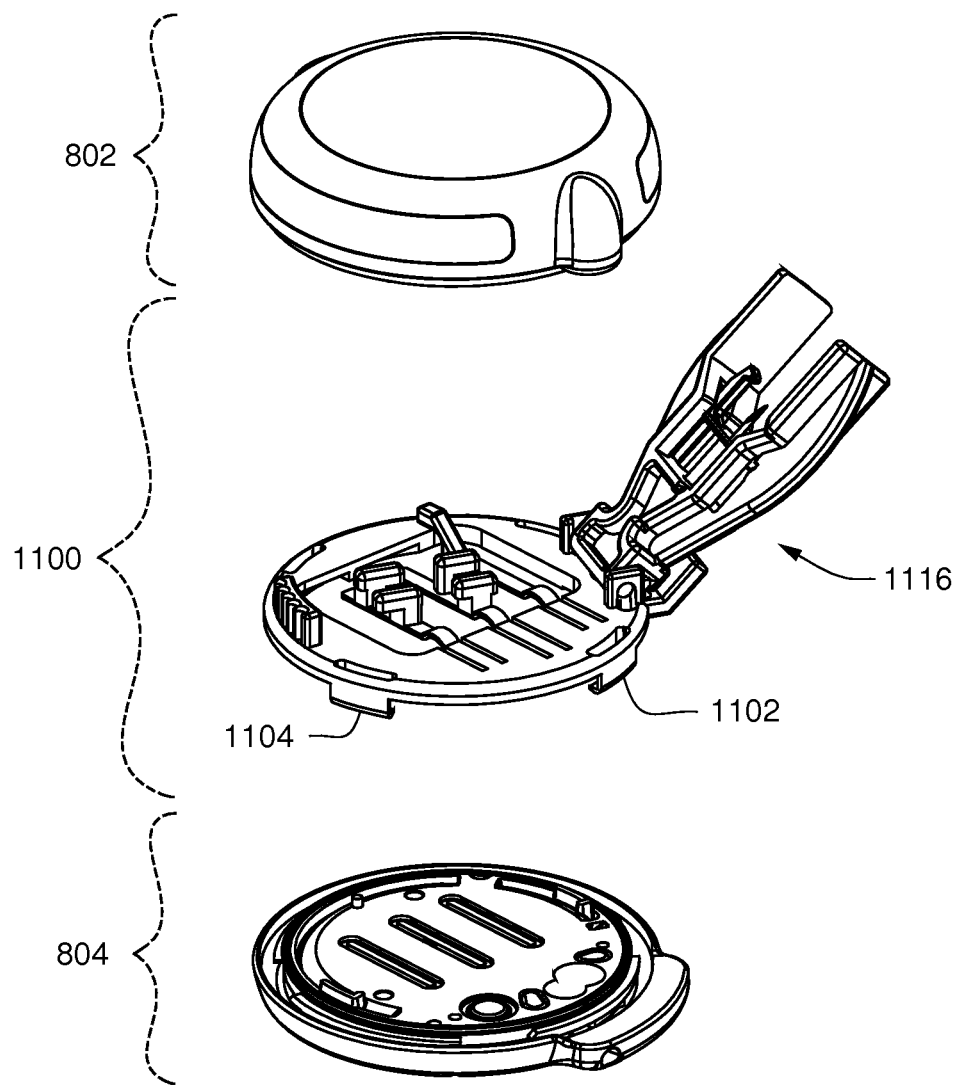
Figure 68:
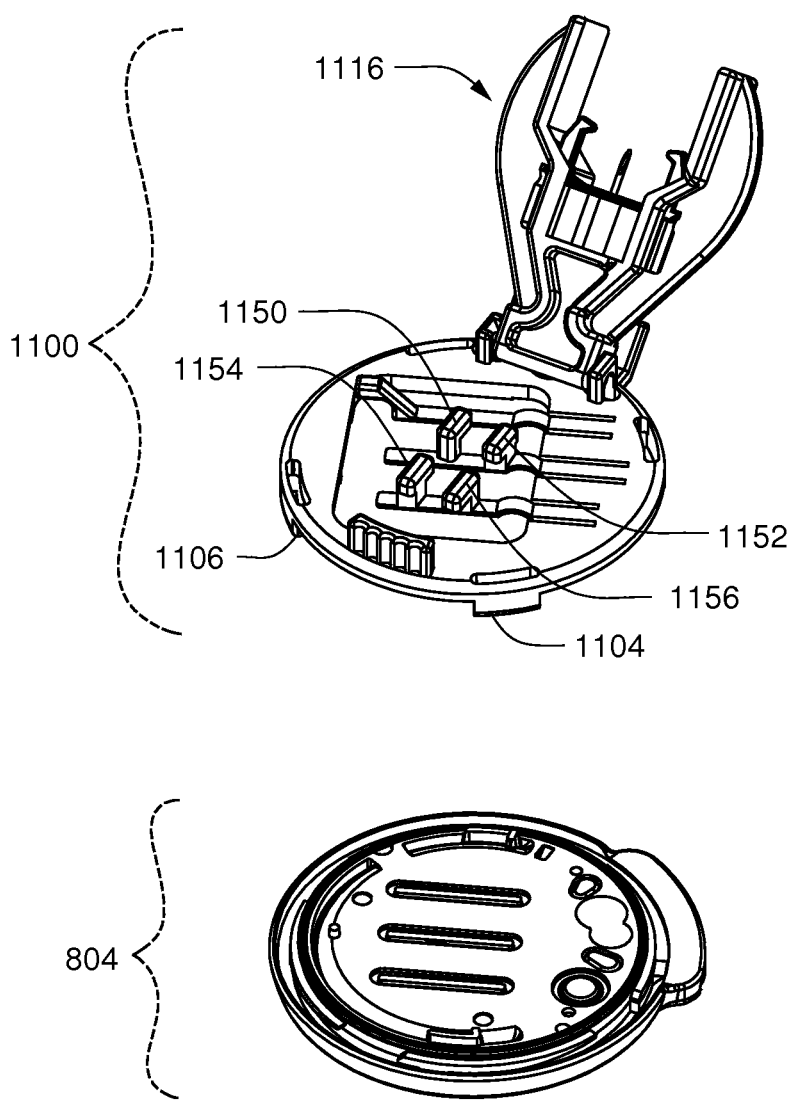
FIGS. 68-74 are various views of the fill adapter of FIG. 66.
Figure 69:
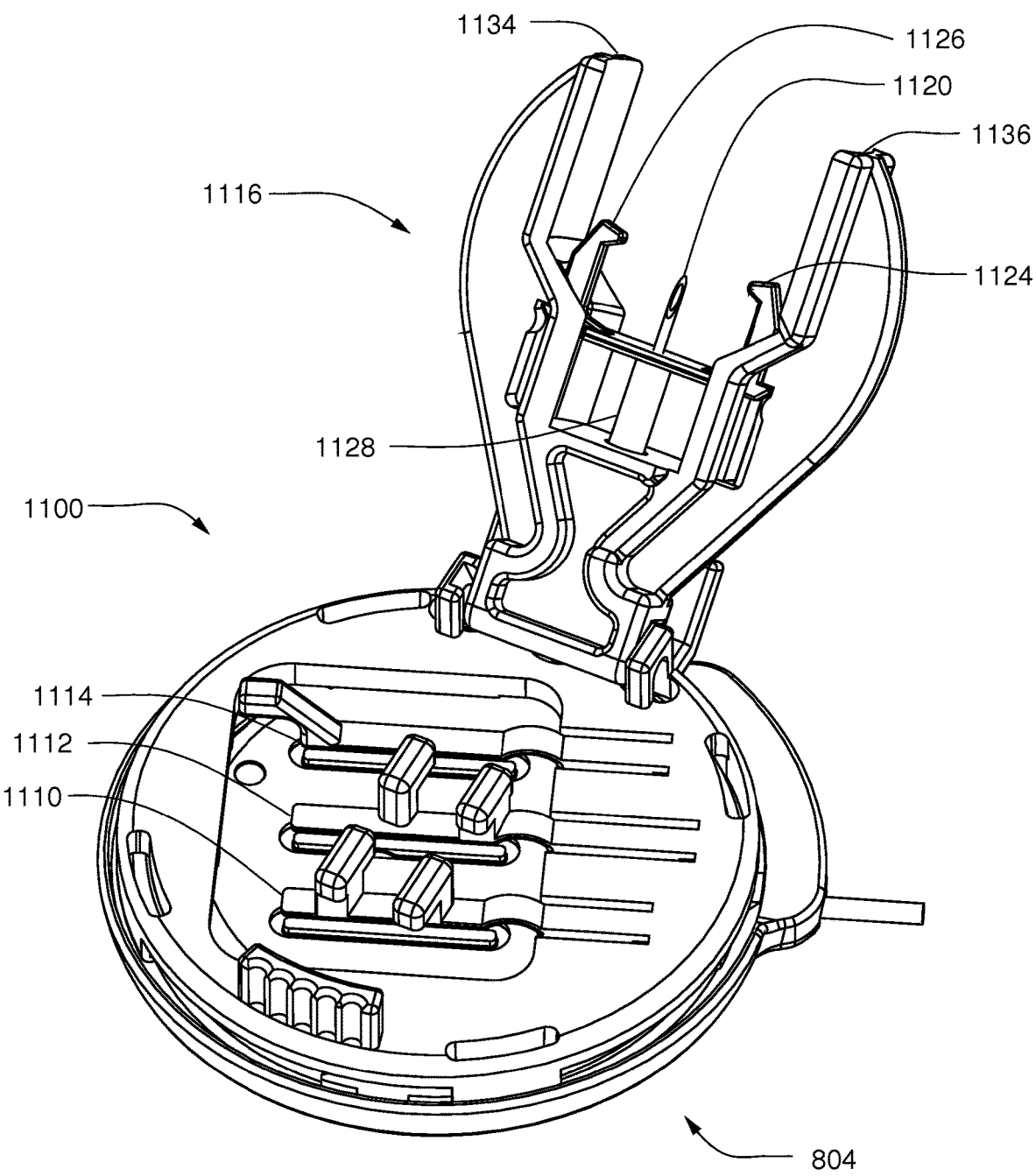

According to an alternative embodiment, and referring also to FIG. 65, fill adapter 1050 may be configured to releasably engage disposable housing assembly 804 via a plurality of locking tabs (e.g., locking tabs 1052, 1054). Additionally, fill adapter 1050 may include a plurality of button assemblies (e.g., button assemblies 1056, 1058, 1060) that may interact with ribs 964, 966, 968 of disposable housing assembly 804 to adjust a fill volume of reservoir 908. Fill adapter 1050 may further include filling aid 1062, having guide passage 1064 configured to align a needle of a syringe with the septum of disposable housing 804, e.g., for accessing reservoir 908 for the purpose of filling reservoir 908 with an infusible fluid. Filling aid 1062 may be connected to base plate 1066, e.g., as an integral component therewith, by gluing, heat sealing, compression fit, or the like.

Referring also to FIGS. 66-74, vial fill adapter 1100 may be configured to facilitate filling reservoir 908 of disposable housing assembly 804 directly from a vial. Similar to fill adapter 1000, vial fill adapter 1100 may include locking tabs 1102, 1104, 1106, 1108 that may be configured to engage radial tabs 934, 936, 938, 940 of disposable housing assembly in a manner generally similar to tabs 942, 944, 946, 948 of locking ring assembly 806. Accordingly, vial fill adapter 1100 may be releasably engaged with disposable housing assembly 804 by aligning vial fill adapter 1100 with disposable housing assembly 804 and rotating vial fill adapter 1100 and disposable housing assembly 804 relative to one another to releasably engage locking tabs 1102, 1104, 1106, 1108 with radial tabs 934, 936, 938, 940.

As discussed above, disposable housing assembly 804 may be configured to facilitate controlling the quantity of infusible fluid delivered to reservoir 908 during filling. For example, membrane assembly 902 of disposable housing assembly 804 may include ribs 964, 966, 968 that may be depressed and at least partially displaced into reservoir 908, thereby reducing the volume of reservoir 908. Accordingly, when infusible fluid is delivered to reservoir 908, the volume of fluid that may be accommodated by reservoir 908 may be correspondingly reduced. Ribs 964, 966, 968 may be accessible via openings 958, 960, 962 in top portion 904 of disposable housing assembly 804.

Vial fill adapter 1100 may include one or more button assemblies (e.g., button assemblies 1110, 1112, 1114) corresponding to ribs 964, 966, 968 (e.g., shown in FIG. 52A). That is, when vial fill adapter 1100 is releasably engaged with disposable housing assembly 804, buttons 1110, 1112, 1114 may be aligned with ribs 964, 966, 968. Button assemblies 1110, 1112, 1114 may be, for example, cantilever members capable of being depressed. When vial fill adapter 1100 is releasably engaged with disposable housing assembly 804, one or more of button assemblies 1110, 1112, 1114 may be depressed, and may correspondingly displace a respective one of ribs 964, 966, 698 into reservoir 908, thereby reducing the volume of reservoir 908.

For example, assume for illustrative purposes that reservoir 908 has a maximum capacity of 3.00 mL. Further, assume that button assembly 1110 is configured to displace rib 964 into disposable housing assembly 804, resulting in a 0.5 mL reduction in the 3.00 mL capacity of disposable housing assembly 804. Further, assume that button assembly 1112 is configured to displace rib 966 into disposable housing assembly 804, also resulting in a 0.5 mL reduction in the 3.00 mL capacity of disposable housing assembly 804. Further, assume that button assembly 1114 is configured to displace rib 968 into disposable housing assembly 804, also resulting in a 0.50 mL reduction in the 3.00 mL capacity of disposable housing assembly 804. Therefore, if the user wishes to fill reservoir 908 within disposable housing assembly 804 with 2.00 mL of infusible fluid, the user may depress button assemblies 1112 and 1114 (resulting in the displacement of ribs 966 and 968 into disposable housing assembly 804), effectively reducing the 3.00 mL capacity of reservoir 908 within disposable housing assembly 804 to 2.0 mL.

Figure 71:
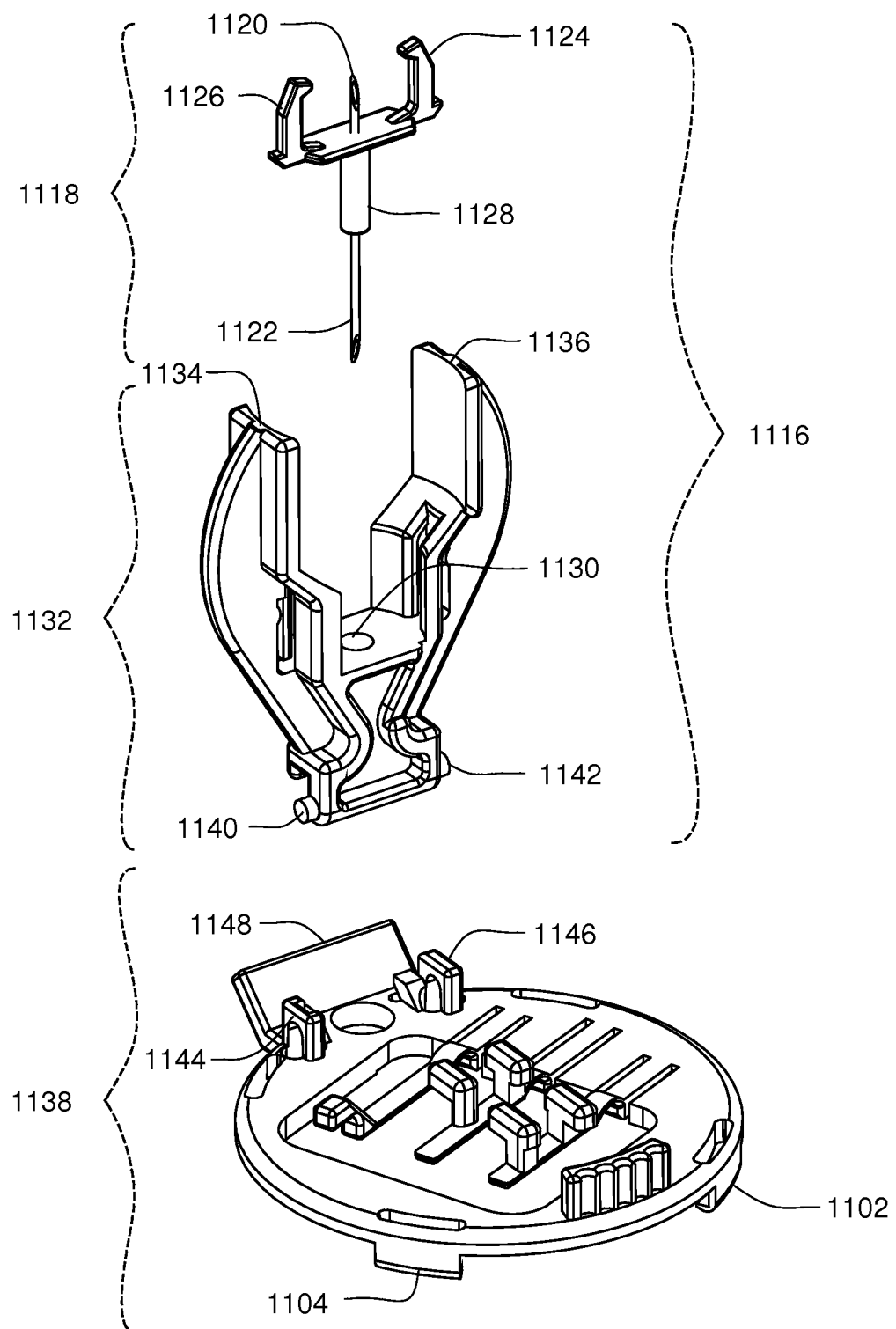

Vial fill adapter 1100 may further include vial filling aid assembly 1116 that may be configured to fluidly couple a vial of infusible fluid to reservoir 908 of disposable housing assembly 804 via a septum. With particular reference to FIG. 71, vial filling aid assembly may include double ended needle assembly 1118. Double ended needle assembly 1118 may include first needle end 1120 configured to penetrate the septum of a vial (not shown) and second needle end 1122 configured to penetrate the septum of disposable housing assembly 804. As such, the vial and reservoir 908 may be fluidly coupled allowing infusible fluid to be transferred from the vial to reservoir 908. Double ended needle assembly 1118 may include vial engagement portion 1124 adjacent first end 1120. Vial engagement arms 1124, 1126 may be configured to releasably engage, e.g., a vial cap, to assist in maintaining the fluid connection between double ended needle assembly 1118 and the vial. Additionally, double ended needle assembly 1118 may include body 1128 that may be slidably received in opening 1130 of vial filling aid body 1132. Vial filling aid body 1132 may include stabilizer arms 1134, 1136, e.g., which may be configured to stabilize the vial during filling of disposable housing assembly 804. In one embodiment, the vial may be engaged with double ended needle assembly 1118 e.g., such that first end 1120 may penetrate the septum of the vial and the cap of the vial may be engaged by engagement arms 1124, 1126. Body 1128 may be slidably inserted into opening 1130 such that second end 1122 of double ended needle assembly 1118 may penetrate the septum of disposable body assembly 804.

Figure 72:
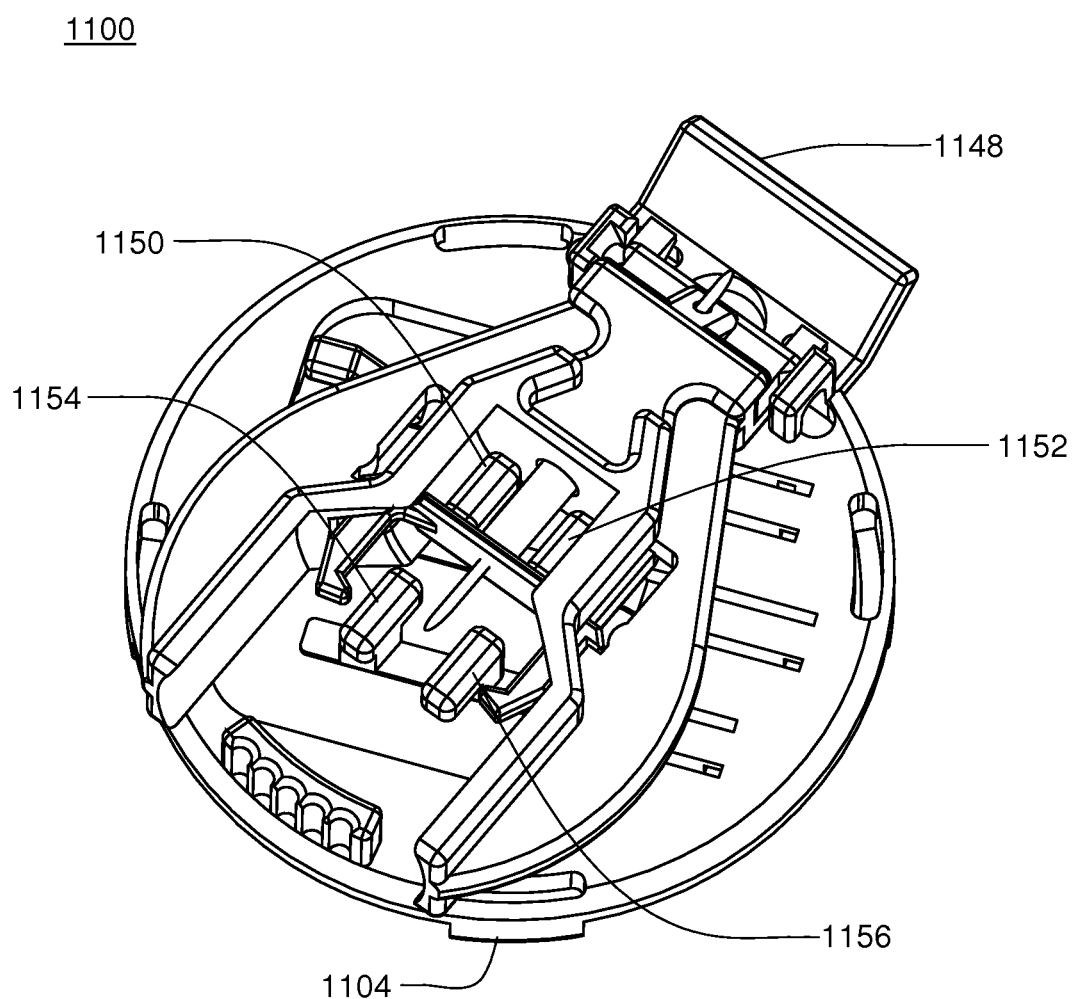
Figure 73:
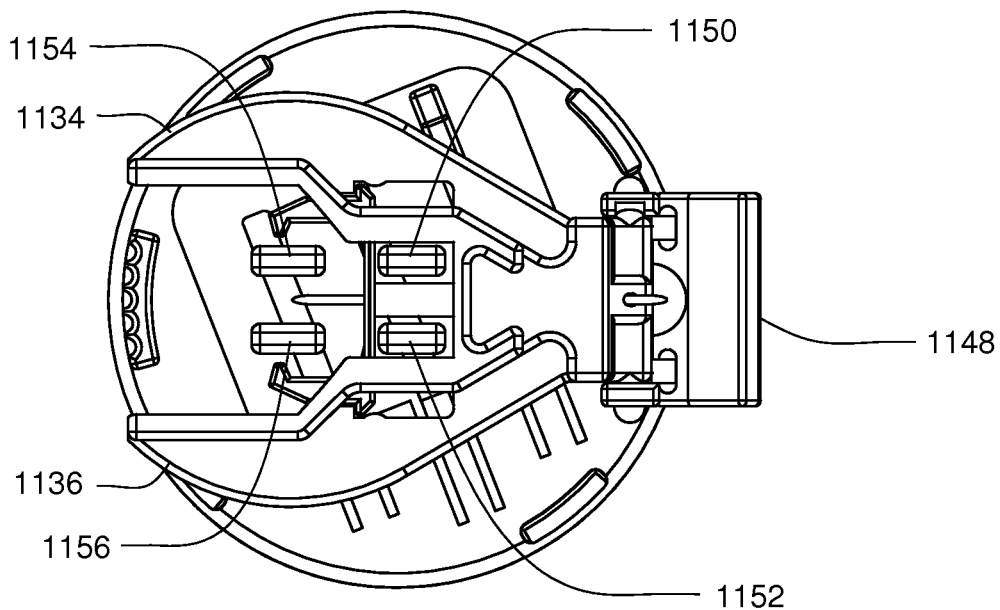
Figure 74:
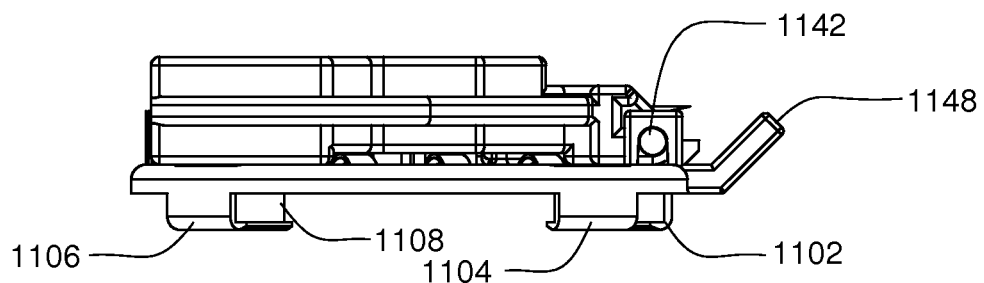
Figure 75:
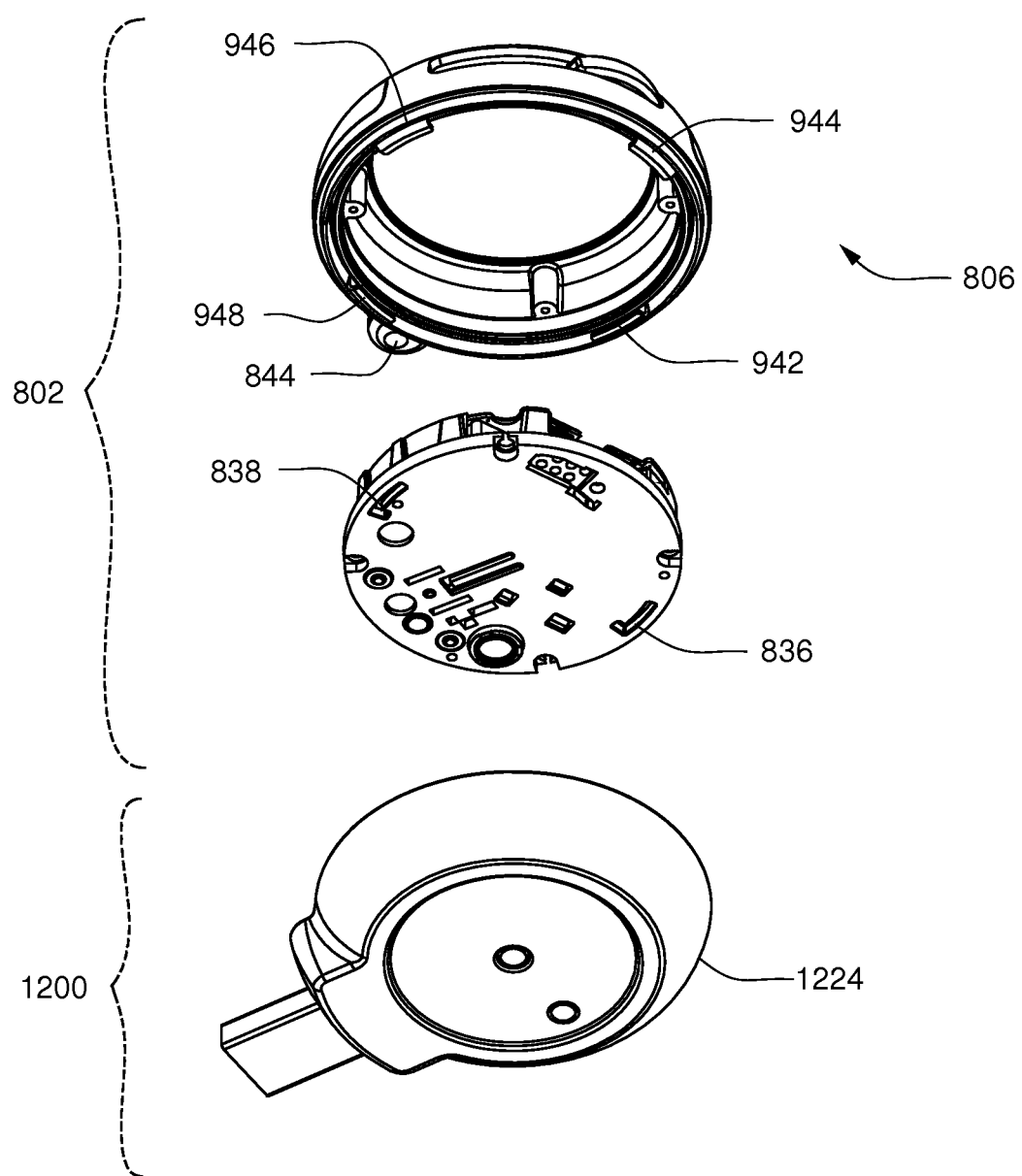
Figure 76:
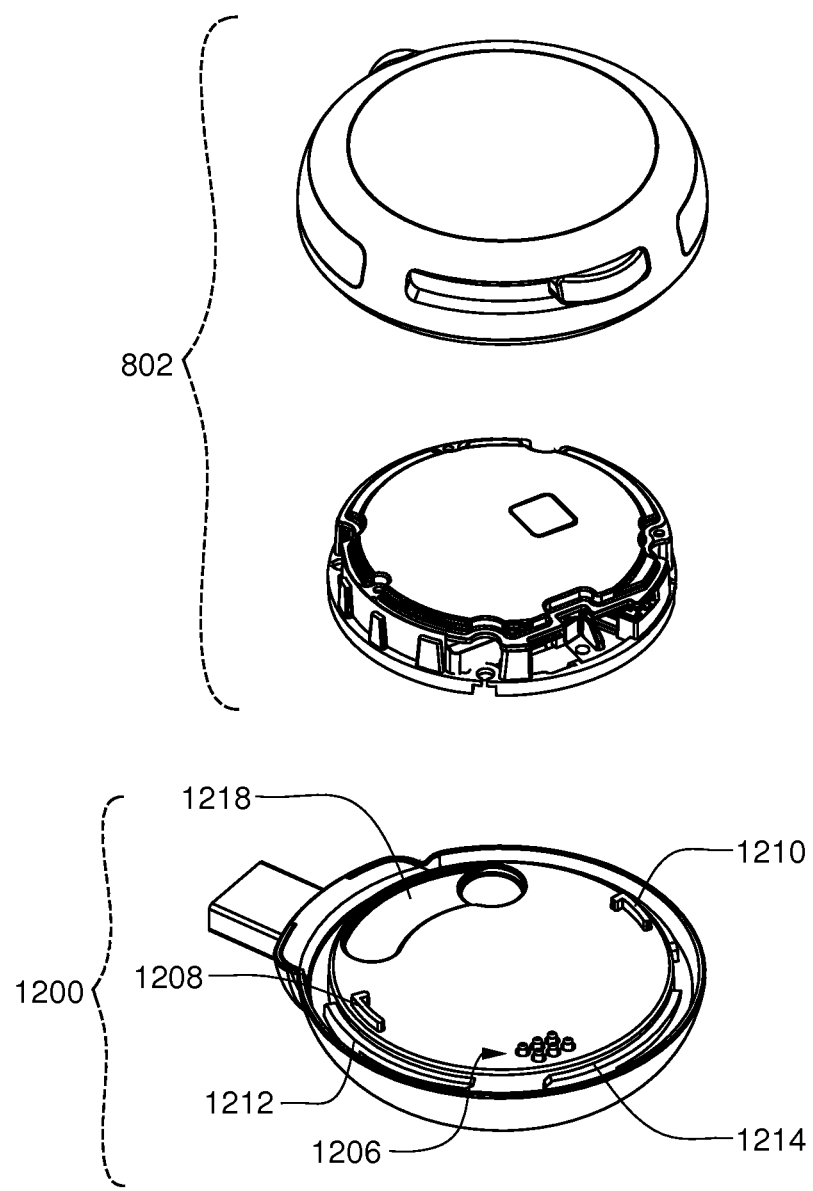

Similar to fill adapter 1000, vial filling aid assembly 1116 may be configured to be pivotally coupled to vial fill adapter base plate 1138. For example, vial filling aid 1116 may include pivot members 1140, 1142 that may be configured to be received in pivot supports 1144, 1146 (e.g., shown in FIG. 71), thereby allowing vial filling aid 1116 to pivot between an open position (e.g., as shown in FIGS. 66-70) and a closed position (e.g., as shown in FIGS. 72-74). The closed position may be suitable, e.g., for packaging vial fill adapter 1100, storage of vial fill adapter 1100, or the like. In order to ensure that vial filling aid 1116 is properly oriented for filling reservoir 908, vial fill adapter 1100 may include support member 1148. To properly orient vial filling aid 1116, a user may pivot vial filling aid 1116 to a fully open position, wherein vial filling aid 1116 may contact support member 1148. Additionally, vial fill adapter base plate 1138 may include one or more locking features (e.g., locking tabs 1150, 1152) that may engage vial filing aid 1116, and may maintain vial filling aid 1116 in the closed position. Vial fill adapter base plate 1138 may also include features (e.g., tabs 1154, 1156) that may be configured to assist in retaining double ended needle assembly 1118, e.g., by preventing slidable separation of double ended needle assembly 1118 from vial filling aid body 1132.

Figure 70:
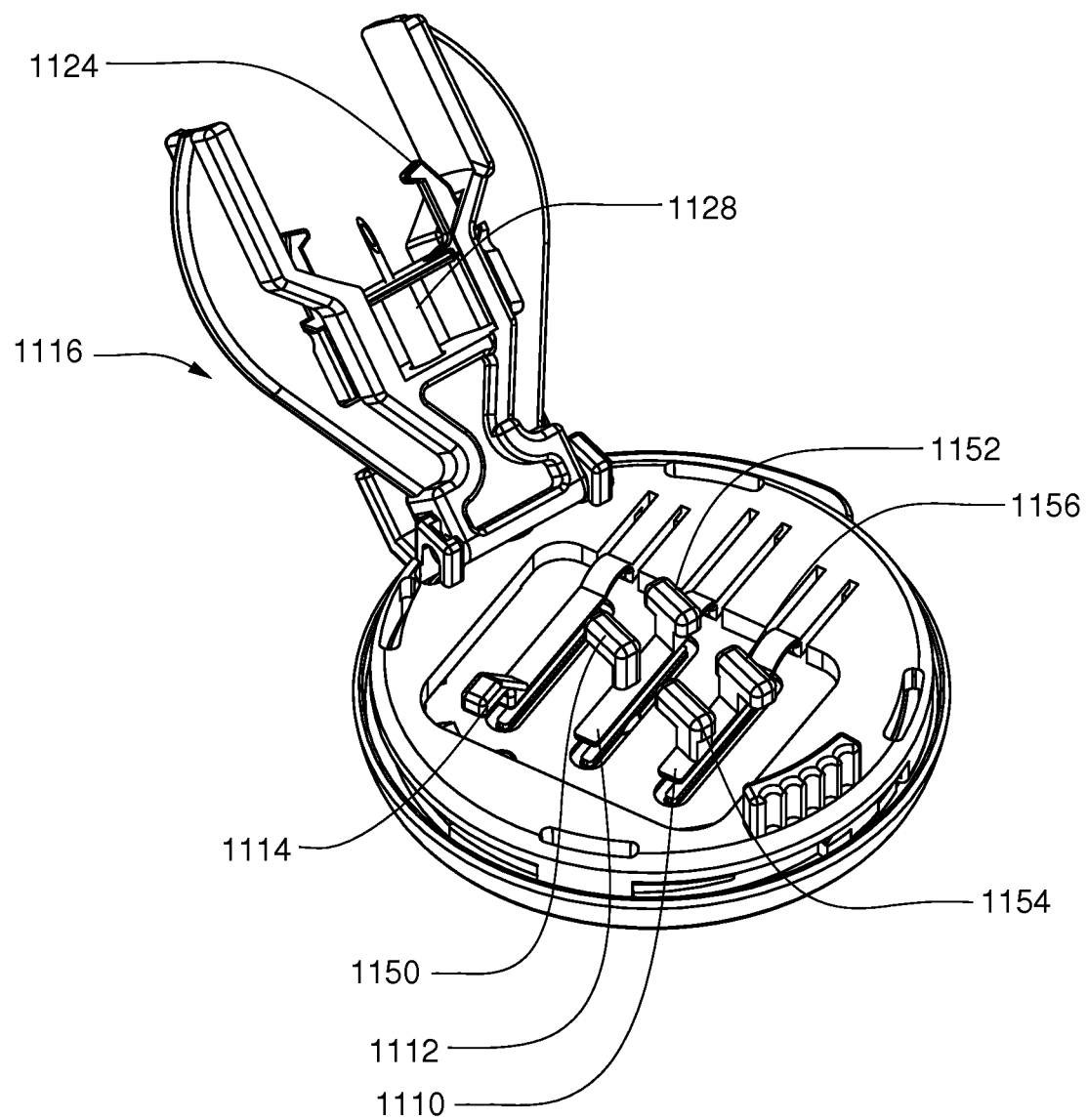

As shown in FIGS. 72-74, filling aid assembly 1116 is in a closed position. In this configuration, support member 1148 may additionally function as a needle guard. When removing filling aid assembly 1116 from disposable housing assembly 804, support member 1148 may function to safely allow a user to squeeze the ends and rotate filling aid assembly 1116 for removal. As shown in FIG. 70, in the open position, support member 1148 may function as a stop to maintain proper orientation.

Referring again to FIGS. 57-73, the exemplary embodiments of the fill adapter include a grip feature (e.g., 1166 in FIG. 72). Grip feature 1166 may provide a grip interface for removal of the fill adapter from disposable housing assembly 804. Although shown in one configuration in these figures, in other embodiments, the configuration may vary. In still other embodiments, a grip feature may not be included.

According to one embodiment, fill adapter base plate 1020 and vial fill adapter base plate 1138 may be interchangeable components. Accordingly, a single base plate (e.g., either fill adapter base plate 1020 or vial fill adapter base plate 1138 may be used with either filling aid 1010 or vial filling aid 1116. Accordingly, the number of distinct components that are required for both filling adapters may be reduced, and a user may have the ability to select the filling adapter that may be the most suitable for a given filling scenario.

The various embodiments of the fill adapters may provide many safely benefits, including but not limited to: providing a system for filling the reservoir without handling a needle; protecting the reservoir from unintentional contact with the needle, i.e., destruction of the integrity of the reservoir through unintentional puncture; designed to be ambidextrous; in some embodiments, may provide a system for maintaining air in the reservoir.

As discussed above, reusable housing assembly 802 may include battery 832, e.g., which may include a rechargeable battery. Referring also to FIGS. 75-80, battery charger 1200 may be configured to recharge battery 832. Battery charger 1200 may include housing 1202 having top plate 1204. Top plate 1204 may include one or more electrical contacts 1206, generally, configured to be electrically coupled to electrical contacts 834 of reusable housing assembly 802. Electrical contacts 1206 may include, but are not limited to, electrical contact pads, spring biased electrical contact members, or the like. Additionally, top plate 1204 may include alignment tabs 1208, 1210, which may be configured to mate with openings 836, 838 in base plate 818 of reusable housing assembly 802 (e.g., as shown in FIG. 35C). The cooperation of alignment tabs 1208, 1210 and openings 836, 838 may ensure that reusable housing assembly 802 is aligned with battery charger 1200 such that electrical contacts 1206 of battery charger 1200 may electrically couple with electrical contacts 834 of reusable housing assembly 802.

Figure 77:
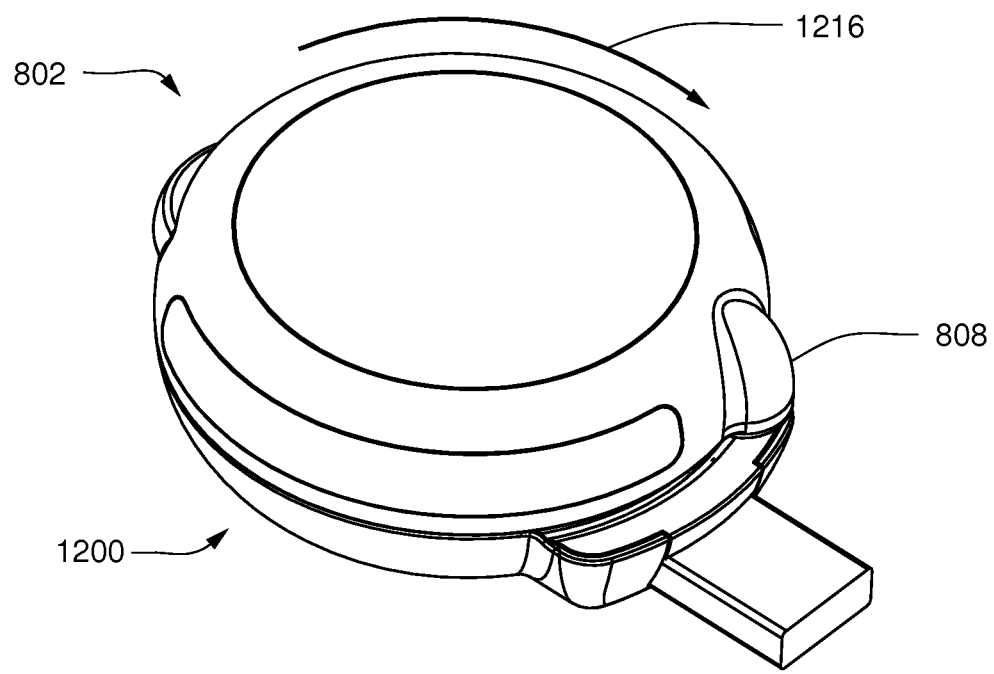
Figure 78:
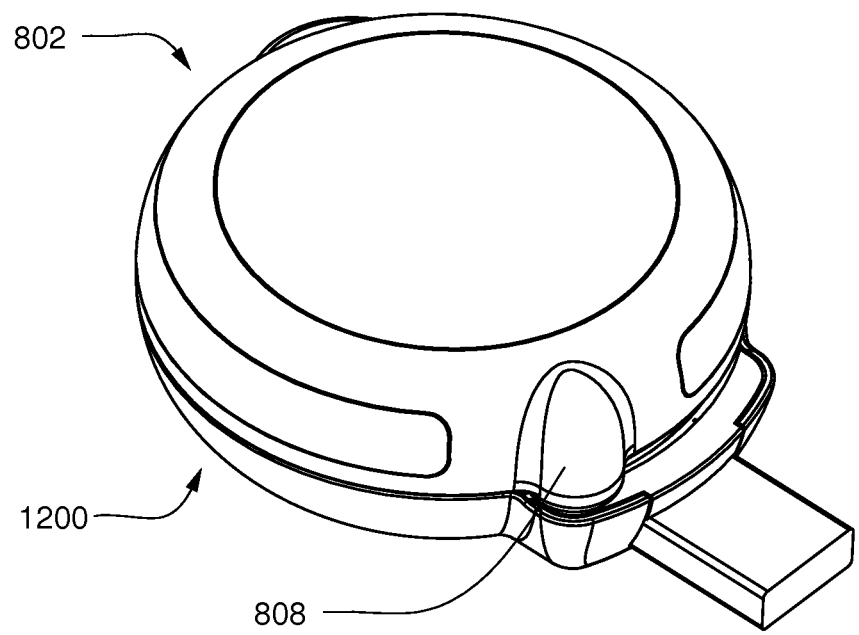

With reference also to FIGS. 77 and 78, battery charger 1200 may be configured to releasably engage reusable housing assembly 802. For example, in a similar manner as disposable housing assembly 804, battery charger 1200 may include one or more locking tabs (e.g., locking tabs 1212, 1214 shown in FIG. 76). The locking tabs (e.g., locking tabs 1212, 1214) may be engaged by tabs 942, 944, 946, 948 of locking ring assembly 806. As such, reusable housing assembly 802 may be aligned with battery charger 1200 (via alignment tabs 1208, 1210) with locking ring 806 in a first, unlocked position, as shown in FIG. 77. Locking ring 806 may be rotated relative to battery charger 1200 in the direction of arrow 1216 to releasably engage tabs 942, 944, 946, 948 of locking ring 806 with the locking tabs (e.g., locking tabs 1212, 1214) of battery charger 1200, as shown in FIG. 78.

Figure 80:
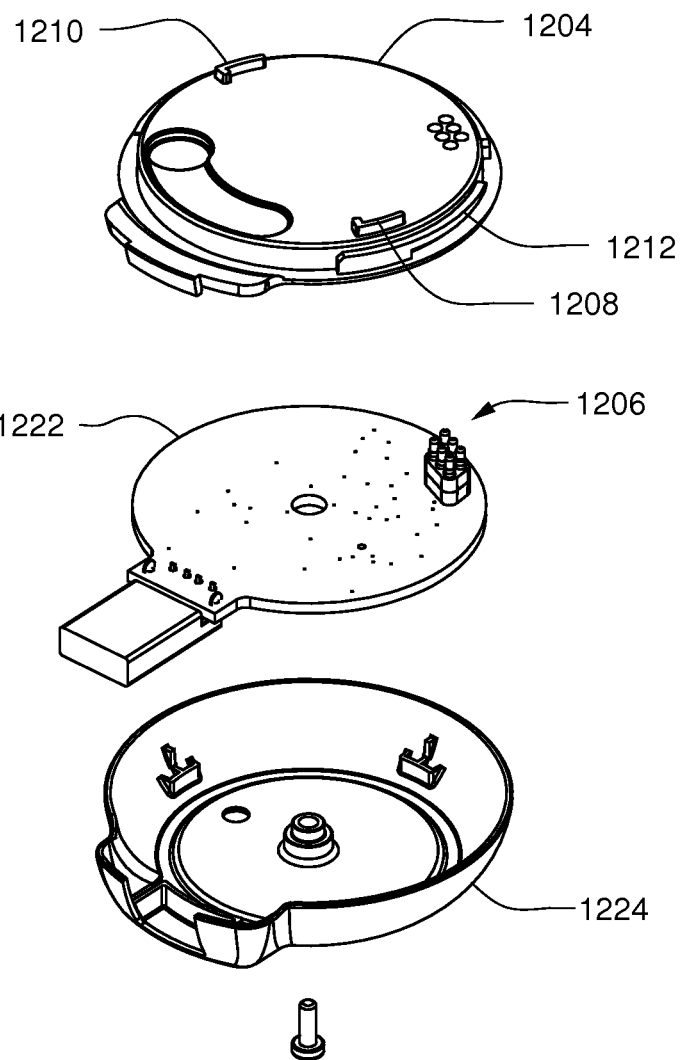

In an embodiment, battery charger 1200 may include recessed region 1218, e.g., which may, in the exemplary embodiments, provide clearance to accommodate reusable housing assembly 802 pumping and valving components. Referring also to FIGS. 79 & 80, battery charger 1200 may provide electrical current to electrical contacts 1206 (and thereby to reusable housing assembly 802 via electrical contacts 834) for recharging battery 832 of reusable housing assembly 802. In some embodiments, when a signal indicative of a fully engaged reusable housing is not provided, current may not be provided to electrical contacts 1206. According to such an embodiment, the risk associated with an electrical short circuit (e.g., resulting from foreign objects contacting electrical contacts 1206) and damage to reusable housing assembly 802 (e.g., resulting from improper initial alignment between electrical contacts 1206 and electrical contacts 834) may be reduced. Additionally, battery charger 1200 may not unnecessarily draw current when battery charger is not charging reusable housing assembly 802.

Still referring to FIGS. 79 and 80, battery charger 1200 may include a lower housing portion 1224 and top plate 1204. Printed circuit board 1222 (e.g., which may include electrical contacts 1206) may be disposed within a cavity included between top plate 1204 and lower housing portion 1224.

Figure 81:
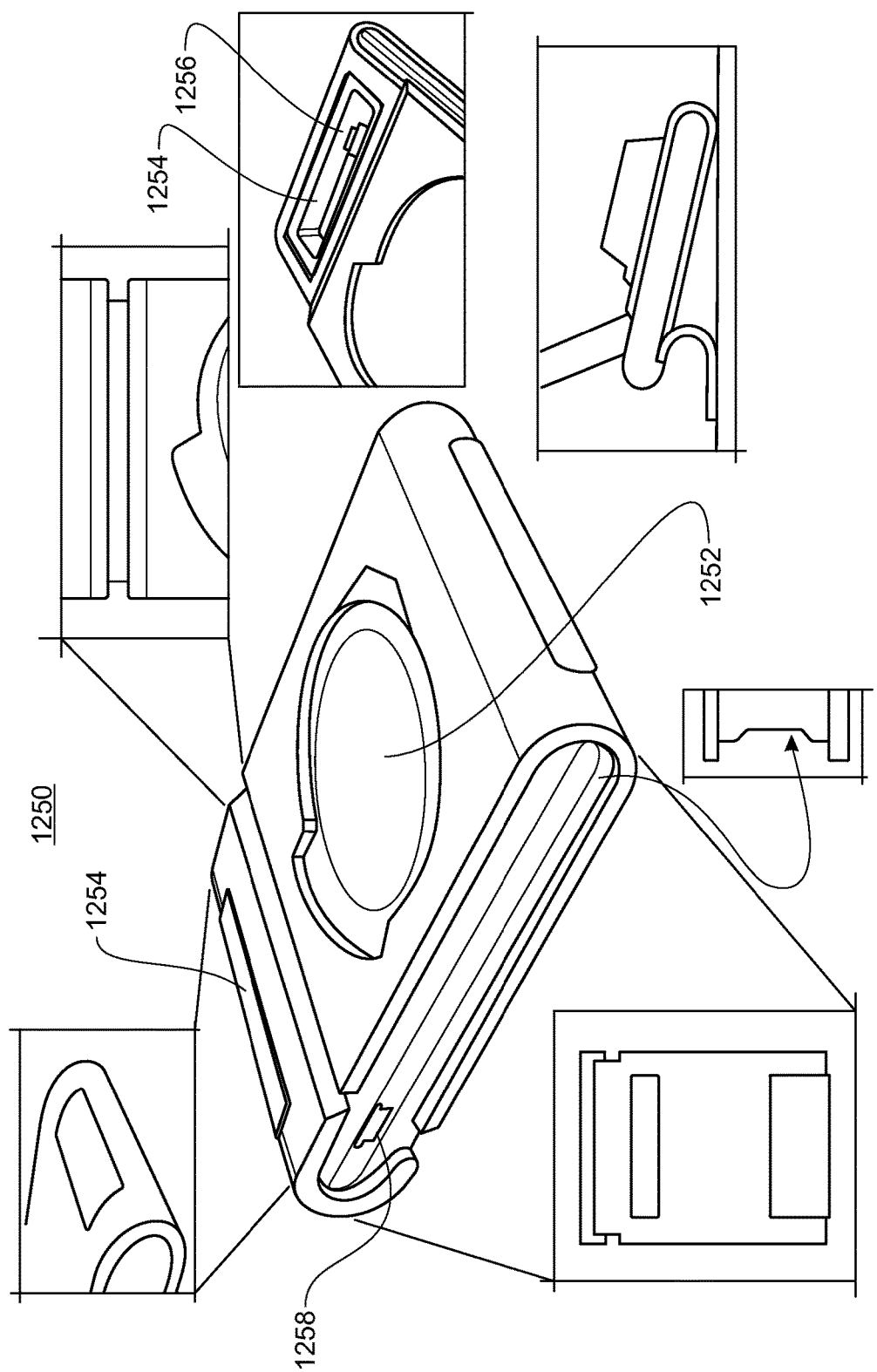
Figure 82:
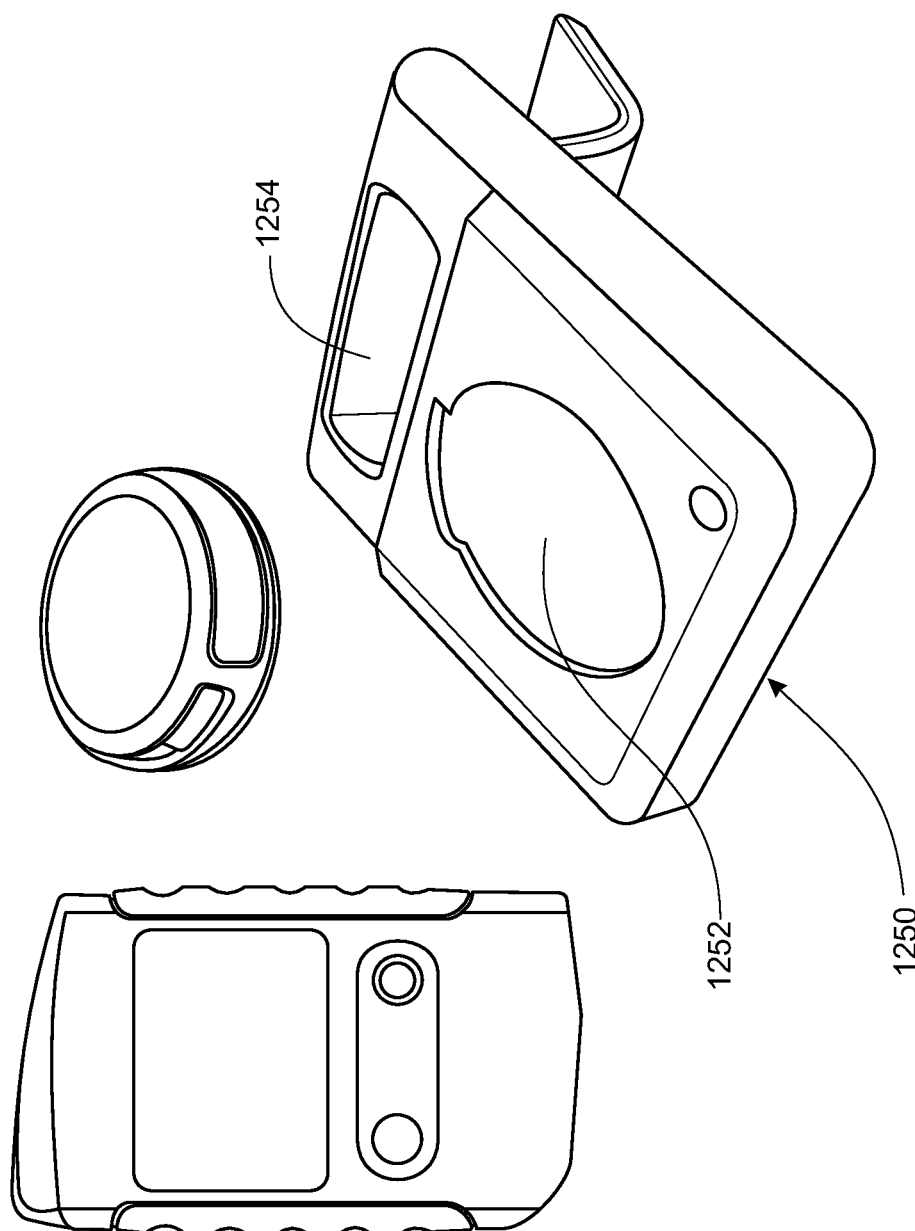

Referring also to FIGS. 81-89, various embodiments of battery charger/docking stations are shown. FIGS. 81 and 82 depicts desktop charger 1250 including recess 1252 configured to mate with and recharge a reusable housing assembly (e.g., reusable housing assembly 802). The reusable housing assembly may rest in recess 1252 and or may be releasably engaged in recess 1252, in a similar manner as discussed above. Additionally, desktop charger 1250 may include recess 1254 configured to mate with a remote control assembly (e.g., remote control assembly 300). Recess 1254 may include a USB plug 1256, e.g., which may be configured to couple with the remote control assembly when the remote control assembly is disposed within recess 1254. USB plug 1256 may allow for data transfer to/from the remote control assembly, as well as charging of remote control assembly. Desktop charger 1250 may also include USB port 1258 (e.g., which may include a mini-USB port), allowing desktop charger to receive power (e.g., for charging the reusable housing assembly and/or the remote control assembly). Additionally/alternatively USB port 1258 may be configured for data transfer to/from remote control assembly and/or reusable housing assembly, e.g., by connection to a computer (not shown).

Referring to FIGS. 83A-83B, similar to the previous embodiment, desktop charger 1260 may include recess 1262 for mating with a reusable housing assembly (e.g., reusable housing assembly 1264). Desktop charger may also include recess 1266 configured to receive a remote control assembly (e.g., remote control assembly 1268). One or more of recess 1262, 1266 may include electrical and/or data connections configure to charge and/or transfer data to/from reusable housing assembly 1262 and/or remote control assembly 1268, respectively.

Referring to FIGS. 84A-84B, another embodiment of a desktop charger is shown. Similar to desktop charger 1260, desktop charger 1270 may include recesses (not shown) for respectively mating with reusable housing assembly 1272 and remote control assembly 1274. As shown, desktop charger 1270 may hold reusable housing assembly 1272 and remote control assembly 1274 in a side-by-side configuration. Desktop charger 1270 may include various electrical and data connection configured to charge and/or transfer data to/from reusable housing assembly 1272 and/or remote control assembly 1274, as described in various embodiments above.

Referring to FIG. 85A-85D, collapsible charger 1280 may include recess 1282 for receiving reusable housing assembly 1284 and remote control assembly 1286. Collapsible charger 1280 may include various electrical and data connection configured to charge and/or transfer data to/from reusable housing assembly 1284 and/or remote control assembly 1286, as described in various embodiments above. Additionally, as shown in FIGS. 85B-85D, collapsible charger 1280 may include pivotable cover 1288. Pivotable cover 1288 may be configured to pivot between an open position (e.g., as shown in FIG. 85B), in which reusable housing assembly 1284 and remote control assembly 1286 may be docked in collapsible charger 1280, and a closed position (e.g., as shown in FIG. 85D), in which recess 1282 may be covered by pivotable cover 1288. In the closed position, recess 1282, as well as any electrical and/or data connections disposed therein, may be protected from damage.

Figure 86:
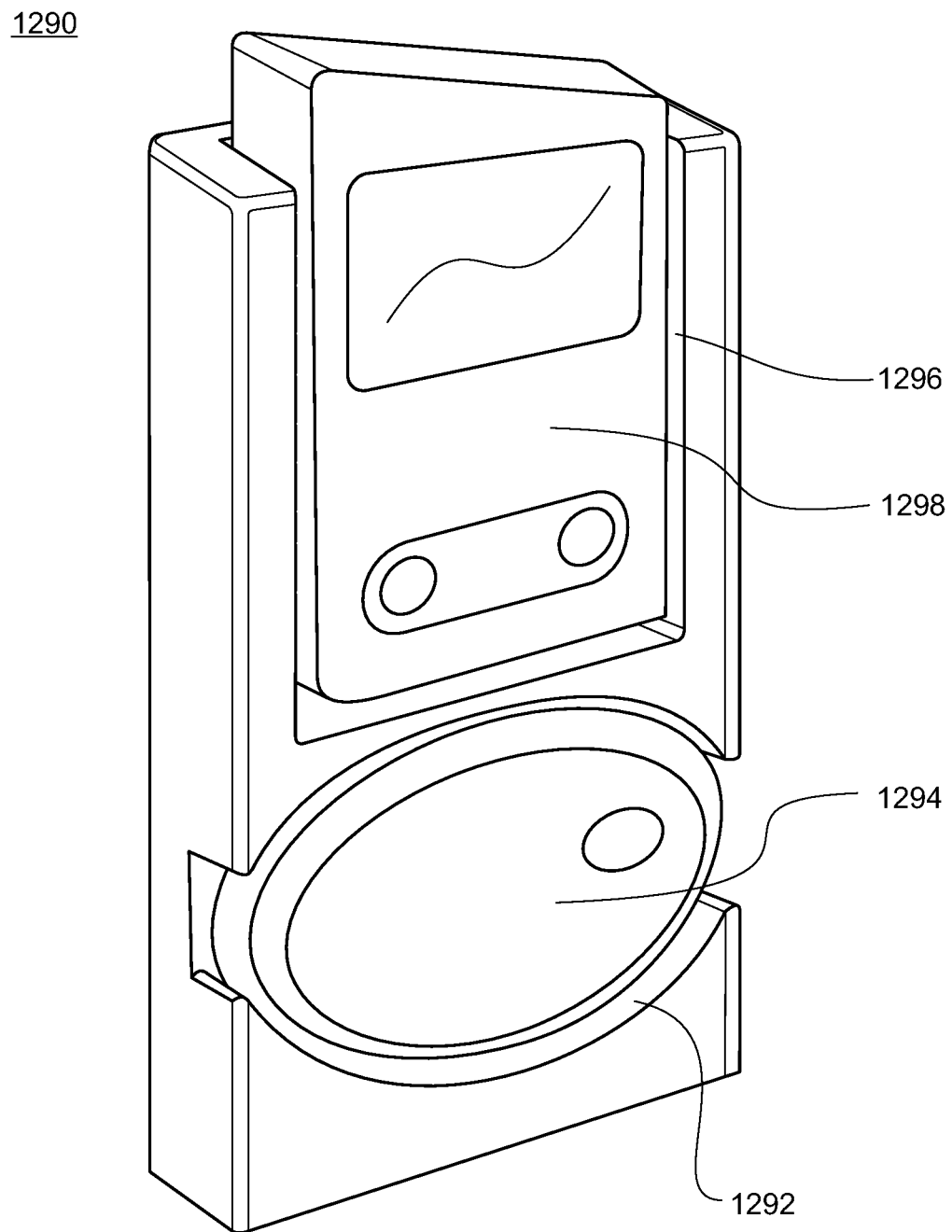

Referring to FIG. 86, wall charger 1290 may include recess 1292 configured to receive reusable housing assembly 1294. Additionally, wall charger 1290 may include recess 1296 configured to receive remote control assembly 1298. Reusable housing assembly 1294 and remote control assembly 1298 may be positioned in a stacked configuration, e.g., thereby providing a relatively slim profile. A rear portion of wall charger 1290 may include an electrical plug, configured to allow wall charger to be plugged into an electrical receptacle. As such, wall charger 1290, while plugged into the electrical receptacle, may achieve a wall mounted configuration. Additionally, while plugged into the electrical receptacle, wall charger 1290 may be provided with power for charging reusable housing assembly 1294 and/or remote control assembly 1298.

Figure 87:
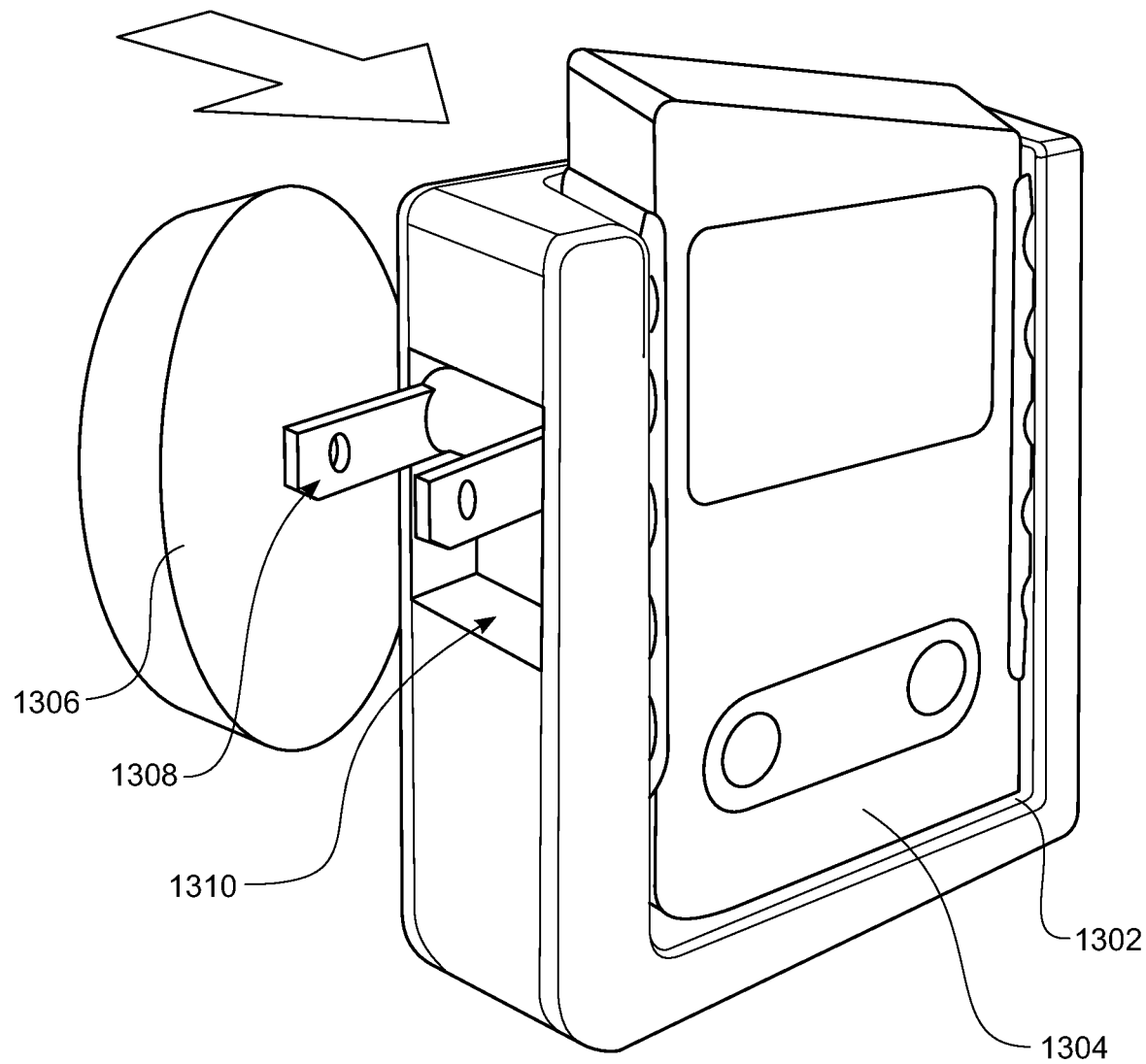

Referring to FIG. 87, wall charger 1300 may include recess 1302 configured to receive remote control assembly 1304. Additionally, wall charger may include a recess (not shown) configured to receive reusable housing assembly 1306. Wall charger 1300 may be configured to position remote control assembly 1304 and reusable housing assembly 1306 in a back-to-back configuration, which may provide a relatively thin profile. Additionally, wall charger 1300 may include an electrical plug 1308 configured to be plugged into an electrical receptacle. Electrical plug 1308 may include a stowable configuration, in which electrical plug 1308 may be pivotable between a deployed position (e.g., as shown), and a stowed position. In the deployed position, electrical plug 1308 may be oriented to be plugged into an electrical receptacle. In the stowed position electrical plug 1308 may be disposed within recess 1310, which may protect electrical plug 1308 from damage and/or from damaging other items.

Figure 88:
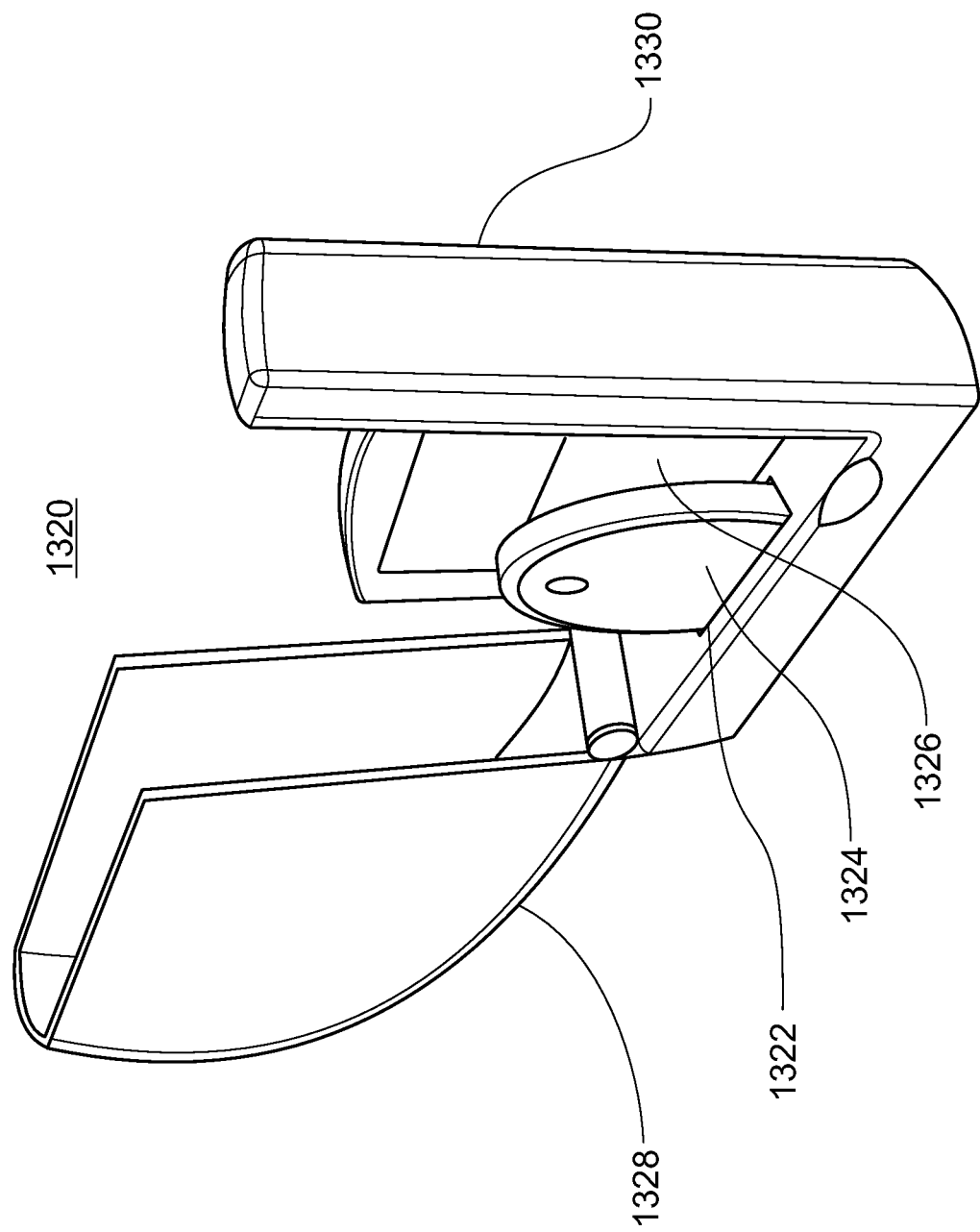

Referring to FIG. 88, charger 1320 may include recess 1322 configured to receive reusable housing assembly 1324. Charger 1320 may additionally include a recess (not shown) configured to receive remote control assembly 1326. Charger 1320 may additionally include cover 1328. Cover 1328 may be configured to pivot between an open position (as shown) and a closed position. When cover 1328 is in the open position, reusable housing assembly 1324 and remote control assembly 1326 may be accessible (e.g., allowing a user to remove/install reusable housing assembly 1324 and/ or remote control assembly 1326 from/into charger 1320. When cover 1324 is in the closed position, cover 1328 and charger body 1330 may substantially enclose reusable housing assembly 1324 and/or remote control assembly 1326 and/or recess 1322 and the recess configured to receive remote control assembly 1326, thereby providing damage and/or tamper protection for reusable housing assembly 1324, remote control assembly 1326 and/or any electrical and/or data connection associated with charger 1320.

Referring to FIGS. 89A-89B, wall charger 1350 may include recess 1352 configured to receive remote control assembly 1354. Wall charger 1350 may also include recess 1356 configured to receive reusable housing assembly 1358. Wall charger 1350 may be configured to position remote control assembly 1354 and reusable housing assembly 1358 in a generally side-by-side configuration, thereby providing a relatively slim profile. Charger 1350 may additionally include electrical plug 1360, e.g., which may be configured to be plugged into an electrical receptacle. Electrical plug 1360 may include a stowable configuration, in which electrical plug 1360 may be pivotable between a deployed position (e.g., as shown), and a stowed position. In the deployed position, electrical plug 1360 may be oriented to be plugged into an electrical receptacle. In the stowed position electrical plug 1360 may be disposed within recess 1362, which may protect electrical plug 1308 from damage and/or from damaging other items.

Infusion pump therapy may include volume and time specifications. The amount of fluid dispensed together with the dispense timing may be two critical factors of infusion pump therapy. As discussed in detail below, the infusion pump apparatus and systems described herein may provide for a method of dispensing fluid together with a device, system and method for measuring the amount of fluid dispensed. However, in a circumstance where the calibration and precision of the measurement device calibration is critical, there may be advantages to determining any compromise in the precision of the measurement device as soon as possible. Thus, there are advantages to off-board verification of volume and pumping.

As discussed above, infusion pump assembly 100 may include volume sensor assembly 148 configured to monitor the amount of fluid infused by infusion pump assembly 100. Further and as discussed above, infusion pump assembly 100 may be configured so that the volume measurements produced by volume sensor assembly 148 may be used to control, through a feedback loop, the amount of infusible fluid that is infused into the user.

Figure 90B:
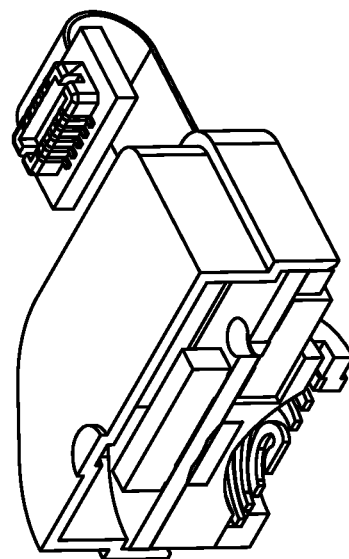
FIGS. 90A-90C are various views of a volume sensor assembly included within the infusion pump assembly of FIG. 1.
Figure 90A:
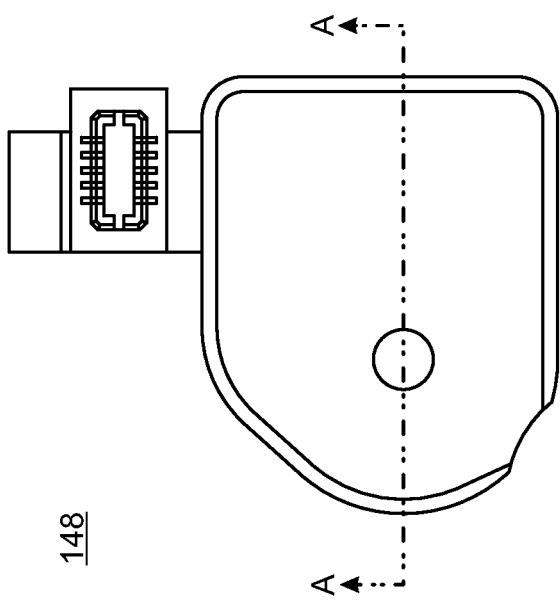
Figure 90C:
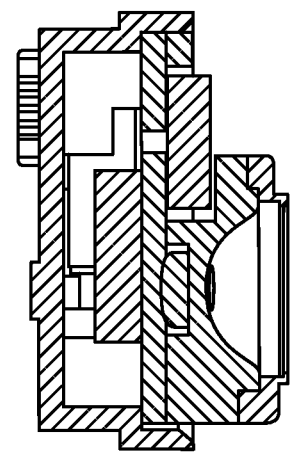
Figure 91C:
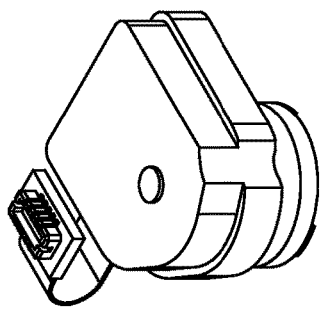
FIGS. 91A-91I are various views of a volume sensor assembly included within the infusion pump assembly of FIG. 1.
Figure 91F:
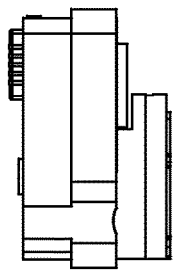
Figure 91I:
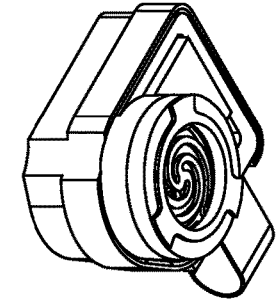
Figure 91B:
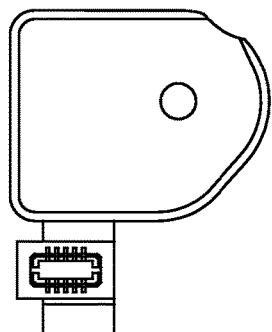
Figure 91E:
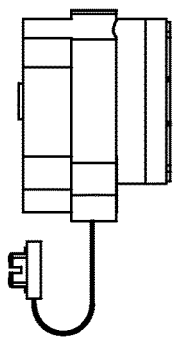
Figure 91H:
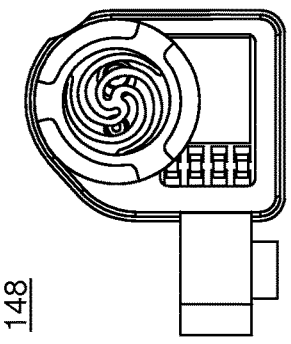
Figure 91A:
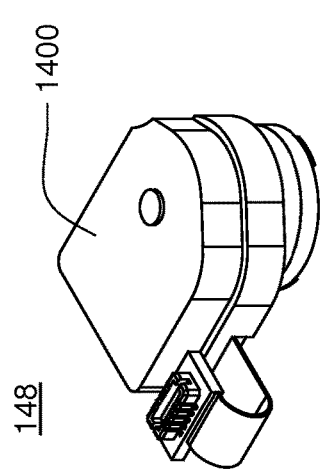
Figure 91D:
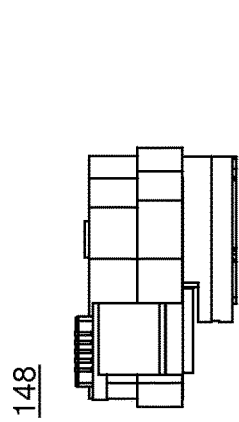
Figure 91G:
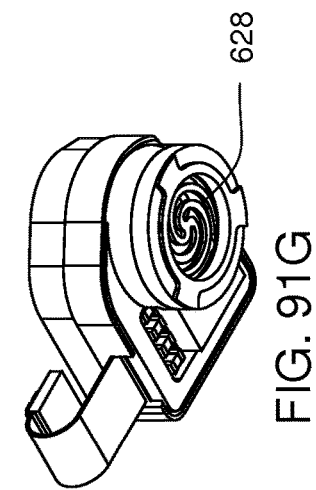
Figure 92C:
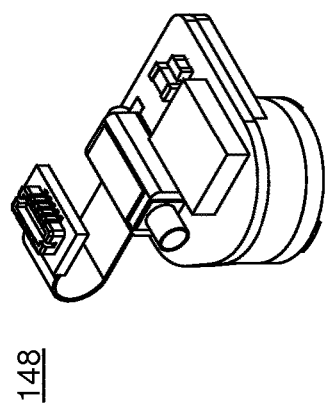
FIGS. 92A-92I are various views of a volume sensor assembly included within the infusion pump assembly of FIG. 1.
Figure 92F:
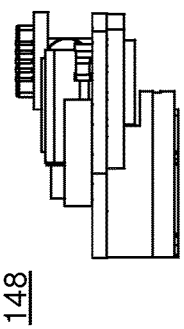
Figure 92I:
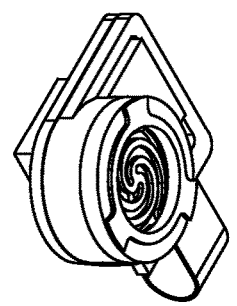
Figure 92B:
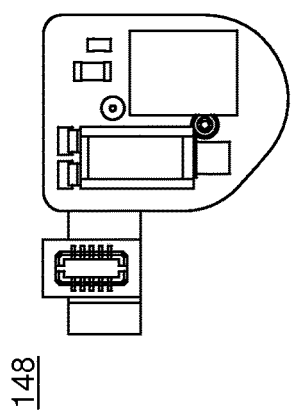
Figure 92E:
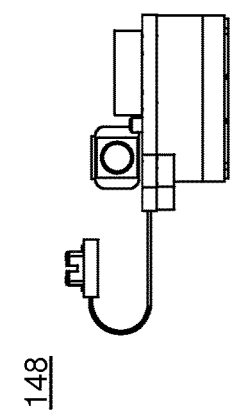
Figure 92H:
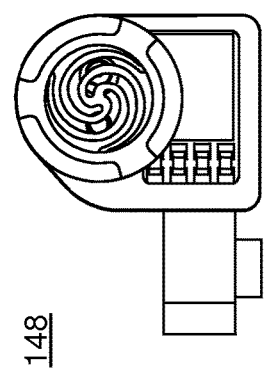
Figure 92A:
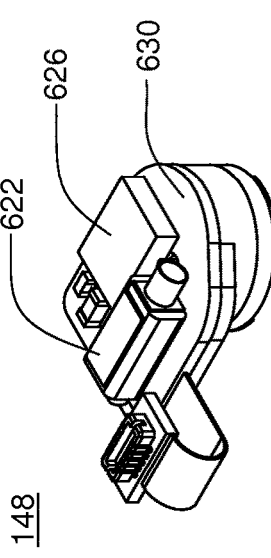
Figure 92D:
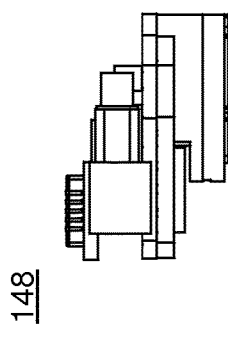
Figure 92G:
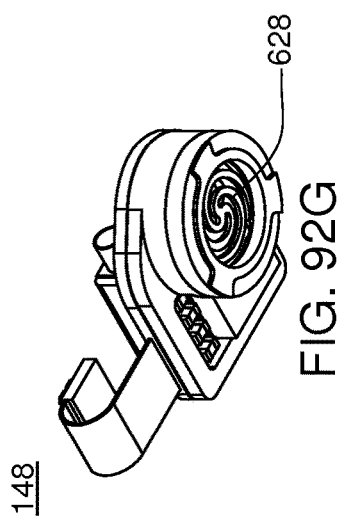
Figure 93C:
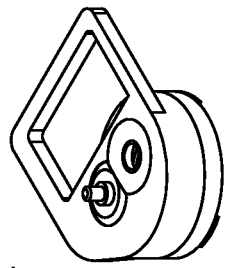
FIGS. 93A-93I are various views of a volume sensor assembly included within the infusion pump assembly of FIG. 1.
Figure 93F:
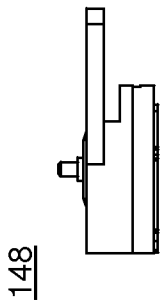
Figure 93I:
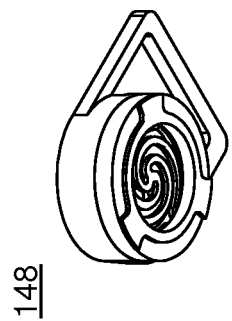
Figure 93B:
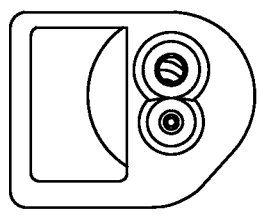
Figure 93E:
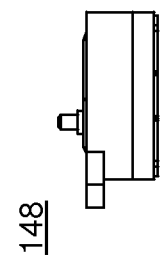
Figure 93H:
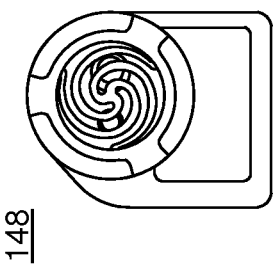
Figure 93A:
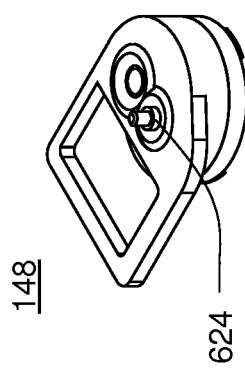
Figure 93D:
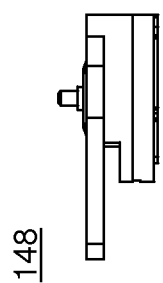
Figure 93G:
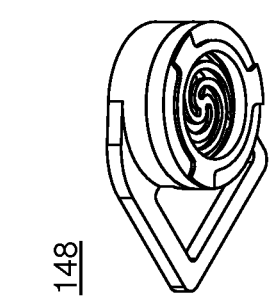
Figure 94C:
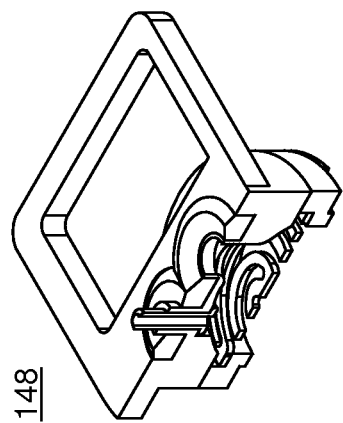
FIGS. 94A-94F are various views of a volume sensor assembly included within the infusion pump assembly of FIG. 1.
Figure 94F:
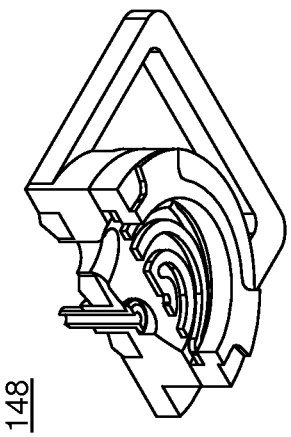
Figure 94B:
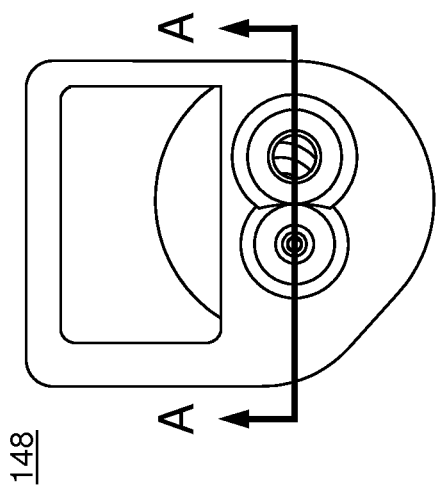
Figure 94E:
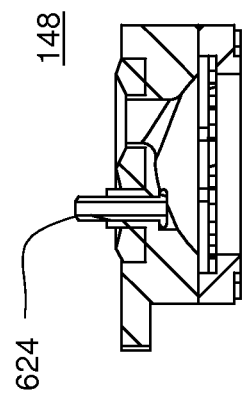
Figure 94A:
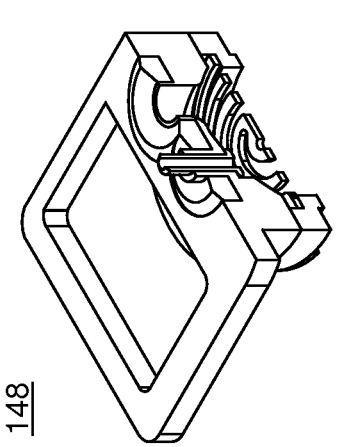
Figure 94D:
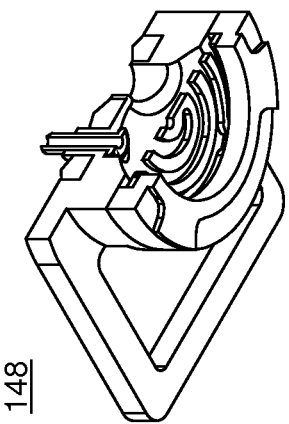
Figure 95:
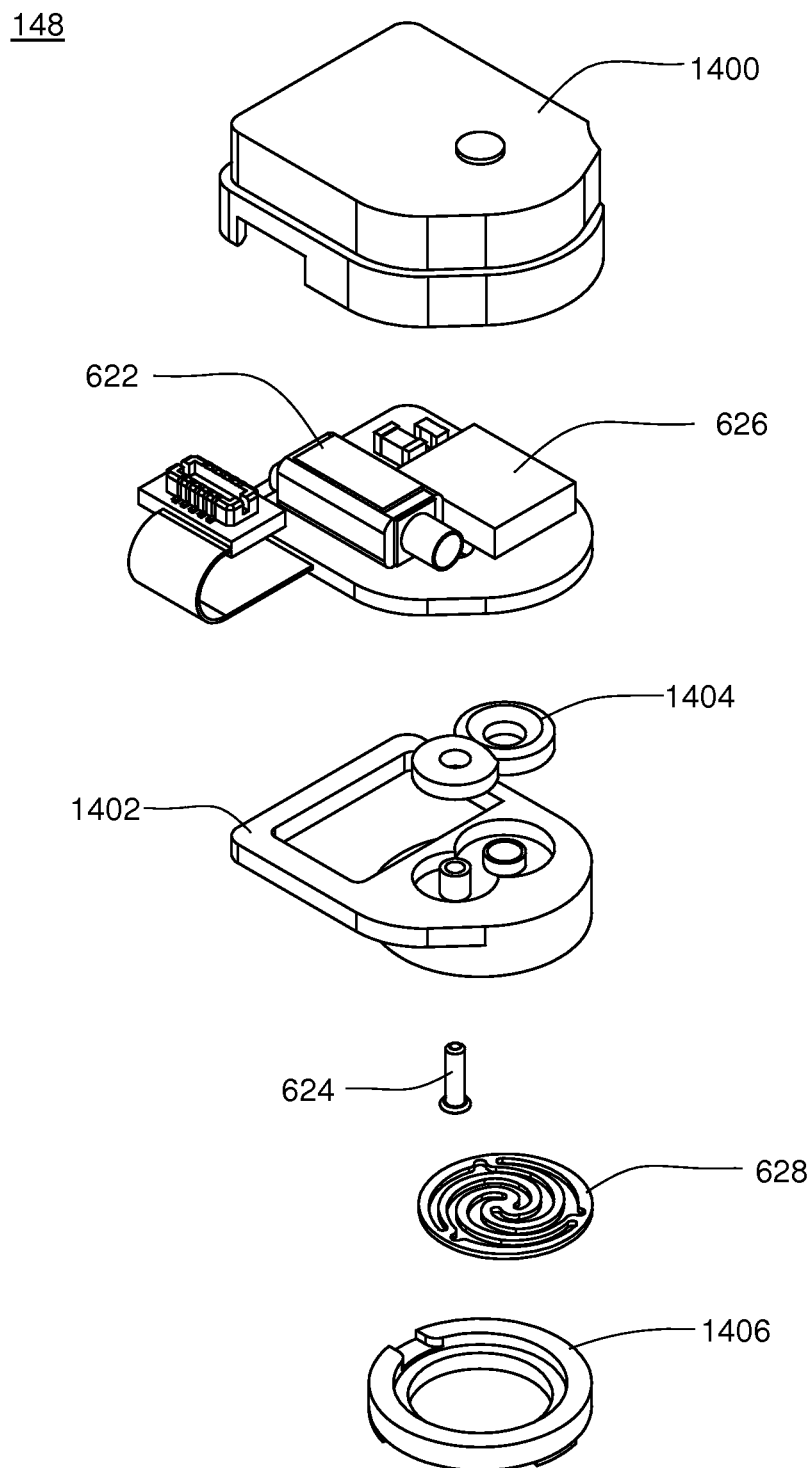
FIG. 95 is an exploded view of a volume sensor assembly included within the infusion pump assembly of FIG. 1.

Referring also to FIGS. 90A-90C, there is shown one diagrammatic view and two cross-sectional views of volume sensor assembly 148. Referring also to FIGS. 91A-91I, there is shown various isometric and diagrammatic views of volume sensor assembly 148 (which is shown to include upper housing 1400). Referring also to FIGS. 92A-92I, there is shown various isometric and diagrammatic views of volume sensor assembly 148 (with upper housing 1400 removed), exposing speaker assembly 622, reference microphone 626, and printed circuit board assembly 830. Referring also to FIGS. 93A-93I, there is shown various isometric and diagrammatic views of volume sensor assembly 148 (with printed circuit board assembly 830 removed), exposing port assembly 624. Referring also to FIGS. 94A-94F, there is shown various isometric and diagrammatic cross-sectional views of volume sensor assembly 148 (with printed circuit board assembly 830 removed), exposing port assembly 624. Referring also to FIG. 95, there are shown an exploded view of volume sensor assembly 148, exposing upper housing 1400, speaker assembly 622, reference microphone 626, seal assembly 1404, lower housing 1402, port assembly 624, spring diaphragm 628, and retaining ring assembly 1406.

Figure 96:
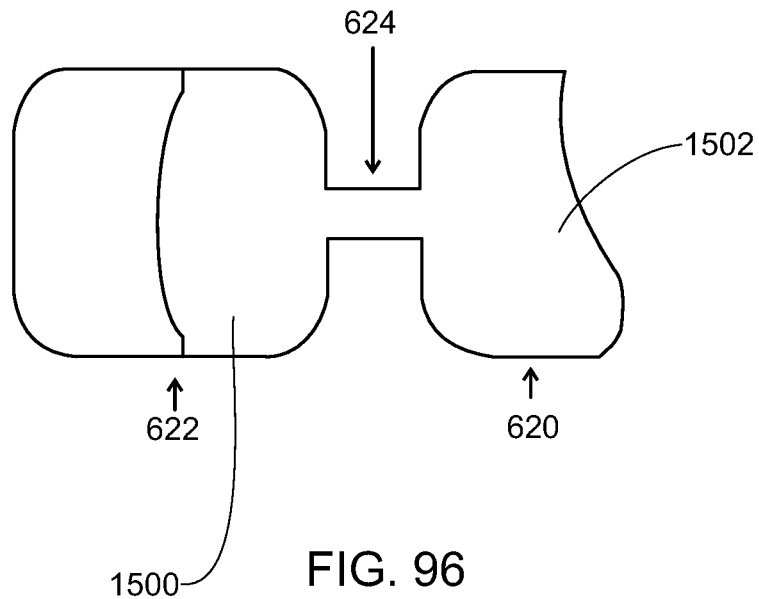
FIG. 96 is a diagrammatic view of a volume sensor assembly included within the infusion pump assembly of FIG. 1.

The following discussion concerns the design and operation of volume sensor assembly 148 (which is shown in a simplified form in FIG. 96). For the following discussion, the following nomenclature may be used:

| Symbols | |
|---|---|
| P | Pressure |
| p | Pressure Perturbation |
| V | Volume |
| v | Volume Perturbation |
| γ | Specific Heat Ratio |
| R | Gas Constant |
| ρ | Density |
| Z | Impedance |
| f | Flow friction |
| A | Cross sectional Area |
| L | Length |
| ω | Frequency |
| ζ | Damping ratio |
| α | Volume Ratio |
| Subscripts | |
| 0 | Speaker Volume |
| 1 | Reference Volume |
| 2 | Variable Volume |
| k | Speaker |
| r | Resonant Port |
| z | Zero |
| p | Pole |

Derivation of the Equations for Volume Sensor Assembly 148:

Modeling the Acoustic Volumes

The pressure and volume of an ideal adiabatic gas may be related by:

$$PV^\gamma = K \quad [\text{EQ \#1}]$$

where K is a constant defined by the initial conditions of the system.

EQ #1 may be written in terms of a mean pressure, P, and volume, V, and a small time-dependent perturbation on top of those pressures, p(t), v(t) as follows:

$$(P+p(t))(V+v(t))^\gamma = K \quad [\text{EQ \#2}]$$

Differentiating this equation may result in:

$$\dot{p}(t)(V+v(t))^\gamma + \gamma(V+v(t))^{\gamma-1}(P+p(t))\dot{v}(t) = 0 \quad [\text{EQ \#3}]$$

which may simplify to:

$$\dot{p}(t) + \gamma \frac{P+p(t)}{V+v(t)} \dot{v}(t) = 0 \quad [\text{EQ \#4}]$$

If the acoustic pressure levels are much less than the ambient pressure, the equation may be further simplified to:

$$\dot{p}(t) + \frac{\gamma P}{V} \dot{v}(t) = 0 \quad [\text{EQ \#5}]$$

How good is this assumption? Using the adiabatic relation it may be shown that:

$$\frac{P}{V} = \left(\frac{P+p(t)}{V+v(t)}\right)\left(\frac{P+p(t)}{P}\right)^{-\frac{\gamma+1}{\gamma}} \quad [\text{EQ \#6}]$$

Accordingly, the error in the assumption would be:

$$\text{error} = 1 - \left(\frac{P+p(t)}{P}\right)^{-\frac{\gamma+1}{\gamma}} \quad [\text{EQ \#7}]$$

A very loud acoustic signal (120 dB) may correspond to pressure sine wave with amplitude of roughly 20 Pascal. Assuming air at atmospheric conditions ($\gamma=1.4$, P=101325 Pa), the resulting error is 0.03%. The conversion from dB to Pa is as follows:

$$\lambda = 20\log_{10}\left(\frac{p_{rms}}{p_{ref}}\right) \text{ or } p_{rms} = p_{ref} 10^{\frac{\lambda}{20}} \quad [\text{EQ \#8}]$$

where $$p_{ref} = 20 \cdot \mu\text{Pa}.$$

Applying the ideal gas law, $P=\rho RT$, and substituting in for pressure may result in the following:

$$\dot{p}(t) + \frac{\gamma RT\rho}{V} \dot{v}(t) = 0 \quad [\text{EQ \#9}]$$

EQ #9 may be written in terms of the speed of sound, $a = \sqrt{\gamma RT}$ as follows:

$$\dot{p}(t) + \frac{\rho a^2}{V} \dot{v}(t) = 0 \quad [\text{EQ \#10}]$$

Acoustic impedance for a volume may be defined as follows:

$$Z_v = \frac{p(t)}{\dot{v}(t)} = -\frac{1}{\left(\frac{V}{\rho a^2}\right)s} \quad [\text{EQ \#11}]$$

Modeling the Acoustic Port

The acoustic port may be modeled assuming that all of the fluid in the port essentially moves as a rigid cylinder reciprocating in the axial direction. All of the fluid in the channel is assumed to travel at the same velocity, the channel is assumed to be of constant cross section, and the "end effects" resulting from the fluid entering and leaving the channel are neglected.

If we assume laminar flow friction of the form $\Delta p = f\rho\dot{v}$, the friction force acting on the mass of fluid in the channel may be written as follows:

$$F = f\rho A^2 \dot{x} \quad [\text{EQ \#12}]$$

A second order differential equation may then be written for the dynamics of the fluid in the channel:

$$\rho L A \ddot{x} = \Delta p A - f\rho A^2 \dot{x} \quad [\text{EQ \#13}]$$

or, in terms of volume flow rate:

$$\dot{v} = -\frac{fA}{L}v + \Delta p \frac{A}{\rho L} \quad [\text{EQ \#14}]$$

The acoustic impedance of the channel may then be written as follows:

$$Z_p = \frac{\Delta p}{\dot{v}} = \frac{\rho L}{A}\left(s + \frac{fA}{L}\right) \quad [\text{EQ \#15}]$$

System Transfer Functions

Using the volume and port dynamics defined above, volume sensor assembly 148 may be described by the following system of equations: (k=speaker, r=resonator)

$$\dot{p}_0 - \frac{\rho a^2}{V_0}\dot{v}_k = 0 \quad [\text{EQ \#16}]$$

$$\dot{p}_1 + \frac{\rho a^2}{V_1}(\dot{v}_k - \dot{v}_r) = 0 \quad [\text{EQ \#17}]$$

$$\dot{p}_2 + \frac{\rho a^2}{V_2}\dot{v}_r = 0 \quad [\text{EQ \#18}]$$

$$\dot{v}_r = -\frac{fA}{L}\dot{v}_r + \frac{A}{\rho L}(p_2 - p_1) \quad [\text{EQ \#19}]$$

One equation may be eliminated if $p_0$ is treated as the input substituting in $$\dot{v}_k = \frac{V_0}{\rho a^2} \dot{p}_0.$$

$$\dot{p}_1 + \frac{V_0}{V_1} \dot{p}_0 - \frac{\rho a^2}{V_1} \dot{v}_r = 0 \quad \text{[EQ \#20]}$$

$$\dot{p}_2 + \frac{\rho a^2}{V_2} \dot{v}_r = 0 \quad \text{[EQ \#21]}$$

$$\ddot{v}_r = -\frac{fA}{L} \dot{v}_r + \frac{A}{\rho L} p_2 - \frac{A}{\rho L} p_1 \quad \text{[EQ \#22]}$$

Cross System Transfer Function

The relationship between the speaker volume and the variable volume may be referred to as the Cross System transfer function. This transfer function may be derived from the above equations and is as follows:

$$\frac{p_2}{p_0} = -\frac{V_0}{V_1} \frac{\omega_n^2}{s^2 + 2\zeta\omega_n s + \alpha\omega_n^2} \quad \text{[EQ \#23]}$$

where $$\omega_n^2 = \frac{a^2 A}{L} \frac{1}{V_2}, \zeta = \frac{fA}{2L\omega_n} \text{ and } \alpha = \left(1 + \frac{V_2}{V_1}\right) \quad \text{[EQ \#24]}$$

Figure 97:
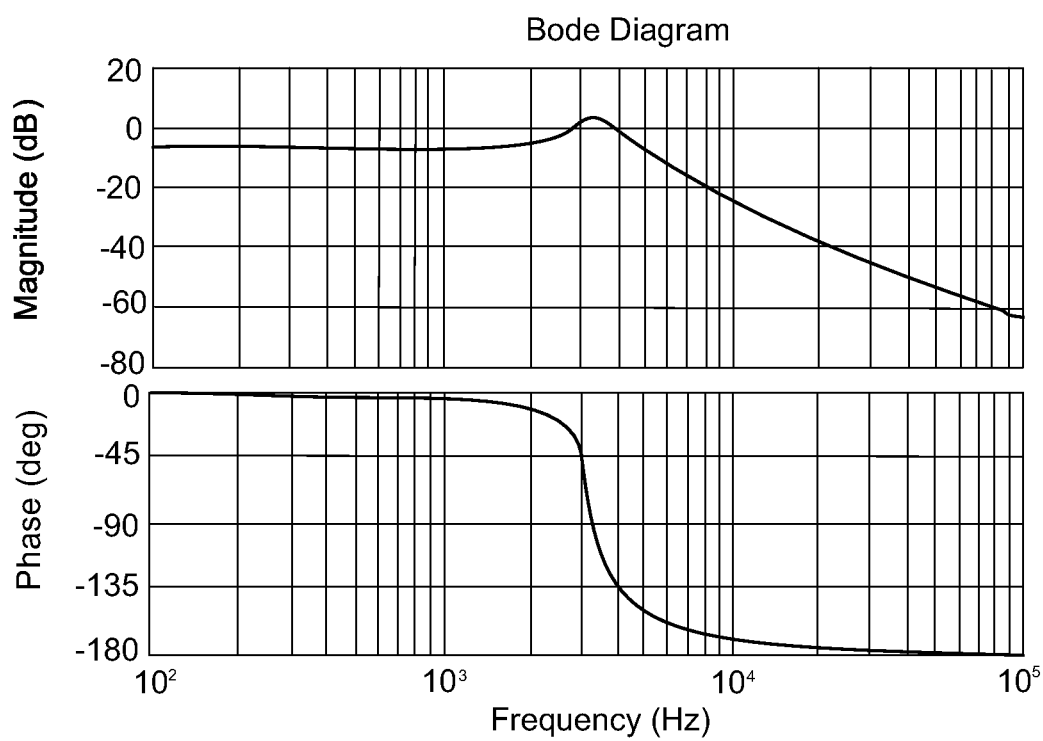
FIG. 97 is a two-dimensional graph of a performance characteristic of the volume sensor assembly of FIG. 96.

Referring also to FIG. 97, a bode plot of EQ #23 is shown.

The difficulty of this relationship is that the complex poles depend on both the variable volume, $V_2$, and the reference volume, $V_1$. Any change in the mean position of the speaker may result in an error in the estimated volume.

Cross Port Transfer Function

Figure 98:
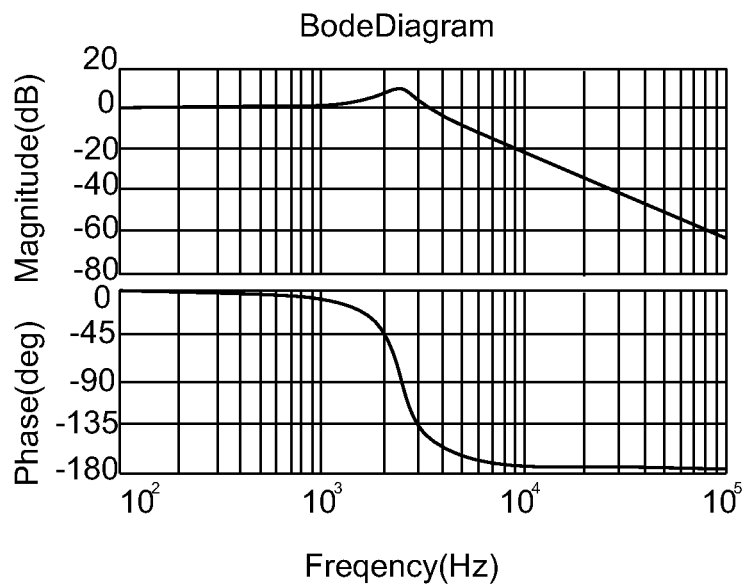
FIG. 98 is a two-dimensional graph of a performance characteristic of the volume sensor assembly of FIG. 96.

The relationship between the two volumes on each side of the acoustic port may be referred to as the Cross Port transfer function. This relationship is as follows:

$$\frac{p_2}{p_1} = \frac{\omega_n^2}{s^2 + 2\zeta\omega_n s + \omega_n^2} \quad \text{[EQ \#25]}$$

which is shown graphically in FIG. 98.

This relationship has the advantage that the poles are only dependent on the variable volume and not on the reference volume. It does, however, have the difficulty that the resonant peak is actually due to the inversion of the zero in the response of the reference volume pressure. Accordingly, the pressure measurement in the reference chamber will have a low amplitude in the vicinity of the resonance, potentially increasing the noise in the measurement.

Cross Speaker Transfer Function

Figure 99:
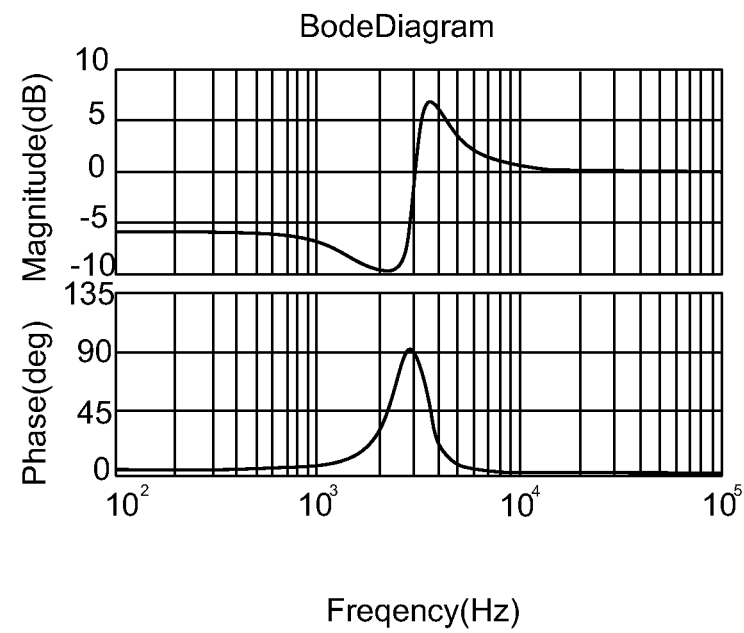
FIG. 99 is a two-dimensional graph of a performance characteristic of the volume sensor assembly of FIG. 96.

The pressures may also be measured on each side of the speaker. This is referred to as the cross speaker transfer function:

$$\frac{p_1}{p_0} = -\frac{V_0}{V_1} \frac{s^2 + 2\zeta\omega_n s + \omega_n^2}{s^2 + 2\zeta\omega_n s + \alpha\omega_n^2} \quad \text{[EQ \#26]}$$

which is shown graphically in FIG. 99.

This transfer function has a set of complex zeros in addition to the set of complex poles.

Looking at the limits of this transfer function: as $$s \to 0, \frac{p_1}{p_0} \to -\frac{V_0}{V_1 + V_2};$$

and as $$s \to \infty, \frac{p_1}{p_0} \to -\frac{V_0}{V_1}.$$

Resonance Q Factor and Peak Response

The quality of the resonance is the ratio of the energy stored to the power loss multiplied by the resonant frequency. For a pure second-order system, the quality factor may be expressed as a function of the damping ratio:

$$Q = \frac{1}{2\zeta} \quad \text{[EQ \#27]}$$

The ratio of the peak response to the low-frequency response may also be written as a function of the damping ratio:

$$|G|_{\omega_d} = \frac{1}{\zeta\sqrt{5 - 4\zeta}} \quad \text{[EQ \#28]}$$

This may occur at the damped natural frequency:

$$\omega_d = \omega_n \sqrt{1 - \zeta} \quad \text{[EQ \#29]}$$

Volume Estimation

Volume Estimation Using Cross-Port Phase

The variable volume (i.e., within volume sensor chamber 620) may also be estimated using the cross-port phase. The transfer function for the pressure ratio across the resonant port may be as follows:

$$\frac{p_2}{p_1} = \frac{\omega_n^2}{s^2 + bs + \omega_n^2} \quad \text{[EQ \#30]}$$

At the 90° phase point, $\omega = \omega_n$; where $$\omega_n^2 = \frac{1}{V_2} \frac{a^2 A}{L}$$

The resonant frequency may be found on the physical system using a number of methods. A phase-lock loop may be employed to find the 90° phase point—this frequency may correspond to the natural frequency of the system. Alternatively, the resonant frequency may be calculated using the phase at any two frequencies:

The phase, φ, at any given frequency will satisfy the following relation:

$$\tan\phi = \frac{b\omega}{\omega^2 - \omega_n^2} \quad \text{[EQ \#31]}$$

where $$b = \frac{fA}{L}.$$

Solving for $V_2$ results in:

$$V_2 = \frac{\frac{a^2 A}{L}}{\omega^2 - f\omega\cot\phi} \quad \text{[EQ \#32]}$$

Accordingly, the ratio of the phases at two different frequencies $\omega_1$ and $\omega_2$ can be used to compute the natural frequency of the system:

$$\alpha\omega_n^2 = \omega_1\omega_2 \frac{\left(\omega_1 \frac{\tan\phi_1}{\tan\phi_2} - \omega_2\right)}{\left(\omega_2 \frac{\tan\phi_1}{\tan\phi_2} - \omega_1\right)} \quad \text{[EQ \#33]}$$

For computational efficiency, the actual phase does not need to be calculated. All that is needed is the ratio of the real and imaginary parts of the response (tan $\phi$).

Re-writing EQ #33 in terms of the variable volume results in:

$$\frac{1}{V_2} = \frac{1}{a^2}\frac{L}{A}\omega_1\omega_2 \frac{\left(\omega_1 \frac{\tan\phi_1}{\tan\phi_2} - \omega_2\right)}{\left(\omega_2 \frac{\tan\phi_1}{\tan\phi_2} - \omega_1\right)} \quad \text{[EQ \#34]}$$

Volume Estimation Using Swept Sine

The resonant frequency of the system may be estimated using swept-sine system identification. In this method, the response of the system to a sinusoidal pressure variation may be found at a number of different frequencies. This frequency response data may then used to estimate the system transfer function using linear regression.

The transfer function for the system may be expressed as a rational function of s. The general case is expressed below for a transfer function with an $n^{th}$ order numerator and an $m^{th}$ order denominator. N and D are the coefficients for the numerator and denominator respectively. The equation has been normalized such that the leading coefficient in the denominator is 1.

$$G(s) = \frac{N_n s^n + N_{n-1} s^{n-1} + \ldots + N_0}{s^m + D_{m-1} s^{m-1} + D_{m-2} s^{m-2} + \ldots + D_0} \quad \text{[EQ \#35]}$$

or $$G(s) = \frac{\sum_{k=0}^{n} N_k s^k}{s^m + \sum_{k=0}^{m-1} D_k s^k} \quad \text{[EQ \#36]}$$

This equation may be re-written as follows:

$$Gs^m = \sum_{k=0}^{n} N_k s^k - G \sum_{k=0}^{m-1} D_k s^k \quad \text{[EQ \#37]}$$

Representing this summation in matrix notation resulting in the following:

$$\begin{bmatrix} G_1 s_1^m \\ \vdots \\ G_k s_k^m \end{bmatrix} = \begin{bmatrix} s_1^n & \ldots & s_1^0 & -G_1 s_1^{m-1} & \ldots & -G_1 s_1^0 \\ \vdots & & \vdots & \vdots & & \vdots \\ s_k^n & \ldots & s_k^0 & -G_k s_k^{m-1} & \ldots & -G_k s_k^0 \end{bmatrix} \begin{bmatrix} N_n \\ \vdots \\ N_0 \\ D_{m-1} \\ \vdots \\ D_0 \end{bmatrix} \quad \text{[EQ \#38]}$$

where k is the number of data points collected in the swept sine. To simplify the notation, this equation may be summarized using the vectors:

$$y = XC \quad \text{[EQ \#39]}$$

where y is k by 1, x is k by (m+n−1) and c is (m+n−1) by 1. The coefficients may then be found using a least square approach. The error function may be written as follows:

$$e = y - Xc \quad \text{[EQ \#40]}$$

The function to be minimized is the weighted square of the error function; W is a k×k diagonal matrix.

$$e^T W e = (y - Xc)^T W (y - Xc) \quad \text{[EQ \#41]}$$

$$e^T W e = y^T W y - (y^T W X c)^T - y^T W X c + c^T X^T W X c \quad \text{[EQ \#42]}$$

As the center two terms are scalars, the transpose may be neglected.

$$e^T W e = y^T W y - 2 y^T W X c + c^T X^T W X c \quad \text{[EQ \#43]}$$

$$\frac{\partial e^T W e}{\partial c} = -2 X^T W y + 2 X^T W X c = 0 \quad \text{[EQ \#44]}$$

$$c = (X^T W X)^{-1} X^T W y \quad \text{[EQ \#45]}$$

It may be necessary to use the complex transpose in all of these cases. This approach may result in complex coefficients, but the process may be modified to ensure that all the coefficients are real. The least-square minimization may be modified to give only real coefficients if the error function is changed to be $$e^T W e = Re(y - Xc)^T W Re(y - Xc) + Im(y - Xc)^T W Im(y - Xc) \quad \text{[EQ \#46]}$$

Accordingly, the coefficients may be found with the relation:

$$c = (Re(X)^T W Re(X) + Im(X)^T W Im(X))^{-1} (Re(X)^T W Re(y) + Im(X)^T W Im(y)) \quad \text{[EQ \#47]}$$

Solution for a 2nd Order System

For a system with a $0^{th}$ order numerator and a second order denominator as shown in the transfer function:

$$G(s) = \frac{N_0}{s^2 + D_1 s + D_0} \quad \text{[EQ \#48]}$$

The coefficients in this transfer function may be found based on the expression found in the previous section:

$$c = (Re(X)^T W Re(X) + Im(X)^T W Im(X))^{-1}(Re(X)^T W Re(y) + Im(X)^T W Im(y)) \quad [\text{EQ \#49}]$$

where:

$$y = \begin{bmatrix} G_1 s_1^2 \\ \vdots \\ G_k s_k^2 \end{bmatrix}, X = \begin{bmatrix} 1 & -G_1 s_1 & -G_1 \\ \vdots & \vdots & \vdots \\ 1 & -G_k s_k & -G_k \end{bmatrix}, \text{ and } c = \begin{bmatrix} N_0 \\ D_1 \\ D_0 \end{bmatrix} \quad [\text{EQ \#50}]$$

To simplify the algorithm, we may combine some of terms:

$$c = D^{-1} b \quad [\text{EQ \#51}]$$

where:

$$D = Re(X)^T W Re(X) + Im(X)^T W Im(X) \quad [\text{EQ \#52}]$$

$$b = Re(X)^T W Re(y) + Im(X)^T W Im(y) \quad [\text{EQ \#53}]$$

To find an expression for D in terms of the complex response vector G and the natural frequency $s = j\omega$, X may be split into its real and imaginary parts:

$$Re(X) = \begin{bmatrix} 1 & \omega_k Im(G_1) & -Re(G_1) \\ \vdots & \vdots & \vdots \\ 1 & \omega_k Im(G_k) & -Re(G_k) \end{bmatrix}, \quad [\text{EQ \#54}]$$

$$Im(X) = \begin{bmatrix} 0 & -\omega_k Re(G_1) & -Im(G_1) \\ \vdots & \vdots & \vdots \\ 0 & -\omega_k Re(G_k) & -Im(G_k) \end{bmatrix}$$

The real and imaginary portions of the expression for D above may then become:

$$Re(X)^T W Re(X) = \begin{bmatrix} \sum_{i=1}^{k} w_i & \sum_{i=1}^{k} w_i Im(G_i)\omega_i & -\sum_{i=1}^{k} w_i Re(G_i) \\ \sum_{i=1}^{k} w_i Im(G_i)\omega_i & \sum_{i=1}^{k} w_i Im(G_i)^2 \omega_i^2 & -\sum_{i=1}^{k} w_i Im(G_i) Re(G_i)\omega_i \\ -\sum_{i=1}^{k} w_i Re(G_i) & -\sum_{i=1}^{k} w_i Im(G_i) Re(G_i)\omega_i & \sum_{i=1}^{k} w_i Re(G_i)^2 \end{bmatrix} \quad [\text{EQ \#55}]$$

$$Im(X)^T W Im(X) = \begin{bmatrix} 0 & 0 & 0 \\ 0 & \sum_{i=1}^{k} w_i Re(G_i)^2 \omega_i^2 & \sum_{i=1}^{k} w_i Im(G_i) Re(G_i)\omega_i \\ 0 & \sum_{i=1}^{k} w_i Im(G_i) Re(G_i)\omega_i & \sum_{i=1}^{k} w_i Im(G_i)^2 \end{bmatrix} \quad [\text{EQ \#56}]$$

Combining these terms results in the final expression for the D matrix, which may contain only real values.

$$D = \begin{bmatrix} \sum_{i=1}^{k} w_i & \sum_{i=1}^{k} w_i Im(G_i)\omega_i & -\sum_{i=1}^{k} w_i Re(G_i) \\ \sum_{i=1}^{k} w_i Im(G_i)\omega_i & \sum_{i=1}^{k} w_i (Re(G_i)^2 + Im(G_i)^2)\omega_i^2 & 0 \\ -\sum_{i=1}^{k} w_i Re(G_i) & 0 & \sum_{i=1}^{k} w_i (Re(G_i)^2 + Im(G_i)^2) \end{bmatrix} \quad [\text{EQ \#57}]$$

The same approach may be taken to find an expression for the b vector in terms of G and $\omega$. The real and imaginary parts of y are as follows:

$$Re(y) = \begin{bmatrix} -Re(G_1)\omega_1^2 \\ \vdots \\ -Re(G_k)\omega_k^2 \end{bmatrix}, Im(y) = \begin{bmatrix} -Im(G_1)\omega_1^2 \\ \vdots \\ -Im(G_k)\omega_k^2 \end{bmatrix} \quad [\text{EQ \#58}]$$

Combining the real and imaginary parts results in the expression for the b vector as follows:

$$b = Re(X)^T W Re(y) + Im(X)^T W Im(y) = \begin{bmatrix} -\sum_{i=1}^{k} w_i Re(G_i)\omega_i^2 \\ 0 \\ \sum_{i=1}^{k} w_i (Re(G_i)^2 + Im(G_i)^2)\omega_i^2 \end{bmatrix} \quad [\text{EQ \#59}]$$

The next step is to invert the D matrix. The matrix is symmetric and positive-definite so the number of computations needed to find the inverse will be reduced from the general 3×3 case. The general expression for a matrix inverse is:

$$D^{-1} = \frac{1}{\det(D)} adj(D) \quad [\text{EQ \#60}]$$

If D is expressed as follows:

$$D = \begin{bmatrix} d_{11} & d_{12} & d_{13} \\ d_{12} & d_{22} & 0 \\ d_{13} & 0 & d_{33} \end{bmatrix} \quad [\text{EQ \#61}]$$

then the adjugate matrix may be written as follows:

$$adj(D) = \quad [\text{EQ \#62}]$$

$$\begin{bmatrix} \begin{vmatrix} d_{22} & 0 \\ 0 & d_{33} \end{vmatrix} & -\begin{vmatrix} d_{12} & 0 \\ d_{13} & d_{33} \end{vmatrix} & \begin{vmatrix} d_{12} & d_{22} \\ d_{13} & 0 \end{vmatrix} \\ -\begin{vmatrix} d_{12} & d_{13} \\ 0 & d_{33} \end{vmatrix} & \begin{vmatrix} d_{11} & d_{13} \\ d_{13} & d_{33} \end{vmatrix} & -\begin{vmatrix} d_{11} & d_{12} \\ d_{13} & 0 \end{vmatrix} \\ \begin{vmatrix} d_{12} & d_{13} \\ d_{22} & 0 \end{vmatrix} & -\begin{vmatrix} d_{11} & d_{13} \\ d_{12} & 0 \end{vmatrix} & \begin{vmatrix} d_{11} & d_{12} \\ d_{12} & d_{22} \end{vmatrix} \end{bmatrix} = \begin{bmatrix} a_{11} & a_{12} & a_{13} \\ a_{12} & a_{22} & a_{23} \\ a_{13} & a_{32} & a_{33} \end{bmatrix}$$

Due to symmetry, only the upper diagonal matrix may need to be calculated.

The Determinant may then be computed in terms of the adjugate matrix values, taking advantage of the zero elements in the original array:

$$det(D) = a_{12}d_{12} + a_{22}d_{22} \quad [\text{EQ \#63}]$$

Finally, the inverse of D may be written as follows:

$$D^{-1} = \frac{1}{\det(D)} adj(D) \quad [\text{EQ \#64}]$$

Since we are trying to solve:

$$c = D^{-1}b = \frac{1}{\det(D)} adj(D) b \quad [\text{EQ \#65}]$$

then:

$$c = \frac{1}{\det(D)} \begin{bmatrix} a_{11} & a_{12} & a_{13} \\ a_{12} & a_{22} & a_{23} \\ a_{13} & a_{32} & a_{33} \end{bmatrix} \begin{bmatrix} b_1 \\ 0 \\ b_3 \end{bmatrix} = \frac{1}{\det(D)} \begin{bmatrix} a_{11}b_1 + a_{13}b_3 \\ a_{12}b_1 + a_{23}b_3 \\ a_{13}b_1 + a_{33}b_3 \end{bmatrix} \quad [\text{EQ \#66}]$$

The final step is to get a quantitative assessment of how well the data fits the model. Accordingly, the original expression for the error is as follows:

$$e^T W e = Re(y-Xc)^T W Re(y-Xc) + Im(y-Xc)^T W Im(y-Xc) \quad [\text{EQ \#67}]$$

This may be expressed in terms of the D matrix and the b and c vectors as follows:

$$e^T W e = h - 2c^T b + c^T D c \quad [\text{EQ \#68}]$$

where:

$$h = Re(y^T) W Re(y) + Im(y^T) W Im(y) \quad [\text{EQ \#69}]$$

$$h = \sum_{i=1}^{k} w_i (Re(G_i)^2 + Im(G_i)^2) \omega_i^4 \quad [\text{EQ \#70}]$$

The model fit error may also be used to detect sensor failures.

Alternate Solution for a 2nd Order System $$G(s) = \frac{N_n s^n + N_{n-1} s^{n-1} + \ldots + N_0}{s^m + D_{m-1} s^{m-1} + D_{m-2} s^{m-2} + \ldots + D_0} \quad [\text{EQ \#71}]$$

or $$G(s) = \frac{\sum_{k=0}^{n} N_k s^k}{s^m + \sum_{k=0}^{m-1} D_k s^k} \quad [\text{EQ \#72}]$$

This equation may be re-written as follows:

$$G = \sum_{k=0}^{n} N_k s^{k-m} - G \sum_{k=0}^{m-1} D_k s^{k-m} \quad [\text{EQ \#73}]$$

Putting this summation into matrix notation results in the following:

$$\begin{bmatrix} G_1 \\ \vdots \\ G_k \end{bmatrix} = \begin{bmatrix} s_1^{n-m} & \ldots & s_1^{-m} & -G_1 s_1^{-1} & \ldots & -G_1 s_1^{-m} \\ \vdots & & \vdots & \vdots & & \vdots \\ s_k^{n-m} & \ldots & s_k^{-m} & -G_k s_k^{-1} & \ldots & -G_k s_k^{-m} \end{bmatrix} \begin{bmatrix} N_n \\ \vdots \\ N_0 \\ D_{m-1} \\ \vdots \\ D_0 \end{bmatrix} \quad [\text{EQ \#74}]$$

For a system with a $0^{th}$ order numerator and a second order denominator as shown in the transfer function:

$$G(s) = \frac{N_0}{s^2 + D_1 s + D_0} \quad [\text{EQ \#75}]$$

The coefficients in this transfer function may be found based on the expression found in the previous section:

$$c = (Re(X)^T W Re(X) + Im(X)^T W Im(X))^{-1} (Re(X)^T W Re(y) + Im(X)^T W Im(y)) \quad [\text{EQ \#76}]$$

where $$y = \begin{bmatrix} G_1 \\ \vdots \\ G_k \end{bmatrix}, \quad [\text{EQ \#77}]$$

$$X = \begin{bmatrix} s_1^{-2} & -G_1 s_1^{-1} & -G_1 s_1^{-2} \\ \vdots & \vdots & \vdots \\ s_k^{-2} & -G_k s_k^{-1} & -G_k s_k^{-2} \end{bmatrix},$$

and $$c = \begin{bmatrix} N_0 \\ D_1 \\ D_0 \end{bmatrix}$$

To simplify the algorithm, some terms may be combined:

$$c = D^{-1} b \quad [\text{EQ \#78}]$$

where:

$$D = Re(X)^T W Re(X) + Im(X)^T W Im(X) \quad [\text{EQ \#79}]$$

$$b = Re(X)^T W Re(y) + Im(X)^T W Im(y) \quad [\text{EQ \#80}]$$

To find an expression for D in terms of the complex response vector G and the natural frequency $s=j\omega$, split X may be split into its real and imaginary parts:

$$\text{Re}(X) = \begin{bmatrix} -\omega_1^{-2} & -\omega_1^{-1}\text{Im}(G_1) & \omega_1^{-2}\text{Re}(G_1) \\ \vdots & \vdots & \vdots \\ -\omega_k^{-2} & -\omega_k^{-1}\text{Im}(G_k) & \omega_k^{-2}\text{Re}(G_k) \end{bmatrix} \quad [\text{EQ \#81}]$$

$$\text{Im}(X) = \begin{bmatrix} 0 & -\omega_1^{-1}\text{Re}(G_1) & \omega_1^{-2}\text{Im}(G_1) \\ \vdots & \vdots & \vdots \\ 0 & -\omega_k^{-1}\text{Re}(G_k) & \omega_k^{-2}\text{Im}(G_k) \end{bmatrix} \quad [\text{EQ \#82}]$$

The real and imaginary portions of the expression for D above may then become:

$$\text{Re}(X)^T W \text{Re}(X) = \begin{bmatrix} \sum_{i=1}^{k} w_i \omega_i^{-4} & \sum_{i=1}^{k} w_i \text{Im}(G_i)\omega_i^{-3} & -\sum_{i=1}^{k} w_i \text{Re}(G_i)\omega_i^{-4} \\ \sum_{i=1}^{k} w_i \text{Im}(G_i)\omega_i^{-3} & \sum_{i=1}^{k} w_i \text{Im}(G_i)^2 \omega_i^{-2} & -\sum_{i=1}^{k} w_i \text{Im}(G_i)\text{Re}(G_i)\omega_i^{-3} \\ -\sum_{i=1}^{k} w_i \text{Re}(G_i)\omega_i^{-4} & -\sum_{i=1}^{k} w_i \text{Im}(G_i)\text{Re}(G_i)\omega_i^{-3} & \sum_{i=1}^{k} w_i \text{Re}(G_i)^2 \omega_i^{-4} \end{bmatrix} \quad [\text{EQ \#83}]$$

$$\text{Im}(X)^T W \text{Im}(X) = \begin{bmatrix} 0 & 0 & 0 \\ 0 & \sum_{i=1}^{k} w_i \text{Re}(G_i)^2 \omega_i^{-2} & -\sum_{i=1}^{k} w_i \text{Im}(G_i)\text{Re}(G_i)\omega_i^{-3} \\ 0 & -\sum_{i=1}^{k} w_i \text{Im}(G_i)\text{Re}(G_i)\omega_i^{-3} & \sum_{i=1}^{k} w_i \text{Im}(G_i)^2 \omega_i^{-4} \end{bmatrix} \quad [\text{EQ \#84}]$$

Combining these terms results in the final expression for the D matrix, which may contain only real values.

$$D = \begin{bmatrix} \sum_{i=1}^{k} w_i \omega_i^{-4} & \sum_{i=1}^{k} w_i \text{Im}(G_i)\omega_i^{-3} & -\sum_{i=1}^{k} w_i \text{Re}(G_i)\omega_i^{-4} \\ \sum_{i=1}^{k} w_i \text{Im}(G_i)\omega_i^{-3} & \sum_{i=1}^{k} w_i (\text{Re}(G_i)^2 + \text{Im}(G_i)^2)\omega_i^{-2} & -2\sum_{i=1}^{k} w_i \text{Im}(G_i)\text{Re}(G_i)\omega_i^{-3} \\ -\sum_{i=1}^{k} w_i \text{Re}(G_i)\omega_i^{-4} & -2\sum_{i=1}^{k} w_i \text{Im}(G_i)\text{Re}(G_i)\omega_i^{-3} & \sum_{i=1}^{k} w_i (\text{Re}(G_i)^2 + \text{Im}(G_i)^2)\omega_i^{-4} \end{bmatrix} \quad [\text{EQ \#85}]$$

The same approach may be taken to find an expression for the b vector in terms of G and ω. The real and imaginary parts of y areas follows:

$$\text{Re}(y) = \begin{bmatrix} -\text{Re}(G_1) \\ \vdots \\ -\text{Re}(G_k) \end{bmatrix}, \text{Im}(y) = \begin{bmatrix} -\text{Im}(G_1) \\ \vdots \\ -\text{Im}(G_k) \end{bmatrix} \quad [\text{EQ \#86}]$$

Combining the real and imaginary parts results in the expression for the b vector as follows:

$$b = \text{Re}(X)^T W \text{Re}(y) + \text{Im}(X)^T W \text{Im}(y) = \begin{bmatrix} -\sum_{i=1}^{k} w_i \text{Re}(G_i)\omega_i^{-2} \\ -\sum_{i=1}^{k} w_i (\text{Im}(G_i) + \text{Re}(G_i)\omega_i^{-1}) \\ \sum_{i=1}^{k} w_i (\text{Re}(G_i)^2 + \text{Im}(G_i)^2)\omega_i^{-2} \end{bmatrix} \quad [\text{EQ \#87}]$$

Implementing Acoustic Volume Sensing
Collecting the Frequency Response Data and Computing the Complex Response To implement volume sensor assembly 148, volume sensor assembly 148 should determine the relative response of reference microphone 626 and invariable volume microphone 630 to the acoustic wave set up by speaker assembly 622. This may be accomplished by driving speaker assembly 622 with a sinusoidal output at a known frequency; the complex response of microphones 626, 630 may then be found at that driving frequency. Finally, the relative response of microphones 626, 630 may be found and corrected for alternating sampling by e.g., an analog-to-digital convertor (i.e., ADC).

Additionally, the total signal variance may be computed and compared to the variance of pure tone extracted using the discrete Fourier transform (i.e., DFT). This may result in a measure of how much of the signal power comes from noise sources or distortion. This value may then be used to reject and repeat bad measurements.

Computing the Discrete Fourier Transform

The signal from the microphone may be sampled synchronously with the output to speaker assembly 622 such that a fixed number of points, N, are taken per wavelength. The measured signal at each point in the wavelength may be summed over an integer number of wavelengths, M, and stored in an array x by the ISR for processing after all the data for that frequency has been collected.

A DFT may be performed on the data at the integer value corresponding to the driven frequency of the speaker. The general expression for the first harmonic of a DFT is as follows:

$$x_k = \frac{2}{MN} \sum_{n=0}^{N-1} x_n e^{\frac{2\pi i}{N} kn} \quad \text{[EQ \#88]}$$

The product MN may be the total number of points and the factor of two may be added such that the resulting real and imaginary portions of the answer match the amplitude of the sine wave:

$$x_n = \text{re}(x_k)\cos\left(\frac{2\pi}{N} kn\right) + \text{im}(x_k)\sin\left(\frac{2\pi}{N} kn\right) \quad \text{[EQ \#89]}$$

This real part of this expression may be as follows:

$$\text{re}(x) = \frac{2}{MN} \sum_{n=0}^{N-1} x_n \cos\left(\frac{2\pi}{N} n\right) \quad \text{[EQ \#90]}$$

We may take advantage of the symmetry of the cosine function to reduce the number of computations needed to compute the DFT. The expression above may be equivalent to:

$$\text{re}(x) = \frac{2}{MN}\left[\left(x_0 - x_{\frac{1}{2}N}\right) + \sum_{n=1}^{\frac{1}{4}N-1} \sin\left(\frac{\pi}{2} - \frac{2\pi}{N}n\right)\left[\left(x_n - x_{\frac{1}{2}N+n}\right) - \left(x_{\frac{1}{2}N+n} - x_{N-n}\right)\right]\right] \quad \text{[EQ \#91]}$$

Similarly, for the imaginary portion of the equation:

$$\text{im}(x) = -\frac{2}{MN} \sum_{n=0}^{N-1} x_n \sin\left(\frac{2\pi}{N} n\right) \quad \text{[EQ \#92]}$$

which may be expressed as follows:

$$\text{im}(x) = -\frac{2}{MN}\left[\left(x_{\frac{1}{4}N} - x_{\frac{3}{4}N}\right) + \sum_{n=1}^{\frac{1}{4}N-1} \sin\left(\frac{2\pi}{N}n\right)\left[\left(x_n - x_{\frac{1}{2}N+n}\right) + \left(x_{\frac{1}{2}N+n} - x_{N-n}\right)\right]\right] \quad \text{[EQ \#93]}$$

The variance of this signal may be calculated as follows:

$$\sigma^2 = \frac{1}{2}(\text{re}(x)^2 + \text{im}(x)^2) \quad \text{[EQ \#94]}$$

The maximum possible value of the real and imaginary portions of x may be $2^{11}$; which corresponds to half the AD range. The maximum value of the tone variance may be $2^{21}$; half the square of the AD range.

Computing the Signal Variance

The pseudo-variance of the signal may be calculated using the following relation:

$$\sigma^2 = \frac{1}{NM^2} \sum_{n=0}^{N-1} x_n^2 - \frac{1}{N^2 M^2}\left(\sum_{n=0}^{N-1} x_n\right)^2 \quad \text{[EQ \#95]}$$

The result may be in the units of AD counts squared. It may only be the "pseudo-variance" because the signal has been averaged over M periods before the variance is calculated over the N samples in the "averaged" period. This may be a useful metric, however, for finding if the "averaged" signal looks like a sinusoid at the expected frequency. This may be done by comparing the total signal variance to that of the sinusoid found in the discrete Fourier transform.

The summation may be on the order of $$\sum_{n=0}^{N-1} x_n^2 = O(NM^2 2^{24})$$

for a 12-bit ADC. If $N<2^7=128$ and $M<2^6=64$, then the summation will be less than $2^{43}$ and may be stored in a 64-bit integer. The maximum possible value of the variance may result if the ADC oscillated between a value of 0 and $2^{12}$ on each consecutive sample. This may result in a peak variance of $\frac{1}{4}(2^{12})^2 = 2^{22}$ so the result may be stored at a maximum of a $\frac{1}{2}^9$ resolution in a signed 32-bit integer.

Computing the Relative Microphone Response

The relative response (G) of microphones 626, 630 may be computed from the complex response of the individual microphones:

$$G = \frac{x_{var}}{x_{ref}} = \frac{x_{var}}{x_{ref}} \frac{x_{ref}^*}{x_{ref}^*} \quad \text{[EQ \#96]}$$

$$\text{Re}(G) = \frac{\text{Re}(x_{var})\text{Re}(x_{ref}) + \text{Im}(x_{var})\text{Im}(x_{ref})}{\text{Re}(x_{ref})^2 + \text{Im}(x_{ref})^2} \quad \text{[EQ \#97]}$$

$$\text{Im}(G) = \frac{\text{Re}(x_{ref})\text{Im}(x_{var}) - \text{Re}(x_{var})\text{Im}(x_{ref})}{\text{Re}(x_{ref})^2 + \text{Im}(x_{ref})^2} \quad \text{[EQ \#98]}$$

The denominator of either expression may be expressed in terms of the reference tone variance computed in the previous section as follows:

$$Re(x_{ref})^2 + Im(x_{ref})^2 = 2\sigma_{ref}^2 \quad \text{[EQ \#99]}$$

Correcting for A/D Skew

The signals from microphones 626, 630 may not be sampled simultaneously; the A/D ISR alternates between microphones 626, 630, taking a total of N samples per wavelength for each of microphones 626, 630. The result may be a phase offset between two microphones 626, 630 of $$\frac{\pi}{N}.$$

To correct for this phase offset, a complex rotation may be applied to the relative frequency response computed in the previous section:

$$G_{rotated} = G \cdot \left( \cos\left(\frac{\pi}{N}\right) + i\sin\left(\frac{\pi}{N}\right) \right) \quad \text{[EQ #100]}$$

Reference Models

Second and Higher Order Models

Figure 100:
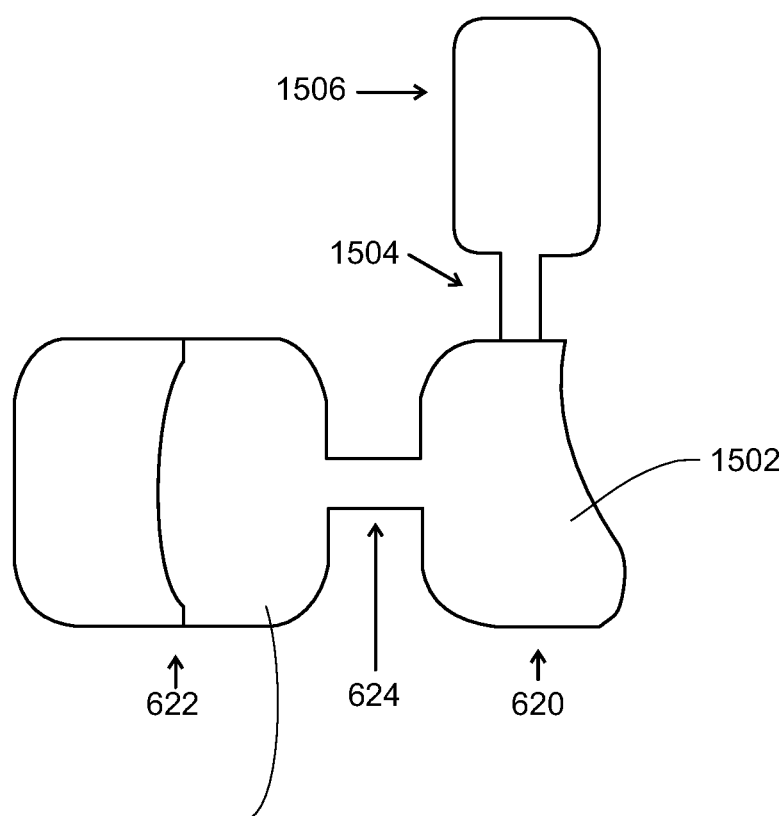
FIG. 100 is a diagrammatic view of a volume sensor assembly included within the infusion pump assembly of FIG. 1.

Leakage through the seals (e.g., seal assembly 1404) of volume sensor chamber 620 may be modeled as a second resonant port (e.g., port 1504, FIG. 100) connected to an external volume (e.g., external volume 1506, FIG. 100).

The system of equations describing the three-chamber configuration may be as follows:

$$\dot{p}_1 + \frac{\rho a^2}{V_1}(\dot{v}_k - \dot{v}_{r12}) = 0 \quad \text{[EQ #101]}$$

$$\dot{p}_2 + \frac{\rho a^2}{V_2}(\dot{v}_{r12} - \dot{v}_{r23}) = 0 \quad \text{[EQ #102]}$$

$$\ddot{v}_{r12} = -\frac{f_{12} A_{12}}{L_{12}} \dot{v}_{r12} + \frac{A_{12}}{\rho L_{12}}(p_2 - p_1) \quad \text{[EQ #103]}$$

$$\dot{p}_3 + \frac{\rho a^2}{V_3} \dot{v}_{r23} = 0 \quad \text{[EQ #104]}$$

$$\ddot{v}_{r23} = -\frac{f_{23} A_{23}}{L_{23}} \dot{v}_{r23} + \frac{A_{23}}{\rho L_{23}}(p_3 - p_2) \quad \text{[EQ #105]}$$

Figure 101:
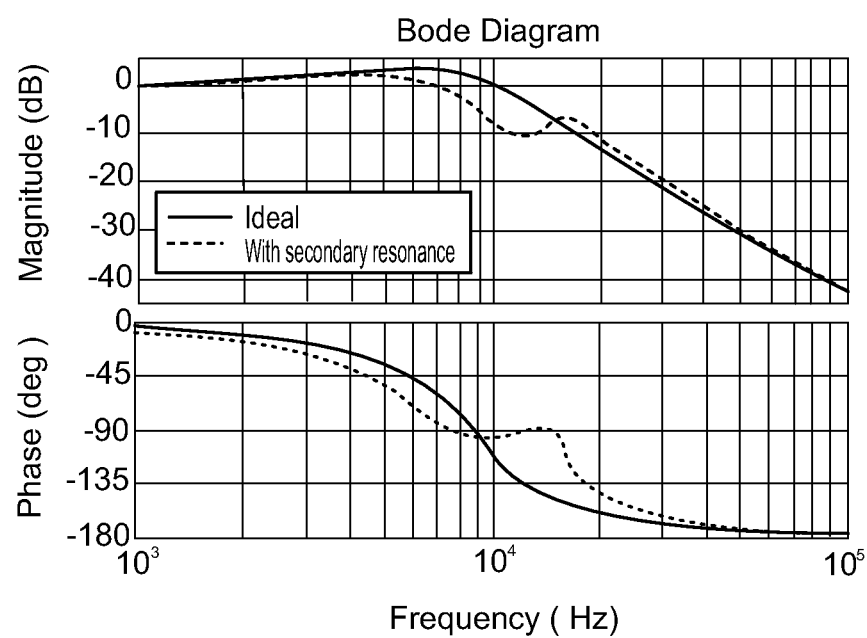
FIG. 101 is a two-dimensional graph of a performance characteristic of the volume sensor assembly of FIG. 100.

Putting these equations into state-space results in the following:

$$\begin{bmatrix} \dot{p}_1 \\ \dot{p}_2 \\ \dot{p}_3 \\ \dot{v}_{12} \\ \dot{v}_{13} \end{bmatrix} = \begin{bmatrix} 0 & 0 & 0 & \frac{\rho a^2}{V_1} & 0 \\ 0 & 0 & 0 & -\frac{\rho a^2}{V_2} & \frac{\rho a^2}{V_2} \\ 0 & 0 & 0 & 0 & -\frac{\rho a^2}{V_3} \\ -\frac{A_{12}}{\rho L_{12}} & \frac{A_{12}}{\rho L_{12}} & 0 & -b_{12} & 0 \\ 0 & -\frac{A_{23}}{\rho L_{23}} & \frac{A_{23}}{\rho L_{23}} & 0 & -b_{23} \end{bmatrix} \quad \text{[EQ #106]}$$

$$\begin{bmatrix} p_1 \\ p_2 \\ p_3 \\ v_{12} \\ v_{23} \end{bmatrix} + \begin{bmatrix} -\frac{\rho a^2}{V_1} \\ 0 \\ 0 \\ 0 \\ 0 \end{bmatrix} [\dot{v}_k]$$

the frequency response of which may be represented graphically in the Bode diagram shown in FIG. 101 and which may also be written in transfer function form:

$$\frac{p_2}{p_1} = \frac{\omega_{12}^2(s^2 + b_{23}s + \omega_{23}^2)}{(s^2 + b_{12}s + \omega_{12}^2)(s^2 + b_{23}s + \omega_{23}^2) + \frac{V_3}{V_2}\omega_{23}^2(s + b_{12})s} \quad \text{[EQ #107]}$$

Expanding the denominator results in the following:

$$\frac{p_2}{p_1} = \frac{\omega_{12}^2(s^2 + b_{23}s + \omega_{23}^2)}{s^4 + (b_{12} + b_{23})s^3 + \left(b_{12}b_{23} + \omega_{12}^2 + \omega_{23}^2\left(1 + \frac{V_3}{V_2}\right)\right)s^2 + \left(b_{23}\omega_{12}^2 + b_{12}\omega_{23}^2\left(1 + \frac{V_3}{V_2}\right)\right)s + \omega_{12}^2\omega_{23}^2} \quad \text{[EQ #108]}$$

A bubble underneath the diaphragm material in the variable volume will follow the same dynamic equations as a leakage path. In this case, the diaphragm material may act as the resonant mass rather than the leakage port. Accordingly, the equation may be as follows:

$$m\ddot{z} = \Delta p A - b_m \dot{x} \quad \text{[EQ #109]}$$

wherein m is the mass of the diaphragm, A is the cross sectional area of the diaphragm that can resonate, and $b_m$ is the mechanical damping. EQ #106 may be written in terms of the volume flow rate:

$$\ddot{v} = -\frac{b}{m}\dot{v} + \Delta p \frac{A^2}{m} \quad \text{[EQ #110]}$$

wherein the volume of the air bubble is $V_3$. If the bubble volume is substantially smaller than the acoustic volume $V_3 \ll V_2$ than the transfer function may be simplified to:

$$\frac{p_2}{p_1} = \frac{\omega_{12}^2(s^2 + b_{23}s + \omega_{23}^2)}{(s^2 + b_{12}s + \omega_{12}^2)\left(s^2 + b_{23}s + \omega_{23}^2\left(1 + \frac{V_3}{V_2}\right)\right)} \quad \text{[EQ #111]}$$

Second Order with Time Delay

The volume sensor assembly 148 equations derived above assume that the pressure is the same everywhere in the acoustic volume. This is only an approximation, as there are time delays associated with the propagation of the sound waves through the volume. This situation may look like a time delay or a time advance based on the relative position of the microphone and speakers.

Figure 102:
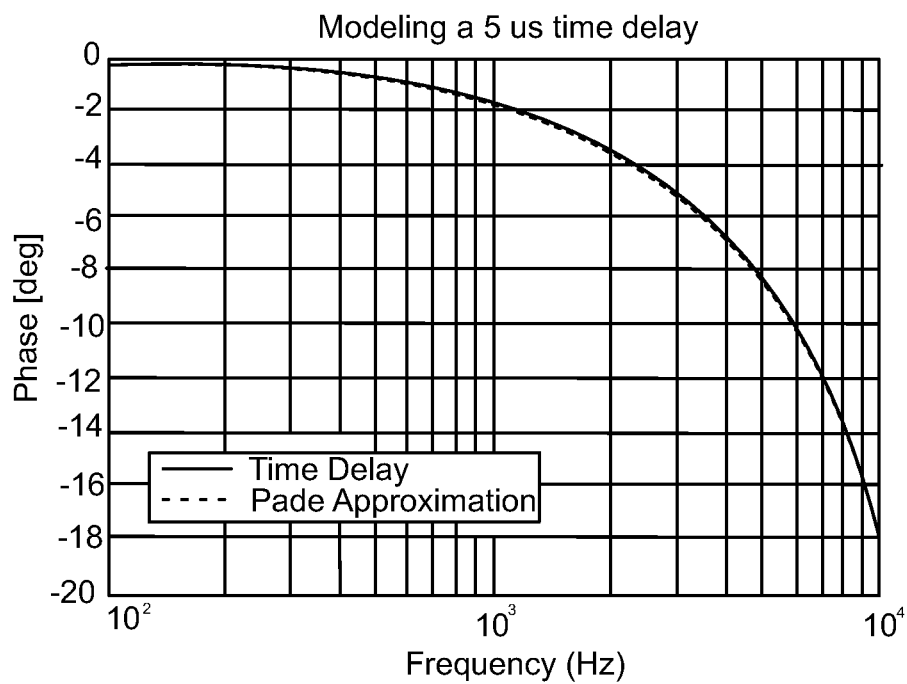
FIG. 102 is a two-dimensional graph of a performance characteristic of the volume sensor assembly of FIG. 100.

A time delay may be expressed in the Laplace domain as:

$$G(s) = e^{-\Delta T s} \quad \text{[EQ #112]}$$

which makes for a non-linear set of equations. However, a first-order Pade approximation of the time delay may be used as follows:

$$G(s) = -\frac{s + \frac{2}{\Delta T}}{s - \frac{2}{\Delta T}} \quad \text{[EQ #113]}$$

which is shown graphically in FIG. 102.

Three Chamber Volume Estimation

Figure 103:
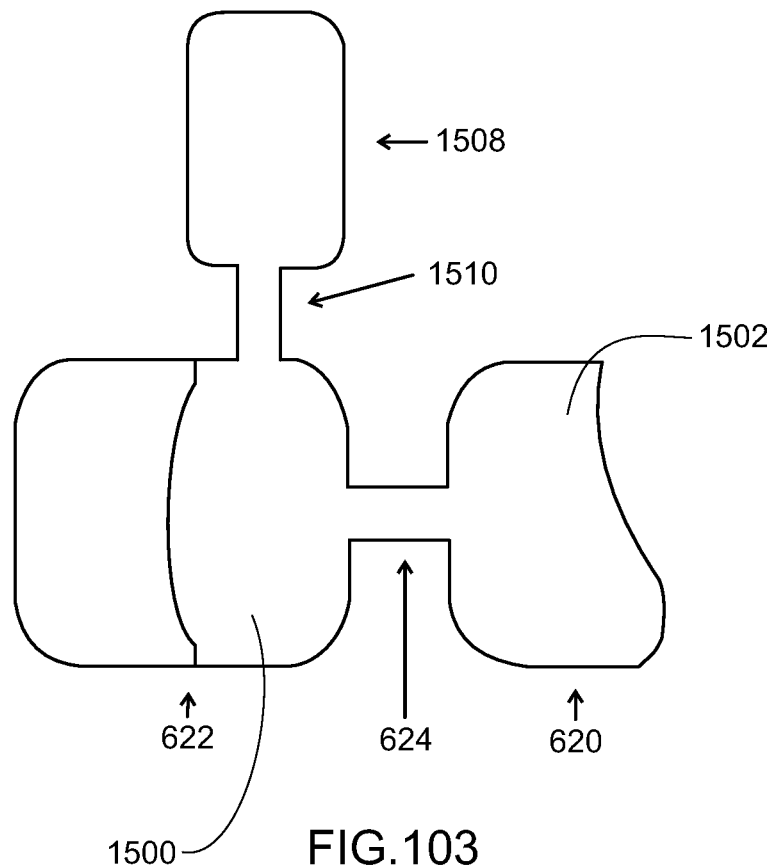
FIG. 103 is a diagrammatic view of a volume sensor assembly included within the infusion pump assembly of FIG. 1.

Volume sensor assembly 148 may also be configured using a third reference volume (e.g., reference volume 1508;

FIG. 103) connected with a separate resonant port (e.g., port 1510; FIG. 103). This configuration may allow for temperature-independent volume estimation.

The system of equations describing the three-chamber configuration are as follows:

$$\dot{p}_1 + \frac{\rho a^2}{V_1}(\dot{v}_k - \dot{v}_{r12} - \dot{v}_{r13}) = 0 \quad \text{[EQ \#114]}$$

$$\dot{p}_2 + \frac{\rho a^2}{V_2}\dot{v}_{r12} = 0 \quad \text{[EQ \#115]}$$

$$\ddot{v}_{r12} = -\frac{f_{12}A_{12}}{L_{12}}\dot{v}_{r12} + \frac{A_{12}}{\rho L_{12}}(p_2 - p_1) \quad \text{[EQ \#116]}$$

$$\dot{p}_3 + \frac{\rho a^2}{V_3}\dot{v}_{r13} = 0 \quad \text{[EQ \#117]}$$

$$\ddot{v}_{r13} = -\frac{f_{13}A_{13}}{L_{13}}\dot{v}_{r13} + \frac{A_{13}}{\rho L_{13}}(p_2 - p_1) \quad \text{[EQ \#118]}$$

Using these equations and solving for the transfer function across each of the resonant ports results in the following:

$$\frac{p_2}{p_1} = \frac{\omega_{n12}^2}{s^2 + 2\zeta_{12}\omega_{n12}s + \omega_{n12}^2} \quad \text{[EQ \#119]}$$

where $$\omega_{n12} = \frac{1}{V_2}\frac{a^2 A_{12}}{L_{12}} \text{ and } \zeta = \frac{f_{12}A_{12}}{2L_{12}\omega_{n12}} \quad \text{[EQ \#120]}$$

$$\frac{p_3}{p_1} = \frac{\omega_{n13}^2}{s^2 + 2\zeta_{13}\omega_{n13}s + \omega_{n13}^2} \quad \text{[EQ \#121]}$$

where $$\omega_{n13} = \frac{1}{V_3}\frac{a^2 A_{13}}{L_{13}} \text{ and } \zeta = \frac{f_{13}A_{13}}{2L_{13}\omega_{n13}} \quad \text{[EQ \#122]}$$

The volume of volume sensor chamber 620 may be estimated using the ratio of the natural frequency of the two resonant ports as follows:

$$\frac{\omega_{n13}^2}{\omega_{n12}^2} = \frac{V_2}{V_3}\frac{A_{13}}{A_{12}}\frac{L_{12}}{L_{13}} \quad \text{[EQ \#123]}$$

EQ #120 illustrates that the volume of volume sensor chamber 620 may be proportional to reference volume 1508. The ratio of these two volumes (in the ideal model) may only depend on the geometry of the resonant port (e.g., port 1510; FIG. 103) and has no dependence upon temperature.

Exponential Volume Model

Assume the flow out through the flow resistance has the following form:

$$\dot{V}_{out} = \frac{V_{avs}}{\tau} \quad \text{[EQ \#124]}$$

Assuming a fixed input flow rate from the pump chamber, the volume of volume sensor chamber 620 is based upon the following differential equation:

$$\dot{V}_{avs} = \dot{V}_{in} - \dot{V}_{out} = \dot{V}_{in} - \frac{V_{avs}}{\tau} \quad \text{[EQ \#125]}$$

which gives the following solution assuming a zero initial volume:

$$V_{avs} = \dot{V}_{in}\tau\left(1 - e^{-\frac{t}{\tau}}\right) \quad \text{[EQ \#126]}$$

Accordingly, the output flow rate flows:

$$\dot{V}_{out} = \dot{V}_{in}\left(1 - e^{-\frac{t}{\tau}}\right) \quad \text{[EQ \#127]}$$

The volume delivered during the pump phase may be written:

$$V_{out} = \dot{V}_{in}\left[t - \tau\left(1 - e^{-\frac{t}{\tau}}\right)\right] \quad \text{[EQ \#128]}$$

Device Calibration

The model fit allows the resonant frequency of the port to be extracted from the sine sweep data. The next step is to relate this value to the delivered volume. The ideal relationship between the resonant frequency and the delivered volume to be expressed as follows:

$$\omega_n^2 = \frac{a^2 A}{L}\frac{1}{V_2} \quad \text{[EQ \#129]}$$

The speed of sound will vary with temperature, so it may be useful to split out the temperature effects.

$$\omega_n^2 = \frac{\gamma R A}{L}\frac{T}{V_2} \quad \text{[EQ \#130]}$$

The volume may then be expressed as a function of the measured resonant frequency and the temperature:

$$V_2 = C\frac{T}{\omega_n^2} \quad \text{[EQ \#131]}$$

Where c is the calibration constant $$C = \frac{\gamma R A}{L}$$

Implementation Details

End Effects

The air resonating in the port (e.g., port assembly 624) may extend out into the acoustic volumes at the end of each oscillation. The distance the air extends may be estimated based on the fundamental volume sensor assembly equations. For any given acoustic volume, the distance the air extends into the volume may be expressed as a function of the pressure and port cross-sectional area:

$$x = \frac{V}{\rho a^2 A} p \qquad \text{[EQ \#132]}$$

If we assume the following values:

$$V = 28.8 \times 10^{-6} L \qquad \text{[EQ \#133]}$$

$$\rho = 1.292 \frac{\text{kg}}{\text{m}^3} \qquad \text{[EQ \#134]}$$

$$a = 340 \frac{\text{m}}{\text{s}} \qquad \text{[EQ \#135]}$$

$$d = 0.5 \cdot \text{mm} \qquad \text{[EQ \#136]}$$

$$p = 1 \cdot Pa \text{ (Approximately 100 dB)} \qquad \text{[EQ \#137]}$$

Accordingly, the air will extend roughly 1.9 mm in to the acoustic chamber.

Sizing V1 (i.e., the Fixed Volume) Relative to V2 (i.e., the Variable Volume)

Sizing $V_1$ (e.g., fixed volume 1500) may require trading off acoustic volume with the relative position of the poles and zeros in the transfer function. The transfer function for both $V_1$ and $V_2$ (e.g., variable volume 1502) are shown below relative to the volume displacement of speaker assembly 622.

$$\frac{p_2}{v_k} = -\frac{\rho a^2}{V_1} \frac{\omega_n^2}{s^2 + 2\zeta\omega_n s + \alpha\omega_n^2} \qquad \text{[EQ \#138]}$$

$$\frac{p_1}{v_k} = \frac{\rho a^2}{V_1} \frac{s^2 + 2\zeta\omega_n s + \alpha\omega_n^2}{s^2 + 2\zeta\omega_n s + \omega_n^2} \qquad \text{[EQ \#139]}$$

where $$\omega_n^2 = \frac{a^2 A}{L} \frac{1}{V_2}, \zeta = \frac{fA}{2L\omega_n} \text{ and } \alpha = \left(1 + \frac{V_2}{V_1}\right) \qquad \text{[EQ \#140]}$$

As $V_1$ is increased the gain may decrease and the speaker may be driven at a higher amplitude to get the same sound pressure level. However, increasing $V_1$ may also have the benefit of moving the complex zeros in the $p_1$ transfer function toward the complex poles. In the limiting case where $V_1 \to \infty$, $\alpha \to 1$ and you have pole-zero cancellation and a flat response. Increasing $V_1$, therefore, may have the benefit of reducing both the resonance and the notch in the $p_1$ transfer function, and moving the $p_2$ poles toward $\omega_n$; resulting in a lower sensitivity to measurement error when calculating the $p_2/p_1$ transfer function.

Figure 104:
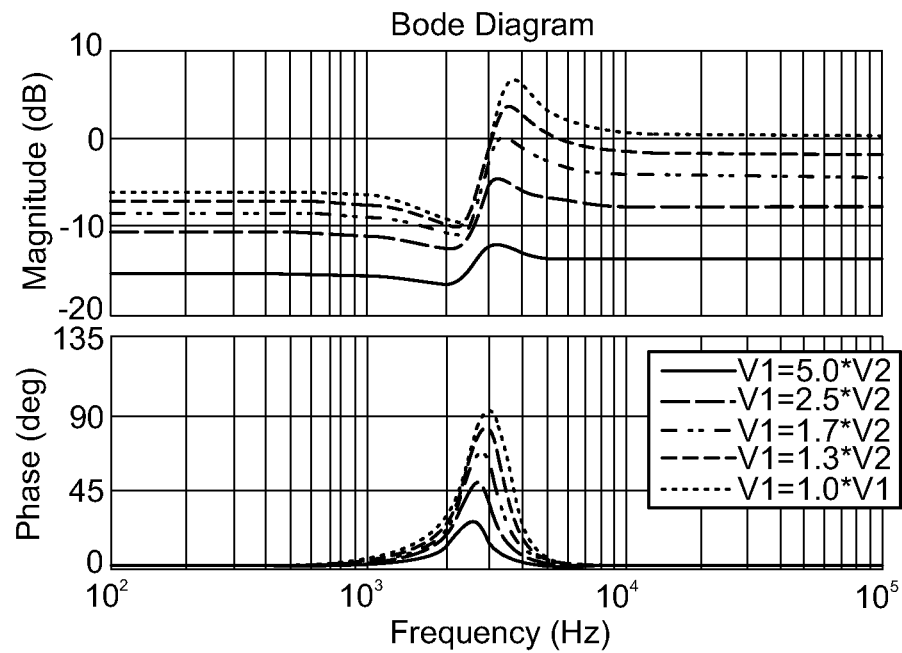
FIG. 104 is a two-dimensional graph of a performance characteristic of a volume sensor assembly included within the infusion pump assembly of FIG. 1.

FIG. 104 is a graphical representation of:

$$\frac{p_1}{v_k} \qquad \text{[EQ \#141]}$$

Figure 105:
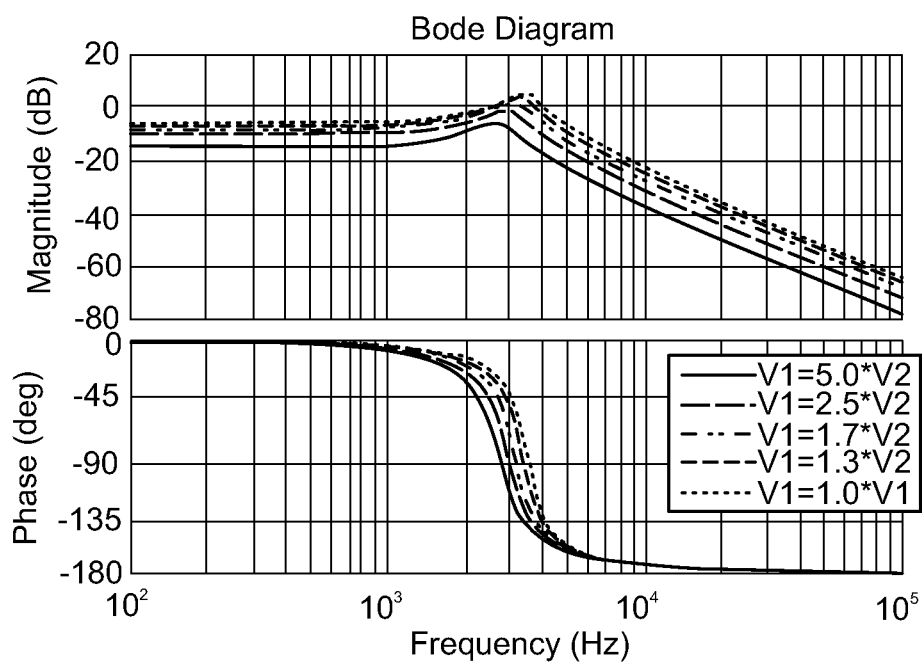
FIG. 105 is a two-dimensional graph of a performance characteristic of a volume sensor assembly included within the infusion pump assembly of FIG. 1.
Figure 106:
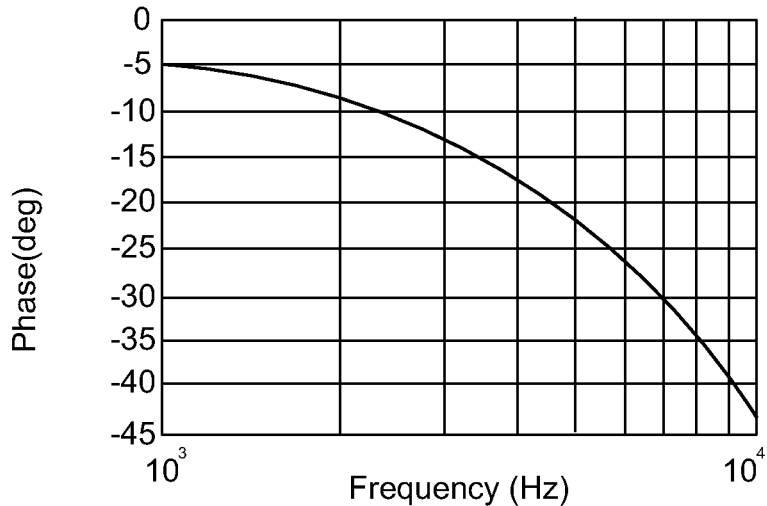
FIG. 106 is a two-dimensional graph of a performance characteristic of a volume sensor assembly included within the infusion pump assembly of FIG. 1.

FIG. 105 is a graphical representation of $$\frac{p_2}{v_k} \qquad \text{[EQ \#142]}$$

Aliasing

Higher frequencies may alias down to the frequency of interest, wherein the aliased frequency may be expressed as follows:

$$f = |f_n - n f_s| \qquad \text{[EQ \#143]}$$

where $f_s$ is the sampling frequency, $f_n$ is the frequency of the noise source, n is a positive integer, and f is the aliased frequency of the noise source.

The demodulation routine may effectively filter out noise except at the specific frequency of the demodulation. If the sample frequency is set dynamically to be a fixed multiple of the demodulation frequency, then the frequency of the noise that can alias down to the demodulation frequency may be a fixed set of harmonics of that fundamental frequency.

For example, if the sampling frequency is eight times the demodulation frequency, then the noise frequencies that can alias down to that frequency are as follows:

$$\frac{f_n}{f} = \left\{\frac{1}{n\beta+1}, \frac{1}{n\beta-1}\right\} = \left\{\frac{1}{7}, \frac{1}{9}, \frac{1}{15}, \frac{1}{17}, \frac{1}{23}, \frac{1}{25}, \ldots\right\} \qquad \text{[EQ \#144]}$$

where $$\beta = \frac{f_s}{f} = 8.$$

For $\beta=16$, the following series would result:

$$\frac{f_n}{f} = \left\{\frac{1}{15}, \frac{1}{17}, \frac{1}{31}, \frac{1}{33}, \ldots\right\} \qquad \text{[EQ \#145]}$$

Performance

Sensitivity to Temperature

The sensitivity to temperature may be split into a gain change and a noise change. If the temperature is off by a factor of dT, the resulting gain error may be:

$$V_2 = c\left(\frac{T_2}{\omega_2^2} - \frac{T_1}{\omega_1^2}\right) \qquad \text{[EQ \#147]}$$

Accordingly, if the same temperature is used for both sine sweeps, any error in the temperature measurement may look like a gain change to the system.

$$e_{gain} = 1 - \frac{T_{measured}}{T_{actual}} \qquad \text{[EQ \#148]}$$

Therefore, for a 1° K temperature error, the resulting volume error may be 0.3% at 298° K. This error may include both the error in the temperature sensor and the difference between the sensor temperature and the temperature of the air within volume sensor assembly 148.

The measurement, however, may be more susceptible to noise in the temperature measurement. A temperature change during the differential sine sweeps may result in an error that looks more like an offset rather than a gain change:

$$V_{error} = \frac{c}{\omega^2} \Delta T \qquad \text{[EQ \#149]}$$

Figure 107:
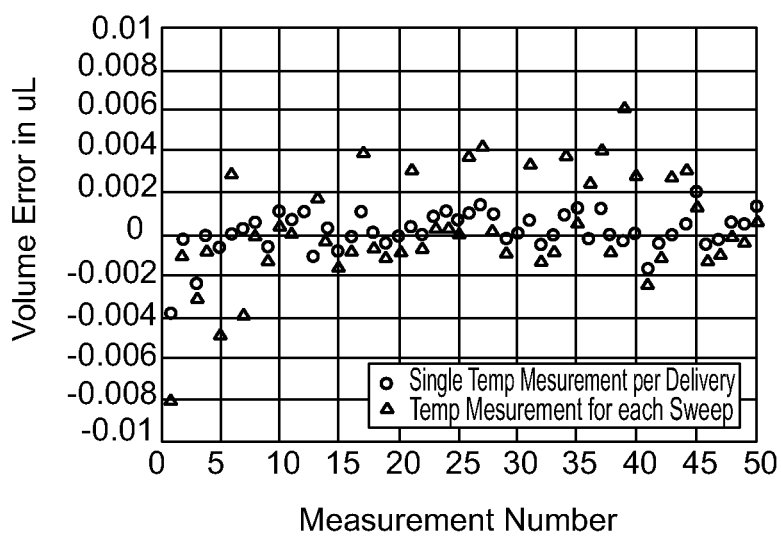
FIG. 107 is a two-dimensional graph of a performance characteristic of a volume sensor assembly included within the infusion pump assembly of FIG. 1.

Accordingly, if the measurement varies by 0.1 K during the two measurement sine sweeps, the difference may be 0.012 uL. Therefore, it may be better to use a consistent temperature estimate for each delivery rather than taking a separate temperature measurement for each sine sweep (as shown in FIG. 107).

Figure 108:
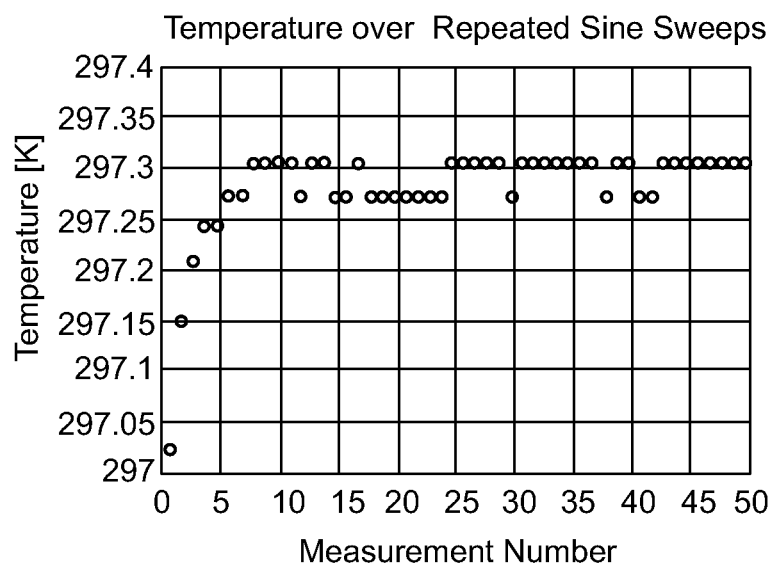
FIG. 108 is a two-dimensional graph of a performance characteristic of a volume sensor assembly included within the infusion pump assembly of FIG. 1.

The LM73 temperature sensor has a published accuracy of +/−1° C. and a resolution of 0.03 C. Further, the LM73 temperature sensor seems to consistently have a startup transient of about 0.3° C. that takes about five sine sweeps to level out (as shown in FIG. 108).

Figure 109:
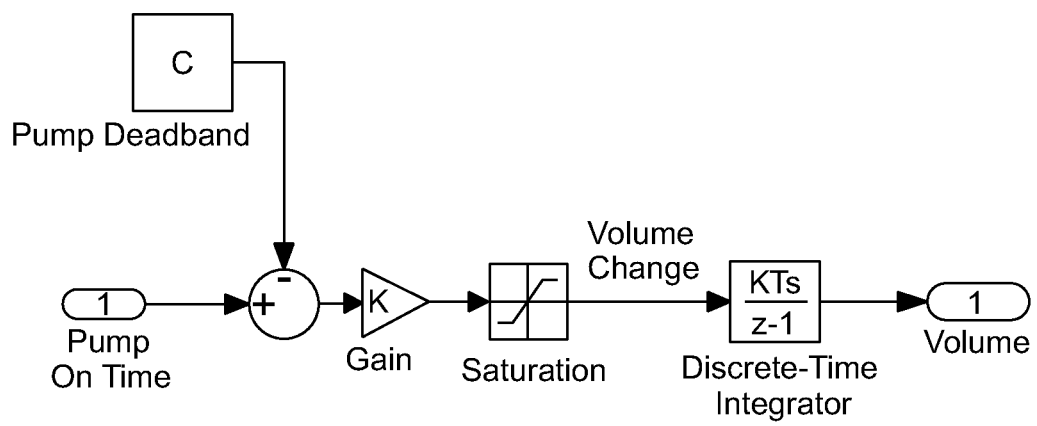
FIG. 109 is a diagrammatic view of a control model for a volume sensor assembly included within the infusion pump assembly of FIG. 1.

Since the above-described infusion pump assemblies (e.g., infusion pump assembly 100, 100', 400, 500) provides discrete deliveries of infusible fluid, the above-described infusion pump assemblies may be modeled entirely in the discrete domain (in the manner shown in FIG. 109), which may be reduced to the following:

$$G_p(z) = \frac{Kz}{z-1} \quad [\text{EQ \#150}]$$

A discrete-time PI regulator may perform according to the following:

$$G_c(z) = K_p\left(1 + \frac{T_s}{T_I}\frac{z}{z-1}\right) \quad [\text{EQ \#151}]$$

The AVS system described above works by comparing the acoustic response in fixed volume 1500 and variable volume 1502 to a speaker driven input and extracting the volume of the variable volume 1502. As such, there is a microphone in contact with each of these separate volumes (e.g., microphones 626, 630). The response of variable volume microphone 630 may also be used in a more gross manner to detect the presence or absence of disposable housing assembly 114. Specifically, if disposable housing assembly 114 is not attached to (i.e., positioned proximate) variable volume 1502, essentially no acoustic response to the speaker driven input should be sensed. The response of fixed volume 1500, however, should remain tied to the speaker input. Thus, the microphone data may be used to determine whether disposable housing assembly 114 by simply ensuring that both microphones exhibit an acoustic response. In the event that microphone 626 (i.e., the microphone positioned proximate fixed volume 1500) exhibits an acoustic response and microphone 630 (i.e., the microphone positioned proximate variable volume 1502) does not exhibit an acoustic response, it may be reasonably concluded that disposable housing assembly 114 is not attached to reusable housing assembly 102. It should be noted that a failure of variable volume microphone 630 may also appear to be indicative of disposable housing assembly 114 not being attached, as the failure of variable volume microphone 630 may result in a mid-range reading that is nearly indistinguishable from the microphone response expected when disposable housing assembly 114 is not attached.

For the following discussion, the following nomenclature may be used:

| Symbols | |
|---|---|
| $\alpha_{max}(f)$ | maximum read at a given frequency |
| $\alpha_{min}(f)$ | minimum read at a given frequency |
| $\delta$ | difference between max and min sums |
| f | individual frequency |
| F | set of sine sweep frequencies |
| N | number of frequencies in each sine sweep, F |
| $\phi$ | boolean disposable attached flag |
| $\sigma$max | sum of maximum ADC reads |
| $\sigma$min | sum of minimum ADC reads |
| T | max/min ADC difference threshold |
| Subscripts | |
| i | sweep number |
| ref | reference volume |
| var | variable volume |

As part of the demodulation routine employed in each frequency response calculation, the minimum and maximum readings of both fixed volume microphone 626 and variable volume microphone 630 may be calculated. The sum of these maximum and minimum values may be calculated over the entire sine-sweep (as discussed above) for both microphone 626 and microphone 630 as follows.

$$\sigma\max = \sum^{f\in F} \alpha_{max}(f) \quad [\text{EQ \#152}]$$

$$\sigma\min = \sum^{f\in F} \alpha_{min}(f) \quad [\text{EQ \#153}]$$

and the difference between these two summations may be simplified as follows:

$$\delta = \sigma\max - \sigma\min \quad [\text{EQ \#154}]$$

While δ may be divided by the number of sine sweeps to get the average minimum/maximum difference for the sine sweep (which is then compared to a threshold), the threshold may equivalently be multiplied by N for computational efficiency. Accordingly, the basic disposable detection algorithm may be defined as follows:

$$\phi_i = \begin{cases} 1 & \text{if } \delta_{var} > N*T \\ 0 & \text{if } \delta_{var} < N*T \text{ \& } \delta_{ref} > N*T \end{cases} \quad [\text{EQ \#155}]$$

The additional condition that the maximum/minimum difference be greater than the threshold is a check performed to ensure that a failed speaker is not the cause of the acoustic response received. This algorithm may be repeated for any sine-sweep, thus allowing a detachment of disposable housing assembly 114 to be sensed within e.g., at most two consecutive sweeps (i.e., in the worst case scenario in which disposable housing assembly 114 is removed during the second half of an in-progress sine sweep).

Thresholding for the above-described algorithm may be based entirely on numerical evidence. For example, examination of typical minimum/maximum response differences may show that no individual difference is ever less than five hundred ADC counts. Accordingly, all data examined while disposable housing assembly 114 is detached from reusable housing assembly 102 may show that all minimum/maximum response differences as being well under five hundred ADC counts. Thus, the threshold for δ may be set at T=500.

While volume sensor assembly 148 is described above as being utilized within an infusion pump assembly (e.g., infusion pump assembly 100), this is for illustrative purposes only and is not intended to be a limitation of this disclosure, as other configurations are possible and are considered to be within the scope of this disclosure. For example, volume sensor assembly 148 may be used within a process control environment for e.g., controlling the quantity of chemicals mixed together. Alternatively, volume sensor assembly 148 may be used within a beverage dispensing system to control e.g., the quantity of ingredients mixed together.

While volume sensor assembly 148 is described above as utilizing a port (e.g., port assembly 624) as a resonator, this is for illustrative purposes only, as other configurations are possible and are considered to be within the scope of this disclosure. For example, a solid mass (not shown) may be suspended within port assembly 624 and may function as a resonator for volume sensor assembly 148. Specifically, the mass (not shown) for the resonator may be suspended on a diaphragm (not shown) spanning port assembly 624. Alternatively, the diaphragm itself (not shown) may act as the mass for the resonator. The natural frequency of volume sensor assembly 148 may be a function of the volume of variable volume 1502. Accordingly, if the natural frequency of volume sensor assembly 148 can be measured, the volume of variable volume 1502 may be calculated.

The natural frequency of volume sensor assembly 148 may be measured in a number of different ways. For example, a time-varying force may be applied to the diaphragm (not shown) and the relationship between that force and the motion of the diaphragm (not shown) may be used to estimate the natural frequency of volume sensor assembly 148. Alternately the mass (not shown) may be perturbed and then allowed to oscillate. The unforced motion of the mass (not shown) may then be used to calculate the natural frequency of volume sensor assembly 148.

The force applied to the resonant mass (not shown) may be accomplished in various ways, examples of which may include but are not limited to:
- speaker assembly 622 may create a time-varying pressure within fixed volume 1500;
- the resonant mass (not shown) may be a piezoelectric material responding to a time-varying voltage/current; and
- the resonant mass (not shown) may be a voice coil responding to a time-varying voltage/current The force applied to the resonant mass may be measured in various ways, examples of which may include but are not limited to:
- measuring the pressure in the fixed volume;
- the resonant mass (not shown) may be a piezoelectric material; and
- a strain gauge may be connected to the diaphragm (not shown) or other structural member supporting the resonant mass (not shown).

Similarly, the displacement of the resonant mass (not shown) may be estimated by measuring the pressure in the variable volume, or measured directly in various ways, examples of which may include but are not limited to:
- via piezoelectric sensor;
- via capacitive sensor;
- via optical sensor;
- via Hall-effect sensor;
- via a potentiometer (time varying impedance) sensor;
- via an inductive type sensor; and
- via a linear variable differential transformer (LVDT)

Further, the resonant mass (not shown) may be integral to either the force or displacement type sensor (i.e. the resonant mass (not shown) may be made of piezoelectric material).

The application of force and measurement of displacement may be accomplished by a single device. For example, a piezoelectric material may be used for the resonant mass (not shown) and a time-varying voltage/current may be applied to the piezoelectric material to create a time-varying force. The resulting voltage/current applied to the piezoelectric material may be measured and the transfer function between the two used to estimate the natural frequency of volume sensor assembly 148.

As discussed above, the resonant frequency of volume sensor assembly 148 may be estimated using swept-sine system identification. Specifically, the above-described model fit may allow the resonant frequency of the port assembly to be extracted from the sine sweep data, which may then be used to determine the delivered volume. The ideal relationship between the resonant frequency and the delivered volume may be expressed as follows:

$$\omega_n^2 = \frac{a^2 A}{L} \frac{1}{V_2} \qquad \text{[EQ \#129]}$$

The speed of sound will vary with temperature, so it may be useful to split out the temperature effects.

$$\omega_n^2 = \frac{\gamma R A}{L} \frac{T}{V_2} \qquad \text{[EQ \#130]}$$

The volume may then be expressed as a function of the measured resonant frequency and the temperature:

$$V_2 = C \frac{T}{\omega_n^2} \qquad \text{[EQ \#131]}$$

Where c is the calibration constant $$C = \frac{\gamma R A}{L}.$$

Infusion pump assembly 100 may then compare this calculated volume $V_2$ (i.e., representative of the actual volume of infusible fluid delivered to the user) to the target volume (i.e., representative of the quantity of fluid that was supposed to be delivered to the user). For example, assume that infusion pump assembly 100 was to deliver a 0.100 unit basal dose of infusible fluid to the user every thirty minutes. Further, assume that upon effectuating such a delivery, volume sensor assembly 148 indicates a calculated volume $V_2$ (i.e., representative of the actual volume of infusible fluid delivered to the user) of 0.095 units of infusible fluid.

When calculating volume $V_2$, infusion pump assembly 100 may first determine the volume of fluid within volume sensor chamber 620 prior to the administration of the dose of infusible fluid and may subsequently determine the volume of fluid within volume sensor chamber 620 after the administration of the dose of infusible fluid, wherein the difference of those two measurements is indicative of $V_2$ (i.e., the actual volume of infusible fluid delivered to the user). Accordingly, $V_2$ is a differential measurement.

V2 may be the total air space over the diaphragm in the variable volume chamber. The actual fluid delivery to the patient may be the difference in V2 from when the chamber was full to after the measurement valve was opened and the chamber was emptied. V2 may not directly be the delivered volume. For example, the air volume may be measured and a series of differential measurements may be taken. For occlusion, an empty measurement may be taken, the chamber may be filed, a full measurement may be taken, and then a final measurement may be taken after the exit valve is open. Accordingly, the difference between the first and second measurement may be the amount pumped and the difference between the second and third is the amount delivered to the patient.

Accordingly, electrical control assembly 110 may determine that the infusible fluid delivered is 0.005 units under what was called for. In response to this determination, electrical control assembly 110 may provide the appropriate signal to mechanical control assembly 104 so that any additional necessary dosage may be pumped. Alternatively, electrical control assembly 110 may provide the appropriate signal to mechanical control assembly 104 so that the additional dosage may be dispensed with the next dosage. Accordingly, during administration of the next 0.100 unit dose of the infusible fluid, the output command for the pump may be modified based on the difference between the target and amount delivered.

Figure 110:
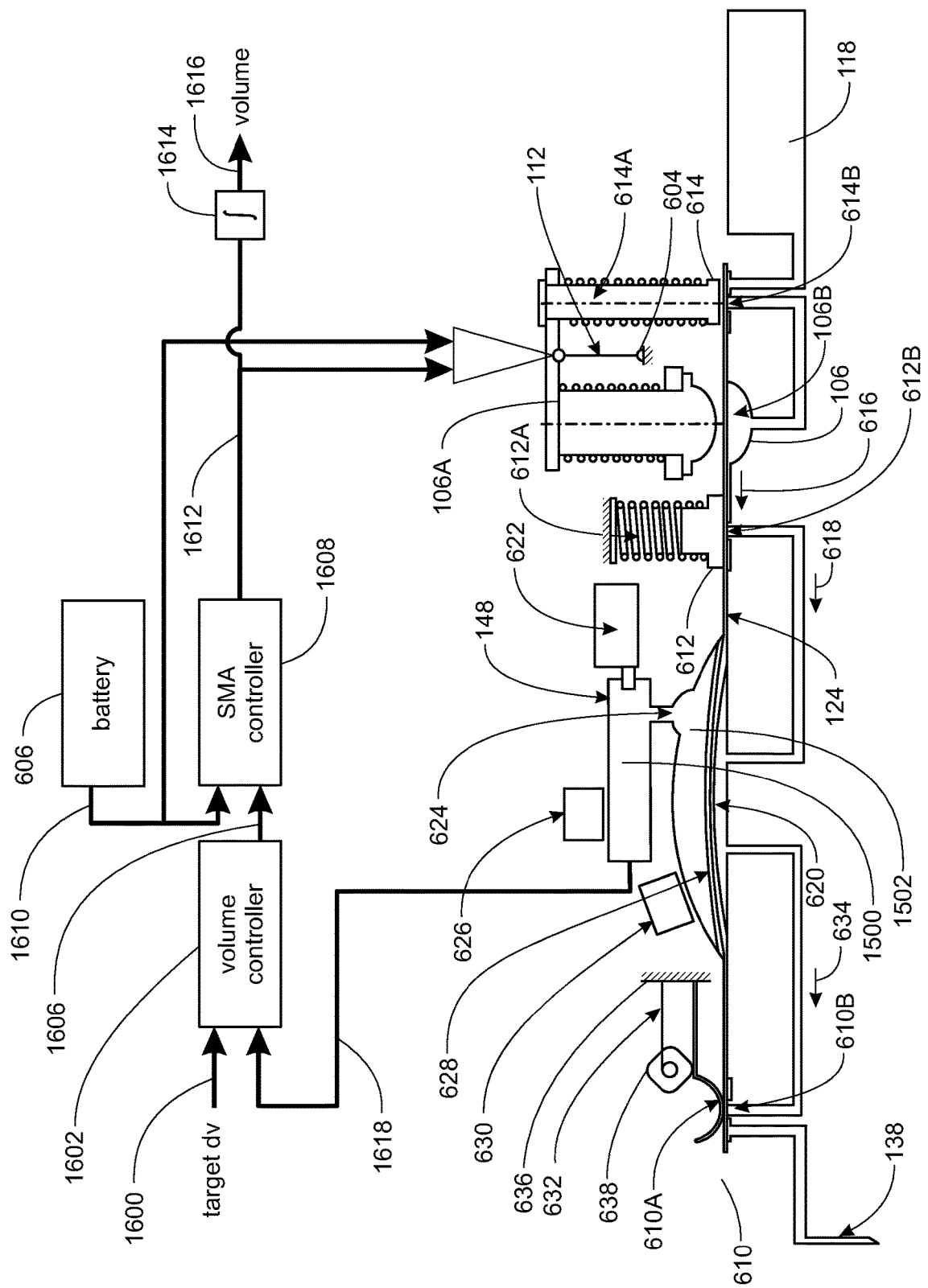
FIG. 110 is a diagrammatic view of an electrical control assembly for the volume sensor assembly included within the infusion pump assembly of FIG. 1.

Referring also to FIG. 110, there is shown one particular implementation of a control system for controlling the quantity of infusible fluid currently being infused based, at least in part, on the quantity of infusible fluid previously administered. Specifically and continuing with the above-stated example, assume for illustrative purposes that electrical control assembly 110 calls for the delivery of a 0.100 unit dose of the infusible fluid to the user. Accordingly, electrical control assembly 110 may provide a target differential volume signal 1600 (which identifies a partial basal dose of 0.010 units of infusible fluid per cycle of shape memory actuator 112) to volume controller 1602. Accordingly and in this particular example, shape memory actuator 112 may need to be cycled ten times in order to achieve the desired basal dose of 0.100 units of infusible fluid (i.e., 10 cycles×0.010 units per cycle=0.100 units). Volume controller 1602 in turn may provide "on-time" signal 1606 to SMA (i.e., shape memory actuator) controller 1608. Also provided to SMA controller 1608 is battery voltage signal 1610.

Specifically, shape-memory actuator 112 may be controlled by varying the amount of thermal energy (e.g., joules) applied to shape-memory actuator 112. Accordingly, if the voltage level of battery 606 is reduced, the quantity of joules applied to shape-memory actuator 112 may also be reduced for a defined period of time. Conversely, if the voltage level of battery 606 is increased, the quantity of joules applied to shape memory actuator 112 may also be increased for a defined period of time. Therefore, by monitoring the voltage level of battery 606 (via battery voltage signal 1610), the type of signal applied to shape-memory actuator 112 may be varied to ensure that the appropriate quantity of thermal energy is applied to shape-memory actuator 112 regardless of the battery voltage level.

SMA controller 1608 may process "on-time" signal 1606 and battery voltage signal 1610 to determine the appropriate SMA drive signal 1612 to apply to shape-memory actuator 112. One example of SMA drive signal 1612 may be a series of binary pulses in which the amplitude of SMA drive signal 1612 essentially controls the stroke length of shape-memory actuator 112 (and therefore pump assembly 106) and the duty cycle of SMA drive signal 1612 essentially controls the stroke rate of shape-memory actuator 112 (and therefore pump assembly 106). Further, since SMA drive signal 1612 is indicative of a differential volume (i.e., the volume infused during each cycle of shape memory actuator 112), SMA drive signal 1612 may be integrated by discrete time integrator 1614 to generate volume signal 1616 which may be indicative of the total quantity of infusible fluid infused during a plurality of cycles of shape memory actuator 112. For example, since (as discussed above) it may take ten cycles of shape memory actuator 112 (at 0.010 units per cycle) to infuse 0.100 units of infusible fluid, discrete time integrator 1614 may integrate SMA drive signal 1612 over these ten cycles to determine the total quantity infused of infusible fluid (as represented by volume signal 1616).

SMA drive signal 1612 may actuate pump assembly 106 for e.g. one cycle, resulting in the filling of volume sensor chamber 620 included within volume sensor assembly 148. Infusion pump assembly 100 may then make a first measurement of the quantity of fluid included within volume sensor chamber 620 (as discussed above). Further and as discussed above, measurement valve assembly 610 may be subsequently energized, resulting in all or a portion of the fluid within volume sensor chamber 620 being delivered to the user. Infusion pump assembly 100 may then make a measurement of the quantity of fluid included within volume sensor chamber 620 (as described above) and use those two measurements to determine $V_2$ (i.e., the actual volume of infusible fluid delivered to the user during the current cycle of shape memory actuator 112). Once determined, $V_2$ (i.e., as represented by signal 1618) may be provided (i.e., fed back) to volume controller 1602 for comparison to the earlier-received target differential volume.

Continuing with the above-stated example in which the differential target volume was 0.010 units of infusible fluid, assume that $V_2$ (i.e., as represented by signal 1618) identifies 0.009 units of infusible fluid as having been delivered to the user. Accordingly, infusion pump assembly 100 may increase the next differential target volume to 0.011 units to offset the earlier 0.001 unit shortage. Accordingly and as discussed above, the amplitude and/or duty cycle of SMA drive signal 1612 may be increased when delivering the next basal dose of the infusible fluid to the user. This process may be repeated for the remaining nine cycles of shape memory actuator 112 (as discussed above) and discrete time integrator 1614 may continue to integrate SMA drive signal 1612 (to generate volume signal 1616) which may define the total quantity of infusible fluid delivered to the user.

Figure 111:
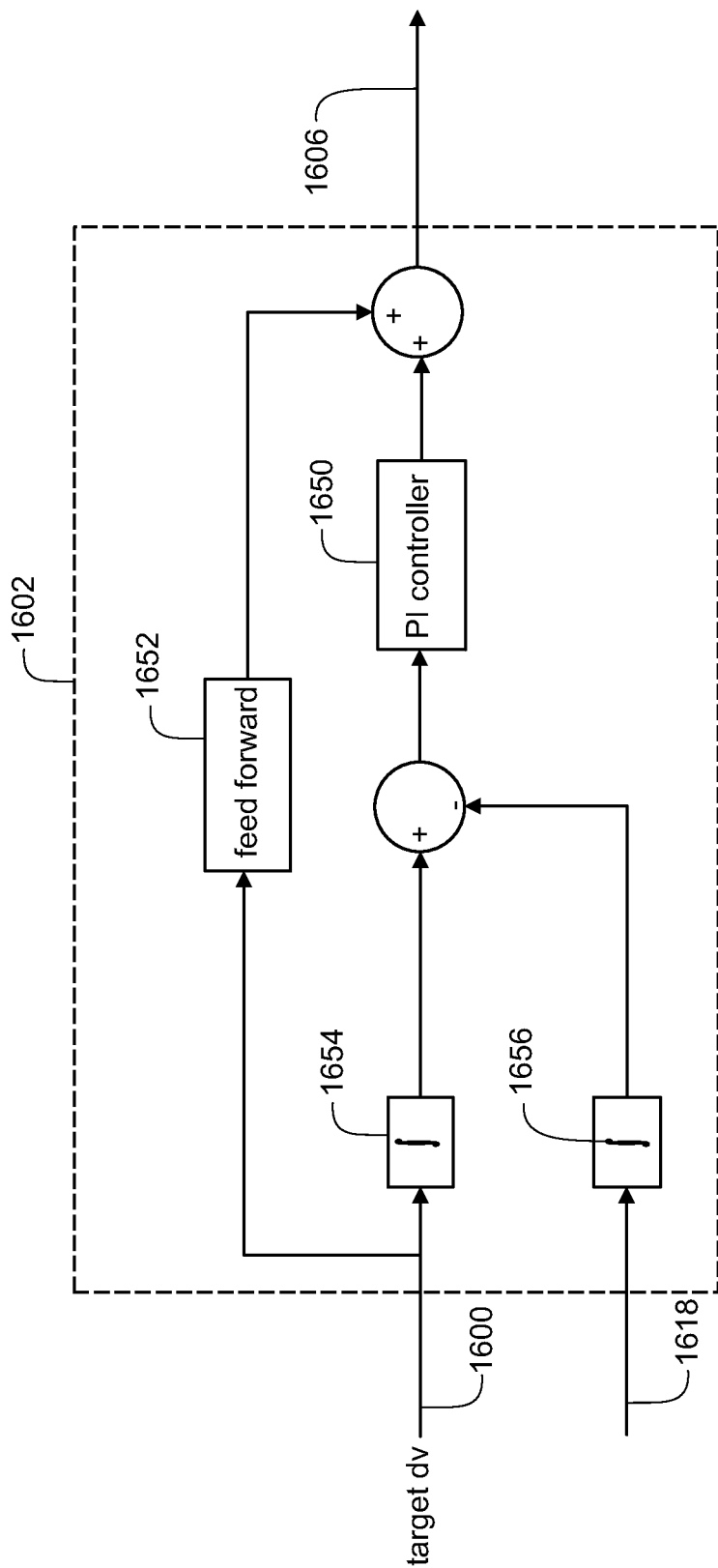
FIG. 111 is a diagrammatic view of a volume controller for the volume sensor assembly included within the infusion pump assembly of FIG. 1.

Referring also to FIG. 111, there is shown one possible embodiment of volume controller 1602. In this particular implementation, volume controller 1602 may include PI (proportional-integrator) controller 1650. Volume controller 1602 may include feed forward controller 1652 for setting an initial "guess" concerning "on-time" signal 1606. For example, for the situation described above in which target differential volume signal 1600 identifies a partial basal dose of 0.010 units of infusible fluid per cycle of shape memory actuator 112, feed forward controller 1652 may define an initial "on-time" of e.g., one millisecond. Feed forward controller 1652 may include e.g., a lookup table that define an initial "on-time" that is based, at least in part, upon target differential volume signal 1600. Volume controller 1602 may further include discrete time integrator 1654 for integrating target differential volume signal 1600 and discrete time integrator 1656 for integrating $V_2$ (i.e., as represented by signal 1618).

Figure 112:
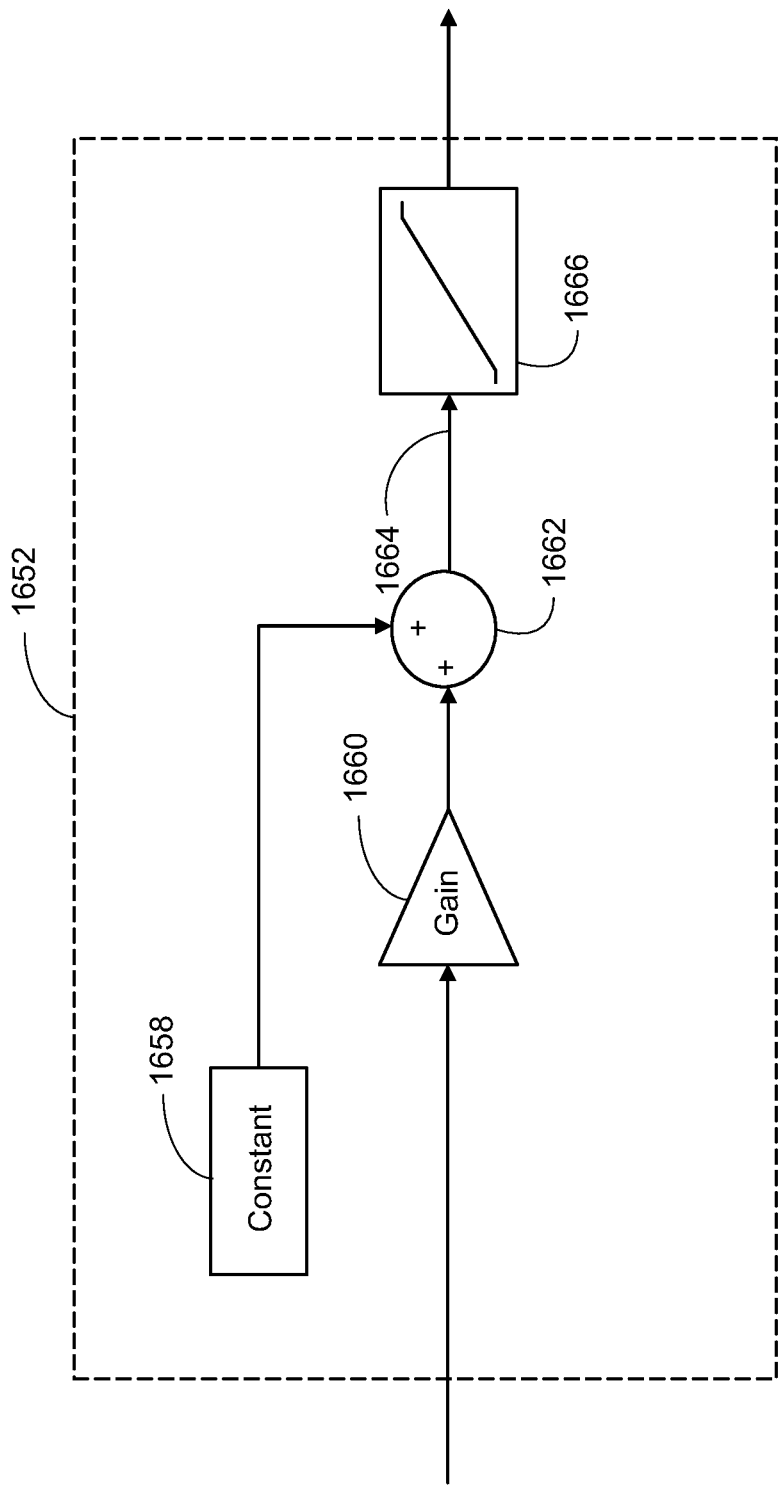
FIG. 112 is a diagrammatic view of a feed forward controller of the volume controller of FIG. 111.

Referring also to FIG. 112, there is shown one possible embodiment of feed forward controller 1652. In this particular implementation, feed forward controller 1652 may define a constant value signal 1658 and may include amplifier 1660 (e.g., a unity gain amplifier), the output of which may be summed with constant value signal 1658 at summing node 1662. The resulting summed signal (i.e., signal 1664) may be provided to as an input signal to e.g., lookup table 1666, which may be processed to generate the output signal of feed forward controller 1652.

As discussed above, pump assembly 106 may be controlled by shape memory actuator 112. Further and as discussed above, SMA controller 1608 may process "on-time" signal 1606 and battery voltage signal 1610 to determine the appropriate SMA drive signal 1612 to apply to shape-memory actuator 112.

Figure 113:
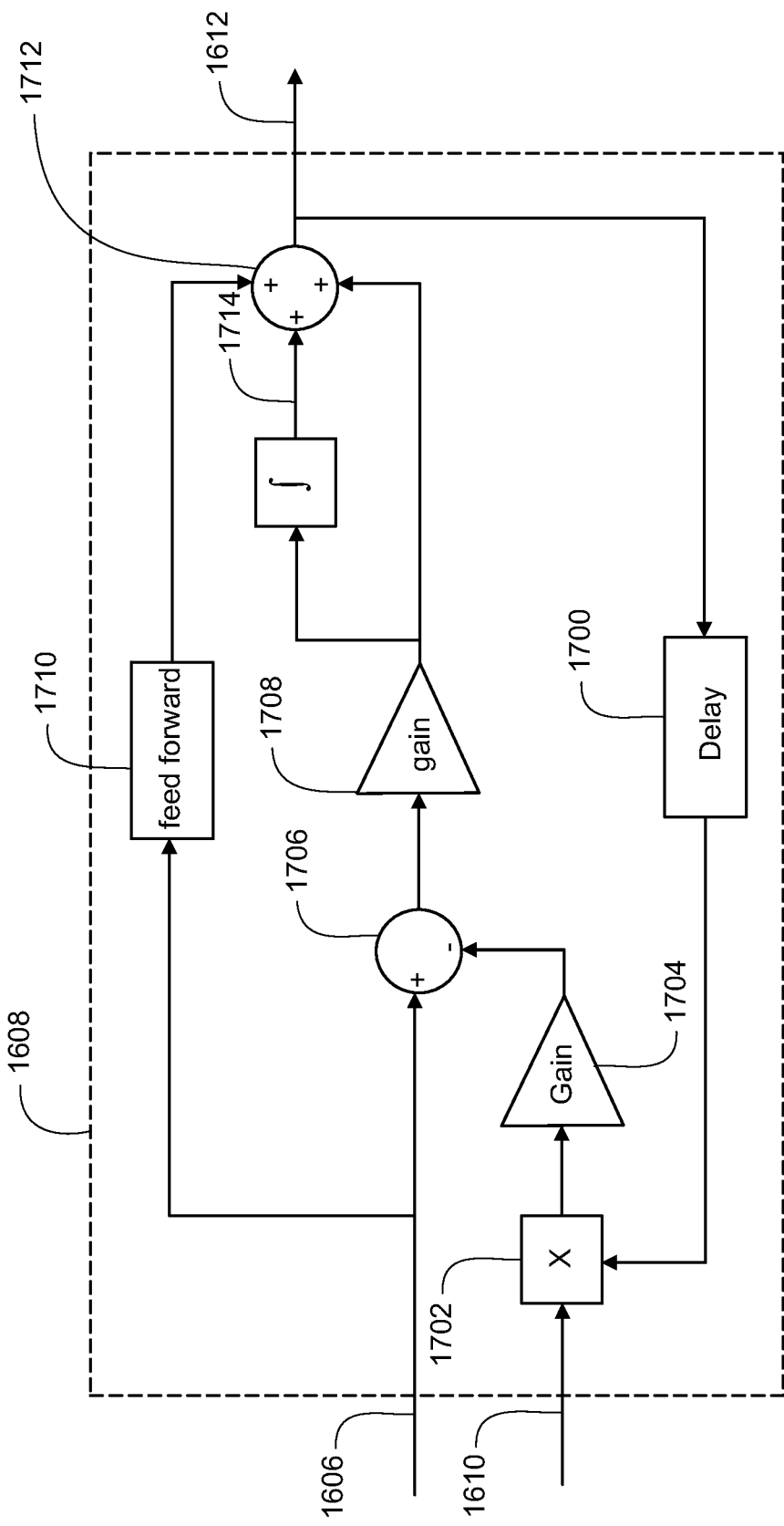
FIGS. 113-114 diagrammatically depicts an implementation of an SMA controller of the volume controller of FIG. 111.
Figure 114:
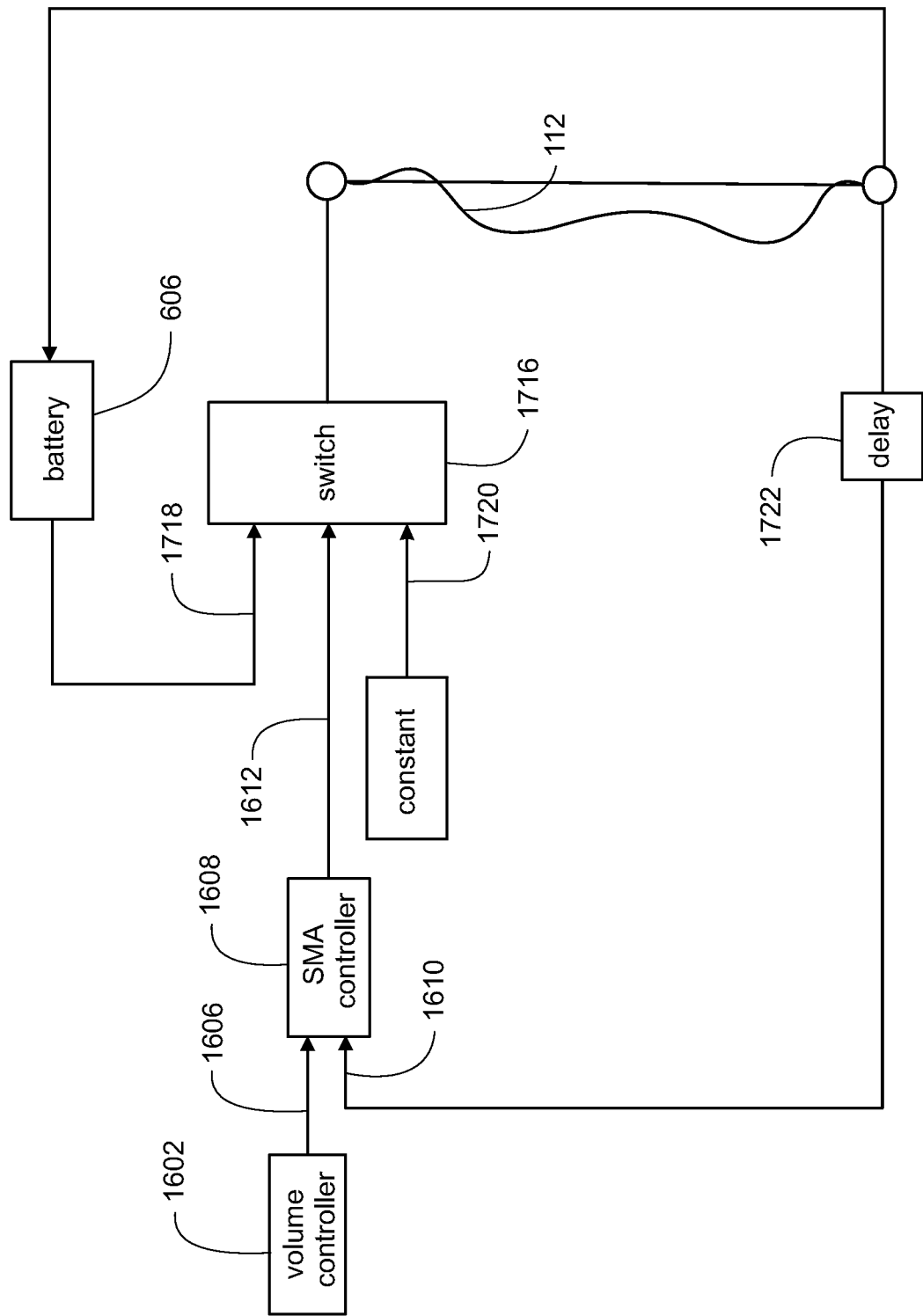

Referring also to FIGS. 113-114, there is shown one particular implementation of SMA controller 1608. As discussed above, SMA controller 1608 may be responsive to "on-time" signal 1606 and battery voltage signal 1610 and may provide SMA drive signal 1612 to shape-memory actuator 112. SMA controller 1608 may include a feedback loop (including unit delay 1700), the output of which may be multiplied with battery voltage signal 1610 at multiplier 1702. The output of multiplier 1702 may be amplified with e.g., unity gain amplifier 1704. The output of amplifier 1704 may be applied to the negative input of summing node 1706 (to which "on-time" signal 1606 is applied). The output of summing node 1706 may be amplified (via e.g., unity gain amplifier 1708). SMA controller may also include feed forward controller 1710 to provide an initial value for SMA drive signal 1612 (in a fashion similar to feed forward controller 1652 of volume controller 1602; See FIG. 112). The output of feed forward controller 1710 may be summed at summing node 1712 with the output of amplifier 1708 and an integrated representation (i.e., signal 1714) of the output of amplifier 1708 to form SMA drive signal 1612.

SMA drive signal 1612 may be provided to control circuitry that effectuates the application of power to shape-memory actuator 112. For example, SMA drive signal 1612 may be applied to switching assembly 1716 that may selectively apply current signal 1718 (supplied from battery 606) and/or fixed signal 1720 to shape-memory actuator. For example, SMA drive signal 1612 may effectuate the application of energy (supplied from battery 606 via current signal 1718) via switching assembly 1716 in a manner that achieves the duty cycle defined by SMA drive signal 1612. Unit delay 1722 may generate a delayed version of the signal applied to shape-memory actuator 112 to form battery voltage signal 1610 (which may be applied to SMA controller 1608).

When applying power to shape-memory actuator 112, voltage may be applied for a fixed amount of time and: a) at a fixed duty cycle with an unregulated voltage; b) at a fixed duty cycle with a regulated voltage; c) at a variable duty cycle based upon a measured current value; d) at a variable duty cycle based upon a measured voltage value; and e) at a variable duty cycle based upon the square of a measured voltage value. Alternatively, voltage may be applied to shape-memory actuator 112 for a variable amount of time based upon a measured impedance.

When applying an unregulated voltage for a fixed amount of time at a fixed duty cycle, inner loop feedback may not be used and shape memory actuator may be driven at a fixed duty cycle and with an on-time determined by the outer volume loop.

When applying a regulated voltage for a fixed amount of time at a fixed duty cycle, inner loop feedback may not be used and shape memory actuator 112 may be driven at a fixed duty cycle and with an on-time determined by the outer volume loop.

When applying an unregulated voltage at a variable duty cycle based upon a measured current value, the actual current applied to shape-memory actuator 112 may be measured and the duty cycle may be adjusted during the actuation of shape-memory actuator 112 to maintain the correct mean current.

When applying an unregulated voltage at a variable duty cycle based upon a measured voltage value, the actual voltage applied to shape-memory actuator 112 may be measured and the duty cycle may be adjusted during the actuation of shape-memory actuator 112 to maintain the correct mean voltage.

When applying an unregulated voltage at a variable duty cycle based upon the square of a measured voltage value, the actual voltage applied to shape-memory actuator 112 may be measured and the duty cycle may be adjusted during the actuation of shape-memory actuator 112 to maintain the square of the voltage at a level required to provide the desired level of power to shape-memory actuator 112 (based upon the impedance of shape-memory actuator 112).

Figure 114A:
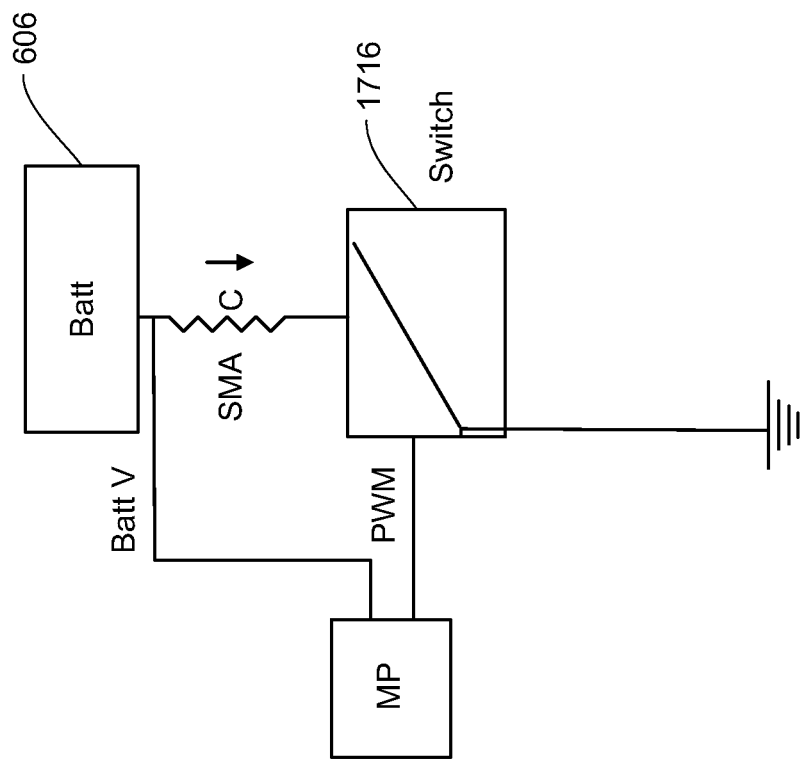
FIG. 114A-114B is an alternate implementation of an SMA controller.
Figure 114B:
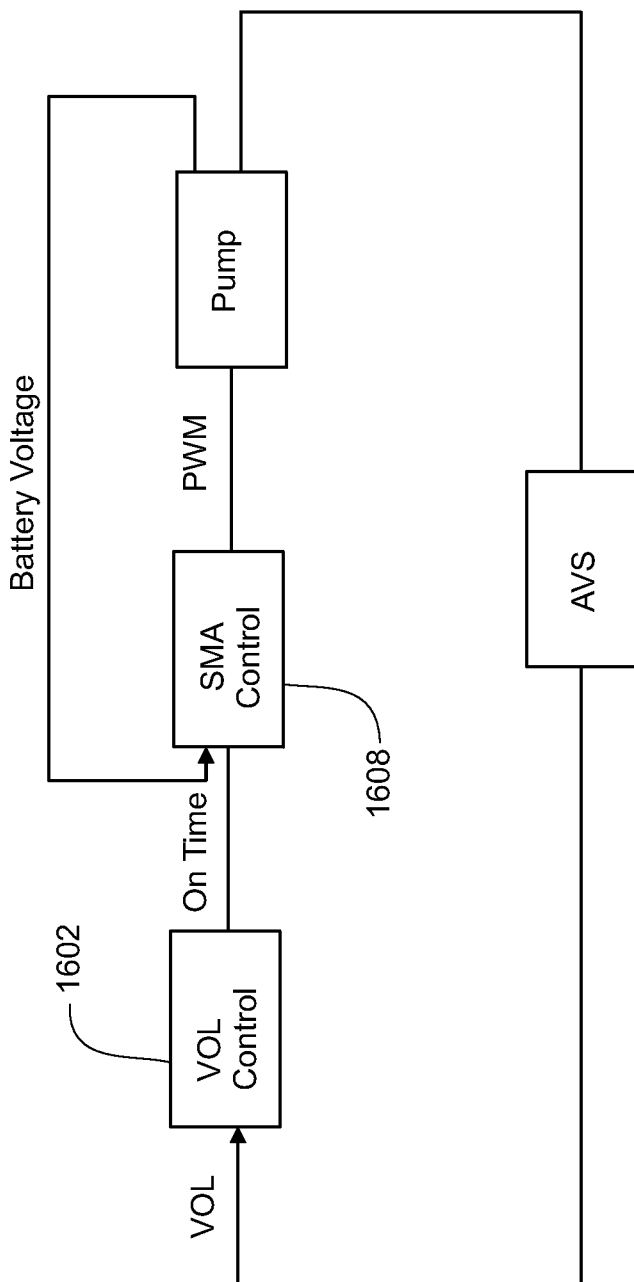

Referring also to FIG. 114A-114B, there is shown other implementations of SMA controller 1608. Specifically, FIG. 114A is an electrical schematic that includes a microprocessor and various control loops that may be configured to provide a PWM signal that may open and close the switch assembly. The switch assembly may control the current that is allowed to flow through the shape memory actuator. The battery may provide the current to the shape memory actuator. Further, 114B discloses a volume controller and an inner shape memory actuator controller. The shape memory actuator controller may provide a PWM signal to the pump, which may be modified based on the battery voltage. This may occur for a fixed ontime, the result being a volume that may be measured by volume sensor assembly 148 and fed back into the volume controller.

In our preferred embodiment, we vary the duty cycle based on the measured battery voltage to give you approximately consistent power. We adjust the duty cycle to compensate for a lower battery voltage. Battery voltage may change for two reasons: 1) as batteries are discharged, the voltage slowly decreases; and 2) when you apply a load to a battery it has an internal impedance so its voltage dips. This is something that happens in any type of system, and we compensate for that by adjusting the duty cycle, thus mitigating the lower or varying battery voltage. Battery voltage may be measured by the microprocessor. In other systems: 1) voltage may be regulated (put a regulator to maintain the voltage at a steady voltage); 2) feedback based on something else (i.e., speed or position of a motor, not necessarily measuring the battery voltage).

Other configurations may be utilized to control the shape memory actuator. For example: A) the shape memory actuator may be controlled at fixed duty cycle with unregulated voltage. As voltage varies, the repeatability of heating the shape memory actuator is reduced. B) a fixed duty cycle, regulated voltage may be utilized which compensate for changes in battery voltage. However, regulate the voltage down is less efficient due to energy of energy. C) the duty cycle may be varied based on changes in current (which may required more complicated measurement circuitry. D) The duty cycle may be varied based on measured voltage. E) The duty cycle may be varied based upon the square of the current or the square of the voltage divided by resistance. F) the voltage may be applied for a variable amount of time based on the measured impedance (e.g., may measure impedance using Wheatstone gauge (not shown)). The impedance of the shape memory actuator may be correlated to strain (i.e., may correlate how much the SMA moves based on its impedance).

Figure 115:
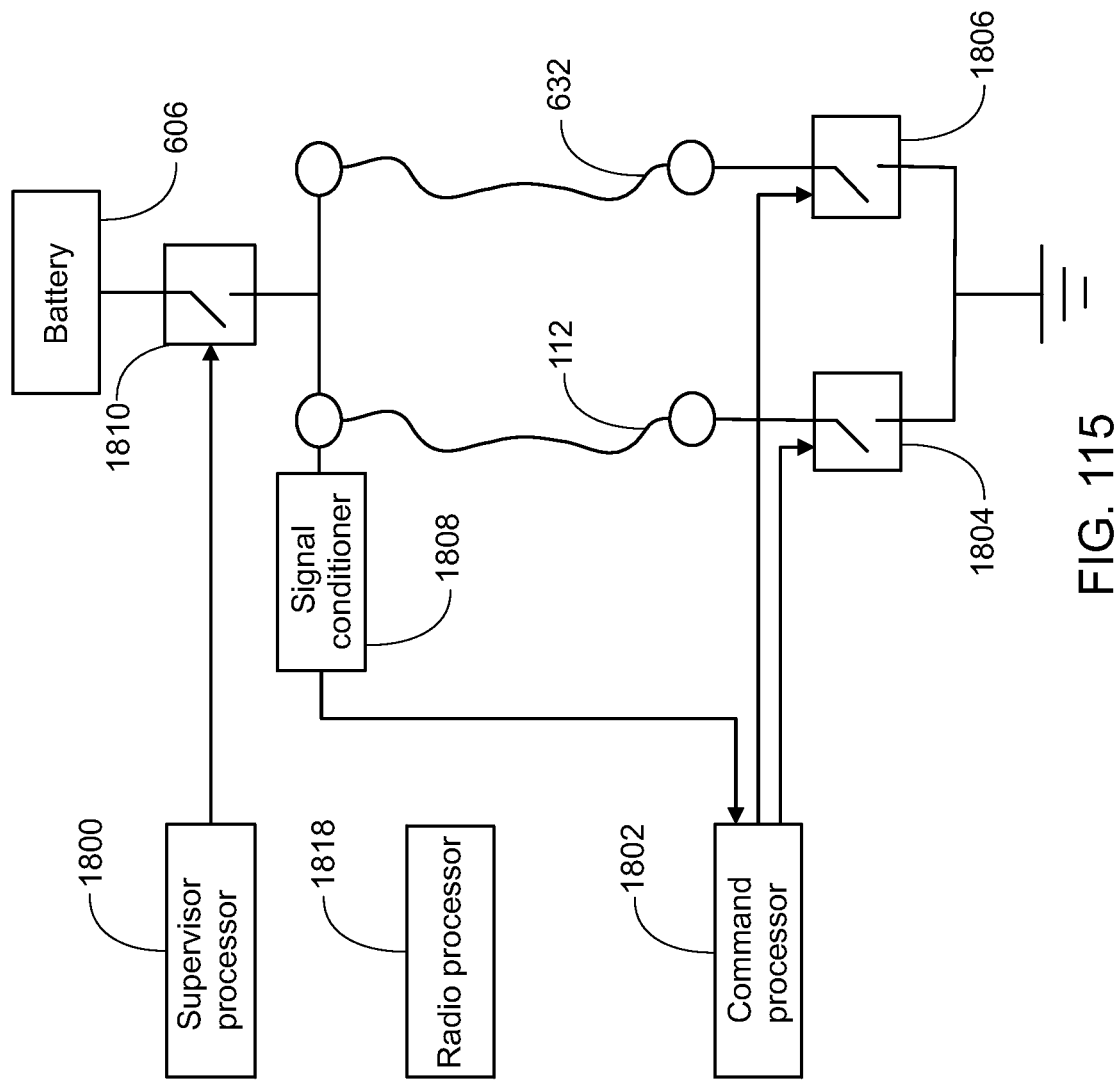
FIG. 115 diagrammatically depicts a multi-processor control configuration that may be included within the infusion pump assembly of FIG. 1.

Referring also to FIG. 115 and as discussed above, to enhance the safety of infusion pump assembly 100, electrical control assembly 110 may include two separate and distinct microprocessors, namely supervisor processor 1800 and command processor 1802. Specifically, command processor 1802 may perform the functions discussed above (e.g., generating SMA drive signal 1612) and may control relay/switch assemblies 1804, 1806 that control the functionality of (in this example) shape memory actuators 112, 632 (respectively). Command processor 1802 may receive feedback from signal conditioner 1808 concerning the condition (e.g., voltage level) of the voltage signal applied to shape memory actuators 112, 632. Command processor 1800 may control relay/switch assembly 1810 independently of relay/switch assemblies 1804, 1806. Accordingly, when an infusion event is desired, both of supervisor processor 1800 and command processor 1802 must agree that the infusion event is proper and must both actuate their respective relays/switches. In the event that either of supervisor processor 1800 and command processor 1802 fails to actuate their respective relays/switches, the infusion event will not occur. Accordingly through the use of supervisor processor 1800 and command processor 1802 and the cooperation and concurrence that must occur, the safety of infusion pump assembly 100 is enhanced.

The supervisor processor may prevent the command processor from delivering when it is not supposed and also may alarm if the command processor does not deliver when it should be delivering. The supervisor processor may deactivate the relay/switch assembly if the command processor actuates the wrong switch, or if the command processor it tries to apply power for too long.

The supervisor processor may redundantly doing calculations for how much insulin should be delivered (i.e., double checking the calculations of the command processor). Command processor may decide the delivery schedule, and the supervisor processor may redundantly check those calculations.

Supervisor also redundantly holds the profiles (delivery profiles) in RAM, so the command processor may be doing the correct calculations, but if is has bad RAM, would cause the command to come up with the wrong result. The Supervisor uses its local copy of the basal profile, etc., to double check.

Supervisor can double check AVS measurements, looks at the AVS calculations and applies safety checks. Every time AVS measurement is taken, it double checks.

Referring also to FIG. 116, one or more of supervisor processor 1800 and command processor 1802 may perform diagnostics on various portions of infusion pump assembly 100. For example, voltage dividers 1812, 1814 may be configured to monitor the voltages (V1 & V2 respectively) sensed at distal ends of e.g., shape memory actuator 112. The value of voltages V1 & V2 in combination with the knowledge of the signals applied to relay/switch assemblies 1804, 1810 may allow for diagnostics to be performed on various components of the circuit shown in FIG. 116 (in a manner similar to that shown in illustrative diagnostic table 1816).

As discussed above and as illustrated in FIGS. 115-116, to enhance the safety of infusion pump assembly 100, electrical control assembly 110 may include a plurality of microprocessors (e.g., supervisor processor 1800 and command processor 1802), each of which may be required to interact and concur in order to effectuate the delivery of a dose of the infusible fluid. In the event that the microprocessors fail to interact/concur, the delivery of the dose of infusible fluid may fail and one or more alarms may be triggered, thus enhancing the safety and reliability of infusion pump assembly 100.

A master alarm may be utilized that tracks the volume error over time. Accordingly, if the sum of the errors becomes too large, the master alarm may be initiated, indicating that something may be wrong with the system. Accordingly, the master alarm may be indicative of a total volume comparison being performed and a discrepancy being noticed. A typical value of the discrepancy required to initiate the master alarm may be 1.00 milliliters. The master alarm may monitor the sum in a leaky fashion (i.e., Inaccuracies have a time horizon).

Figure 117A:
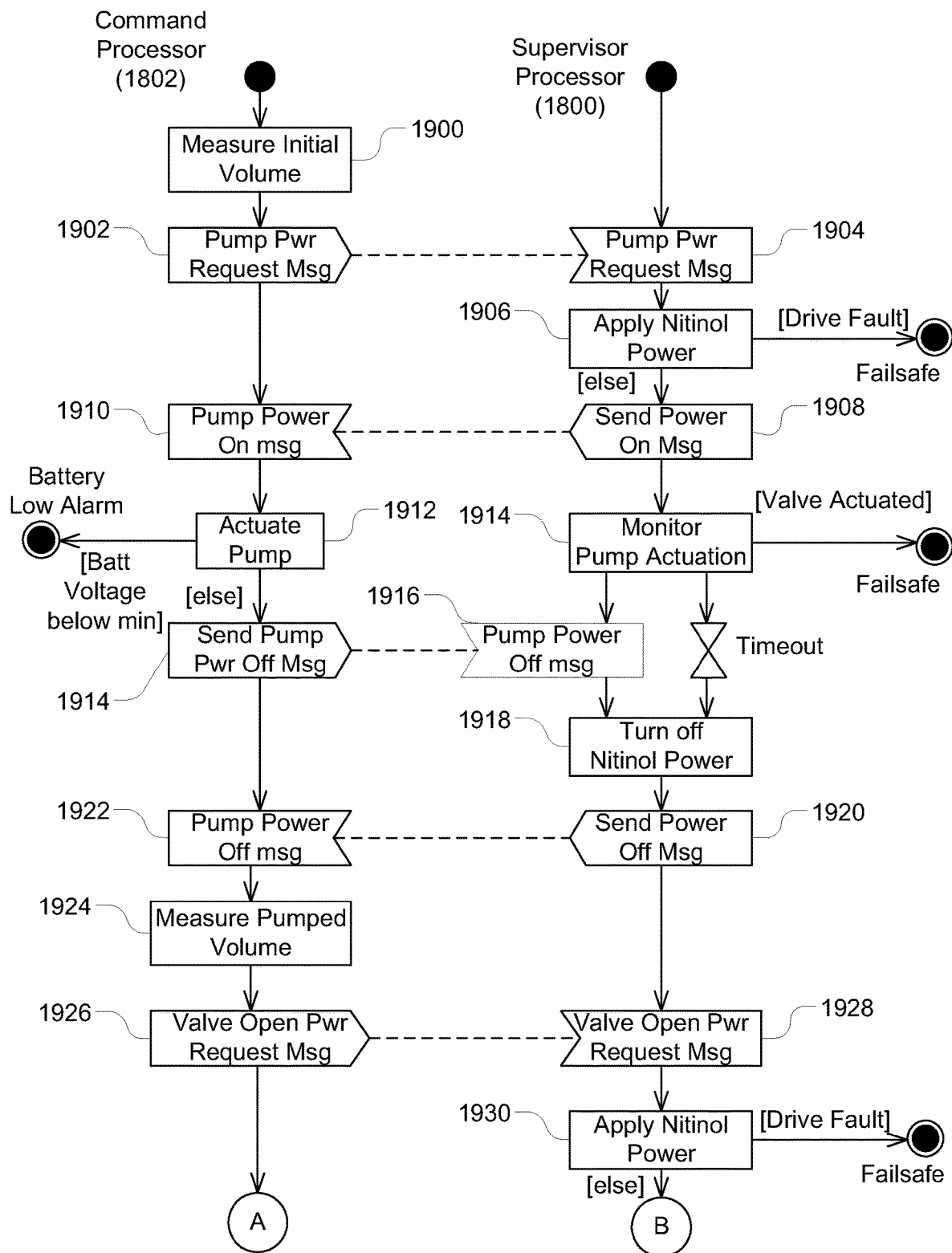
FIG. 117A-117B diagrammatically depicts multi-processor functionality.
Figure 117B:
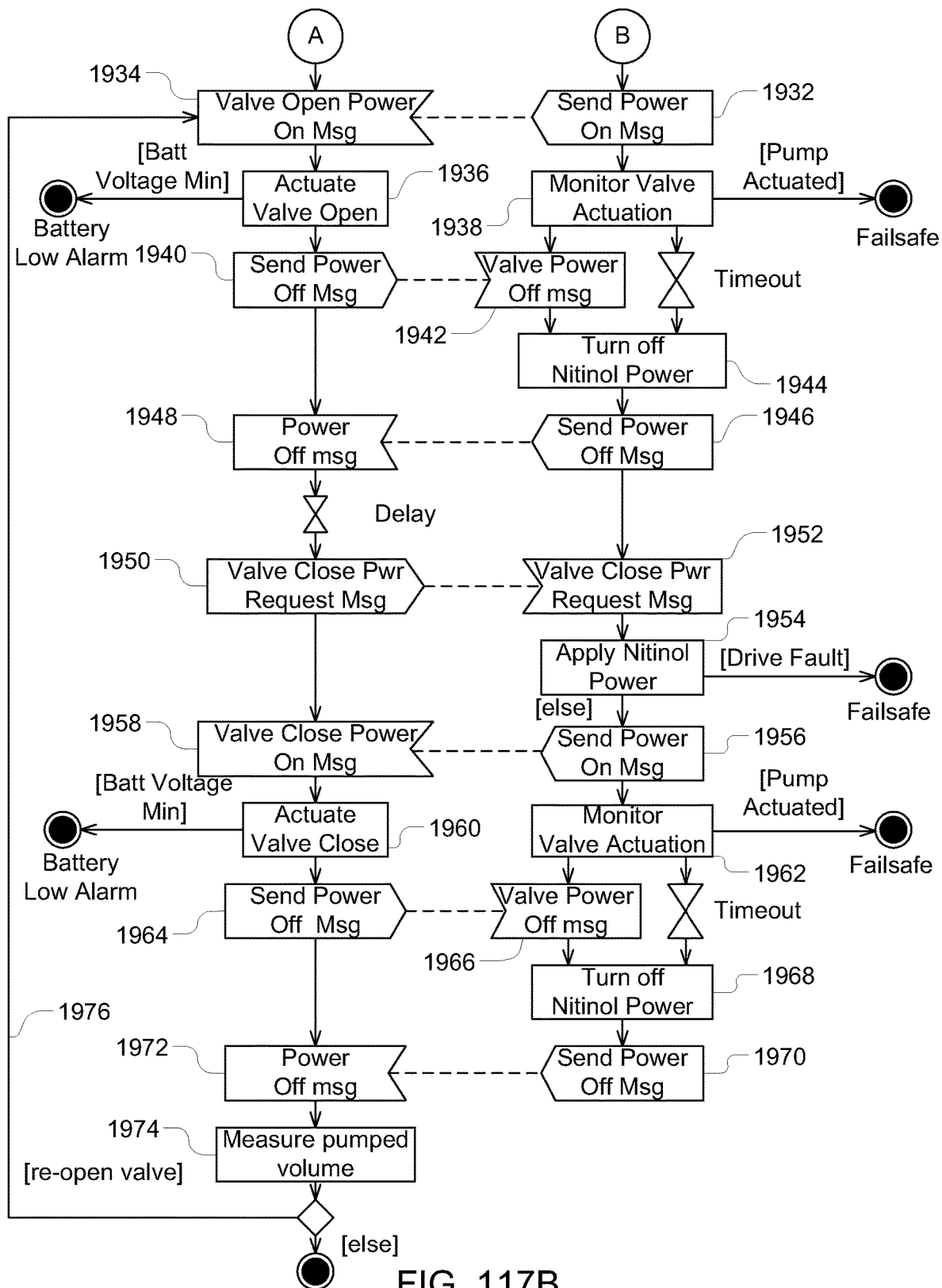

Referring also to FIGS. 117A-117B, there is shown one such illustrative example of such interaction amongst multiple microprocessors during the delivery of a dose of the infusible fluid. Specifically, command processor 1802 may first determine 1900 the initial volume of infusible fluid within volume sensor chamber 620. Command processor 1802 may then provide 1902 a "pump power request" message to supervisor processor 1800. Upon receiving 1904 the "pump power request" message, supervisor processor 1800 may e.g., energize 1906 relay/switch 1810 (thus energizing shape memory actuator 112) and may send 1908 a "pump power on" message to command processor 1802. Upon receiving 1910 the "pump power on" message, command processor 1802 may actuate 1912 e.g., pump assembly 106 (by energizing relay/switch 1804), during which time supervisor processor 1800 may monitor 1914 the actuation of e.g., pump assembly 106.

Once actuation of pump assembly 106 is complete, command processor 1802 may provide 1914 a "pump power off" message to supervisor processor 1800. Upon receiving 1916 the "pump power off" message, supervisor processor 1800 may deenergize 1918 relay/switch 1810 and provide 1920 a "pump power off" message to command processor 1802. Upon receiving 1922 the "pump power off" message, command processor 1802 may measure 1924 the quantity of infusible fluid pumped by pump assembly 106. This may be accomplished by measuring the current quantity of fluid within volume sensor chamber 620 and comparing it with the quantity determined above (in step 1900). Once determined 1924, command processor 1802 may provide 1926 a "valve open power request" message to supervisor processor 1800. Upon receiving 1928 the "valve open power request" message, supervisor processor 1800 may energize 1930 relay/switch 1810 (thus energizing shape memory actuator 632) and may send 1932 a "valve open power on" message to command processor 1802. Upon receiving 1934 the "valve open power on" message, command processor 1802 may actuate 1936 e.g., measurement valve assembly 610 (by energizing relay/switch 1806), during which time supervisor processor 1800 may monitor 1938 the actuation of e.g., measurement valve assembly 610.

Once actuation of measurement valve assembly 610 is complete, command processor 1802 may provide 1940 a "valve power off" message to supervisor processor 1800.

Upon receiving 1942 the "valve power off" message, supervisor processor 1800 may deenergize 1944 relay/switch 1810 and provide 1946 a "valve power off" message to command processor 1802.

Upon receiving 1948 the "valve power off" message, command processor 1802 may provide 1950 a "valve close power request" message to supervisor processor 1800. Upon receiving 1952 the "valve close power request" message, supervisor processor 1800 may energize 1954 relay/switch 1810 (thus energizing shape memory actuator 652) and may send 1956 a "power on" message to command processor 1802. Upon receiving 1958 the "power on" message, command processor 1802 may actuate 1960 an energizing relay/switch (not shown) that is configured to energize shape memory actuator 652, during which time supervisor processor 1800 may monitor 1962 the actuation of e.g., shape memory actuator 652.

As discussed above (and referring temporarily to FIGS. 26A, 26B, 27A, 27B & 28), shape memory actuator 652 may be anchored on a first end using electrical contact 654. The other end of shape memory actuator 652 may be connected to bracket assembly 656. When shape memory actuator 652 is activated, shape memory actuator 652 may pull bracket assembly 656 forward and release valve assembly 634. As such, measurement valve assembly 610 may be activated via shape memory actuator 632. Once measurement valve assembly 610 has been activated, bracket assembly 656 may automatically latch valve assembly 610 in the activated position. Actuating shape memory actuator 652 may pull bracket assembly 656 forward and release valve assembly 634. Assuming shape memory actuator 632 is no longer activated, measurement valve assembly 610 may move to a de-activated state once bracket assembly 656 has released valve assembly 634. Accordingly, by actuating shape memory actuator 652, measurement valve assembly 610 may be deactivated.

Once actuation of shape memory actuator 652 is complete, command processor 1802 may provide 1964 a "power off" message to supervisor processor 1800. Upon receiving 1966 the "power off" message, supervisor processor 1800 may deenergize 1968 relay/switch 1810 and may provide 1970 a "power off" message to command processor 1802. Upon receiving 1972 the "power off" message, command processor 1802 may determine the quantity of infusible fluid within volume sensor chamber 620, thus allowing command processor 1802 to compare this measured quantity to the quantity determined above (in step 1924) to determine 1974 the quantity of infusible fluid delivered to the user.

In the event that the quantity of infusible fluid delivered 1974 to the user is less than the quantity of infusible fluid specified for the basal/bolus infusion event, the above-described procedure may be repeated (via loop 1976).

Figure 118:
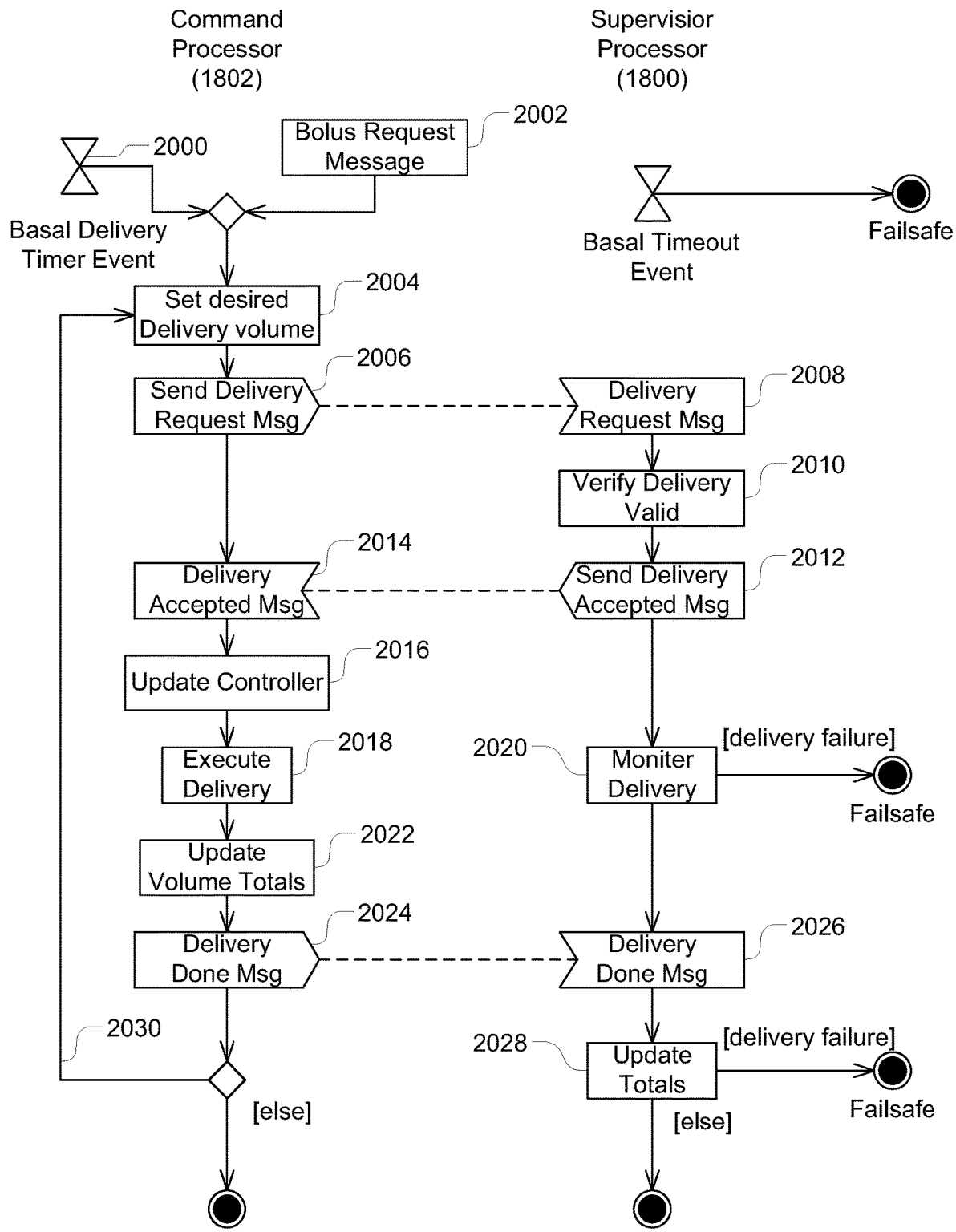
FIG. 118 diagrammatically depicts multi-processor functionality.

Referring also to FIG. 118, there is shown another illustrative example of the interaction amongst processors 1800, 1802, this time during the scheduling of a dose of infusible fluid. Command processor 1802 may monitor 2000, 2002 for the receipt of a basal scheduling message or a bolus request message (respectively). Upon receipt 2000, 2002 of either of these messages, command processor 1802 may set 2004 the desired delivery volume and may provide 2006 a "delivery request" message to supervisor processor 1800. Upon receiving 2008 the "delivery request" message, supervisor processor 1800 may verify 2010 the volume defined 2004 by command processor 1802. Once verified 2010, supervisor processor 1800 may provide 2012 a "delivery accepted" message to command processor 1802. Upon receipt 2014 of the "delivery accepted" message, command processor 1802 may update 2016 the controller (e.g., the controller discussed above and illustrated in FIG. 110) and execute 2018 delivery of the basal/bolus dose of infusible fluid. Command processor 1808 may monitor and update 2022 the total quantity of infusible fluid delivered to the user (as discussed above and illustrated in FIGS. 117A-117B). Once the appropriate quantity of infusible fluid is delivered to the user, command processor 1802 may provide 2024 a "delivery done" message to supervisor processor 1800. Upon receipt 2026 of the "delivery done" message, supervisor processor 1800 may update 2028 the total quantity of infusible fluid delivered to the user. In the event that the total quantity of infusible fluid delivered 2018 to the user is less than the quantity defined above (in step 2004), the infusion process discussed above may be repeated (via loop 2030).

Figure 119:
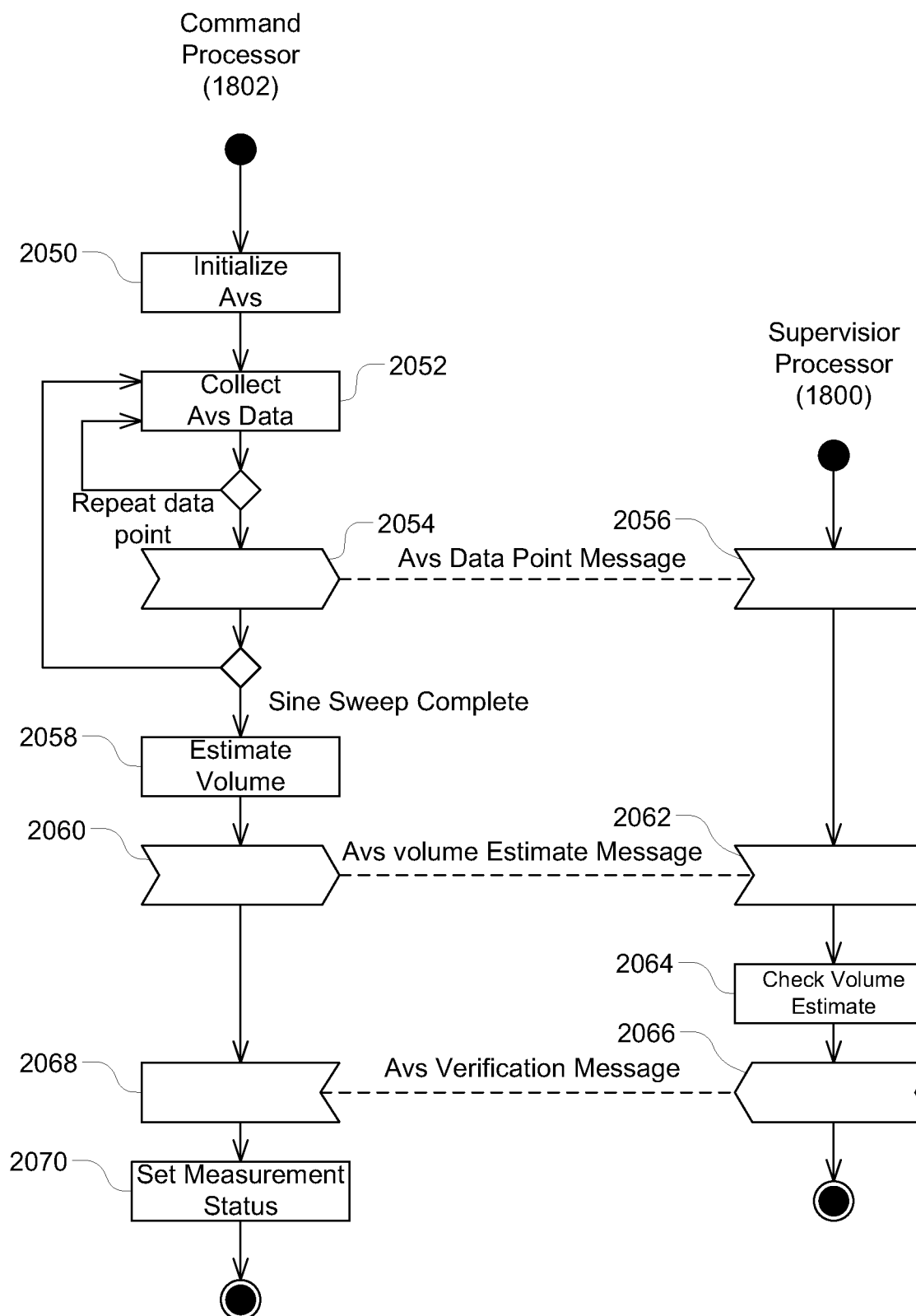
FIG. 119 diagrammatically depicts multi-processor functionality.

Referring also to FIG. 119, there is shown an example of the manner in which supervisor processor 1800 and command processor 1802 may interact while effectuating a volume measurements via volume sensor assembly 148 (as described above).

Specifically, command processor 1802 may initialize 2050 volume sensor assembly 148 and begin collecting 2052 data from volume sensor assembly 148, the process of which may be repeated for each frequency utilized in the above-described sine sweep. Each time that data is collected for a particular sweep frequency, a data point message may be provided 2054 from command processor 1802, which may be received 2056 by supervisor processor 1800.

Once data collection 2052 is completed for the entire sine sweep, command processor 1802 may estimate 2058 the volume of infusible fluid delivered by infusion pump assembly 100. Command processor 1802 may provide 2060 a volume estimate message to supervisor processor 1800. Upon receiving 2062 this volume estimate message, supervisor processor 1800 may check (i.e., confirm) 2064 the volume estimate message. Once checked (i.e., confirmed), supervisor processor 1800 may provide 2066 a verification message to command processor 1802. Once received 2068 from supervisor processor 1800, command processor 1802 may set the measurement status for the dose of infusible fluid delivered by volume sensor assembly 148.

As discussed above and referring temporarily to FIG. 11), the various embodiments of the infusion pump assembly (e.g., infusion pump assembly 100, 100', 400, 500) discussed above may be configured via a remote control assembly 300. When configurable via remote control assembly 300, the infusion pump assembly may include telemetry circuitry (not shown) that allows for communication (e.g., wired or wireless) between the infusion pump assembly and e.g., remote control assembly 300, thus allowing remote control assembly 300 to remotely control the infusion pump assembly. Remote control assembly 300 (which may also include telemetry circuitry (not shown) and may be capable of communicating with the infusion pump assembly) may include display assembly 302 and input assembly 304. Input assembly 304 may include slider assembly 306 and switch assemblies 308, 310. In other embodiments, the input assembly may include a jog wheel, a plurality of switch assemblies, or the like. Remote control assembly 300 may allow the user to program basal and bolus delivery events.

Remote control assembly 300 may include two processors, one processor (e.g., which may include, but is not limited to a CC2510 microcontroller/RF transceiver, available from Chipcon AS, of Oslo, Norway) may be dedicated to radio communication, e.g., for communicating with infusion pump assembly 100, 100', 400, 500. The second processor included within remote control assembly (which may include but are not limited to an ARM920T and an ARM922T manufactured by ARM Holdings PLC of the United Kingdom) may be a command processor and may perform data processing tasks associated with e.g., configuring infusion pump assembly 100, 100', 400, 500.

Further and as discussed above, one embodiment of electrical control assembly 816 may include three microprocessors. One processor (e.g., which may include, but is not limited to a CC2510 microcontroller/RF transceiver, available from Chipcon AS, of Oslo, Norway) may be dedicated to radio communication, e.g., for communicating with a remote control assembly 300. Two additional microprocessors (e.g., supervisor processor 1800 and command processor 1802) may effectuate the delivery of the infusible fluid (as discussed above). Examples of supervisor processor 1800 and command processor 1802 may include, but is not limited to an MSP430 microcontroller, available from Texas Instruments Inc. of Dallas, Tex.

The OS may be a non-preemptive scheduling system, in that all tasks may run to completion before the next task is allowed to run regardless of priority. Additionally, context switches may not be performed. When a task completes executing, the highest priority task that is currently scheduled to run may then be executed. If no tasks are scheduled to execute, the OS may place the processor (e.g., supervisor processor 1800 and/or command processor 1802) into a low power sleep mode and may wake when the next task is scheduled. The OS may only be used to manage main loop code and may leave interrupt-based functionality unaffected.

The OS may be written to take advantage of the C++ language. Inheritance as well as virtual functions may be key elements of the design, allowing for easy creation, scheduling and managing of tasks.

At the base of the OS infrastructure may be the ability to keep track of system time and controlling the ability to place the processor in Low Power Mode (LPM; also known as sleep mode). This functionality along with the control and configuration of all system clocks may be encapsulated by the SysClocks class.

The SysClocks class may contain the functionality to place the processor (e.g., supervisor processor 1800 and/or command processor 1802) into LPM to reduce energy consumption. While in LPM, the slow real time clock may continue to run while the fast system clock that runs the CPU core and most peripherals may be disabled.

Placing the processor into LPM may always be done by the provided SysClocks function. This function may contain all required power down and power up sequences resulting in consistency whenever entering or exiting LPM. Waking from LPM may be initiated by any interrupts based on the slow clock.

The OS may keep track of three aspects of time: seconds, milliseconds and the time of day. Concerning seconds, SysClocks may count seconds starting when the processor comes out of reset. The second counter may be based on the slow system clocks and, therefore, may increment regardless of whether the processor is in LPM or at full power. As a result, it is the boundary at which the processor may wake from sleep to execute previously scheduled tasks. If a task is scheduled to run immediately from an interrupt service routine (ISR), the ISR may wake the processor from LPM on exit and the task may be executed immediately. Concerning milliseconds, in addition to counting the seconds since power on, SysClocks may also count milliseconds while the processor is in full power mode. Since the fast clock is stopped during LPM, the millisecond counter may not increment. Accordingly, whenever a task is scheduled to execute based on milliseconds, the processor may not enter LPM. Concerning time of day, the time of day may be represented within SysClocks as seconds since a particular point time (e.g., seconds since 1 Jan. 2004).

The SysClocks class may provide useful functionality to be used throughout the Command and Supervisor project code base. The code delays may be necessary to allow hardware to settle or actions to be completed. SysClocks may provide two forms of delays, a delay based on seconds or a delay based on milliseconds. When a delay is used, the processor may simply wait until the desired time has passed before continue with its current code path. Only ISRs may be executed during this time. SysClocks may provide all of the required functionality to set or retrieve the current time of day.

The word "task" may be associated with more complex scheduling systems; therefore within the OS, task may be represented by and referred to as Managed Functions. The ManagedFunc class may be an abstract base class that provides all the necessary control members and functionality to manage and schedule the desired functionality.

The ManagedFunc base class may have five control members, two scheduling manipulation member functions, and one pure virtual execute function that may contain the managed functionality. All of the ManagedFunc control members may be hidden from the derived class and may only be directly set by the derived class during creation, thus simplifying the use and enhancing the safety of infusion pump assembly 100, 100', 400, 500.

The Function ID may be set at the time of creation and may never be changed. All Function IDs may be defined within a single .h file, and the base ManagedFunc constructor may strongly enforce that the same ID may not be used for more than one managed function. The ID may also define the priority of a function (with respect to other functions) based upon the function ID assigned, wherein higher priority functions are assigned lower function IDs. The highest priority task that is currently scheduled to execute may execute before lower priority tasks.

All other control members may be used to represent the function's current scheduled state, when it should be executed, and if (upon execution) the function should be rescheduled to execute in a previously set amount of time. Manipulation of these controls and states may be allowed but only through the public member functions (thus enforcing safety controls on all settings).

To control the scheduling of a managed function, the set start and set repeat functions may be used. Each of these member functions may be a simple interface allowing the ability to configure or disable repeat settings as well as control whether a managed function is inactive, scheduled by seconds, milliseconds, or time of day.

Through inheritance, creating a Managed Function may be done by creating a derived class and defining the pure virtual 'execute' function containing the code that needs to be under scheduling control. The ManagedFunc base class constructor may be based upon the unique ID of a function, but may also be used to set default control values to be used at start up.

For example to create a function that runs thirty seconds after start up and every 15 seconds thereafter, the desired code is placed into the virtual execute function and the function ID, scheduled by second state, thirty second start time, and repeat setting of fifteen seconds is provided to the constructor.

The following is an illustrative code example concerning the creation of a managed function. In this particular example, a "heartbeat" function is created that is scheduled to execute for the first time one second after startup of infusion pump assembly 100, 100', 400, 500 and execute every ten seconds thereafter:

```
#include "ManagedFunc.h"
// The SendGoodFunc is a "heartbeat" status message
class SendGoodFunc : public ManagedFunc
{
public:
   // Initialize the managed func to run 2 seconds
   after start up
   // and repeat every second.
   SendGoodFunc( ) :
      ManagedFunc(IPC_SEND_GOOD, SCHEDULED_SEC, 1,
      true, 10) { };
   ~SendGoodFunc( ) { };
   protected:
      void execute(void);
};
void SendGoodFunc::execute(void)
{
   // << code to send the heartbeat >>
}
SendGoodFunc g_sendGoodFunc;
// to manipulate the heartbeat timing simply call:
//   g_sendGoodFunc.setFuncStart(...)              or
g_sendGoodFunc.setRepeat( ... )
```

The actual execution of the Managed Functions may be controlled and performed by the SleepManager class. The SleepManager may contain the actual prioritized list of managed functions. This prioritized list of functions may automatically be populated by the managed function creation process and may ensure that each function is created properly and has a unique ID.

The main role of the SleepManager class may be to have its 'manage' function called repeatedly from the processors main loop and/or from a endless while loop. Upon each call of manage, the SleepManager may execute all functions that are scheduled to run until the SleepManager has exhausted all scheduled functions; at which time the SleepManager may place the processor in LPM. Once the processor wakes from LPM, the manage function may be reentered until the processor is again ready to enter LPM (this process may be repeated until stopped, e.g., by a user or by the system).

If the processor has to be kept in full power mode for an extended period of time (e.g., while an analog-to-digital conversion is being sampled), the SleepManager may provide functionality to disable entering LPM. While LPM is disabled, the manage function may continuously search for a scheduled task.

The SleepManager may also provide an interface to manipulate the scheduling and repeat settings of any managed function through the use of the unique ID of the function, which may allow any section of code to perform any required scheduling without having direct access to or unnecessary knowledge of the desired ManagedFunc object.

Radio circuitry included within each of infusion pump assembly 100, 100', 400, 500 and remote control assembly 300 may effectuate wireless communication between remote control assembly 300 and infusion pump assembly 100, 100', 400, 500. A 2.4 GHz radio communications chip (e.g., a Texas Instruments CC2510 radio transceiver) with an internal 8051 microcontroller may be used for radio communications.

The radio link may balance the following three objectives: link availability; latency; and energy.

Concerning link availability, remote control assembly 300 may provide the primary means for controlling the infusion pump assembly 100, 100', 400, 500 and may provide detailed feedback to the user via the graphical user interface (GUI) of remote control assembly 300. Concerning latency, the communications system may be designed to provide for low latency to deliver data from remote control assembly 300 to the infusion pump assembly 100, 100', 400, 500 (and vice versa). Concerning energy, both remote control assembly 300 and infusion pump assembly 100, 100', 400, 500 may have a maximum energy expenditure for radio communications.

The radio link may support half-duplex communications. Remote control assembly 300 may be the master of the radio link, initiating all communications. Infusion pump assembly 100, 100', 400, 500 may only respond to communications and may never initiate communications. The use of such a radio communication system may provide various benefits, such as: increased security: a simplified design (e.g., for airplane use); and coordinated control of the radio link.

Figure 120A:
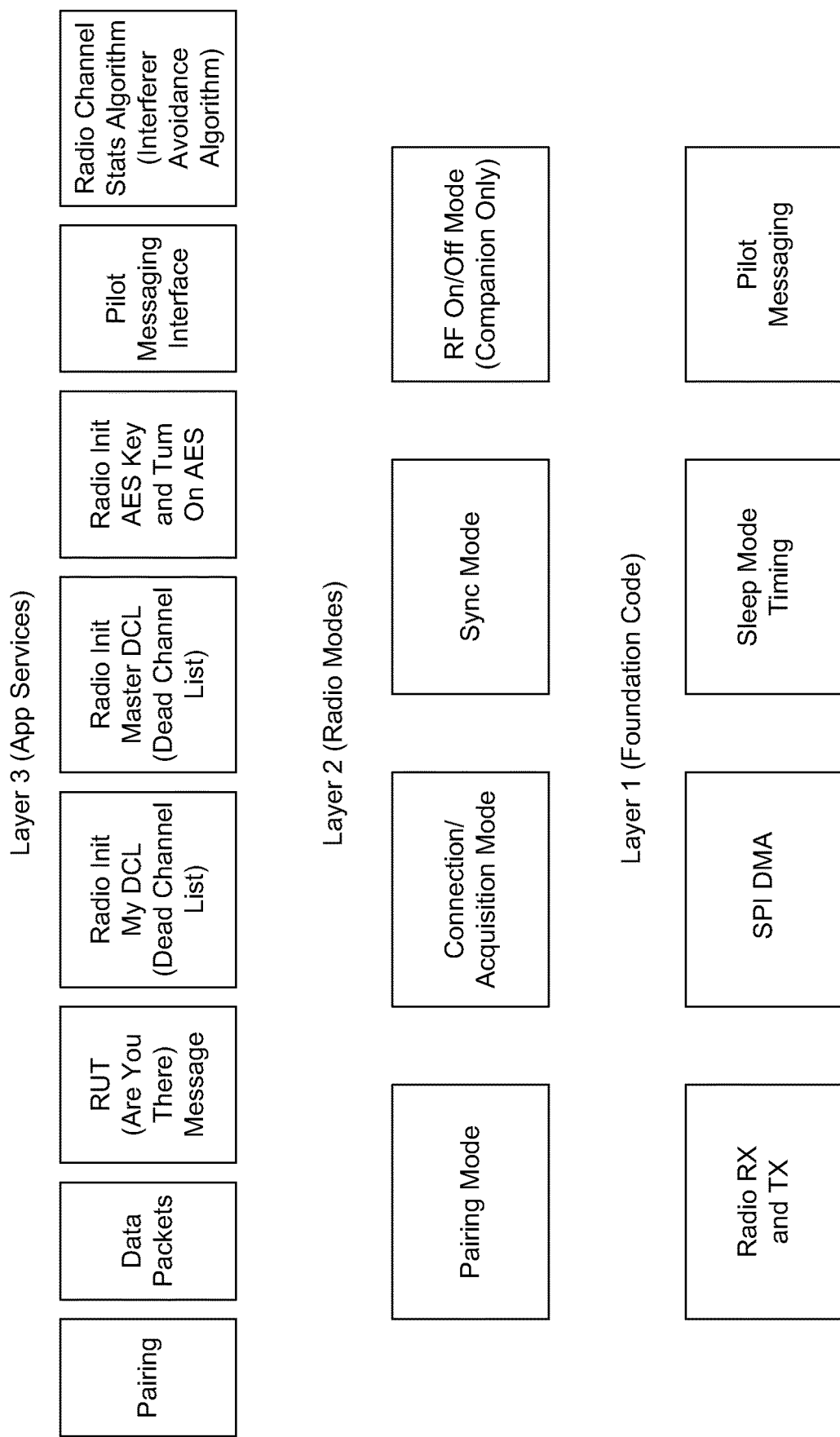
FIG. 120A graphically depicts various software layers; 120B-120C depict various state diagrams;
120D graphically depicts device interaction;
120E graphically depicts device interaction.

Referring also to FIG. 120A, there is shown one illustrative example of the various software layers of the radio communication system discussed above. The radio processors included within remote control assembly 300 and infusion pump assembly 100, 100', 400, 500 may transfer messaging packets between an SPI port and a 2.4 GHz radio link (and vice versa). The radio may always be the SPI slave. On infusion pump assembly 100, 100', 400, 500, radio processor (PRP) 1818 (See FIGS. 115-116) may service two additional nodes over the SPI port that are upstream (namely command processor 1800 and supervisor processor 1802. In some embodiments, on remote control assembly 300, the radio processor (CRP) may service at least one additional node over the SPI port that may be either upstream or down stream, for example, in some embodiments, the above-described remote control processor (UI) and the Continuous Glucose Engine (CGE).

A messaging system may allow for communication of messages between various nodes in the network. The UI processor of remote control assembly 300 and e.g., supervisor processor 1800 may use the messaging system to configure and initiate some of the mode switching on the two system radios. It may be also used by the radios to convey radio and link status information to other nodes in the network.

When the radio of remote control assembly 300 wishes to gather channel statistics from the infusion pump assembly 100, 100', 400, 500 or update the master channel list of the radio of infusion pump assembly 100, 100', 400, 500, the radio of remote control assembly 300 may use system messages. Synchronization for putting the new updated list into effect may use indicators in the heartbeat messages to remove timing uncertainty.

The radio communication system may be written in C++ to be compatible with the messaging software. A four byte radio serial number may be used to address each radio node. A hash table may be used to provide a one-to-one translation between the device "readable" serial number string and the radio serial number. The hash table may provide a more randomized 8-bit logical address so that pumps (e.g., infusion pump assembly 100, 100', 400, 500) or controllers with similar readable serial numbers are more likely to have unique logical addresses. Radio serial numbers may not have to be unique between pumps (e.g., infusion pump assembly 100, 100', 400, 500) and controllers due to the unique roles each has in the radio protocol.

The radio serial number of remote control assembly 300 and the radio serial number of infusion pump assembly 100, 100', 400, 500 may be included in all radio packets except for the RF Pairing Request message that may only include the radio serial number of remote control assembly 300, thus ensuring that only occur with the remote control assembly/infusion pump assembly to which it is paired. The CC2510 may support a one byte logical node address and it may be advantageous to use one byte of the radio serial number as the logical node address to provide a level of filtering for incoming packets.

The Quiet_Radio signal may be used by the UI processor of remote control assembly 300 to prevent noise interference on the board of remote control assembly 300 by other systems on the board. When Quiet_Radio is asserted, the radio application of remote control assembly 300 may send a message to the radio of infusion pump assembly 100, 100', 400, 500 asserting Radio Quiet Mode for a pre-determined period of time. The Quiet_Radio feature may not be required based on noise interference levels measured on the PC board of remote control assembly 300. During this period of time, the radio of remote control assembly 300 may stay in Sleep Mode 2 for up to a maximum of 100 ms. The radio of remote control assembly 300 may come out of Sleep Mode 2 when the Quiet_Radio signal is de-asserted or the maximum time period has expired. The UI processor of remote control assembly 300 may assert Quiet_Radio at least one radio communication's interval before the event needs to be asserted. The radio of remote control assembly 300 may inform the radio of infusion pump assembly 100, 100', 400, 500 that communications will be shutdown during this quiet period. The periodic radio link protocol may have status bits/bytes that accommodate the Quiet_Radio feature unless Quiet_Radio is not required.

The radio software may integrate with the messaging system and radio bootloader on the same processor, and may be verified using a throughput test. The radio software may integrate with the messaging system, SPI Driver using DMA, and radio bootloader, all on the same processor (e.g., the TI CC2510).

The radio of remote control assembly 300 may be configured to consume no more than 32 mAh in three days (assuming one hundred minutes of fast heartbeat mode communications per day). The radio of infusion pump assembly 100, 100', 400, 500 may be configured to consume no more than 25 mAh in three days (assuming one hundred minutes of fast heartbeat mode communications per day).

The maximum time to reacquire communications may be ≤6.1 seconds including connection request mode and acquisition mode. The radio of remote control assembly 300 may use the fast heartbeat mode or slow heartbeat mode setting to its advantage in order to conserve power and minimize latency to the user. The difference between the infusion pump assembly 100, 100', 400, 500 and remote control assembly 300 entering acquisition mode may be that the infusion pump assembly 100, 100', 400, 500 needs to enter acquisition mode often enough to ensure communications may be restored within the maximum latency period. However, the remote control assembly 300 may change how often to enter acquisition mode with the infusion pump assembly 100, 100', 400, 500 when in slow heartbeat mode and heartbeats are lost. The radio of remote control assembly 300 may have knowledge of the user GUI interaction, but the infusion pump assembly 100, 100', 400, 500 may not.

The radio of remote control assembly 300 may set the heartbeat period for both radios. The period may be selectable in order to optimize power and link latency depending on activity. The desired heartbeat period may be communicated in each heartbeat from the radio of remote control assembly 300 to the radio of infusion pump assembly 100, 100', 400, 500. This may not exclusively establish the heartbeat rate of infusion pump assembly 100, 100', 400, 500 due to other conditions that determine what mode to be in. When in fast heartbeat mode, the radio of remote control assembly 300 may set the heartbeat period to 20 ms if data packets are available to send or receive, thus providing low link latency communications when data is actively being exchanged.

When in fast heartbeat mode, the radio of remote control assembly 300 may set the heartbeat period to 60 ms four heartbeats after a data packet was last exchanged in either direction on the radio. Keeping the radio heartbeat period short after a data packet has been sent or received may assure that any data response packet may be also serviced using a low link latency. When in slow heartbeat mode, the heartbeat rate may be 2.00 seconds or 6.00 second, depending upon online or offline status respectively.

The infusion pump assembly 100, 100', 400, 500 may use the heartbeat rate set by the radio of remote control assembly 300. The radio of remote control assembly 300 may support the following mode requests via the messaging system:
Pairing Mode
Connection Mode
Acquisition Mode (includes the desired paired infusion pump assembly 100, 100', 400, 500 radio serial number)
Sync Mode—Fast Heartbeat
Sync Mode—Slow Heartbeat
RF Off Mode The radio of infusion pump assembly 100, 100', 400, 500 may support the following mode requests via the messaging system:
Pairing Mode
Acquisition Mode
RF Off Mode The radio may use a system message to obtain the local radio serial number. On remote control assembly 300, the radio may get the serial number from the UI processor of remote control assembly 300. The radio may use a system message to store the paired radio serial number.

Remote control assembly 300 and the radio of infusion pump assembly 100, 100', 400, 500 may issue a status message using the messaging system to the UI processor of remote control assembly 300 and command processor 1802 whenever the following status changes:
Online Fast: Successful connection
Online Fast: Change from Acquisition Mode to Fast Heartbeat Mode
Online Slow: Successful request change from Fast Heartbeat to Slow Heartbeat
Offline: Automatic change to Search Sync mode due to lack of heartbeat exchanges.
Online Fast: Successful request change from Slow Heartbeat to Fast Heartbeat
Offline: Bandwidth falls below 10% in Sync Mode
Online: Bandwidth rises above 10% in Search Sync mode
Offline: Successful request change to RF Off Mode The radio configuration message may be used to configure the number of radio retries. This message may be sent over the messaging system. The UI processor of remote control assembly 300 will send this command to both the radio of remote control assembly 300 and the radio of infusion pump assembly 100, 100', 400, 500 to configure these radio settings.

There may be two parameters in the radio configuration message: namely the number of RF retries (e.g., the value may be from 0 to 10); and the radio offline parameters (e.g., the value may be from 1 to 100 in percent of bandwidth).

The radio application on both the remote control assembly 300 and infusion pump assembly 100, 100', 400, 500 may have an API that allows the messaging system to configure the number of RF retries and radio offline parameters.

The following parameters may be recommended for the radio hardware configuration:
Base Radio Specifications
MSK
250 kbps over air baud rate
Up to 84 channels
Channel spacing 1000 kHz
Filter bandwidth 812 kHz
No Manchester encoding
Data whitening
4 byte preamble
4 byte sync (word)
CRC appended to packet
LQI (Link Quality Indicator) appended to packet
Automatic CRC filtering enabled
Forward Error Correction (FEC) may or may not be utilized. Although Forward Error Correction (FEC) may be used to increase the effective signal dynamic range by approximately 3 dB, FEC requires fixed packet sizes and doubles the number of over the air bits for the same fixed size message.

The radio may function within 1.83 meters distance under nominal operating conditions (except in pairing mode). It may be a goal that the radio function within 7.32 meters distance under nominal operating conditions. The transmit power level may be 0 dBm (except in pairing mode) and the transmit power level in pairing mode may be −22 dBm. Since the desired radio node address of infusion pump assembly 100, 100', 400, 500 may be not known by the remote control assembly 300 in pairing mode, both infusion pump assembly 100, 100', 400, 500 and remote control assembly 300 may use a lower transmit power to reduce the likelihood of inadvertently pairing with another infusion pump assembly.

AES Encryption may be used for all packets but may not be required, as the Texas Instruments CC2510 radio transceiver includes this functionality. If AES encryption is used, fixed keys may be utilized, as fixed keys provide a quick way to enable encryption without passing keys. However, key exchange may be provided for in future versions of infusion pump assembly 100, 100', 400, 500. The fixed keys may be contained in one separate header source file with no other variables but the fixed keys data, thus allowing for easier management of read access of the file.

Figure 120B:
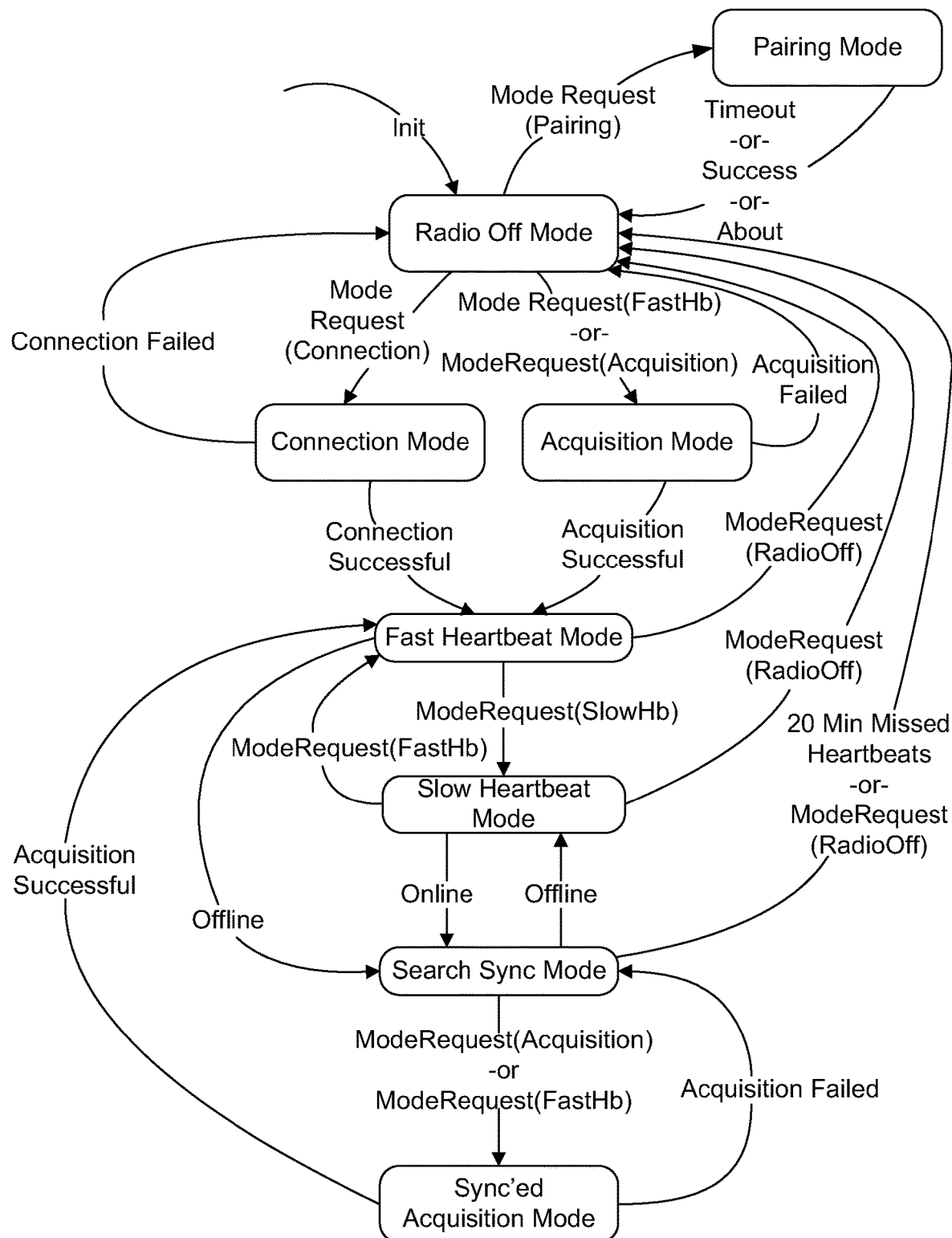
Figure 120C:
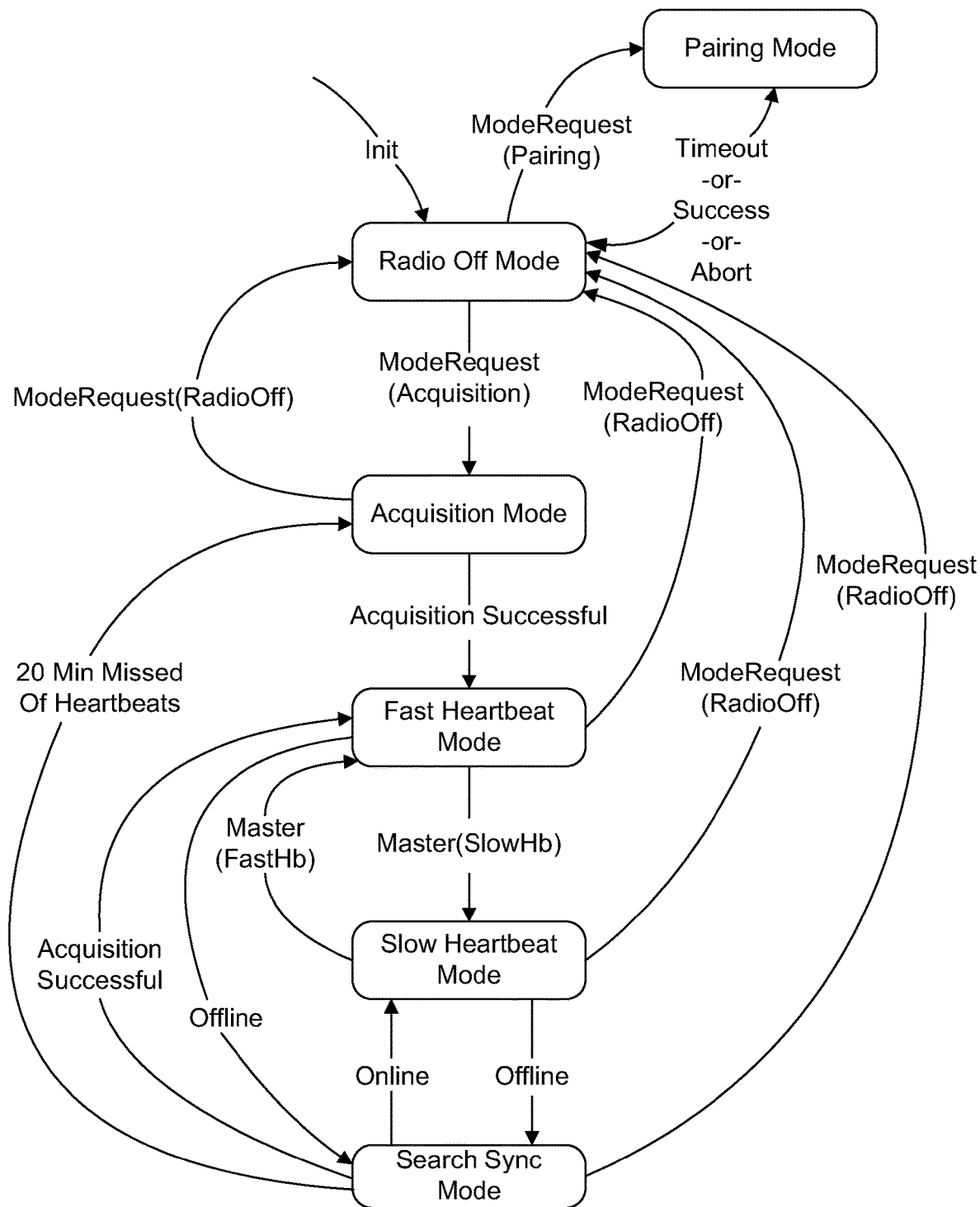

The radio software may support the following eight modes:
Pairing Mode
RF Off Mode
Connection Mode
Acquisition Mode
Fast Heartbeat Mode
Slow Heartbeat Mode
Search Sync Mode
Sync'ed Acquisition Mode
which are graphically depicted in FIGS. 120B-120C.

Pairing may be the process of exchanging radio serial numbers between remote control assembly 300 and infusion pump assembly 100, 100', 400, 500. Remote control assembly 300 may be "paired" with infusion pump assembly 100, 100', 400, 500 when infusion pump assembly 100, 100', 400, 500 knows its serial number. Infusion pump assembly 100, 100', 400, 500 may be "paired" with remote control assembly 300 when remote control assembly 300 knows its serial number.

Figure 120D:
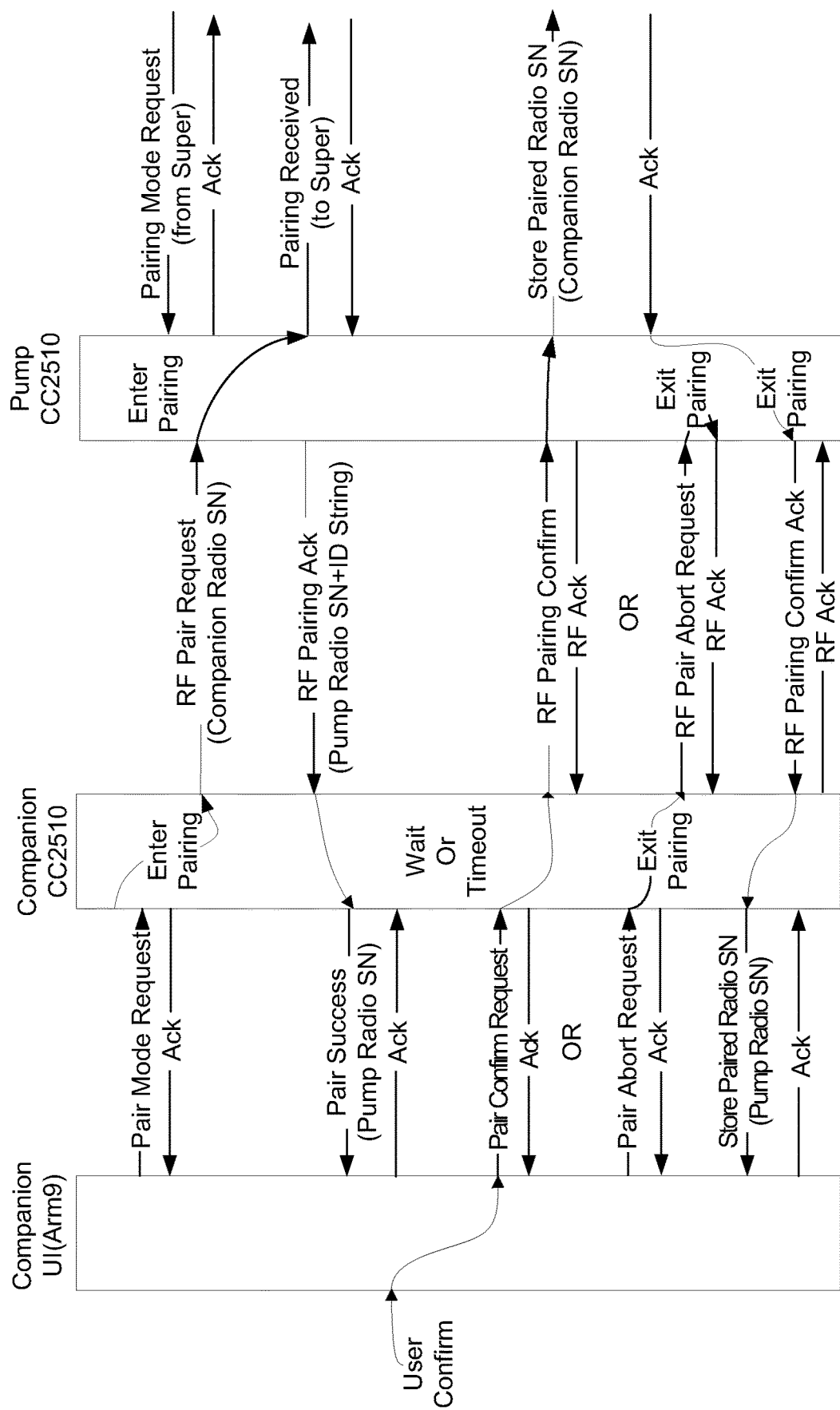

Pairing mode (which is graphically depicted in FIG. 120D) may require that four messages to be exchanged over the RF link:
RF Pairing Request (broadcast from Remote control assembly 300 to any Infusion pump assembly 100, 100', 400, 500)
RF Pairing Acknowledge (from Infusion pump assembly 100, 100', 400, 500 to Remote control assembly 300)
RF Pairing Confirm Request (from Remote control assembly 300 to Infusion pump assembly 100, 100', 400, 500)
RF Pairing Confirm Acknowledge (from Infusion pump assembly 100, 100', 400, 500 to Remote control assembly 300)

Additionally, remote control assembly 300 may cancel the pairing process at any time via the RF pairing abort message (from remote control assembly 300 to infusion pump assembly 100, 100', 400, 500. Pairing mode may not support messaging system data transfers.

The radio of infusion pump assembly 100, 100', 400, 500 may enter pairing mode upon receiving a pairing mode request message. It may be the responsibility of supervisor processor 1800 on infusion pump assembly 100, 100', 400, 500 to request the radio to enter pairing mode if there is no disposable attached to infusion pump assembly 100, 100', 400, 500 and the user has pressed the button of infusion pump assembly 100, 100', 400, 500 for six seconds. The radio of infusion pump assembly 100, 100', 400, 500 may set the appropriate transmit power level for pairing mode. Infusion pump assembly 100, 100', 400, 500 may only be paired with one remote control assembly 300 at a time.

Upon receiving the first valid RF pairing request message while in pairing mode, the radio of infusion pump assembly 100, 100', 400, 500 may use the serial number of remote control assembly 300 for the duration of pairing mode and respond with an RF pairing acknowledge message containing the radio serial number infusion pump assembly 100, 100', 400, 500.

The radio of infusion pump assembly 100, 100', 400, 500 may timeout of pairing mode automatically after 2.0±0.2 seconds if no RF pairing request is received. The radio of infusion pump assembly 100, 100', 400, 500 may issue a pairing request received message after transmitting the RF pairing acknowledge. This message to supervisor processors will allow feedback to the user during the pairing confirm process. The radio of infusion pump assembly 100, 100', 400, 500 may automatically timeout of pairing mode in 1.0±0.1 minutes after sending an RF pairing acknowledge unless an RF pairing confirm request is received. The radio of infusion pump assembly 100, 100', 400, 500 may issue a store paired radio serial number message if an RF pairing confirm request message is received after receiving a RF pairing request message. This action may store the radio serial number of remote control assembly 300 in the non-volatile memory of infusion pump assembly 100, 100', 400, 500 and may overwrite the existing pairing data for the infusion pump assembly 100, 100', 400, 500.

The radio of infusion pump assembly 100, 100', 400, 500 may transmit an RF pairing confirm acknowledge and exit pairing mode after the acknowledgment from the store paired radio serial number message is received. This may be the normal exit of pairing mode on infusion pump assembly 100, 100', 400, 500 and may result in infusion pump assembly 100, 100', 400, 500 powering down until connection mode or paring mode entered by the user.

If the radio of infusion pump assembly 100, 100', 400, 500 exits pairing mode upon successfully receiving a pairing confirm request message, then the radio of infusion pump assembly 100, 100', 400, 500 may revert to the newly paired remote control assembly 300 and may send a pairing completion success message to command processor 1802. The radio of infusion pump assembly 100, 100', 400, 500 may exit pairing mode upon receiving an RF pairing abort message. The radio of infusion pump assembly 100, 100', 400, 500 may exit pairing mode upon receiving a pairing abort request message addressed to it. This may allow command processor 1802 or supervisor processor 1800 to abort the pairing process locally on the infusion pump assembly 100, 100', 400, 500.

The radio of remote control assembly 300 may enter pairing mode upon receiving a pairing mode request message. It may be the responsibility of the UI processor of remote control assembly 300 to request that the radio enter pairing mode under the appropriate conditions. The radio of remote control assembly 300 may set the appropriate transmit power level for pairing mode. The radio of remote control assembly 300 may transmit RF pairing requests until an RF pairing acknowledge is received or pairing is aborted.

The radio of remote control assembly 300 may automatically abort pairing mode if the RF pairing acknowledge message is not received within 30.0±1.0 seconds after entering pairing mode. Upon receiving the first valid RF pairing acknowledge message while in pairing mode, the radio of remote control assembly 300 may send a pairing success message to the UI processor of remote control assembly 300 that includes the serial number of infusion pump assembly 100, 100', 400, 500 and may use that serial number for the duration of pairing mode. This message may provide a means for the UI processor of remote control assembly 300 to have the user confirm the serial number of the desired infusion pump assembly 100, 100', 400, 500. If the radio of remote control assembly 300 receives multiple responses (concerning a single pairing request) from infusion pump assembly 100, 100', 400, 500, the first valid one may be used.

The Radio of remote control assembly 300 may only accept an RF pairing confirm acknowledge messages after an RF pairing acknowledge is received while in pairing mode. The radio of remote control assembly 300 may transmit the RF pairing confirm message upon receiving a pair confirm request message from the UI processor of remote control assembly 300.

The radio of remote control assembly 300 may check that infusion pump assembly 100, 100', 400, 500 confirms the pairing before adding infusion pump assembly 100, 100', 400, 500 to the pairing list. The radio of remote control assembly 300 may issue a store paired radio serial number message if an RF pairing complete message is received. This action may allow the UI processor of remote control assembly 300 to store the new serial number of infusion pump assembly 100, 100', 400, 500 and provide user feedback of a successful pairing. It may be the responsibility of the UI processor of remote control assembly 300 to manage the list of paired infusion pump assemblies.

The radio of remote control assembly 300 may send an RF pairing abort message and exit pairing mode upon receiving a pairing abort request message. This may allow the UI processor of the remote control assembly 300 to abort the pairing process on both the remote control assembly 300 and acknowledged infusion pump assembly 100, 100', 400, 500.

Figure 120E:
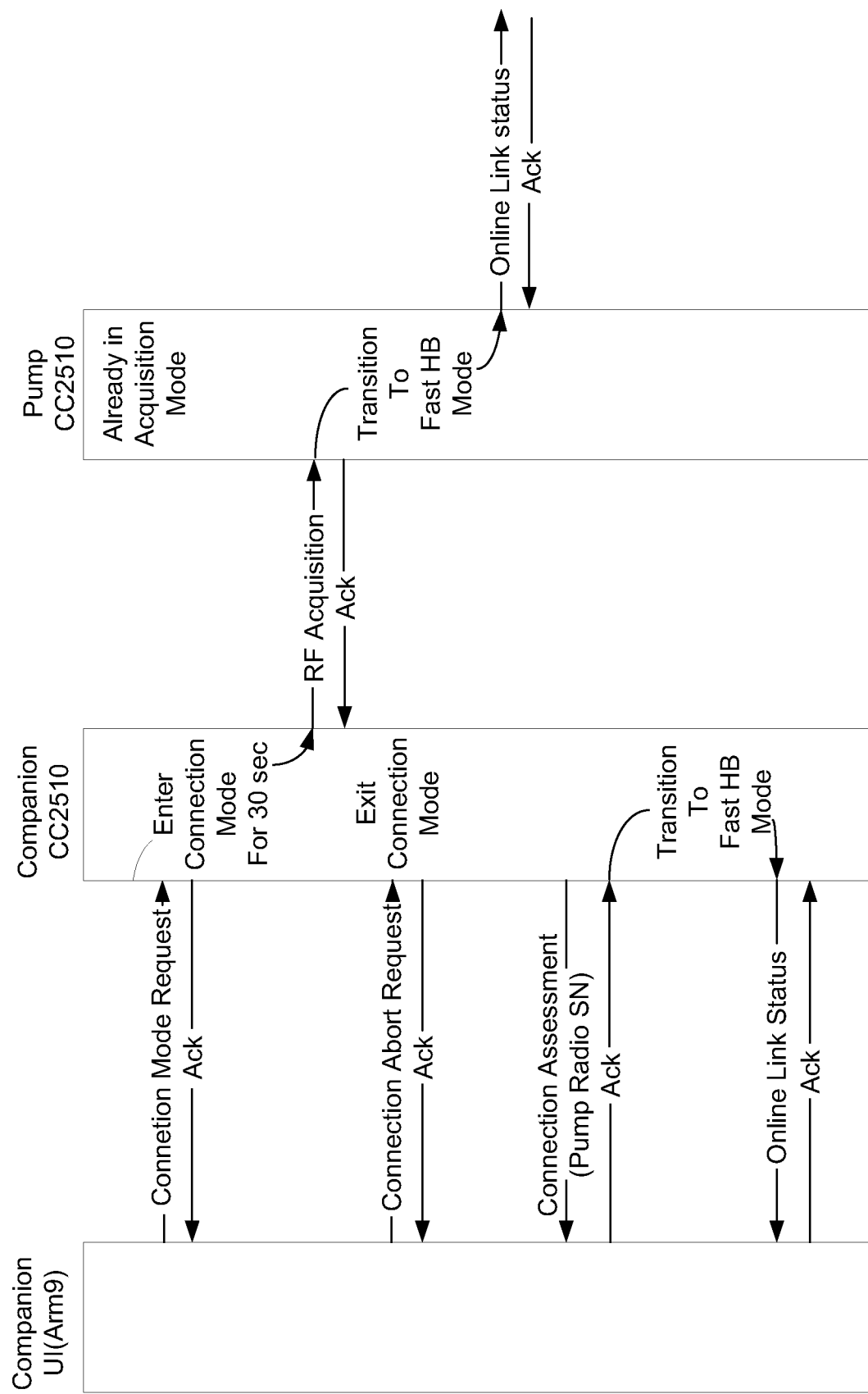

In connection request mode, the radio of remote control assembly 300 may attempt to acquire each infusion pump assembly 100, 100', 400, 500 in its paired infusion pump assembly list and retrieve its "connection ready" status. The "connection" process (which is graphically depicted in FIG. 120E) may allow remote control assembly 300 to quickly identify one of its paired infusion pump assemblies that may be ready to be used. The radio of remote control assembly 300 may be capable of performing the connection request mode with up to six paired infusion pump assemblies. Connection request mode may be only supported on remote control assembly 300 and may be a special form of acquisition mode. In connection request mode, remote control assembly 300 may connect with the first infusion pump assembly to respond. However, each message may be directed to a specific infusion pump assembly serial number.

The radio of remote control assembly 300 may obtain the latest paired infusion pump assembly serial number list upon entering connection mode. The radio of remote control assembly 300 may enter connection mode upon receiving a connection mode request message. It may be the responsibility of the UI processor of remote control assembly 300 to request that the radio enter connection mode when it desires communications with a paired infusion pump assembly. The radio of remote control assembly 300 may issue a connection assessment message to the UI processor of remote control assembly 300 containing the radio serial number of the first infusion pump assembly, if any, that is "connection ready". The radio of remote control assembly 300 may generate the connection assessment message within thirty seconds of entering connection request mode. The radio of remote control assembly 300 may exit connection request mode upon receipt of the connection assessment acknowledgement and transition to fast heartbeat mode. The radio of remote control assembly 300 may exit connection request mode upon receipt of a connection request abort message from the UI processor of remote control assembly 300.

On remote control assembly 300, acquisition mode may be used to find a particular paired infusion pump assembly. The radio of remote control assembly 300 may send RF RUT (aRe yoU There) packets to the desired paired infusion pump assembly. If the infusion pump assembly receives the RF RUT message, it may respond to the radio of remote control assembly 300. Multiple channels may be used in the acquisition mode algorithm to improve the opportunity for the radio of remote control assembly 300 to find the paired infusion pump assembly.

The radio of remote control assembly 300 may enter acquisition mode upon receiving an acquisition mode request or fast heartbeat mode request message while in RF Off Mode. The radio of remote control assembly 300 may enter sync'ed acquisition mode upon receiving an acquisition mode request or fast heartbeat mode request message while in search sync mode. It may be the responsibility of the UI processor of remote control assembly 300 to request that the radio enter acquisition mode when the RF link is off-line and remote control assembly 300 desires communications with infusion pump assembly 100, 100', 400, 500.

The radio of remote control assembly 300 may only communicate with one paired infusion pump assembly 100, 100', 400, 500 (except in pairing and connection modes). When communications are lost, the UI processor of remote control assembly 300 may use acquisition mode (at some periodic rate limited by the power budget) to attempt to restore communications.

Infusion pump assembly 100, 100', 400, 500 may enter acquisition mode under the following conditions:

When in Radio Off Mode and Acquisition Mode may be requested

When Search Sync Mode times out due to lack of heartbeats

Upon entering acquisition mode, the radio of infusion pump assembly 100, 100', 400, 500 may obtain the serial number of the last stored paired remote control assembly 300. The radio of infusion pump assembly 100, 100', 400, 500 may only communicate with the remote control assembly to which it has been "paired" (except while in the "pairing request" mode). The radio of infusion pump assembly 100, 100', 400, 500 may transition from acquisition mode to fast heartbeat mode upon successfully acquiring synchronization with the remote control assembly 300. The acquisition mode of infusion pump assembly 100, 100', 400, 500 may be capable of acquiring synchronization within 6.1 seconds, which may implies that the infusion pump assembly 100, 100', 400, 500 may always be listening at least every ~6 seconds when in acquisition mode.

Data packets may be sent between two paired devices when the two devices are in sync mode and online. The two devices may sync via a heartbeat packet before data packets are exchanged. Each radio may send data packets at known time intervals after the heartbeat exchange. The infusion pump assembly 100, 100', 400, 500 may adjust its timing to anticipate reception of a packet. The radio may support one data packet in each direction on each heartbeat. The radio may provide a negative response to a fast heartbeat mode request if the radio if offline. The radio of remote control assembly 300 may change to fast heartbeat mode if a system request for fast heartbeat mode is received while in slow heartbeat mode and the radio is online.

Upon transitioning to fast heartbeat mode from acquisition mode, the radio of remote control assembly 300 may send the master channel list message. The master channel list may be built by the radio of remote control assembly 300 and sent to the radio of infusion pump assembly 100, 100', 400, 500 to allow a selection of frequency hopping channels based on historical performance. When in fast heartbeat mode or slow heartbeat mode, periodic heartbeat messages may be exchanged between the radio of remote control assembly 300 and the radio of infusion pump assembly 100, 100', 400, 500. The periodicity of these messages may be at the heartbeat rate. The heartbeat messages may allow data packet transfers to take place and may also exchange status information. The two radios may exchange the following status information: Quiet Mode, data availability, buffer availability, heartbeat rate, and prior channel performance. It may be a goal to keep the packet size of the heartbeat messages small in order to conserve power. The radio may provide for a maximum data packet size of eighty-two bytes when in Sync Mode. The messaging system may be designed to support packet payload sizes up to sixty-four bytes. This maximum size was selected as an optimal trade-off between minimum messages types and non-fragmented messages. The eighty-two bytes may be the maximum packet size of the messaging system including packet overhead.

The messaging system has an API that may allow the radio protocol to send an incoming radio packet to it. The messaging system may also have an API that allows the radio protocol to get a packet for transmission over the radio network. The messaging system may be responsible for packet routing between the radio protocol and the SPI port. Data packets may be given to the messaging system for processing. The messaging system may have an API that allows the radio protocol to obtain a count of the number of data packets waiting to be sent over the radio network. The radio protocol may query the messaging system on each heartbeat to determine if data packets are available to send over the radio network. It may be desirable for the software to check the availability of a message just before the heartbeat is sent to minimize round trip message latency.

The radio protocol may be capable of buffering one incoming radio data packet and passing the packet to the messaging system. The radio protocol may send the data packet to the messaging system upon receipt of the data packet. The message system may be responsible for routing radio data packets to the proper destination node. The radio protocol may be capable of buffering one packet from the messaging system.

The radio protocol may be responsible for acknowledging receipt of valid data packets over the RF link via an RF ACK reply packet to the sending radio. The RF ACK packet may contain the source and destination radio serial numbers, RF ACK command identification, and sequence number of the data packet being acknowledged.

The radio transmitting a radio data packet may retransmit that radio data packet on the next heartbeat with the same sequence number if an RF ACK is not received and the retry count is within the maximum RF retries allowed. It may be expected that, from time to time, interference will corrupt a transmission on a particular frequency. An RF retry allows the same packet to be retransmitted at the next opportunity at a different frequency. The sequence number provides a means of uniquely identifying the packet over a short time window. The number of radio packet retries may be configurable using the radio configuration command. Allowing more retries may increase the probability of a packet being exchanged but introduces more latency for a round trip messages. The default number of radio retries at power up may be ten (i.e., the maximum transmission attempts before dropping the message).

A one byte (modulo 256) radio sequence number may be included in all radio data packets over the RF link. Since the radio may be responsible for retrying data packet transmission if not acknowledged, the sequence number may provide a way for the two radios to know if a data packet is a duplicate. The transmitted sequence number may be incremented for each new radio data packet and may be allowed to rollover. When a data packet is successfully received with the same sequence number as the previous successfully received data packet (and in the same direction), the data packet may be ACK'd and the received data packet discarded. This may remove duplicate packets generated by the RF protocol before they are introduced into the network. Note that it may be possible that multiple data packets in a row may need to be dropped with the same sequence number under extreme situations.

If a heartbeat is missed, the radio of remote control assembly 300 and the radio of infusion pump assembly 100, 100', 400, 500 may attempt to send and listen respectively for subsequent heartbeats. The radio of remote control assembly 300 and the radio of infusion pump assembly 100, 100', 400, 500 may automatically change from fast heartbeat mode or slow heartbeat mode to search sync mode if heartbeats are missed for two seconds. This may minimize power consumption when the link is lost by allowing the radios to continue to use their synchronization information, as two seconds allows sufficient time to hop through all channels.

The radio may be considered online while in the following modes:

Fast Heartbeat mode
Slow Heartbeat mode as these are the only conditions where messaging system traffic may be exchanged. All other conditions may be considered offline.

The radio may initialize to radio off mode at the start of code execution from reset. When code first executes on the radio processor, the initial state may be the radio off mode to allow other processors to perform self-tests before requesting the radio to be active. This requirement does not intend to define the mode when waking from sleep mode. The radio may cease RF communications when set to radio off mode. On remote control assembly 300, this mode may be intended for use on an airplane to suppress RF emissions. Since infusion pump assembly 100, 100', 400, 500 only responds to transmissions from remote control assembly 300 (which will have ceased transmitting in airplane mode), radio off mode may only be used on infusion pump assembly 100, 100', 400, 500 when charging.

Command processor 1802 may be informed of airplane mode and that, therefore, the RF was intentionally turned off on remote control assembly 300 so that it does not generate walk-away alerts. However, this may be completely hidden from the radio of infusion pump assembly 100, 100', 400, 500.

The radio of remote control assembly 300 and the radio of infusion pump assembly 100, 100', 400, 500 may periodically attempt to exchange heartbeats in order to reestablish data bandwidth while in search sync mode. The radio of remote control assembly 300 may transition to radio off mode after twenty minutes of search sync mode with no heartbeats successfully exchanged.

The radio of infusion pump assembly 100, 100', 400, 500 may transition to acquisition mode after twenty minutes of search sync mode with no heartbeats successfully exchanged.

Listening during pre-agreed time slots may be the most efficient use of power for infusion pump assembly 100, 100', 400, 500 to re-establish the RF link. After a loss of communications, the crystal tolerance and temperature drift may make it necessary to expand the receive window of infusion pump assembly 100, 100', 400, 500 over time. Staying in search sync mode for extended periods (e.g., 5-20 minutes) after communications loss may cause the instantaneous power consumed to exceed the average power budgeted for the radio of infusion pump assembly 100, 100', 400, 500. The radio of remote control assembly 300 may not be forced to expand its window, so staying in search sync mode may be very power efficient. Acquisition mode may consume more power for remote control assembly 300. Twenty minutes may be used as a compromise to balance power consumption on both the radio of remote control assembly 300 and the radio of infusion pump assembly 100, 100', 400, 500.

The radio of remote control assembly 300 and the radio of infusion pump assembly 100, 100', 400, 500 may transition to slow heartbeat mode if they successfully exchange three of the last five heartbeats. Approximately every six seconds, a burst of five heartbeats may be attempted. If three of these are successful, the bandwidth may be assumed to be sufficient to transition to slow heartbeat mode. The radio of infusion pump assembly 100, 100', 400, 500 may be acquirable while in search sync mode with a latency of 6.1 seconds. This may imply that the infusion pump assembly 100, 100', 400, 500 may always be listening at least every ~6 seconds when in search sync mode.

Radio protocol performance statistics may be necessary to promote troubleshooting of the radio and to assess radio performance. The following radio performance statistics may be maintained by the radio protocol in a data structure:

| NAME | SIZE | DESCRIPTION |
| --- | --- | --- |
| TX Heartbeat Count | 32 Bits | Total transmitted heartbeats |
| RX Heartbeat Count | 32 bits | Total valid received heartbeats |
| CRC Errors | 16 bits | Total packets received over the RF link which were dropped due to bad CRC. This may be a subset of RX Packets Nacked. |
| First Retry Count | 32 bits | Total number of packets which were successfully acknowledged after 1 retry |
| Second Retry Count | 32 bits | Total number of packets which were successfully acknowledged after 2 retries |
| Third Retry Count | 32 bits | Total number of packets which were successfully acknowledged after 3 retries |
| Fourth Retry Count | 32 bits | Total number of packets which were successfully acknowledged after 4 retries |
| Fifth Retry Count | 16 bits | Total number of packets which were successfully acknowledged after 5 retries |
| Sixth Retry Count | 16 bits | Total number of packets which were successfully acknowledged after 6 retries |
| Seventh Retry Count | 16 bits | Total number of packets which were successfully acknowledged after 7 retries |
| Eighth Retry Count | 16 bits | Total number of packets which were successfully acknowledged after 8 retries |
| Ninth Retry Count | 16 bits | Total number of packets which were successfully acknowledged after 9 retries |
| Tenth Retry Count | 16 bits | Total number of packets which were successfully acknowledged after 10 retries |
| Dropped Retry Count | 16 bits | Total number of packets which were dropped after maximum retries attempts |
| Duplicate Packet Count | 16 bits | Total number of received packets dropped due to duplicate packet |
| 1 to 5 Missed Fast Mode Hops | 16 bits | Count of 1 to 5 consecutive missed hops in Fast mode (i.e. not received) |
| 6 to 16 Missed Fast Mode Hops | 16 bits | Count of 6 to 16 consecutive missed hops in Fast mode. |
| 17 to 33 Missed Fast Mode Hops | 16 bits | Count of 17 to 33 consecutive missed hops in Fast mode |

| NAME | SIZE | DESCRIPTION |
|---|---|---|
| 34+ Missed Fast Mode Hops | 16 bits | Count of 34 or more consecutive missed hops in Fast mode |
| 1 to 2 Missed Slow Mode Hops | 16 bits | Count of 1 to 2 consecutive missed hops in Slow mode (i.e. not received) |
| 3 to 5 Missed Slow Mode Hops | 16 bits | Count of 3 to 5 consecutive missed hops in Slow mode |
| 5 to 7 Missed Slow Mode Hops | 16 bits | Count of 5 to 7 consecutive missed hops in Slow mode |
| 8+ Missed Slow Mode Hops | 16 bits | Count of 8 or more consecutive missed hops in Slow mode |
| Destination Radio Serial Number Mismatch | 16 bits | Count of received packets in which the destination made it past the hardware filtering but does not match this radio's serial number. This may be not an error but indicates that the radio may be waking up and receiving (but not processing) packets intended for other radios |
| Total Walkaway Time (minutes) | 16 bits | |
| Total Walkaway Events | 16 bits | Together with total walkaway time provides an average walkaway time |
| Number of Pairing Attempts | 16 bits | |
| Total Time in Acquisition Mode (Infusion pump assembly 100, 100', 400, 500 Only) | 16 bits | |
| Total Acquisition Mode Attempts (Remote control assembly 300 Only) | 16 bits | Successful Acquisition Count 16 bits Count of transitions from Connect or Acquisition Mode to Fast Heartbeat Mode |
| Requested Slow Heartbeat Mode Transitions | 16 bits | |
| Automatic Slow Heartbeat Mode Transitions | 16 bits | |
| Radio offline messages sent | 16 bits | |
| Radio online messages sent | 16 bits | |

A #define DEBUG option (compiler option) may be used to gather the following additional radio performance statistics per each channel (16 bit numbers):
Number of missed hops
CCA good count
CCA bad count
Average RSSI (accumulated for good RX packets only)
Dropped from Frequency Hop List count
Acquisition Mode count (found pair on this channel)

The debug option may be used to gather engineering only statistics. If processor performance, power, and memory allow, it may be desirable to keep this information at runtime. The radio statistics may be made available to the messaging system.

Link quality may be intended to be used on remote control assembly 300 to provide a bar indicator, similar to a cell phone, of the radio link quality. Link quality may be made available to both remote control assembly 300 and infusion pump assembly 100, 100', 400, 500. It may be anticipated that the link quality status will consist of a one byte indicator of the quality of the radio link.

The radio may change frequency for each heartbeat. An adaptive pseudo random frequency hopping algorithm may be used for sync mode and heartbeat attempts in search sync mode. It may be a goal to use sixty-four channels for frequency hopping. An algorithm may be developed to adaptively generate a channel list on remote control assembly 300 for frequency hopping. The radio of remote control assembly 300 may build, maintain, and distribute the master channel list. Prior channel statistics and historical performance information may be obtained from the radio of infusion pump assembly 100, 100', 400, 500 by the radio of remote control assembly 300 using the messaging system as needed to meet performance requirements. By building the channel list from the perspective of both units, the radio interference environment of both units may be considered. The radios may adaptively select hopping channels to meet the round trip message latency, while operating in a desirable RF environment.

Figure 121:
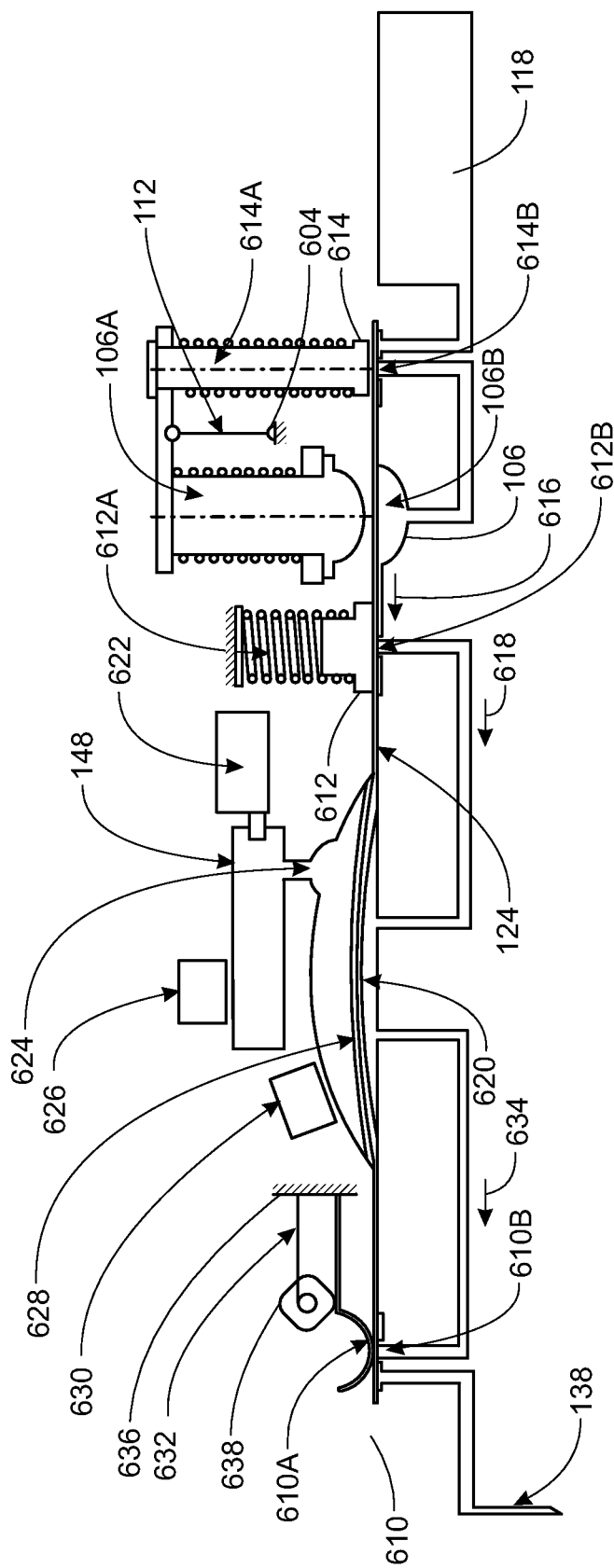
FIG. 121 diagrammatically depicts a volume sensor assembly included within the infusion pump assembly of FIG. 1.

Occlusions and/or leaks may occur anywhere along the fluid delivery path of infusion pump assembly 100. For example and referring to FIG. 121, occlusions/leaks may occur: in the fluid path between reservoir 118 and reservoir valve assembly 614; in the fluid path between reservoir valve assembly 614 and pump assembly 106; in the fluid path between pump assembly 106 and volume sensor valve assembly 612; in the fluid path between volume sensor valve assembly 612 and volume sensor chamber 620; in the fluid path between volume sensor chamber 620 and measurement valve assembly 610; and in the fluid path between measurement valve assembly 610 and the tip of disposable cannula 138. Infusion pump assembly 100 may be configured to execute one or more occlusion/leak detection algorithms that detect and locate such occlusions/leaks and enhance the safety/reliability of infusion pump assembly 100.

As discussed above, when administering the infusible fluid, infusion pump assembly 100 may first determine the volume of infusible fluid within volume sensor chamber 620 prior to the administration of the dose of infusible fluid and may subsequently determine the volume of infusible fluid within volume sensor chamber 620 after the administration of the dose of infusible fluid. By monitoring these values, the occurrence of occlusions/leaks may be detected.

Occlusion Type—Total:

When a total occlusion is occurring, the difference between the initial measurement prior to the administration of the dose of infusible fluid and the final measurement after the administration of the dose of infusible fluid will be zero (or essentially zero), indicating a large residual quantity of infusible fluid within volume sensor chamber 620. Accordingly, no fluid may be leaving volume sensor chamber 620.

Specifically, if the tip of disposable cannula is occluded, the fluid path down stream of volume sensor chamber 620 will fill with fluid and eventually become pressurized to a level equivalent to the mechanical pressure exerted by spring diaphragm 628. Accordingly, upon measurement valve assembly 610 opening, zero (or essentially zero) fluid will be dispensed and, therefore, the value of the initial and final measurements (as made by volume sensor assembly 148) will essentially be equal.

Upon detecting the occurrence of such a condition, a total occlusion indicator may be set and infusion pump assembly 100 may e.g., trigger an alarm, thus indicating that the user needs to seek alternative means for receiving their therapy.

Occlusion Type—Partial:

When a partial occlusion is occurring, the difference between the initial measurement prior to the administration of the dose of infusible fluid and the final measurement after the administration of the dose of infusible fluid will indicate that less than a complete dose of infusible fluid was delivered. For example, assume that at the end of a particular pumping cycle, volume sensor assembly 148 indicated that 0.10 microliters of infusible fluid were present in volume sensor chamber 620. Further, assume that measurement value assembly 610 is subsequently closed and pump assembly 106 is subsequently actuated, resulting in volume sensor chamber 620 being filed with the infusible fluid. Further assume that volume sensor assembly 148 determines that volume sensor chamber 620 is now filled with 1.00 microliters of infusible fluid (indicating a pumped volume of 0.90 microliters).

Accordingly, upon the opening of measurement valve assembly 610, the quantity of infusible fluid included within volume sensor chamber would be expected to drop to 0.10 microliters (or reasonably close thereto). However, in the event of a partial occlusion, due to a slower-than-normal flow rate from volume sensor chamber 620, the quantity of infusible fluid within volume sensor chamber 620 may only be reduced to 0.40 microliters (indicating a delivered volume of 0.60 microliters). Accordingly, by monitoring the difference between the pumped volume (0.90 microliters) and the delivered volume (0.60 microliters), the residual volume may be defined and the occurrence of a partial occlusion may be detected.

Upon detecting the occurrence of such a condition, a partial occlusion indicator may be set and infusion pump assembly 100 may e.g., trigger an alarm, thus indicating that the user needs to seek alternative means for receiving their therapy. However, as this is indicative of a partial occlusion (as opposed to a complete occlusion), the issuance of an alarm may be delayed, as the partial occlusion may clear itself.

Alternatively, infusion pump assembly 100 may: calculate a pump ontime to volume delivered ratio; track it through time; and track by using a fast moving and a slow moving exponential average of the pump ontime. The exponential average may be tracked, in a fashion similar to the leaky sum integrator. The infusion pump assembly 100 may filter signal and look for a fast change. The rate of fluid outflow and/or residual volume may be monitored. If the residual volume does not change, then there may be a total occlusion. If the residual volume changed, they may be a partial occlusion. Alternatively still, the residual values may be summed. If the number of valve actuations or the latch time is being varied, the fluid flow rate may be examined, even if you build up pressure in volume sensor assembly 148.

Total/Partial Empty Reservoir:

When reservoir 118 is becoming empty, it will become more difficult to fill volume sensor chamber 620 to the desired level. Typically, pump assembly 106 is capable of pumping 1.0 microliters per millisecond. For example, assume that an "empty" condition for volume sensor chamber 620 is 0.10 microliters and a "full" condition for volume sensor chamber 620 is 1.00 microliters. However, as reservoir 118 begins to empty, it may become harder for pump assembly 106 to fill volume sensor chamber 620 to the "full" condition and may consistently miss the goal. Accordingly, during normal operations, it may take one second for pump assembly 106 to fill volume sensor chamber 620 to the "full" condition and, as reservoir 118 empties, it may take three seconds to fill volume sensor chamber 620 to the "full" condition. Eventually, if reservoir 118 completely empties, volume sensor chamber 620 may never be able to achieve a "full condition". Accordingly, the inability of pump assembly 106 to fill volume sensor chamber 620 to a "full" condition may be indicative of reservoir 118 being empty. Alternatively, the occurrence of such a condition may be indicative of other situations (e.g., the failure of pump assembly 106 or an occlusion in the fluid path prior to volume sensor chamber 620). Infusion pump assembly 100 may determine the difference between the "full" condition and the amount actually pumped. These differences may be summed and the made up for once the reservoir condition is addressed.

Upon detecting the occurrence of such a condition, an empty indicator may be set and infusion pump assembly 100 may e.g., trigger an alarm, thus indicating that the user needs to e.g., replace disposable housing assembly 114.

Additionally, as reservoir 118 empties, reservoir 118 will eventually result in a "vacuum" condition and the ability of pump assembly 106 to deliver fluid to volume sensor chamber 620 may be compromised. As discussed above, volume controller 1602 may include feed forward controller 1652 for setting an initial "guess" concerning "on-time" signal 1606, wherein this initial guess is based upon a pump calibration curve. For example, in order for pump assembly 106 to deliver 0.010 units of infusible fluid, feed forward controller 1652 may define an initial "on-time" of e.g., one millisecond. However, as reservoir 118 begins to empty, due to compromised pumping conditions, it may take two milliseconds to deliver 0.010 units of infusible fluid. Further, as reservoir 118 approaches a fully empty condition, it make take ten milliseconds to deliver 0.010 units of infusible fluid. Accordingly, the occurrence of reservoir 118 approaching an empty condition may be detected by monitoring the level at which the actual operation of pump assembly 106 (e.g., two milliseconds to deliver 0.010 units of infusible fluid) differs from the anticipated operation of pump assembly 106 (e.g., one millisecond to deliver 0.010 units of infusible fluid).

Upon detecting the occurrence of such a condition, a reserve indicator may be set and infusion pump assembly 100 may e.g., trigger an alarm, thus indicating that the user will need to e.g., replace disposable housing assembly 114 shortly.

Leak Detection:

In the event of a leak (e.g., a leaky valve or a rupture/perforation) within the fluid path, the ability of the fluid path to retain fluid pressure may be compromised. Accordingly, in order to check for leaks within the fluid path, a bleed down test may be performed in which pump assembly 106 is used to pressurize volume sensor chamber 620. Volume sensor assembly 148 may then perform a first volume measurement (as described above) to determine the volume of infusible fluid within volume sensor chamber 620. Infusion pump assembly 100 may then wait a defined period of time to allow for bleed down in the event of a leak. For example, after a sixty second bleed down period, volume sensor assembly 148 may perform a second volume measurement (as described above) to determine the volume of infusible fluid within volume sensor chamber 620. If there are no leaks, the two volume measurements should be essentially the same. However, in the event of a leak, the second measurement may be less then the first measurement. Additionally, depending on the severity of the leak, pump assembly 106 may be incapable of filling volume sensor chamber 620. Typically, a leak check may be performed as part of a delivery of infusible fluid.

In the event that the difference between the first volume measurement and the second volume measurement exceeds an acceptable threshold, a leak indicator may be set and infusion pump assembly 100 may e.g., trigger an alarm, thus indicating that the user needs to seek alternative means for receiving their therapy As discussed above, infusion pump assembly 100 may include supervisor processor 1800, command processor 1802, and radio processor 1818. Unfortunately, once assembled, access to electrical control assembly 110 within infusion pump assembly 100 very limited. Accordingly, the only means to access electrical control assembly 110 (e.g., for upgrading flash memories) may be through the communication channel established between infusion pump assembly 100, 100', 400, 500 and remote control assembly 300, or via electrical contacts 834 used by battery charger 1200.

Electrical contacts 834 may be directly coupled to radio processor 1818 and may be configured to provide I2C communication capability for erasing/programming any flash memory (not shown) included within radio processor 1818. The process of loading a program into radio processor 1818 may provide a means for erasing/programming of the flash memories in both the supervisor processor 1800 and command processor 1802.

When programming supervisor processor 1800 or command processor 1802, the program (i.e., data) to be loaded into flash memory accessible by supervisor processor 1800 or command processor 1802 may be provided in a plurality of data blocks. This is because the radio processor 1818 may not have enough memory to hold the entire flash image of the software as one block.

Figure 122:
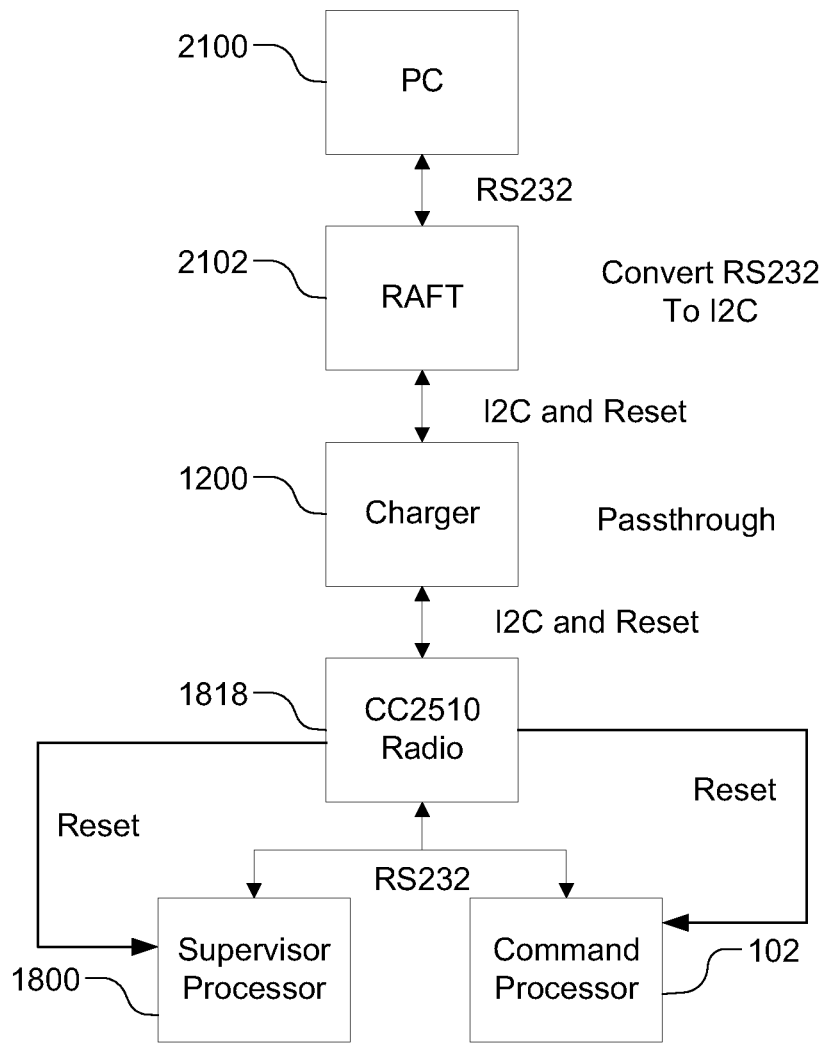
FIG. 122 diagrammatically depicts an inter-connection of the various systems of the infusion pump assembly of FIG. 1.

Referring also to FIG. 122, there is shown one illustrative example of the manner in which the various systems within infusion pump assembly 100, 100', 400, 500 may be interconnected. For example, battery charger 1200 may be coupled to computing device 2100 (e.g., a personal computer) via bus translator 2102, which converts e.g., RS232 formatted data to e.g., I2C formatted data. Bus translator 2102 may execute a pass-through program that effectuates the above-described translation. Battery charger 1200 may be coupled to radio processor 181 via electrical contacts 834 (described above). Radio processor 1818 may then be coupled to supervisor processor 1800 and command processor 1802 via e.g., an RS232 bus. Radio processor 1818 may execute an update program that allows radio processor 1818 to control/orchestrate the updating of the flash memories accessible by supervisor processor 1800 and command processor 1802. Accordingly, through the use of the above-described coupling, software updates obtained by computing device 2100 may be uploaded to flash memory (not shown) accessible by supervisor processor 1800 and command processor 1802. The above-described software updates may be command line program that may be automatically invoked by a script process.

As discussed above, infusion pump assembly 100, 100' 400, 500 may be configured to deliver an infusible fluid to a user. Further and as discussed above, infusion pump assembly 100, 100' 400, 500 may deliver the infusible fluid via sequential, multi-part, infusion events (that may include a plurality of discrete infusion events) and/or one-time infusion events. However, in some embodiments, infusion pump assembly 100, 100' 400, 500 may deliver stacking bolus infusion events. For example, a user may request the delivery of a bolus, e.g., 6 units. While the 6 units are in the process of being delivered to the user, the user may request a second bolus, e.g., 3 units. In some embodiments of infusion pump assembly 100, 100' 400, 500 may deliver the second bolus at the completion of the first bolus.

Examples of other such sequential, multi-part, infusion events may include but are not limited to a basal infusion event and an extended-bolus infusion event. As is known in the art, a basal infusion event refers to the repeated injection of small (e.g. 0.05 unit) quantities of infusible fluid at a predefined interval (e.g. every three minutes) that may be repeated until stopped, e.g., by a user or by the system. Further, the basal infusion rates may be pre-programmed and may include specified rates for pre-programmed time-frames, e.g., a rate of 0.50 units per hour from 6:00 am-3:00 pm; a rate of 0.40 units per hour from 3:00 pm-10:00 pm; and a rate of 0.35 units per hour from 10:00 pm-6:00 am. However, the basal rate may be 0.025 units per hour, and may not change according to pre-programmed time-frames. The basal rates may be repeated regularly/daily until otherwise changed.

Further and as is known in the art, an extended-bolus infusion event may refer to the repeated injection of small (e.g. 0.05 unit) quantities of infusible fluid at a predefined interval (e.g. every three minutes) that is repeated for a defined number of intervals (e.g., three intervals) or for a defined period of time (e.g., nine minutes). An extended-bolus infusion event may occur simultaneously with a basal infusion event.

If multiple infusion events conflict with each other, infusion pump assembly 100, 100' 400, 500 may prioritize the infusion event in the follow manner.

Figure 123:
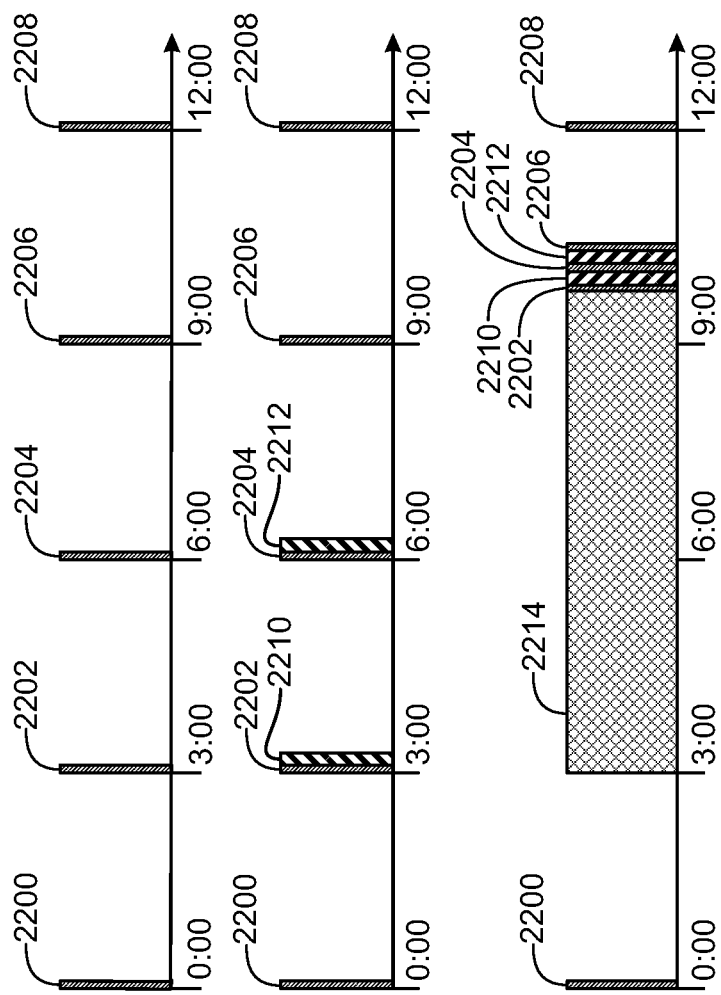
FIG. 123 diagrammatically depicts basal-bolus infusion events.

Referring also to FIG. 123, assume for illustrative purposes only that the user configures infusion pump assembly 100, 100' 400, 500 to administer a basal dose (e.g. 0.05 units) of infusible fluid every three minutes. The user may utilize remote control assembly 300 to define a basal infusion event for the infusible fluid (e.g., 1.00 units per hour).

Infusion pump assembly 100, 100' 400, 500 may then determine an infusion schedule based upon the basal infusion event defined. Once determined, infusion pump assembly 100, 100' 400, 500 may administer the sequential, multi-part, infusion event (e.g., 0.05 units of infusible fluid every three minutes). Accordingly, while administering the sequential, multi-part, infusion event, infusion pump assembly 100, 100' 400, 500: may infuse a first 0.05 unit dose 2200 of the infusible fluid at t=0:00 (i.e., a first discrete infusion event), may infuse a second 0.05 unit dose 2202 of the infusible fluid at t=3:00 (i.e., a second discrete infusion event); may infuse a third 0.05 unit dose 2204 of the infusible fluid at t=6:00 (i.e., a third discrete infusion event); may infuse a fourth 0.05 unit dose 2206 of the infusible fluid at t=9:00 (i.e., a fourth discrete infusion event); and may infuse a fifth 0.05 unit dose 2208 of the infusible fluid at t=12:00 (i.e., a fifth discrete infusion event). As discussed above, this pattern of infusing 0.05 unit doses of the infusible fluid every three minutes may be repeated until stopped, e.g., by a user or by the system, in this example, as this is an illustrative example of a basal infusion event.

Further, assume for illustrative purposes that the infusible fluid is insulin and sometime after the first 0.05 unit dose 2200 of infusible fluid is administered (but before the second 0.05 unit dose 2202 of infusible fluid is administered), the user checks their blood glucose level and realizes that their blood glucose level is running a little higher than normal. Accordingly, the user may define an extended bolus infusion event via remote control assembly 300. An extended bolus infusion event may refer to the continuous infusion of a defined quantity of infusible fluid over a finite period of time. However, as such an infusion methodology is impractical/undesirable for an infusion pump assembly, when administered by such an infusion pump assembly, an extended bolus infusion event may refer to the infusion of additional small doses of infusible fluid over a finite period of time.

Accordingly, the user may utilize remote control assembly 300 to define an extended bolus infusion event for the infusible fluid (e.g., 0.20 units over the next six minutes), which may be confirmed in a manner discussed above. While, in this example, the extended bolus infusion event is described as 0.20 units over the next six minutes, this is for illustrative purposes only and is not intended to be a limitation of this disclosure, as either or both of the unit quantity and total time interval may be adjusted upward or downward. Once defined and/or confirmed, infusion pump assembly 100, 100' 400, 500 may determine an infusion schedule based upon the extended bolus infusion event defined; and may administer the infusible fluid. For example, infusion pump assembly 100, 100' 400, 500 may deliver 0.10 units of infusible fluid every three minutes for the next two interval cycles (or six minutes), resulting in the delivery of the extended bolus dose of infusible fluid defined by the user (i.e., 0.20 units over the next six minutes).

Accordingly, while administering the second, sequential, multi-part, infusion event, infusion pump assembly 100, 100' 400, 500 may infuse a first 0.10 unit dose 2210 of the infusible fluid at t=3:00 (e.g., after administering the second 0.05 unit dose 2202 of infusible fluid). Infusion pump assembly 100, 100' 400, 500 may also infuse a second 0.10 unit dose 2212 of the infusible fluid at t=6:00 (e.g., after administering the third 0.05 unit dose 2204 of infusible fluid).

Assume for illustrative purposes only that after the user programs infusion pump assembly 100, 100' 400, 500 via remote control assembly 300 to administer the first sequential, multi-part, infusion event (i.e., 0.05 units infused every three minute interval repeated continuously) and administer the second sequential, multi-part, infusion event (i.e., 0.10 units infused every three minute interval for two intervals), the user decides to eat a very large meal. Predicting that their blood glucose level might increase considerably, the user may program infusion pump assembly 100, 100' 400, 500 (via remote control assembly 300) to administer a one-time infusion event. An example of such a one-time infusion event may include but is not limited to a normal bolus infusion event. As is known in the art, a normal bolus infusion event refers to a one-time infusion of the infusible fluid.

For illustrative purposes only, assume that the user wishes to have infusion pump assembly 100, 100' 400, 500 administer a bolus dose of thirty-six units of the infusible fluid. Infusion pump assembly 100, 100' 400, 500 may monitor the various infusion events being administered to determine whether a one-time infusion event is available to be administered. If a one-time infusion event is available for administration, infusion pump assembly 100, 100' 400, 500 may delay the administration of at least a portion of the sequential, multi-part, infusion event.

Continuing with the above-stated example, once the user completes the programming of infusion pump assembly 100, 100' 400, 500 to deliver one-time infusion event 2214 (i.e., the thirty-six unit bolus dose of the infusible fluid), upon infusion pump assembly 100, 100' 400, 500 determining that the one-time infusion event is available for administration, infusion pump assembly 100, 100' 400, 500 may delay the administration of each sequential, multi-part infusion event and administer the available one-time infusion event.

Specifically and as discussed above, prior to the user programming infusion pump assembly 100, 100' 400, 500 to deliver one-time infusion event 2214, infusion pump assembly 100, 100' 400, 500 was administering a first sequential, multi-part, infusion event (i.e., 0.05 units infused every three minute interval repeated continuously) and administering a second sequential, multi-part, infusion event (i.e., 0.10 units infused every three minute interval for two intervals).

For illustrative purposes only, the first sequential, multi-part, infusion event may be represented within FIG. 123 as 0.05 unit dose 2200 @ t=0:00, 0.05 unit dose 2202 @ t=3:00, 0.05 unit dose 2204 @ t=6:00, 0.05 unit dose 2206 @ t=9:00, and 0.05 unit dose 2208 @ t=12:00. As the first sequential, multi-part, infusion event as described above is a basal infusion event, infusion pump assembly 100, 100' 400, 500 may continue to infuse 0.05 unit doses of the infusible fluid at three minute intervals indefinitely (i.e., until the procedure is cancelled by the user).

Further and for illustrative purposes only, the second sequential, multi-part, infusion event may be represented within FIG. 123 as 0.10 unit dose 2210 @ t=3:00 and 0.10 unit dose 2212 @ t=6:00. As the second sequential, multi-part, infusion event is described above as an extended bolus infusion event, infusion pump assembly 100, 100' 400, 500 may continue to infuse 0.10 unit doses of the infusible fluid at three minute intervals for exactly two intervals (i.e., the number of intervals defined by the user).

Continuing with the above-stated example, upon infusion pump assembly 100, 100' 400, 500 determining that the thirty-six unit normal bolus dose of the infusible fluid (i.e., one-time infusion event 2214) is available for administration, infusion pump assembly 100, 100' 400, 500 may delay the administration of each sequential, multi-part infusion event and may start administering one-time infusion event 2214 that is available for administration.

Accordingly and for illustrative purposes only, assume that upon completion of the programming of infusion pump assembly 100, 100' 400, 500 to deliver the thirty-six unit normal bolus does of the infusible fluid (i.e., the one-time infusion event), infusion pump assembly 100, 100' 400, 500 begins administering one-time infusion event 2214. Being that one-time infusion event 2214 is comparatively large, it may take longer than three minutes (i.e., the time interval between individual infused doses of the sequential, multi-part, infusion events) and one or more of the individual infused doses of the sequential, multi-part, infusion events may need to be delayed.

Specifically, assume that it will take infusion pump assembly 100, 100' 400, 500 greater than six minutes to infuse thirty-six units of the infusible fluid. Accordingly, infusion pump assembly 100, 100' 400, 500 may delay 0.05 unit dose 2202 (i.e., scheduled to be infused @ t=3:00), 0.05 unit dose 2204 (i.e., scheduled to be infused @ t=6:00), and 0.05 unit dose 2206 (i.e., scheduled to be infused @ t=9:00) until after one-time infusion event 2214 (i.e., the thirty-six unit normal bolus dose of the infusible fluid) is completely administered. Further, infusion pump assembly 100, 100' 400, 500 may delay 0.10 unit dose 2210 (i.e., scheduled to be infused @ t=3:00 and 0.10 unit dose 2212 (i.e., scheduled to be infused @ t=6:00) until after one-time infusion event 2214.

Once administration of one-time infusion event 2214 is completed by infusion pump assembly 100, 100' 400, 500, any discrete infusion events included within the sequential, multi-part, infusion event that were delayed may be administered by infusion pump assembly 100, 100' 400, 500. Accordingly, once one-time infusion event 2214 (i.e., the thirty-six unit normal bolus dose of the infusible fluid) is completely administered, infusion pump assembly 100, 100' 400, 500 may administer 0.05 unit dose 2202, 0.05 unit dose 2204, 0.05 unit dose 2206, 0.10 unit dose 2210, and 0.10 unit dose 2212.

While infusion pump assembly 100, 100' 400, 500 is shown to administer 0.05 unit dose 2202, then 0.10 unit dose 2210, then 0.05 unit dose 2204, then 0.10 unit dose 2212, and then 0.05 unit dose 2206, this is for illustrative purposes only and is not intended to be a limitation of this disclosure, as other configurations are possible and are considered to be within the scope of this disclosure. For example, upon infusion pump assembly 100, 100' 400, 500 completing the administration of one-time infusion event 2214 (i.e., the thirty-six unit normal bolus dose of the infusible fluid), infusion pump assembly 100, 100' 400, 500 may administer all of the delayed discrete infusion events associated with the first sequential, multi-part infusion event (i.e., namely 0.05 unit dose 2202, 0.05 unit dose 2204, and 0.05 unit dose 2206). Infusion pump assembly 100, 100' 400, 500 may then administer all of the delayed discrete infusion events associated with the second sequential, multi-part infusion event (i.e., 0.10 unit dose 2210, and 0.10 unit dose 2212).

While one-time infusion event 2214 (i.e., the thirty-six unit normal bolus dose of the infusible fluid) is shown as being infused beginning at t=3:00, this is for illustrative purposes only and is not intended to be a limitation of this disclosure. Specifically, infusion pump assembly 100, 100' 400, 500 may not need to begin infusing one-time infusion event 2214 at one of the three-minute intervals (e.g., t=0:00, t=3:00, t=6:00, t=9:00, or t=12:00) and may begin administering one-time infusion event 2214 at any time.

While each discrete infusion event (e.g., 0.05 unit dose 2202, 0.05 unit dose 2204, 0.05 unit dose 2206, 0.10 unit dose 2210, and 0.10 unit dose 2212) and one-time infusion event 2214 are shown as being a single event, this is for illustrative purposes only and is not intended to be a limitation of this disclosure. Specifically, at least one of the plurality of discrete infusion events e.g., 0.05 unit dose 2202, 0.05 unit dose 2204, 0.05 unit dose 2206, 0.10 unit dose 2210, and 0.10 unit dose 2212) may include a plurality of discrete infusion sub-events. Further, one-time infusion event 2214 may include a plurality of one-time infusion sub-events.

Figure 124:
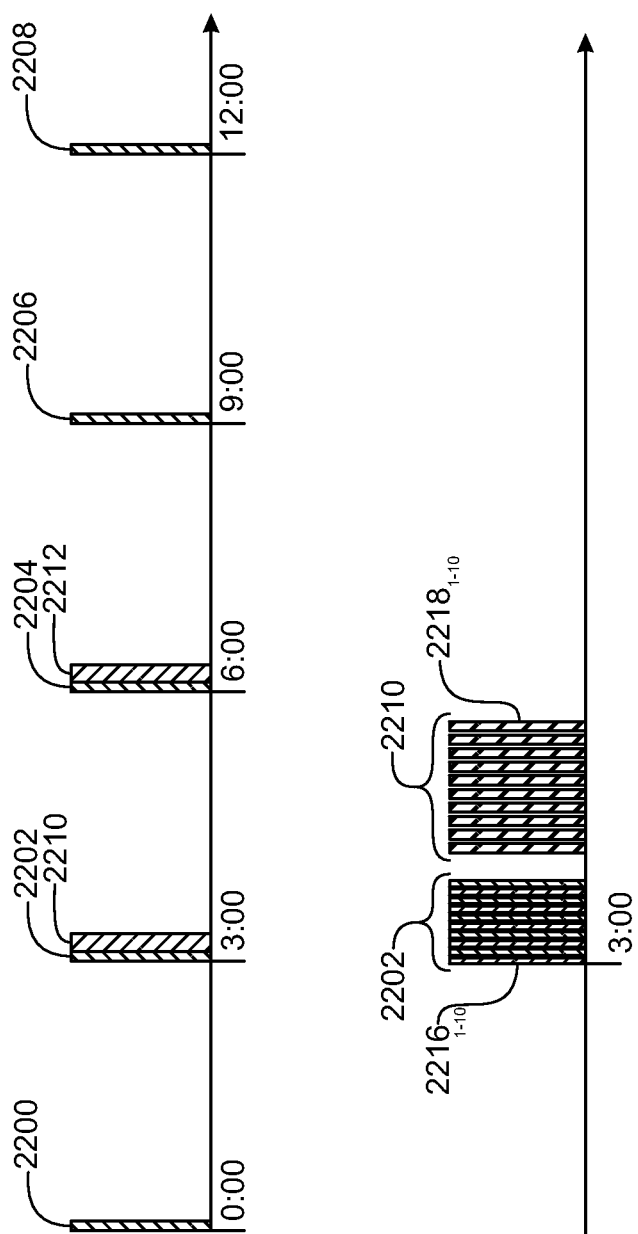
FIG. 124 diagrammatically depicts basal-bolus infusion events.
Figure 125B:
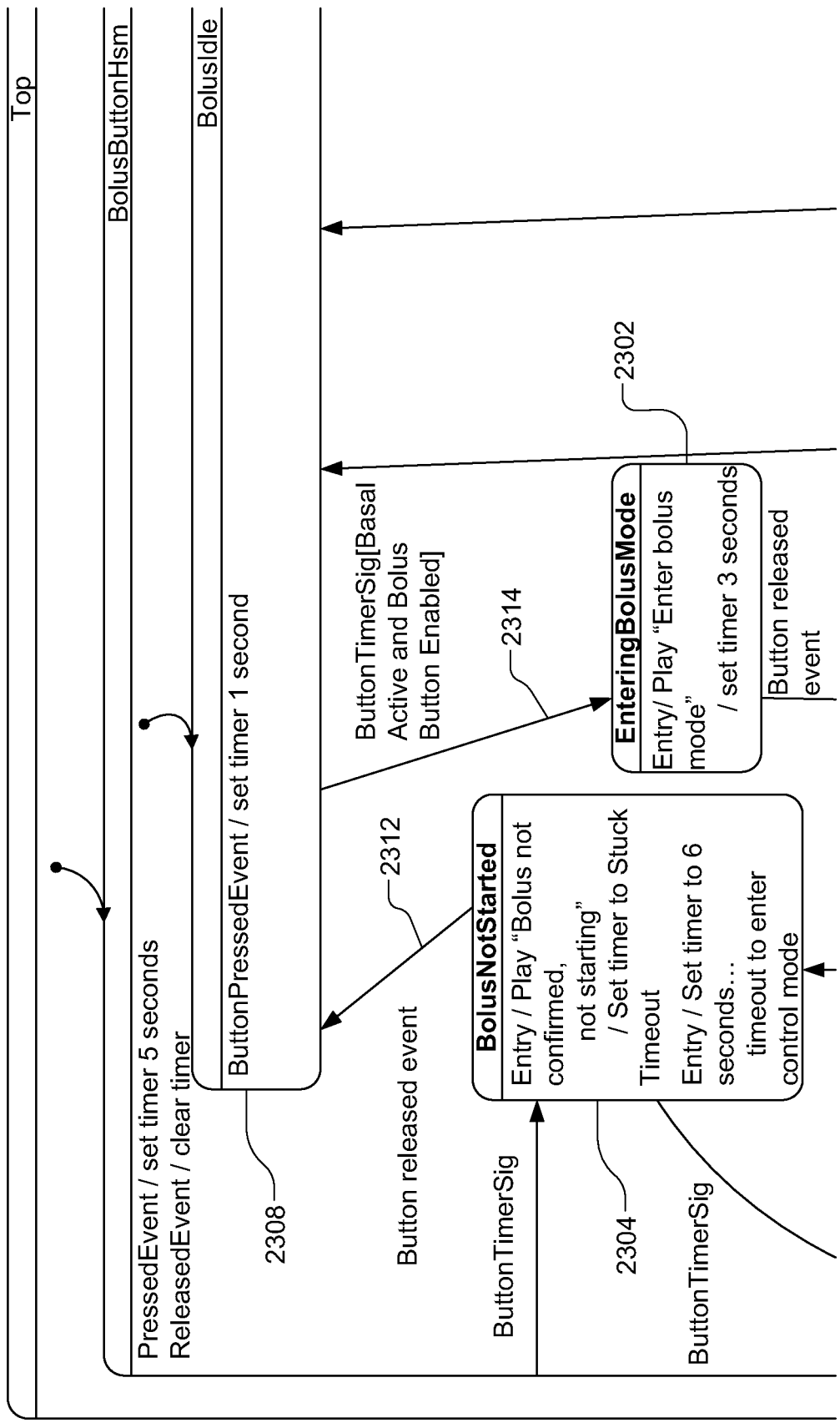
Figure 125C:
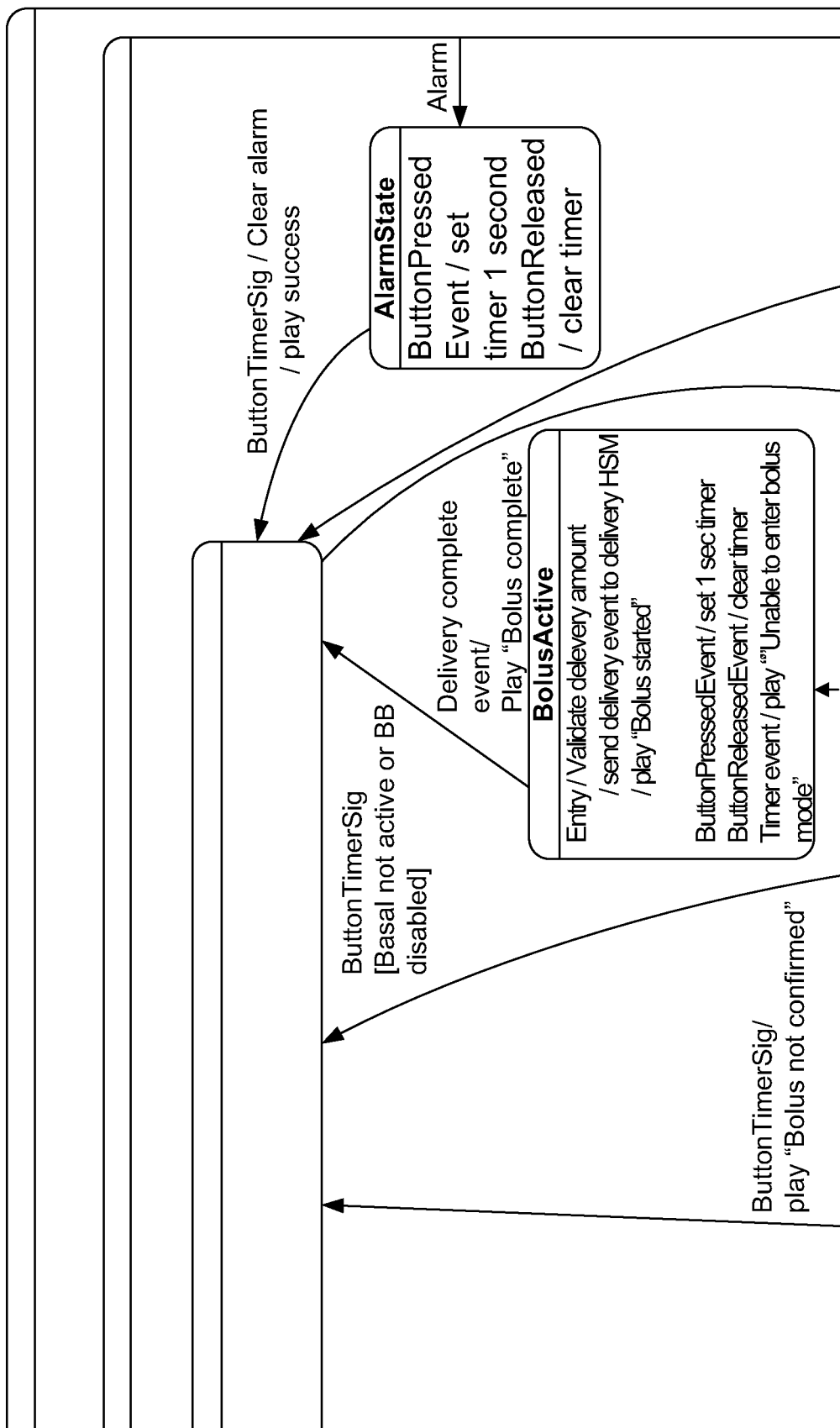
Figure 125D:
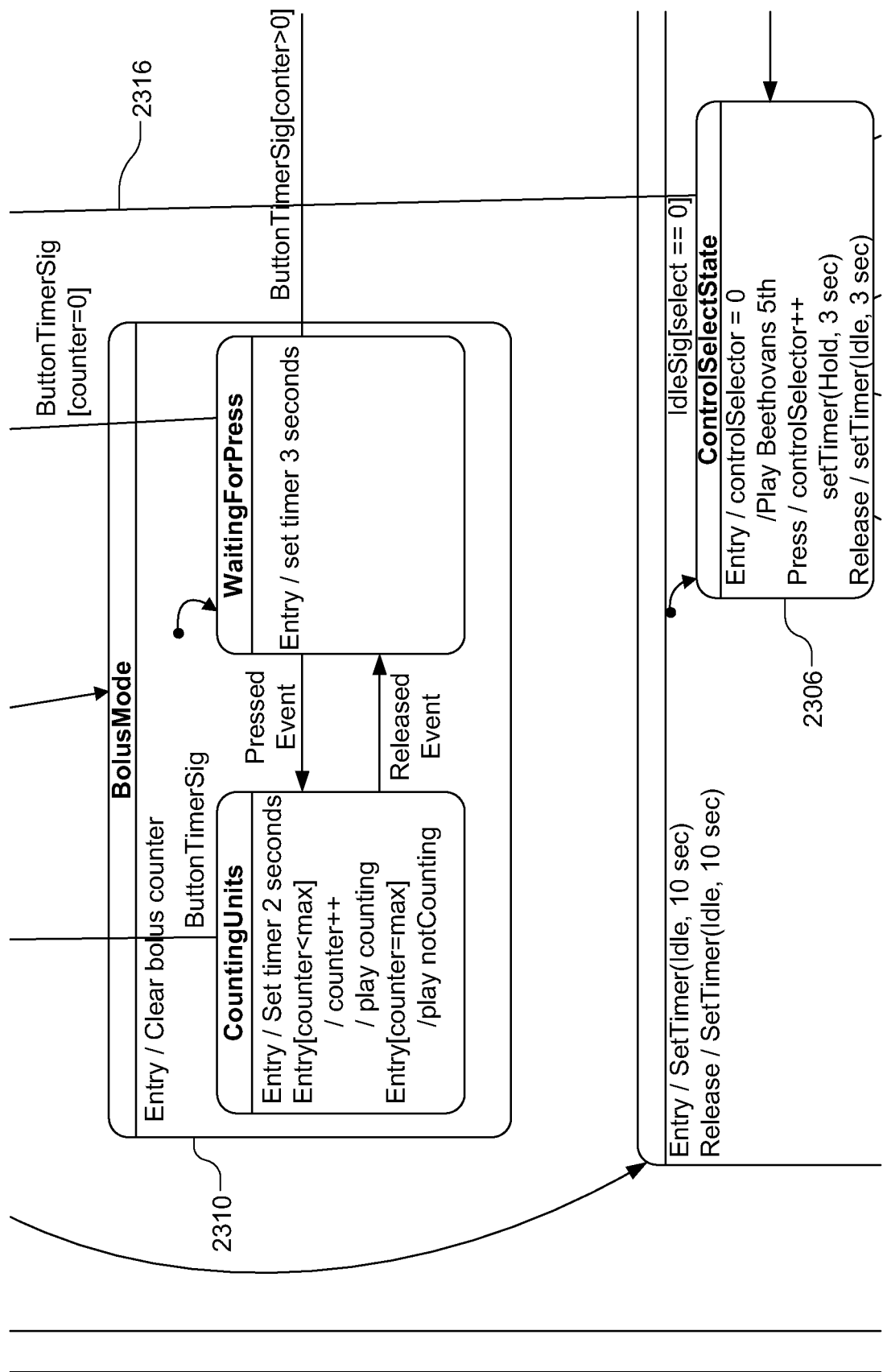
Figure 125E:
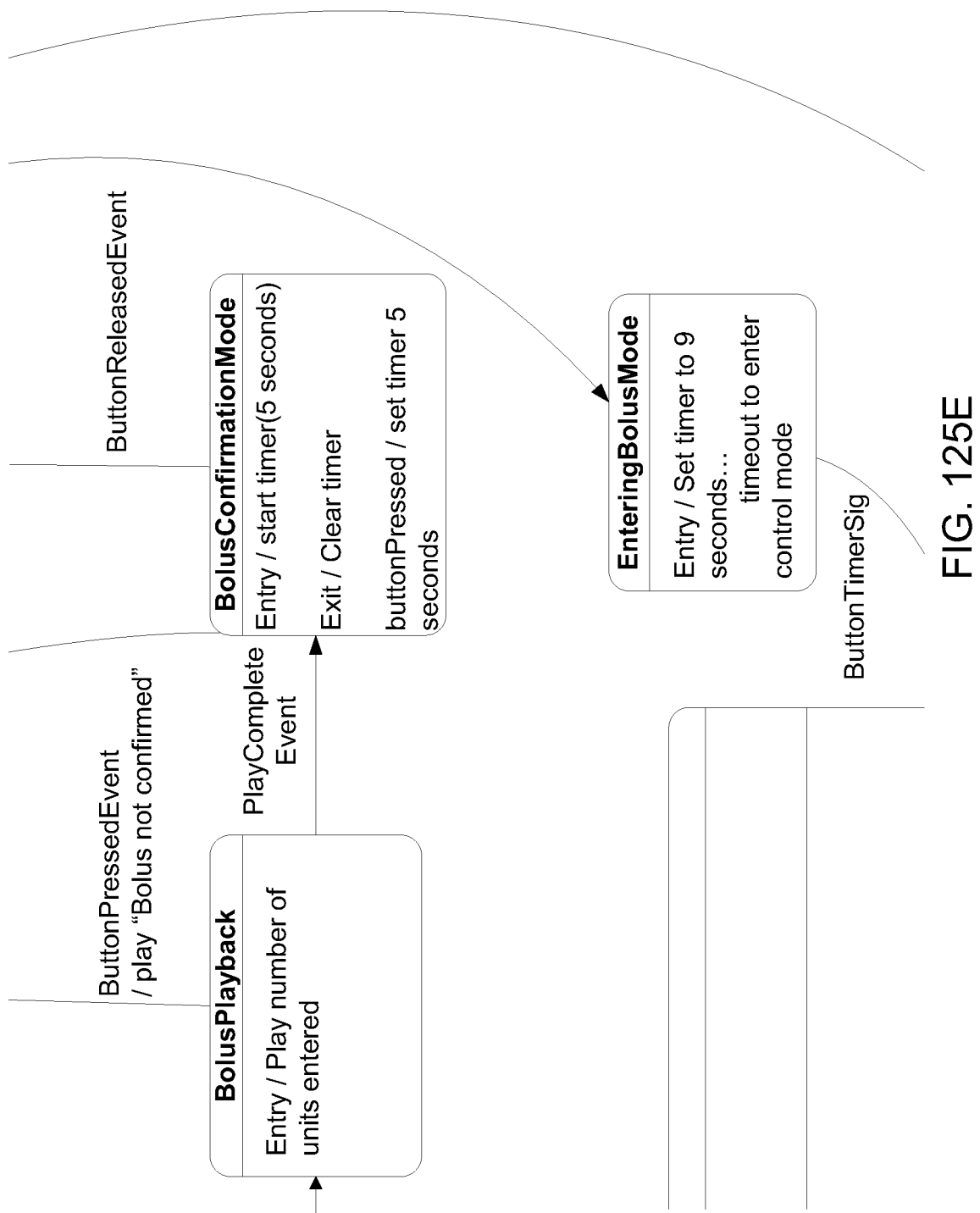
Figure 125F:
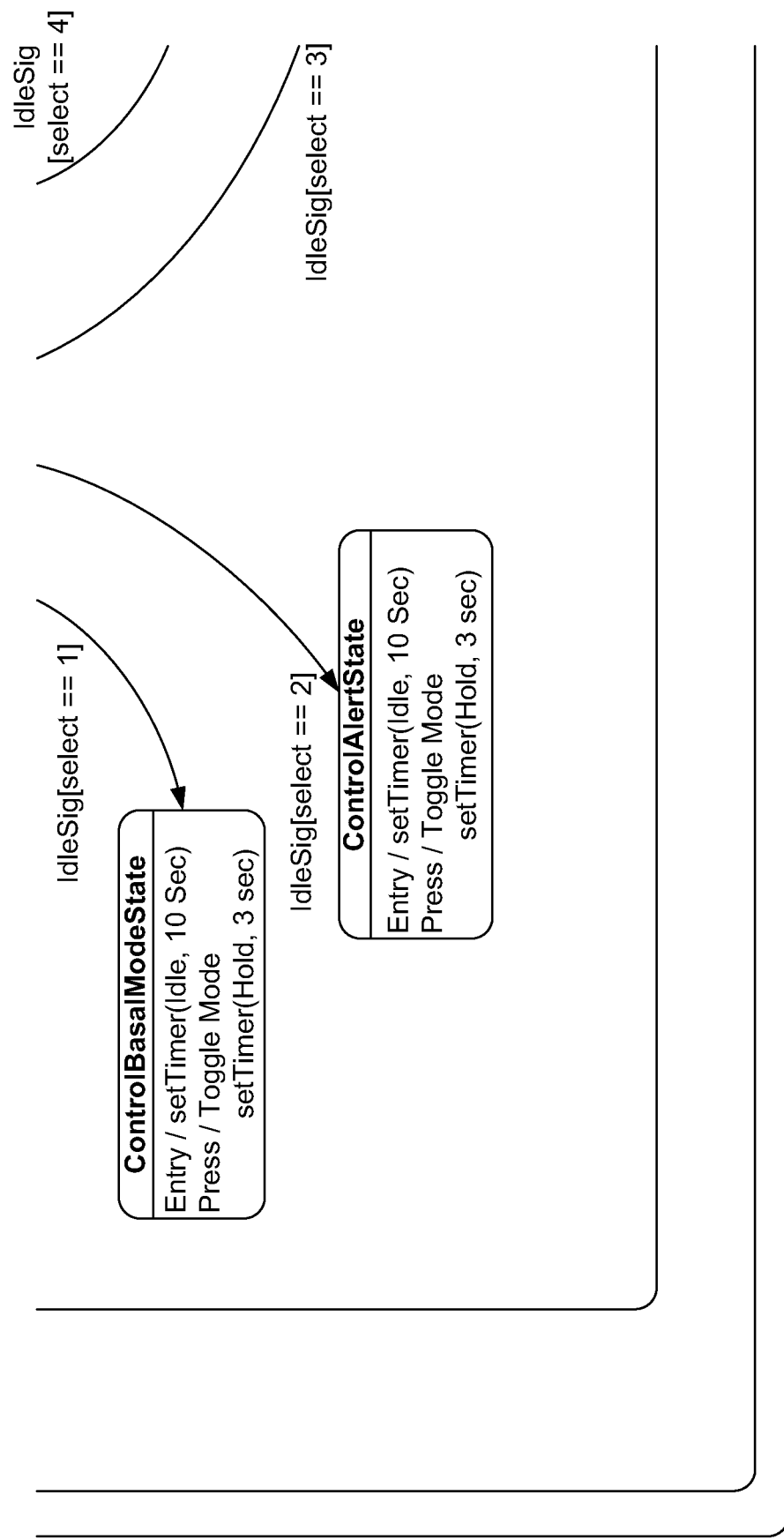
Figure 125G:
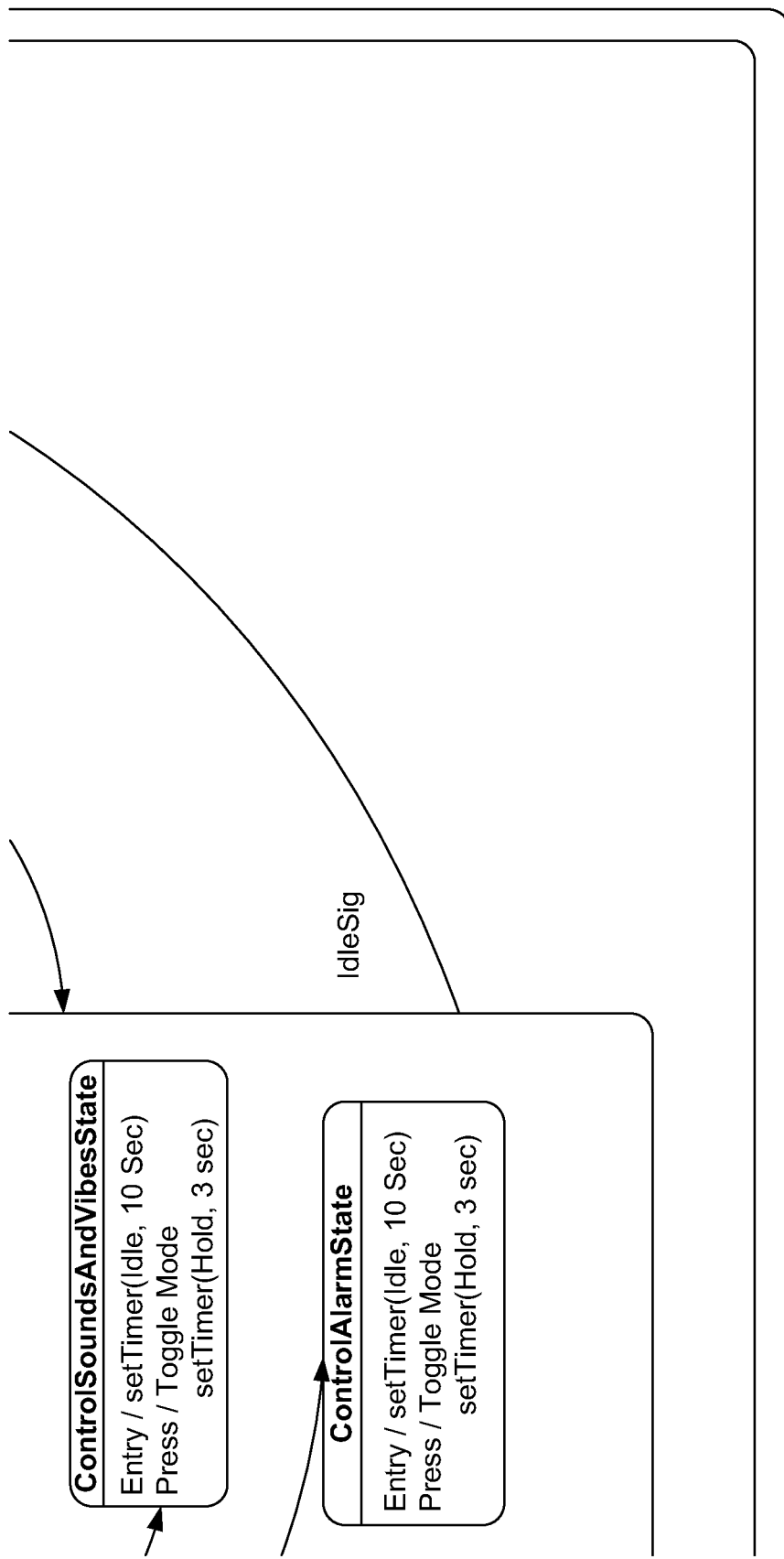
Figure 126A:
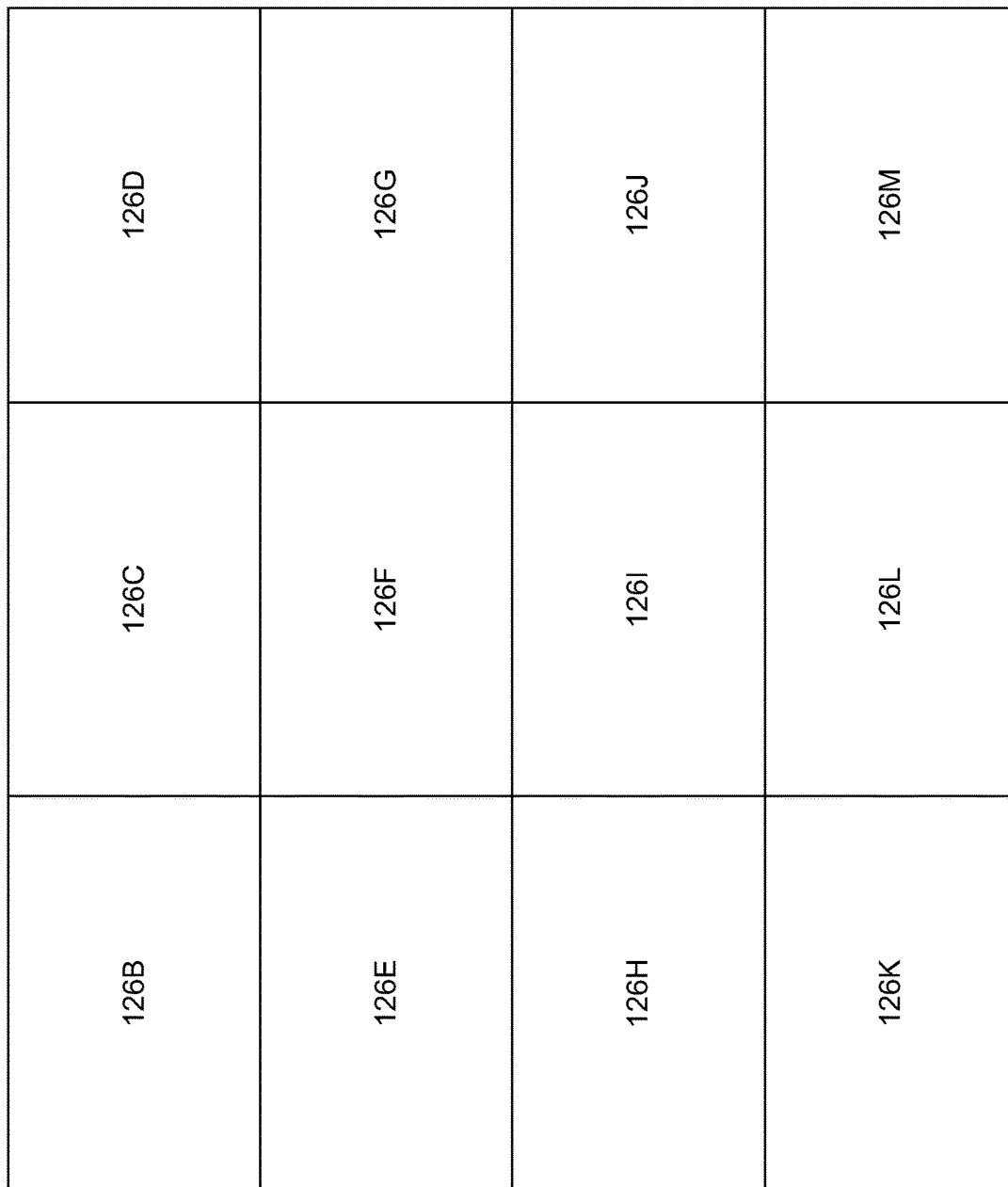
Figure 126B:
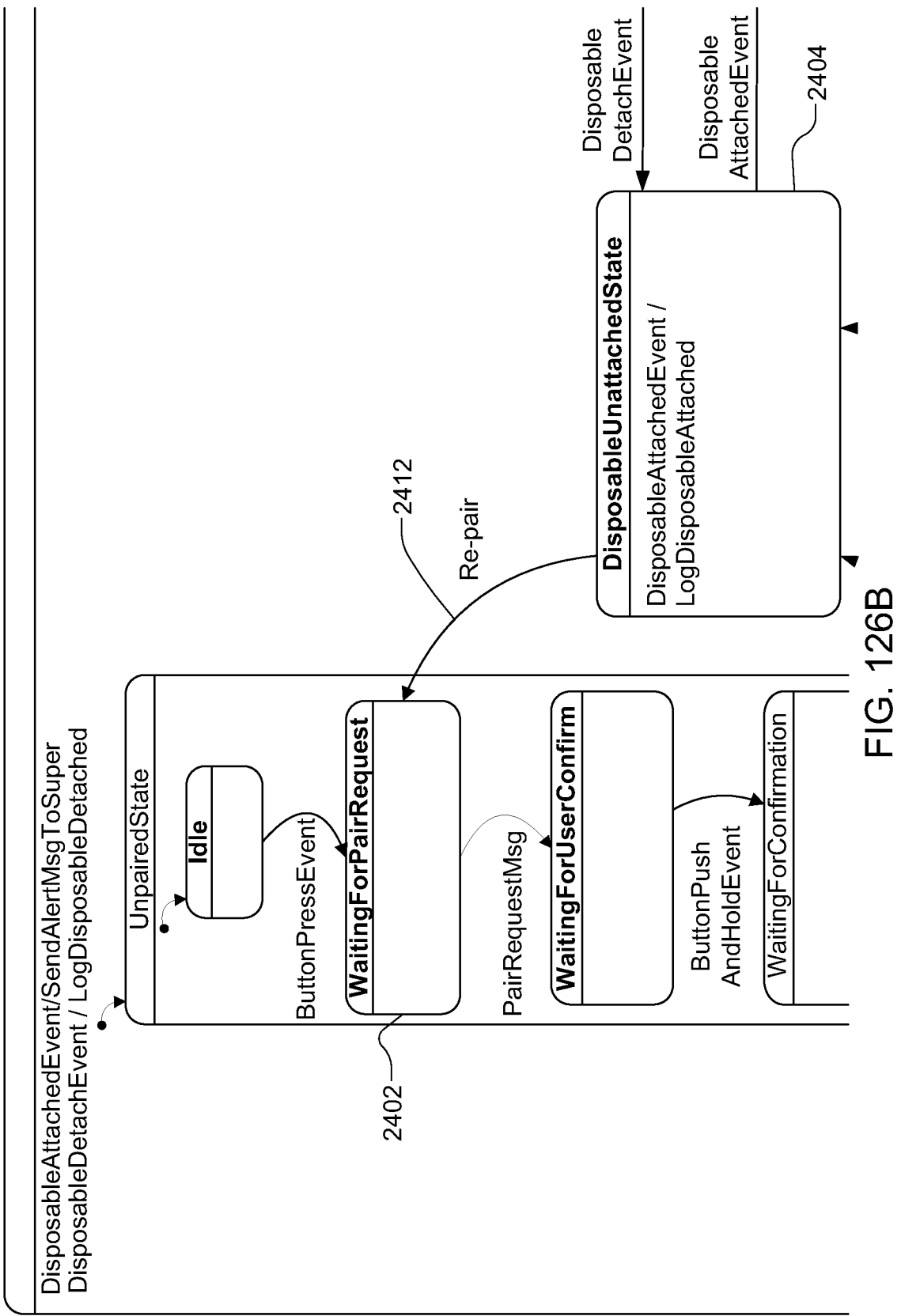
Figure 126C:
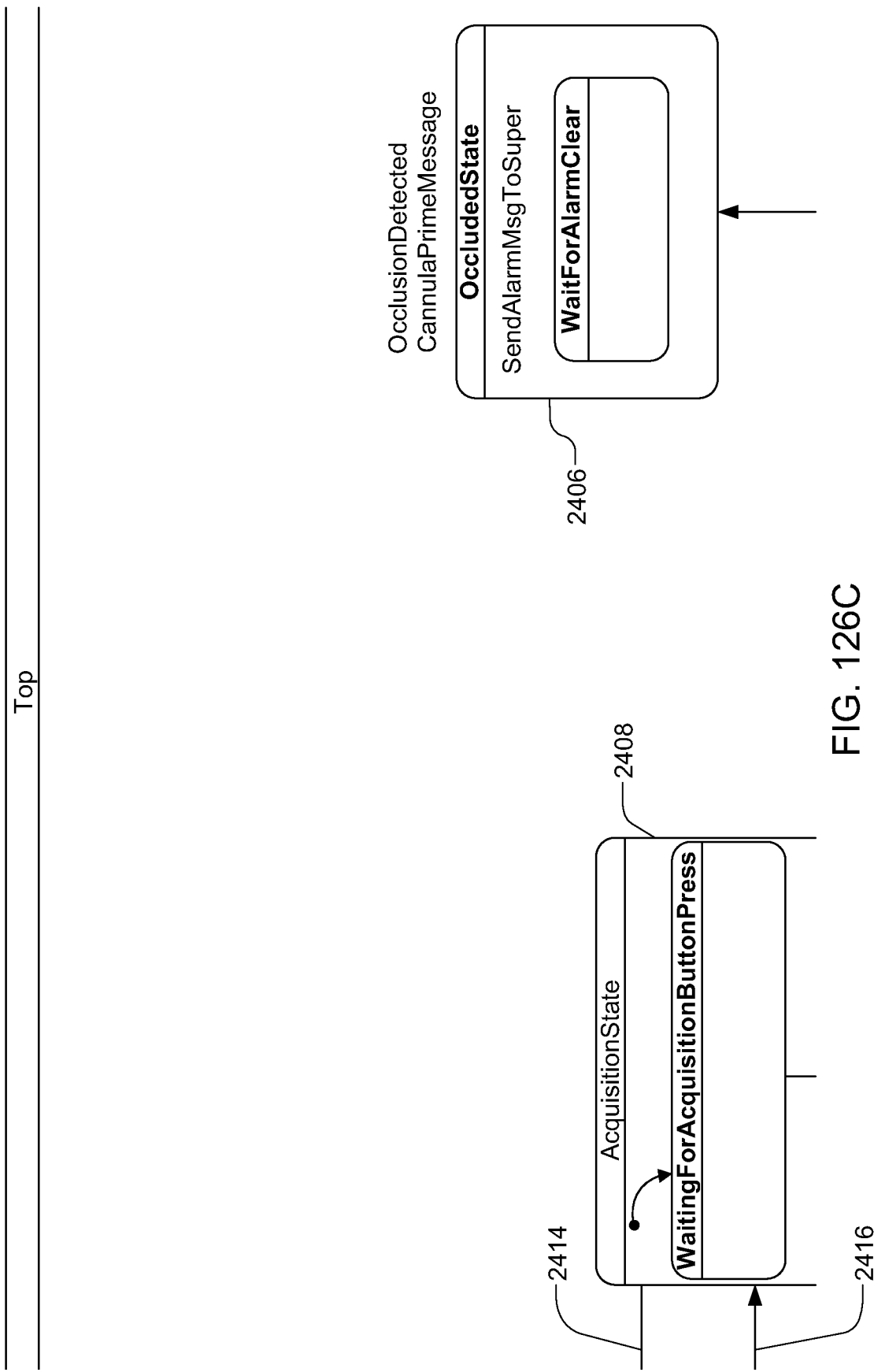
Figure 126D:
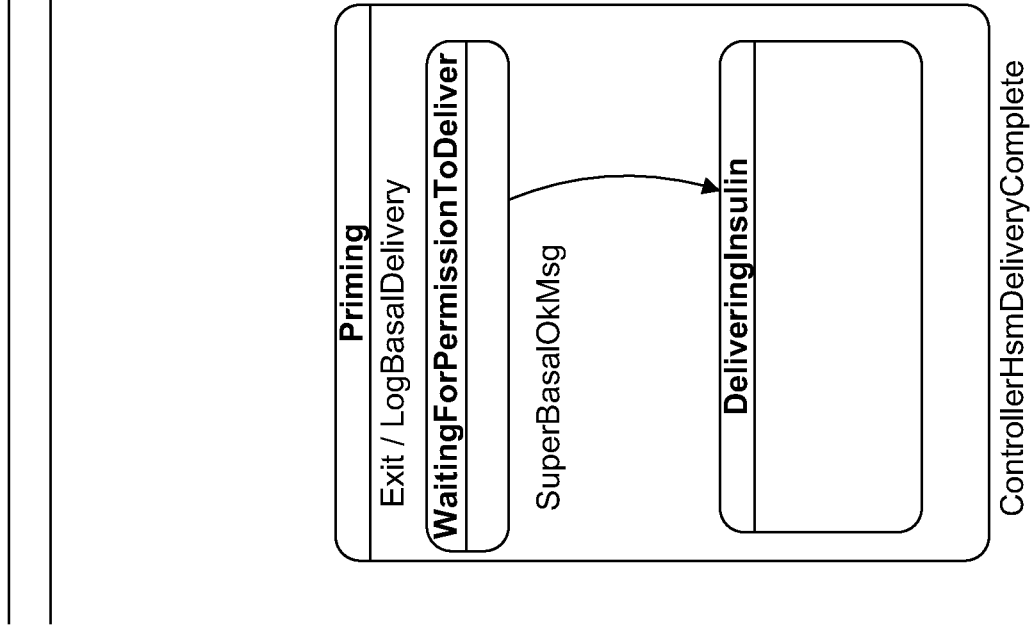
Figure 126E:
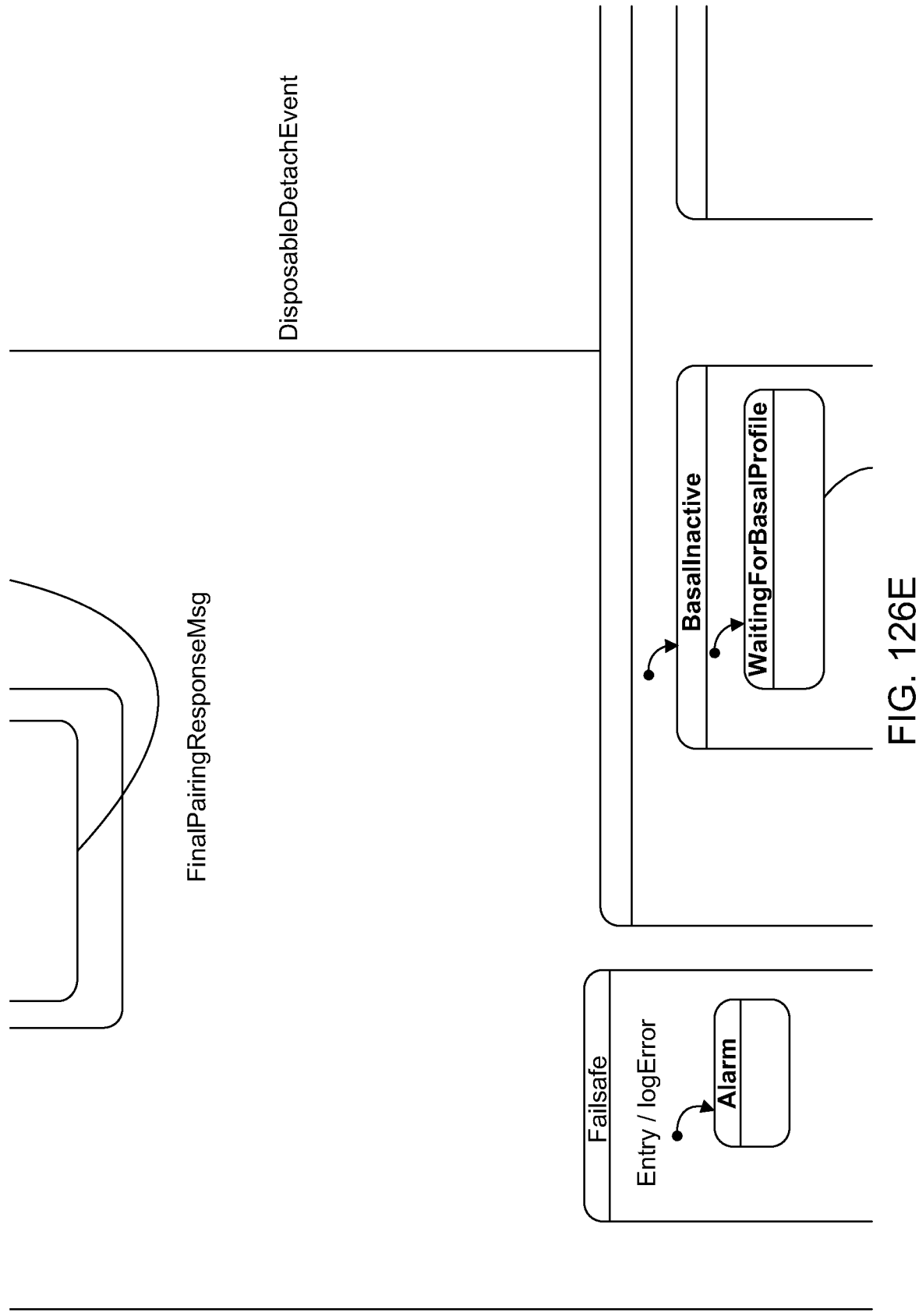
Figure 126F:
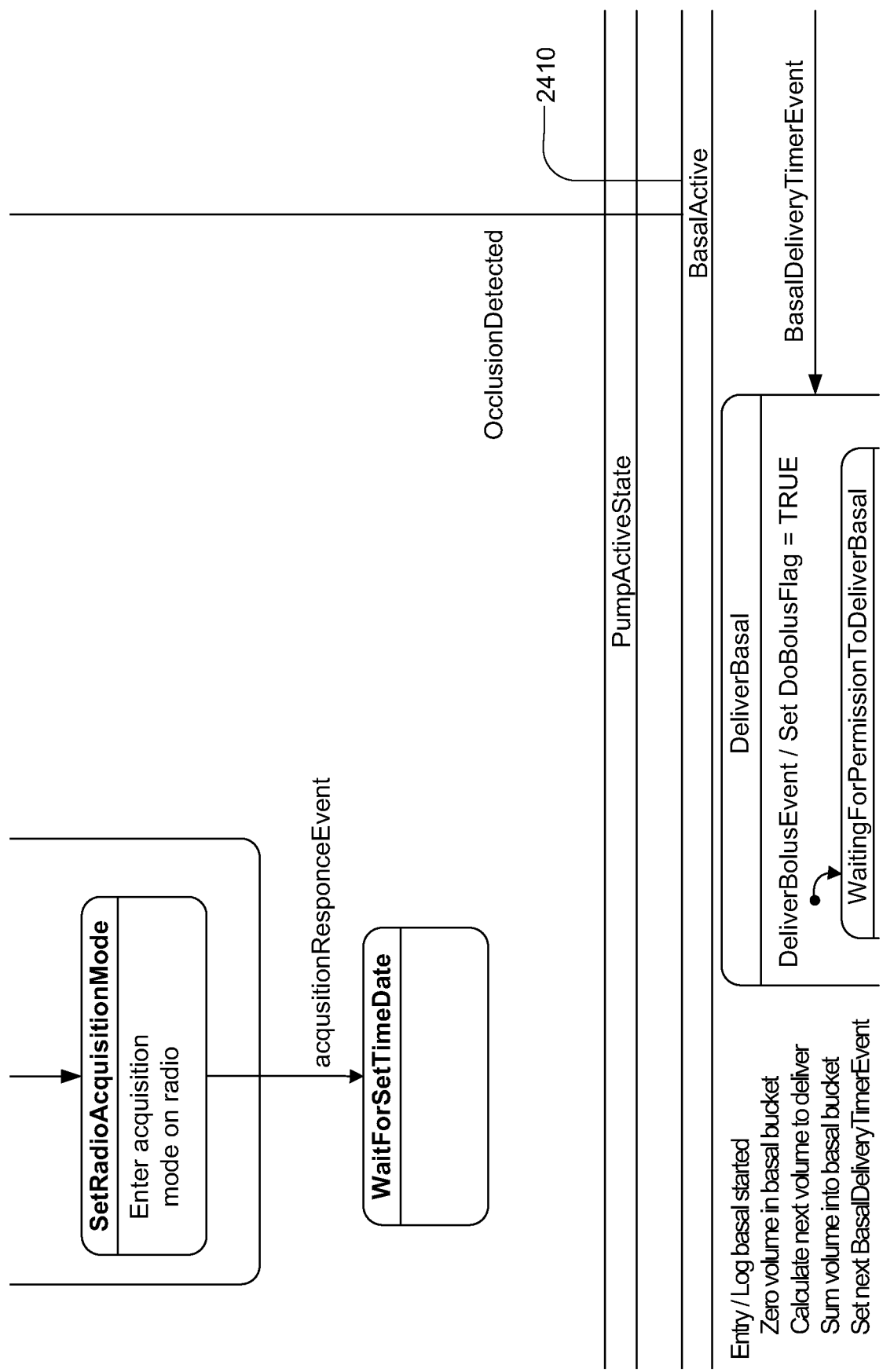
Figure 126G:
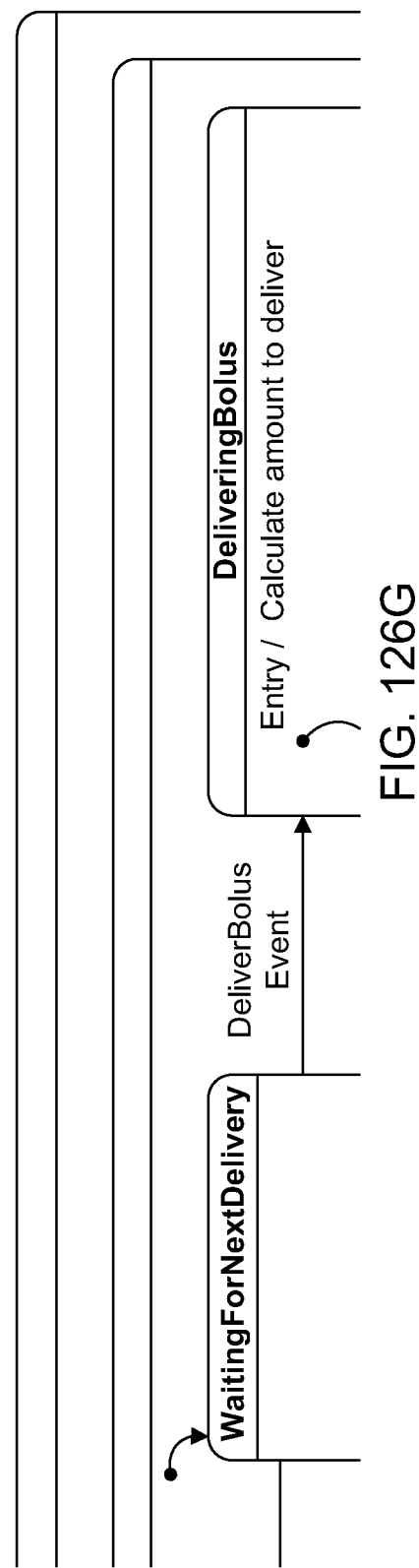
Figure 126H:
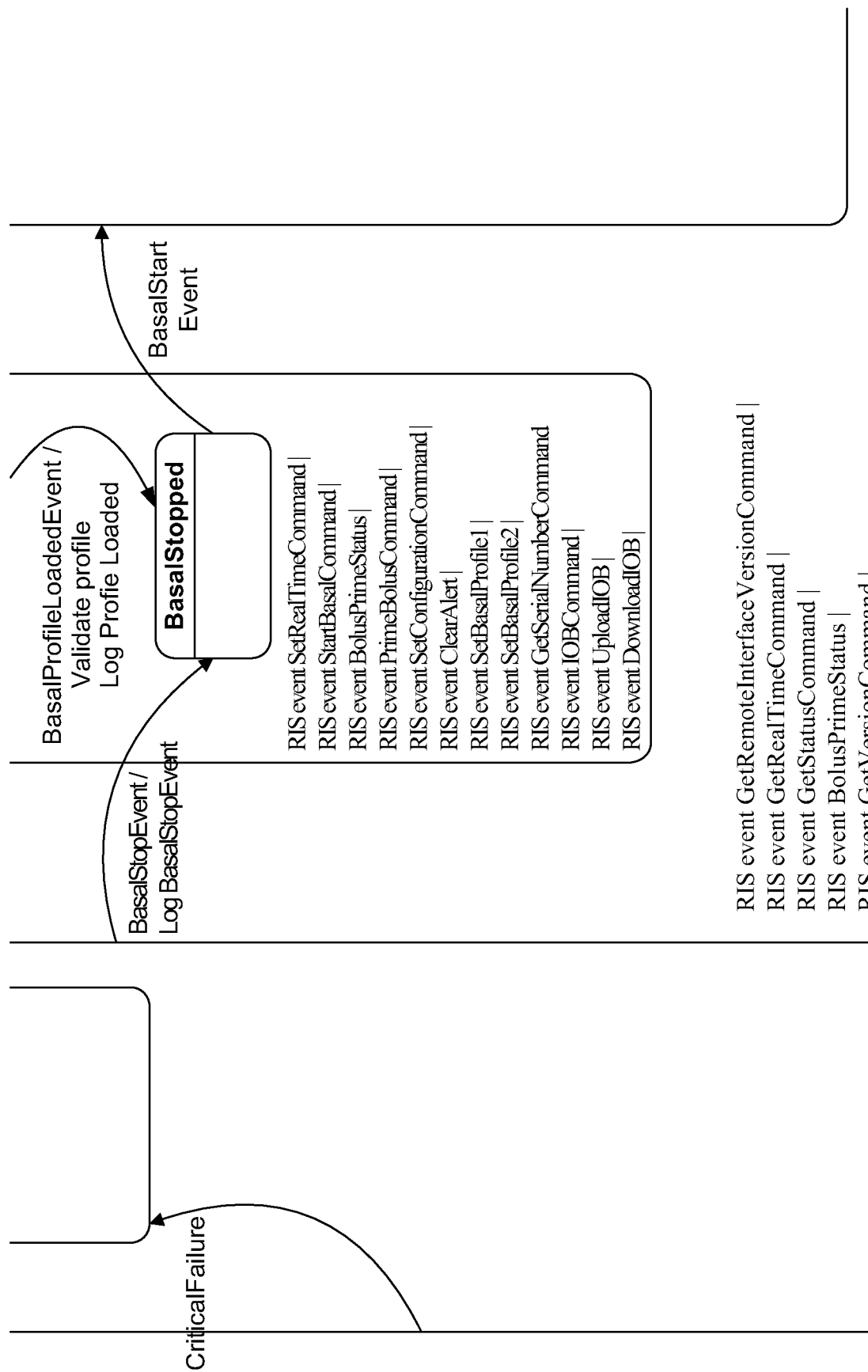
Figure 126I:
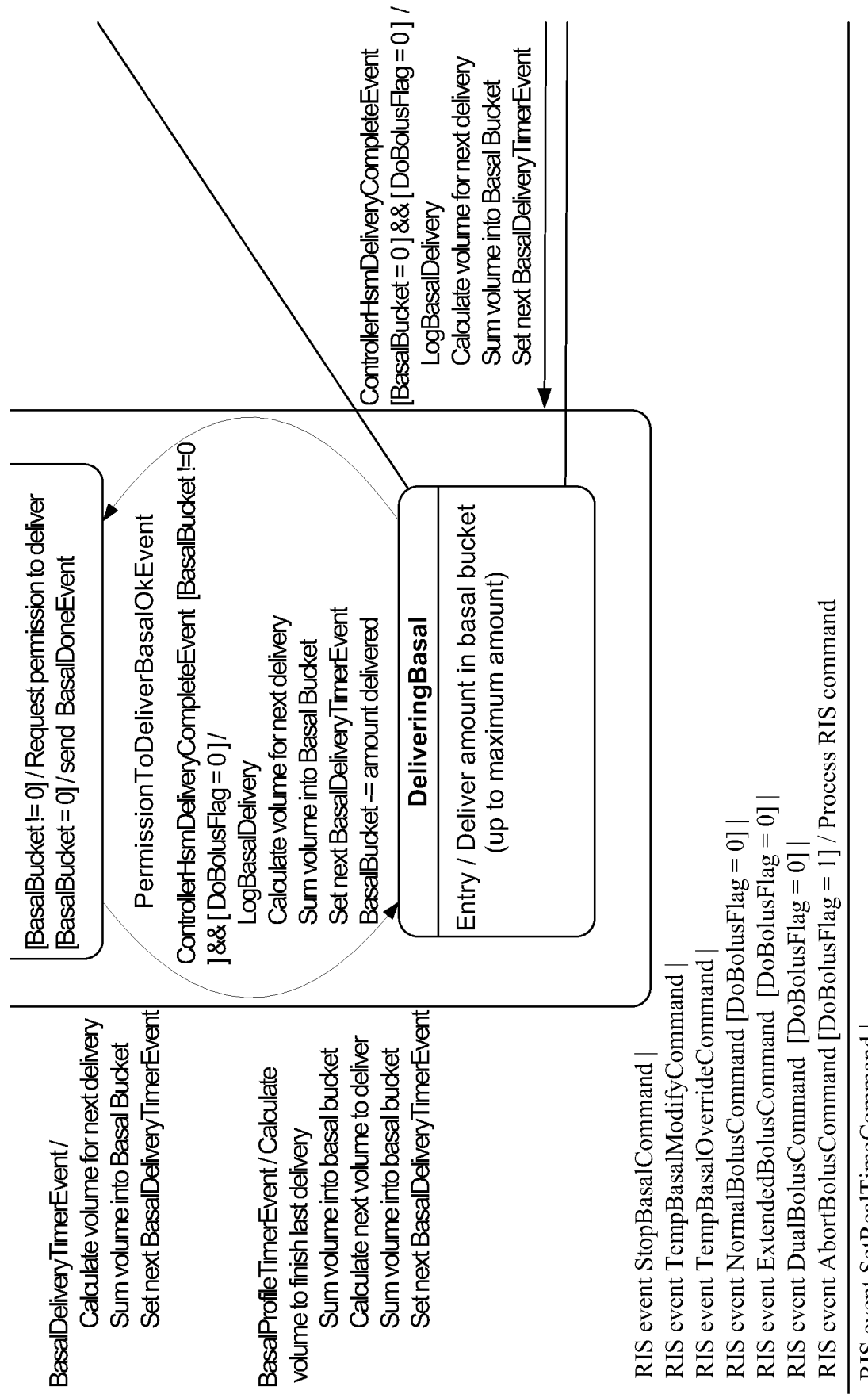
Figure 126J:
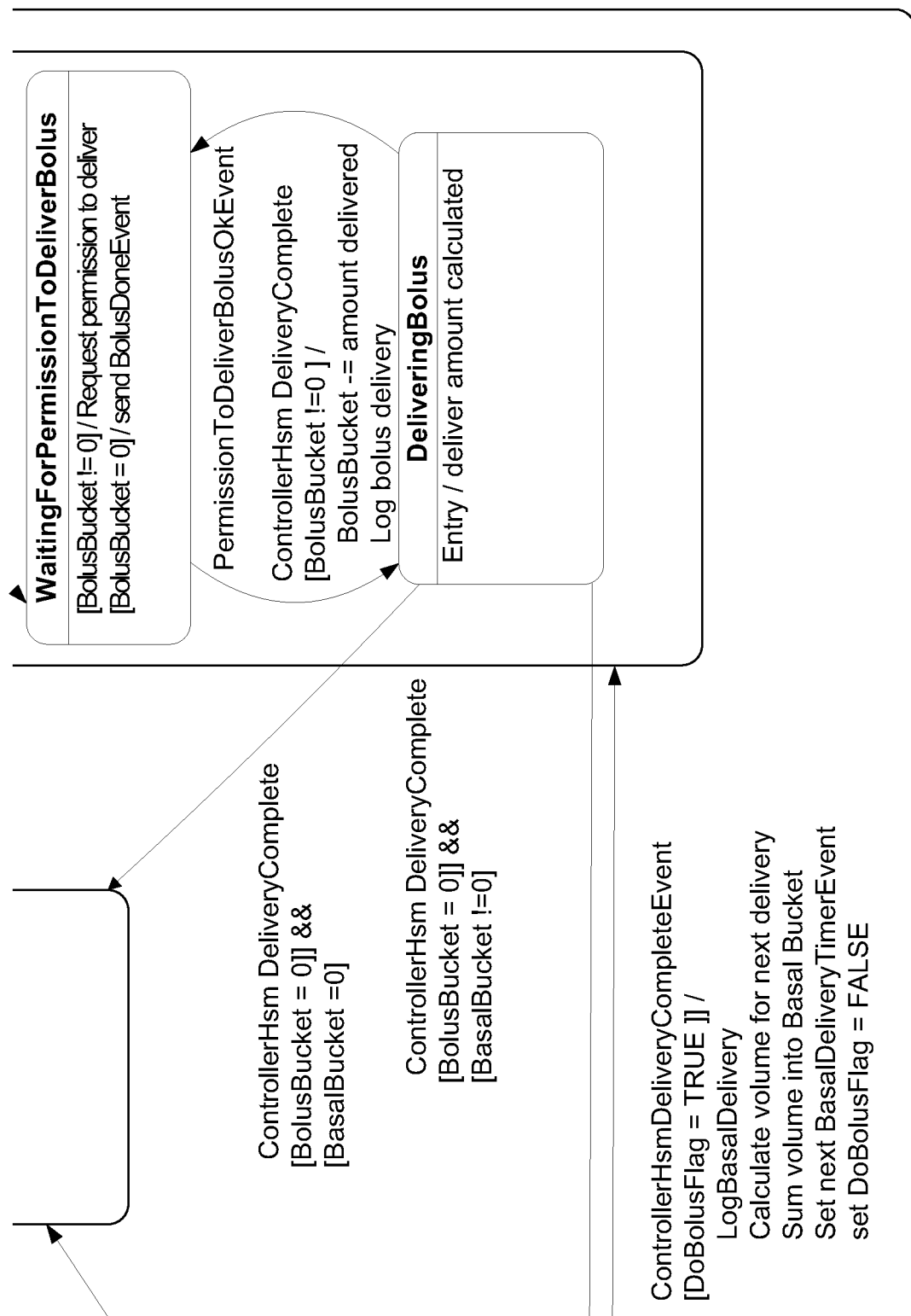
Figure 126M:
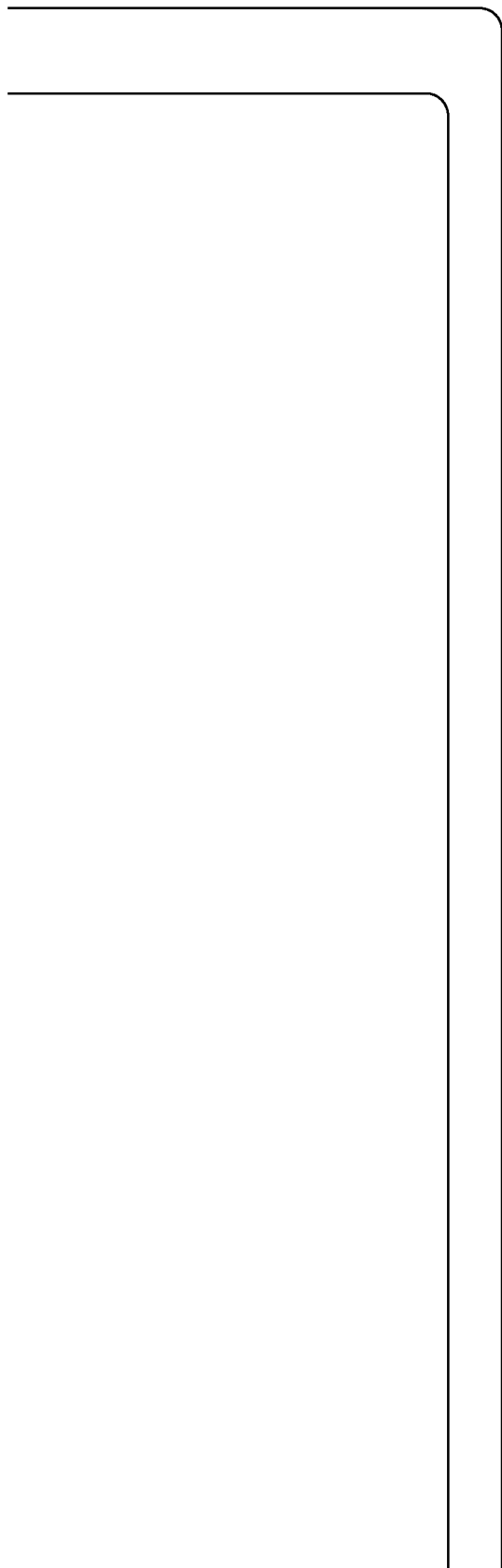

Referring also to FIG. 124 and for illustrative purposes, 0.05 unit dose 2202 is shown to include ten discrete infusion sub-events (e.g., infusion sub-events $2216_{1-10}$), wherein a 0.005 unit dose of the infusible fluid is infused during each of the ten discrete infusion sub-events. Additionally, 0.10 unit dose 2210 is shown to include ten discrete infusion sub-events (e.g., infusion sub-events $2218_{1-10}$), wherein a 0.01 unit dose of the infusible fluid is delivered during each of the ten discrete infusion sub-events. Further, one-time infusion event 2214 may include e.g., three-hundred-sixty one-time infusion sub-events (not shown), wherein a 0.1 unit dose of the infusible fluid is delivered during each of the three-hundred-sixty one-time infusion sub-events. The number of sub-events defined above and the quantity of the infusible fluid delivered during each sub-event is solely for illustrative purposes only and is not intended to be a limitation of this disclosure, as the number of sub-events and/or the quantity of the infusible fluid delivered during each sub-event may be increased or decreased depending upon e.g., the design criteria of infusion pump assembly 100, 100' 400, 500.

Before, after, or in between the above-described infusion sub-events, infusion pump assembly 100, 100' 400, 500 may confirm the proper operation of infusion pump assembly 100, 100' 400, 500 through the use of any of the above-described safety features (e.g., occlusion detection methodologies and/or failure detection methodologies).

Figure 127:
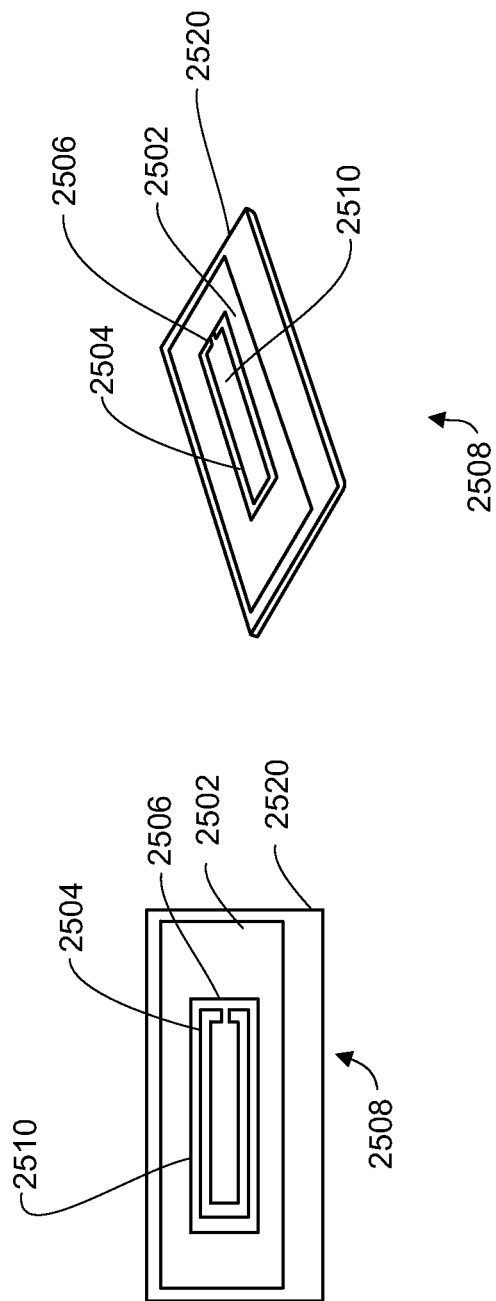
FIG. 127 is an exemplary diagram of a split ring resonator antenna.
Figure 131:
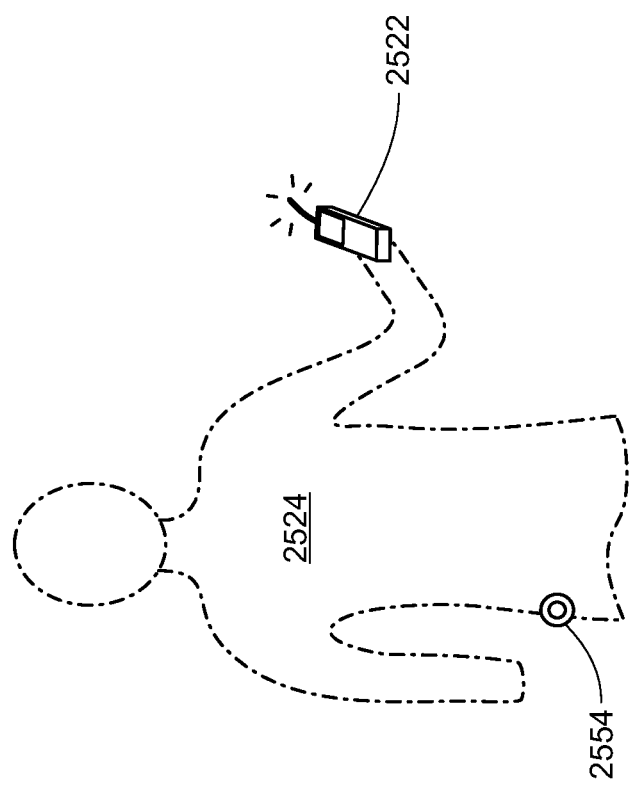
FIG. 131 is an exemplary diagram of a split ring resonator antenna integrated into a device which operates within close proximity to dielectric material.

In the exemplary embodiments, the infusion pump assembly may be wirelessly controlled by a remote control device. In the exemplary embodiments, a split ring resonator antenna may be used for wireless communication between the infusion pump assembly and the remote control device (or other remote device). The term "wirelessly controlled" refers to any device that may receive input, instructions, data, or other, wirelessly. Further, a wirelessly controlled insulin pump refers to any insulin pump that may wirelessly transmit and/or receive data from another device. Thus, for example, an insulin pump may both receive instructions via direct input by a user and may receive instructions wirelessly from a remote controller. Referring to FIG. 127 and FIG. 131, an exemplary embodiment of a split ring resonator antenna adapted for use in a wirelessly controlled medical device, and is used in the exemplary embodiment of the infusion pump assembly, includes at least one split ring resonator antenna (hereinafter "SRR antenna") 2508, a wearable electric circuit, such as a wirelessly controlled medical infusion apparatus (hereinafter "infusion apparatus") 2514, capable of powering the antenna, and a control unit 2522.

In various embodiments, a SRR antenna 2508 may reside on the surface of a non-conducting substrate base 2500, allowing a metallic layer (or layers) to resonate at a predetermined frequency. The substrate base 2500 may be composed of standard printed circuit board material such as Flame Retardant 2 (FR-2), FR-3, FR-4, FR-5, FR-6, G-10, CEM-1, CEM-2, CEM-3, CEM-4, CEM-5, Polyimide, Teflon, ceramics, or flexible Mylar. The metallic resonating bodies comprising a SRR antenna 2508 may be made of two rectangular metallic layers 2502, 2504, made of, for example, platinum, iridium, copper, nickel, stainless steel, silver or other conducting materials. In other various embodiments, a SRR antenna 2508 may contain only one metallic resonating body.

In the exemplary embodiment, a gold-plated copper outer layer 2502, surrounds, without physically contacting, a gold-plated copper inner ring 2504. That is, the inner ring 2504 resides in the cavity 2510 (or aperture) formed by the outer layer 2502. The inner ring 2504 may contain a gap, or split 2506, along its surface completely severing the material to form an incomplete ring shape. Both metallic resonating bodies 2502, 2504 may reside on the same planar surface of the substrate base 2500. In such a configuration, the outer layer 2502 may by driven via a transmission line 2512 coupled to the outer layer 2502, for example. Additionally, in various other embodiments, a transmission line 2512 may be coupled to the inner ring 2504.

Figure 132:
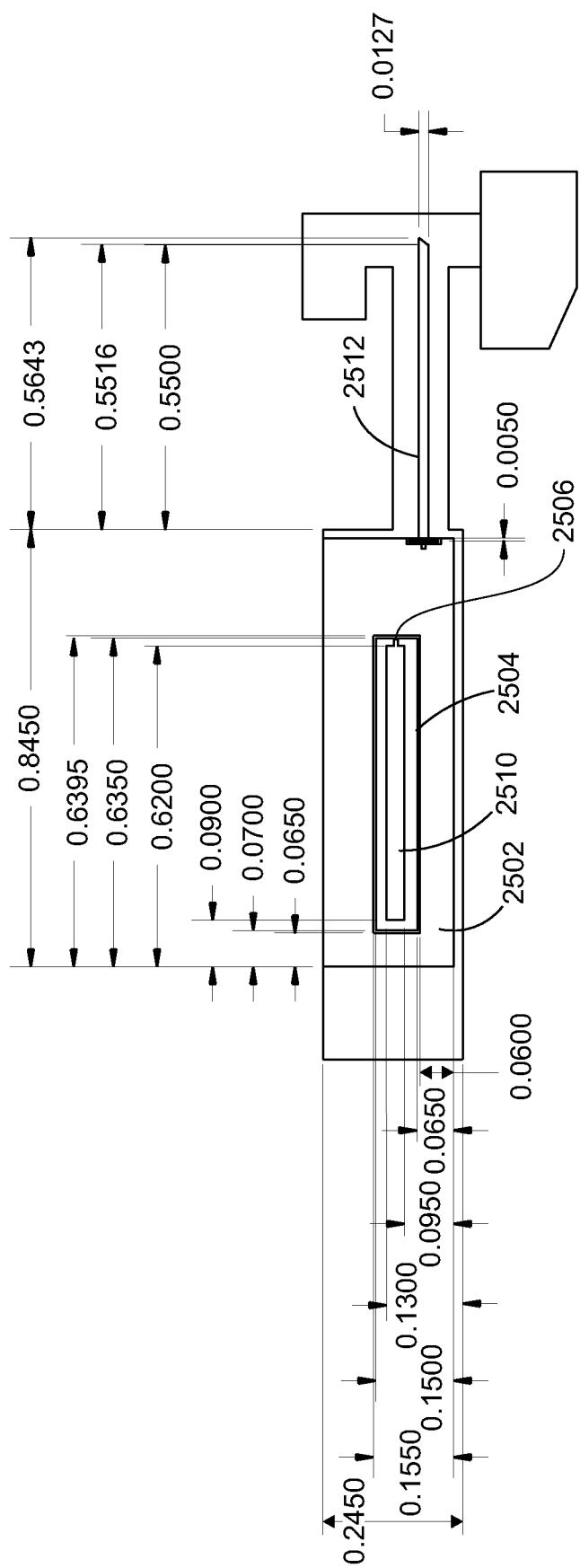
FIG. 132 is a diagram of the dimensions of the inner and outer portion of the exemplary embodiment.

Antenna design software, such as AWR Microwave Office, capable of simulating electromagnetic geometries, such as, antenna performance, may significantly decrease the time required to produce satisfactory dimensions compared to physically fabricating and testing antennas. Accordingly, with aid of such software, the SRR antenna 2508 may be designed such that the geometric dimensions of the resonant bodies 2502, 2504 facilitate an operational frequency of 2.4 GHz. FIG. 132 depicts the exemplary dimensions of the inner ring 2504 and outer layer 2502, and the positioning of the cavity 2510 in which the inner ring 2504 resides. The distance in between the outer layer 2502 and the inner ring 2504 is a constant 0.005 inches along the perimeter of the cavity 2510. However, in other embodiments, the distance between the outer layer and the inner ring may vary and in some embodiments, the operational frequency may vary.

In various embodiments, a SRR antenna 2508 may have dimensions such that it could be categorized as electrically small, that is, the greatest dimension of the antenna being far less than one wavelength at operational frequency.

In various other embodiments, a SRR antenna 2508 may be composed of one or more alternatively-shaped metallic outer layers, such as circular, pentagonal, octagonal, or hexagonal, surrounding one or more metallic inner layers of similar shape. Further, in various other embodiments, one or more metallic layers of a SRR antenna 2508 may contain gaps in the material, forming incomplete shapes.

Figure 130:
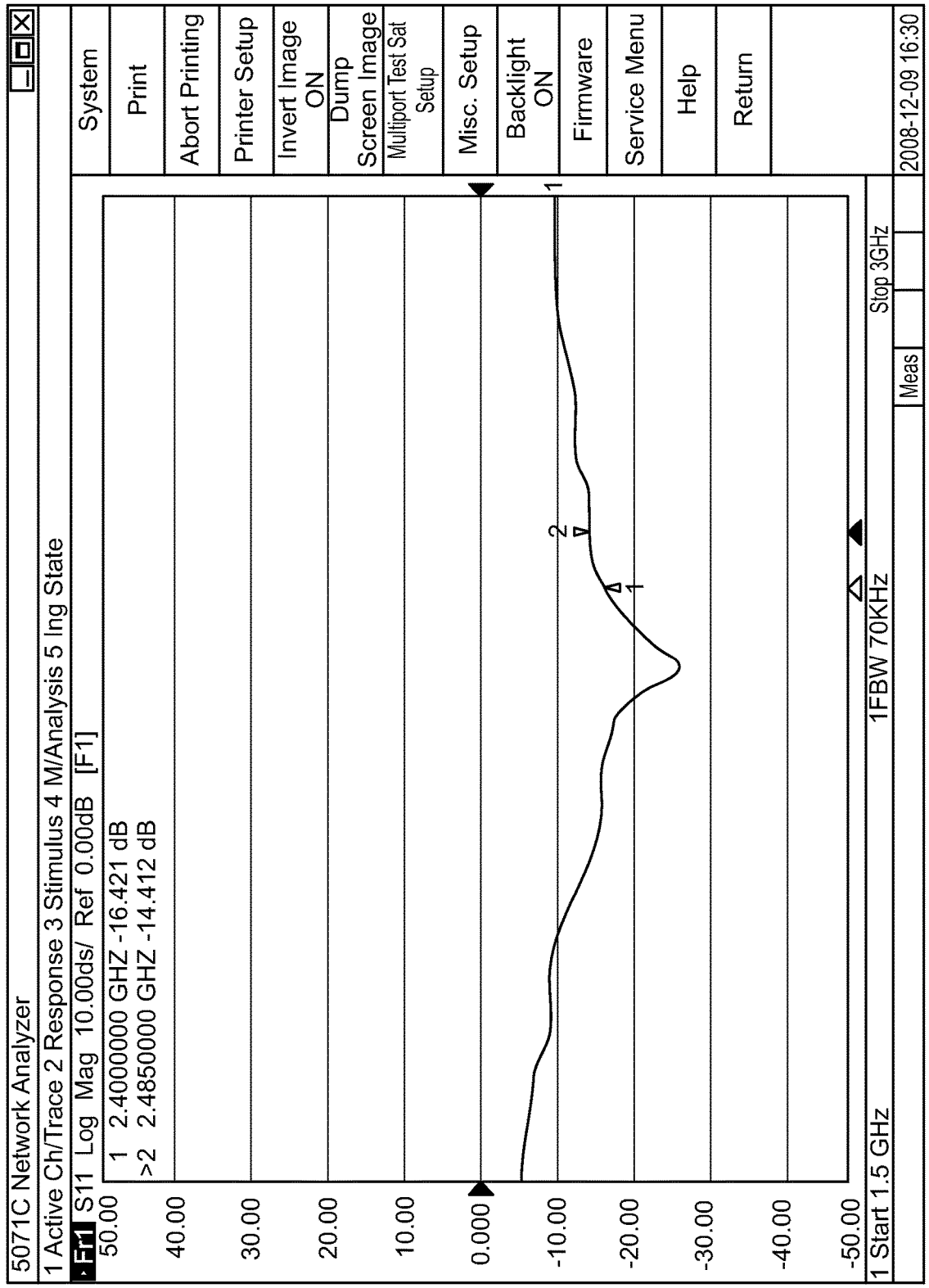
FIG. 130 is a graph of the return loss of a split ring resonator antenna prior to contact with human skin.
Figure 130A:
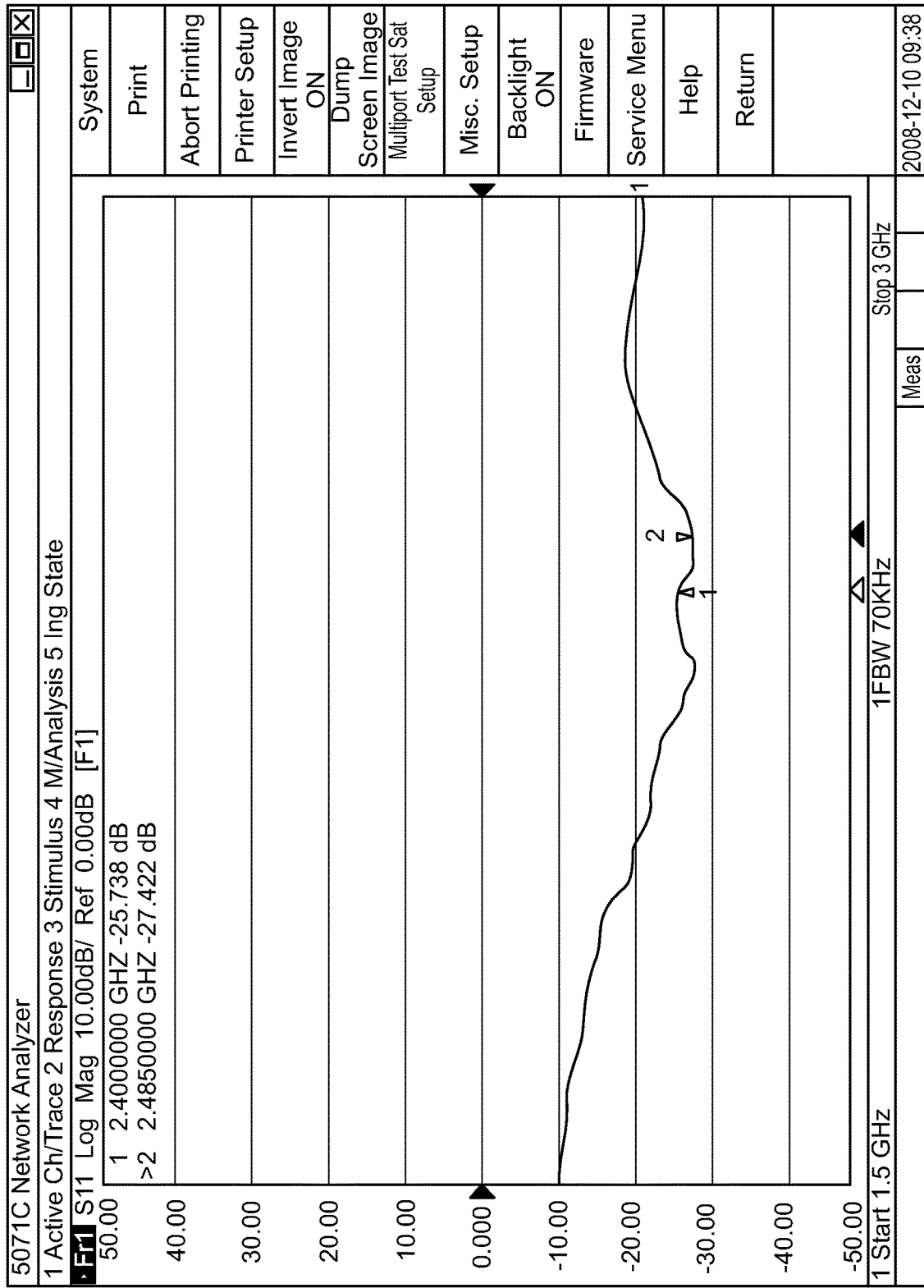
FIG. 130A is a graph of the return loss of a split ring resonator antenna during contact with human skin.

Referring to FIG. 130, a SRR antenna 2508 having the exemplary geometry exhibits acceptable return loss and frequency values when placed in contact with human skin. As shown in FIG. 130, focusing on the band of interest denoted by markers 1 and 2 on the graph, return loss prior to contact with human skin is near −15 dB while monitoring a frequency band centered around 2.44 GHz. Return loss during contact with human skin, as shown in FIG. 130A, remains a suitable value near −25 dB at the same frequency, yielding approximately 97% transmission power.

Figure 133:
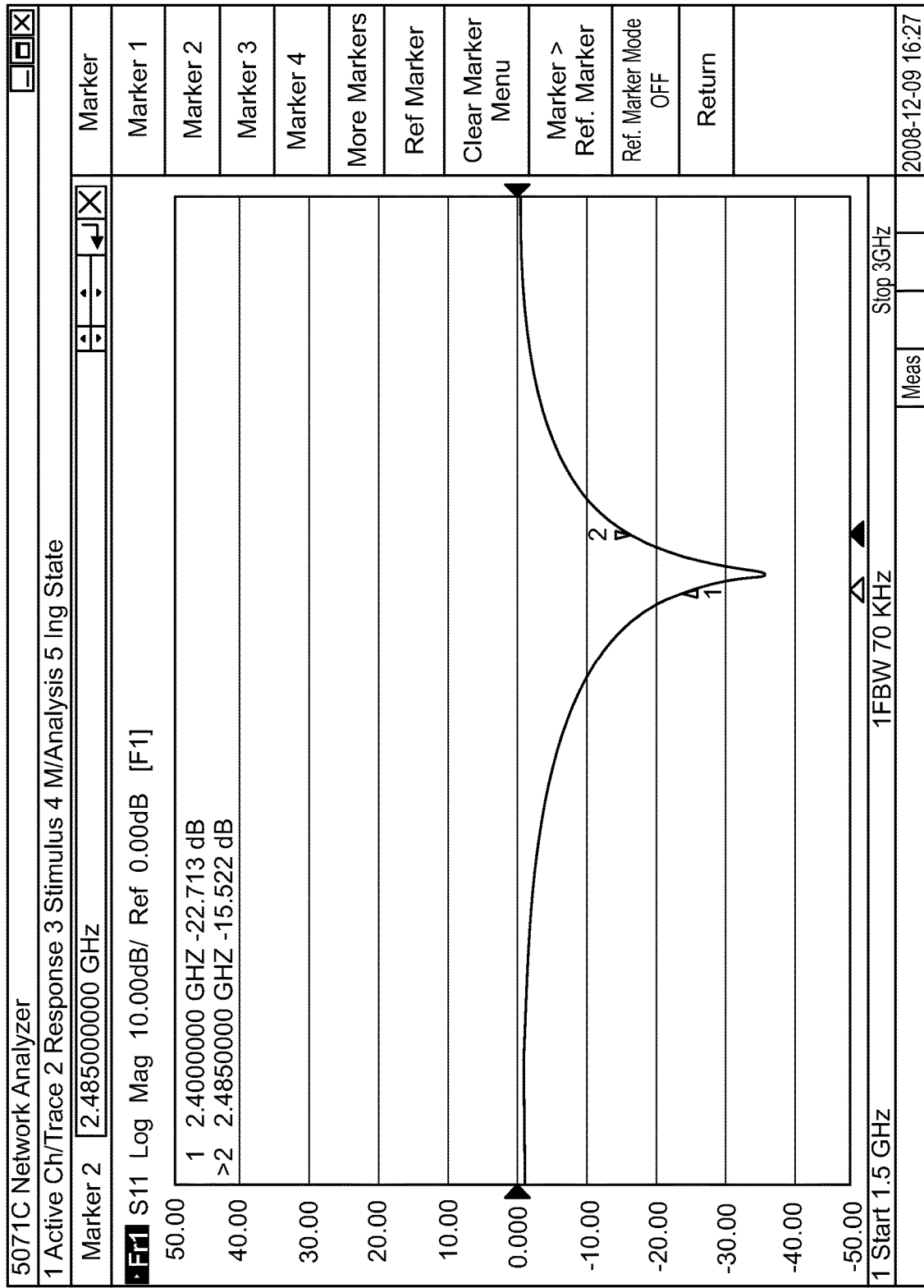
FIG. 133 is a graph of the return loss of a non-split ring resonator antenna prior to contact with human skin.
Figure 133A:
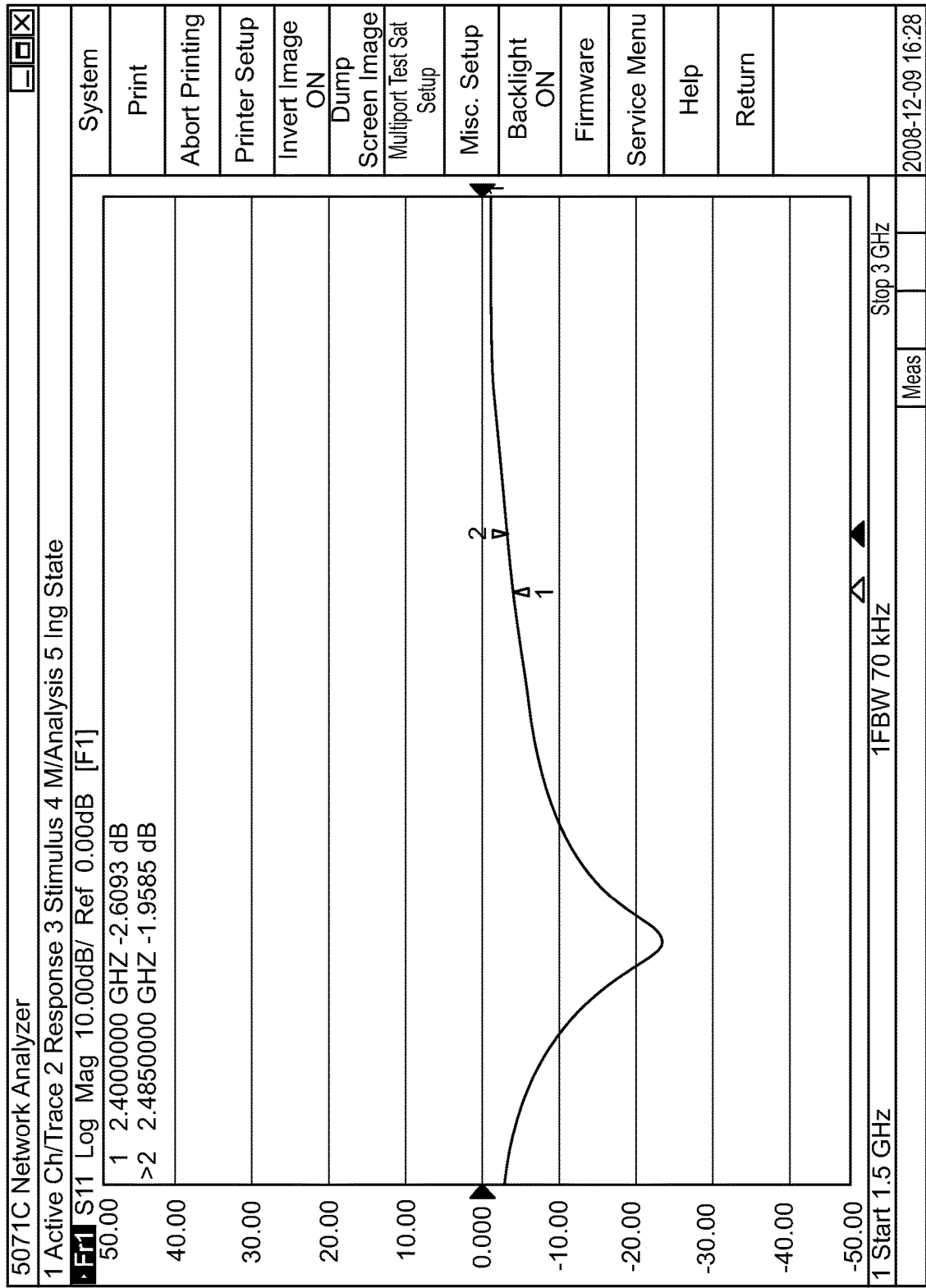
FIG. 133A is a graph of the return loss of a non-split ring resonator antenna during contact with human skin.

These results are favorable especially as compared with a non-split ring resonator antenna type, such as the Inverted-F. Return loss of an Inverted-F antenna may exhibit a difference when the antenna contacts human skin, resulting in a low percentage of power transmitted outward from the antenna. By way of example, as shown in FIG. 133, and again focusing on the band of interest denoted by markers 1 and 2 on the graph, return loss of an Inverted-F antenna prior to contact with human skin is near −25 dB at a frequency centered around 2.44 GHz. Return loss during contact with human skin is nearly −2 dB at the same frequency, yielding approximately 37% power transmission.

Integration with a Wireless Medical Device

Figure 128:
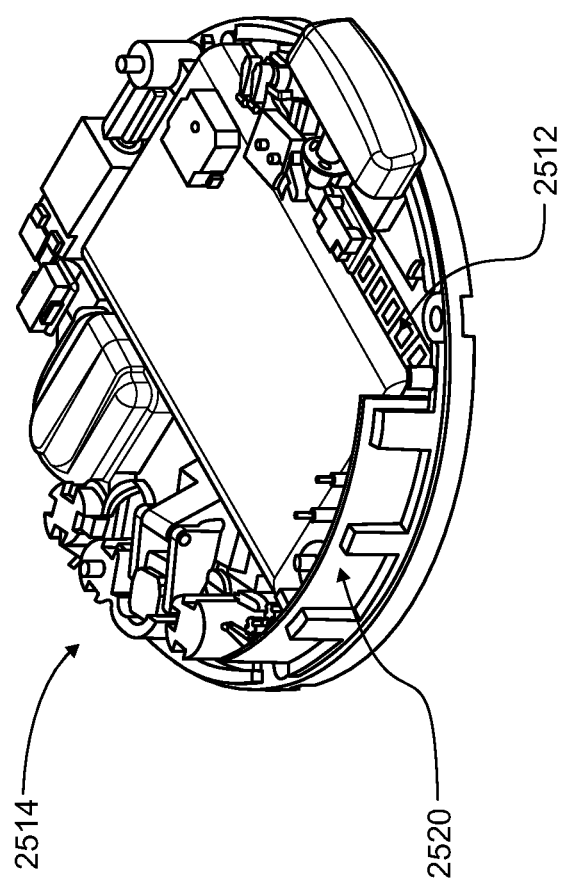
FIG. 128 is an exemplary diagram of a medical device configured to utilize a split ring resonator antenna.

In the exemplary embodiment, referring to FIG. 132 and FIG. 128, one application of a SRR antenna 2508 may be integration into a wearable infusion apparatus 2514 capable of delivering fluid medication to a user/patient 2524. In such an application, the safety of the user/patient is dependent on fluid operation between these electrical components, thus reliable wireless transmission to and from a control unit 2522 is of great importance.

An infusion apparatus 2514 may be worn directly on the human body. By way of example, such a device may be attached on or above the hip joint in direct contact with human skin, placing the SRR antenna 2508 at risk of unintended dielectric loading causing a frequency shift in electrical operation. However, in such an application, electrical characteristics of the SRR antenna 2508 which allow it to be less sensitive to nearby parasitic objects are beneficial in reducing or eliminating degradation to the performance. A controlling component, such as a control unit 2522 (generally shown in FIG. 131), may be paired with an infusion apparatus 2514, and may be designed to transmit and receive wireless signals to and from the infusion apparatus 2514 at a predetermined frequency, such as 2.4 GHz. In the exemplary embodiment, the control unit 2522 serves as the main user interface through which a patient or third party may manage insulin delivery. In other embodiments, infusion apparatus 2514 may utilize a SRR antenna 2508 to communicate with one or more control units 2522.

In various embodiments, a number of different wireless communication protocols may be used in conjunction with the SRR antenna 2508, as the protocol and data types to be transferred are independent of the electrical characteristics of the antenna. However, in the exemplary embodiment, a bi-directional master/slave means of communication organizes the data transfer through the SRR antenna 2508. The control unit 2522 may act as the master by periodically polling the infusion apparatus 2514, or slave, for information. In the exemplary embodiment, only when the slave is polled, the slave may send signals to the control unit 2522 only when the slave is polled. However, in other embodiments, the slave may send signals before being polled. Signals sent by way of this system may include, but are not limited to, control, alarm, status, patient treatment profile, treatment logs, channel selection and negotiation, handshaking, encryption, and check-sum. In some embodiments, transmission through the SRR antenna 2508 may also be halted during certain infusion operations as an added precaution against electrical disruption of administration of insulin to the patient.

In the exemplary embodiment, the SRR antenna 2508 may be coupled to electrical source circuitry via one or more pins 2516 on a transmission line 2512. In various other embodiments a transmission line may comprise a wire, pairs of wire, or other controlled impedance methods providing a channel by which the SRR antenna 2508 is able to resonate at a certain frequency. The transmission line 2512 may reside on the surface of the substrate base 2500 and may be composed of the same material as the SRR antenna 2508, such as gold-plated copper. Additionally, a ground plane may be attached to the surface of the substrate base opposite the transmission line 2512.

The electrical circuitry coupled to the SRR antenna 2508 may apply an RF signal to the end of the transmission line 2512 nearest the circuitry, creating an electromagnetic field throughout, and propagating from, the SRR antenna 2508. The electrical circuitry coupled to the SRR antenna 2508 facilitates resonance at a predetermined frequency, such as 2.4 GHz. Preferably, transmission line 2512 and SRR antenna 2508 both have impedances of 50 Ohms to simplify circuit simulation and characterization. However, in other various embodiments, the transmission line and split ring resonator antenna may have other impendence values, or a different resonating frequency.

Figure 129:
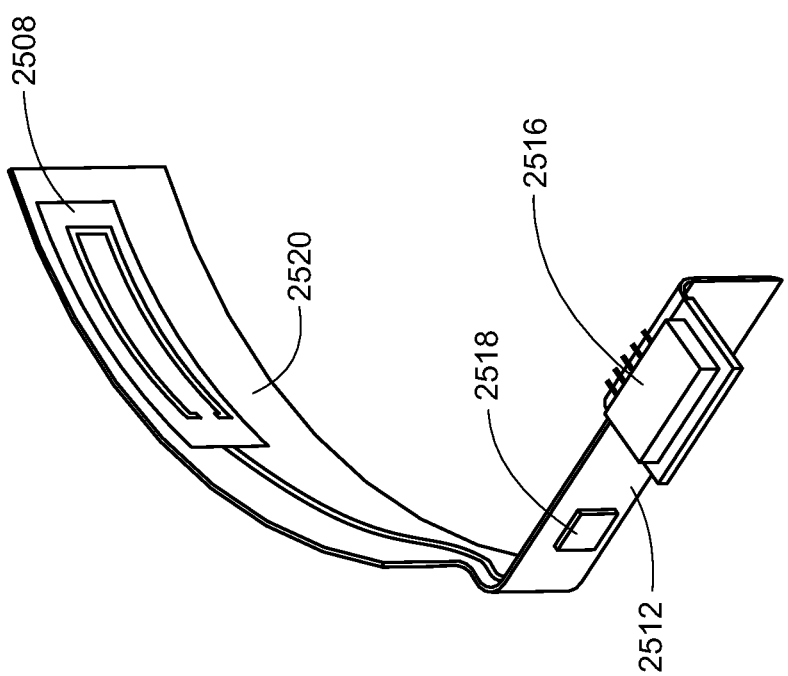
FIG. 129 is an exemplary diagram of a split ring resonator antenna and transmission line from a medical infusion device.

Referring to FIG. 129, a signal processing component(s) 2518, such as, a filter, amplifier, or switch, may be integrated into the transmission line 2512, or at some point between the signal source connection pins 2516 and the SRR antenna 2508. In the exemplary embodiment, the signal processing component 2518 is a band-pass filter to facilitate desired signal processing, such as, allowing only the exemplary frequency to be transmitted to the antenna, and rejecting frequencies outside that range. In the exemplary embodiment, a Combline band-pass filter 2518 may be included in the transmission line 2512 between the antenna and the signal source. However in other embodiments, any other signal processing device, for example, but not limited to, filters, amplifiers, or any other signal processing devices known in the art.

In various embodiments, a SRR antenna 2508 may be composed of metallic bodies capable of resonating on a flexible or rigid substrate. As shown in FIG. 128 and FIG. 3, the exemplary embodiment incorporates a curved SRR antenna on a flexible Polyimide substrate 2520. Polyimide may be the exemplary material because it tends to be more flexible than alternative substrates. This configuration may allow for simplified integration into circular-shaped devices (such as a wirelessly controlled medical infusion apparatus 2514), devices with irregular-shaped external housing, or devices in which saving space is paramount.

In various embodiments, both control unit 2522 and base unit 2514 may incorporate a split SRR antenna 2508. This configuration may prove beneficial where the control unit is meant to be handheld, in close proximity to human skin, or is likely to be in close proximity to a varying number of materials with varying dielectric constants.

In various other embodiments, a SRR antenna 2508 may be integrated into a human or animal limb replacement. As prosthetic limbs are becoming more sophisticated the electrical systems developed to control and simulate muscle movements require much more wiring and data transfer among subsystems. Wireless data transfer within a prosthetic limb may reduce weight through reduced physical wiring, conserve space, and allow greater freedom of movement. However, common antennas in such a system may be susceptible to dielectric loading. Similar to the previously mentioned benefits of integrating a SRR antenna 2508 into a wirelessly controlled medical infusion apparatus, a prosthetic limb, such as a robotic arm, may also come into contact with human skin or other dielectric materials and benefit from the reduction of electrical disturbances associated with such an antenna. In other various embodiments, the SRR antenna 2508 may be integrated into any device comprised of the electrical components capable of powering and transmitting/receiving data to an antenna and susceptible to electrical disturbances associated with proximity to dielectric materials.

In various embodiments, a SRR antenna 2508 may be integrated into a configuration of medical components in which one or more implantable medical devices, operating within the human body, communicate wirelessly to a handheld, body-mounted, or remote control unit. In certain embodiments, both body-mounted and in-body wireless devices may utilize a SRR antenna 2508 for wireless communication. Additionally, one or more of the components utilizing a SRR antenna 2508 may be completely surrounded by human skin, tissue or other dielectric material. By way of example, such a configuration may be used in conjunction with a heart monitoring/control system where stability and consistency of wireless data transmission are of fundamental concern.

In various other embodiments, a SRR antenna 2508 may be integrated into the embodiments of the infusion pump assembly. Configuration of medical components in which one or more electrical sensors positioned on, or attached to, the human body wirelessly communicate to a remote transceiving unit. By way of example, a plurality of electrodes positioned on the body may be coupled to a wireless unit employing a SRR antenna 2508 for wireless transmission to a remotely located electrocardiogram machine. By way of further example, a wireless temperature sensor in contact with human skin may employ SRR antenna 2508 for wireless communication to a controller unit for temperature regulation of the room in which the sensor resides.

As discussed and described above, in some embodiments of the infusion pump system the SMA may control both the pump assembly (including the pump assembly 106, however, in various other embodiments, the SMA may also control of various embodiments of the pump assembly), and the various embodiments shown and described herein of the measurement valve assembly. However, in some embodiments, the SMA may be controlled using at least one optical position sensor assembly ("optical sensor") wherein the position of the pump assembly plunger ("pump plunger") and the measurement valve plunger is measured using at least one optical position sensor, and in the exemplary embodiments, at least one pump assembly plunger optical sensor and at least one measurement valve plunger optical position sensor. Thus, in these embodiments, the command processor provides closed-loop control of the pump plunger position and measurement valve plunger position by comparing the optical sensor output to a target position and then modifying the PWM of the low-side field effect transistors ("FET"). In addition, voltages are measured at various positions such the SMA controller may detect various conditions of the system including, but not limited to, one or more of the following: a broken SMA wire, failed FET and/or a depleted battery assembly and/or power source. Thus, the actual plunger position may be determined for, in some embodiments, both the pump plunger and the measurement valve plunger, and target plunger positions may be established.

Referring now to FIGS. 145-149B various embodiments of the optical position sensor in the infusion pump system is shown. Some embodiments of the apparatus, methods and systems will be described below with reference to an exemplary embodiment. The exemplary embodiment is described with respect to a medical infusion pump, which in some embodiments may be an infusion pump, which may, in some embodiments, be an insulin pump, as shown and described herein, however, the optical position sensor described herein may also be used with various other infusion pumps and/or medical delivery devices and/or medical systems including, but not limited to, those described in U.S. Pat. No. 7,498,563 issued Mar. 3, 2009 and entitled Optical Displacement Sensor for Infusion Devices, U.S. Pat. No. 7,306,578 issued Dec. 11, 2007 and entitled Loading Mechanism for Infusion Pump, U.S. patent application Ser. No. 11/704,899 filed Feb. 9, 2007, now U.S. Publication No. US-2007-0228071-A1, and entitled Fluid Delivery Systems and Methods, U.S. patent application Ser. No. 11/704,896 filed Feb. 9, 2007, now U.S. Publication No. US-2007-0219496-A1, published Sep. 20, 2007 and entitled Pumping Fluid Delivery Systems and Methods Using Force Application Assembly, U.S. patent application Ser. No. 11/704,886 filed Feb. 9, 2007, now U.S. Publication No. US-2007-0219480-A1, published Sep. 20, 2007 and entitled Patch-Sized Fluid Delivery Systems and Methods, U.S. patent application Ser. No. 11/704,897 filed Feb. 9, 2007, now U.S. Publication No. US-2007-0219597-A1, published Sep. 20, 2007 and entitled Adhesive and Peripheral Systems and Methods for Medical Devices, U.S. patent application Ser. No. 12/560,106 filed Sep. 15, 2009, now U.S. Publication No. US-2010-0185142-A1, published Jul. 22, 2010 and entitled Systems and Methods for Fluid Delivery, and U.S. patent application Ser. No. 12/649,681 filed Dec. 30, 2009, now U.S. Publication No. US-2010-0198182-A1, published Aug. 5, 2010 and entitled Method, System and Apparatus for Verification of Volume and Pumping, which are each hereby incorporated herein by reference in their entireties. Reference herein to a disposable may refer to, in some embodiments, the disposable housing assembly and/or disposable portion and/or reservoir portion of the various infusion pumps described in any of the above-discussed infusion pumps.

However, the apparatus, systems and methods described herein may be used in any infusion pump or apparatus. Further, the apparatus, systems and methods described herein may be used to verify the movement of any plunger, pump actuator, valve and/or other moveable part within any medical device to confirm that movement and/or displacement occurred. Further, in addition to confirmation of movement, the determination of the distance of movement, i.e. the total displacement, may also be used in some embodiments.

Referring also to FIG. 150, the various embodiments of the infusion pump apparatus, methods and systems include the control of the pump and one or more active valves by contraction of a SMA wire, which, in the exemplary embodiments, is NITINOL wire. The SMA wire works by applying current through the wire, which induces heating the wire, and causes a phase change that result in a contraction of the wire length. The change in wire length may be exploited by e.g. lever and/or pulley mechanisms to actuate the pump plunger 2902 and measurement valve 2908.

The infusion pump system 2900 drives the SMA wires, which may include two, 2910, 2912 as shown in the exemplary embodiment shown in FIG. 150, directly from the battery voltage by switching the battery voltage across the wire to cause a contraction/actuation of the respective component and then switches off the battery voltage to stop the contraction. The wire/component starting position is, in some embodiments, restored by spring forces that oppose the SMA wire contraction force.

In the exemplary embodiment, each of the SMA wires 2910, 2912 provides proportional control, i.e. the SMA wire contracts over time and displaces the respective component over time. Despite this implementation, the valve components 2904, 2906, 2908 act to occlude or un-occlude fluid flow, which is a discrete, non-proportional and binary function. However, the pump piston is operated over a range of stroke lengths, so proportional control of the pump plunger 2902 is a functional goal in the exemplary embodiment.

In some embodiments, proportional control of the pump plunger 2902 may be achieved by monitoring the volume delivered into the volume measurement chamber 2920 and measured by the volume measurement sensor assembly/system 2946 and adjusting the amount of time that the pump plunger 2902 SMA wire 2910 is activated, i.e., adjusting the ontime. This may result in a closed-loop control of aliquot pumping volume as a function of SMA wire activation time on a stroke by stroke basis. The controller scheme in some embodiments also includes additional control variables which may increase the accuracy of the aliquot pumping volume to converge on a given target delivery volume.

Several factors may affect SMA activation including, but not limited to, one or more of the following: energy into the wire (voltage, current, time), ambient temperature, heat sinking, pre-tension, SMA wire variations (diameter, alloy composition, electrical resistance), and/or assembly variations. Changes in physical parameters, such as the ones listed above, may result in an inter-pump and intra-pump variation in the ontime of the pump plunger SMA 2910 that may be expected to result in a given pumped volume per stroke of the pump plunger 2902 (which may also be referred to as a given pump delivery volume). As a result, both an offset in time and a change in the slope of the on-time versus pump aliquot volume relationship may occur.

Referring now also to FIG. 145, a graph that shows the same pump system 2900 tested over a temperature range of 18 to 38 degrees Celsius results in a SMA actuation onset time from about 180 to about 310 ms. As may be seen, the slope is also aggravated at lower temperatures. Variation in the offset and slope of ontime versus pump delivery volume may add complexity to the pump system 2900 as compensation for the variation(s) may be necessary to achieve accurate pump delivery volume. This phenomenon may also affect the components, e.g., valves and plungers, actuated by SMA wire in a similar fashion, though valve function is not proportional.

At least in part due to the sensitivity of SMA actuation time to multiple physical variations it may be desirable, in some embodiments, to directly control one or more components, e.g., the pump plunger 2902 and/or measurement valve 2908 actuator position. This may be beneficial for many reasons, including, but not limited to, as the position of the pump plunger 2902 and measurement valve actuator 2908 may be a closer indication of proportional performance than SMA on-time. Various embodiments of methods, systems and apparatus for achieving this goal are described below.

The ability to sense the position of the pump plunger 2902 and/or the measurement valve actuator 2908 in the infusion pump system 2900 may be desired. Although as has been discussed herein, SMA wire may be used in the exemplary embodiments to actuate the pump plunger and the measurement valves 2940, in other embodiments, various motors may be used to actuate the pump and/or the valve(s) including but not limited to a peristaltic pump, a rotary pump and a piezoelectric actuator. Thus, disclosed herein, irrespective of the pump actuator, are methods, apparatus and systems for sensing the position of various components in the infusion pump system, including but not limited to, sensing the position of one or more components which may include, but are not limited to, the pump or displacement component, and one or more active valves and/or passive valves. Thus, in some embodiments, it may be desirable to sense the position of inactive valves, e.g., the reservoir valve 2904 and/or the volume measurement chamber inlet valve 2906.

There are various devices that may be used to sense the position of the pump plunger 2902 and/or measurement valve actuator 2908. These include, but are not limited to, one or more of the following: ultrasonic, optical (reflective, laser interferometer, camera, etc), linear caliper, magnetic, mechanical contact switch, infrared might measurement, etc. However, in the exemplary embodiment, due to the small structure of the infusion pump assembly and/or pump system 2900, it may be desirable to use a small component so as to utilize a small space with the sensing component(s). In various embodiments, the device battery life also may also be considered since the battery size may be limited by the overall size of the device and battery capacity may be a premium. Sensing distance may also be a consideration in various embodiments. For example, where the displacement of the one or more components, e.g., the pump plunger 2902 and/or the measurement valve actuator 2908 component may be very small (for example, in the exemplary embodiment, a full displacement of the pump plunger 2902 may be about 1 mm and a full displacement of the measurement valve actuator may be about 0.2 mm). The displacement distances are examples for some embodiments, in other embodiments, the displacement distances may vary.

In the exemplary embodiment, a small reflective optical sensor assembly (hereinafter "optical sensor") that fits into the exemplary embodiments of the infusion pump system 2900 hardware, as shown and described, for example, herein, may be used. In some embodiments, the at least one optical sensor is located in the reusable housing assembly. However, in other embodiments, part of the at least one optical sensor may be located in the disposable housing assembly and another part of the at least one optical sensor may be located in the reusable housing assembly. The optical sensor, in the various embodiments, has a sensing range that accommodates the components for which the optical sensor may be sensing, e.g., in some embodiments, the pump plunger 2902 and/or measurement valve actuator 2908 displacements. In the exemplary embodiment any optical sensor may be used, including, but not limited to a Sharp GP2S60, manufactured by Sharp Electronics Corporation which is a U.S. subsidiary of Sharp Corporation of Osaka, Japan. In these embodiments, this optical sensor contains an infra red emitting diode and infra red sensing detector in a single component package. Light from the emitter is unfocused and bounces off the sensing surface, some of which is reflected to the detector. This results in a sensed intensity of light by the detector that varies as a function of distance/angle to the reflector. Referring now to FIG. 146, the curve illustrates the sensitivity of the optical sensor to displacement of a reflective surface.

Referring also to FIG. 147, in various embodiments, one or more optical sensors may be used in the pump system 2900. The one or more optical sensors may be included in the pump system 2900 such that they may detect the movement and distance of movement/displacement of one or more valves 2904, 2906, 2908 and/or the pump plunger 2902. With respect to the pump system 2900, FIG. 147 represents various embodiments of the location for one or more optical sensors 2956, 2958 to sense the pump plunger 2902, as well as an embodiment of the location of an optical sensor 2954 to sense the measurement valve 2908.

With respect to the embodiments of the location of the optical sensors 2956, 2958 to sense the pump plunger 2902, although both of these locations may sense the pump plunger 2902, the distance from the respective sensor 2956, 2958 to the component, e.g. pump plunger 2902 in this example, varies the sensitivity of the optical sensor 2956, 2958. Thus, it may be beneficial to use one or the other optical sensor location 256, 2958, depending on, for example, but not limited to, the desired data. In some embodiments, the optical sensors may be placed on the underneath of the printed circuit board. The placement of the optical sensors on the underneath of the circuit board allows for independent sensing of the various components desired in the pump system 2900, for example, but not limited to, the pump plunger 2902 head, measurement valve actuating arm 2952 and/or the measurement valve 2908.

Still referring the FIG. 147, the embodiment shown includes three optical sensors 2954, 2956, 2958, placed, in some embodiments, on the bottom of the PCB (not shown) over both pump plunger and valve components to detect motion of the respective components. The optical sensor 2958 shown over the pump plunger 2902 and the optical sensor 2956 of the pump plunger actuator arm 2960 essentially sense the same motion, i.e., the movement of the pump plunger 2902, however, each of the optical sensor 2956, 2958 are a different distance from the respective component being sensed, i.e., the pump plunger 2902, and thus, each optical sensor 2956, 2958, may result in a different sensitivity of detection. In some embodiments, one of the optical sensors, e.g., 2956, 2958, may be preferred for detecting onset motion, i.e., the start of the pump plunger 2902 motion towards the pump chamber 2916, due to the starting distance from the optical sensor. Both the pump plunger 2902 head and the pump plunger actuator arm 2960, in some embodiments, are made from white DELRIN. Thus, in these embodiments, the surface is naturally reflective. In various embodiments, various materials may be used to manufacture these components such that they include a naturally reflective surface. However, in some embodiments, coatings may be added to the surface of the various components to increase reflection, if desired. In some embodiments, changes to the geometry of the surfaces may also be made to modify the reflection.

In some embodiments, the optical sensor 2954 positioned over the measurement valve actuator arm 2952 senses rotation. Thus, the change in reflective intensity is due to a rotational change of the reflecting surface. In the some embodiments, the measurement valve actuator arm 2952 may be made from a metallic MEMS part. However, in other embodiments, the measurement valve actuator arm and/or other parts to be sensed, including the tab discussed below, by the optical sensor may be made from DELRIN or other materials. In other embodiments, features may be added to change or modify the reflective pattern. These changes may include, but are not limited to, adding a tab that extends under the optical sensor 2954. Additionally, in some embodiments, optical coatings or polishing of the metal surface, or other treatments/methods, may be used to increase the refection intensity.

Referring now also to FIGS. 148A-149B, various embodiments of an optical sensor are shown. Although in various embodiments, for illustration purposes, the optical sensor arrangement may be shown with respect to a measurement valve actuator 2908 or a pump plunger 2902, this is for illustration purposes only, other embodiments of the various embodiments of the optical sensor arrangements may include where the optical sensor arrangement is used with any component, including, but not limited to, one or more valves and/or one or more pump plungers.

Referring now to FIGS. 148A-148B, an optical sensor detector 2962 is shown with an LED, and/or light source 2964 and a slot wheel 2966. In some embodiments, the optical sensor detector 2962 may include one or more detectors, and depending on the rotation of the slot wheel 2966, which, in some embodiments, may indicate the position of either a valve and/or a pump plunger, the LED 2964 will shine through a different slot in the slot wheel 2966 and the one of the detectors 2962 will detect the light, indicating the position of the slot wheel 2966.

Referring now to FIGS. 149A-149B, another embodiments of an optical sensor, similar to the embodiments shown and described above with respect to FIGS. 148A-148B, is shown. In this embodiment, the slot wheel 2966 includes a variation in the slots.

In various embodiments, the optical sensors 2954, 2956, 2958, utilize infra red light, thus ambient light may not be a variable. In some embodiments, each optical sensor's light emitting source may be controlled independently, which may be beneficial for many reasons, including but not limited to, so that optical cross-talk between the sensors may be avoided (e.g., in some embodiments, raster through the sensors one at a time). Optical sensors may be sensitive to drift and temperature over time, thus, in some embodiments, a "dark" sensor reading, and/or a temperature sensor reading (in some embodiments, at least one temperature sensor may be incorporated into the pump system, and in some embodiments, at least one temperature sensor may be included in the optical sensor system) may be taken before turning on the respective emitting light source in order to compensate for offset. In some embodiments, normalizing the starting reading before inducing motion may be used to compensate for a change in gain.

In various embodiments, sensing the pump plunger 2902 may be used in a number of ways, including but not limited to, onset of motion detection and determination of pump plunger 2902 position.

Sensing when the pump plunger 2902 has started to move may be beneficial for many reasons, including but not limited to, one or more of the following: removing the offset variation in the SMA wire activation on-time, in embodiments where ontime is used to control the SMA wire. Also, in some embodiments the closed-loop controller compensation may be less confounded because it may be compensating only for variation in slope of ontime versus volume. This may reduce the pump aliquot volume variability and result in more accurate fluid delivery versus time.

Since the pump plunger 2902 moves fluid by displacement, the position of the pump plunger 2902 may be correlated with the amount/volume of fluid displaced/pumped. Controlling the position of the pump piston has many benefits, some of which are discussed below.

Correlation of the pumped volume with the position of the pump plunger 2902 may enable the pump system 2900/infusion device to deliver a desired volume of fluid. Additionally, correlation of pump volume may reduce delivery variation. A more precise infusion pump, combined, in some embodiments, with an accurate measurement system, for example, various embodiments of the volume measurement sensor assembly described herein, may improve volume delivery consistency.

Improved correlation of pumping volume to pump plunger 2902 position may enable more accurate transitions from low volume to high volume delivery. In some embodiments, the pump controller may pump fluid as a function of SMA wire activation time. Thus, pumping fluid at a fixed volume may be beneficial. However, in some embodiments, to temporarily increase the delivery volume, the pump system 2900 may increase the aliquot delivery rate and hold the volume constant. With more accurate pumping volume the pump may temporarily aliquot higher volumes to meet e.g., a bolus delivery, and return to the basal delivery, which, in some embodiments, may be a lower pumping volume, without losing accuracy of either basal rate or bolus volume in the process.

Another benefit may include where, in some embodiments, aliquot pumping time is a variable used to promote fixed volume aliquot delivery; aliquot delivery time may be more independent and possibly speed up bolus volume delivery. Also, determining the pump plunger 2902 position may also enable a direct determination of malfunction. If, for example, a failure occurs with the pump plunger 2902 actuator 2960, the control system having determined the position of the pump plunger 2902, may, in some embodiments, alert the pump system that the pump has failed, e.g., failed open, closed, and/or somewhere in between. In some embodiments, this may promote safety for the user/patient as the system may identify failure at a faster rate, preventing over and/or under delivery.

In the various embodiments where SMA wire is used for pump actuation and/or active valve actuation, SMA wire activation ontime may be monitored as a function of pump plunger 2902 position to determine if the SMA wire is "wearing out" prematurely, i.e., if the SMA wire expected "life" is being effected. This may be determined, in some embodiments, by monitoring the ontime necessary to achieve a given pump position over time.

In some embodiments, sensing when the pump plunger 2902 has stopped moving may impart greater certainty to the pump system 2900 regarding when the pump plunger 2902 has bottomed out and prevent over-driving the pump plunger 2902. Over driving the SMA wire may reduce the "life" of the SMA wire and continuing to drive either the pump or a valve after reaching the desired position is also a waste of electrical/battery power. Thus, identifying when the pump plunger 2902 has stopped moving, and or, identifying when the measurement valve actuator 2908 has reached the desired location, may increase battery life and/or reduce the power needs of the system, and/or prevent premature SMA wire failure.

Similarly as with the pump piston, the various valve pistons may be optically sensed to detect motion of the valve and/or the position of the valve, either of which may have benefits, including but not limited to, one or more of the following.

In some embodiments, where one or more valves is controlled by SMA wire, sensing when the valve piston has started to move may remove the offset variation in the SMA wire activation ontime and may give greater certainty to when the valve starts to open and/or close. Additionally, sensing when the valve has stopped moving may give greater certainty to when the valve has opened/closed and prevent over-driving the valve actuator. As over driving the SMA wire may reduce the "life" of the wire and continuing to drive any actuator after the valve state is reached is a waste of electrical power. Thus, identifying when a valve has stopped moving may increase battery life and/or reduce the power needs of the system, and/or prevent premature SMA failure. Also, sensing the valve position may enable the determination of a valve being stuck in an undesirable position, for example, but not limited to, the measurement valve actuator 2908 being stuck in the open position.

Optical Position Sensor Control of Infusion Pump System

Although described herein as an infusion pump system, the optical sensor control of pumping may be used in various medical devices. For purposes of this description, the term "pump" broadly refers to valves and actuators used to move fluid from the reservoir to the user.

In some embodiments, the pump may be used to move the fluid from the reservoir to the volume measurement chamber and then to the user. Referring to FIG. 150, a schematic of an embodiment of an infusion pump system 2900 is shown. In some embodiments, pumping may be accomplished using a pump plunger 2902 and three separate valves 2904, 2906, 2908, where the pump plunger 2902 is controlled by an independently actuated SMA 2910, and one valve, the measurement valve 2908, is controlled by an independently actuated SMA wire 2912. As discussed herein, SMA may be actuated by changing its temperature (in this case by applying an electrical current) which changes its crystalline structure and causes the SMA to contract. In the infusion pump system 2900, the SMA wires 2910, 2912 are attached to linkages used to move the valve and pump plungers. The positions of the pump plunger 2902 and the measurement valve 2908 are measured using optical sensors (as shown and discussed above with respect to FIGS. 145-149B). The current applied to the SMA is modified based on the optical sensor measurements to provide proportional control of the pump plunger 2902 and measurement valve 2908 positions.

In some embodiments, the pump sequence is as follows. First, the pump plunger SMA 2902 is actuated which simultaneously moves the reservoir valve plunger 2914, which occludes the flow path between the pump chamber 2916 and the reservoir 2918. The pump plunger 2902 forces the fluid in the pump chamber 2916 past the passive volume measurement sensor chamber inlet check valve 2906 and into the volume measurement sensor chamber 2920. The fluid is held in the volume measurement sensor chamber 2920 by the measurement valve 2908 while a volume measurement taken. Once the volume measurement is completed, the measurement valve SMA 2912 is actuated, which opens the measurement valve 2908 and the fluid is released from the volume measurement sensor chamber 2920 to the tubing set 2922, which may, in some embodiments, lead to a user/patient which may, in some embodiments, lead to the delivery of medical fluid to the user/patient.

Referring now also to FIG. 151, the actuation of each SMA wire 2910, 2912 is accomplished using two field effect transistors (FET). A high side FET, which, in some embodiments, is controlled by the supervisor processor 2926 (described above), and provides an on/off switch between the battery supply voltage and the SMA wires 2910, 2912. In some embodiments, the high side FET is normally off and may prevent or reduce the occurrence of a single-point electrical fault from actuating the pump. A low-side FET, which, in some embodiments, is pulse-width modulated (PWM), is controlled by the command processor 2924 and provides control of the amount of current flowing through the SMA wire 2910, 2912.

In some embodiments, both the position of the pump plunger 2902 and measurement valve plunger 2908 is measured using at least two optical position sensors. However, in some embodiments, a single optical sensor may be used to measure both the pump plunger 2902 and the measurement valve plunger 2908. This allows the command processor 2924 to provide closed-loop control of the plunger pump 2902 and measurement valve plunger 2908 position by comparing the optical sensor output to a target position and modifying the PWM of the low-side FET. In addition, in some embodiments, voltages are measured at various positions. This enables, in some embodiments, the SMA controller to detect various conditions of the system including, but not limited to, one or more of the following: a broken SMA wire, a failed FET, and/or a depleted battery.

For the following discussion, the following nomenclature may be used:
m Total mass of the nitinol wire
$T_n$ Current nitinol temperature
$T_i$ Initial nitinol temperature
$T_a$ Ambient temperature
I Current
V Applied voltage
R Electrical Resistance
h Heat transfer coefficient [W/K]
C Heat capacity [J/kg/K]
η Duty cycle SMA Modeling A thermal model of the SMA wires and a linear model of the pump plunger 2902 is described below. As discussed below, the position of the pump plunger 2902 is measured. In some embodiments, the displacement of the pump plunger 2902 is measurement, i.e., the distance travelled from the starting point to the ending point may be measured.

Modeling the SMA Wire

The basic heat transfer equation for a constant current going through a wire with resistance R may be as follows. This neglects any of the thermal effects of the phase change in the SMA.

$$mC\frac{dT_N}{dt} = \dot{Q}_{in} - \dot{Q}_{out} = I^2R - h(T_N - T_a) \quad [EQ\ \#156]$$

Solving this equation gives the expression:

$$T_N = T_a + (T_i - T_a)e^{-\frac{t}{\tau}} + \frac{I^2R}{h}(1 - e^{-\frac{t}{\tau}})e^{-\frac{t}{\tau}} \quad [EQ\ \#157]$$

Where $\tau = \frac{mC}{h}$

Thus, at time 0 the SMA temperature will be $T_i$, and at t→∞ the temperature will approach a steady state value of $$\left(T_a + \frac{I^2R}{h}\right). \quad [EQ\ \#158]$$

Solving for the required on time to get the SMA to a given temperature:

$$\frac{t}{\tau} = \ln\left(\frac{1 - \frac{h}{I^2R}(T_i - T_a)}{1 - \frac{h}{I^2R}(T_N - T_a)}\right) \quad [EQ\ \#159]$$

This may be approximated using a Taylor's Expansion as:

$$t \approx \frac{mC}{I^2R}\left[(T_N - T_i) - \frac{1}{2}\frac{h}{I^2R}[(T_a - T_N)^2 - (T_a - T_i)^2]\right] \quad [EQ\ \#160]$$

This may also be written in terms of the applied voltage:

$$t \approx \frac{mCR}{V^2}\left[(T_N - T_i) - \frac{1}{2}\frac{hR}{V^2}[(T_a - T_N)^2 - (T_a - T_i)^2]\right] \quad [EQ\ \#161]$$

Thus, the ontime needed to produce a given strain in the SMA will be inversely proportional to the square of the applied voltage. In some embodiments, unregulated voltage is applied to the SMA for energy efficiency, thus, the applied voltage may vary with the battery voltage.

The internal battery impedance causes a voltage drop as the load is applied during each cycle of the PWM. In addition, the battery open circuit voltage drops over the course of the actuation. Both the battery open circuit voltage and impedance will change as the battery is discharged. The net result is that the electrical power applied to the SMA for a fixed duty cycle is variable. The repeatability of the SMA actuator may be improved by, in some embodiments, measuring the battery voltage and adjusting the duty cycle to provide power that is more consistent. In some embodiments, however, the position of the measurement valve plunger 2908 and the pump plunger 2902 may be measured directly and incorporated into a feedback loop. This may minimize any effects of the battery voltage variation.

Pulse Pump Modeling

An example of a relationship between the linear displacement of the pump plunger 2902 (as measured by the optical sensor) and the delivered volume is shown in FIG. 152. In some embodiments, the pump plunger 2902 may exhibit a dead zone where the pump plunger 2902 may not be in contact with the membrane covering the pump chamber 2906. Once the pump plunger 2902 reaches the pump chamber 2916 membrane there may be a relatively linear relationship between pump plunger 2902 displacement and volume until the pump plunger 2902 contacts the bottom of the pump chamber 2906.

A model of the pump plunger 2902 is shown in FIG. 153 as a gain 2930 element with a dead zone 2928 and saturation 2932 limit. The idealized linear model of a pump plunger 2902 that neglects the dead zone 2928 and saturation 2932 is then a static gain element 2930:

$$\Delta v(k) = K\delta_{target}(k) \qquad [\text{EQ \#162}]$$

where Δv(k) is the change in volume during a single pump pulse, which refers to one actuation of the pump plunger 2902 by the SMA, the pump plunger 2902 moving from a starting point towards the pump chamber 2916 and reaching an end point, then returning to a stopping point. The total volume delivered may be the sum of the individual pulses:

$$v(n) = \sum_{k=0}^{n} K\delta_{target}(k) \qquad [\text{EQ \#163}]$$

This may be expressed as a transfer function in the discrete domain:

$$G_p(z) = \frac{v(z)}{\delta_{target}(z)} = K\frac{z}{z-1} \qquad [\text{EQ \#164}]$$

SMA Controller
Feedback Controller

Referring now to FIGS. 154B and 154C, during a typical actuation, as shown in the FIGS., target position as a function of time and actual position as measured by the optical sensor as a function of time are shown in FIG. 154B. FIG. 154C shows the controlled variable, the duty cycle 2902 is the duty cycle that may be changed in response to errors in following the position trajectory. It should be noted that the term "ADC counts" refer to the counts as read by the analog to digital converter ("ADC") on the MSP 430 command processor. The ADC counts are proportional to the voltage of the at least one optical sensor. Thus, the output of the at least one optical sensor will be a voltage which is read by the ADC (analog to digital converter).

In some embodiments, and referring also to FIGS. 154A, 154B and 154C, the SMA controller may use a proportional controller 2936 with a fixed feed-forward 2934 to control the position of the pump plunger 2902 or measurement valve plunger 2908. The heating of the SMA wire 2910, 2912 may be an integrating process, thus, uses a proportional controller 2936 for controlling the position of the plungers 2902, 2908. In some embodiments, a fixed duty-cycle feed forward 2934 term may be used to provide fast initial heating of the SMA wire 2910, 2912. The output of the controller is limited to a valid PWM range (0% to 100%), where valid may be, in some embodiments, referring to a combination of that which the system may perform together with potential SMA stress and/or strain and/or saturation factors which may contribute to overall SMA wire life. In some embodiments, the signal from the one or more optical sensor is low passed filtered 2938 with, in some embodiments, a single-pole discrete filter. In some embodiments, the PWM frequency is 20 kHz, which moves it outside the audible range, which may be beneficial for many reasons, including, but not limited to, one or more of the following: user comfort and improving the user experience while pumping as the PWM frequency is outside the audible range. In some embodiments, the PWM output is updated at a frequency of 5 kHz, but in other embodiments, the frequency may vary.

Voltage Sensing and Timing

In some embodiments, the battery voltage sensing is done through a resistor-divider to an ADC input on the MSP430. The minimum time needed to sample the voltage may be represented in EQ #165:

$$t_{sample} > (R_s + 2\ k\Omega)\ln 2^{13}(40\ pF) + 800\ ns \qquad [\text{EQ \#165}]$$

where $R_s$ is the source impedance. The minimum sampling time may therefore be 1.77 microseconds. A sampling time of 2 microseconds may be used in some embodiments, however, in other embodiments the sampling time may be greater than or less than 2 microseconds. In some embodiments the minimum sampling time may be less than 1.77 microseconds or greater than 1.77 microseconds depending on the value of $R_s$. In some embodiments, the sampling is done synchronous with the PWM and timed to be a fixed interval from the end of the high cycle of the PWM. Referring now to FIG. 155, in some embodiments, as presented in FIG. 155, the ontime of the PWM duty cycle cannot be/should not be less than the ADC sampling time. As a result, in this embodiment, the voltage measurement will be higher than the actual battery voltage for duty cycles under 4%. In the exemplary embodiment, the control algorithm is updated every $4^{th}$ PWM period to give time for the Interrupt Service Routine ("ISR"): to complete. However, in various embodiments, the control algorithm may be updated using intervals other than every $4^{th}$ PWM period.

SMA Target Trajectory

In some embodiments, the outer "volume" loop (described in more detail below with respect to the volume controller) provides a target final pump plunger 2902 position to the inner pump plunger 2902 position control loop. The inner pump plunger 2902 position controller, in some embodiments, brings the pump plunger 2902 to this target position with minimum overshoot because once fluid is moved past the measurement valve 2940 it may not be brought back to the pump chamber 2916. Thus, it may be desirable in some embodiments to minimize and/or prevent overshoot, and this may be desirable for many reasons, including, but not limited to, safety to the user as it may be beneficial to prevent an "overdelivery" of medical fluid. In some embodiments, this may be accomplished where the pump plunger 2902 position controller generates a position trajectory, i.e., a series of pump plunger 2902 target positions as a function of time that may be followed by the SMA actuator. This may be compared with other embodiments including a step change in target position which may increase the incidence of overshoot in some instances.

Referring also to FIG. 156, the pump plunger 2902 target position, in some embodiments, has two parts, which are shown: an initial flat region and a linear region. The initial flat region 2942 is where the pump plunger 2902 position is not changing to allow the SMA 2910 to reach the transition temperature. The linear region 2944 is where the pump plunger 2902 is brought to its final position over a fixed time interval. Because the time interval is fixed, the target pump plunger velocity may be less for smaller actuations. In some embodiments, this may be beneficial for many reasons, including, but not limited to, improved controller accuracy for small volume deliveries.

Referring to FIG. 157, the measurement valve plunger 2908, in some embodiments, may be controlled differently from the pump plunger 2902 (as described above) because it is binary in its operation, i.e., the measurement valve 2940 is either in an open position or a closed position. The measurement valve plunger 2908 position controller, therefore, in some embodiments, moves the measurement valve plunger 2908 to the "open" position and then, in some embodiments, holds the measurement valve plunger 2908 in the open position which may allow the fluid ample time to fully drain from the measurement chamber 2920. This method may be beneficial for many reasons, including, but not limited to, adding the "open and hold" phase to the measurement valve plunger 2908 trajectory which may require less strain on the SMA wire 2912, which may increase the SMA wire 2912 "life"/duration of useful/usable performance for actuation. Thus, adding the "open and hold" phase, rather than, in some embodiments, continuing to move the measurement valve plunger 2908, may require less strain on the SMA wire 2912, thus, increasing the SMA wire 2912 "life".

Safety Check and Fault Handling

The pump controller in various embodiments includes a number of safety checks designed to provide greater safety to the pump system 2900 operation. These including, but are not limited to, preventing the SMA actuator from "browning out" the electrical system if the battery voltage is too low and guarding against electrical failures in the SMA drive circuit. Thus, the pump controller monitors and ensures that the SMA wire and the drive circuit, or source of electrical energy, functions so as to allow for function of the pump system 2900.

In some embodiments, these safety checks include supply voltage monitoring. In some embodiments, the supply voltage is measured once during each period of the low-side switch PWM and is used in the feedback controller. However, in other embodiments, the pump controller may measure the supply voltage more or less often. However, this measurement is also checked, in some embodiments, to verify that the supply voltage is within the range of expected battery voltages. Where the measurement is outside this range, the actuation may be stopped and in some embodiments, an alarm may be posted by the command processor. The failure of this integrity check could indicate one or more, but not limited to, the following: a failure of voltage sensing circuit, a failure of the battery, and/or a depleted battery. Although supply voltage monitoring is not the primary mechanism for detecting a depleted battery—that may also be done by the battery gauge—in the event of a failure of the battery gauge, supply voltage monitoring allows the pump system 2900 to terminate the high-current SMA actuation before actuating same may deplete or "pull down" the battery voltage to a level below a threshold needed for the processor voltage regulators.

The integrity of the switches and SMA wires 2910, 2912, are also monitored during each actuation. This safety routine verifies the safety of the system which may, in some embodiments, may including, but are not limited to, one or more of the following: verification that the switches are functioning correctly; and verification that the measurement valve plunger 2908 and the pump plunger 2902 are not actuated simultaneously. These verifications may provide greater safety to the pump system 2900 for many reasons, including, but limited to, actuating the pump plunger 2902, i.e., pumping fluid from the reservoir, while the measurement valve plunger 2908 is in the open position, thereby pumping fluid to the tubing set 2922 without holding the fluid in the measurement chamber 2920. In some embodiments, this may be desirable and beneficial, e.g., in those embodiments where the volume measurement sensor 2946 includes a method for determining the volume of the fluid in the measurement chamber 2020 which includes holding the fluid in the measurement chamber 2020 during the actual volume measurement. Some embodiments of the volume measurement sensor 2946 may not require the measurement valve 2940, but for those that do, the safety routine described above ensures the volume measurement sensor 2946 may perform measurements according to the method. In some embodiments, to perform these safety-checks the supervisor processor monitors the voltage above the low-side switches using three digital inputs. Referring also to FIG. 158, the electrical architecture is shown for a single strand of SMA wire. However, in some embodiments, the SMA wires share the same high-side switch, but have their own low-side switch and voltage monitor line.

Still referring to FIG. 158, in some embodiments, the safety-check routine proceeds as follows. The command processor 2924 requests SMA power from the supervisor processor 2926. The supervisor processor 2926 receives the message and proceeds to perform the following: the supervisor processor 2926 verifies that the high-side SMA voltage is low. If the voltage is high, the supervisor processor 2926 may indicates that the power FET has failed closed. The supervisor processor 2926 closes the SMA power switch 2948 and the supervisor processor 2926 verifies that the high-side SMA voltage is high. If it is low the supervisor processor 2926 indicates that the high-side FET has failed open. The supervisor processor 2926 verifies that the low-side SMA voltage is high. If the voltage is low the supervisor processor 2926 indicates that the SMA wire is broken or the low side FET has failed closed. The supervisor processor 2926 then sends a message to the command Processor 2924 that the SMA power is on. The command processor 2924 receives the SMA power on message and starts the SMA actuation. At the same time, the supervisor processor 2926 monitors the SMA monitor lines verifying that only the designated SMA wire is being actuated and that the low-side FET has not failed open. The command processor 2924 completes the actuation and sends a SMA power-off message to the supervisor processor 2926. At this point, the supervisor processor 2926 turns off the SMA power and sends a confirmation message.

In various embodiments, the pump system 2900 may include additional safety checks and/or, the process for the above-described safety checks may vary. In some embodiments, in addition to the safety checks described above, the supervisor processor 2926 may turn off the SMA power switch 2948 and alarm if the supervisor processor 2926 does not receive a "power off" request from the command processor 2924 within a fixed period of time. Thus, in some embodiments, if the command processor 2924, for example, freezes mid-SMA actuation, and continues to actuate the SMA, and thus, does not command the SMA power switch 2948 to turn off, the supervisor processor 2926 may determine that the command processor 2924 has not turned off the SMA power switch, and the supervisor processor 2926 may post an alarm. This protects the pump system 2900 from command processor 2924 faults which may provide another safety layer to the pump system 2900.

Optical Sensor Monitoring

In the exemplary embodiment, the command processor 2924 checks the integrity of each of the at least two optical sensors during every actuation. However, as discussed above, in some embodiments, the pump system 2900 may include at least one optical sensor where the optical sensor is used to determine the position of the pump plunger 2902 but not the measurement valve plunger 2908. In some embodiments, the pump plunger 2902 may include at least two optical sensors determining the position of the pump plunger 2902. Further, and as discussed above, in some embodiments, the pump system 2900 may include additional optical sensor to determine the position of additional valves and or membrane position. Thus, for purposes of the discussion, the term "optical sensor" is not meant to be limited to a single optical sensor, rather, applies to the at least one optical sensor that may be included in the pump system 2900 in some embodiments. Where more than one optical sensor is included in the pump system 2900, in some embodiments, the discussion below may apply to each optical sensor.

In some embodiments, the command processor 2924 may check the optical sensor signal output, which, in some embodiments, may include confirming that the optical sensor is within an expected range at the start of actuation. :Sensor Check: range check, looking at the optical sensor and if not within the expected range at the start of the actuation, then it may conclude it's broken] before each actuation. In some embodiments, if the output of the optical sensor is outside the normal operating range the command processor 2924 may post an alarm.

The command processor may, in some embodiments, post an alarm if the output of the optical sensor does not change significantly during an actuation. This may be beneficial for this optical sensor output may indicate, e.g., an electrical fault which may produce an optical sensor output that is in range but not related to the plunger displacement for which the optical sensor is determining. Also, in some embodiments, allowances may be made for optical sensor noise and/or drift.

Saturation

Referring also to FIGS. 159A and 159B, in some embodiments, to maximize the "life" of the SMA wire (which include at least one SMA wire, and in some embodiments, may be more than one SMA wire), it may be desirable to minimize the number of times the pump plunger/measurement valve plunger (and/or any valve/plunger that is being actuated by a SMA) "bottoms out" at the end of its travel. When the plunger reaches the end of its travel, it cannot move any further so it falls behind the target position. If the tracking error (the difference between the target position and actual position) exceeds a fixed threshold, the plunger is assumed to have "bottomed out" and the power to the SMA wire is turned off. Allowances are made to prevent false detects.

If the plunger is detected to have "bottomed out" twice in a row, the maximum allowed target position may be reduced to prevent the plunger from bottoming out again. In some embodiments, the maximum target position may not be reduced the first time the plunger is detected to have "bottomed out" to prevent any false detections of plunger saturation from limiting the plunger travel.

Delivery Controller

The delivery controller delivers a discrete dose of fluid (which in some embodiments, as discussed above, may be any fluid, including, but not limited to, a medical fluid, e.g., insulin) each time it is commanded by the therapy layer. The delivery controller, in some embodiments, does not track nor control the therapy, e.g., basal programs, boluses, or the timing of the delivery; rather, the therapy is controlled by the therapy layer. The delivery controller, in some embodiments, has a primary responsibility to deliver a dose of fluid when commanded and to measure the actual fluid delivered (using the volume measurement sensor 2946), and also, to adjust the pump plunger 2902 command to minimize any volume delivery error. Thus, where the pump plunger 2902 target position is met, the delivery controller determines whether the volume of fluid delivered is as expected and if not, to adjust the pump plunger 2902 command.

In addition, in some embodiments, the delivery controller may confirm and process a variety of system checks including, but not limited to, detecting occlusions, detecting an empty reservoir, and/or system faults that may affect the delivery of fluid to the tubing set 2922, which, in some embodiments, may be connected by way of a cannula to the patient/user of the system. If one or more faults are detected by the delivery controller, the delivery controller may, and in some embodiments, will always, enter a failsafe state preventing further delivery until and unless the at least one detected fault is resolved. The delivery controller reports faults detected to the therapy layer. The term failsafe may refer to a state of non-delivery in response to a determined failure, following alerting the user/patient that the system is entering a failsafe mode.

For the following discussion, the following nomenclature may be used:

Term Definition
$G_p(z)$ Pulse pump discrete transfer function
$G_c(z)$ Controller discrete transfer function
$K_p$ Controller loop gain
$T_1$ Controller Integrator time constant
z Complex argument for the discrete transform $$x(z) = Z\{x(n)\} = \sum_{n=0}^{\infty} x(n)z^{-n}$$

e Delivery error
r(z) Target volume trajectory
K Pulse pump gain

Volume Controller

Referring also now to FIG. 160, in some embodiments, the primary function of the delivery controller may be to provide closed-loop control of the delivered fluid volume. The delivery controller accomplishes this function, in some embodiments, by taking the measured volume change (this is the difference between the AVS/volume measurement sensor measurement with the AVS/volume measurement sensor chamber full and the AVS measurement with the chamber empty), comparing it to the target volume, and setting the pump plunger 2902 target displacement accordingly. Referring also to FIG. 161, the schematic shows the outer volume loop as well as the inner voltage loop described above.

As shown in FIGS. 161-162, the volume controller architecture on the total delivered volume and a feed-forward term based on the target volume for the current delivery is shown. As shown in this embodiment, the target volume and measured volume changes (dV AVS) are integrated before being passed into the feedback controller; there is no direct feedback on the error from an individual delivery.

Feedback Controller

Referring now to FIG. 162, in some embodiments, the volume controller may include the architecture, as shown, with integrator saturation and anti-windup. The discrete transfer function is shown below for the region where the integrator is active. A unit time delay is included to account for the 1-frame delay between the volume measurement and its use in the feedback loop.

$$G_c(z) = K_p\left(1 + \frac{1}{T_I}\frac{z}{z-1}\right)\frac{1}{z} \qquad [\text{EQ \#166}]$$

The pump plunger 2902 displacement versus volume delivered transfer function (input is the pump plunger position, and the output is the volume delivered) between total volume delivered and pump plunger 2902 may be modeled as a simple discrete integrator.

$$G_p(z) = \frac{v(z)}{t_{on}(z)} = K\frac{z}{z-1}$$ [EQ #167]

The forward path transfer function may then be written as follows. An additional unit time delay may be added to account for the fact that the AVS measurement/volume measurement sensor measurement will be from the previous delivery. A corresponding unit delay was also added to the target input.

$$G_c(z)G_p(z) = K_p\left(1+\frac{1}{T_I}\frac{z}{z-1}\right)K\left(\frac{z}{z-1}\right)\frac{1}{z} = K_pK\frac{\left(1+\frac{1}{T_I}\right)z-1}{(z-1)^2}$$ [EQ #168]

The steady-state volume error for this type of controller when following an input r(z) is shown below:

$$\frac{e(z)}{r(z)} = \frac{1}{1+G_cG_p} = \frac{(1-z^{-1})^2}{(1-z^{-1})^2 + KK_p\left[\left(\frac{1}{T_I}+1\right)-z^{-1}\right]z^{-1}}$$ [EQ #169]

The pump system 2900 may typically be following a ramp target volume trajectory (piecewise constant delivery rate). This input may be described in the discrete domain as follows:

$$r(z) = C\frac{z}{(z-1)^2}$$ [EQ #170]

The steady state flowing error can then be found using the discrete final value theorem applied to the plant and controller derived above:

$$\lim_{t\to\infty} e(t) = \lim_{z\to 1}[(1-z^{-1})e(z)] =$$ [EQ #171]

$$\lim_{z\to 1}\left[\left(\frac{(1-z^{-1})^3}{(1-z^{-1})^2 + KK_p\left[\left(\frac{1}{T_I}+1\right)-z^{-1}\right]z^{-1}}\right)\left(\frac{z^{-1}}{(1-z^{-1})^2}\right)\right] = 0$$

So a PI controller will theoretically have zero steady state error when following a ramp input in volume.

Controller Feed-Forward

Referring also to FIG. 163, in some embodiments, to improve the trajectory following of the controller, a non-linear feed-forward term may be added to, e.g., compensate for the pulse pump dead-band. In some embodiments, this feed-forward term provides a "best guess" of the pump plunger 2902 displacement for a given target volume by inverting the idealized pump plunger 2902 model described above with respect to the delivery controller. Pump system 2900 characteristics are different for different reusable housing assemblies, disposable housing assemblies, and reservoir fill volumes, i.e., the volume of fluid in the reservoir.

Thus, this feed-forward term may generally produce some error that may need to be corrected by the feedback controller.

Initialization of the Feed-Forward Parameters

The gain and offset used in the feed forward controller, shown in FIG. 164, are initialized during the start-up test based on the measured pump characteristics.

Least Square Recursive Filter

The gain and offset parameters of the feed-forward controller are adjusted as the pump is operating. Thus, the slope and offset of the model are continuously updated based on the AVS measurements/volume measurement sensor measurements to improve the accuracy of the feed-forward model. The "learning" algorithm may be based on a linear exponentially forgetting least square recursive filter. The time constant is set such that it adapts slowly compared to the feedback controller (FIG. 162) and the two do not have significant interaction. If the feed-forward term was never changed, it would have no effect on the stability of the feedback controller.

The feed-forward model is updated using a recursive least-square estimator. The function we are fitting is as follows:

$$y(n) = mx(n) + b$$ [EQ #172]

The dependent variable x is the delivered volume and the independent variable, y, is the pump plunger 2902 target position/displacement. In vector form, this may be written:

$$y(n) = w^T x(n)$$ [EQ #173]

$$w = \begin{bmatrix} m_n \\ b_n \end{bmatrix} \text{ and } x_n = \begin{bmatrix} x_{n,11} \\ 1 \end{bmatrix}$$

It may be noted that $x_n$ is the vector x at time step n, and $x_{n,11}$ is the $1^{st}$ element of the vector x at the time step n. The function being optimized is:

$$y_n = m_n x_n + b_n = w^T x = \begin{bmatrix} m_n & b_n \end{bmatrix}\begin{bmatrix} x_{n,11} \\ 1 \end{bmatrix}$$ [EQ #174]

The error for a given time step, n may be written:

$$e_n = y_n - (n_{n-1}x_n + b_{n-1})$$ [EQ #175]

To update the w vector based on the error signal, the gain matrix is first updated:

$$g_n = \begin{bmatrix} p_{n-1,11}x_{n,11} + p_{n-1,12} \\ p_{n-1,21}x_{n,11} + p_{n-1,22} \end{bmatrix}$$ [EQ #176]

$$\{\lambda + p_{n-1,11}x^2 + (p_{n-1,12} + p_{n-1,21})x_{n,11} + p_{n-1,22}\}^{-1}$$

The inverse is of a scalar so no matrix inversion is required. The covariance matrix may then be updated for the next time step:

$$P_n = \lambda^{-1}\begin{bmatrix} p_{n-1,11}(1-g_{n,11}x_{n,11}) - & p_{n-1,21}(1-g_{n,11}x_{n,11}) - \\ p_{n-1,12}g_{n,11} & p_{n-1,22}g_{n,11} \\ p_{n-1,12}(1-g_{n,12}) - & p_{n-1,22}(1-g_{n,12}) - \\ p_{n-1,11}g_{n,12}x_{n,11} & p_{n-1,21}g_{n,12}x_{n,11} \end{bmatrix}$$ [EQ #177]

The coefficients can then be updated based on the gain vector and the error:

$$\begin{bmatrix} m_n \\ b_n \end{bmatrix} = \begin{bmatrix} m_{n-1} \\ b_{n-1} \end{bmatrix} + e_n g_n \qquad \text{[EQ \#178]}$$

Taking advantage that the covariance matrix is symmetric, the method and/or algorithm may be written more computationally efficiently. This may, in some embodiments, be beneficial for many reasons, including, but not limited to, efficient implementation in software.

In some embodiments, the filter is only valid if the pump plunger 2902 is operating in its linear range, so the value may only be updated if the measured volume is in the range of 0.1 uL to 2.1 uL, for example, where this range is in the linear range. In some embodiments, the recursive filter may not be effective if the measurements are not sufficiently "signal rich", i.e., where too many deliveries are performed at a single operating point the linear fit may converge to a solution that may not be valid once the pump plunger 2902 being operation over the full range. To guard against this possible "localized" solution, the algorithm, in some embodiments, may not be updated where the diagonal terms of the covariance matrix exceed a set threshold.

Delivery Fault Detection

In addition to providing closed-loop control of the volume delivered by the pump system 2900, the delivery controller, in some embodiments, may also detect fault conditions associated with fluid delivery. A variety of fault detection methods are described below, one or more of which may be included in various embodiments of the delivery controller.

In some embodiments, the delivery controller monitors, amongst possible additional functions, the total volume error, which may be defined as the cumulative volume error of all the deliveries since the delivery controller was last reset. If the delivered volume exceeds the target volume by more than a specified amount, which indicates an over-delivery, the delivery controller, in some embodiments, may post a pump fault and switch to a failsafe mode, which is described above. Conversely, if the target volume exceeds the measured volume by a specified amount, which indicates under-delivery, the delivery controller, in some embodiments, may post a pump fault and switch the pump system 2902 to a failsafe mode, which is described above. In some embodiments, the under-delivery tolerance may be programmable by the user/patient and further, in some embodiments, the tolerance may include a high and low sensitivity setting.

Thus, where the delivery controller determines that the cumulative volume error is such that a either an over-delivery or under-delivery threshold has been met, which threshold may be set based on safety to the user/patient, the delivery controller may signal a pump fault condition and the pump system 2902 may be shut down, with at least one indication to the user/patient, such that the pump system 2902 avoids over delivery and under delivery at unsafe levels. Thus, in various embodiments, the pump system 2902 includes a determination of the volume of over delivery and/or under delivery and a threshold tolerance of same where when the threshold is reached, the pump system 2902 may enter failsafe mode.

Occlusion Detection

In some embodiments, the deliver controller monitors the volume of fluid that both flows into and out of the volume measurement chamber 2920 and, in some embodiments, may determine whether the tubing set 2922 may be occluded. In some embodiments, there are two parallel methods used for detecting an occlusion, which may be termed the total occlusion method and the partial occlusion method. The total occlusion detection method monitors the flow into and out of the volume measurement chamber 2920 during a single delivery of fluid. The partial occlusion detection method monitors for a gradual build-up of fluid in the volume measurement chamber 2920.

The residual volume for an individual delivery may be defined as the difference between the volume flow into the volume measurement chamber 2920, which may be referred to as the "pumped volume" and the volume flowing out of the volume measurement chamber 2920, which may be referred to as the "delivered volume":

$$v_{res} = \Delta v_{pump} - \Delta v_{delivered} \qquad \text{[EQ \#179]}$$

This is equivalent to the difference between the final and initial variable volume estimates:

$$v_{res} = V_{final} - V_{initial} \qquad \text{[EQ \#180]}$$

Under normal operation, in some embodiments, the residual volume may be close to zero at steady state. In some embodiments, the residual volume may be the fundamental metric for detecting both total and partial occlusions.

Total Occlusion

In the event of a total occlusion of the fluid exit path, which may also be referred to as the tubing set 2922 and the cannula as well as the fluid path in the disposable housing assembly downstream from the volume measurement chamber 2920, the residual volume in the volume measurement chamber 2920 may be approximately the same size as the volume pumped, i.e., the volume of fluid pumped into the volume measurement chamber 2920. Thus, in these circumstances, fluid has been pumped into the volume measurement chamber 2920, however, little or no fluid may have left the volume measurement chamber 2920. In these circumstances, in some embodiments, a threshold residual volume may be used as an indicator of a total occlusion. In some embodiments, the total occlusion detection threshold may be set based on the cumulative pumped volume, i.e., the total volume of fluid pumped. A linearized model of the fluid flow out of the volume measurement chamber 2920 may have the form:

$$V_{avs} \propto \frac{V_{avs}}{\tau} \qquad \text{[EQ \#181]}$$

Where $V_{avs}$ is the volume of the variable volume chamber 2950.

Larger pumped volumes/larger volumes of fluid pumped into the volume measurement chamber 2920, may result in larger delivered volumes for the same measurement valve 2940 open time and tubing set 2922 flow impedance. In some embodiments, therefore, the residual volume threshold for occlusion is therefore calculated as a fraction of the total volume pumped:

$$T_o = \rho_o \Delta v_{pump} \qquad \text{[EQ \#182]}$$

where $\rho_o$ is a value less than one. An exemplary value for $\rho_o$ is 0.15, which means the delivery controller may detect a total occlusion if less than 85% of the fluid pumped into the volume measurement chamber 2920 is delivered/pumped out of the volume measurement chamber 2920 (and in some embodiments to the tubing set 2922 and to the user/patient). Determination of a total occlusion may be as follows:

$$\Phi_O = \begin{cases} 1 & \text{if } v_{res} > T_o \\ 0 & \text{otherwise} \end{cases} \qquad \text{[EQ \#183]}$$

Where $_o$ is the total occlusion detection indicator. In some embodiments, the pump system 2902 may not alarm immediately after the total occlusion detection indicator has been set to "1", rather in some embodiments, an alarm may be posted once the total occlusion detection indicator remains positive for a preset number of consecutive deliveries to allow time for the occlusion to clear through regular operation of the pump system 2902, which, in some circumstances, may be accomplished. In various embodiments, the number of occluded deliveries permitted is variable and may, in some embodiments, be pre-set/preprogrammed and/or may be based on a user/patient configurable occlusion sensitivity setting.

In some embodiments, in the event that an occlusion clears on its own, the fluid may once again flow out of the volume measurement chamber 2920. Thus, in some embodiments, the logic for clearing the total occlusion is related to the delivered volume, $v_{del}$ being greater than a given threshold. This cleared-occlusion threshold may be, in some embodiments, calculated as a fraction of the total volume pumped for a given delivery plus the accumulated residual volume, if any, from previous deliveries, which may be represented as follows:

$$T_u = \rho_u(\Delta v_{pump} + v_{residual,total}) \qquad \text{[EQ \#184]}$$

Or $$\Phi_O = \begin{cases} 0 & \text{if } v_{del} > T_u \\ 1 & \text{otherwise} \end{cases} \qquad \text{[EQ \#185]}$$

Combining these two, the total occlusion update logic is as follows:

$$\Phi_O[n+1] = \begin{cases} 1 & \text{if } v_{res}[n+1] > T_O \\ 0 & \text{if } v_{del}[n+1] > T_u \\ & \text{otherwise } \Phi_O[n] \end{cases} \qquad \text{[EQ \#186]}$$

In some embodiments, an increase in the residual volume may be an indication that an occlusion has occurred, however, the residual volume returning to zero may not necessarily be an indication that an occlusion has cleared. This is because the pump plunger 2902 may, in some instances, only be able to pump one or two deliveries following an occlusion due to the build up of back-pressure in the volume measurement chamber 2920. Thus, once the pump system 2900 has reached this condition, the change in residual volume becomes close to zero, thus, no fluid flows into the volume measurement chamber 2920 and no fluid volume flows out of the volume measurement chamber 2920. As a result, in some embodiments, the delivered volume, instead of the residual volume, may be used for the condition to clear a total occlusion indication.

In various embodiments, partial occlusions result in an accumulation of residual volume in the volume measurement chamber 2920, but this accumulation may occur over time at a low enough rate that the total occlusion detection logic may not detect the accumulation. As a result, in some embodiments, a second method, i.e., partial occlusion method, may be used which integrates the residual volume of individual deliveries and uses this sum to detect a slow build-up of volume characteristic of a partial occlusion. Additionally, any volume that leaks from the volume measurement chamber 2920 between deliveries may be subtracted out of the total of the residual volume of individual deliveries so as to prevent confusing an inter-delivery leak with a partial occlusion. A "leaky" integration, as shown in EQ #187 and EQ #188 may be performed so that the cumulative effect of measurement error may be minimized.

The Integrator $$S_{var} = \gamma_{var} * S_{var} + (v_{res} - v_{interleak}) \qquad \text{[EQ \#187]}$$

The partial occlusion indicator, $\Phi_{var}$, is then set based on the following logic:

$$\Phi_{var} = \begin{cases} 1 & \text{if } S_{var} > T_{var} \\ 0 & \text{otherwise} \end{cases} \qquad \text{[EQ \#188]}$$

As with the total occlusion detection and occlusion alarm, a partial occlusion detection may not trigger an occlusion alarm until a minimum number of consecutive deliveries are detected/determined to be occluded. This allows time for partial occlusions to clear through regular operation of the pump system 2902, which, in some circumstances, may be accomplished. Additionally, in some embodiments, the partial occlusion alarm may not be posted unless the total trajectory error exceeds a certain threshold.

In some embodiments, the partial occlusion threshold may be a limit on how much fluid volume may remain in the volume measurement chamber 2920 between deliveries. If there is too much residual volume in the volume measurement chamber 2920 the pump plunger 2902 may be unable to deliver a full pump-stroke due to the increased back pressure. In some embodiments, this sets an upper limit for the allowed residual volume. Thus, if the maximum target delivery volume for a single delivery is $\Delta v_{max}$ and the maximum total volume of the volume measurement chamber 2920 before the pack-pressure prevents further pumping is $V_{max}$ then the maximum partial occlusion threshold is:

$$T_{var,max} = \Delta V_{max} - \Delta v_{max} \qquad \text{[EQ \#189]}$$

This threshold is on the order of $T_{var} = 1.0$ μL. If a cumulative total of more than 1.0 μL of volume remains in the volume measurement chamber 2920 a partial occlusion may be detected. Again, an alarm may not be posted unless the under-delivery and number of consecutive occluded delivery conditions have also been met.

Empty Reservoir Detection

The empty reservoir detection algorithm, may, in some embodiments, evaluate the ability of the pump plunger 2902 to deliver fluid from the reservoir 2918 to the volume measurement chamber 2920. The pump system 2902, in some embodiments, may use two parameters for this evaluation, which may include, but is not limited to, the pumping error and the total trajectory error. The pumping error may be the difference between the target and actual pumped volumes. An internal "empty reservoir indicator", which may be set if the pump is under-delivering. In some embodiments, if under-delivery occurs two consecutive deliveries while the pump plunger 2902 is at its maximum actuation, the maximum target volume may be decreased, allowing pumping to continue with smaller and more frequent deliveries. If the maximum target volume is reduced by this method below a minimum threshold, an empty reservoir alarm may be posted. Alternatively, in some embodiments, if the difference between the measured volume delivered and the total target volume requested exceeds a threshold, an empty reservoir may be assumed by the pump system 2902 and an alarm may be posted. In some embodiments, empty reservoir alarms may also be posted due to an up-stream occlusion, leak, or possibly a faulty pump plunger shape memory actuator 2910.

Maximum Target Volume Reduction Empty Reservoir Alarm

In some embodiments, as the reservoir 2918 empties, the maximum volume that the pump chamber 2916 membrane restoring force may pull from the reservoir 2918 may decrease. Consequently, the maximum volume that the pump plunger 2902 may deliver to the measurement chamber 2920 and then to the tubing set 2922 may also decrease. To minimize the volume left in the reservoir 2918 when the disposable housing assembly may be discarded, the delivery controller may dynamically decrease the maximum target volume as this occurs. Thus, in some embodiments, this may allow the pump system 2900 to continue administering fluid/therapy by delivering smaller deliveries more frequently.

The basis for this empty reservoir detection maximum volume reduction, in some embodiments, may be the difference between the goal/target volume for each delivery, $v_{target}$, and the volume pumped into the volume measurement chamber 2920, $v_{pump}$. This difference may be defined as the pumped volume error, $v_{error}$:

$$v_{error} = v_{target} - v_{pump} \quad \text{[EQ \#190]}$$

An internal indicator may be set whenever this difference is greater than zero, $v_{error} > 0$ and the pump plunger 2902 is either saturating or at its maximum allowed value. If this occurs in two consecutive deliveries, the maximum target delivery volume may be decremented and the therapy layer may be called to reschedule the next delivery. In some embodiments, an exception to this method may be made during a bolus. When bolusing, the target delivery volume for the entire bolus may be, in some embodiments, calculated at the start of the bolus. Therefore, the maximum target volume may not decrement during a bolus.

In some embodiments, once the maximum target volume has been reduced to the minimum delivery volume, any further saturated under-delivering may result in an empty reservoir alarm.

Under Delivery Empty Reservoir Alarm

In some embodiments, the pump system 2900 may alarm for an empty reservoir when either the maximum allowed target volume is reduced below a minimum by way of a dynamic reduction, as described above, or, in some embodiments, whenever the pump system 2900 is under-delivering by more than a given amount/threshold. The basis for the under-delivery empty reservoir detection algorithm may be the difference between the total target volume, $V_{target}$, and the measured volume, $V_{measured}$. This difference may be defined as the total trajectory error, $V_{error}$:

$$V_{error} = V_{target} - V_{pumped} \quad \text{[EQ \#191]}$$

The under delivery empty reservoir metric therefore may be:

$$\Phi_{empty} = \begin{cases} 1 & \text{if } V_{error} > V_{threshold} \\ 0 & \text{otherwise} \end{cases} \quad \text{[EQ \#192]}$$

In some embodiments, additional conditions are not placed on this metric for alarming. The pump system 2900 may alarm in this way if the reservoir 2918 is emptying while a bolus is in progress and hence, no maximum volume reduction may be possible. In some embodiments, the pump system 2900 may also/rather alarm in this way when the ability of the pump chamber 2916 is reduced faster than the maximum volume reduction algorithm may reduce the maximum volume.

Acoustic Leak and Bubble Detection

In some embodiments of the pump system 2900, the delivery controller may include an algorithm for detecting acoustic leaks and resonant air bubbles in the volume measurement chamber 2920. The detection algorithm may be based on the premise that the volume measurement sensor damping ratio for the second-order resonance may, in some embodiments, remain substantially constant during all the sine-sweeps of an individual delivery.

In some embodiments, therefore, the comparison of the model fit calculated damping ratios in the pumped and un-pumped states may be used as a metric for the detection of, for example, gross acoustic leaks or large air bubbles. This metric may be separate from the absolute check on damping ratio performed, in some embodiments, as a volume measurement sensor level integrity check.

In some embodiments, the method for detecting acoustic leaks and bubbles in the volume measurement chamber 2920 may include the following steps. First, define the maximum and minimum damping ratios from a single set of sine sweep data:

$$\zeta_{max} = \max(\zeta_1, \zeta_2, \zeta_3)$$

$$\zeta_{min} = \min(\zeta_1, \zeta_2, \zeta_3) \quad \text{[EQ \#193]}$$

The differential damping metric may then be defined as the percent difference between these two values:

$$S_{diffDamp} = 100 * \frac{\zeta_{min} - \zeta_{max}}{\zeta_{min} + \zeta_{max}} \quad \text{[EQ \#194]}$$

And the differential damping acoustic leak indicator may be set as a threshold on this value:

$$\Phi_{diffDamp} = \begin{cases} 1 & \text{if } S_{diffDamp} > T_{diffDamp} \\ 0 & \text{otherwise} \end{cases} \quad \text{[EQ \#195]}$$

As differentiated from the occlusion and empty reservoir indicators, described above, a differential damping indicator may be, in some embodiments, sufficient to trigger an acoustic leak alarm and thus the differential damping indicator may always, in some embodiments, result in an acoustic leak alarm.

The thresholds for this metric may be based entirely on experimental evidence. In some embodiments, a very conservative threshold of, e.g., a ten percent difference between the damping ratios of any two sine sweeps from a single delivery may be set, or $T_{diffDamp} = 5$. However, in various embodiments, the threshold may be higher or lower.

Leak Detection

In some embodiments, the delivery controller may check for leaking fluid leaking out of the volume measurement chamber 2920 either, for example, but not limited to, upstream past the measurement valve 2940 or downstream past the measurement valve 2940. It may be beneficial for many reasons to perform checks and detect leaks as, for example, leaks may generate issues both during a delivery and between delivery if residual volume leaks out of the volume measurement chamber 2920. Thus, in some embodiments, two different leak tests may be performed by the pump system 2900, including, but not limited to, an inter-delivery leak test to check for leaks during a delivery and an intra-delivery leak test to check for loss of residual volume between deliveries.

The intra-delivery leak test may be performed, in some embodiments, when the volume measurement chamber 2920 is full of fluid. A first volume measurement may be taken after the pump plunger 2902 has been actuated. The fluid may be left in the volume measurement chamber 2920 for a fixed period of time, e.g., 1 second, and then a second volume measurement may be taken. In some embodiments, in general, these two volume measurements should be the same. Thus, any difference between these measurements, that is, above the expected measurement noise, which, in some embodiments, may be approximately 1 nL, may generally be attributed to a leaking valve. The intra-delivery leak test, in some embodiments, may be performed during each delivery, i.e., each basal or bolus delivery, however, in various embodiments, the intra-delivery test may be performed more, or less, often.

The inter-delivery leak test, in some embodiments, may be performed when the measurement chamber 2920 is empty except for the normally generally small amount of residual volume that may persist in the chamber between deliveries. For the inter-delivery leak test, the last volume estimate of the previous delivery is compared to the first volume estimate of the new delivery. As in the case of the intra-delivery leak test, these measurements should generally be the same. The expected measurement noise, in some embodiments, may be marginally higher than in the case of the intra-delivery leak test. Still, any volume change outside this expected noise floor may also generally be attributed to a leaking valve. The inter-delivery leak test may be performed before each basal delivery. In some embodiments, the intra-delivery test may not be performed during a bolus delivery because there is a minimal delay between consecutive deliveries. However, in some embodiments, the intra-delivery test may be performed during a bolus delivery.

Generalized Leak Algorithm

A similar algorithm may be used to detect both inter and intra delivery leaks. The basis for the detection algorithms is the leaked volume defined as the difference between the consecutive volume estimates:

$$v_{leak} = v_{avs,2} - v_{avs,1} \quad [\text{EQ \#196}]$$

This leaked volume may be integrated over consecutive deliveries using a leaky integrator. In this case, the metric for leak detection, $S_{leak}$, will be defined as follows.

$$S_{leak} = \gamma_{leak} S_{leak} + v_{leak} \quad [\text{EQ \#197}]$$

where $\gamma_{leak} < 1.0$ is the rate of decay. The leak detection logic is then:

$$\Phi_{leak} = \begin{cases} 1 & \text{if } S_{leak} > T_{leak} \\ 0 & \text{otherwise} \end{cases} \quad [\text{EQ \#198}]$$

In some embodiments, the leak thresholds for the inter-delivery leak algorithm may be set whereby the measured leaked volume is the volume that was over-delivered in the case of a leaking measurement valve. In the case of a leaking measurement chamber inlet valve 2906, there may be no over-delivery but, in some embodiments, the leak measurement may not differentiate between this and a measurement valve leak. In the case of an inter-delivery leak, in some embodiments, the potential over-delivery will generally be bounded by the amount of residual volume.

In some embodiments, the intra-leak detection threshold may be set by taking into account that the actual leaked volume may be greater than the volume measured during the leak test. In some embodiments, the leak test may be performed/completed over a short interval, for example, approximately 1 second, but where the fluid is pressurized in the volume measurement chamber 2920 for a longer period of time, this may allow for additional volume to leak out.

Exit Valve Fail Detection

In some embodiments, as described above, the pump system 2900 includes a measurement valve 2940 which maintains the fluid in the measurement chamber 2920 unless and until the measurement has been completed by the volume measurement sensor. Thus, in some embodiments, it may be beneficial to determine if a leak is present in the measurement valve 2940, i.e., where fluid is leaking from the volume measurement chamber 2920 prior to the completion of the volume measurement, thus, detecting possibly inaccurate volume measurements as soon as they occur. The measurement valve 2940 fail detection metric, in some embodiments, compares the expected outcome of an actuation to the observed outcome. In the event of a full measurement valve 2940 failure, for example, the volume pumped may appear to be near zero, as the fluid exits nearly as fast or as fast as it is pumped into the measurement chamber 2920. Using a feed forward model estimate for the actuator response, in some embodiments, measurement valve 2940 failures may be guarded against in the following manner, where slope, m, and offset, b, are the actuator model:

$$v_{buffer} = 3 * v_{target} \quad [\text{EQ \#199}]$$

$$\delta_{threshold} = (v_{buffer} * m) + b$$

$$v_{threshold} = 0.1 * v_{target}$$

$$\Phi_{noMeasuredVolume} = v_{pumped} < v_{threshold}$$

$$\Phi_{highControllerEffort} = \delta_{target} > \delta_{threshold}$$

$$\Phi_{plungerSaturated} = true \text{ if the plunger is saturated}$$

Note: both $\delta_{threshold}$ and $v_{threshold}$ are limited to a reasonable range of values $$\Phi_{exitValveFail} =$$

$$\begin{cases} 1 & \text{if } \Phi_{noMeasuredVolume} \text{ and either } (\Phi_{highControllerEffort} \text{ or } \Phi_{plungerSaturated}) \\ 0 & \text{otherwise} \end{cases}$$

Thus, in some embodiments, following this method, where the delivery controller commands an actuation that the current model predicts should result in three times the target volume pumped, but where the volume observed to be pumped is less than a tenth of the targeted pumped volume, then in some embodiments, a measurement valve 2940 failure may be assumed and an alarm may be posted.

In some embodiments, the intra-leak method assumes that a leak is continuous. However, discontinuous leaks, i.e., where this assumption would not hold true, may occur. Thus, in some embodiments, to detect a leak of this type, the local relationship between the target pump plunger 2902 position commanded and the subsequent volume pumped may be monitored. An indication of a discontinuous leak may be that a change in the target position does not necessarily correspond to a change in the volume pumped. Thus, if the relationship between the target position of the plunger and the volume pumped becomes uncorrelated, a discontinuous leak may be suspected by the pump system 2900. Referring now also to FIG. 164, in these cases, in some embodiments, a double pump plunger 2902 stroke delivery may be performed. If the measurement valve 2940 is operating normally, a second actuation of the pump plunger 2902 would result in additional volume measured in the measurement chamber 2920. However, if the measurement valve 2940 performs like a pressure relief valve, the additional pumped volume is expected to leak discontinuously and the volume in the measurement chamber 2920 may remain substantially unchanged. In some embodiments, while performing a discontinuous leak check, the pump plunger 2902 position change targeted for each of the two strokes may be one that should, during regular pump system 2900 function, result in one-half the targeted volume pumped for each stroke, based on the current actuator model.

In some embodiments, in addition to the various safety-checks performed by the command processor 2924, there are a set of secondary checks performed by the supervisor processor 2926. In some embodiments, the supervisor processor 2926 may control the power to the pump system 2900 so the active participation of both processors 2924, 2926 is needed for the pump system 2900 to deliver fluid. The supervisor processor 2926 may provide oversight at a number of different levels and, in some embodiments, may not turn on power to the pump system 2900 unless all of the integrity checks pass. Some of the secondary checks performed by the supervisor processor 2926 may include, but are not limited to, one or more of the following.

In some embodiments, a therapy monitor on the supervisor processor 2926 may determine the volume and timing of fluid delivery independent of the command processor 2924. Thus, in some embodiments, the supervisor processor 2926 may prevent the command processor 2924 from delivering fluid if both the timing and volume are not in agreement.

In some embodiments, the delivery monitor provides oversight of the volume measurement sensor using a redundant temperature sensor, redundant storage of the calibration parameter, and independent range-checking of the results and back-calculation of the volume measurement sensor model-fit errors.

In some embodiments, the delivery controller checks for failed switches (open or closed) and broken SMA, and also guards against simultaneous or out-of-sequence actuation of the pump plunger 2902 and measurement valve 2940. The delivery controller may also limit the time the power is applied to SMA. In some embodiments, the delivery controller may independently track the target fluid volume and delivered fluid volume. In some embodiments, the delivery controller may post an alarm and prevent further delivery if it detects a substantial over or under delivery.

Verifying the integrity of a system or device prior to use is desirable. With respect to medical devices, the integrity of the system or device may be verified to, for example, but not limited to, ensure the safety of the user/patient. The detection of fault conditions is at least one method of verifying the integrity of the system or device. In many embodiments, detecting fault conditions at start-up is desirable to avoid downstream errors and failures while the medical device is delivering therapy or otherwise medically serving a user or patient.

Some embodiments of the infusion device methods and systems will be described below with reference to an exemplary embodiment. The exemplary embodiment is described with respect to a medical infusion pump, which in some embodiments may be an insulin pump, as shown and described in herein. Reference herein to a disposable may refer to, in some embodiments, the various embodiments of the disposable housing assembly and/or reservoir portion of the infusion pump described herein.

Although the term "start-up test" may be used herein, the systems and methods described herein may be used at any time. However, in many embodiments, the systems and methods are used at start-up as well as at various other times during the use of the medical device. These include, but are not limited to, when various faults are detected by the system during operation. The start-up test may be beneficial for many reasons, including but not limited to, identifying defective or faulty disposables prior to their use in administering a medical therapy, and/or detecting a fault condition with a medical device that is in ongoing use. Thus, the start-up test may increase the safety of medical devices.

In some embodiments of the method and system, the method and system may be used to determine whether a disposable housing assembly has faults prior to use for delivering therapy. Thus, in some embodiments, the start-up test/procedure/method may be performed each time a disposable housing assembly is attached to a reusable housing assembly. The faults may include, but are not limited to, one or more of the following: disposable leaks, disposable valve malfunction, disposable reservoir malfunction, and/or pump/reusable/disposable malfunction. In some embodiments of the systems and methods, where the integrity of the disposable is not verified for two sequential disposable housing assemblies, the lack of integrity of the reusable pump may be confirmed/assumed. In some embodiments, the system may indicate that a new pump/reusable may be recommended, and once another reusable is attached to a disposable, the start-up test may be repeated on a disposable, which may include, repeating the start-up test on one or more previously failed disposable housing assemblies. In some embodiments, this method may be used to consistently verify the integrity of the pump.

Referring now to FIGS. 165-166, in some embodiments, after a priming function has been completed, which may be performed for many reasons, including, but not limited to, initial priming of a new disposable housing assembly and/or priming after disconnect of a tubing set 2922 from a cannula. However, in any case, once a priming function has been completed, and before a cannula is attached to administer therapeutic medications, the system may, in some embodiments, perform a verification of the measurement valve 2940 integrity. This may be completed by actuating the pump plunger 2902 to deliver a threshold volume of fluid. This may be done by actuating the pump plunger 2902 with increasingly longer ontime, taking a volume measurements sensor 2946 measurement, and following, determining the volume pumped, and if the volume pumped is less than a threshold volume, actuating the pump plunger 2902 again using an increasingly longer ontime. However, where the pump system 2900, after repeating this process, reaches the maximum ontime (which, in some embodiments, is a preprogrammed time) and has not reached the threshold volume, i.e., pumped more than the minimum for a measurement valve 2908, 2940 failure detection but less than the minimum to pass the start-up test. Thus, in these circumstances, in some embodiments, the pump system 2900 may conclude that the pump plunger 2902 SMA actuator 2910 and the reservoir may be faulty.

With respect to measurement valve 2908, 2940 integrity, there are many benefits to confirming the integrity prior to administering therapy to a user/patient. These benefits include, but are not limited to, preventing over delivery. Thus, confirming the integrity of the pump system 2900 prior to administering therapy to a user/patient, safety of the system may be maintained.

With respect to the increasing ontime, in various embodiments using ontime to control the delivery of the medical fluid, this may be performed to verify a measurement valve 2940 failure versus a pump plunger 2902/pump plunger SMA actuator 2910 failure. The maximum ontime, in some embodiments, may be determined using many variables, including, but not limited to, the ontime that a reasonable pump plunger 2902/pump plunger SMA actuator 2910 requires to actuate. Thus, where the system is experiencing the maximum ontime and there is no volume measured by the volume measurement sensor assembly 2946, i.e., the volume measured is less than the measurement valve 2908, 2940 failure detection threshold, than it may be determined and/or confirmed that the measurement valve 2940, 2908 may have failed.

In some embodiments, however, the pump may be functioning, however, is weakened. Thus, in some embodiments, this differentiation may be confirmed by removing the disposable housing assembly, and attaching a new/another disposable housing assembly. Where the same results are repeated, it may be determined and/or confirmed that the pump plunger 2902 and/or pump plunger SMA actuator 2910 is weak and may be replaced. In some embodiments, the controller may recommend the reusable housing assembly of the pump system 2900 be replaced. In some embodiments, the controller may include a safety system that prevents the continued use of the reusable housing assembly that has been determined to be weak, thus, ensuring the potentially failed reusable housing assembly is not reused.

Additionally, where the system is confirming whether the pump is weak or the disposable is faulty, replacing the disposable with a new disposable may also confirm whether the reservoir 2918 in the first disposable housing assembly included a faulty reservoir which may indicate for example, but not limited, one or more of the following: that the reservoir valve 2904 is not functioning properly, e.g., is not able to be opened, i.e., is stuck in the closed position, and/or that the reservoir 2918 is not filled enough. Thus, where a fault is found with one disposable housing assembly, in some embodiments, the pump system 2900 may require the user/patient to replace the disposable housing assembly with another disposable housing assembly. In some embodiments, where a fault is found with the second disposable housing assembly, the pump system 2900, in some embodiments, may require another reusable housing assembly. Thus, in some embodiments, this system reduces the need of the system to determine whether the fault was caused by a leaking measurement valve 2940 or a faulty reservoir 2910 and/or faulty reservoir valve 2904. In either case, the reusable housing assembly is replaced. However, the system and methods described herein ensure that a faulty reusable housing assembly is detected and confirmed prior to continued use for providing therapy to a user/patient.

In some embodiments, when the threshold volume has been met as determined by the volume measurement sensor assembly 2947, in some embodiments, a leak test is performed. The threshold volume may be any volume preprogrammed into the system. In the exemplary embodiment, this volume may be 1 microliter, however, in other embodiments, the volume may be less than or greater than 1 microliter. The leak test, in some embodiments, includes holding the volume of fluid in the volume measurement chamber 2920 for a predetermined time, e.g., a number of seconds, which are preprogrammed/predetermined, and in the exemplary embodiments, may be approximately 2 to 5 seconds, however, in other embodiments, may be less than or greater than this time. The volume measurement sensor assembly 2947 then completes another volume measurement to determine whether any volume leaked from the volume measurement chamber 2920. Thus, in some embodiments, this leak test may determine and/or detect a slow leak as opposed to a fast leak (which may be determined/detected as discussed above).

In some embodiments, once the leak test is completed, the pump system 2900 opens the measurement valve 2940 to empty the volume of fluid from the volume measurement chamber 2920. In some embodiments, the pump system 2900 may alert the user/patient to shake the volume of fluid off the tubing set 2922 prior to connection to the cannula.

Following, in some embodiments, the system confirms the integrity of the battery, the volume measurement sensor assembly 2946, and the temperature before signaling to the user/patient that they may connect to the device, i.e., connecting the tubing set 2922 to the cannula. Thus, the start-up test presents an opportunity for the pump system 2900 to perform a delivery, conform the integrity of the disposable housing assembly and the reusable housing assembly. Additionally, the pump system executes 2900 all of the standard run-time integrity tests, i.e., the integrity tests performed after each delivery in the normal course of the therapy, providing an opportunity to detect other failures before therapy has started.

Additionally, in some embodiments, prior to any start-up test, the pump system 2900 may alert and/or alarm the user/patient of the start-up test and that the user/patient should ensure they are not connected to the medical device. In some embodiments, a user interface and/or controller device (e.g., remote control assembly) may require the user/patient to verify that they are disconnected, and thus, this may contribute to increased safety and prevention of inadvertent and/or accidental over delivery/delivery.

The start-up test, in some embodiments, may provide an initial data point for modeling the ontime versus volume delivered (in embodiments where this system of pump control is used). Thus, in some embodiments, the final volume pumped into the volume measurement chamber 2920 may be determined and be used as an initial model data point. From this initial data point, the slope and offset for the ontime may be determined or estimated. Thus, although the slope and offset may be adjusted through the ongoing operation of the pump, the start-up test may present an initial slope and offset which is a more valuable and useful starting point for the estimator as compared with no initial data. This may improve the accuracy of the estimator and the accuracy of the initial deliveries of the pump. In various embodiments, for example, those described above and below where an ontime control system is not used, the start-up procedure and method may be used to provide the initial date point for the embodiment of the control system.

In some embodiments, the infusion pump may perform a start-up test each time the user changes the infusion set/tubing set 2922. In some embodiments, the start-up test may be performed before the user connects the infusion set/ tubing set 2922 to the cannula. This may be beneficial for many reasons, including but not limited to, detecting faults before there is any potential for over or under delivery to the user. Thus, in some embodiments, the start-up test may have one or more of the following benefits: detects measurement valve 2940 failures and may update the pump model to improve the start-up transient. In addition, the start-up method may also execute all of the standard run-time integrity tests which may provide an opportunity for the pump system 2900 to detect other failures before the fluid delivery/therapy has started.

In the exemplary embodiment, the start-up may accomplish many tasks, including, but not limited to, initializing the feed forward actuator model offset, initializing the target measurement valve 2040 position near minimum, and performing pump system 2900 integrity checks. In practice, the start-up method may be similar to a standard delivery but with a few key differences outlined in detail below. Referring now to FIG. 167, a schematic of one embodiment of the start-up test method is shown. The start-up method may be broken into three distinct phases, namely, a pumping phase, a leak check phase and a valving phase. The pumping phase includes collecting data for the pump plunger 2902 modeling by way of pump SMA actuator 2910 re-actuation. The leak check phase includes checking pumped volumes against expected values after pumping fluid into the measurement chamber 2920 and after a delay. The valving phase includes releasing the pumped fluid from the measurement chamber 2929 and the measurement valve 2908 actuation target position is set by way of re-actuation of the measurement valve SMA actuator 2908.

Referring now also to FIGS. 168-170, where the pump plunger 2902 target position is plotted against the volume of fluid pumped to the volume measurement chamber 2920, during a start-up, the pump plunger 2902 may be re-actuated multiple times without actuation of the measurement valve 2940. At each re-actuation, the pump plunger 2902 target position change may be incremented. The size of this increment may vary based on the total volume that has already been pumped into the volume measurement chamber 2920 by previous re-actuations.

Initially, the goal of the start-up procedure is to accurately set the actuator model offset. In some embodiments, the target position may be initialized at a value which is low enough to ensure that the pump will not move fluid. The increment for re-actuation, $\delta_1$, in some embodiments, is set at a small value so that when the pump plunger 2902 moves from the dead band into its linear region, the first delivery will be small. In order to estimate the offset, based on this single first pumped volume, a default pump slope is assumed. The offset may be therefore:

$$\delta_{offset} = \delta_{target} - m_{default} v_{pumped} \quad [\text{EQ \#200}]$$

Where $m_{default}$ is the default slope, $\delta_{target}$ is the target position change for the first pumped volume delivery, and $v_{pumped}$ is the first pumped volume. The error in this estimate is directly proportional to the error in the slope, $\varepsilon$, and the size of $v_{pumped}$.

$$e = \delta_{offset,calculated} - \delta_{offset,actual}$$

$$e = v_{pumped} m_{default} - v_{pumped}(m_{actual} + \varepsilon)$$

$$e = v_{pumped} \varepsilon \quad [\text{EQ \#201}]$$

Referring to FIG. 168, thus, the smaller $v_{pumped}$ is, the less susceptible the offset calculation is to deviation from the average slope, $m_{default}$, used for the calculation. As such, the pumped volume limit for this phase, $V_1$, is close to zero. Once an actuation has moved any fluid, an accurate offset may be calculated. The offset may be calculated for every actuation which results in a pumped volume less than $V_1$, even those which move no fluid. In the event that no non-zero volumes are pumped which are less than $V_1$, the last zero volume data point is used to determine the offset. This result may be within $\delta_1$ of the actual offset.

Referring now to FIG. 170, after the first non-zero volume has been pumped and the initial pump offset calculated, the goal of re-actuation, in some embodiments, is to model the slope of the actuator using the least squares estimator described above. The increment of position change, $\delta_2$, in this phase is set so that multiple points may be collected for the regression analysis, therefore, improving the model.

Referring now to FIG. 169, as the volume measurement chamber 2920 fills with fluid, the dynamics of pumping may begin to change. Once a certain volume, $V_2$, has been achieved, the pumped volume for a given pump plunger 2902 position change (i.e., pump plunger 2902 displacement) may no longer reflect the normal empty chamber actuator response. After this point, the actuator model may no longer be updated. The third position change increment for re-actuation, $\delta_3$, is based on the normal pump controls described above. The goal of this phase, in some embodiments, is to fill the volume measurement chamber 2920 to the minimum hold volume, $V_{min,startup}$.

During the start-up procedure, integrity checks may also be completed in some embodiments. These may include, but are not limited to, one or more of the following. For example, if the pump target position reaches saturation, and the pumped volume remains close to zero, in some embodiments, the measurement valve 2940 is assumed to have failed in the open position. As may be determined from inspection, this is slightly different from the regular delivery for measurement valve 2940 failure because it is based solely on saturation rather than either saturation or the pump feed-forward model.

If the volume delivered to the volume measurement chamber 2920 for a pre-determined pump plunger 2902 position change, i.e., displacement, is substantially less than the expected volume, in some embodiments, it may be determined that the pump is experiencing a "weak pump" fault.

At the conclusion of the pump plunger 2902 actuation phase of the start-up test, the total volume pumped into the volume measurement chamber 2920 is determined. Where the minimum threshold for alarm is not met, the start-up procedure may conclude that both the measurement valve 2940 and the measurement chamber inlet check valve 2906 are functioning normally.

During start-up, the pump system 2900 tests for inter-delivery leaks using a similar procedure as performed for the run-time tests. In some embodiments, during the start-up procedure, after fluid has been pumped to the volume measurement chamber 2920 and a baseline "pumped" fluid measurement is taken/completed, a second measurement is taken after a fixed delay. If there is any volume change between these two measurements (outside the measurement noise), it may be concluded in some embodiments that it is likely due to fluid leaking past the measurement valve 2940 and/or the measurement chamber inlet check valve 2906. The start-up test leak-check procedure, in some embodiments, is the same as the run-time leak detection, however, the test parameters, e.g., waiting time between measurements, leak alarm thresholds, may be different.

In some embodiments, as with the pump plunger 2902, the measurement valve SMA 2912 is re-actuated multiple times during the start up test. In some embodiments, following each actuation, the volume in the volume measurement chamber 2920 may be compared to the volume in the volume measurement chamber 2920 before the pump plunger 2902 was actuated. In some embodiments, where there is still a residual volume in the volume measurement chamber 2920, the measurement valve SMA 2910 may be re-actuated. In some embodiments, the measurement valve 2940 target position change may be incremented from its default value with each re-actuation. When an actuation results in the residual volume dropping to near zero, the re-actuations may be stopped, and, in some embodiments, the last targeted measurement valve 2920 position change becomes the new default position change for future deliveries. In some embodiments, this may be beneficial for one or more reasons, including, by making the increment small, a near minimum measurement valve 2920 target position may be achieved. This may be desirable in some embodiments, for many reasons, including, but not limited to, it reducing the strain on the measurement valve SMA 2912 for each actuation, which may potentially increase the SMA time to failure/shorten the "life" of the SMA.

In some embodiments, the start-up occlusion detection may be the same or similar to the run time occlusion detection as described above. However, in some embodiments, the start-up occlusion detection may not require the occlusion detection criteria to be met for consecutive deliveries before alarming. As discussed above, the occlusion detection criteria is that the volume delivered, as determined by the volume measurement sensor, is greater than some fraction of the volume pumped.

In some embodiments, for each measurement valve 2940 re-actuation of the start-up test, the measurement valve 2940 target position may be incremented. In some embodiments, when the start-up test is complete, the last targeted measurement valve 2940 position may become the starting target measurement valve 2940 position for the first subsequent run time delivery.

In some embodiments, rather than the infusion pump system including a volume measurement sensor assembly, the pump system may include one or more optical sensors used as a feedback measurement. For example, referring also to FIGS. 171-172, in some embodiments, rather than a delivered volume determination from a volume measurement sensor assembly (see FIGS. 161-162), the volume delivered may be presumed/assumed from at least one pump plunger 2902 optical sensor input which may be correlated to a volume delivered based on a model of the pump assembly. In some embodiments, the pump assembly, which may be integrated into a reusable housing assembly, may be calibrated at manufacture, and therefore, a model of pump plunger 2902 displacement versus volume of fluid pumped, may be generated. In some embodiments, additional modeling may be completed with respect to disposable housing assemblies, thus, in some embodiments, each disposable housing assembly may be calibrated with a reusable housing assembly, and, in some embodiments, each disposable housing assembly may include, e.g., a calibration code, for example, which may either be input manually into e.g., a remote control assembly and/or read by the reusable housing assembly and/or remote control assembly, for example, using an RFID reader and writer and/or a bar code scanner. In some embodiments, each reusable housing assembly may include one or more disposable housing assemblies that have been calibrated with the reusable housing assembly. In some embodiments, each disposable housing assembly may be calibrated at manufacture.

The code, in some embodiments, may indicate the model for the controller to follow. Thus, variations in disposable housing assemblies may be input into the controller and pump predictive model; therefore, the model may be substantially accurate with respect to predicting an assumed volume delivered.

However, in some embodiments of the infusion pump system, a series of one or more models may be established. For example, in some embodiments, for each disposable housing assembly, a code, or indication of the model, may be assigned based on a calibration procedure at manufacture. In these embodiments, therefore, each disposable housing assembly may not be explicitly calibrated to a specific reusable housing assembly, however, the calibration procedure may fit the disposable housing assembly into a category or code that most closely represents the expected performance based on the calibration procedure.

Thus, in some embodiments of these embodiments of the infusion pump system, the displacement of the pump plunger 2902, as discussed above, may follow a trajectory. The at least one optical sensor may determine the actual displacement of the pump plunger 2902 and the volume delivered may be assumed/predicted based on a model. In various embodiments, the pump plunger 2902 may include one or more optical sensors to determine the displacement of the pump plunger 2902. Examples of the optical sensors and the placement of these optical sensors may include those described above with respect to FIGS. 145-149B In some embodiments, variations in the disposable housing assembly, for example, SMA wire actuation and membrane spring back/return to starting position following pump, etc., may be accounted for in a predictive model. Thus, in some embodiments, the number of actuations of the pump plunger 2902 may translate to a variation in the feed forward term to compensate for a change in the prediction of the ADC counts to pump plunger 2902 displacement. In some embodiments, the SMA wire may vary upon use, and/or the membrane of the pump chamber 2916 may vary upon use, and therefore, the assumed volume of fluid pumped from the reservoir 2918 for a pump plunge 2902 displacement may vary with the number of pump actuations. In some embodiments, as the volume in the reservoir is depleted, the expected volume delivered for ADC count may vary, and therefore, the volume in the reservoir at the start of the pump may be factored into the one or more models.

In some embodiments, the actual displacement of the pump plunge 2902 upon actuation may vary from the trajectory. The volume controller may feed back the actual pump plunger 2902 displacement information, sensed by the at least one optical sensor. The difference between the displacement requested and the actual displacement may be fed into one or more of the upcoming deliveries, therefore, compensating for a displacement error.

Thus, the displacement of the pump plunger 2902 may, in some embodiments, essentially be translated into an assumed/presumed volume delivery. Using the at least one optical sensor, the actual displacement of the pump plunger 2902 for each actuation of the pump plunger 2902 may be determined. The displacement may be fed back to the target pump plunger 2902 displacement, and the volume controller may determine whether and how to compensate for the actual displacement, if determined necessary. In some embodiments, as discussed above, the pump plunger 2902 displacement, and in some embodiments, taken together with the number of actuations of the pump plunger 2902 for a given disposable housing assembly, as well as the reservoir volume, may determine the volume delivered based on a model.

In some embodiments, whether and how to compensate for the determined actual displacement of the pump plunger 2902 may depend on one or more factors. These may include the size of the difference, whether the difference may indicate an over delivery or an under delivery, the number of consecutive actual displacement readings that may show error, etc. Thus, in some embodiments, a threshold error may be required prior to the controller adjusting the displacement trajectory.

In some embodiments of these embodiments of the infusion pump system, the system may include additional optical sensors to sense the movement of valves. For example, in some embodiments, the pump system may include at least one optical sensor to sense the movement of the reservoir valve 2904 and/or a pump chamber exit valve 2906, which may be similar to the valves described and shown above, for example, with respect to FIG. 150. The pump chamber exit valve 2906 may function in a similar manner to the volume measurement chamber valve 2906, only the pump chamber exit valve 2906, once opened, may allow fluid to flow from the pump chamber 2916 to the tubing set 2922. Thus, as discussed above, in these embodiments, the volume measurement sensor assembly 2946, together with the measurement valve, may be removed from the pump system 2900.

Thus, in these embodiments, confirmation of the valves 2904, 2906 opening and closing may confirm fluid was pumped from the reservoir 2918 and fluid was pumped out of the pump chamber 2916 and to the tubing set 2922. Following, where the optical sensors do not sense the opening and/or closing of one or more valves, the system may post an alarm. However, as discussed above with respect to various alarms posted to the system, in some embodiments, the alarms may be posted after a threshold is met. For example, in some embodiments, an alarm may be posted if the optical sensor determines that two consecutive pump plunger 2902 actuations occurred and two consecutive errors were detected on one or more of the valves 2904, 2906.

As discussed above with respect to the at least one optical sensor for the pump plunger 2902, in some embodiments, greater than one optical sensor may be used to collect sensor input from redundant optical sensors. In some embodiments, for example, as shown in FIG. 147, the two optical sensors for the pump plunger 2902 may be located in two different locations in the pump system 2900 thereby collecting sensor data from two different angles which may provide, in some embodiments, a more developed determination of the pump plunger 2902 displacement.

In some embodiments, the two or more optical sensors may be used for redundancy and also, to determine whether one of the optical sensors may have an error. Thus, in some embodiments, upon collection of optical sensor data from two or more optical sensors, the system may, comparing the two sets of data, determine that one of the sensors may have an error as the data points vary more than a preset threshold. However, in some embodiments, where the optical sensor data collected by the at least one optical sensor is so far away from the expected value, i.e., exceeds one or more thresholds, the system may post an alarm and conclude the at least one optical sensor has failed and/or is in error.

In various embodiments, the various membranes in the disposable housing assembly, including, but not limited to, the membrane assembly and the reservoir membrane, may include a coating, for example, in some embodiments, the coating may be parylene and the membrane may be SANTOPRENE, a thermoplastic elastomer made by ExxonMobil Corporation, Irving, Tex., U.S.A. However, in various other embodiments, the coating may vary and may include any form of parylene, for example, or other coating materials. In various embodiments parylene C may be used. In various embodiments, the parylene coating may be 3 microns in thickness, however in some embodiments the parylene coating may be 1 micron thick and in some embodiments, the reservoir membrane may include a different thickness of coating than the fluid pathway membrane. In some embodiments, the reservoir membrane may include a 3 micron thickness parylene coating and the fluid pathway membranes may include a 1 micron parylene coating. In carious embodiments, the thickness of the parylene may vary and may be less than 1 micron and/or greater than 3 microns.

In some embodiments, the coating may be applied using a tumble method, and in various embodiments, the membranes are coated on both sides (i.e., the fluid side and the dry side/non fluid side of the membrane). In various embodiments, various methods may be used to apply the coating to the membrane.

In various embodiments, the reservoir in the disposable housing assembly may be a 3 cc volume reservoir. However, in other embodiments, the volume of the reservoir may be less than or greater than 3 cc.

Referring now also to FIGS. 173A and 173B, in some embodiments, the parylene coating of the membrane may change the durometer of the membrane material and therefore, in some embodiments, the reservoir membrane may be designed to compensate for this change. In some embodiments, the reservoir membrane 4000 may be "inverted", that is, may be biased such that it collapses onto the bottom of the reservoir. In these embodiments, the reservoir membrane 4000 includes a perimeter seal 4002 (which in some embodiments may be a bead seal) that allows for the assembly of the reservoir membrane 4000 such that two plates may "pinch seal" the reservoir membrane 4000.

In various embodiments, the reservoir membrane 4000 may also include a septum 4004. In various embodiments, the septum 4004 may be made from SANTOPRENE and may be parylene coated. The septum 4004, in these embodiments, is configured such that the septum 4004 is substantially rounded, thus, when the disposable housing assembly is assembled (which, in some embodiments, may include laser welding) the septum 4004 may be pushed into a mating hole that is smaller than the septum 4004 diameter, thus, placing a compression force on the septum 4004. In addition, in some embodiments, there is axial compression. This compression may seal the septum 4004. In some embodiments, this configuration of the septum 4004 may be desirable when using a parylene coating as the parylene may make the septum more difficult to seal. In these embodiments of the septum 4004, the septum 4004 is configured such that the filling needle (e.g., a needle used to fill the reservoir with fluid) enters the septum 4004 at approximately a 45 degree angle.

In various embodiments, the reservoir membrane 4000 may include a bump feature 4008 approximate to the septum 4004 location. The bump feature 4008 may be shaped as shown, or may be a different shape. The bump feature 4008 may prevent and/or reduce the likelihood of accidental/unintentional piercing of the membrane 4000 by the filling needle which may reduce the likelihood of leaks in the reservoir. The bump feature 4008 may, in some embodiments, also serve as an air trap such that the filling needle may remove air after filling the reservoir to a desired volume with fluid.

Figure 174A:
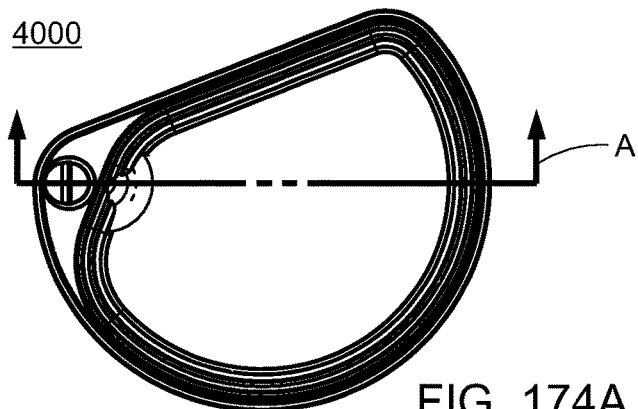
Figure 174B:
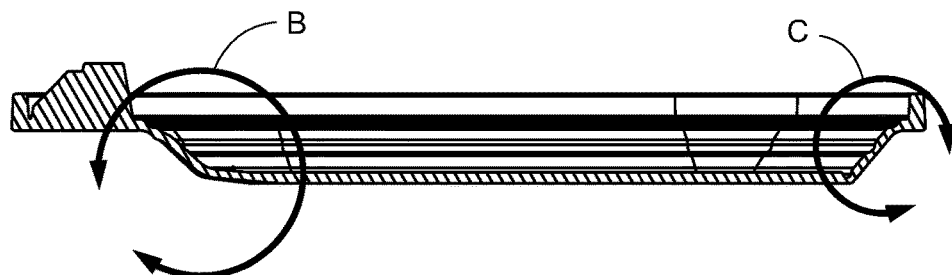
Figure 174C:
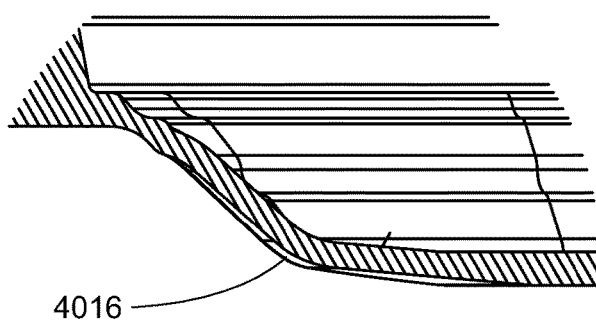
Figure 174D:
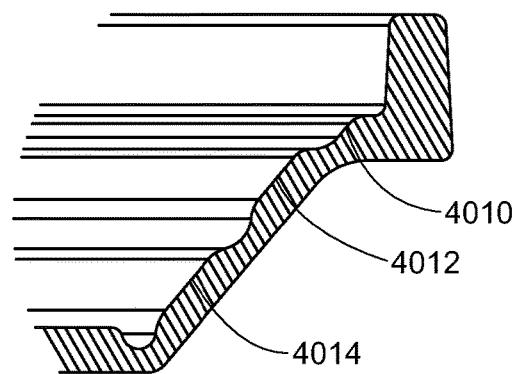

Referring now also to FIGS. 174A-174D, in some embodiments the reservoir membrane 4000 may include one or more features that minimize and/or reduce and/or remove positive pressure from being exerted onto the contents of the reservoir. In some embodiments, one or more notches may be introduced onto the reservoir membrane 4000. Referring now to FIG. 174D, showing the sectional view of FIG. 174A taken at "A", is an enlarged view of the section "C" shown in FIG. 174B, the notches 4010, 4012, 4014 essentially "weaken" the elastomeric properties of the reservoir membrane 4000 and these features allow the reservoir membrane 4000 to unfold completely or substantially completely when the reservoir is filled to capacity. The notches 4010, 4012, 4014 may also lessen the force on the fluid at these points. Thus, in some embodiments, the one or more notches may be located at one or more points where the force is greatest and/or in some embodiments, may be located to reduce the force to a maximum threshold amount. In various embodiments, the number, size and or location of the notches may vary.

In some embodiments the reservoir membrane 4000 may include features that reduce the dead volume of the reservoir such that air and/or fluid are not trapped in the reservoir. Referring now to FIG. 174C, which is an enlarged sectional view of section "B" in FIG. 174B (which is a cross sectional view of FIG. 174A taken at "A"). In some embodiments, a feature 4016 may be included and in some embodiments, the feature 4016 may be located near the septum 4004. In some embodiments, this feature is configured to ensure air is not "stuck" in the corner of the reservoir. In various embodiments, the features 4016 may be configured differently and/or located differently.

Referring now to FIG. 175, another embodiment of the actuator assembly 4018 is shown. In this embodiment, the crimp assembly 4020, which anchors the shape memory alloy wires 4022, 4024 may include post assemblies 4026, 4028. In some embodiments, the crimp assembly 4020 may include glue to anchor the memory shape alloy wires 4022, 4024 to the crimp assembly 4020. In some embodiments, glue may be advantageous for many reasons, including, but not limited to, limiting the thermal change of the shape memory alloy wires 4022, 4024 (i.e., serving as a thermal heat sink) and/or may serve as an additional mechanical attachment and/or may provide strain relief. In various embodiments, glue of various durometers may be selected to aid in strain relief. In some embodiments, the post assemblies 4026, 4028 may be used with and/or without glue at the crimp assembly 4020. In some embodiments, the post assemblies 4026, 4028 may be advantageous, for example, for they maintain the shape memory alloy wires 4022, 4024 and prevent and/or minimize and/or reduce lateral rotation and/or angular deflection.

Referring now to FIGS. 176A and 176B, another embodiment of the actuator assembly 4030 is shown. In this embodiment, the crimp assembly 4032, which anchors the shape memory alloy wires 4036, 4038 may include dove tail assembly 4034. In some embodiments, the crimp assembly 4032 may include glue to anchor the memory shape alloy wires 4036, 4038 to the crimp assembly 4032. In some embodiments, the glue may be applied over the crimp assembly 4032 and over the shape memory alloy wires 4036, 4038 connection to the crimp assembly 4032. In some embodiments, glue may be advantageous for many reasons, including, but not limited to, limiting the thermal change of the shape memory alloy wires 4036, 4038 and/or may serve as an additional mechanical attachment and/or may provide strain relief. In various embodiments, glue of various durometers may be selected to aid in strain relief. In some embodiments, the dove tail assembly 4034 may be used with and/or without glue at the crimp assembly 4032. In some embodiments, the dove tail assembly 4034 may be advantageous, for example, for it maintains the shape memory alloy wires 4036, 4038 and allows for lateral rotation and/or angular deflection.

Referring now to FIGS. 177A and 177B, a partial rendition of another embodiment of the actuator assembly 4046 is shown. In this embodiment, a hook 4040 is added to the crimp assembly 4048. As the actuator assembly 4046 rotates, the hook 4040 rotates and therefore, the shape memory alloy wires 4042, 4044 receive reduced/minimum bending stress. In some embodiments of this embodiment, the crimp assembly 4048 may be used with glue and/or without glue.

Referring now to FIGS. 178A and 178B, a partial rendition of another embodiment of the actuator assembly 4050 is shown. In this embodiment, a hook 4052 is added to the actuator assembly 4050. The shape memory alloy wire 4054 forms a single wire that wraps around a hook 4052. In some embodiments, the hook 4052 may be shaped differently and may include, for example, a holder to hold the shape memory alloy wire 4054. In some embodiments of this embodiment, the hook 4052 may be used with glue and/or without glue, and in some embodiments, the shape memory alloy wire 4054 may be glued approximately at the entire contact point between the shape memory alloy wire 4054 and the hook 4052. In some embodiments, the shape memory alloy wire 4054 may be glued at the entire contact point between the shape memory alloy wire 4054 and the actuator assembly 4050. In some embodiments, the glue may not be applied as extensively.

Referring now to FIGS. 179A and 179B, a partial rendition of another embodiment of the actuator assembly 4056 is shown. In this embodiment, a hook 4058 is added to the actuator assembly 4056. The shape memory alloy wire 4060, 4062 includes either two single strands or a strand that may wrap around the anchor. The shape memory alloy wire 4060, 4062 connects to connectors 4064, 4068. Connectors 4064, 4068 also connect to a strand of non-shape memory alloy wire 4060, which, in some embodiments, may be a strand of KEVLAR wire, or an electrically conductive wire. The strand of non-shape memory alloy wire 4060 wraps around the hook 4058. In some embodiments, the hook 4058 may be shaped differently and may include, for example, a holder to hold the non-shape memory alloy wire 4060. In some embodiments of this embodiment, the hook 4058 may be used with glue and/or without glue, and in some embodiments, the non-shape memory alloy wire 4060 may be glued approximately at the entire contact point between the non-shape memory alloy wire 4060 and the hook 4058. In some embodiments, the non-shape memory alloy wire 4060 may be glued at the entire contact point between the non-shape memory alloy wire 4060 and the actuator assembly 4056. In some embodiments, the glue may not be applied as extensively. In these embodiments, the bend and flex would occur on the non-shape memory alloy wire 4060. In various embodiments described above, there is an electrical connection between the connectors shown. In some embodiments, an electrically conductive wire may be included.

Referring now also to FIG. 180, another embodiment of the dove tail crimp embodiment is shown.

Referring now also to FIGS. 241A and 241B, another embodiment of the shape memory alloy 7016 and the actuator assembly 4056 are shown. In this embodiment, the shape memory alloy includes a crimp 7018 rather than, for example, an electrical contact. Thus, in this embodiment, a single shape memory alloy 7016 wire is used that is crimped, which mechanically fastens the shape memory alloy 7016 to the actuator assembly 4056.

In some embodiments, the actuator assembly 4056 may include additional material in various sections to impart additional stiffness to the actuator assembly 4056. This may be beneficial/desirable for many reasons, including, but not limited to, reducing the distance that the shape memory alloy wire travels.

In various embodiments, a torsion spring may be included in the actuator assembly. In some embodiments, the actuator assembly may include a pocket for the torsion spring, therefore, stopping the torsion spring during its upward position, therefore, the torsion spring, at this position, does not apply force to the actuator assembly, including the shape memory alloy.

In some embodiments, the actuator assembly may be made from plastic. In other embodiments, the actuator assembly may be made from metal and in these embodiments may serve as a heat sink. In the embodiments where the non-shape memory alloy wire or the shape memory alloy wire wraps around a hook, in some of these embodiments, the wire may wrap more than once around the hook. In some embodiments, the crimp may be an inline crimp and may float in space, where one piece of shape-memory alloy wire is attached to the crimp and a second, non-shape memory alloy wire is attached to the crimp. In some embodiments, the second, non-shape memory alloy wire may be a shape-memory alloy wire that has been "deactivated" such that the actuation properties of the shape memory alloy wire are no longer present in the wire. In some embodiments, the non-shape memory alloy wire may be KEVLAR or platinum, for example, but other materials may be used. In some embodiments, one shape-memory alloy wire may be used to pull the plunger pump down and one shape-memory alloy wire may be used to pull the plunger pump up. In some embodiments, the shape-memory alloy wire (and/or the non-shape memory alloy wire) may be potted, for example, in some embodiments by using glue, to the electrical contacts.

Referring now to FIGS. 181-184, various embodiments of the configuration of the measurement valve and the shape memory alloy configurations are shown.

Referring now to FIGS. 242 and 243, views of the measurement valve assembly 7020 are shown. The plunger assembly includes an optical flag 7022, and the bell crank assembly 7026 includes an optical flag 7024. In various embodiments, one or both of these optical flag 7022, 7024 may be monitored, however, in some embodiments, one of these optical flags 7022, 7024 are monitored. For example, in some embodiments, the optical flag 7022 may be monitored therefore monitoring the movement of the plunger 7032. In this embodiment of the bell crank 7026, two arms 7028, 7030 that lift the plunger 7032.

Referring now to FIGS. 185A and 185B, one embodiment of a packaging for the disposable housing assembly 4072 is shown. In some embodiments of this embodiment, the housing 4070 includes formed areas for the disposable housing assembly 4072, fill adapter 4076 and the tubing assembly (tubing and cannula contact assembly) 4074, which, in various embodiments, is bonded to the disposable housing assembly 4072. In various embodiments, the housing 4070 is made from PET (polyethylene terephthalate). In some embodiments, the housing 4070 may be formed using other materials. In some embodiments, the housing 4070 may be formed using thermoforming, and, in some embodiment, using thermoforming with vacuum assist. In some embodiments, plug assist may also be used. In various other embodiments, the housing 4070 may be formed using other techniques. In various embodiments the packaging may be designed to accommodate the disposable housing assembly 4072 and/or the disposable housing assembly attached to a fill adapter 4076, as well as the tubing assembly 7074. The housing 4070 may therefore include compartments 4078, 4080 to accommodate the various disposables. In various embodiments, once the disposable housing assembly 4072 and the cannula assembly 4074 are loaded into the housing 4070, a cover (not shown) is placed onto the housing 4070. In some embodiments, the cover may be made from TYVEK, in other embodiments; the cover may be made from another material. In various embodiments, the cover removably bonds to the housing 4070 and provides a barrier to maintain sterility inside the housing 4070.

Referring now to FIGS. 186A and 186B, another embodiment of a disposable packaging is shown. In some embodiments of this embodiment, the housing 4086 includes formed areas 4082, 4084 for the disposable housing assembly 4072, fill adapter 4076 and the tubing assembly (tubing and cannula contact assembly) 4074, which, in various embodiments, is bonded to the disposable housing assembly 4072. In various embodiments, the housing 4086 may be made from PET (polyethylene terephthalate). In some embodiments, the housing 4086 may be formed using other materials. In some embodiments, the housing 4086 may be formed using thermoforming, and, in some embodiment, using thermoforming with vacuum assist. In some embodiments, plug assist may also be used. In various other embodiments, the housing 4086 may be formed using other techniques. In various embodiments the packaging may be designed to accommodate the disposable housing assembly 4072 and/or the disposable housing assembly attached to a fill adapter 4076, as well as the tubing assembly 7074. The housing 4086 may therefore include compartments 4082, 4084 to accommodate the various disposables. In various embodiments, once the disposable housing assembly 4072 and the cannula assembly 4074 are loaded into the housing 4086, a cover (not shown) is placed onto the housing 4086. In some embodiments, the cover may be made from TYVEK, in other embodiments; the cover may be made from another material. In various embodiments, the cover removably bonds to the housing 4086 and provides a barrier to maintain sterility inside the housing 4086. As shown in FIG. 186B, in some embodiments, the housing 4086 may include features in the compartments, for example, in compartment 4084, that provide additional functionality to the housing 4086. For example, in FIG. 186B, the compartment 4084 in the housing 4086 functions to maintain the fill adapter 4076 in a position that may be beneficial/desirable for filling the disposable housing assembly 4072 reservoir.

In various embodiments, the shape of the housing of the packaging may vary. Some embodiments may include additional compartments and or features to accommodate additional disposables, which may include, but are not limited to, a filling syringe and/or a filling syringe and a filling needle.

Referring now to FIGS. 187A-187J, various views of another embodiment of disposable packing are shown. In these embodiments, a cover assembly 4088 may be included that is configured to mateably attach to the base assembly 4090 in a removable fashion and may be made from the same material as the base assembly 4090. However, in various other embodiments, the cover may be different from that shown in FIGS. 187A-187J and may be made from TYVEK, in other embodiments; the cover may be made from another material. In various embodiments of this embodiment, the cover may removably bond to the base assembly 4090 and provide a barrier to maintain sterility inside the base assembly 4090. In various embodiments, the base assembly 4090 is configured to receive the disposable assembly 4092, which, in various embodiments, may include a disposable housing assembly 4094, a fill adapter 4096 and a cannula assembly 4098.

In some embodiments of this embodiment, the base assembly 4090 and the cover assembly 4088 include formed areas that are configured to receive the disposable housing assembly 4094, fill adapter 4096 and the tubing assembly (tubing and cannula contact assembly) 4098, which, in various embodiments, is bonded to the disposable housing assembly 4094. In various embodiments, the base assembly 4090 and cover assembly 4088 may be made from PET (polyethylene terephthalate). In some embodiments, the base assembly 4090 and cover assembly 4088 may be formed using other materials. In some embodiments, the base assembly 4090 and cover assembly 4088 may be formed using thermoforming, and, in some embodiment, using thermoforming with vacuum assist. In some embodiments, plug assist may also be used. In various other embodiments, the base assembly 4090 and cover assembly 4088 may be formed using other techniques.

In various embodiments the packaging may be designed to accommodate the disposable housing assembly 4094 and/or the disposable housing assembly attached to a fill adapter 4096, as well as the cannula assembly 4098. The packaging may therefore include various compartments and features to accommodate the various disposables. In various embodiments, once the disposable housing assembly 4094 and the cannula assembly 4098 are loaded into the base assembly 4090, the cover assembly 4088 is placed onto the base assembly 4090. In some embodiments, the cover assembly 4088 may include a TYVEK cover. In some embodiments the cover assembly 4088 may be made from the same material as the base assembly 4090 or, of a different material. In various embodiments, the cover assembly 4088 removably attaches and/or mates to the base assembly 4090 and, together with the TYVEX, provides a barrier to maintain sterility inside the base assembly 4090.

Figure 187A:
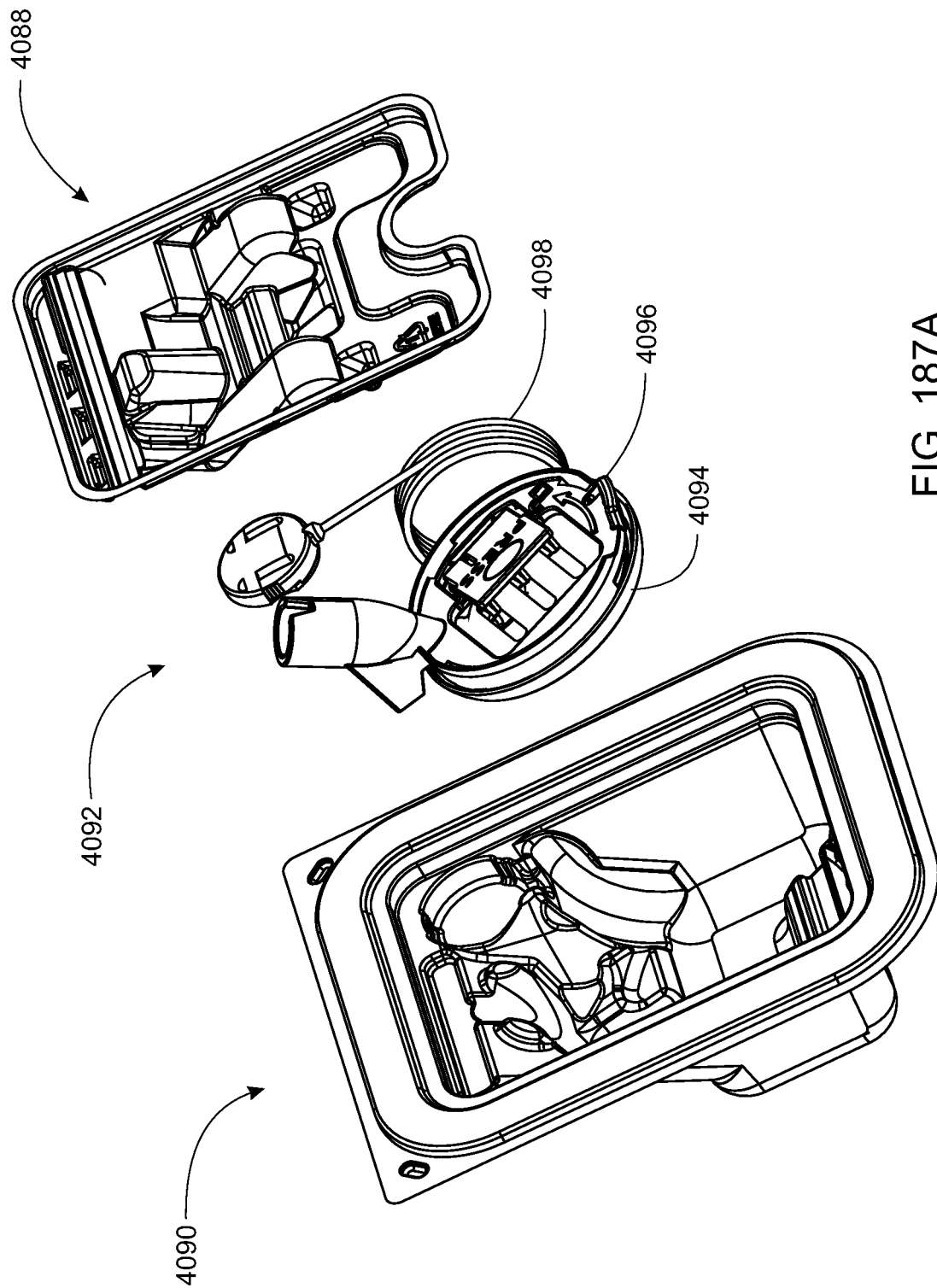
Figure 187B:
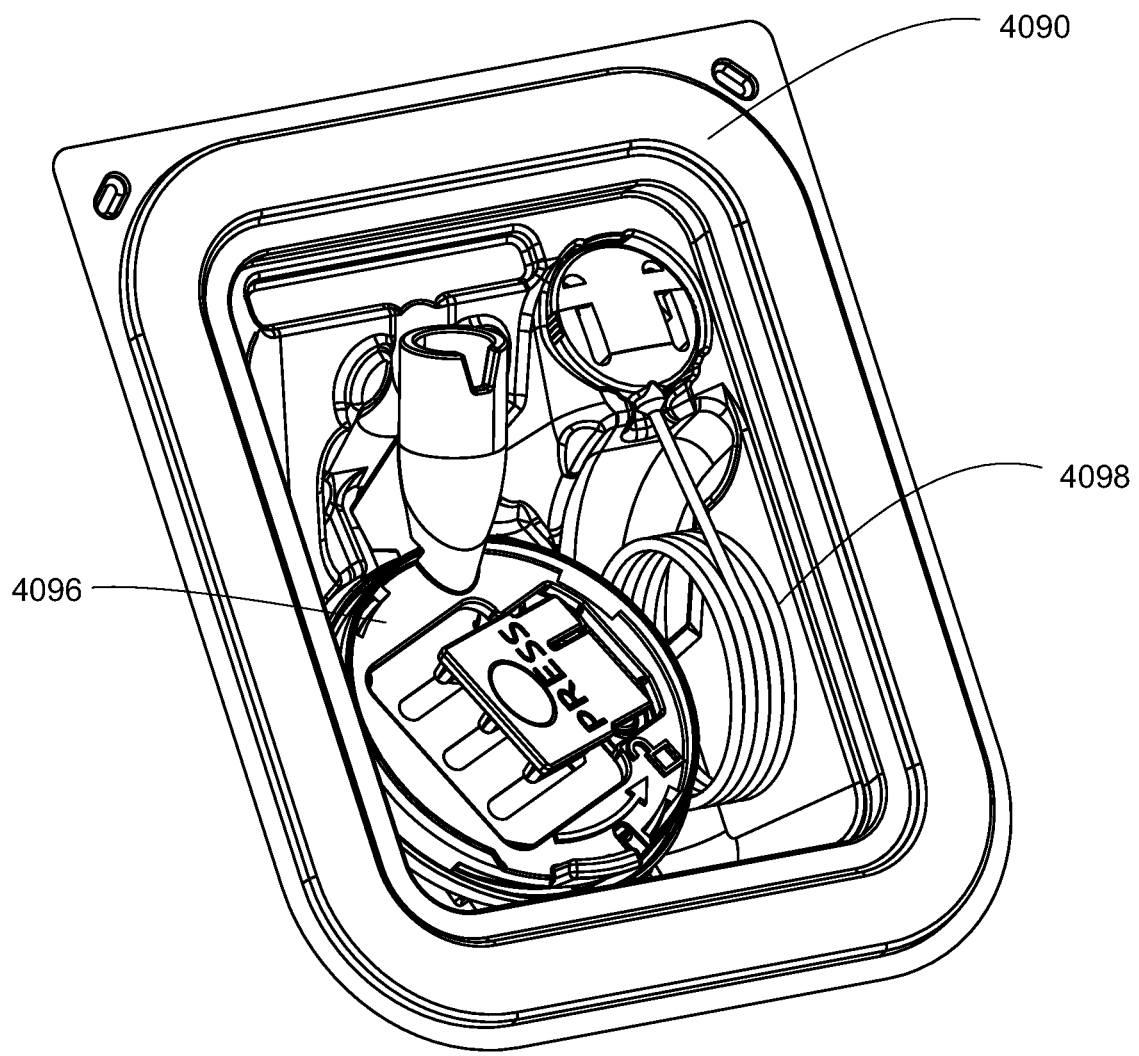
Figure 187C:
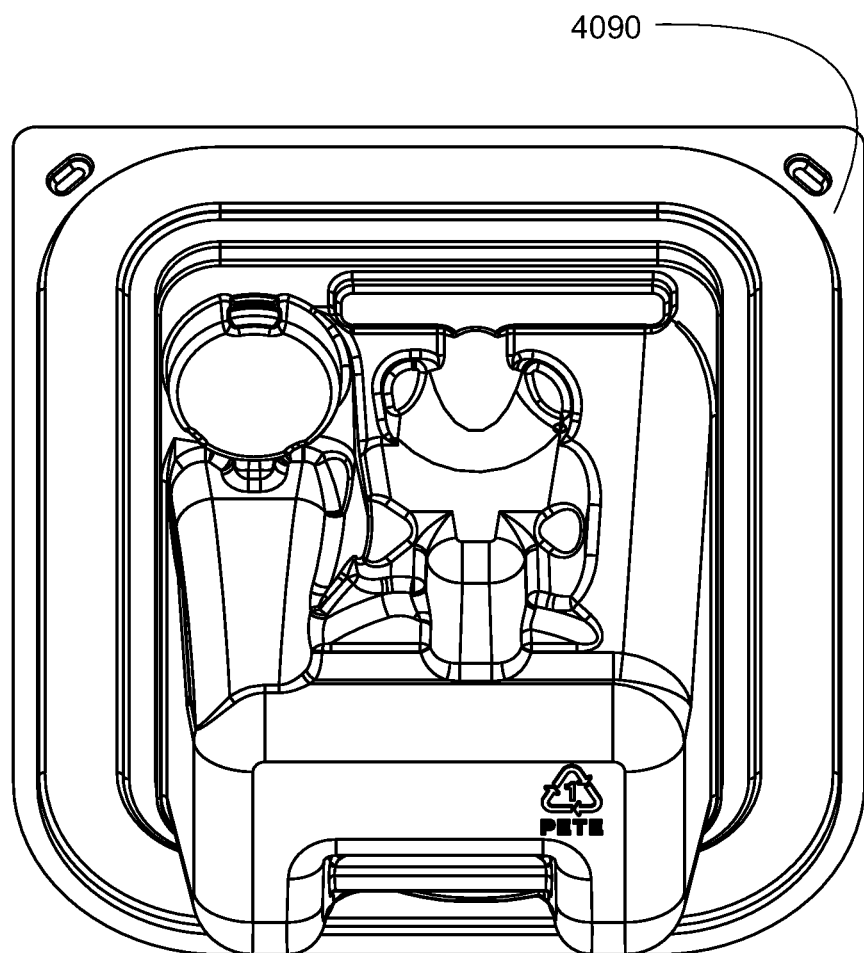
Figure 187D:
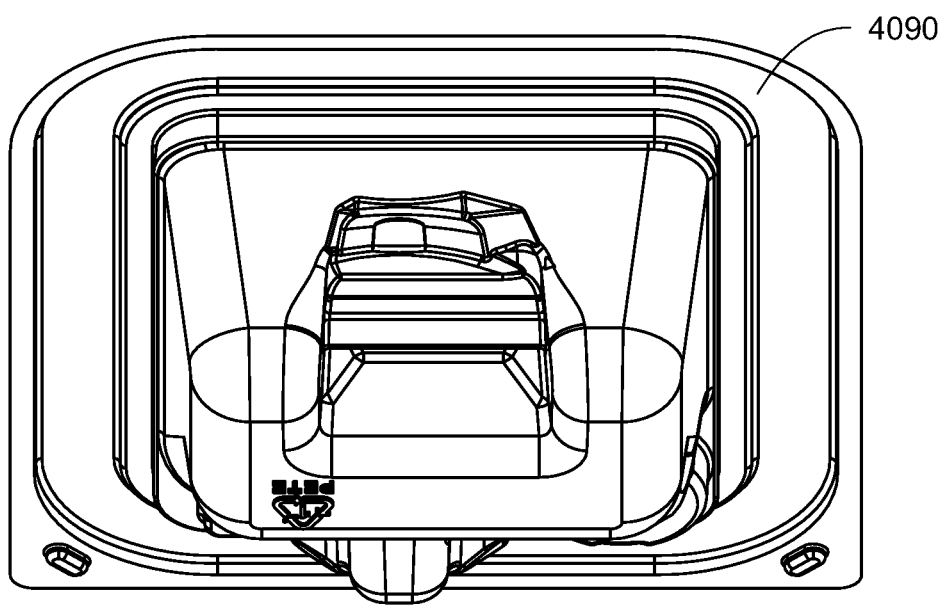
Figure 187E:
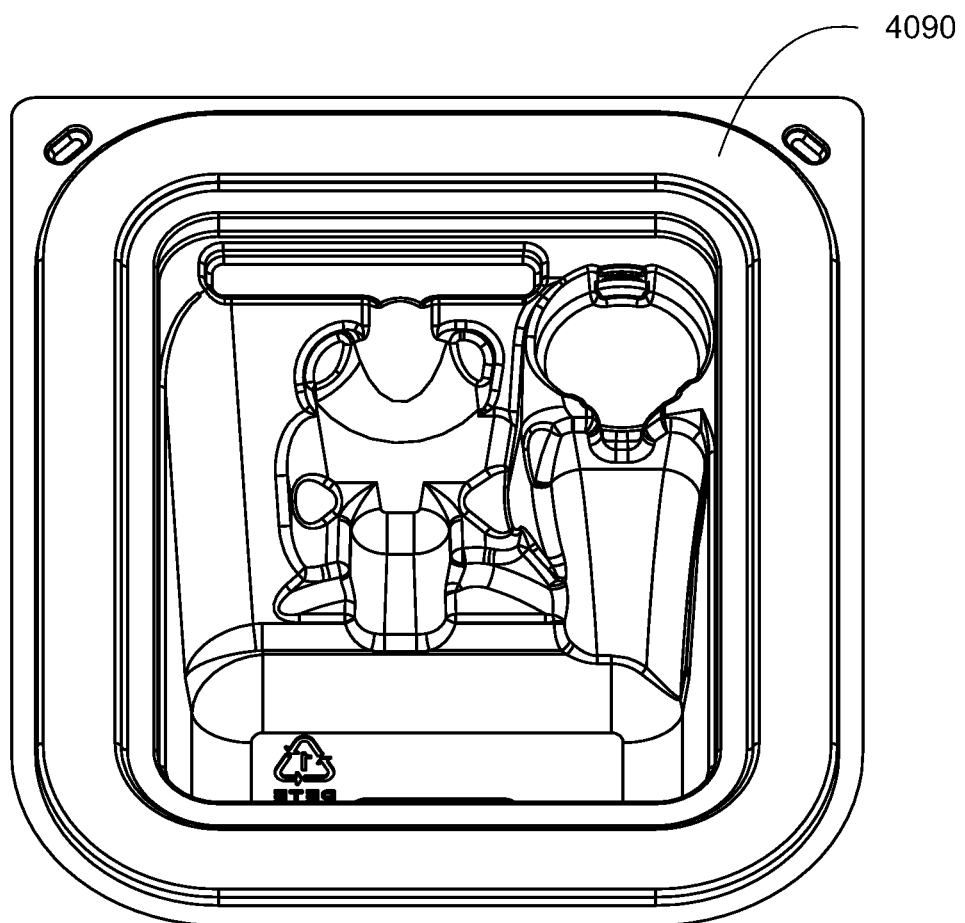
Figure 187F:
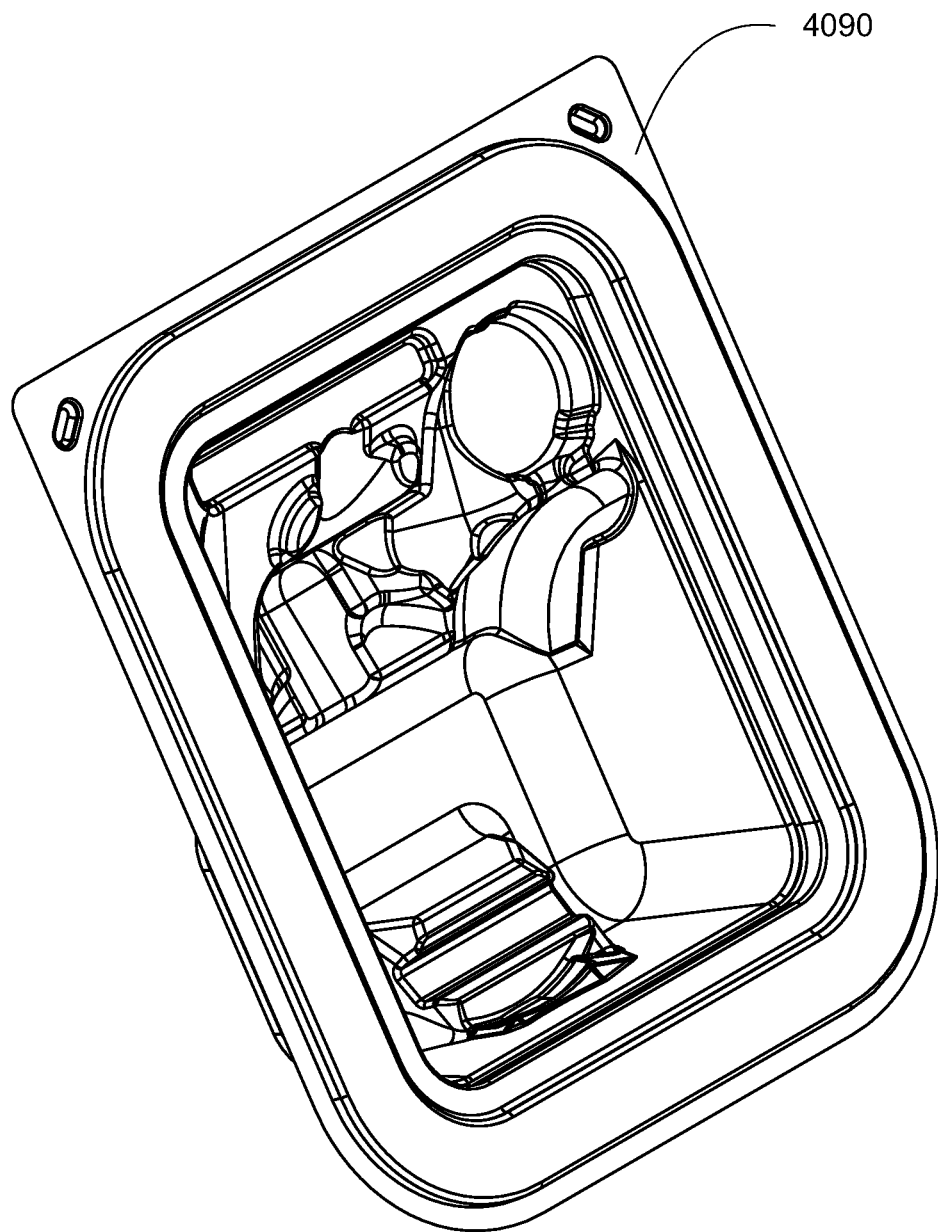
Figure 187G:
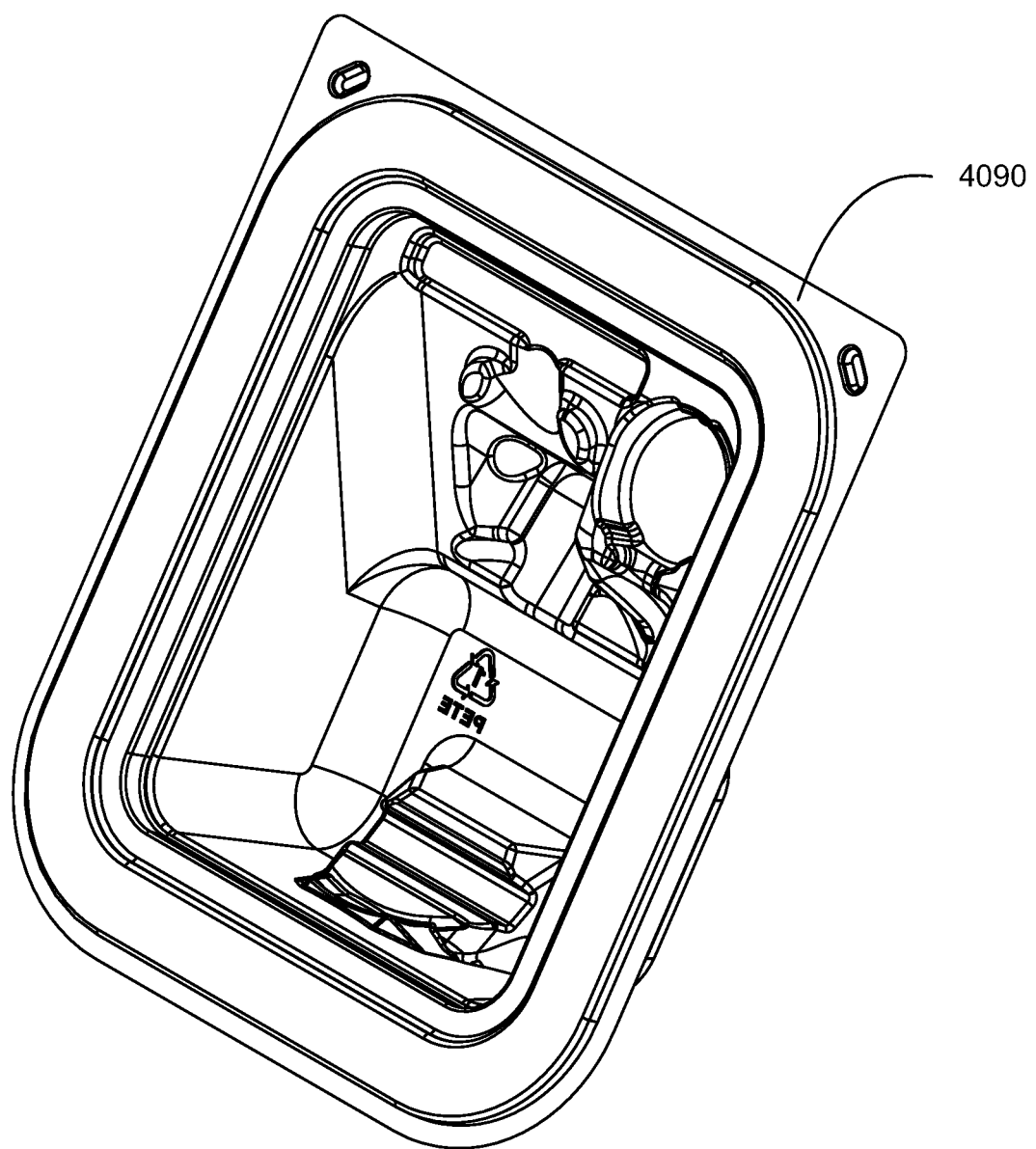
Figure 187H:
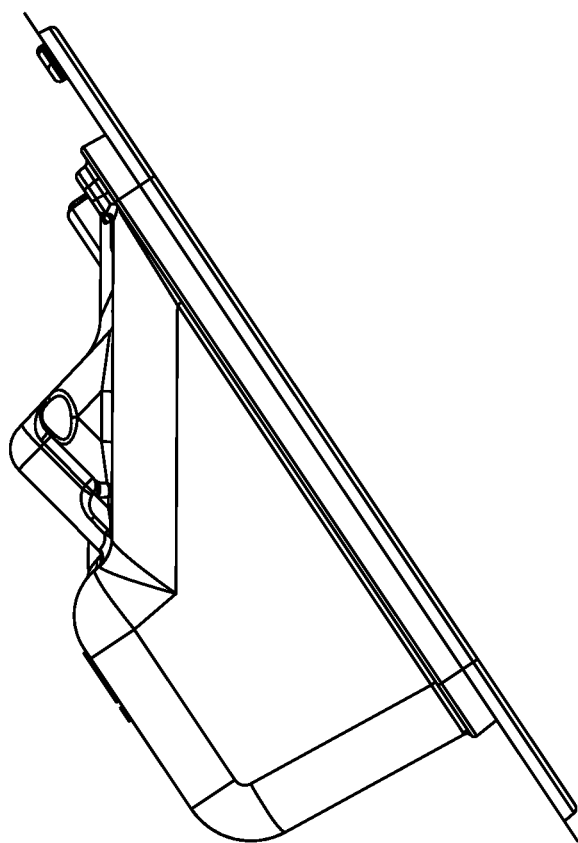
Figure 187I:
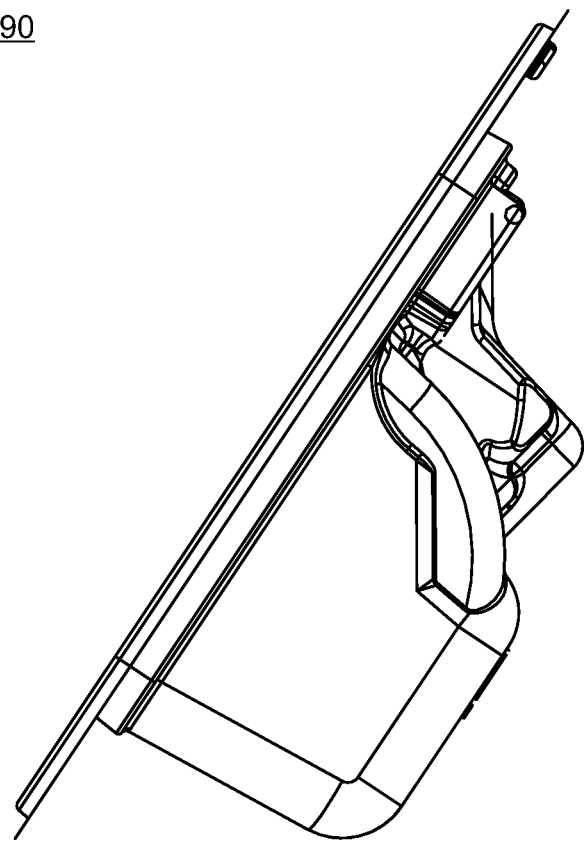
Figure 187J:
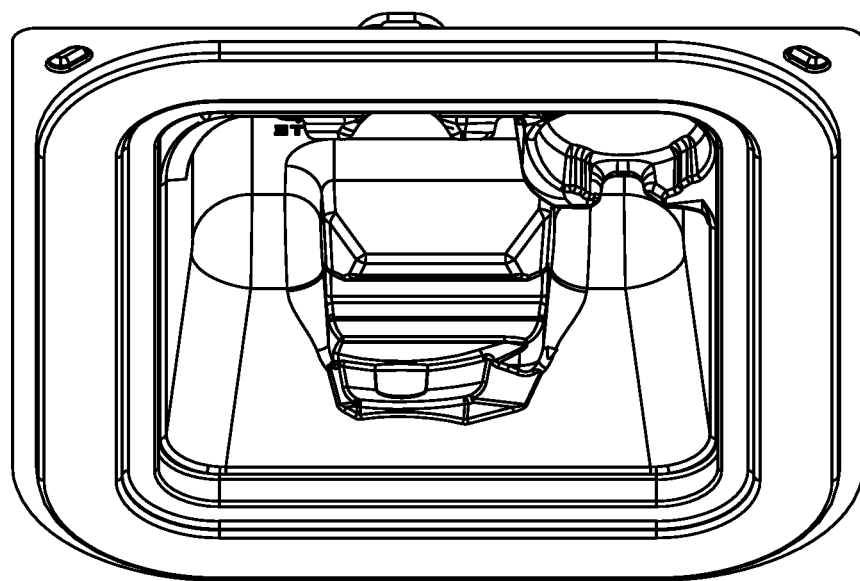

As shown in FIGS. 187A-187J, in some embodiments, the base assembly 4090 and the cover assembly 4088 may include various features in the compartments, which may provide additional functionality to the base assembly 4090 and the cover assembly 4088. For example, as shown in FIG. 187B, the compartment in the base assembly 4090 functions to maintain the fill adapter 4096 in a position that may be beneficial/desirable for filling the disposable housing assembly 4094 reservoir. In some embodiments, the compartment features maintain the fill adapter 4096 and disposable housing assembly 4094 at a 45 degree angle for filling the reservoir in the disposable housing assembly 4094. In various embodiments of the cover assembly 4088, compartments may be included to assist in maintaining the position of the fill adapter 4096 inside the base assembly 4090. In some embodiments, the cover assembly 4088 may include a well or other to accommodate the cannula connector during priming of the disposable housing assembly 4094.

In various embodiments, the base assembly 4090 may be configured to be self standing and this may be desirable/advantageous for many reason, including, but not limited to, the filling of the disposable housing assembly 4094 may be accomplished by a user using one hand, the packaging itself provides for a sterile work surface and maintains the disposable housing assembly 4094 inside the sterile work surface while filling to reduce/avoid contamination.

In some embodiments, the packaging may include user instructions for use wrapped around the outside of the packaging. In some embodiments, the shape and dimensions of the packaging may vary. Some embodiments may include additional compartments and or features to accommodate additional disposables or other devices, which may include, but are not limited to, a filling syringe and/or a filling syringe and a filling needle.

Many medical devices are subject to an ethylene oxide (EO) sterilization process to kill potentially harmful pathogens prior to use on or in a human or other animal. The process involves placing the parts to be sterilized in a chamber and subjecting them to phases of vacuum, humidification, heat and EO gas. The EO gas permeates through the packaging materials and comes in contact with the component's/device's surface(s). However, the EO gas also permeates and is absorbed by the materials during this process. Due to the volatility of EO, it is harmful to human tissue/biological processes and may have harmful interaction with substances, e.g. drugs, that come into contact with the components (e.g. insulin or other therapeutics), thus, the EO gas must be sufficiently removed from the sterilized parts before they may be used.

EO removal may be done using, for example, one of the following two processes. One includes using several vacuum cycles at the end of the sterilization cycle to purge the airspace of EO. Another is where the sterilized components are subject to an "aeration" process whereby the parts may be quarantined for a period of time that has been shown to provide sufficiently low levels of EO and EO variant "residues" (hereby referred to simply as "EO") exhausting from the components/devices. The vacuum cycle is effective in removing residual EO from the airspace and likely drawing some EO out of materials. During aeration, the EO residuals come out of the sterilized materials by diffusion. The EO is gaseous in nature, so the molecules must make their way to the surface of the component/device and then exhaust into the atmosphere. This process may take hours to days to weeks depending upon the EO dosing and material properties (which may include, but are not limited to, one or more of the following: affinity to absorb/hold onto the EO). Below is described a process to expedite the aeration process to allow sterilized components/devices to be used sooner and to better ensure that the components/devices are sufficiently aerated and EO residues are low enough to be considered safe for general human/animal use and/or drug interaction.

Many factors may affect the amount of time elapsed before a sufficiently low EO residual level is reached, these may include, but are not limited to, material used, temperature and packaging. With respect to material, the material density may play a role, thus, a more dense plastic may absorb less EO than, for example, rubber, but less dense rubber may more quickly release the EO/variants as compared with a plastic. With respect to temperature, temperature directly affects the rate of diffusion and raising the temperature raises the energy level of the gas molecules making them more mobile to exhaust from the material. With respect to packaging, on many cases, sterilized components reside in packages that allow them to be handled which indicates that, in many cases, there is an inherent barrier to prevent de-sterilization. In some instances, packaging may include a non-permeable barrier, for example, a plastic sheet and/or shell, and a removable semi-permeable barrier, for example, TYVEK. This packaging may also be enclosed in other packaging, for example, for shipment, such as cardboard boxes or multiple boxes. EO may readily penetrate the packaging during the sterilization process in part because of the motive vacuum force used at the onset of the process to actively move the EO particles into all airspace within the chamber. The EO then permeates the component material as it dwells due to the nature of diffusion (for example, particles move from a higher density volume into a lower density volume). During the vacuum flush cycles, any air born EO may be evacuated from the air space and the vacuum may draw an amount of absorbed gas from the component/device materials. During aeration, the higher concentration of the EO gas in the materials diffuses out into the lower EO concentration air space around the components, eventually making its way out of the packaging and into the atmosphere.

In some embodiments, for any device/component configuration or material, an impediment to driving EO levels down quickly may be the packaging. Diffusion rate for any gas is maximized when the density of molecules in the reference space (i.e., where the dense molecules are headed) is kept low. Diffusion acts to homogenize the density of gas in a volume and the large the gradient (density discrepancy) the more quickly the volume of higher density will reduce. In some cases, the aeration takes place in a well ventilated volume, for example, a room or chamber with moving air/ventilation, but the packaging acts to trap exhausted EO and reduce the diffusion gradient. There are often multiple trapped volumes around the sterilized components including the product packaging and one or more bulk packaging containers, for example, cardboard boxes. This results, in many cases, in the EO having to not only diffuse out of the sterilized parts, but the packaging itself. The produce packaging is unavoidable, but the bulk packing boxes act to block convection offered by the ventilated volume around the packaging.

In some embodiments, to decrease the EO levels more quickly, ventilating the sterilizer bulk packaging may allow convection to increase the EO gradient. Convection, in some embodiments, may inherently assist with equalization of the temperature throughout the packaging more efficiently since there may be less insulated airspace. In some embodiments, this process/method may include, but is not limited to, one or more of the following:

In some embodiments, a sterilizer bulk package may be used that contains individually packed components to be sterilized. A sterilizer bulk package containing slots, holes, mesh, etc., to provide a containment structure that may be ventilated form the space within the bulk pack to the atmosphere in the chamber/room where the aeration is taking place. A sterilizer bulk package may be disposable or reusable. In some embodiments, place the sterilizer bulk package into a standard cardboard box for shipping after aeration. Next, transfer the individually paced components to a standard cardboard box for shipping after aeration. The sterilizer bulk package may, in some embodiments, contain features that leave airspace between the individually packed components (i.e., spacer) to promote airflow around all sides of the components/devices/parts.

Sterilizer bulk package, in some embodiments, may incorporate features to mate the packaging directly to a duct that pushes air through the packaging. In some embodiments, this may include modification of a typical aeration chamber to duct air through the parts directly, in addition to moving through the airspace around the packaging.

The sterilizer bulk pack may, in some embodiments, contain a built in fan or multiple fans for increasing convection directly within the box. In some embodiments, this may be used with respect to a reusable device/pack/component.

The sterilizer bulk pack may contain, in some embodiments, elements to locally apply heat to the parts and expedite the process. This could be combined, in some embodiments, with direct convection within the box to increase the efficiently of the heating process. In some embodiments, this may be used with respect to a reusable device/pack/component.

While the process/methods described herein may be applicable to anything that is EO sterilized, in some embodiments, the process/methods may be used in critical applications where the residual EO levels must be significantly lower than what it considered "safe" for a human, for example, devices that come into contact with infused drugs that will be infused into a human, which may include, but is not limited to, insulin. Insulin and other drugs containing amino acid chains are highly sensitive to EO and exposure results in conversion of therapeutic molecules into non-therapeutic or perhaps harmful molecules. The residual EO levels in some cases may be required to be less than 1 part per million (PPM) in order to avoid having a significant impact on the drug potency. Driving the EO residual concentration down into the 1 PPM range implies the impact of the EO gradient (i.e., airspace must be <<1 PPM to maximize the diffusion potential).

Referring now also to FIG. 188, in some embodiments, it may be desirable to, rather than the pump architecture described and shown herein, include a pump architecture that includes two pumps and the pumps include inverted pump mechanisms. Therefore, rather than the pump actuator actuating in a manner such that the pump chamber gets smaller, the pump actuator starts in the down position, i.e., the pump actuator is in the pump chamber. When pumping fluid from the reservoir is desired, in this configuration, the plunger pump is pulled up, out of the pump chamber, and therefore, if there is air in the pump chamber, there is zero volume remaining in the pump chamber at the end of the pump stroke and the air will be pumped past the 1 way valve. In addition, in this configuration, the AVS/measurement chamber does not store pressure when performing the reading, therefore, the first/beginning and second/end reading are performed at the same pressure. Thus, if there is air in the measurement chamber, because the first and second readings are performed at the same pressure, the air is not compressed and therefore, the readings will be accurate despite the air present in the measurement chamber, the air is not part of the calculation. In some embodiments, there is a second inverted pump actuator/pump mechanism downstream the AVS/measurement chamber.

In various embodiments, a reverse pumping sequence may be used as the pump architecture. Thus, rather than having the Pump Piston and Reservoir Valve "normally open", the two components could be "normally closed". With the Pump Piston bottomed out in the Pump Chamber, the variable volume delivered to the AVS chamber/measurement chamber may drawn in from the Reservoir and be fully delivered on each Pump stroke, which affords the opportunity for maximum hydraulic force on each stroke. Air would not accumulate in the chamber because there would be minimal residual volume in the Pump Chamber between strokes and the Pump Piston would be in continuous contact with the Pump Chamber Membrane, thus minimizing the air interface with the membrane and the effect of air permeation through the membrane.

This could be implemented in several ways including but not limited to, one or more of the following:

System 1: Single Actuator, Active Pump/Active Valve

In some embodiments, this system would be essentially the same as the embodiments described above, but the mechanism may be designed to operate in reverse.

System 2: Dual Actuator, Active Pump/Active Valve

In some embodiments, this system would require separating the common articulating mechanism that drives the Pump and Valve pistons into just a Pump Piston/bellcrank and would require a second Reservoir Valve/bellcrank. It would also require adding an additional shape-memory alloy/NITINOL actuator to move the independent Reservoir Valve bellcrank/piston. This method would impart a lower load on the existing Pump NITINOL for actuating the Pump Piston alone.

System 3: Single Actuator, Active Pump/Passive Valve

In some embodiments, this system may involve removing the entire existing Reservoir Valve actuator functionality from the reusable Pump and placing this functionality in the Disposable Base. As with system 2, the common articulating mechanism that drives the Pump and Valve pistons would be separated into just a Pump Piston/bellcrank and the existing shape-memory allow/NITINOL actuator would drive the Pump Piston. The valve function may become a passive check valve that is part of the disposable Vase. Because the Reservoir must be open when there is a vacuum in the Pump Chamber (in order to draw fluid from the Reservoir) this functionality cannot be implemented in the reusable Pump, as is done with the AVS check valve. Some aspects of this passive check-valve concept:

Positive pressure in the Pump Chamber may close the valve.

Negative pressure in the Pump Chamber may open the valve.

The valve may be biased normally closed to lessen the chance of reduced efficiency from the valve leaking during small volume/low rate strokes.

The flow restriction when the valve is may be minimized to reduce the fill time of the Pump Chamber.

An example of an implementation of this system is shown in FIGS. 189A-189C.

In some embodiments, an o-ring seal may be added to the inlet valve as an additional sealing method to prevent ingress of fluid, from the reservoir, from entering the pump chamber. In some embodiments, the o-ring seal may be made from SANTOPRENE or another material and in some embodiments, the SANTOPRENE may not include a parylene coating. In some embodiments, the SANTOPRENE does include a parylene coating.

In some embodiments, silicone oil, or another type of oil or hydrophobic compound, may be added to the fluid lines in the disposable housing assembly at manufacture. In some embodiments, the silicone oil may enhance air bubble removal, where air bubbles develop in the fluid lines.

Tubing Connection to Disposable Housing Assembly

Referring now also to FIG. 190, in some embodiments, the disposable housing assembly 5000, which may include any of the various embodiments of the disposable housing assembly described herein, may, rather than a cannula (or tubing) assembly attached to the exit, include a luer connector 5002. In some embodiments, this may be advantageous for the luer connector 5002 may attach to any number of cannula assemblies/tubing assemblies by a standard connector 5004.

In some embodiments, the disposable housing assembly 5000 may be configured such that tubing, which, in some embodiments may be connected to a cannula assembly, may be introduced directly into the exit. In some embodiments, the tubing may be fastened with adhesive or another mechanism. However, in some embodiments, the tubing may be inserted and the reusable housing assembly, together with the disposable housing assembly, may maintain the tubing connected to the disposable housing assembly and maintain the tubing communication with the fluid path in the disposable housing assembly. In various other embodiments, the tubing may be inserted with an overmold that snaps into the exit. In some embodiments, the tubing may be inserted with an overmold that glues or otherwise adheres to the exit.

Referring now to FIG. 198, a disposable housing assembly 6000 which, in various embodiments, may include any of the various embodiments of the disposable housing assembly 6000 described herein is shown with tubing 6002 that has been inserted into the exit of the disposable housing assembly 6000. In some embodiments, the disposable housing assembly 6000 includes a tapered exit, tapered in either direction. In some embodiments, the disposable housing assembly 6000 exit includes a compliant seal 6006, which, in some embodiments, may be a face seal or radial seal. Thus, in some embodiments, the tapered entry and the compliant seal 6006 form a tubing 6002 interface in the disposable housing assembly 6000. In some embodiments, the tubing 6002 slides into the compliant seal 6006. Referring also to FIG. 48, in some embodiments, the tubing interface may be located in the base portion of the disposable housing assembly, however, in some embodiments, the tubing interface may be located between the base portion of the disposable housing assembly and the fluid pathway cover.

Referring now also to FIGS. 55A-56C, the reusable housing assembly is shown and, when rotated about the disposable housing assembly and connected to the disposable housing assembly, a nub 808, having a spring actuated tab 2980, on the locking ring assembly catches the tubing and pushes the tubing into a recess in the disposable housing assembly. In some embodiments, before the reusable housing assembly is rotated about the disposable housing assembly, there may include sufficient friction between the disposable housing assembly and the tubing to maintain the position of the tubing.

In various embodiments, the disposable housing assembly includes a tube recess that may be configured to maintain the tubing such that kinking is prevented and/or minimized. This may be desirable for many reasons, including, but not limited to, prevention and/or minimizing occlusions/restricted flow within the tubing.

In various embodiments, once the reusable housing assembly is rotated about the disposable housing assembly, the tubing is locked in position and therefore, a force on the tubing, for example, where the tubing is being pulled in a direction opposite the disposable housing assembly, may not dislodge and/or separate the tubing from being fluidly connected to the fluid path.

In various embodiments, the seal, which, as discussed above, may include a face seal, may form a hydraulic seal between the fluid path of the disposable housing assembly and the inner lumen of the tubing.

Figure 136:
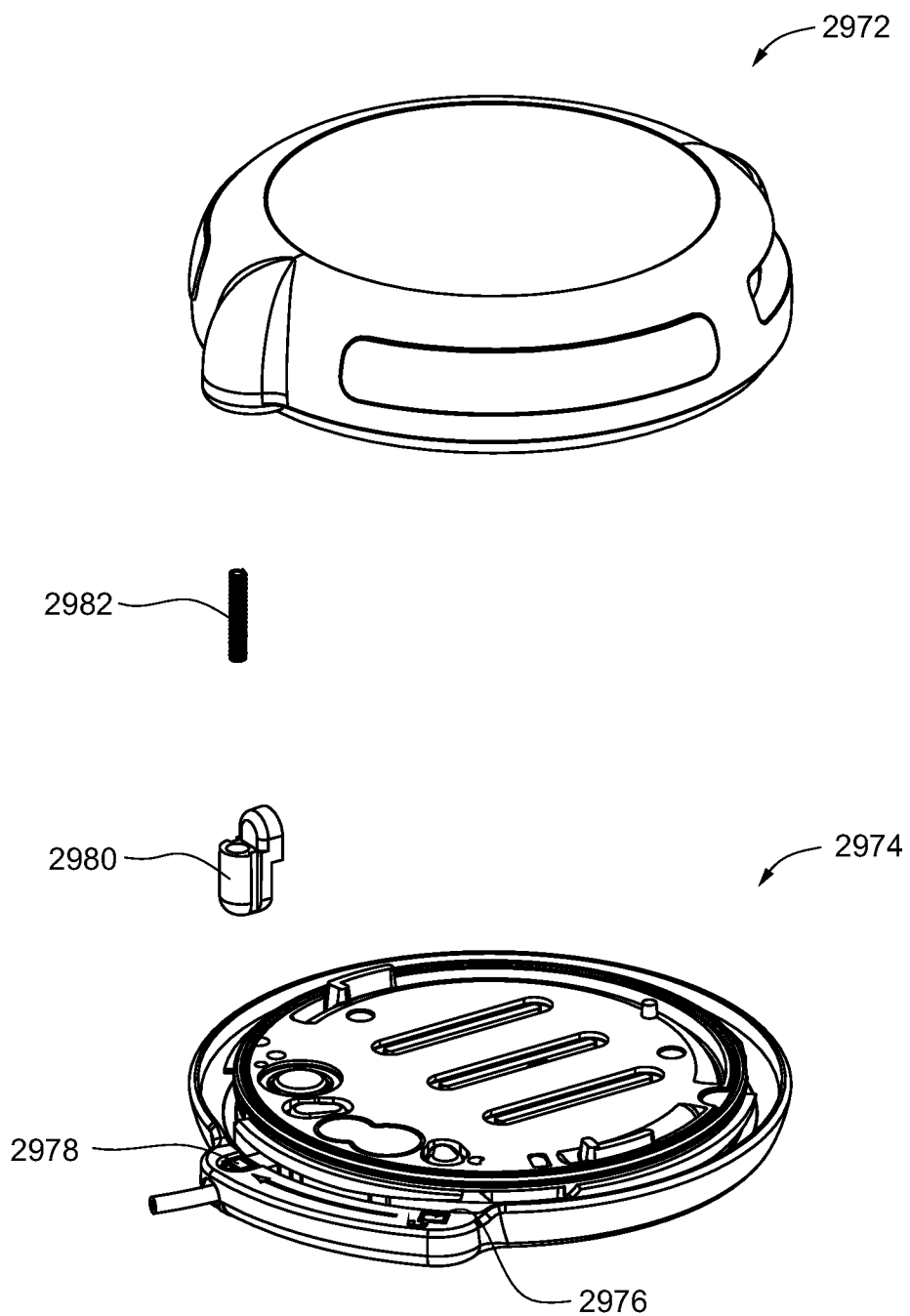
FIG. 136 shows a partially exploded view of one embodiments of the reusable housing assembly together with one embodiment of the disposable housing assembly with icons.

Referring now also to FIG. 199 and FIG. 136, in some embodiments, a plug 6008 or an at least partially compliant part may be connected to the tubing 6002. In some embodiments, the plug 6008 may be overmolded onto the tubing 6002. In some embodiments, the plug 6008 may be inserted into the exit of the disposable housing assembly 6000 which, in some embodiments, may include a mating recess. A face seal may be formed between the tubing/plug and the fluid path in the disposable housing assembly 6000. When the reusable housing assembly 6004 is connected to the disposable housing assembly 6000 by being rotated about the disposable housing assembly 6000 a nub, having a spring actuated tab 2980, on the locking ring assembly pushes down and secures the plug in place. As described above in greater detail, in some embodiments, the locking ring assembly may include a tab 2980 which includes a spring loaded plunger that may apply a load to the plug. Displacement of the plug when the tab pushes on the plug reinforces the hydraulic seal between the fluid path in the disposable housing assembly and the inner lumen of the tubing.

In some embodiments, the plug 6008 may include a rigid plate or rigid part and/or a portion of the plug 6008 may be rigid, which may, in some embodiments, distribute the loading across the compliant plug when the tab exerts force onto the plug 6008. In some embodiments, there may be a feature between the disposable housing assembly 6000 and the rigid portion of the plug 6008 to hold the plug 6008 in place before the reusable housing assembly 6004 is attached to the disposable housing assembly 6000.

Referring now also to FIG. 200A and FIG. 200B in some embodiments, a rigid plug 6008 may be connected to the tubing 6002. In some embodiments, the plug 6008 may be overmolded onto the tubing 6002. In some embodiments, the plug 6008 may be adhered to the tubing 6002, e.g., glued to the tubing 6002. In some embodiments, the plug 6008 may be inserted into the exit of the disposable housing assembly 6000 which, in some embodiments, may include a mating recess. In some embodiments, the plug 6008 may be inserted through the top of the "tab" on the disposable housing assembly 6000. An o-ring seal 6006 may be located between the plug 6008 and the base portion of the disposable housing assembly 6000. A face seal or radial seal may be formed between the tubing/plug and the fluid path in the disposable housing assembly 6000. When the reusable housing assembly 6004 is connected to the disposable housing assembly 6000 by being rotated about the disposable housing assembly 6000 a nub, having a spring actuated tab 2980, on the locking ring assembly pushes down and secures the plug in place. Thus, in this embodiment, the plug 6008 is attached to the disposable housing assembly 6000 from the top, but the tubing 6002 will be connected into the exit of the disposable housing assembly 6000. As described above in greater detail, in some embodiments, the locking ring assembly may include a tab 2980 which includes a spring loaded plunger that may apply a load to the plug. Displacement of the plug when the tab pushes on the plug reinforces the hydraulic seal between the fluid path in the disposable housing assembly and the inner lumen of the tubing.

In some embodiments, there may be a feature between the disposable housing assembly 6000 and the rigid plug 6008 to hold the plug 6008 in place before the reusable housing assembly 6004 is attached to the disposable housing assembly 6000.

Referring now also to FIGS. 201A and 201B, in some embodiments, a connector 6010 may be attached to the tubing 6002. In various embodiments of various embodiments of the connector 6010, the tubing 6002 may be connected to a cannula assembly (not shown). In some embodiments, the connector 6010 may be configured for both handling by a user and for interaction with the disposable housing assembly 6000. In some embodiments, as shown in FIGS. 201A and 201B, the connector 6010 may be "butterfly" shaped. In some embodiments, the connector 6010 is rigid and/or partially rigid and is overmolded onto the tubing 6002. The connector 6010 may include a plug portion and a tab or wing portion. However, in some embodiments, the disposable housing assembly includes the tab or wing portion. The connector 6010 mates with the exit of the disposable housing assembly 6000, e.g., in some embodiments, the plug portion of the connector 6010 is inserted into the disposable housing portion 6000 exit. In some embodiments, a compliant component may be located on the connector 6010, however in other embodiments, the compliant component 6006, e.g., a seal, may be in the disposable housing portion 6000. When the connector 6010 is connected to the disposable housing component 6000, the compliant component 6006 forms a hydraulic seal e.g., radial seal or face-seal. In some embodiments, the connector 6010 may bend and flip, i.e., butterfly, relative to the disposable housing assembly 6000 and, in some embodiments; the connector 6010 may include one or more features that connect the connector 6010 to the disposable housing assembly 6000. For example, in the butterfly embodiment, the wings of the butterfly may snap onto the disposable housing assembly 6000. In some embodiments, the wings of the butterfly and/or the connector 6010 may be adhesively connected to the disposable housing assembly 6000. In some embodiments, one side of the butterfly connector may include an adhesive strip with an adhesive covering. Before bending and flipping the wings, the adhesive covering may be removed. The wings may then be bent such that they adhere to the disposable housing assembly 6000.

When the reusable housing assembly 6004 is connected to the disposable housing assembly 6000 by being rotated about the disposable housing assembly a nub, having a spring actuated tab 2980, on the locking ring assembly pushes down and secures the plug in place. As described above in greater detail, in some embodiments, the locking ring assembly may include a tab 2980 which includes a spring loaded plunger that may apply a load to the plug portion of the connector. In some embodiments, displacement of the plug when the tab pushes on the plug reinforces the hydraulic seal between the fluid path in the disposable housing assembly and the inner lumen of the tubing.

Referring now also to FIG. 202, in some embodiments, a connector 6010 may be attached to the tubing 6002. In some embodiments, the connector 6010 may be configured for both handling by a user and for interaction with the disposable housing assembly 6000. In some embodiments, as shown in FIG. 202, the connector 6010 may be "L" shaped. However, in other embodiments, the shape of the connector 6010 may vary, shapes include, but are not limited to, "T" shapes, "L" shapes, and others as well as variations of "L" and "T" shapes. In some embodiments, the connector 6010 is rigid and/or partially rigid and is overmolded onto the tubing 6002. In some embodiments, the tubing 6002 is adhered to the connector 6010, e.g., the tubing 6002 may be glued to an opening in the connector 6010. In some embodiments, the connector 6010 may include a plug portion and a tab or wing portion. The connector 6010 mates with the exit of the disposable housing assembly 6000, e.g., in some embodiments, the plug portion of the connector 6010 is inserted into the disposable housing portion 6000 exit. In some embodiments, a compliant component 6006 may be located on the connector 6010, however in other embodiments, the compliant component 6006, e.g., a seal, may be in the disposable housing portion 6000. When the connector 6010 is connected to the disposable housing assembly 6000, the compliant component 6006 forms a hydraulic seal e.g., radial seal or face-seal. In some embodiments, the connector 6010 may be rotated relative to the disposable housing assembly 6000 and, in some embodiments; the connector 6010 may include one or more features that connect the connector 6010 to the disposable housing assembly 6000. For example, in the "L" shape embodiment, the bottom part of the "L" may snap onto the disposable housing assembly 6000. In some embodiments, the connector 6010 may be adhesively connected to the disposable housing assembly 6000. Connecting the connector 6010 to the disposable housing assembly 6000 prior to the connection of the reusable housing assembly 6004 to the disposable housing assembly 6000 may be desirable for maintaining the position of the connector 6010 during filling and priming of the disposable housing assembly 6000. Once the connector 6010 is connected to the disposable housing assembly 6000, the tubing 6002 is fluidly connected to the fluid pathway in the disposable housing assembly 6000 through the connector 6010.

When the reusable housing assembly 6004 is connected to the disposable housing assembly 6000 by being rotated about the disposable housing assembly 6000 a nub, having a spring actuated tab 2980, on the locking ring assembly pushes down and secures the plug in place. As described above in greater detail, in some embodiments, the locking ring assembly may include a tab 2980 which includes a spring loaded plunger that may apply a load to the connector. Displacement of the plug when the tab pushes on the connector 6010 reinforces the hydraulic seal between the fluid path in the disposable housing assembly 6000 and the inner lumen of the tubing 6002.

Figure 203B:
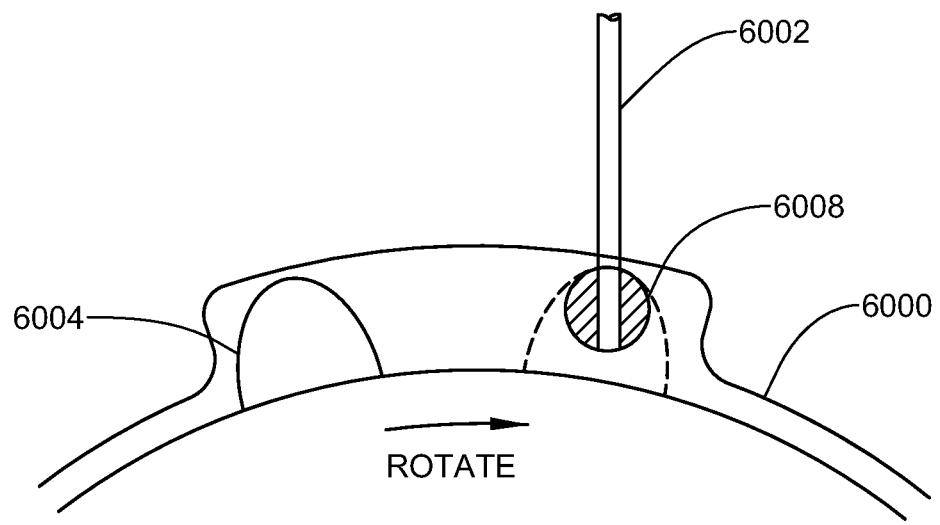

Referring now also to FIGS. 203A and 203B, in some embodiments, a rigid plug 6008 may be connected to the tubing 6002. In some embodiments, the plug 6008 may be overmolded onto the tubing 6002. In some embodiments, the plug 6008 may be adhered to and/or glued to the tubing 6002, however, in various embodiments; any mechanism for attaching the plug 6008 to the tubing 6002 may be used. In some embodiments, the plug 6008 may be inserted into the exit of the disposable housing assembly 6000 which, in some embodiments, may include a mating recess. A compliant face-seal or radial seal (seal 6008) may be located between the plug 6008 and the base portion of the disposable housing assembly 6000 or between the base portion and the fluid pathway of the disposable housing assembly 6000. A face seal or radial seal may be formed between the tubing/plug and the fluid path in the disposable housing assembly. In some embodiments, a complaint face-seal or radial seal may be located on the rigid plug. As shown in FIG. 203A, in some embodiments, the locking ring assembly may include a tab with a slot 6012. When the reusable housing assembly 6004 is connected to the disposable housing assembly 6000 by being rotated about the disposable housing assembly 6000 the slot 6012 in the tab goes around the tubing but captures the plug on the tubing. In some embodiments, the locking ring assembly may include a cam-like feature between the tab and the locking ring and the plug to compress/secure the plug. In these embodiments, the tubing may be maintained in place and the hydraulic seal may be reinforced.

In some embodiments, there may be a feature between the disposable housing assembly 6000 and the rigid plug 6008 to hold the plug 6008 in place before the reusable housing assembly 6004 is attached to the disposable housing assembly 6000. In some embodiments, a snap-like feature is included between the disposable housing assembly and the plug 6008 to hold the plug 6008 in place before the reusable housing assembly 6004 is connected to the disposable housing assembly 6000. In other embodiments, the feature may include, but is not limited to, adhesive, catches, snaps, loops, hooks, and any other feature that maintains the connector on the disposable housing assembly before the reusable housing assembly 6000 is connected.

In various embodiments, an embodiment of a connector may be used. These embodiments may include one or more of the various embodiments discussed above with respect to connectors. However, below, various embodiments of connectors are discussed. The descriptions of these embodiments are not limiting, each may additionally include one or more features described above with respect to connectors. Additionally, in various embodiments, one or more features from one or more embodiments may be combined with one or more features from one or more different embodiments, to form additional embodiments.

Referring now also to FIGS. 204A, 204B and 204C, in some embodiments, a rigid push and rotate connector 6010 may be used. In some embodiments, the location of the exit may be modified to be located on the opposite side of the disposable housing assembly "tab". In some embodiments, the shape of the connector 6010 may be similar to that of the surface adjacent to the exit of the disposable housing assembly ("tab"), however, in various other embodiments, the shape of the connector 6010 may be any shape. In some embodiments, the connector 6010 is attached to the tubing 6002 by adhering the connector 6010 to the tubing 6002, e.g., gluing, or overmolding the connector to the tubing. In various embodiments, the connector 6010 may include a plug portion and a top portion connected to the plug portion.

In various embodiments, a compliant component 6006 is either attached to the connector 6010 or located in the disposable housing assembly 6000. The compliant component 6006 forms a face or radial seal when the connector 6010 is mated/connected to the disposable housing assembly 6000. In various embodiments, the disposable housing assembly 6000 includes a taper or snap interface for the connector 6010.

In various embodiments, the plug 6008 of the connector 6010 is inserted into the disposable housing assembly 6000 with the tab 6018 portion pointing upward. Once the plug 6008 portion is inside the disposable housing assembly 6000, the tab 6018 portion may be rotated to rest above the disposable housing portion 6000 adjacent to the exit (i.e., adjacent to the "tab portion" on the disposable housing assembly). In some embodiments, mating locking features 6016, 6020 (6020 not shown) may be included on the tab 6018 portion of the connector 6010 and the disposable housing assembly 6000 such that the connector 6010 is held in place before the reusable housing assembly 6004 is attached to the disposable housing assembly 6000. In some embodiments, the mating locking features 6016, 60120 may include, but are not limited to, snap buttons and/or catch features. In some embodiments, a hook or other feature may be located on the opposite end of the tab 6018 portion of the connector 6010 such that it loops over the end of the tab 6018 portion of the disposable housing assembly 6000 and maintains the position of the connector 6010.

When the reusable housing assembly 6004 is connected to the disposable housing assembly 6000, by being rotated about the disposable housing assembly 6000, a nub, having a spring actuated tab 2980, on the locking ring assembly pushes down and secures the connector 6010 to the disposable housing assembly 6000.

In some embodiments, the connector 6010 may include a feature for example, a finger relief 6022, for removing the connector 6010 from the disposable housing assembly 6000. In some embodiments, translation of force on the finger relief 6022 in a direction away from the disposable housing assembly 6000 releases the connector 6010 latching and allows for rotation of the connector 6010 away from the disposable housing assembly 6000.

In the various embodiments, the connector is shown attached to a tubing. In various embodiments, the other end of the tubing may be attached to a cannula. In some embodiments, the tubing may be removably attached to the connector by attachment using a standard or other luer connection. However, in some embodiments, the tubing may be non-removably attached to the connector. In some embodiments, the connector may be attached to the disposable housing assembly and the tubing may then be attached to the connector while the connector is attached to the disposable housing assembly. In some embodiments, including exemplary embodiments shown and described herein, the tubing may be bonded or attached to the connector and the connector is then attached to the disposable housing assembly. In some embodiments, a user may attach the tubing to the connector, however, in other embodiments, the tubing may be attached during manufacture, and the user attaches the connector to the disposable housing assembly.

The connector may be any shape, including, but not limited to, the shape shown in herein. In various embodiments, the connector may be various shapes and sizes and may include one or more of the features Referring now also to FIG. 205, in various embodiments, the tubing 6002 may be connected to the various embodiments of the connector 6010 or plug 6008 using glue 6024 or adhesive. In various embodiments, the connector 6010 and/or plug 6008 may include an opening configured to receive the tubing 6002. In various embodiments, the opening in the connector 6010 may include a taper to maintain a minimum bend radius with respect to the tubing 6002. An example of an opening on a connector 6010 is shown in FIG. 205. This configuration may be desirable and beneficial for many reasons, including but not limited to, minimizing and/or preventing kinking of the tubing and or minimizing and/or preventing occlusions/flow restrictions in the tubing.

Referring now also to FIGS. 206-210, another embodiment of a connector is shown. In some embodiments, the connector includes a tab 6018 and a plug 6008. Tubing 6002 is connected to the connector 6010. In some embodiments, the other end of the tubing 6002 is connected to a cannula 6026. This embodiment is shown in FIG. 207. Referring now also to FIG. 208, the plug 6008 may be any of the embodiments shown and described herein. Other plug embodiments are also contemplated. The plug 6008 is inserted into the exit 6028 of the disposable housing assembly 6000. In some embodiments, the disposable housing assembly 6000 may include an interlocking feature, disposable housing assembly interlocking feature 6020, that mates with an interlocking feature, connector interlocking feature 6016, on the connector 6010. Upon insertion of the plug 6008 and rotation of the connector 6010, the interlocking features 6016, 6020 may mate and removably lock and/or attach. In some embodiments, once the plug 6008 is inserted and the connector 6010 rotated, the connector 6010 may not be removed unless and until the connector 6010 is rotated. In some embodiments, the connector 6010 may have additional locking/interlocking features and or different interlocking features than those shown herein.

Once the reusable housing assembly is rotated about the disposable housing assembly and connected to the disposable housing assembly, the connector, in this embodiment, will be unable to be removed from the disposable housing assembly as the connector will be prevented from rotating by the nub, having a spring actuated tab 2980, in the locking ring assembly of the reusable housing assembly.

In various embodiments, the connector includes a plug and in some embodiments, the connector is a plug 6008. Various embodiments of the plug 6008 are described with reference to FIGS. 211-217. Referring now also to FIG. 211-217, these embodiments of the plug are shown as examples of various embodiments that may be used with any of the embodiments of the connector shown and/or described herein. Further, embodiments contemplated include any connector that may accomplish that which is described herein. Any of these embodiments of the connector may include one or more of the embodiments of the plug shown and/or described herein.

Figure 211:
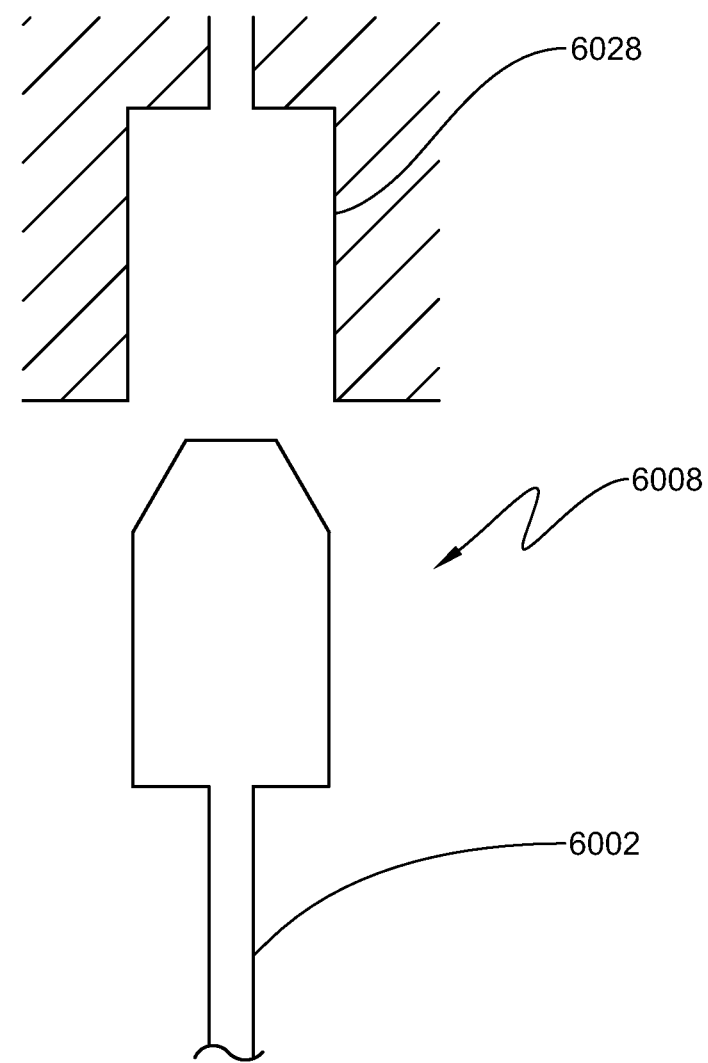

Referring to FIG. 211, an embodiment of a plug 6008 is shown with an embodiment of an exit 6028 to the disposable housing assembly. In some embodiments, the plug may include a luer-type feature which may, in some embodiments, be modified with a latch mechanism. In these embodiments, the plug 6008 may be made from rigid material. In some embodiments, the plug 6008 may include a shallow taper having shallow clearance.

Figure 212:
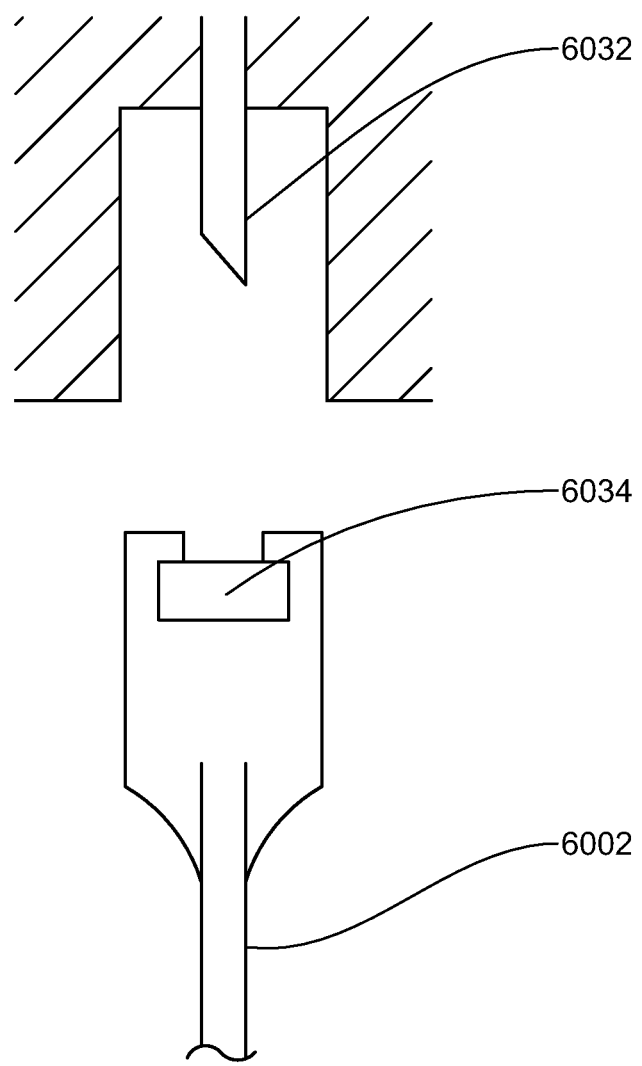

Referring now to FIG. 212, in some embodiments, the disposable housing assembly 6000 may include a needle fixture 6032. In these embodiments, the plug 6008 may include a captured septum 6034. In these features, additional compliant materials, e.g., seals, may not be desired in the disposable housing assembly 6000, as discussed in various embodiments above. However, in some embodiments, the use of seals, as described in above-embodiments, may be used.

Figure 213:
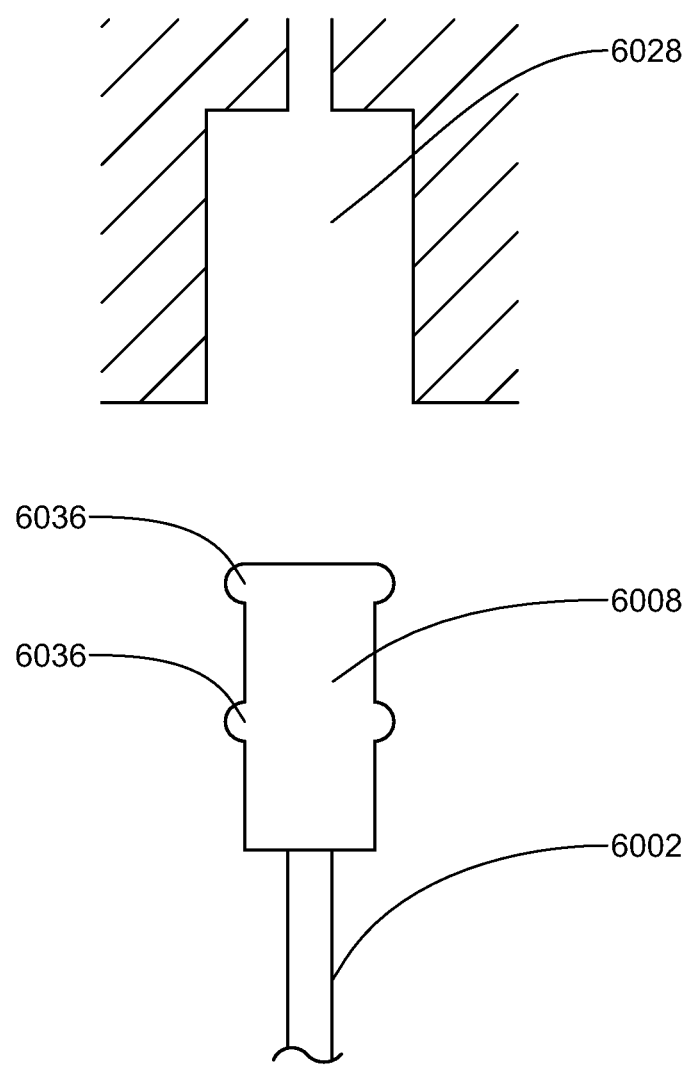

Referring now to FIG. 213, in some embodiments, the plug 6008 may be an elastomeric material with one or more integrated o-rings 6036. In some embodiments of this embodiment of the plug 6008, the plug 6008 may be overmolded, solvent bonded or adhesively bonded to the tubing. In some embodiments, the plug 6008 may be made from polyurethane, however, in other embodiments; the plug 6008 may be made from other materials. In some embodiments, the plug 6008 may be glued and/or adhered to the tubing. In some embodiments, the plug 6008 may be overmolded to the tubing 6002.

Figure 214:
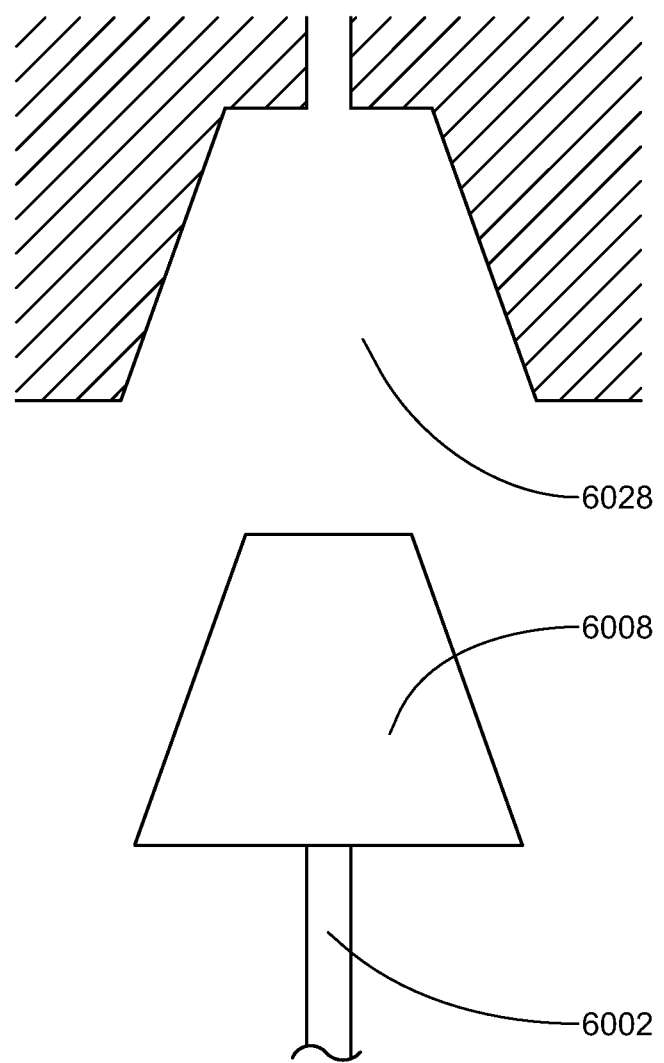

Referring now to FIG. 214, in some embodiments, the disposable housing assembly may include a tapered exit 6028. In some embodiments, the plug 6008 may include a tapered feature. In some embodiments, the plug 6008 may be made from polyurethane, however, in other embodiments; the plug 6008 may be made from other materials. In some embodiments, the plug 6008 may be glued and/or adhered to the tubing. In some embodiments, the plug 6008 may be overmolded to the tubing.

Figure 215:
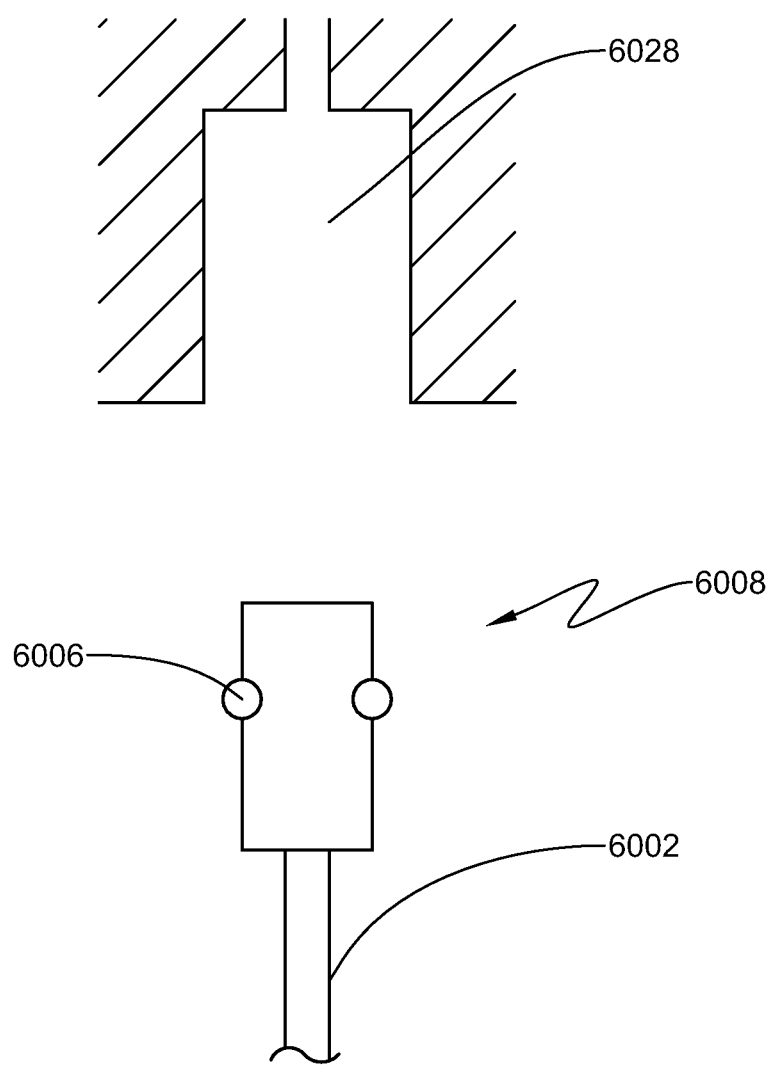

Referring now to FIG. 215, in some embodiments, the disposable housing assembly exit 6028 may include a minimal taper port. The plug 6008 may include at least one o-ring 6006. In some embodiments, the plug 6008 may be made from rigid plastic and the o-ring may be made from an elastomeric material for sealing. In some embodiments, the plug 6008 may be glued and/or adhered to the tubing 6002. In some embodiments, the plug 6008 may be overmolded to the tubing 6002.

Figure 216:
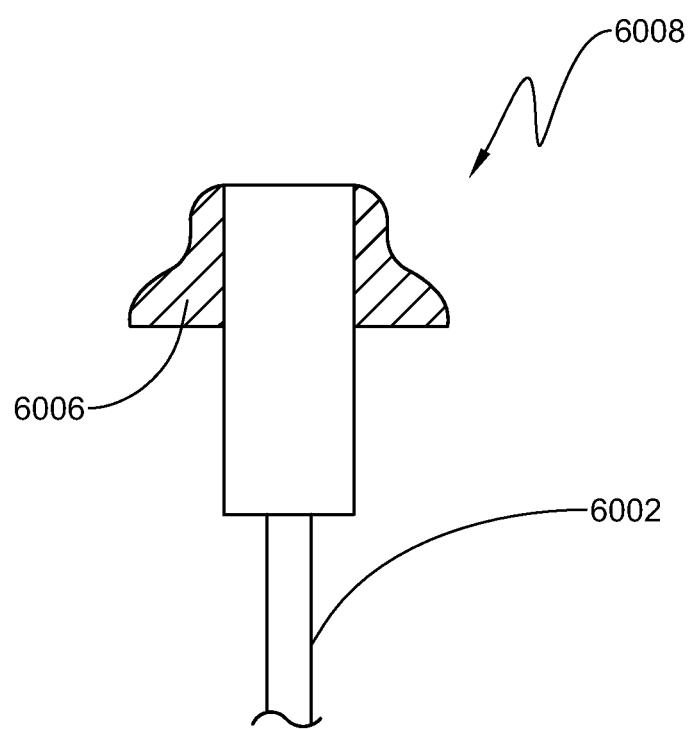
Figure 217:
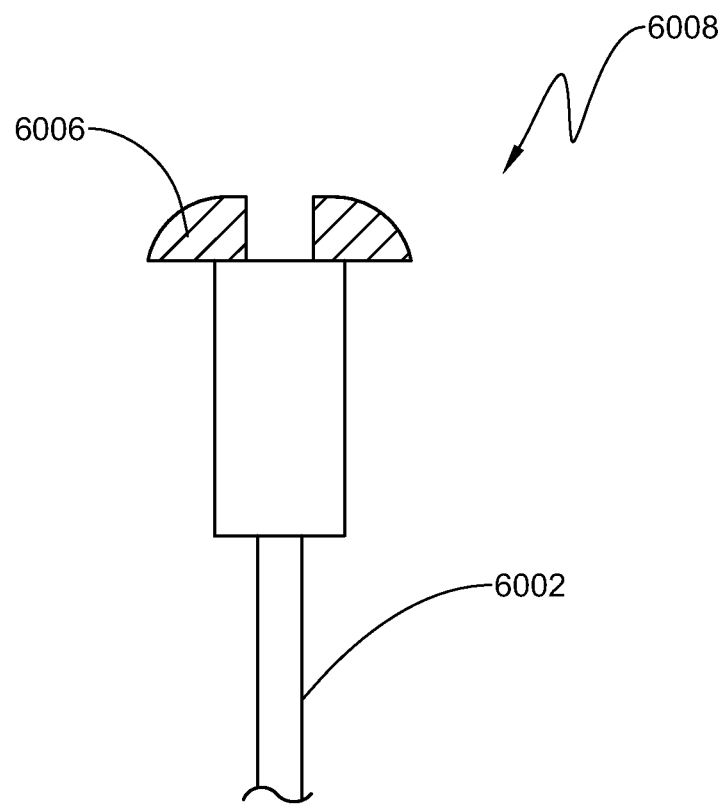

Referring now to FIG. 216, in some embodiments, the plug 6008 may include at least one seal 6006 feature which may include, but is not limited to, one or more of the following: a lip seal, a wiper seal, a radial seal, a face-seal and/or an X seal. Various other seals may be used. Referring now also to FIG. 217, in some embodiments, the plug 6008 may include a face-seal 6006. In some embodiments, the plug 6008 may be glued and/or adhered to the tubing. In some embodiments, the plug 6008 may be overmolded to the tubing 6002.

In various embodiments, the plug may be made from a rigid material or from a compliant and/or semi-compliant material. In some embodiments, the plug may be made from an elastomeric material or any combination thereof.

In various other embodiments, the shape and size of the connector may vary, and/or, in various other embodiments, other types of mating locking features may be used, which include, but are not limited to, latches, catches, snap fits, adhesives, and other mechanisms for securing a connector to the tab of the disposable housing assembly.

Referring now also to FIGS. 218A-218C, another embodiment of a connector 6010 is shown. The connector 6010 may include a tab portion 6018, a protrusion portion 6038, and a plug 6008. In some embodiments, the tab portion 6018 of the connector 6010 may include mating locking features that interact with the tab portion of the disposable housing assembly 6030. As shown, in some embodiments, the mating locking features may include a catch 6014 on the end of the tab portion 6018 of the connector 6010. In some embodiments, the catch 6014 may be a snap fit and/or a loose snap fit and may include features such that the tab portion 6018 of the connector 6010 snaps onto the side/end of the tab portion 6018 of the disposable housing assembly 6000 and may, in some embodiments, include a portion that secures underneath the end of the tab portion 6018 of the disposable housing assembly 6000. In various other embodiments, the shape and size of the connector 6010 may vary, and/or, in various other embodiments, other types of mating locking features may be used, which include, but are not limited to, latches, catches, snap fits, adhesives, and other mechanisms for securing a connector 6010 to the tab 6030 of the disposable housing assembly 6000.

Figure 219A:
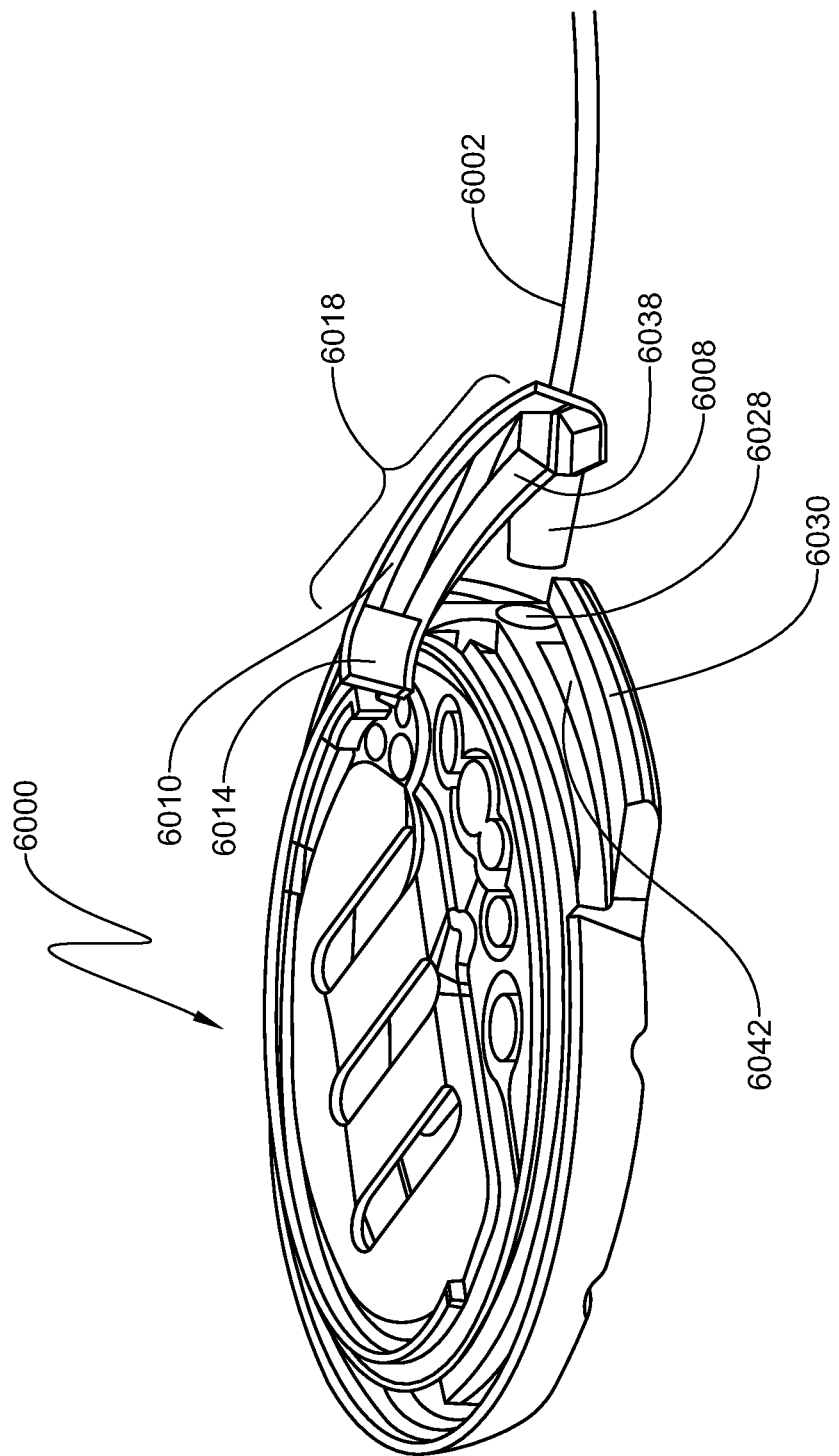
Figure 219B:
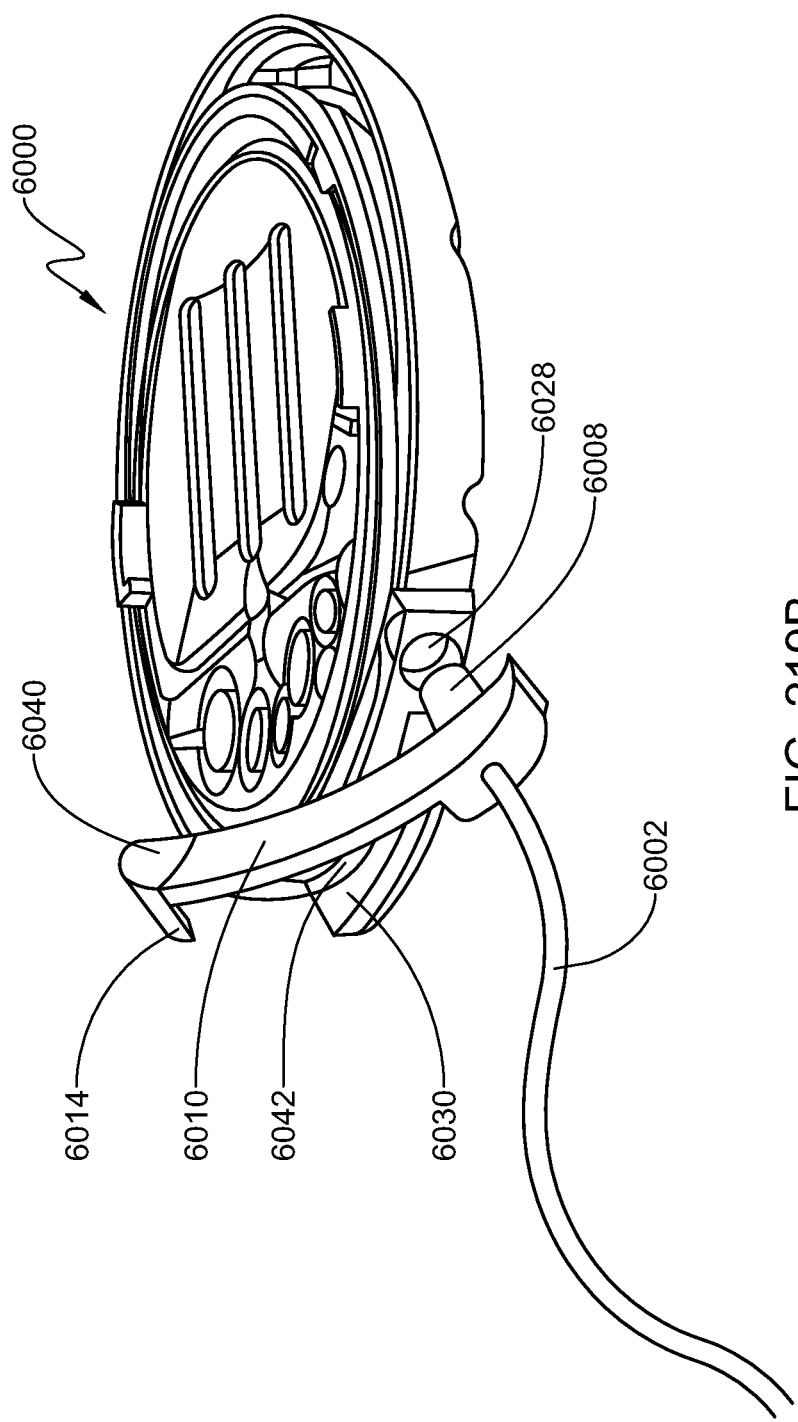
Figure 219C:
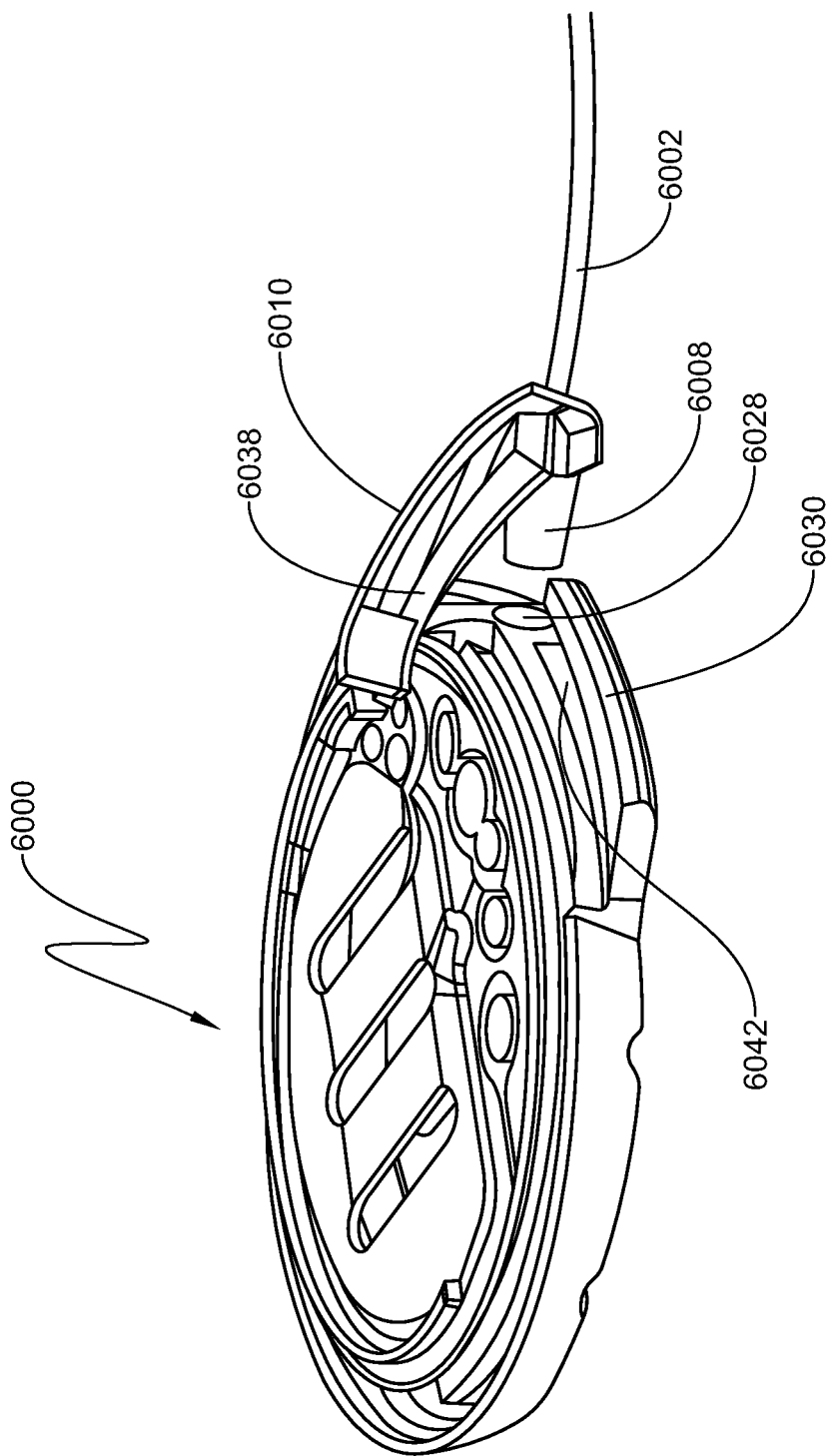
Figure 219D:
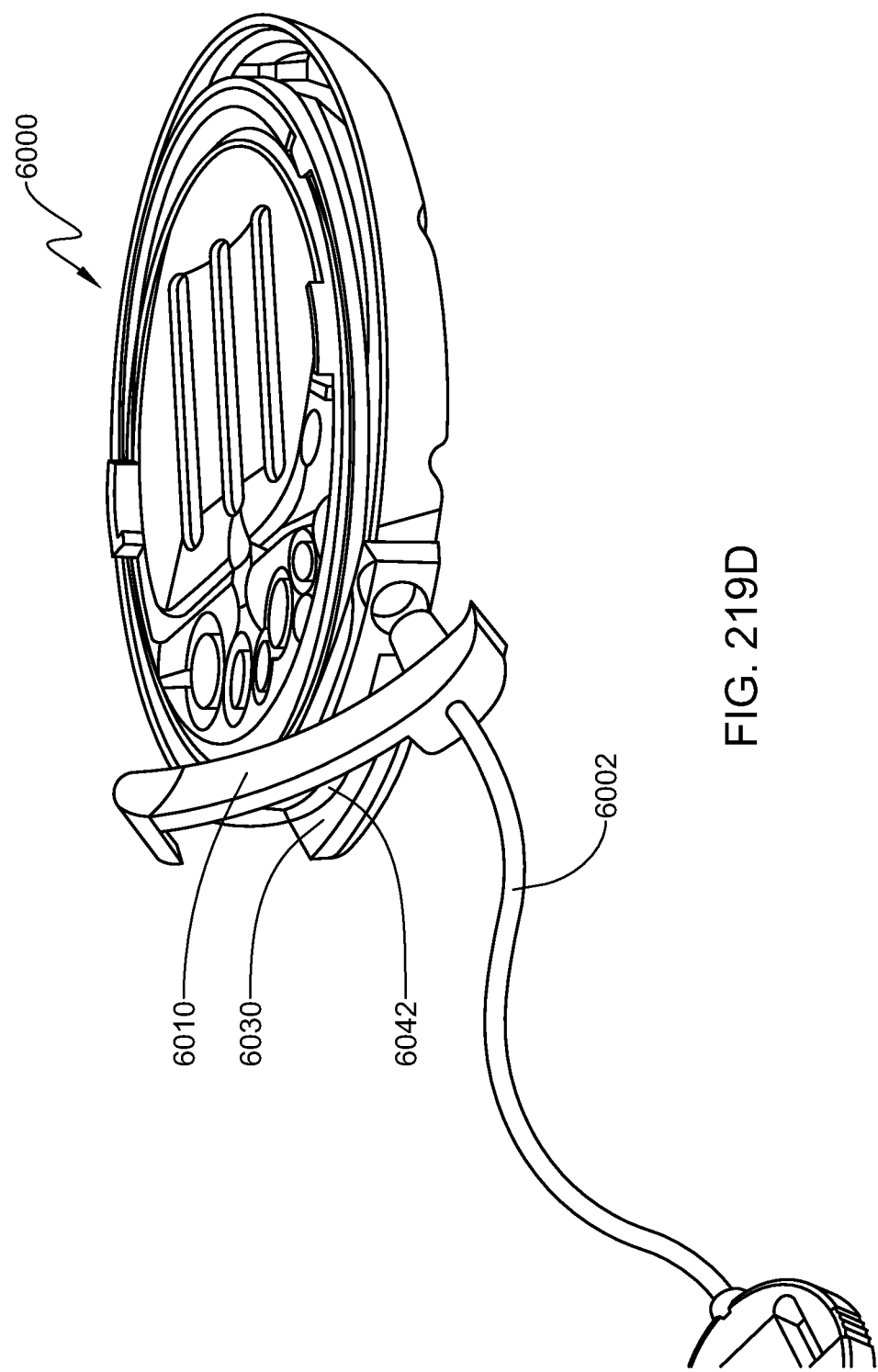
Figure 219E:
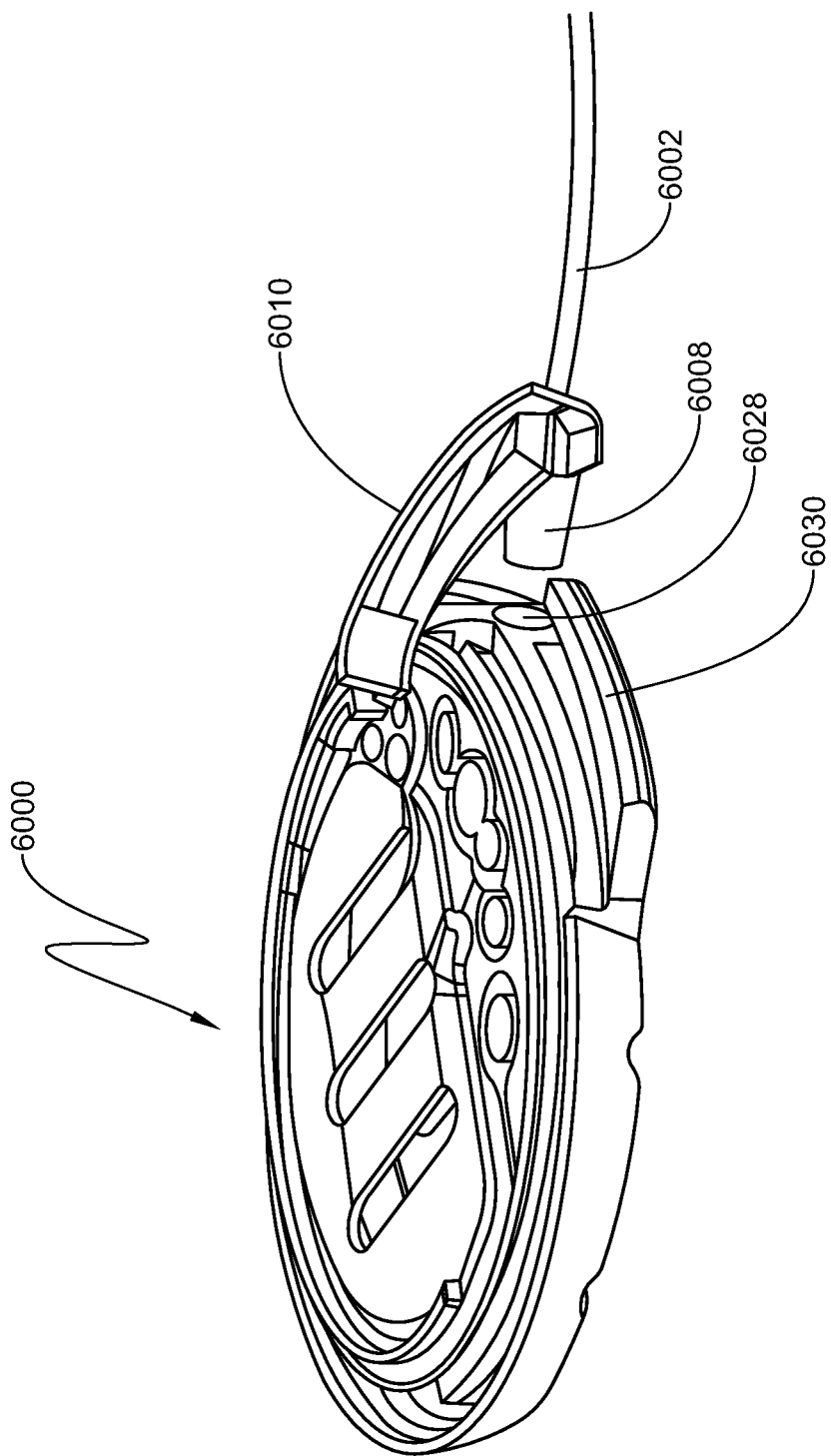
Figure 219F:
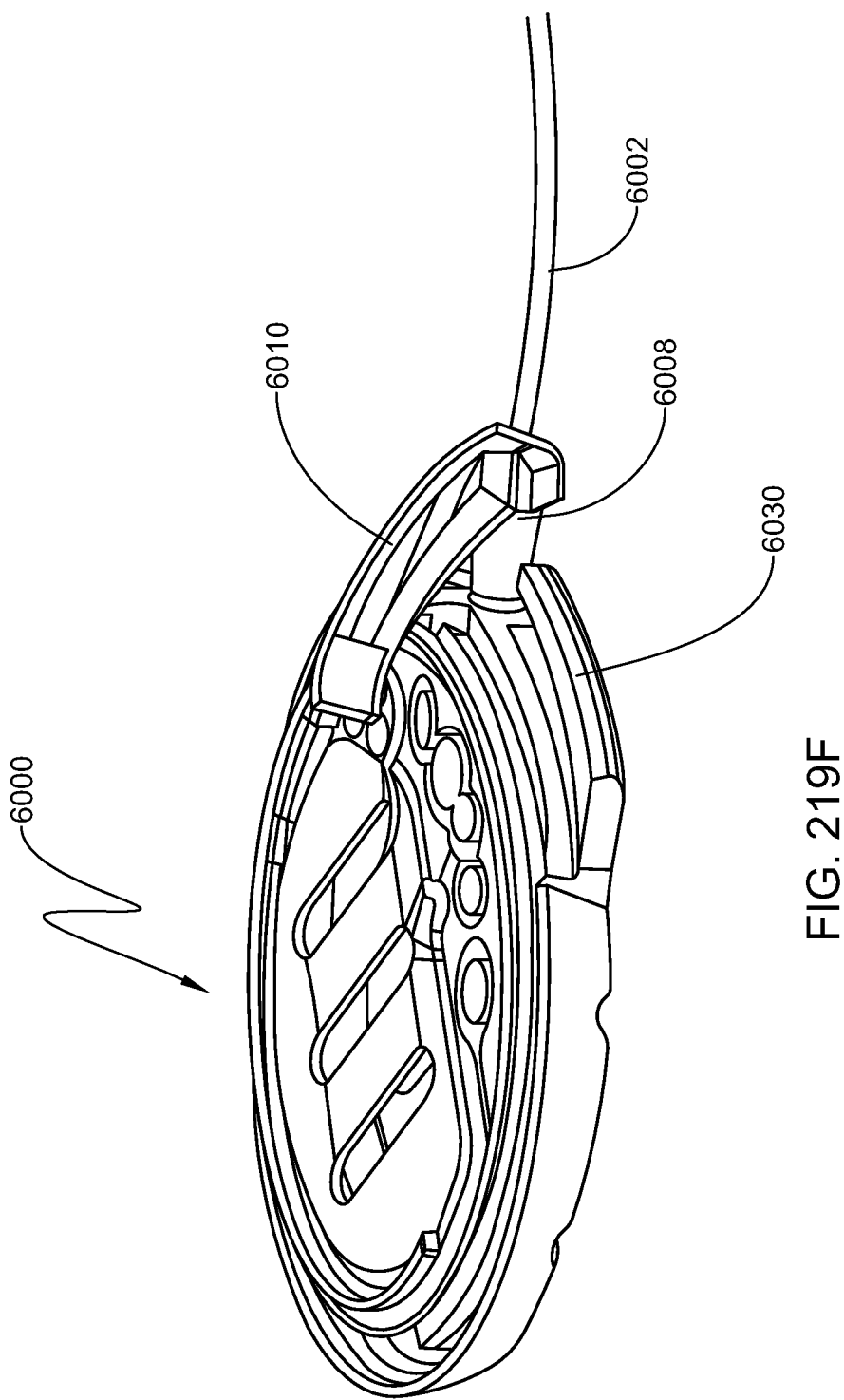
Figure 219G:
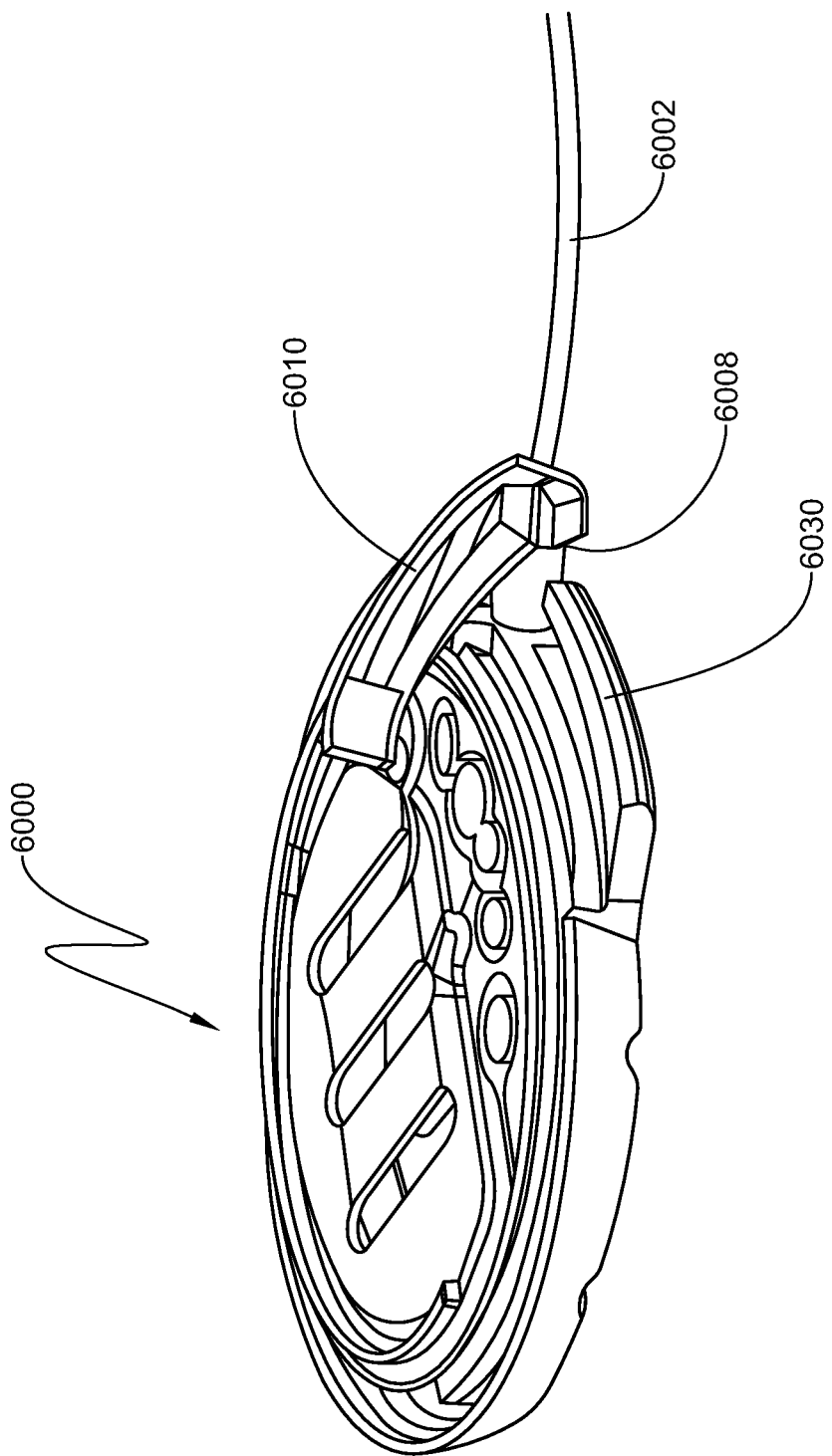
Figure 219H:
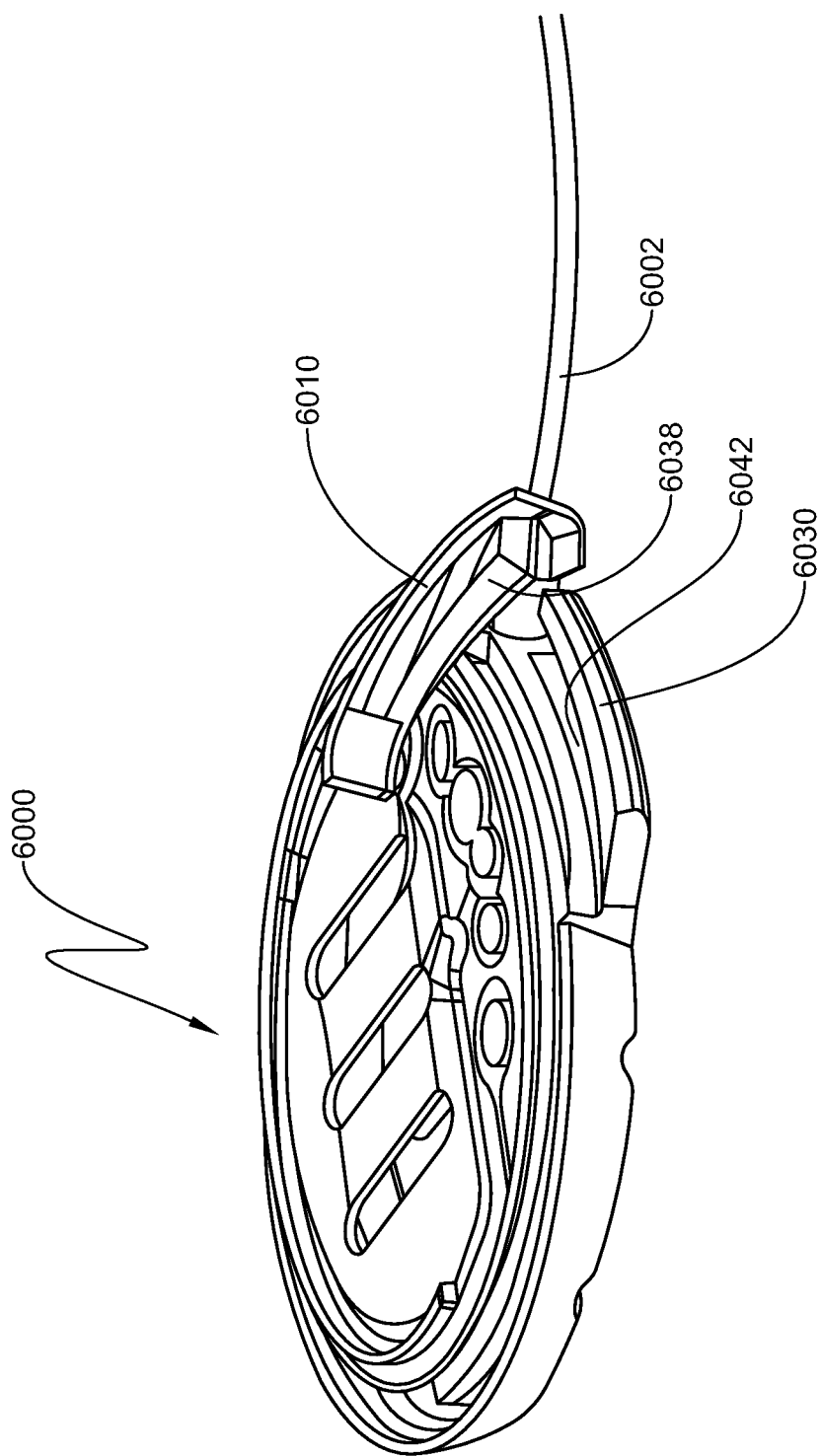
Figure 219I:
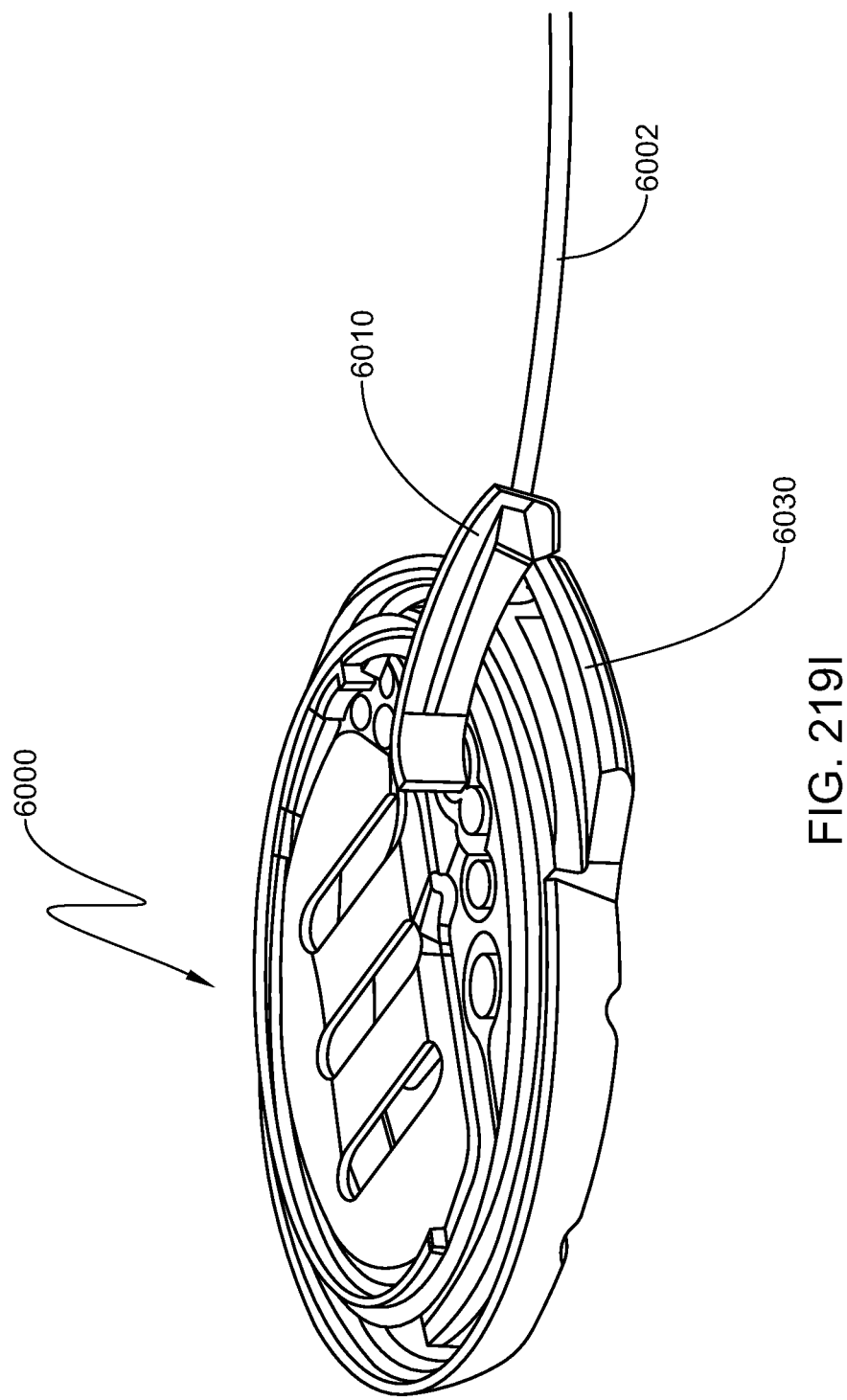
Figure 219J:
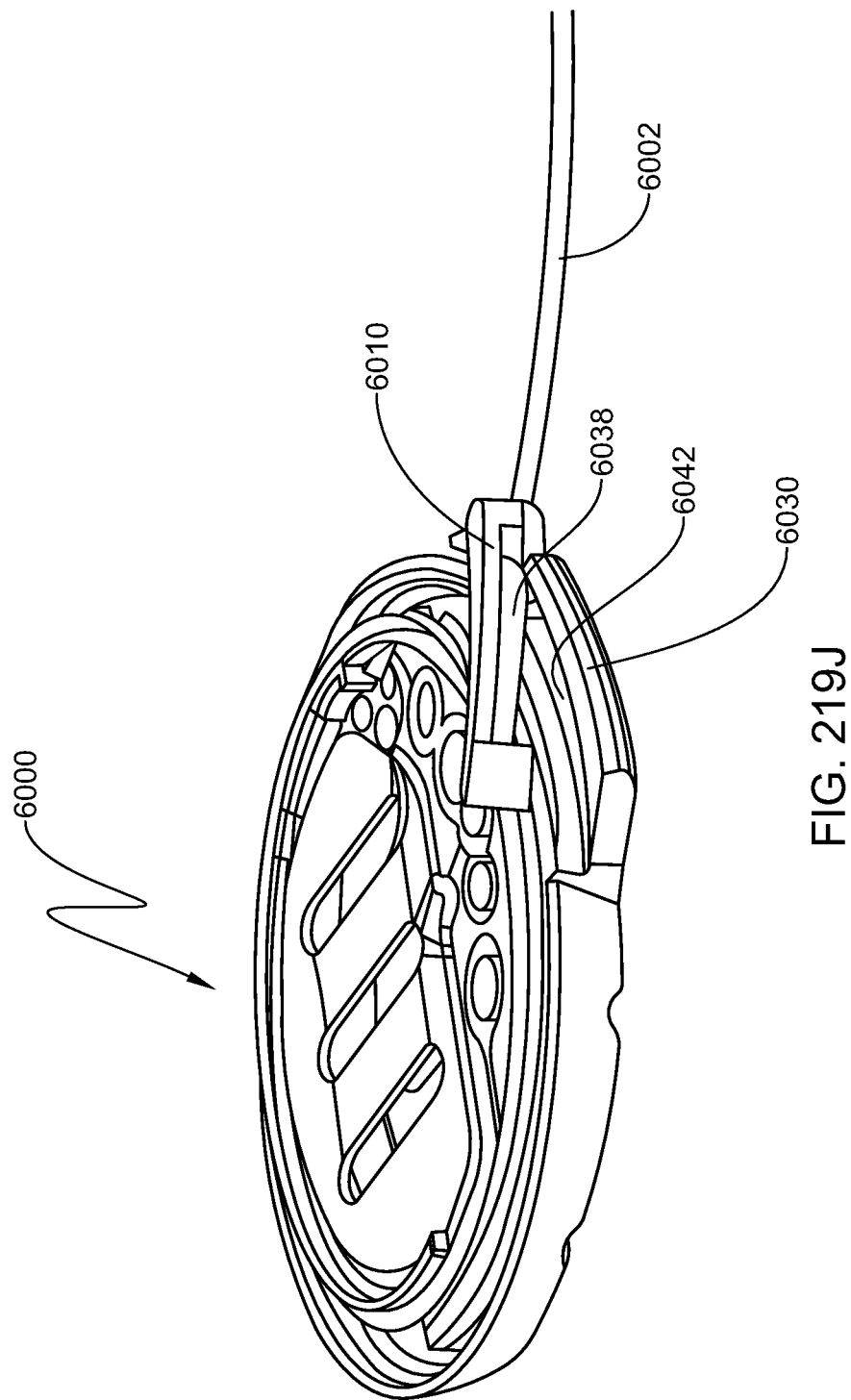
Figure 219K:
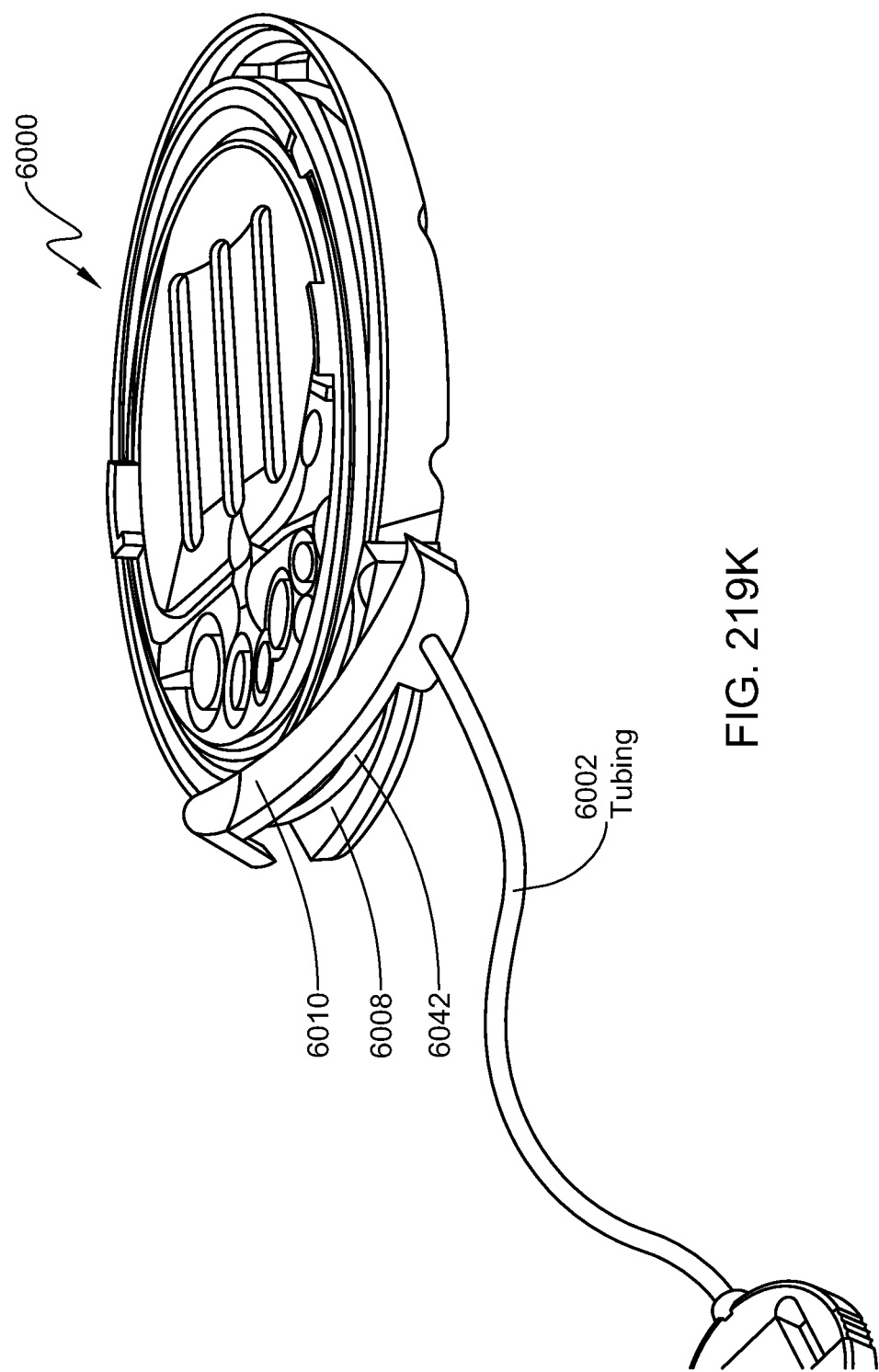
Figure 219L:
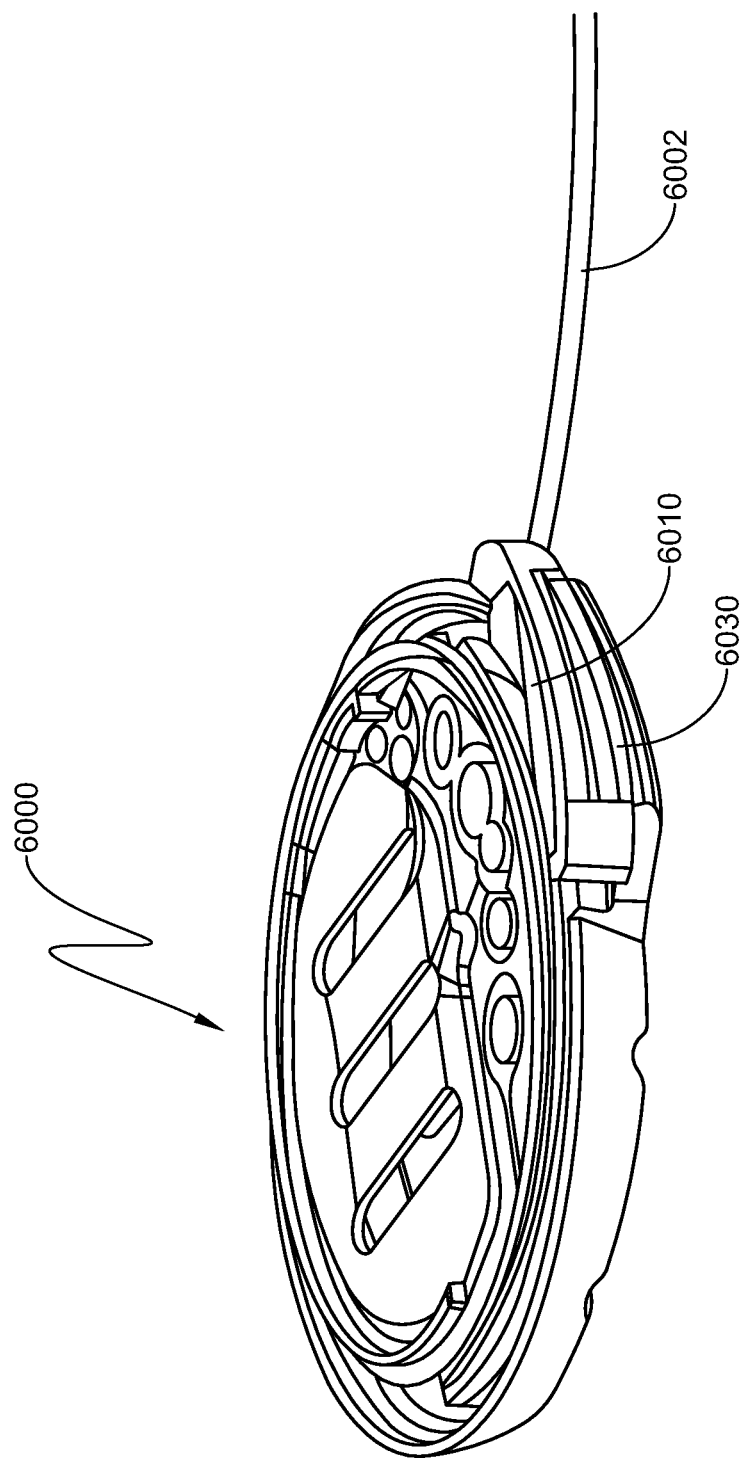
Figure 219M:
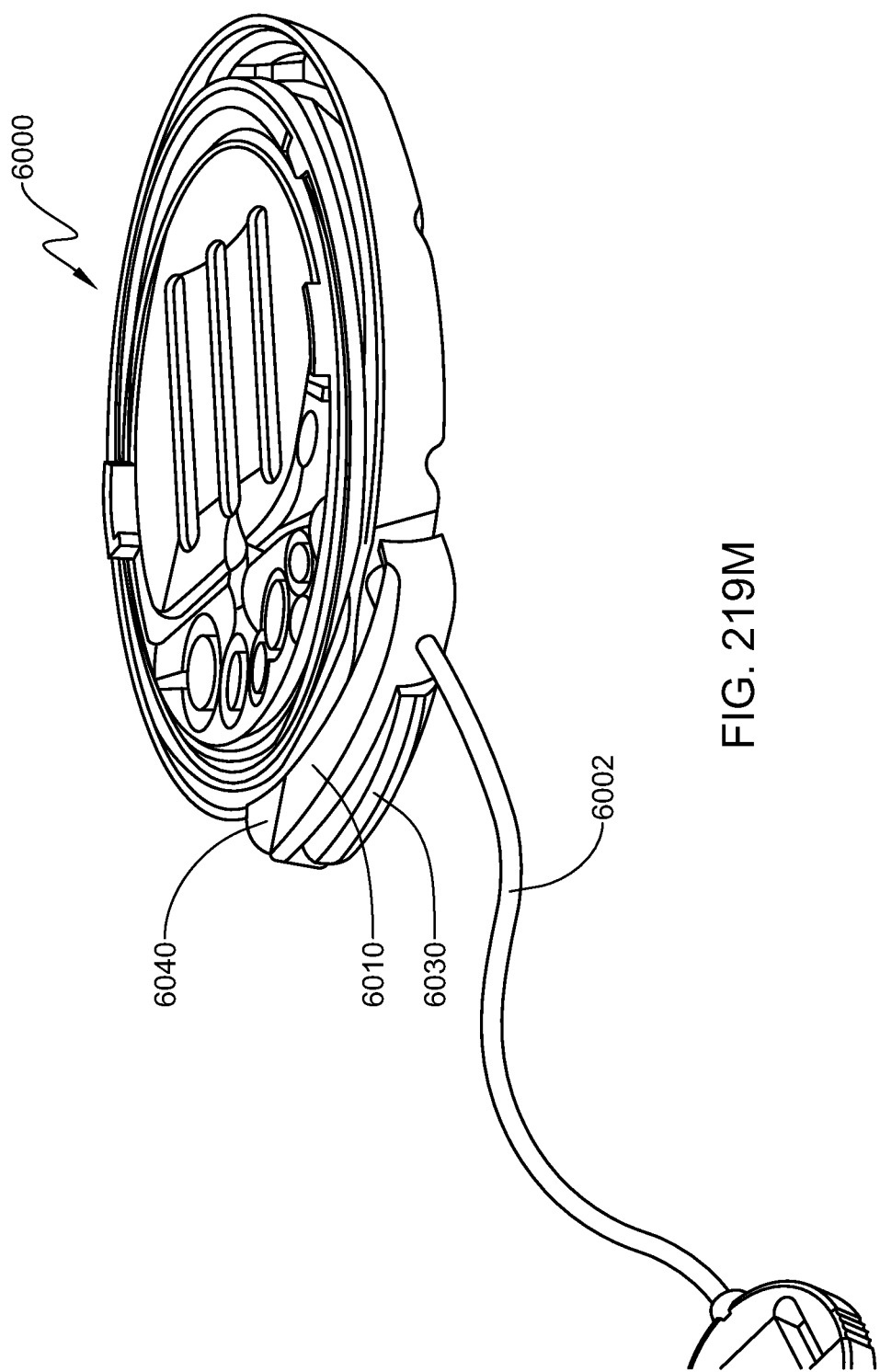

In some embodiments, the connector 6010 includes a protrusion 6038 on the underside. The protrusion 6010 may be tapered in some embodiments. In some embodiments, the protrusion 6038 may be at least slightly curved. Referring now also to FIG. 219B and FIG. 221, in various embodiments, the protrusion 6038 is configured to interact with a groove portion 6042 on the tab portion 6030 of the disposable housing assembly 6000. Referring now also to FIGS. 219A-219M, when the connector 6010 is being attached to the disposable housing assembly 6000, the protrusion 6038 on the connector 6030 rests on the groove 6042. The protrusion 6038 is configured to cam/interfere with the tab portion 6018 of the disposable housing assembly 6000. Thus, in some embodiments, the protrusion 6038 and groove 6042 work together to assist in the insertion of the plug 6008 into the exit 6028. Additionally, in various embodiments, the protrusion 6038 and groove 6042 may contribute to maintaining the plug 6008 in the exit 6028. Thus, the protrusion 6038 and groove 6042, together with the catch 6014, contribute to maintaining and/or enforcing both the insertion of the plug 6008 into the exit 6028 and maintaining and/or enforcing the position of the connector 6010 such that after the plug 6008 is inserted into the exit 6028, the plug 6008 is maintained in the exit 6028 unless and until a user desires to remove the plug 6008 from the exit 6028. Additionally, once the protrusion 6038 and groove 6042 are mated, the plug 6008 is fully inserted and therefore, may, in some embodiments, serve as an indication that the plug 6008 has been fully inserted into the exit 6028.

In some embodiments, the connector 6010 may be made from rigid plastic. In some embodiments, the protrusion 6038 may be overmolded with a thin layer of compliant materials. In some embodiments, as discussed below, the plug 6008 may include an overmold of compliant material and/or be made from compliant material. In some embodiments, the protrusion 6038 may be made from compliant material. In some embodiments, the groove 6042 on the tab portion 6030 of the disposable housing assembly 6000 may include a compliant material. In embodiments where either the groove 6042 includes compliant material and/or the protrusion 6038 includes compliant material, use of compliant material may increase the "squish" between the protrusion 6038 and the groove 6042 and therefore, resulting in a highly compressed and/or tight fit between the protrusion 6038 and the groove 6042.

Referring now also to FIG. 136, in some embodiments, the connector 6010 may include icons that indicate "locked" and "unlocked", similar to those shown and described above with respect to FIG. 136. Thus, in some embodiments, the "locked" and "unlocked" position may also be visually indicated to a user/patient using icons that may be molded, silk-screened, pad printed, injection molded, etched, printed and/or cut-out, e.g., translucent cut-outs of icons, on the connector. In some embodiments using translucent cut-outs, the tab portion 6030 of the disposable housing may be a contrasting color to the connector for visually viewing the tab portion color through the cut-outs. Thus, the icons may indicate whether the reusable housing assembly 6004 is in a locked or unlocked relationship with the disposable housing assembly 6000. In various embodiments, the icons may be any form that may indicate "locked" and "unlocked", or a similar indication, to aid in the user/patient's understanding of the orientation/position between the reusable housing assembly 6004 and the disposable housing assembly 6000. In some embodiments, an arrow icon may also appear between the "locked" and "unlocked" icons.

The plug 6008 may include any embodiment described herein, however, in some embodiments; the plug 6008 may be tapered and may either be rigid with an overmold of elastomeric/compliant material or be made from elastomeric/compliant material. In some embodiments, the tubing 6002 attaches to the connector 6010 as described above. In some embodiments, the tubing 6002 may attach to the connector 6010 and there may be a rigid plastic channel within the connector 6010 and through the plug 6008. In some embodiments, the tubing 6002 may extend into the connector 6010 and in some embodiments; the tubing 6002 may extend all the way through the connector 6010 and through the plug 6008. In some embodiments, the tubing 6002 may extend past the end of the plug 6008.

In these various embodiments, there is maintained a continuous flow lumen from the exit 6028 to the cannula 6026. This may be desirable and/or beneficial for many reasons, including, but not limited to, minimizing and/or eliminating dead volume, minimizing priming volume and/or prevention of or minimizing the occurrence of air traps.

Referring again to FIG. 222, in some embodiments, the tab portion 6030 of the disposable housing assembly 6000 may include a cut-out which may be referred to as a finger cut-out 6044. This cut-out 6044 may be used to assist in removing the connector 6010 from the disposable housing assembly 6000. In some embodiments, the user may grab the connector 6010 at the area of the cut-out 6044, with a thumb and forefinger and pull up on the connector 6010 to remove the connector 6010 from the disposable housing assembly 6000. Thus, any embodiment of the disposable housing assembly 6000 may include a cut-out 6044 on the tab portion 6030.

Referring now also to FIGS. 219A-219M, various views of the embodiment of the connector shown in FIGS. 218A-218C are shown, where the connector 6010 is being attached to the disposable housing assembly 6000. As shown in FIGS. 219A-219M, the connector 6010, including a tab portion 6018 and a plug 6008, may be attached to the disposable housing portion 6000 either by being releasably attached or non-releasably attached. In various embodiments, the connector 6010 may be attached to the disposable housing assembly 6000 as shown in FIGS. 219A-219M.

As discussed above, in various embodiments, the plug of the connector is inserted into the exit of the disposable housing assembly with the tab portion pointing in the general upward direction. Once the plug portion is inside the disposable housing assembly, the tab portion of the connector may be rotated to rest above the tab portion of the disposable housing portion, which is adjacent to the exit. In some embodiments, mating locking features may be included on the tab portion of the connector and the disposable housing assembly such that the connector is held in place before the reusable housing assembly is attached to the disposable housing assembly. In some embodiments, the mating locking features may include, but are not limited to, snap buttons and/or catch features. In some embodiments, a hook or other feature may be located on the opposite end of the tab portion of the connector such that it loops over the end of the tab portion of the disposable housing assembly and maintains the position of the connector.

In various embodiments, once the connector 2010 is attached to the disposable housing assembly 6000, the connector 2010 may only be removed when intended, i.e., the connector 6010 is maintained on the disposable housing assembly 6000 unless and until a user desires to remove the connector 6010. As discussed above, in some embodiments, the connector 6010 may be non-removably attached, however, in some embodiments; the connector 6010 may be removably attached.

Figure 220A:
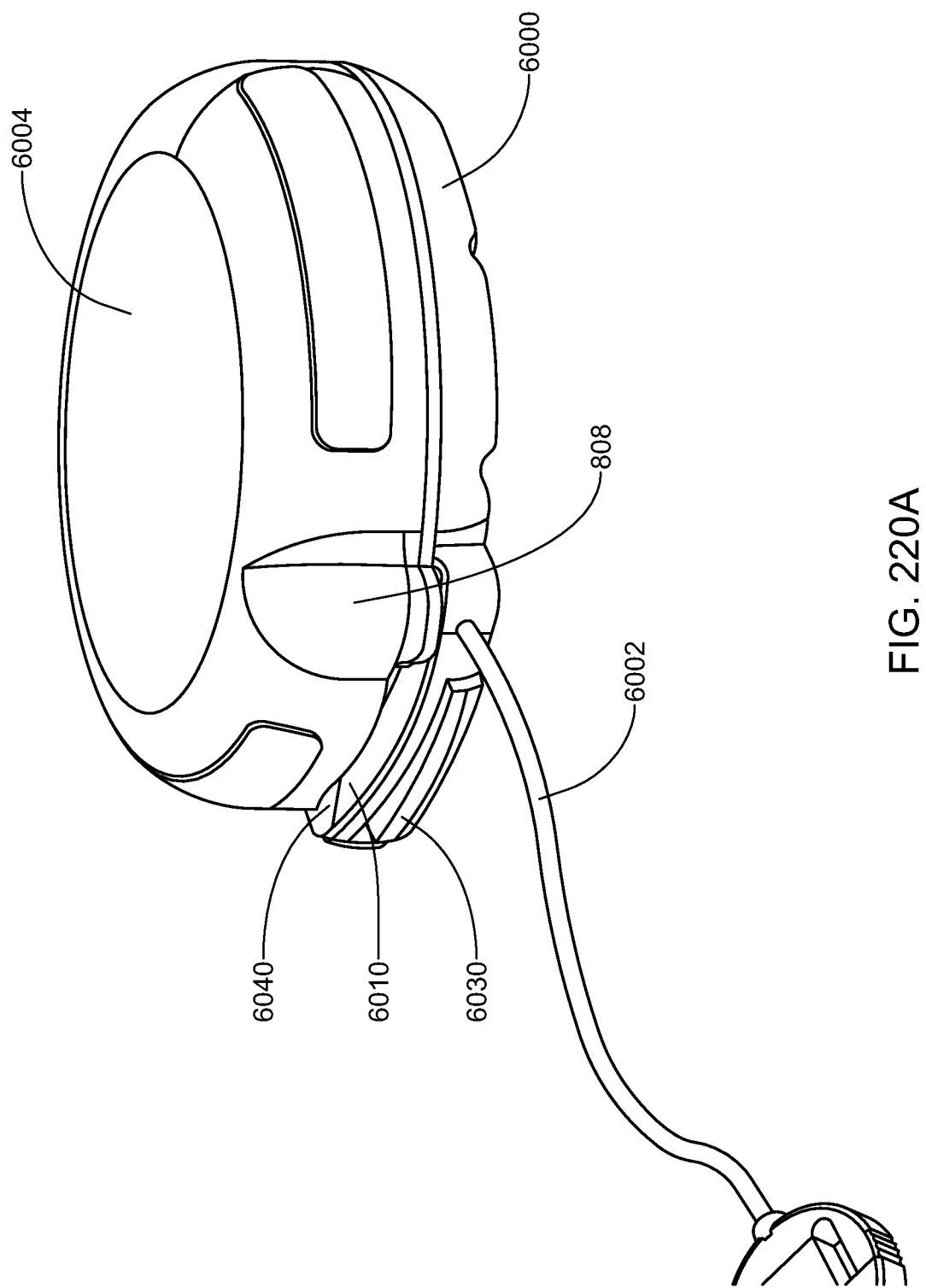
Figure 220B:
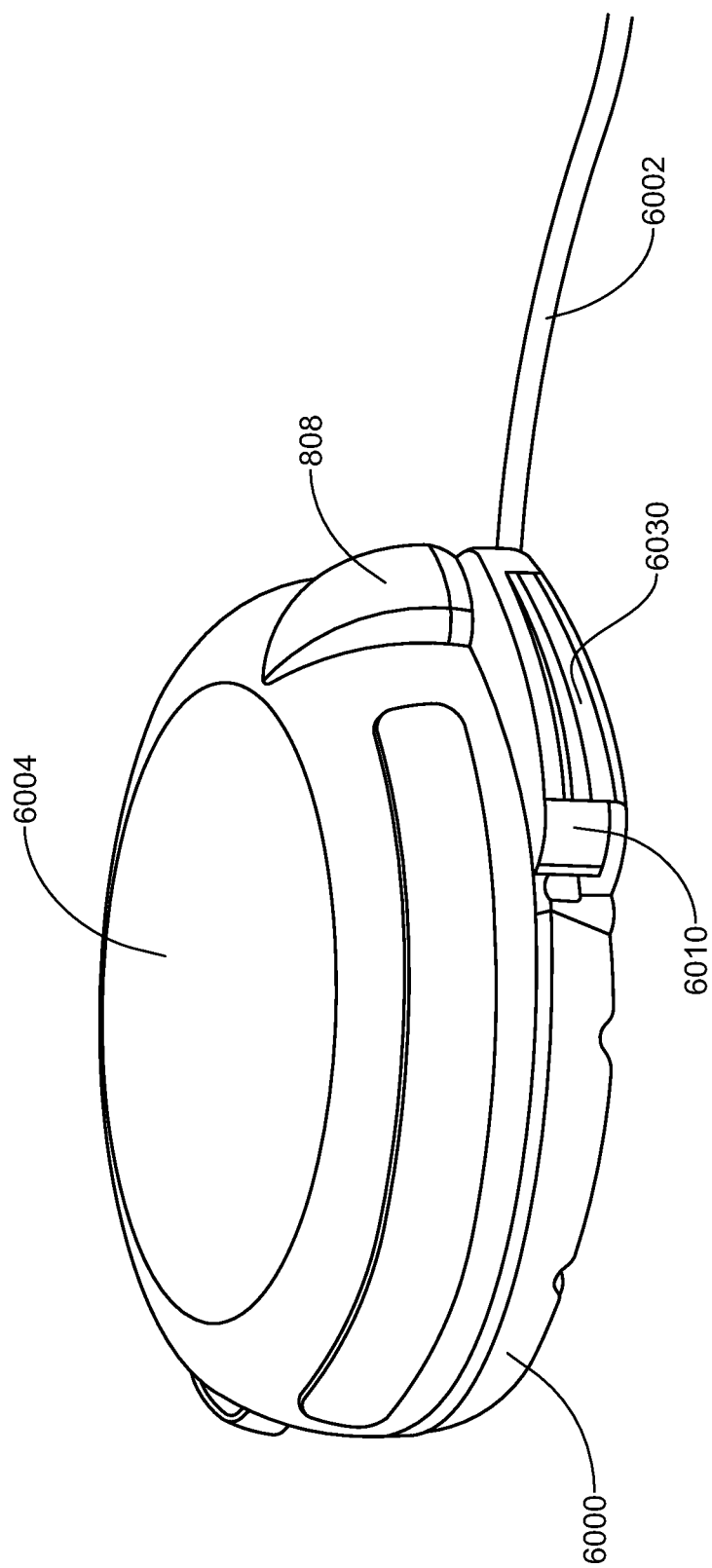
Figure 220C:
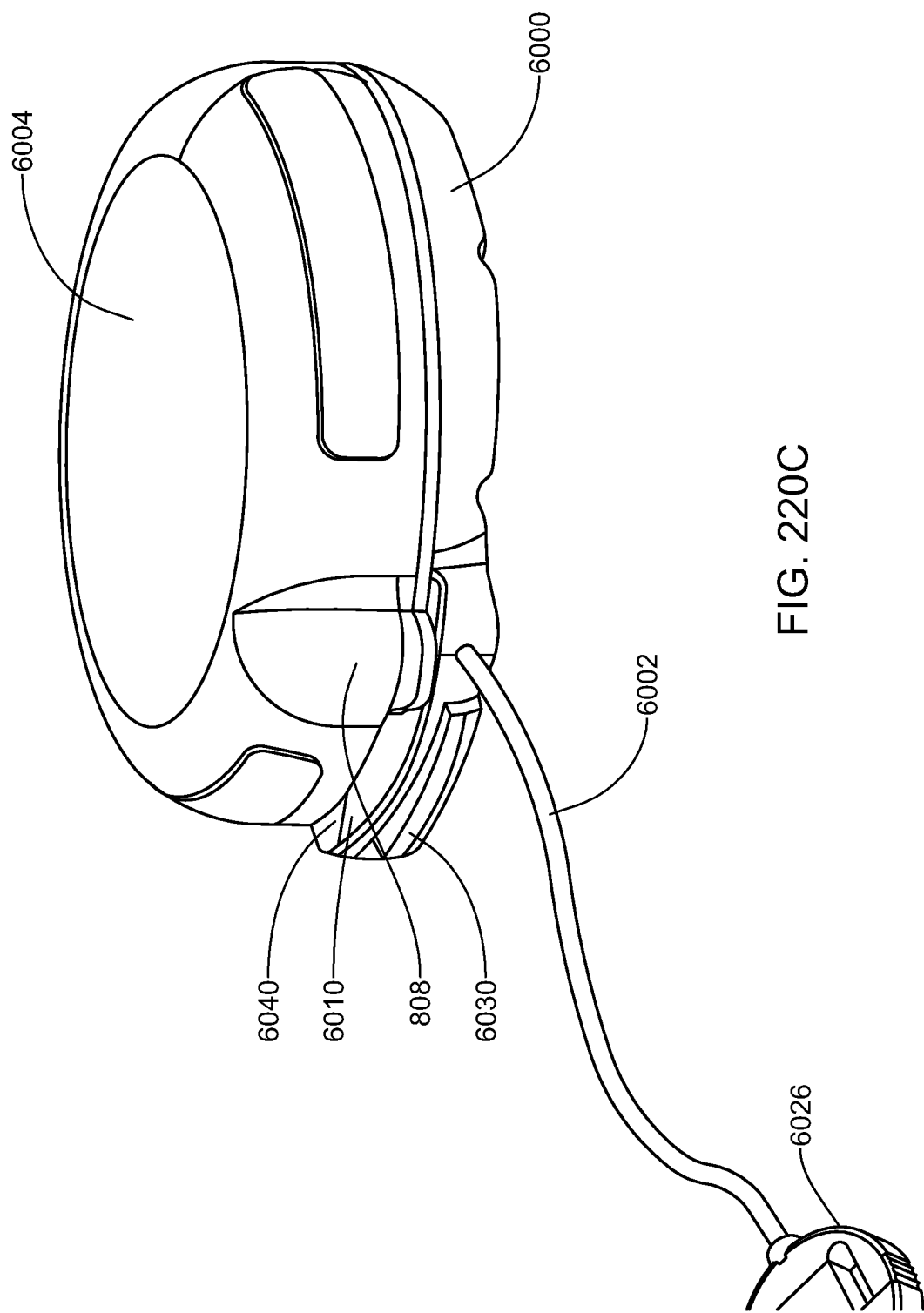
Figure 220D:
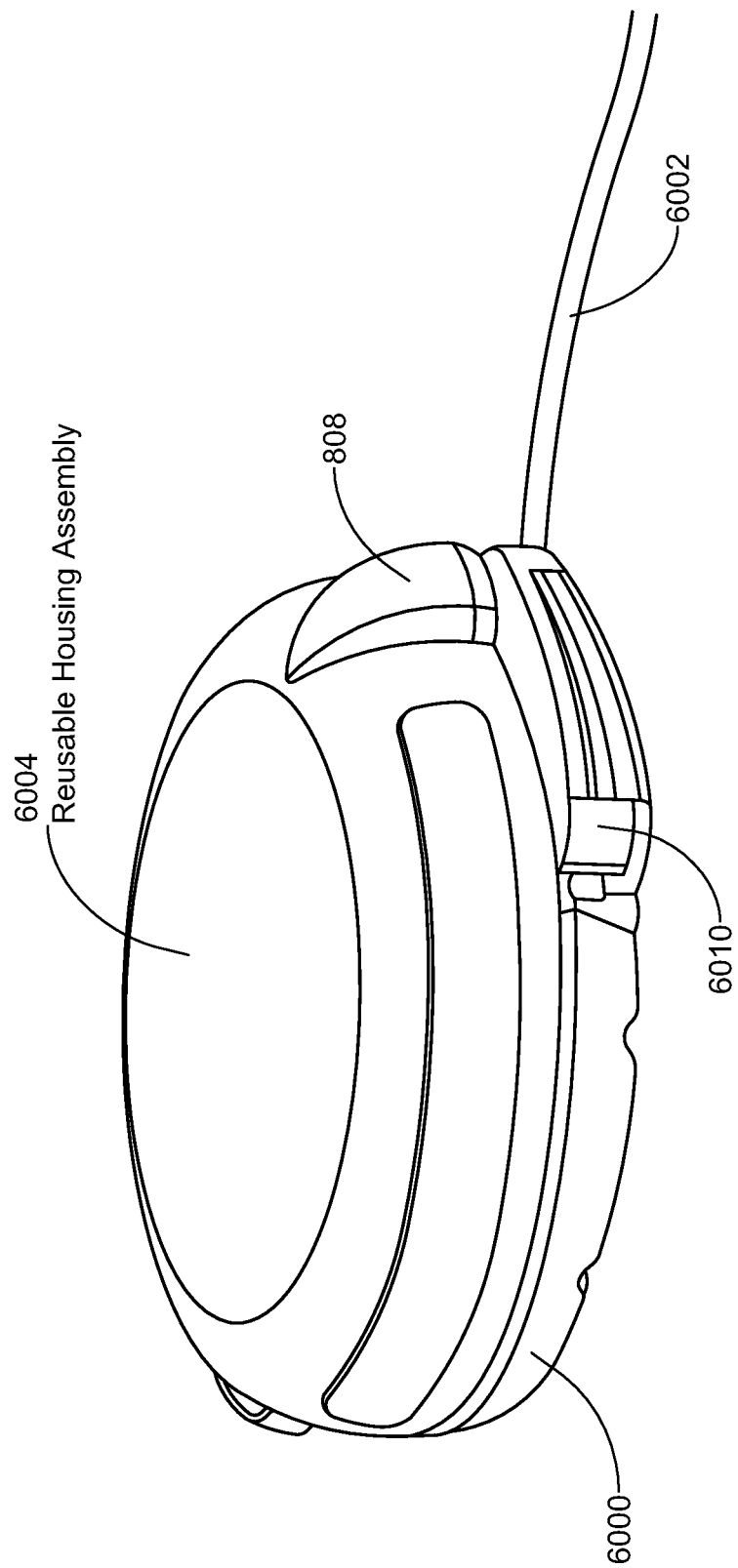
Figure 220E:
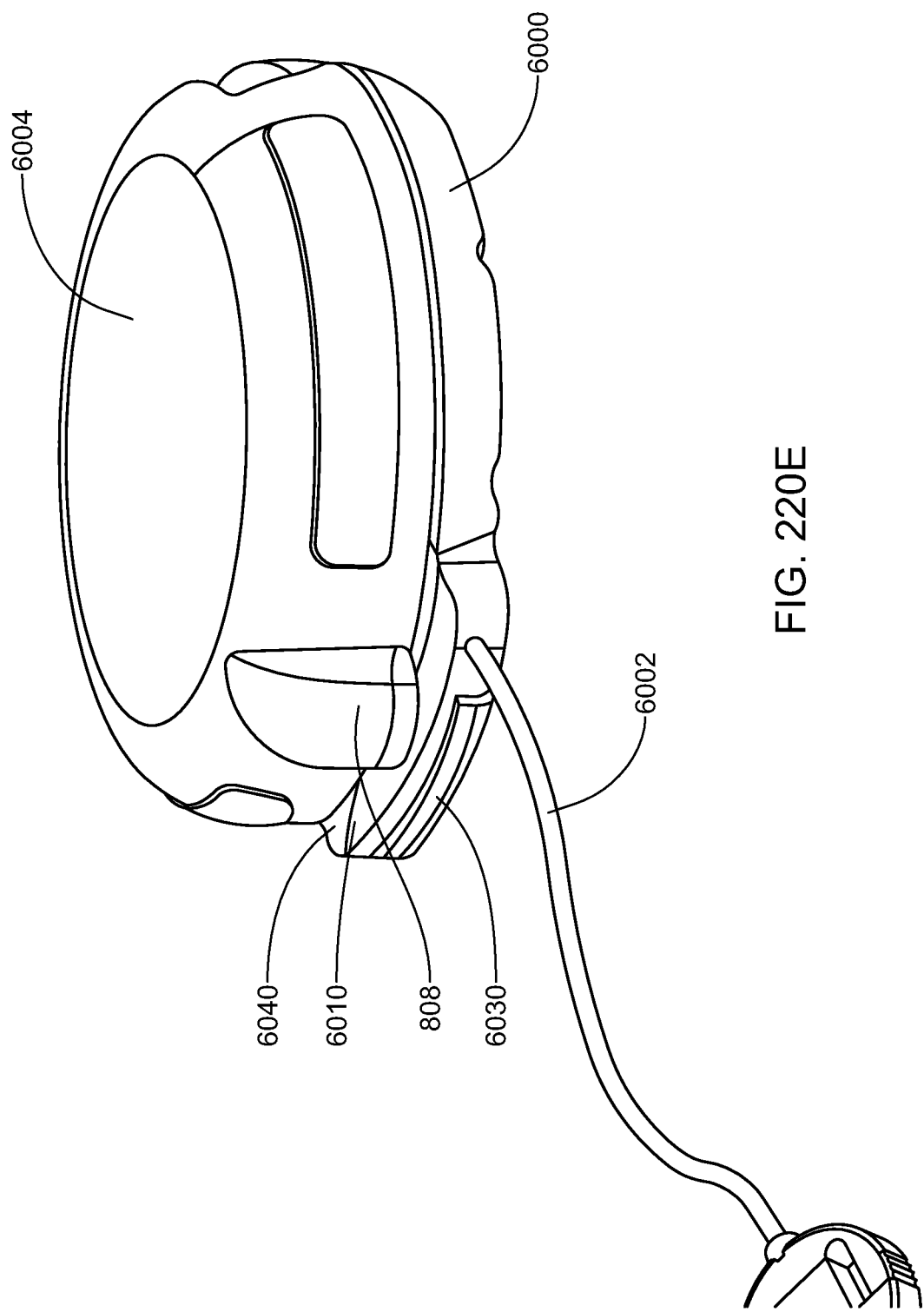
Figure 220F:
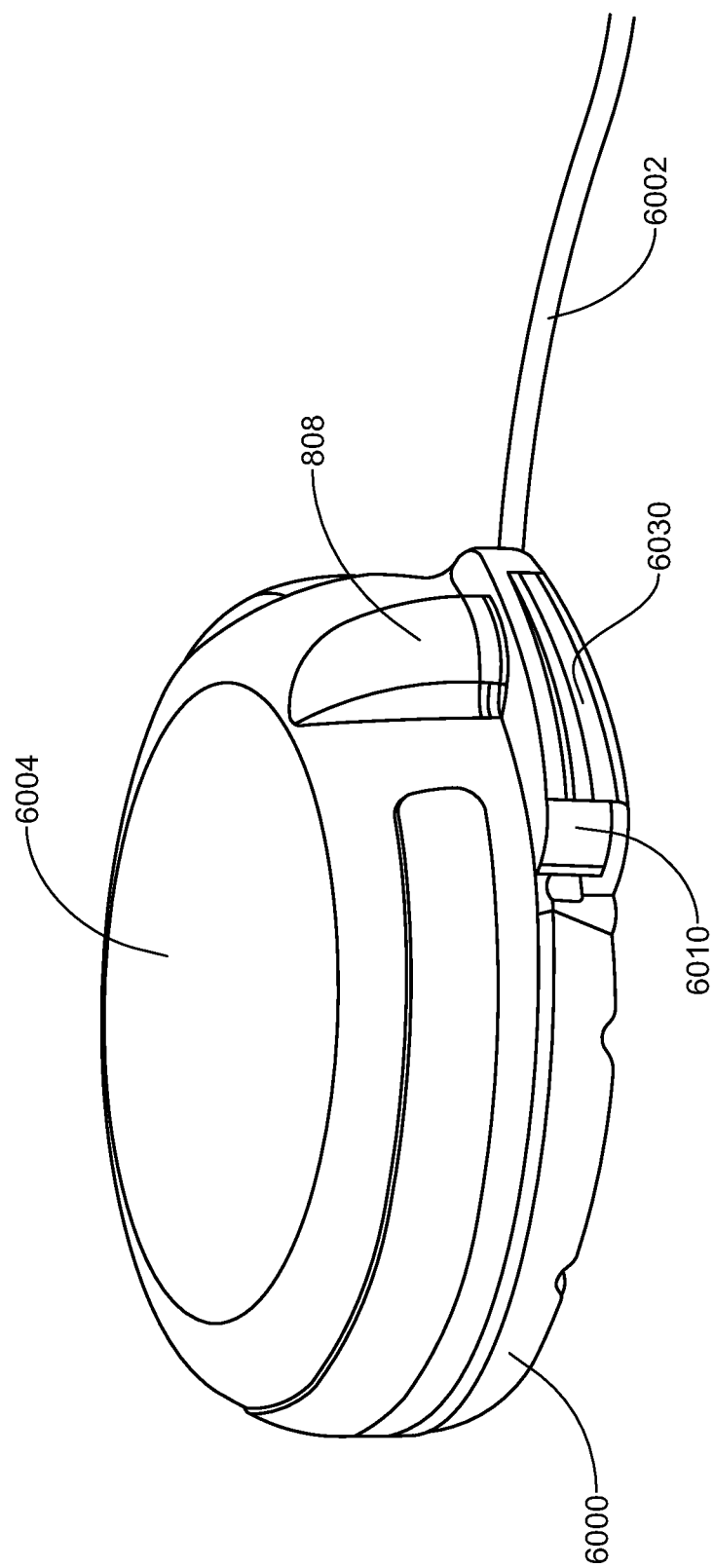
Figure 220G:
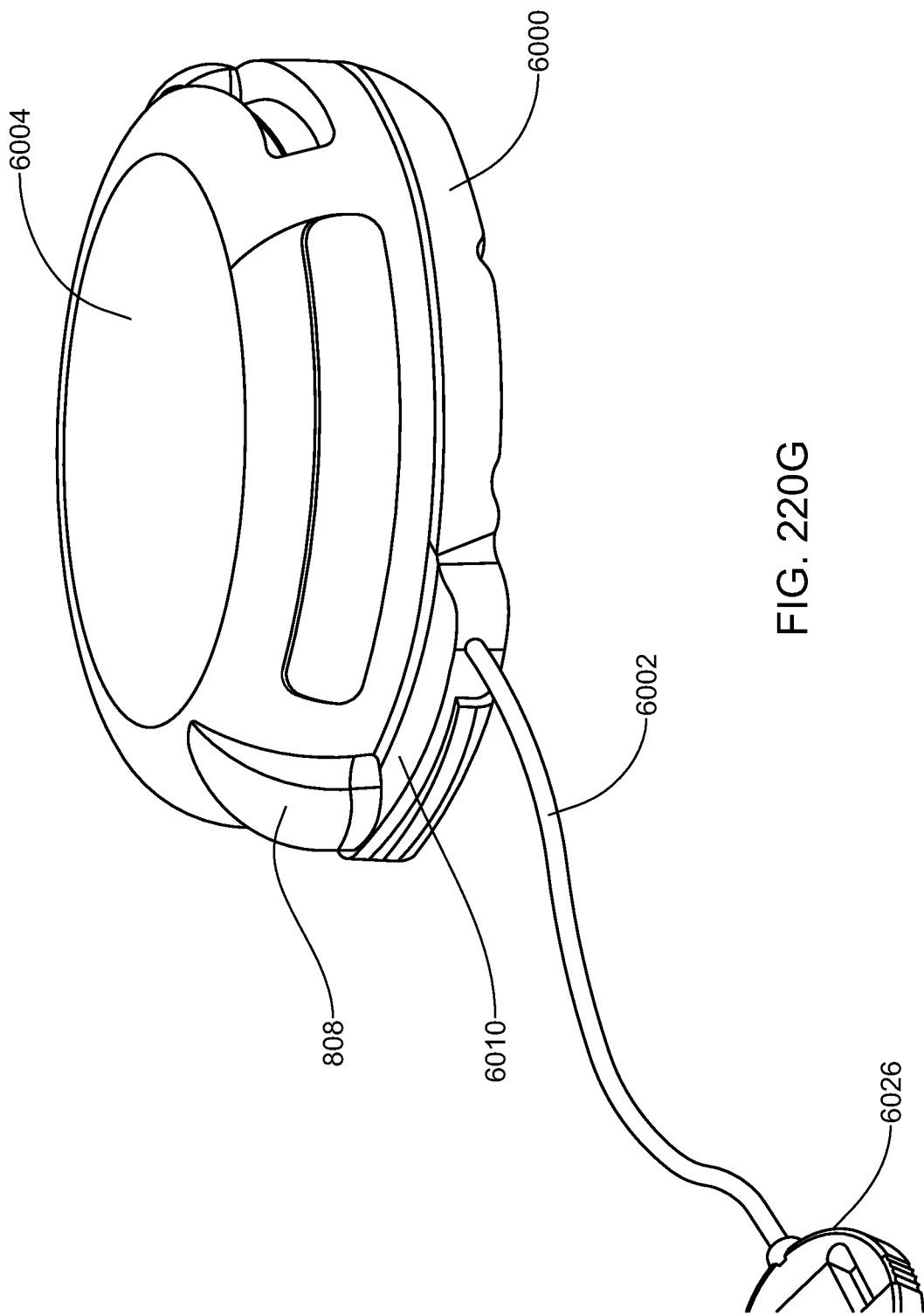
Figure 220H:
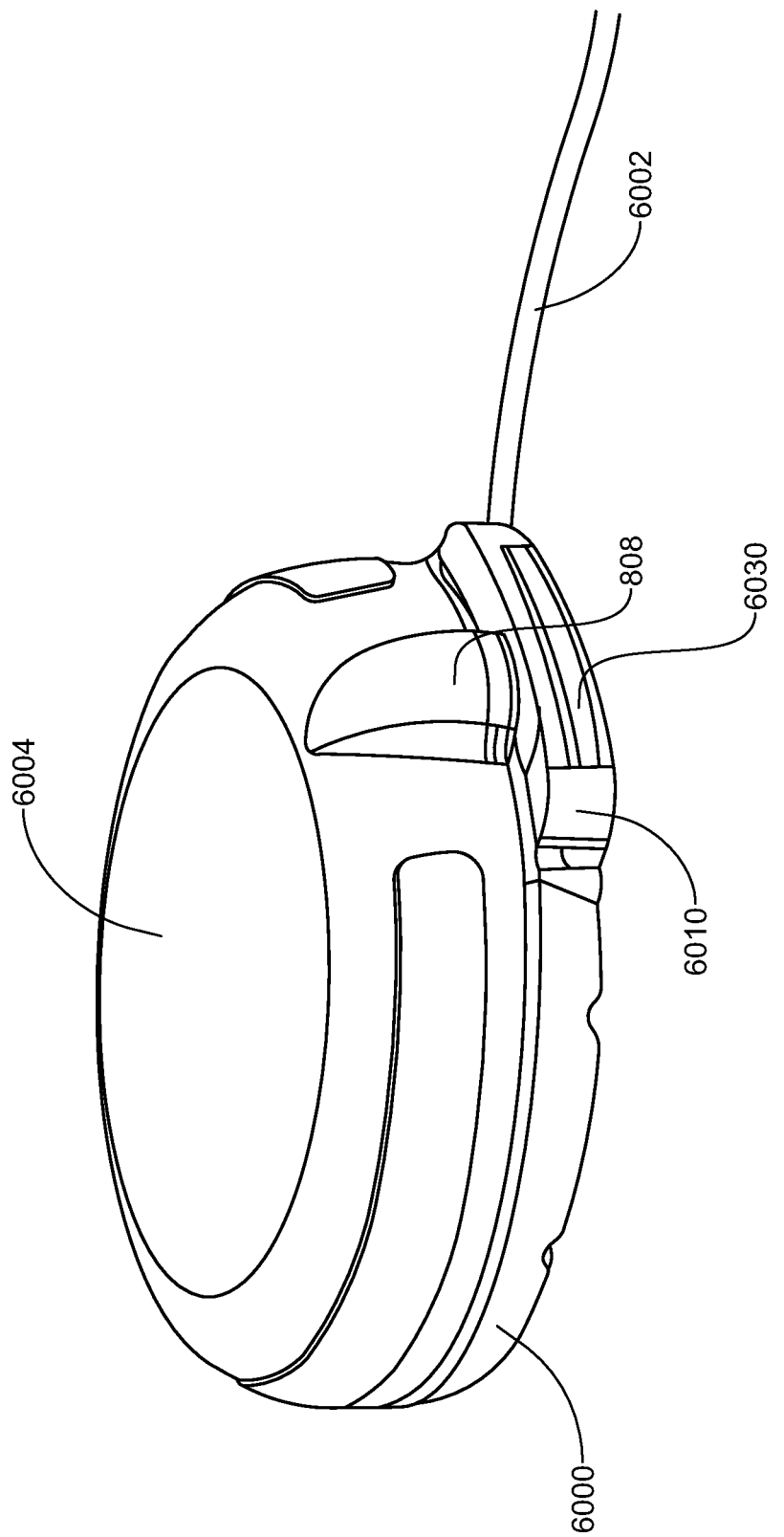
Figure 220I:
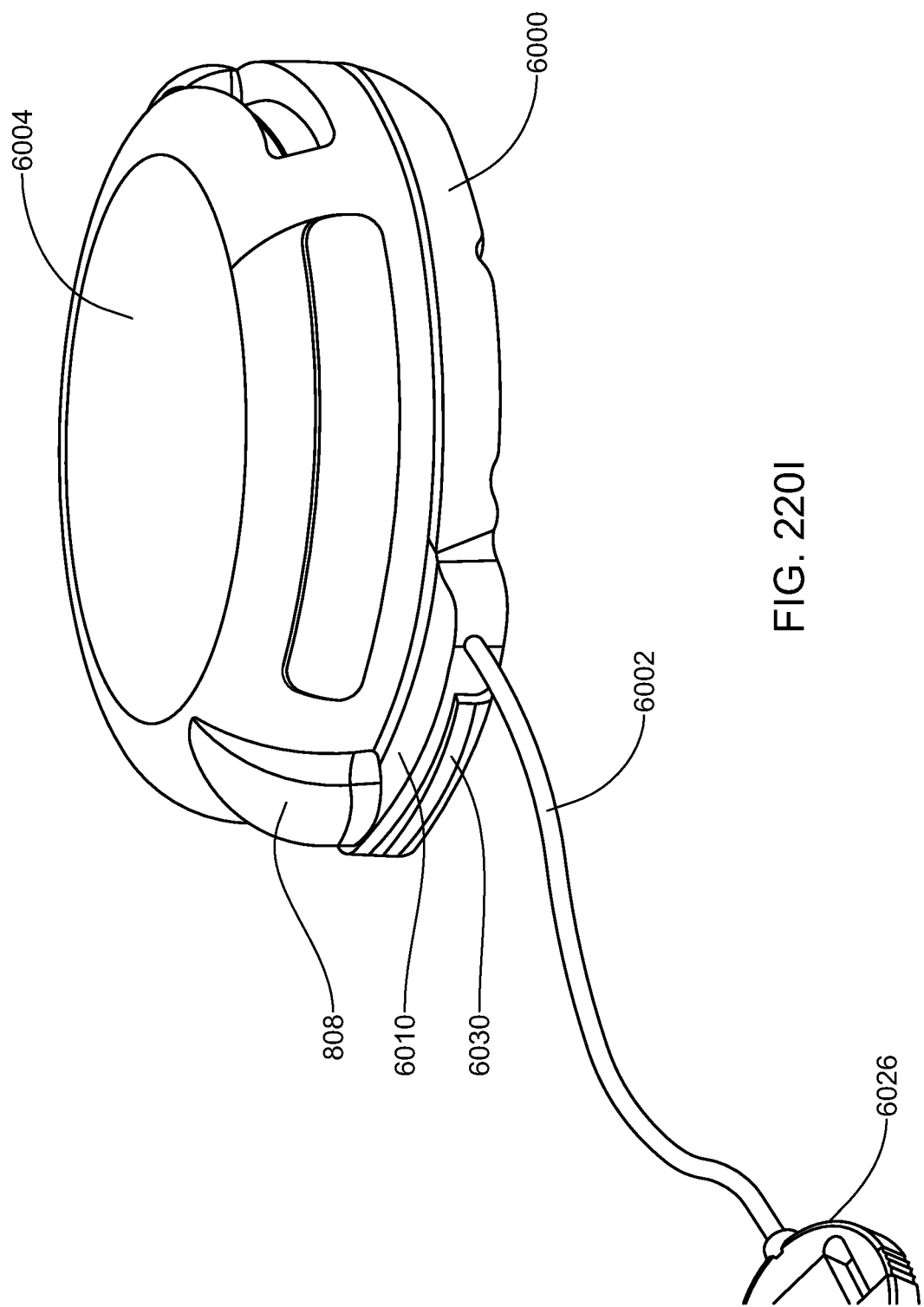
Figure 220J:
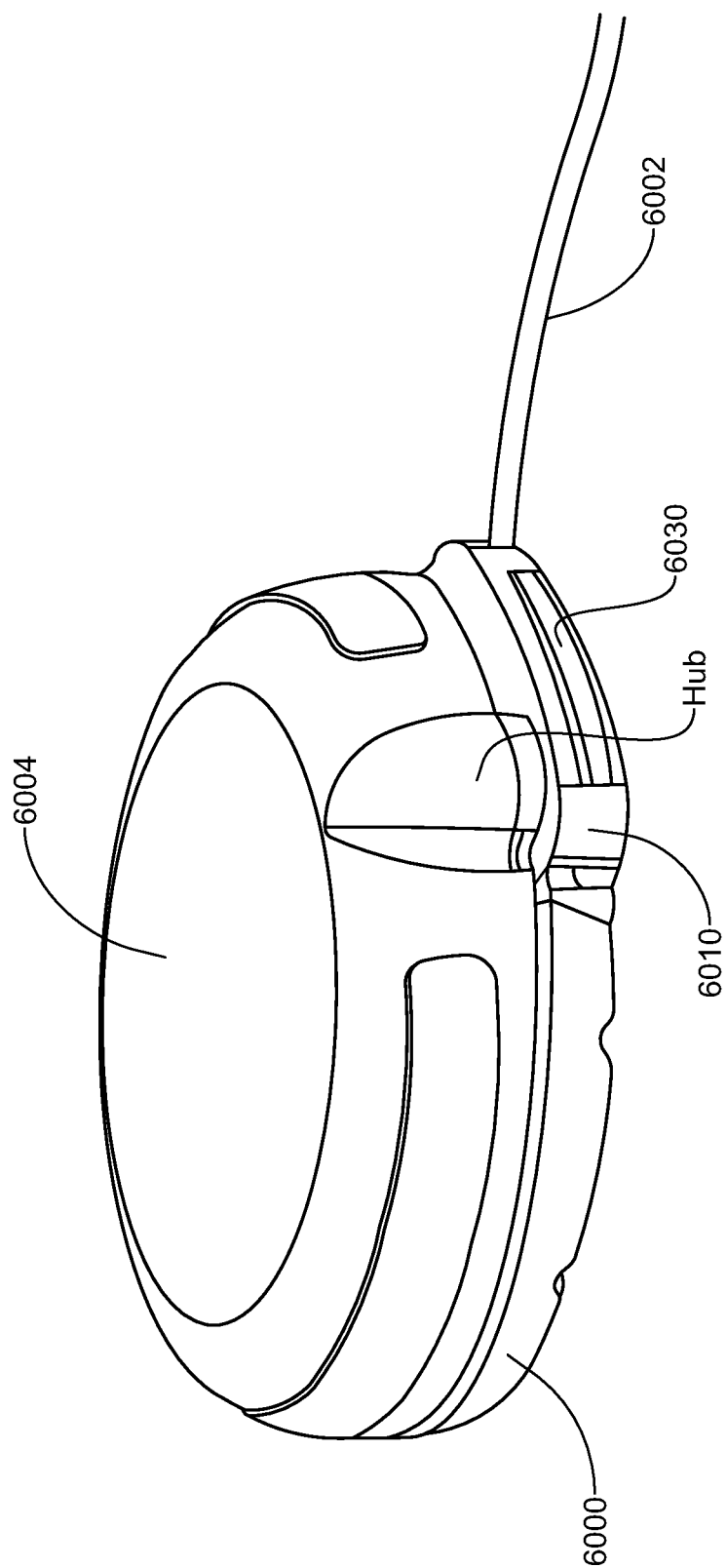

Referring now also to FIGS. 220A-220J, once the connector 6010 is attached to the tab portion 6030 of the disposable housing assembly 6000, the reusable housing assembly 6040 may be connected/attached to the disposable housing assembly 6000 by being rotated about the disposable housing assembly 6000. As shown, as the reusable housing assembly 6004 is rotatably connected to the disposable housing assembly 6000, the nub 808, having a spring actuated tab 2980 (not shown), on the reusable housing assembly 6004 interacts with the tab portion 6018 of the connector. As shown in FIG. 220E, in some embodiments, the connector 6010 may include an indent portion 6040 which may be configured to interact with the nub 808 and/or spring plunger/tab of the locking ring assembly of the reusable housing assembly 6004. As shown in FIG. 220I, once the reusable housing assembly 6004 is attached to the disposable housing assembly 6000, the spring plunger/tab in the nub 808, having a spring actuated tab 2980, may be released, making a "click" sound. The "click" may also produce a tactile feedback that may be perceived by the user/patient. This tactile and audio feedback is indicative to the user that the reusable housing assembly 6004 is fully connected to the disposable housing assembly 6000. In some embodiments, the nub 808, having a spring actuated tab 2980, rests on the tab portion 6018 of the connector 6010, and in some embodiments, the nub 808, having a spring actuated tab 2980, may rest on the indent portion 6040 of the tab portion 6018 of the connector 6010. The nub 808, having a spring actuated tab 2980, presses downward on the connector 6010, maintaining the connector 6010 in an attached position. In some embodiments, once the reusable housing assembly 6004 is attached to the disposable housing assembly 6000, the connector 6010 may not be removed from the disposable housing assembly 6000. Rather, in these embodiments, the reusable housing assembly 6004 must first be detached from the disposable housing assembly 6000 before the connector 6010 may be removed from the disposable housing assembly 6000. In some embodiments, once the connector 6010 is attached to the disposable housing assembly 6000, it may not be removed.

Referring now also to FIGS. 223A and 223B, in some embodiments, a stopcock valve 6046 may be non-removably, or in some embodiments, removably, connected to the tab section 6030 of the disposable housing assembly 6000. Once the connector 6010 is inserted into the stopcock style valve 6046, the reusable housing assembly 6004 may be connected/attached to the disposable housing assembly 6000 by being rotated about the disposable housing assembly 6000. As the reusable housing assembly 6004 is rotatably connected to the disposable housing assembly 6000, the nub 808, having a spring actuated tab 2980, on the reusable housing assembly 6004 interacts with the swivel connector 6048, activating the stopcock style valve 6046, and, in some embodiments, the rotation of the reusable housing assembly 6000 about the disposable housing assembly 6004 prevents the swivel connector 6048 from being removed from the stopcock style valve 6046. In some embodiments, once the reusable housing assembly 6004 is attached to the disposable housing assembly 6000, the spring plunger/tab in the nub 808, having a spring actuated tab 2980, may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the swivel connector 6048 is connected such that it will be maintained in the stopcock valve 6046 until and unless the user wishes to remove the connection. In some embodiments, the nub 808, having a spring actuated tab 2980, presses downward on the swivel connector 6048, maintaining the swivel connector 6048 in an attached position. In some embodiments, once the reusable housing assembly 6004 is attached to the disposable housing assembly 6000, the swivel connector 6048 may not be removed from the disposable housing assembly 6000. Rather, in these embodiments, the reusable housing assembly 6004 must first be detached from the disposable housing assembly 6000 before the swivel connector 6048 may be removed from the disposable housing assembly 6000. In some embodiments, once the swivel connector 6048 is attached to the disposable housing assembly 6000, it may not be removed.

Referring now to FIG. 224, in some embodiments, the connector may be a latching connector 6010 that attaches to the tab 6030 of the disposable housing assembly 6000. In some embodiments, the latching connector 6010 may include a radial or a face seal, and in some embodiments, the latching connector 6010 may include a septum/needle interface. For example, in some embodiments, the latching connector 6010 may include a needle portion and the tab of the disposable housing assembly 6030 may include a septum. In some embodiments, the latching connector 6010 may attach to the disposable housing assembly 6000 from the side, as shown, however, in other embodiments, the latching connector 6010 may attach to the disposable housing assembly 6000 from the top and or from the bottom. In some embodiments, once the latching connector 6010 is connected to the disposable housing assembly 6000, the reusable housing assembly 6004 may be connected/attached to the disposable housing assembly 6000 by being rotated about the disposable housing assembly 6000. As the reusable housing assembly 6004 is rotatably connected to the disposable housing assembly 6000, the nub 808, having a spring actuated tab 2980, on the reusable housing assembly 6004 may interact with the latching connector 6010, such that the rotation of the reusable housing assembly 6004 about the disposable housing assembly 6000 prevents the latching connector 6010 from being removed from the disposable housing assembly 6000. In some embodiments, once the reusable housing assembly 6004 is attached to the disposable housing assembly 6000, the spring plunger/tab in the nub 808 may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the latching connector 6010 is connected such that it will be maintained connected to the disposable housing assembly 6000 until and unless the user wishes to remove the latching connector 6010. In some embodiments, the nub 808, having a spring actuated tab 2980, presses downward on the latching connector 6010, maintaining the latching connector 6010 in an attached position. In some embodiments, once the reusable housing assembly 6004 is attached to the disposable housing assembly 6000, the latching connector 6010 may not be removed from the disposable housing assembly 6000. Rather, in these embodiments, the reusable housing assembly 6004 must first be detached from the disposable housing assembly 6000 before the latching connector 6010 may be removed from the disposable housing assembly 6000. In some embodiments, once the latching connector 6010 is attached to the disposable housing assembly 6000, it may not be removed.

Referring now also to FIGS. 225A and 225B, in some embodiments, the connector 6010 may be a perimeter connector 6010 that attaches to the perimeter of the disposable housing assembly 6000. In some embodiments, the perimeter connector 6010 may be attached to the disposable housing assembly 6000 by being connected to the disposable housing assembly 6000 from the bottom of the disposable housing assembly 6000. However, in some embodiments, the perimeter connector 6010 may be connected to the disposable housing assembly 6000 by being connected to the disposable housing assembly 6000 from the top, as shown in FIG. 225B. Referring now to FIG. 226, in some embodiments, the perimeter connector 6010 may be connected to the disposable housing assembly 6000 by first being connected to the tab of the disposable housing assembly 6000 and then being applied over the top of the disposable housing assembly 6000.

Referring now also to FIG. 136, in some embodiments, the connector 6010 may include icons that indicate "locked" and "unlocked", similar to those shown and described above with respect to FIG. 136. Thus, in some embodiments, the "locked" and "unlocked" position may also be visually indicated to a user/patient using icons that may be molded, silk-screened, pad printed, injection molded, etched, printed and/or cut-out, e.g., translucent cut-outs of icons, on the connector 6010. In some embodiments using translucent cut-outs, the tab portion 6030 of the disposable housing assembly 6000 may be a contrasting color to the connector 6010 for visually viewing the tab portion 6030 color through the cut-outs. Thus, the icons may indicate whether the reusable housing assembly 6004 is in a locked or unlocked relationship with the disposable housing assembly 6000. In various embodiments, the icons may be any form that may indicate "locked" and "unlocked", or a similar indication, to aid in the user/patient's understanding of the orientation/position between the reusable housing assembly 6004 and the disposable housing assembly 6000. In some embodiments, an arrow icon may also appear between the "locked" and "unlocked" icons.

In various embodiments of the perimeter connector 6010, once the perimeter connector 6010 is connected to the disposable housing assembly 6000, the reusable housing assembly 6004 may be connected/attached to the disposable housing assembly 6000 by being rotated about the disposable housing assembly 6000. As the reusable housing assembly 6004 is rotatably connected to the disposable housing assembly 6000, the locking ring and/or nub 808, having a spring actuated tab 2980, on the reusable housing assembly 6004 may interact with the perimeter connector 6010, such that the rotation of the reusable housing assembly 6003 about the disposable housing assembly 6000 prevents the perimeter connector 6010 from being removed from the disposable housing assembly 6000. In some embodiments, once the reusable housing assembly 6004 is attached to the disposable housing assembly 6000, the spring plunger/tab in the nub 808 may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the perimeter connector 6010 is connected such that it will be maintained connected to the disposable housing assembly 6000 until and unless the user wishes to remove the connector 6010. In some embodiments, the nub 808, having a spring actuated tab 2980, presses downward on the perimeter connector, maintaining the perimeter connector 6010 in an attached position. In some embodiments, features in the locking ring interact with the perimeter connector 6010 and maintain the perimeter connector 6010 in position with respect to the disposable housing assembly 6000. In some embodiments, once the reusable housing assembly 6004 is attached to the disposable housing assembly 6000, the perimeter connector 6010 may not be removed from the disposable housing assembly 6000. Rather, in these embodiments, the reusable housing assembly 6004 must first be detached from the disposable housing assembly 6000 before the perimeter connector 6010 may be removed from the disposable housing assembly 6000. In some embodiments, once the perimeter connector 6010 is attached to the disposable housing assembly 6000, it may not be removed.

In some embodiments of the various embodiments of the perimeter connector 6010, the disposable housing assembly 6000 inserts into the perimeter connector 6010 which, in some embodiments, may include guides to align the perimeter connector 6010 with the disposable housing assembly 6000. In some embodiments, a fluid seal, which, in various embodiments, may be a face seal or a radial seal, connects the fluid path in the disposable housing assembly 6000 to the perimeter connector 6010/tubing 6002. In various embodiments, the perimeter connector 6010 is removably attached to the disposable housing assembly 6000, however, in some embodiments; the perimeter connector 6010 is non-removably attached to the disposable housing assembly 6000.

Referring now to FIGS. 227A-227C, in some embodiments the connector 6010 may be a folding snap connector 6010. As shown in FIG. 227A, in some embodiments, the folding snap connector 6010 may attach to the tab of the disposable housing assembly 6000 and fold under the tab 6030 such that the folding snap connector 6010 is attached to the disposable housing assembly 6000. In some embodiments, the folding snap connector 6010 includes a fluid interface sealed with a face or radial seal. In various embodiments, the folding snap connector 6010 is removably attached to the disposable housing assembly 6000, however, in some embodiments; the folding snap connector 6010 is non-removably attached to the disposable housing assembly 6000.

In various embodiments of the folding snap connector 6010, once the folding snap connector 6010 is connected to the disposable housing assembly 6000, the reusable housing assembly 6004 may be connected/attached to the disposable housing assembly 6000 by being rotated about the disposable housing assembly 6000. As the reusable housing assembly 6004 is rotatably connected to the disposable housing assembly 6000, the locking ring and/or nub 808, having a spring actuated tab 2980, on the reusable housing assembly 6004 may interact with the folding snap connector 6010, such that the rotation of the reusable housing assembly 6004 about the disposable housing assembly 6000 prevents the folding snap connector 6010 from being removed from the disposable housing assembly 6000. In some embodiments, once the reusable housing assembly 6004 is attached to the disposable housing assembly 6000, the spring plunger/tab in the nub 808 may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the folding snap connector 6010 is connected such that it will be maintained connected to the disposable housing assembly 6000 until and unless the user wishes to remove the folding snap connector 6010. In some embodiments, the nub 808, having a spring actuated tab 2980, presses downward on the folding snap connector 6010, maintaining the folding snap connector 6010 in an attached position. In some embodiments, features in the locking ring interact with the folding snap connector 6010 and maintain the folding snap connector 6010 in position with respect to the disposable housing assembly 6000. In some embodiments, once the reusable housing assembly 6004 is attached to the disposable housing assembly 6000, the folding snap connector 6010 may not be removed from the disposable housing assembly 6000. Rather, in these embodiments, the reusable housing assembly 6004 must first be detached from the disposable housing assembly 6000 before the folding snap connector 6010 may be removed from the disposable housing assembly 6000. In some embodiments, once the folding snap connector 6010 is attached to the disposable housing assembly 6000, it may not be removed.

Referring now to FIG. 228A, in some embodiments, the connector 6010 may be a perimeter connector 6010 which may include a plug 6008 which attaches to the fluid path through a tab feature 6030 on the disposable housing assembly. In some embodiments, the perimeter connector 6010 may connect by rotatably connecting to the disposable housing assembly 6000, as shown in FIG. 228B. In various embodiments, the perimeter connector 6010 is removably attached to the disposable housing assembly 6000, however, in some embodiments; the perimeter connector 6010 is non-removably attached to the disposable housing assembly.

In various embodiments of the perimeter connector 6010, once the perimeter connector 6010 is connected to the disposable housing assembly 6000, the reusable housing assembly 6004 may be connected/attached to the disposable housing assembly 6000 by being rotated about the disposable housing assembly 6000. As the reusable housing assembly 6004 is rotatably connected to the disposable housing assembly 6000, the locking ring and/or nub 808, having a spring actuated tab 2980, on the reusable housing assembly 6004 may interact with the perimeter connector 6010, such that the rotation of the reusable housing assembly 6004 about the disposable housing assembly 6000 prevents the perimeter connector 6010 from being removed from the disposable housing assembly 6000. In some embodiments, once the reusable housing assembly 6004 is attached to the disposable housing assembly 6000, the spring plunger/tab in the nub 808 may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the perimeter connector 6010 is connected such that it will be maintained connected to the disposable housing assembly 6000 until and unless the user wishes to remove the perimeter connector 6010. In some embodiments, the nub 808, having a spring actuated tab 2980, presses downward on the perimeter connector 6010, maintaining the perimeter connector 6010 in an attached position. In some embodiments, features in the locking ring interact with the perimeter connector 6010 and maintain the perimeter connector 6010 in position with respect to the disposable housing assembly 6000. In some embodiments, once the reusable housing assembly 6004 is attached to the disposable housing assembly 6000, the perimeter connector 6010 may not be removed from the disposable housing assembly 6000. Rather, in these embodiments, the reusable housing assembly 6004 must first be detached from the disposable housing assembly 6000 before the perimeter connector 6010 may be removed from the disposable housing assembly 6000. In some embodiments, once the perimeter connector 6010 is attached to the disposable housing assembly 6000, it may not be removed.

Referring now to FIG. 229, in some embodiments, the connector 6010 may include a plug 6008 and may fit into a tab portion 6030 on the disposable housing assembly 6000. In various embodiments, the plug 6008 attaches to the fluid path through a tab feature 6030 on the disposable housing assembly 6000. Referring now to FIG. 230, in some embodiments, the tab 6030 and plug 6008 on the disposable housing assembly 6000 may connect to the connector 6010 through movement as shown by the arrows. In various embodiments, the connector 6010 is removably attached to the disposable housing assembly 6000, however, in some embodiments; the connector 6010 is non-removably attached to the disposable housing assembly 6000. As discussed above with respect to various other embodiments, the plug 6008 in this embodiment may include any embodiment described herein, however, in some embodiments; the plug 6008 may be tapered and may either be rigid with an overmold of elastomeric/compliant material or be made from elastomeric/compliant material. In some embodiments, the tubing 6002 attaches to the connector 6010 as described above. In some embodiments, the tubing 6002 may attach to the connector 6010 and there may be a rigid plastic channel within the connector 6010 and through the plug 6008. In some embodiments, the tubing 6002 may extend into the connector 6010 and in some embodiments; the tubing 6002 may extend all the way through the connector 6010 and through the plug 6008. In some embodiments, the tubing 6002 may extend past the end of the plug 6008.

In these various embodiments, there is maintained a continuous flow lumen from the exit 6028 to the cannula 6026. This may be desirable and/or beneficial for many reasons, including, but not limited to, minimizing and/or eliminating dead volume, minimizing priming volume and/or prevention of or minimizing the occurrence of air traps.

In various embodiments of the connector 6010, once the connector 6010 is connected to the disposable housing assembly 6010, the reusable housing assembly 6004 may be connected/attached to the disposable housing assembly 6000 by being rotated about the disposable housing assembly 6000. As the reusable housing assembly 6004 is rotatably connected to the disposable housing assembly 6000, the locking ring and/or nub 808, having a spring actuated tab 2980, on the reusable housing assembly 6004 may interact with the connector 6010, such that the rotation of the reusable housing assembly 6004 about the disposable housing assembly 6000 prevents the connector 6010 from being removed from the disposable housing assembly 6000. In some embodiments, once the reusable housing assembly 6004 is attached to the disposable housing assembly 6000, the spring plunger/tab in the nub 808 may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the connector 6010 is connected such that it will be maintained connected to the disposable housing assembly 6000 until and unless the user wishes to remove the connector 6010. In some embodiments, the nub 808, having a spring actuated tab 2980, presses downward on the connector 6010, maintaining the connector 6010 in an attached position. In some embodiments, features in the locking ring interact with the connector 6010 and maintain the connector 6010 in position with respect to the disposable housing assembly 6000. In some embodiments, once the reusable housing assembly 6004 is attached to the disposable housing assembly 6000, the connector 6010 may not be removed from the disposable housing assembly 6000. Rather, in these embodiments, the reusable housing assembly 6004 must first be detached from the disposable housing assembly 6000 before the connector 6010 may be removed from the disposable housing assembly 6000. In some embodiments, once the connector 6010 is attached to the disposable housing assembly 6000, it may not be removed.

Referring now also to FIGS. 231A-231E another embodiment of a connector 6010 is shown. In some embodiments, the connector 6010 may be a pinch connector 6010. In various embodiments, the pinch connector 6010 may include fingers 6058, 6060, clips 6052, 6066, grips 6050, a plug 6008 and/or a post 6054. The tubing 6002 is fluidly connected to the connector 6010 using any of the embodiments described herein. In various embodiments of the pinch connector 6010 embodiment, the corresponding disposable housing assembly 6000 tab 6030 includes an opening 6064 for receiving the fingers 6058, 6060, an indent 6040, as described above, an exit 6028 for receiving the plug 6008, a clip receiver 6056 on each end for receiving the clips 6052, 6066 and an opening 6064 for receiving the post 6054.

In various embodiments, the pinch connector 6010 may include grips 6050, and in various embodiments, grips 6050 are included on both the top side and bottom side of the pinch connector 6010. In the embodiments shown, the grips 6050 are ribs, however, in various other embodiments, the grips 6050 may include a textured surface, bumps, lumps, protrusions or indentations in any size, shape and/or number. The fingers 6058, 6060 are actuated by pressure being applied to both the top side and bottom side grips 6050.

In various embodiments, the fingers 6058, 6060 include a lip 6062. Upon pressure being exerted onto the grips 6050, the fingers 6058, 6060 move towards one another and the fingers 6058, 6060 may be inserted into the opening 6064 in the tab 6030 of the disposable housing assembly 6000. Upon pressure being removed from the grips 6050, the fingers 6058, 6060 move away from one another and the lips 6062 rest against a surface such that the lips 6062 aid in maintaining the fingers 6058, 6060 inside the opening 6064. Once inside the opening 6064, the fingers 6058, 6060 may be viewed from the bottom of the tab 6030 of the disposable housing assembly 6000 through the tab window 6066. This may be beneficial for many reasons, including, but not limited to, the user may view and ensure that the fingers 6058, 6060 have been inserted into the disposable housing assembly 6000. In various embodiments, the fingers 6058, 6060 interlock with the disposable housing assembly 6000 and this may be desirable for many reasons, including, but not limited to, limiting and/or preventing the pinch connector 6010 from rocking while attached to the disposable housing assembly 6000.

Inserting the fingers 6058, 6060 into the opening 6064 also inserts the plug 6008 into the exit of the disposable housing assembly 6000 as well as the post 6054 into the tab 6030. In some embodiments, the post 6054 and plug 6008 together provide lateral stability to the pinch connector 6010 while attached to the disposable housing assembly 6000.

The plug 6008 may be any of the embodiments as described above. In some embodiments, the plug 6008 includes a radial seal. In some embodiments, the radial seal may provide resistance while the plug 6008 is being inserted into the exit. This may be desirable for many reasons, including, but not limited to, that this may ensure the plug 6008 has been inserted into the exit a desirable distance before the radial seal begins.

In some embodiments, the pinch connector 6010 includes a clip 6052, 6066 on each end which is received by the clip receiver 6056 on each end of the tab of the disposable housing assembly. In some embodiments, the clips including a spring quality and snap into place on the clip receiver. In some embodiments, the "snap" produces an audio indication to the user that the pinch connector has been connected to the disposable housing assembly. The "snap" may also produce a tactile feedback that may be perceived by the user/patient. In some embodiments, the clips 6052, 6066 may be beneficial for providing added stability to the connection between the pinch connector 6010 and the disposable housing assembly 6000.

In various embodiments, the pinch connector 6010 is removably attached to the disposable housing assembly 6000, however, in some embodiments; the pinch connector 6010 is non-removably attached to the disposable housing assembly 6000

In various embodiments of the pinch connector 6010, once the pinch connector 6010 is connected to the disposable housing assembly 6000, the reusable housing assembly 6004 may be connected/attached to the disposable housing assembly 6000 by being rotated about the disposable housing assembly 6000. As the reusable housing assembly 6004 is rotatably connected to the disposable housing assembly 6000, the locking ring and/or nub 808, having a spring actuated tab 2980, on the reusable housing assembly 6004 may interact with the pinch connector 6010, such that the rotation of the reusable housing assembly 6003 about the disposable housing assembly 6000 prevents the pinch connector 6010 from being removed from the disposable housing assembly 6000. In some embodiments, once the reusable housing assembly 6004 is attached to the disposable housing assembly 6000, the spring plunger/tab in the nub 808 may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the pinch connector 6010 is connected such that it will be maintained connected to the disposable housing assembly 6000 until and unless the user wishes to remove the pinch connector 6010. In some embodiments, the nub, having a spring actuated tab 2980, presses downward on the pinch connector 6010, maintaining the pinch connector 6010 in an attached position. In some embodiments, features in the locking ring interact with the pinch connector 6010 and maintain the pinch connector in position with respect to the disposable housing assembly 6000. In some embodiments, the pinch connector 6010 may include an indent portion 6040 which may be configured to interact with the nub 808 and/or spring plunger/tab of the locking ring assembly of the reusable housing assembly 6004. In some embodiments, once the reusable housing assembly 6004 is attached to the disposable housing assembly 6000, the pinch connector 6010 may not be removed from the disposable housing assembly 6000. Rather, in these embodiments, the reusable housing assembly 6004 must first be detached from the disposable housing assembly 6000 before the pinch connector 6010 may be removed from the disposable housing assembly 6000. In some embodiments, once the pinch connector 6010 is attached to the disposable housing assembly 6000, it may not be removed.

Referring now also to FIGS. 232A-232E, another embodiment of a connector 6010 is shown. In this embodiment, the connector 6010 is a top down connector 6010. In various embodiments of the top down connector 6010, the plug 6008 may be located on the disposable housing assembly 6000 and the top down connector 6010 may include a plug receiver 6068, i.e., an opening configured to receive the plug 6008. Although this embodiment is shown in the above-referenced figures, in some embodiments, the plug 6008 may be located on the top down connector 6010 and the disposable housing assembly 6000 may include a plug receiver 6068, or an exit 6028, as referred to in various other embodiments described herein.

In various embodiments, the plug 6008 may be any embodiment of a plug 6008 described herein. For example, in some embodiments, the plug 6008 may include a radial seal.

In various embodiments of this embodiment of the top down connector 6010, the disposable housing assembly 6000 may include a tab 6030 wherein a portion of the tab includes a cut-out portion for receiving the top down connector 6010. In various embodiments of this embodiment, when the top down connector 6010 is connected to the disposable housing assembly 6000, the tab 6030 and the top down connector 6010 may be flush with one another.

In various embodiments of the top down connector 6010, the top down connector 6010 may include an indent 6040, as described in various embodiments of connectors herein. However, in some embodiments of the top down connector 6010, an indent 6040 may not be included. In those embodiments including an indent 6040, the size and shape of the indent may vary and be any size and/or shape.

The top down connector 6010 may be any shape and size, however, in some embodiments, the top down connector 6010 includes a grip tab 6070 which may be sized and shaped to accommodate a "pinch grip" from a user, i.e., a grip using the thumb and index finger. In various embodiments, the size and shape of the grip tab 6070 may vary. In some embodiments, the grip tab 6070 may include an overmold and in some embodiments, the overmold may be a flexible overmold. This may be beneficial for many reasons, including, but not limited to, the overmold and/or flexible overmold may be preferable for wearing against the skin of a user, for example, the overmold and/or flexible overmold may be more comfortable against a user's skin.

In some embodiments, the size and shape of the tab portion 6030 of the disposable housing assembly 6000 may vary. Additionally, in embodiments where there is a cut-out portion of the tab portion 6030 of the disposable housing assembly 6000, the size and shape of the cut-out portion may vary and may be any size and/or shape.

As discussed above, in various embodiments, the disposable housing assembly 6000 may include the plug 6008 and the top down connector 6010 may include a plug receiver 6068. This embodiment may be included in any one or more of the various embodiments of connectors 6010 described herein and is not limited to the top down connector 6010. In these embodiments, the plug 6008 and the plug receiver 6068 may include any of the various embodiments of the plug 6008 and plug receiver 6068 described herein.

In some embodiments of the top down connector 6010, the top down connector may include male interlock features 6016 on both ends of the top down connector 6010. These male interlock features 6016 are configured to be received by female interlock features 6020 on the disposable housing assembly 6000 tab 6030. Once the male interlock features 6016 are placed within the female interlock features 6020, the top down connector 6010 is secured onto the disposable housing assembly 6000. In some embodiment, the top down connector 6010 may not include interlock features and may be secured by other means. In various embodiments, the top down connector 6010 is removably attached to the disposable housing assembly 6000, however, in some embodiments; the connector 6010 is non-removably attached to the disposable housing assembly 6000 by various means, some which are discussed herein. In some embodiments, once the male interlock features 6016 are received by the female interlock features 6020, a "click" and or a tactile feedback may result. This may be beneficial for many reasons, including, but not limited to, providing an indication to the user that the top down connector 6010 is connected to the disposable housing assembly 6000.

In some embodiments, the tab portion 6030 may include a side-cut for accommodation of the grip tab 6070. In some embodiments, the side-cut may be made on the cut-out portion of the tab 6030. In some embodiments, the side-cut accommodates the grip tab 6070 such that, when the top down connector 6010 is attached to the disposable housing assembly 6000, the grip tab 6070 does not overlap with the tab 6030 on the disposable housing assembly 6000. This may be beneficial for many reasons, including, but not limited to, the ease of connection of the top down connector 6010 to the disposable housing assembly 6000 by pinch gripping the grip tab 6070.

In various embodiments of the top down connector 6010, once the top down connector 6010 is connected to the disposable housing assembly 6000, the reusable housing assembly 6004 may be connected/attached to the disposable housing assembly 6000 by being rotated about the disposable housing assembly 6000. As the reusable housing assembly 6004 is rotatably connected to the disposable housing assembly 6000, the locking ring and/or nub 808, having a spring actuated tab 2980, on the reusable housing assembly 6004 may interact with the top down connector 6010, such that the rotation of the reusable housing assembly 6004 about the disposable housing assembly 6000 prevents the top down connector 6010 from being removed from the disposable housing assembly 6000. In some embodiments, once the reusable housing assembly 6004 is attached to the disposable housing assembly 6000, the spring plunger/tab in the nub 808 may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the top down connector 6010 is connected such that it will be maintained connected to the disposable housing assembly 6000 until and unless the user wishes to remove the top down connector 6010. In some embodiments, the nub 808, having a spring actuated tab 2980, presses downward on the top down connector 6010, maintaining the connector in an attached position. In some embodiments, features in the locking ring interact with the top down connector 6010 and maintain the top down connector 6010 in position with respect to the disposable housing assembly 6000. In some embodiments, the top down connector 6010 may include an indent portion 6040 which may be configured to interact with the nub 808 and/or spring plunger/tab of the locking ring assembly of the reusable housing assembly 6004. In some embodiments, once the reusable housing assembly 6004 is attached to the disposable housing assembly 6000, the top down connector 6010 may not be removed from the disposable housing assembly 6000. Rather, in these embodiments, the reusable housing assembly 6004 must first be detached from the disposable housing assembly 6000 before the top down connector 6010 may be removed from the disposable housing assembly 6000. In some embodiments, once the top down connector 60010 is attached to the disposable housing assembly 6000, it may not be removed.

In some embodiments of the top down connector 6010, the tab 6030 of the disposable housing assembly 6000 may include a post and the top down connector 6010 may include an opening for receiving the post. Placing the top down connector 6010 onto the disposable housing assembly 6000 also places the plug 6008 into the plug receiver 6068 as well as the post into the opening for receiving the post. In some embodiments, the post and plug 6008 together may provide lateral stability to the top down connector while attached to the disposable housing assembly. In some embodiments, the top down connector 6010 may include a post and the disposable housing connector 6000 may include an opening for receiving the post.

Referring now also to FIGS. 233A-233G, another embodiment of a connector 6010 is shown. The connector 6010 may include a body portion/tab 6018, a post 6054, and a plug receiver 6068. In some embodiments, the body portion 6018 of the connector 6010 may include mating locking features that interact with the tab portion 6030 of the disposable housing assembly 6000. In some embodiments, the body portion 6018 may include features that interact with other portions of the disposable housing assembly 6000. As shown, in some embodiments, the connector 6010 may include a post 6054 on the end of the body portion 6018 of the connector 6010. In some embodiments, the post 6054 may be a removably secure fit, and/or a snap fit and/or a loose snap fit and may include features such that the post 6054 portion of the connector 6010 snaps and/or rests onto the opening on the disposable housing assembly 6000. In various other embodiments, the shape and size of the connector 6010 may vary, and/or, in various other embodiments, other types of features such as mating locking features may be used, which include, but are not limited to, latches, catches, snap fits, adhesives, and other mechanisms for securing a connector to the tab of the disposable housing assembly 6000.

In some embodiments, the connector 6010 may include a locking ring feature 6072 on the underside. The locking ring feature 6072 in some embodiments may be tapered and/or in some embodiments, the locking ring feature 6072 may be at least slightly curved. In some embodiments, the locking ring feature 6072 may interact with the locking ring of the reusable housing assembly 6004 and may act together with the locking ring to secure the connector 6010 to the disposable housing assembly 6000.

As discussed above, in various embodiments, the plug 6008 of the disposable housing assembly 6000 is inserted into the plug receiver 6068 of the connector 6010 with the body portion 6018 pointing in the general upward direction. Once the plug 6008 is inside the connector 6010, the body portion 6018 of the connector 6010 may be rotated to rest adjacent to the tab portion 6030 of the disposable housing portion. In some embodiments, mating locking features (for example, in some embodiments, a catch feature 6014) may be included on the body portion 6018 of the connector 6010 and the disposable housing assembly 6000 such that the connector 6010 is held in place before the reusable housing assembly 6004 is attached to the disposable housing assembly 6000. In some embodiments, the mating locking features may include, but are not limited to, post and opening, snap, buttons and/or catch features 6014. In some embodiments, a hook or other feature may be located on the opposite end of the body portion 6018 of the connector 6010 such that it loops over the end of the tab portion 6030 of the disposable housing assembly 6000 and maintains the position of the connector 6010. In the embodiment shown in FIGS. 233A-233G, the mating locking features include a post 6054 on the connector 6010 and an opening 6064 on the disposable housing assembly 6000.

In various embodiments, once the connector 6010 is attached to the disposable housing assembly 6000, the connector 6010 may only be removed when intended, i.e., the connector 6010 is maintained on the disposable housing assembly 6000 unless and until a user desires to remove the connector 6010. As discussed above, in some embodiments, the connector 6010 may be non-removably attached, however, in some embodiments; the connector 6010 may be removably attached.

While the connector 6010 is being attached to the disposable housing assembly 6000, the post 6054 on the connector 6010 rests on the opening 6064. In some embodiments, the post 6054 and opening 6010 may work together to further stabilize the connection of the connector 6010 to the disposable housing assembly 6000. Additionally, in various embodiments, the post 6054 and opening may contribute to maintaining the plug 6008 in the plug receiver 6068. Thus, in some embodiments, the post 6054 and opening may contribute to maintaining and/or enforcing both the insertion of the plug 6008 into the opening and/or maintaining and/or enforcing the position of the connector 6010 such that after the plug 6008 is inserted into the plug receiver 6068, the plug 6008 is maintained in the plug receiver 6068 unless and until a user desires to remove the plug 6008 from the plug receiver 6068. Additionally, once the post 6054 and opening 6064 are mated, the plug 6008 is fully inserted and therefore, may, in some embodiments, serve as an indication that the plug 6008 has been fully inserted into the plug receiver 6068.

As shown in, for example, FIGS. 233A and 233B, in some embodiments, the disposable housing assembly 6000 may include a plug 6008. In some embodiments, as shown in the embodiments in FIGS. 233A and 233B, the plug 6008 may be positioned such that the connector 6010 approaches the plug 6008 from the side (rather than the top, as shown in the top down connector embodiments). Also, in some embodiments, the tab 6030 of the disposable housing assembly 6000 may be shaped as shown in FIGS. 233A and 233B. In some embodiments, the connector 6010, once attached to the disposable housing assembly 6000, may extend the tab portion 6030 of the disposable housing assembly 6000. In some embodiments, once the connector 6010 is attached to the disposable housing assembly 6000, the connector 6010 and tab 6030 may be flush and continuous.

In some embodiments, the connector 6010 may include an indent 6040, as shown. The indent 6040 may be shaped as shown or, in various embodiments, may be shaped and sized differently.

In various embodiments, the opening 6064 on the disposable housing assembly 6000 may be located adjacent to the tab portion 6030. In some embodiments, for example, as shown in FIGS. 233A and 233B, the opening 6064 may be configured such that it receives the post 6054 on the connector 6010 from the top. Some embodiments may not include a post 6054 and opening 6064. In some embodiments, the location and/or orientation of the opening 6064 may vary. In some embodiments, the location and/or orientation of the post 6054 may vary.

In some embodiments, the connector 6010 may be made from rigid plastic. In some embodiments, the locking ring feature and/or the post may be overmolded with a thin layer of compliant materials. In some embodiments, as discussed above, the plug 6008 may include an overmold of compliant material and/or be made from compliant material. In some embodiments, the locking ring feature and/or the post 6054 may be made from compliant material. In embodiments where the post 6054 includes compliant material, use of compliant material may increase the "squish" between the post 6054 and the opening 6064 and therefore, resulting in a highly compressed and/or tight fit between the post 6054 and the opening 6064.

Referring now also to FIG. 136, in some embodiments, the connector 6010 may include icons that indicate "locked" and "unlocked", similar to those shown and described above with respect to FIG. 136. Thus, in some embodiments, the "locked" and "unlocked" position may also be visually indicated to a user/patient using icons that may be molded, silk-screened, pad printed, injection molded, etched, printed and/or cut-out, e.g., translucent cut-outs of icons, on the connector. In some embodiments using translucent cut-outs, the tab portion 6030 of the disposable housing assembly 6000 may be a contrasting color to the connector for visually viewing the tab portion 6030 color through the cut-outs. Thus, the icons may indicate whether the reusable housing assembly 6004 is in a locked or unlocked relationship with the disposable housing assembly 6000. In various embodiments, the icons may be any form that may indicate "locked" and "unlocked", or a similar indication, to aid in the user/patient's understanding of the orientation/position between the reusable housing assembly 6004 and the disposable housing assembly 6000. In some embodiments, an arrow icon may also appear between the "locked" and "unlocked" icons.

The plug 6008 may include any embodiment described herein, however, in some embodiments; the plug 6008 may be tapered and may either be rigid with an overmold of elastomeric/compliant material or be made from elastomeric/compliant material. In some embodiments, the tubing 6002 attaches to the connector 6010 as described above. In some embodiments, the tubing 6002 may attach to the connector 6010 and there may be a rigid plastic channel within the connector 6010 and through the plug 6008. In some embodiments, the tubing 6002 may extend into the connector 6010 and in some embodiments; the tubing 6002 may extend all the way through the connector 6010 and through the plug 6008. In some embodiments, the tubing 6002 may extend past the end of the plug 6008.

In these various embodiments, there is maintained a continuous flow lumen from the exit 6028 to the cannula 6026. This may be desirable and/or beneficial for many reasons, including, but not limited to, minimizing and/or eliminating dead volume, minimizing priming volume and/or prevention of or minimizing the occurrence of air traps.

Some embodiments of the connector 6010 may also include a catching feature 6014 on the opposite side as the post 6054. The catching feature 6014, when the connector 6010 is connected to the disposable housing assembly 6000, interferes with the disposable housing assembly 6000 and prevents the connector 6000 from rotating further. Thus, in some embodiments, the connector 6010 and the disposable housing assembly 6000 form an interference fit in at least one location. Together with the post 6054 and opening 6064 feature, in some embodiments, once the connector 6010 is attached, the connector 6010 may be held in place by these mating features.

The connector body portion 6018 may include gripping features, however, in the some embodiments; the connector 6010 is sized such that a user may grip the connector 6010 for insertion/attachment with the disposable housing assembly 6000. In some embodiments including grip features which, in various embodiments, may include, but are not limited to, one or more of the following: a textured surface, bumps, lumps, protrusions or indentations in any size, shape and/or number.

In various embodiments of the connector 6010, once the connector 6010 is connected to the disposable housing assembly 6000, the reusable housing assembly 6004 may be connected/attached to the disposable housing assembly 6000 by being rotated about the disposable housing assembly 6000. As the reusable housing assembly 6004 is rotatably connected to the disposable housing assembly 6000, the locking ring and/or nub 808, having a spring actuated tab 2980, on the reusable housing assembly 6004 may interact with the connector 6010, such that the rotation of the reusable housing assembly 6004 about the disposable housing assembly 6000 prevents the connector 6010 from being removed from the disposable housing assembly 6000. In some embodiments, once the reusable housing assembly 6004 is attached to the disposable housing assembly 6000, the spring plunger/tab in the nub 808 may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the connector 6010 is connected such that it will be maintained connected to the disposable housing assembly 6000 until and unless the user wishes to remove the connector 6010. In some embodiments, the nub 808, having a spring actuated tab 2980, presses downward on the connector 6010, maintaining the connector 6010 in an attached position. In some embodiments, features in the locking ring interact with the locking ring feature on the connector 6010 and contribute to maintain the connector 6010 in position with respect to the disposable housing assembly 6000. In some embodiments, the body portion 6018 of the connector 6010 may include an indent portion 6040 which may be configured to interact with the nub 808 and/or spring plunger/tab of the locking ring assembly of the reusable housing assembly 6004. In some embodiments, once the reusable housing assembly 6004 is attached to the disposable housing assembly 6000, the connector 6010 may not be removed from the disposable housing assembly 6000. Rather, in these embodiments, the reusable housing assembly 6004 must first be detached from the disposable housing assembly 6000 before the connector 6010 may be removed from the disposable housing assembly 6000. In some embodiments, once the connector 6010 is attached to the disposable housing assembly 6000, it may not be removed.

In the embodiment shown in FIGS. 233A-233G, the connector 6010 connects to the disposable housing assembly 6000 by the connector 6010 being rotated clockwise with respect to the disposable housing assembly 6000. In other embodiments, the various features described may be configured differently and the connector 6010 may be connected to the disposable housing assembly 6000 by the connector 6010 being rotated counter-clockwise with respect to the disposable housing assembly 6000.

In some embodiments, the disposable housing assembly may include a plug according to the various embodiment described herein, however, in some embodiments, the plug may be located in a different location and/or orientation than is shown herein. In various embodiments, the disposable housing assembly may include one or more mating features that correspond to one or more mating features on a connector. In some embodiments, these mating features may be located and/or orientated differently than is shown herein.

Referring now also to FIGS. 234A-234G, another embodiment of a connector 6010 is shown. The connector 6010 may include a body portion 6018, a catch feature 6014, a latching feature 6016, and a plug 6008. In some embodiments, the body portion 6018 of the connector 6010 may include mating locking features that interact with corresponding features in the disposable housing assembly. In some embodiments, the body portion 6018 may include features that interact with other portions of the disposable housing assembly 6000. As shown, in some embodiments, the connector 6010 may include a male latching feature 6016 on the end of the body portion 6018 of the connector 6010. In some embodiments, the latching feature 6016 may mate with a corresponding latching feature (a female latching feature 6020) on the disposable housing assembly 6000. In some embodiments, the latch may be a removably secure fit, and/or a snap fit and/or a loose snap fit. In various other embodiments, the shape and size of the connector 6010 may vary, and/or, in various other embodiments, other types of features such as mating locking features may be used, which include, but are not limited to, latches, catches, snap fits, adhesives, and other mechanisms for securing a connector 6010 to the tab of the disposable housing assembly 6000.

In some embodiments, the connector 6010 may include a locking ring feature on the underside. The locking ring feature in some embodiments may be tapered and/or in some embodiments, the locking ring feature may be at least slightly curved. In some embodiments, the locking ring feature may interact with the locking ring of the reusable housing assembly and may act together with the locking ring to secure the connector to the disposable housing assembly.

As discussed above, in various embodiments, the plug 6008 of the connector 6010 is inserted into the exit 6028 of the disposable housing portion 6000 with the body portion 6018 pointing in the general upward direction. Once the plug 6008 is inside the exit, the body portion 6018 of the connector 6010 may be rotated to rest adjacent to the tab portion of the disposable housing portion 6000. In some embodiments, mating locking features may be included on the body portion 6018 of the connector 6010 and the disposable housing assembly 6000 such that the connector 6010 is held in place before the reusable housing assembly 6004 is attached to the disposable housing assembly 6000. In some embodiments, the mating locking features may include, but are not limited to, post and opening, snap, buttons, latch features and/or catch features. In some embodiments, a hook or other feature may be located on the opposite end of the body portion of the connector such that it loops over the end of the tab portion of the disposable housing assembly and maintains the position of the connector. In the embodiment shown in FIGS. 234A-234F, the mating locking features include a male latching feature 6016 on the connector 6010 and a female latching feature 6020 on the disposable housing assembly 6000.

In various embodiments, once the connector 6010 is attached to the disposable housing assembly 6000, the connector 6010 may only be removed when intended, i.e., the connector 6010 is maintained on the disposable housing assembly 6000 unless and until a user desires to remove the connector 6010. As discussed above, in some embodiments, the connector 6010 may be non-removably attached, however, in some embodiments; the connector 6010 may be removably attached.

While the connector 6010 is being attached to the disposable housing assembly 6000, the male latching feature 6016 is mated with the female latching feature 6020. In some embodiments, male and female latching features 6016, 6020 may work together to further stabilize the connection of the connector 6010 to the disposable housing assembly 6000. Additionally, in various embodiments, the male and female latching features 6016, 6020 may contribute to maintaining the plug 6008 in the exit 6028. Thus, in some embodiments, the male and female latching features 6016, 6020 may contribute to maintaining and/or enforcing both the insertion of the plug 6008 into the exit 6028 and/or maintaining and/or enforcing the position of the connector 6010 such that after the plug 6008 is inserted into the exit 6028, the plug 6008 is maintained in the exit 6028 unless and until a user desires to remove the plug 6008 from the exit 6028. Additionally, once the male and female latching features 6016, 6020 are mated, the plug 6008 is fully inserted and therefore, may, in some embodiments, serve as an indication that the plug 6008 has been fully inserted into the exit 6028.

As shown in FIGS. 234A and 234B, in some embodiments, the connector 6010 may include a plug 6008. In some embodiments, as shown in the embodiments in FIGS. 234A and 234B, the plug 6008 may be positioned such that the connector 6010 approaches the disposable housing assembly 6000 exit 6028 from the side. Also, in some embodiments, the tab 6030 of the disposable housing portion 6000 may be shaped as shown in FIGS. 234A and 234B. In some embodiments, the connector 6010, once attached to the disposable housing assembly 6000, may extend the tab portion 6030 of the disposable housing assembly 6000. In some embodiments, once the connector 6010 is attached to the disposable housing assembly 6000, the connector 6010 and tab 6030 may be flush and continuous.

In some embodiments, the connector 6010 may include an indent 6040, as shown. The indent 6040 may be shaped as shown or, in various embodiments, may be shaped and sized differently.

In various embodiments, the female latching feature 6020 on the disposable housing assembly 6000 may be located adjacent to the tab portion 6030. In some embodiments, for example, as shown in FIGS. 234A-234D, the female latching feature 6020 may be configured such that it receives the male latching feature 6016 on the connector 6010 from the top. Some embodiments may not include mating latching features 6016. In some embodiments, the location and/or orientation of the female latching feature 6020 may vary. In some embodiments, the location and/or orientation of the male latching feature 6016 may vary.

In some embodiments, the connector 6010 may be made from rigid plastic. In some embodiments, the locking ring feature and/or the latching features may be overmolded with a thin layer of compliant materials. In some embodiments, as discussed above, the plug 6008 may include an overmold of compliant material and/or be made from compliant material. In some embodiments, the locking ring feature and/or the latching feature may be made from compliant material. In embodiments where the male or female latching features 6016, 6020 include compliant material, use of compliant material may increase the "squish" between the male latching feature 6016 and the female latching feature 6020 and therefore, resulting in a highly compressed and/or tight fit between the male and female latching features 6016, 6020.

Referring now also to FIG. 136, in some embodiments, the connector 6010 may include icons that indicate "locked" and "unlocked", similar to those shown and described above with respect to FIG. 136. Thus, in some embodiments, the "locked" and "unlocked" position may also be visually indicated to a user/patient using icons that may be molded, silk-screened, pad printed, injection molded, etched, printed and/or cut-out, e.g., translucent cut-outs of icons, on the connector 6010. In some embodiments using translucent cut-outs, the tab portion 6030 of the disposable housing assembly 6000 may be a contrasting color to the connector 6010 for visually viewing the tab portion 6030 color through the cut-outs. Thus, the icons may indicate whether the reusable housing assembly 6004 is in a locked or unlocked relationship with the disposable housing assembly 6000. In various embodiments, the icons may be any form that may indicate "locked" and "unlocked", or a similar indication, to aid in the user/patient's understanding of the orientation/position between the reusable housing assembly 6004 and the disposable housing assembly 6000. In some embodiments, an arrow icon may also appear between the "locked" and "unlocked" icons.

The plug 6008 may include any embodiment described herein, however, in some embodiments; the plug 6008 may be tapered and may either be rigid with an overmold of elastomeric/compliant material or be made from elastomeric/compliant material. In various embodiments, the plug 6008 may include a seal, for example, in some embodiments, the plug 6008 may include a radial seal.

In some embodiments, the tubing 6002 attaches to the connector 6010 as described above. In some embodiments, the tubing 6002 may attach to the connector 6010 and there may be a rigid plastic channel within the connector 6010 and through the plug 6008. In some embodiments, the tubing 6002 may extend into the connector 6010 and in some embodiments; the tubing 6002 may extend all the way through the connector 6010 and through the plug 6008. In some embodiments, the tubing 6002 may extend past the end of the plug 6008.

In these various embodiments, there is maintained a continuous flow lumen from the exit to the cannula 6026. This may be desirable and/or beneficial for many reasons, including, but not limited to, minimizing and/or eliminating dead volume, minimizing priming volume and/or prevention of or minimizing the occurrence of air traps.

Some embodiments of the connector 6010 may also include a catch/catching feature 6014 on the opposite side as the male latching feature 6016. The catch feature 6014, when the connector 6010 is connected to the disposable housing assembly 6000, interferes with the disposable housing assembly 6000 and prevents the connector 6010 from rotating further. Thus, in some embodiments, the connector 6010 and the disposable housing assembly 6000 form an interference fit in at least one location. Together with the male and female latching features 6016, 6020, in some embodiments, once the connector 6010 is attached, the connector 6010 may be held in place by these mating features 6016, 6020.

The connector body portion 6018 may include gripping features, however, in the some embodiments; the connector 6010 is sized such that a user may grip the connector 6010 for insertion/attachment with the disposable housing assembly 6000. In some embodiments including grip features which, in various embodiments, may include, but are not limited to, one or more of the following: a textured surface, bumps, lumps, protrusions or indentations in any size, shape and/or number.

In various embodiments of the connector 6010, once the connector 6010 is connected to the disposable housing assembly 6000, the reusable housing assembly 6004 may be connected/attached to the disposable housing assembly 6000 by being rotated about the disposable housing assembly 6000. As the reusable housing assembly is rotatably connected to the disposable housing assembly 6000, the locking ring and/or nub 808, having a spring actuated tab 2980, on the reusable housing assembly 6004 may interact with the connector 6010, such that the rotation of the reusable housing assembly 6004 about the disposable housing assembly 6000 prevents the connector 6010 from being removed from the disposable housing assembly 6000. In some embodiments, once the reusable housing assembly 6004 is attached to the disposable housing assembly 6000, the spring plunger/tab in the nub 808 may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the connector 6010 is connected such that it will be maintained connected to the disposable housing assembly 6000 until and unless the user wishes to remove the connector 6010. In some embodiments, the nub 808, having a spring actuated tab 2980, presses downward on the connector 6010, maintaining the connector 6010 in an attached position. In some embodiments, features in the locking ring interact with a locking ring feature on the connector 6010 and contribute to maintain the connector 6010 in position with respect to the disposable housing assembly 6000. In some embodiments, the body portion 6018 of the connector 6010 may include an indent portion which may be configured to interact with the nub 808 and/or spring plunger/tab of the locking ring assembly of the reusable housing assembly 6004. In some embodiments, once the reusable housing assembly 6004 is attached to the disposable housing assembly 6000, the connector 6010 may not be removed from the disposable housing assembly 6000. Rather, in these embodiments, the reusable housing assembly 6004 must first be detached from the disposable housing assembly 6000 before the connector 6010 may be removed from the disposable housing assembly 6000. In some embodiments, once the connector 6010 is attached to the disposable housing assembly 6000, it may not be removed.

In the embodiment shown in FIGS. 234A-234G, the connector 6010 connects to the disposable housing assembly 6000 by the connector 6010 being rotated clockwise with respect to the disposable housing assembly 6000. In other embodiments, the various features described may be configured differently and the connector 6010 may be connected to the disposable housing assembly 6000 by the connector 6010 being rotated counter-clockwise with respect to the disposable housing assembly 6000.

In some embodiments, the disposable housing assembly 6000 may include a plug 6008 and the connector 6010 may include a plug receiver 6068 according to the various embodiment described herein. In some embodiments, the plug 6008 may be located in a different location and/or orientation than is shown herein. In various embodiments, the disposable housing assembly 6000 may include one or more mating features that correspond to one or more mating features on a connector 6010. In some embodiments, these mating features may be located and/or orientated differently than is shown herein.

Referring now also to FIGS. 235A-235E, another embodiment of a connector 6010 and a disposable housing assembly 6000 are shown. The connector 6010 may include a body portion 6018, a catch feature 6015, a latching feature 6016, and a plug 6008. In some embodiments, the body portion 6018 of the connector 6010 may include mating locking features that interact with corresponding features in the disposable housing assembly 6000. In some embodiments, the body portion 6018 may include features that interact with other portions of the disposable housing assembly 6000. As shown, in some embodiments, the connector 6010 may include a male latching feature 6016 on the end of the body portion 6018 of the connector 6010. In some embodiments, the male latching feature 6016 may mate with a corresponding female latching feature 6020 on the disposable housing assembly 6000. In some embodiments, the latch may be a removably secure fit, and/or a snap fit and/or a loose snap fit. In various other embodiments, the shape and size of the connector 6010 may vary, and/or, in various other embodiments, other types of features such as mating locking features may be used, which include, but are not limited to, latches, catches, snap fits, adhesives, and other mechanisms for securing a connector to the tab of the disposable housing assembly 6000.

In some embodiments, the connector 6010 may include a locking ring feature on the underside. The locking ring feature in some embodiments may be tapered and/or in some embodiments, the locking ring feature may be at least slightly curved. In some embodiments, the locking ring feature may interact with the locking ring of the reusable housing assembly 6004 and may act together with the locking ring to secure the connector to the disposable housing assembly 6000.

As discussed above, in various embodiments, the plug 6008 of the connector 6010 is inserted into the exit 6028 of the disposable housing assembly 6000 with the body portion 6018 pointing in the general upward direction. Once the plug 6008 is inside the exit 6028, the body portion 6018 of the connector 6010 may be rotated to rest adjacent to the tab portion 6030 of the disposable housing portion 6000. In some embodiments, mating locking features may be included on the body portion 6018 of the connector 6010 and the disposable housing assembly 6000 such that the connector 6010 is held in place before the reusable housing assembly 6004 is attached to the disposable housing assembly 6000. In some embodiments, the mating locking features may include, but are not limited to, post and opening, snap, buttons, latch features and/or catch features. In some embodiments, a hook or other feature may be located on the opposite end of the body portion 6018 of the connector 6010 such that it loops over the end of the tab portion 6030 of the disposable housing assembly 6000 and maintains the position of the connector 6010. In the embodiment shown in FIGS. 235A-235E, the mating locking features include a male latching feature 6016 on the connector 6010 and a female latching feature 6020 on the disposable housing assembly 6000. The male latching feature 6016 is a bump and the female latching feature 6020 is an opening that accommodates the bump.

In various embodiments, once the connector 6010 is attached to the disposable housing assembly 6000, the connector 6010 may only be removed when intended, i.e., the connector 6010 is maintained on the disposable housing assembly 6000 unless and until a user desires to remove the connector 6010. As discussed above, in some embodiments, the connector 6010 may be non-removably attached, however, in some embodiments; the connector 6010 may be removably attached.

While the connector 6010 is being attached to the disposable housing assembly 6000, the male latching feature 6016 is mated with the female latching feature 6020. In some embodiments, male and female latching features 6016, 6020 may work together to further stabilize the connection of the connector 6010 to the disposable housing assembly 6000. Additionally, in various embodiments, the male and female latching features 6016, 6020 may contribute to maintaining the plug 6008 in the exit 6028. Thus, in some embodiments, the male and female latching features 6016, 6020 may contribute to maintaining and/or enforcing both the insertion of the plug 6008 into the exit 6028 and/or maintaining and/or enforcing the position of the connector 6010 such that after the plug 6008 is inserted into the exit 6028, the plug 6008 is maintained in the exit 6028 unless and until a user desires to remove the plug 6008 from the exit 6028. Additionally, once the male and female latching features 6016, 6020 are mated, the plug 6008 is fully inserted and therefore, may, in some embodiments, serve as an indication that the plug 6008 has been fully inserted into the exit 6028.

As shown in FIGS. 235A-235C, in some embodiments, the connector 6010 may include a plug 6008. In some embodiments, as shown in the embodiments in FIGS. 235A-235C, the plug 6008 may be positioned such that the connector 6010 approaches the disposable housing assembly 6000 exit 6028 from the side. Also, in some embodiments, the tab 6030 of the disposable housing portion 6000 may be shaped as shown in FIGS. 235D and 235E. In some embodiments, the connector 6010, once attached to the disposable housing assembly 6000, may extend the tab portion 6030 of the disposable housing assembly 6000. In some embodiments, once the connector 6010 is attached to the disposable housing assembly 6000, the connector 6010 and tab 6030 may be flush and continuous.

In some embodiments, the connector 6010 may include an indent 6040, as shown. The indent 6040 may be shaped as shown or, in various embodiments, may be shaped and sized differently.

In various embodiments, the female latching feature 6020 on the disposable housing assembly 6000 may be located adjacent to the tab portion 6030. In some embodiments, for example, as shown in FIGS. 235D-235E, the female latching feature 6020 may be configured such that it receives the male latching feature 6016 on the connector 6010 from the top. Some embodiments may not include mating latching features 6016, 6020. In some embodiments, the location and/or orientation of the female latching feature 6020 may vary. In some embodiments, the location and/or orientation of the male latching feature 6016 may vary.

In some embodiments, the connector 6010 may be made from rigid plastic. In some embodiments, the locking ring feature and/or the latching features may be overmolded with a thin layer of compliant materials. In some embodiments, as discussed above, the plug 6008 may include an overmold of compliant material and/or be made from compliant material. In some embodiments, the locking ring feature and/or the latching feature may be made from compliant material. In embodiments where the male or female latching feature 6016, 6020 includes compliant material, use of compliant material may increase the "squish" between the male latching feature 6016 and the female latching feature 6020 and therefore, resulting in a highly compressed and/or tight fit between the male and female latching features 6016, 6020.

Referring now also to FIG. 136, in some embodiments, the connector 6010 may include icons that indicate "locked" and "unlocked", similar to those shown and described above with respect to FIG. 136. Thus, in some embodiments, the "locked" and "unlocked" position may also be visually indicated to a user/patient using icons that may be molded, silk-screened, pad printed, injection molded, etched, printed and/or cut-out, e.g., translucent cut-outs of icons, on the connector 6010. In some embodiments using translucent cut-outs, the tab portion 6030 of the disposable housing assembly 6000 may be a contrasting color to the connector 6010 for visually viewing the tab portion 6030 color through the cut-outs. Thus, the icons may indicate whether the reusable housing assembly 6004 is in a locked or unlocked relationship with the disposable housing assembly 6000. In various embodiments, the icons may be any form that may indicate "locked" and "unlocked", or a similar indication, to aid in the user/patient's understanding of the orientation/position between the reusable housing assembly 6004 and the disposable housing assembly 6000. In some embodiments, an arrow icon may also appear between the "locked" and "unlocked" icons.

The plug 6008 may include any embodiment described herein, however, in some embodiments; the plug 6008 may be tapered and may either be rigid with an overmold of elastomeric/compliant material or be made from elastomeric/compliant material. In various embodiments, the plug 6008 may include a seal, for example, in some embodiments; the plug 6008 may include a radial seal.

In some embodiments, the tubing 6002 attaches to the connector 6010 as described above. In some embodiments, the tubing 6002 may attach to the connector 6010 and there may be a rigid plastic channel within the connector 6010 and through the plug 6008. In some embodiments, the tubing 6002 may extend into the connector 6010 and in some embodiments; the tubing 6002 may extend all the way through the connector 6010 and through the plug 6008. In some embodiments, the tubing 6002 may extend past the end of the plug 6008.

In these various embodiments, there is maintained a continuous flow lumen from the exit 6028 to the cannula 6026. This may be desirable and/or beneficial for many reasons, including, but not limited to, minimizing and/or eliminating dead volume, minimizing priming volume and/or prevention of or minimizing the occurrence of air traps.

Some embodiments of the connector 6010 may also include a catch feature 6014 on the opposite side as the male latching feature 6016. The catch feature 6014, when the connector 6010 is connected to the disposable housing assembly 6000, interferes with the disposable housing assembly 6000 and prevents the connector 6010 from rotating further. Thus, in some embodiments, the connector 6010 and the disposable housing assembly 6000 form an interference fit in at least one location. Together with the male and female latching features 6016, 6020, in some embodiments, once the connector 6010 is attached, the connector 6010 may be held in place by these mating features. In some embodiments, the catch feature 6014 may be ramped and therefore, may, in some embodiments, aid in the attaching of the connector 6014 to the disposable housing assembly 6000.

The connector body portion 6018 may include gripping features, however, in the some embodiments; the connector is sized such that a user may grip the connector 6010 for insertion/attachment with the disposable housing assembly 6000. In some embodiments including grip features which, in various embodiments, may include, but are not limited to, one or more of the following: a textured surface, bumps, lumps, protrusions or indentations in any size, shape and/or number.

In various embodiments of the connector 6010, once the connector 6010 is connected to the disposable housing assembly 6000, the reusable housing assembly 6004 may be connected/attached to the disposable housing assembly 6000 by being rotated about the disposable housing assembly 6000. As the reusable housing assembly 6004 is rotatably connected to the disposable housing assembly 6000, the locking ring and/or nub 808, having a spring actuated tab 2980, on the reusable housing assembly 6004 may interact with the connector 6010, such that the rotation of the reusable housing assembly 6004 about the disposable housing assembly 6000 prevents the connector 6010 from being removed from the disposable housing assembly 6000. In some embodiments, once the reusable housing assembly 6004 is attached to the disposable housing assembly 6000, the spring plunger/tab in the nub 808 may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the connector 6010 is connected such that it will be maintained connected to the disposable housing assembly 6000 until and unless the user wishes to remove the connector 6010. In some embodiments, the nub 808, having a spring actuated tab 2980, presses downward on the connector, maintaining the connector 6010 in an attached position. In some embodiments, features in the locking ring interact with a locking ring feature on the connector 6010 and contribute to maintain the connector 6010 in position with respect to the disposable housing assembly 6000. In some embodiments, the body portion 6018 of the connector 6010 may include an indent portion 6040 which may be configured to interact with the nub 808 and/or spring plunger/tab of the locking ring assembly of the reusable housing assembly 6004. In some embodiments, once the reusable housing assembly 6004 is attached to the disposable housing assembly 6000, the connector 6010 may not be removed from the disposable housing assembly 6000. Rather, in these embodiments, the reusable housing assembly 6004 must first be detached from the disposable housing assembly 6000 before the connector 6010 may be removed from the disposable housing assembly 6000. In some embodiments, once the connector 6010 is attached to the disposable housing assembly 6000, it may not be removed.

In the embodiment shown in FIGS. 235A-235E, the connector 6010 connects to the disposable housing assembly 6000 by the connector 6010 being rotated clockwise with respect to the disposable housing assembly 6000. In other embodiments, the various features described may be configured differently and the connector may be connected to the disposable housing assembly 6000 by the connector 6010 being rotated counter-clockwise with respect to the disposable housing assembly 6000.

In some embodiments, the disposable housing assembly 6000 may include a plug 6008 and the connector 6010 may include a plug receiver 6068 according to the various embodiment described herein. In some embodiments, the plug 6008 may be located in a different location and/or orientation than is shown herein. In various embodiments, the disposable housing assembly 6000 may include one or more mating features that correspond to one or more mating features on a connector 6010. In some embodiments, these mating features may be located and/or orientated differently than is shown herein.

In various embodiments, the tubing 6002, whether connected to a connector 6010 or directly to the disposable housing assembly 6000, may connect to a cannula assembly 6026 on the opposite end. The cannula assembly 6026 may be any cannula assembly 6026 known in the art and may include a cannula, whether plastic or metal, and/or an interface between the tubing 6002 and a cannula which, in some embodiments, may include a septum or a needle interface. In some embodiments, the cannula assembly 6026 includes all of these elements.

Referring now also to FIGS. 236A-236X, together with FIG. 238, another embodiment of a connector 6010 and a disposable housing assembly 6000 are shown. The connector 6010 may include a body portion 6018, a catch feature 6014, a male latching feature 6016, and a plug 6008. In some embodiments, the body portion 6018 of the connector 6010 may include one or more mating locking features that interact with corresponding features in the disposable housing assembly 6000. In some embodiments, the body portion 6018 may include features that interact with other portions of the disposable housing assembly 6000. As shown, in some embodiments, the connector 6010 may include a male latching feature 6016 on the end of the body portion 6018 of the connector 6010. In some embodiments, the male latching feature 6016 may mate with a corresponding latching feature, for example, in some embodiments, the corresponding latching feature may be a female latching feature 6020, on the disposable housing assembly 6000. In some embodiments, the latch may be a removably secure fit, and/or a snap fit and/or a loose snap fit. In various other embodiments, the shape and size of the connector 6010 may vary, and/or, in various other embodiments, other types of features such as mating locking features may be used, which include, but are not limited to, latches, catches, snap fits, adhesives, and other mechanisms for securing a connector to the tab of the disposable housing assembly.

In some embodiments, the connector 6010 may include a locking ring feature on the underside. The locking ring feature in some embodiments may be tapered and/or in some embodiments, the locking ring feature may be at least slightly curved. In some embodiments, the locking ring feature may interact with the locking ring of the reusable housing assembly 6004 and may act together with the locking ring to secure the connector 6010 to the disposable housing assembly 6000.

In some embodiments, the connector 6010 may include icons that indicate "locked" 6076 and "unlocked" 6078. Thus, in some embodiments, the "locked" and "unlocked" position may also be visually indicated to a user/patient using icons 6076, 6078 that may be molded, silk-screened, pad printed, injection molded, etched, printed and/or cut-out, e.g., translucent cut-outs of icons, on the connector. In some embodiments using translucent cut-outs, the tab portion 6030 of the disposable housing assembly 6000, or another portion of the disposable housing assembly 6000, may be a contrasting color to the connector 6010 for visually viewing the tab 6030 portion color through the cut-outs. Thus, the icons 6076, 6078 may indicate whether the reusable housing assembly 6004 is in a locked or unlocked relationship with the disposable housing assembly 6000. In various embodiments, the icons may be any form that may indicate "locked" and "unlocked", or a similar indication, to aid in the user/patient's understanding of the orientation/position between the reusable housing assembly 6004 and the disposable housing assembly 6000. In some embodiments, an arrow icon 6080 may also appear between the "locked" and "unlocked" icons.

In various embodiments, the connector 6010 is attached to a length of tubing 6002. In some embodiments, the tubing 6002 attaches to the connector 6010 through the tubing opening 6082. In some embodiments, the tubing opening 6082 may be a tapered opening which may be larger on the outside. This may be beneficial for many reasons, including, but not limited to, gluing the tubing 6002 into the tubing opening 6002. The larger opening on the outside may maintain or aid to maintain the glue at the outer portion of the tubing opening 6082 such that the amount of glue is reduced, minimized and/or prevented from wicking up along the tubing 6002 inside the tubing opening 6-82. This is beneficial for many reasons, including, but not limited to, preventing or reduction of the potential for glue to induce a kink in the tubing 6002.

As discussed above, in various embodiments, the plug 6008 of the connector 6010 is inserted into the exit 6028 of the disposable housing portion 6000 with the body portion 6018 pointing in the general upward direction. Once the plug 6008 is inside the exit 6028, the body portion 6010 of the connector 6010 may be rotated to rest adjacent to the tab portion 6030 of the disposable housing portion 6000. In some embodiments, mating locking features may be included on the body portion 6018 of the connector 6010 and the disposable housing assembly 6000 such that the connector 6010 is held in place before the reusable housing assembly 6004 is attached to the disposable housing assembly 6000. In some embodiments, the mating locking features may include, but are not limited to, post and opening, snap, buttons, latch features and/or catch features. In some embodiments, a hook or other feature may be located on the opposite end from the post of the body portion of the connector such that it loops over the end of the tab portion of the disposable housing assembly 6000 and maintains the position of the connector 6010. In the embodiment shown in FIGS. 236A-236D and FIGS. 236I-236M, the mating locking features include a male latching feature 6016 on the connector 6010 and a female latching feature 6020 on the disposable housing assembly 6000.

In various embodiments, once the connector 6010 is attached to the disposable housing assembly 6000, the connector 6010 may only be removed when intended, i.e., the connector 6010 is maintained on the disposable housing assembly 6000 unless and until a user desires to remove the connector 6000. As discussed above, in some embodiments, the connector 6010 may be non-removably attached, however, in some embodiments; the connector 6010 may be removably attached. In some embodiments, one or more mating locking features may include one or more frangible portions such that once the connector 6010 is connected to the disposable housing assembly 6000, if the connector 6010 is removed, one or more frangible portions will break and prevent reuse.

While the connector 6010 is being attached to the disposable housing assembly 6000, the male latching feature 6016 is mated with the female latching feature 6020. In some embodiments, male and female latching features 6016, 6020 may work together to further stabilize the connection of the connector 6010 to the disposable housing assembly 6000. Additionally, in various embodiments, the male and female latching features 6016, 6020 may contribute to maintaining the plug 6008 in the exit 6028. Thus, in some embodiments, the male and female latching features 6016, 6020 may contribute to maintaining and/or enforcing both the insertion of the plug 6008 into the exit 6028 and/or maintaining and/or enforcing the position of the connector 6010 such that after the plug 6008 is inserted into the exit 6028, the plug 6008 is maintained in the exit 6028 unless and until a user desires to remove the plug 6008 from the exit 6028. Additionally, once the male and female latching features 6016, 6020 are mated, the plug 6008 is fully inserted and therefore, may, in some embodiments, serve as an indication that the plug 6008 has been fully inserted into the exit 6028.

As shown in FIGS. 236A and 236B, in some embodiments, the connector 6010 may include a plug 6008. In some embodiments, as shown in the embodiments in FIGS. 236A and 236B, the plug 6008 may be positioned such that the connector 6010 approaches the disposable housing assembly 6000 exit from the side. Also, in some embodiments, the tab 6030 of the disposable housing assembly 6000 may be shaped as shown in FIGS. 236A and 236C. In some embodiments, the connector 6010, once attached to the disposable housing assembly 6000, may extend the tab portion 6030 of the disposable housing assembly 6000. In some embodiments, once the connector 6010 is attached to the disposable housing assembly 6000, the connector 6010 and tab 6030 may be flush and continuous.

In some embodiments, the connector 6010 may include an indent 6040, as shown. The indent 6040 may be shaped as shown or, in various embodiments, may be shaped and sized differently. As shown in the embodiments in FIGS. 236A-236E, the indent 6040, in some embodiments, may include one or more icons. In some embodiments the connector 6010 may include at least one indent 6040, and in some embodiments, the connector 6010 may include greater than one indent 6040. In some embodiments, the connector 6010 may include at least one indent 6040 and/or at least one feature including, but not limited to, an indent, bump, rib, textured surface, lumps, protrusions or indentations in any size, shape and/or number.

In various embodiments, the female latching feature 6020 on the disposable housing assembly 6000 may be located adjacent to the tab portion 6030. In some embodiments, for example, as shown in FIGS. 236C-236D and FIGS. 236I-236L, the female latching feature 6020 may be configured such that it receives the male latching feature 6016 on the connector 6010 from the top. Some embodiments may not include mating latching features. In some embodiments, the location and/or orientation of the female latching feature may vary. In some embodiments, the location and/or orientation of the male latching feature may vary. In some embodiments, the male latching feature may interlock with the female latching feature such that a portion of the male latching feature clips under the female latching feature.

In some embodiments, the connector 6010 may be made from rigid plastic and in some embodiments, the connector 6010 may be made from TERLUX, however, in various other embodiments, the connector 6010 may be made from other materials, including, but not limited to, polycarbonate, TOPAS or other various plastics. In some embodiments, the locking ring feature and/or the latching features may be overmolded with a thin layer of compliant materials. In some embodiments, as discussed above, the plug 6008 may include an overmold of compliant material and/or be made from compliant material. In some embodiments, the locking ring feature and/or the latching feature may be made from compliant material. In embodiments where the male or female latching feature includes compliant material, use of compliant material may increase the "squish" between the male latching feature and the female latching feature and therefore, resulting in a highly compressed and/or tight fit between the male and female latching features.

The plug 6008 may include any embodiment described herein, however, in some embodiments; the plug 6008 may be tapered and may either be rigid with an overmold of elastomeric/compliant material or be made from elastomeric/compliant material. In various embodiments, the plug 6008 may include a seal, for example, in some embodiments; the plug may include a radial seal. In some embodiments, the seal may be made from medical grade silicone.

In some embodiments, the tubing 6002 attaches to the connector 6010 as described above. In some embodiments, the tubing 6002 may attach to the connector 6010 and there may be a rigid plastic channel within the connector 6010 and through the plug 6008. In some embodiments, the tubing 6002 may extend into the connector 6010 and in some embodiments; the tubing 6002 may extend all the way through the connector 6010 and through the plug 6008. In some embodiments, the tubing 6002 may extend past the end of the plug 6008.

In these various embodiments, there is maintained a continuous flow lumen from the exit 6028 to the cannula assembly 6026. This may be desirable and/or beneficial for many reasons, including, but not limited to, minimizing and/or eliminating dead volume, minimizing priming volume and/or prevention of or minimizing the occurrence of air traps.

Referring now still to FIGS. 236A-236H and 236L-236T, some embodiments of the connector 6010 may also include a catch feature 6014 on the opposite side as the male latching feature 6016. The catch feature 6014, when the connector 6010 is connected to the disposable housing assembly 6000, interferes with the disposable housing assembly 6000 and prevents the connector 6010 from rotating further. Thus, in some embodiments, the connector 6010 and the disposable housing assembly 6000 form an interference fit in at least one location. Together with the male and female latching features 6016, 6020, in some embodiments, once the connector 6010 is attached, the connector 6010 may be held in place by these mating features. In some embodiments, the catch feature 6014 may include a ramp 6084 and therefore, may, in some embodiments, aid in the attaching of the connector 6010 to the disposable housing assembly 6000. Referring now to FIG. 236Q and FIG. 236R, in some embodiments, the catch 6014 of the connector 6010 may interfere with a disposable housing assembly interference feature 6086. As shown, if the plug 6008 is not mostly inserted into the exit 6028, the catch 6014 and the disposable housing assembly interference feature 6086 meet and this prevents the connector 6010 from being fully connected to the disposable housing assembly 6000. This configuration additionally prevents the reusable housing assembly 6004 from attaching to the disposable housing assembly 6000. This may be beneficial for many reasons, including, but not limited to, ensuring that the plug 6008 is fully inserted into the exit 6028 before the reusable housing assembly 6004 is attached and before any delivery by the pump begins. Additionally, the ramp 6084 of the catch 6014 aids in ensuring that the plug 6008 is fully inserted. In some embodiments, where the plug 6008 is mostly inserted into the exit 6028, but not completely inserted, when the reusable housing assembly 6004 is attached to the disposable housing assembly 6000, pressure from the reusable housing assembly 6004, together with the ramp 6084 of the catch 6014, inserts the plug 6008 fully. Thus, while the plug 6008 is almost fully inserted, the plug 6008 may be fully inserted by the motion of the reusable housing assembly 6004 being attached to the disposable housing assembly 6000 due, in part, to the ramp 6084 of the catch 6014 (which acts as a cam). Thus, if a user inserts the plug 6008 of the connector 6010, even if the plug 6008 is not fully seeded in the exit 6028, once the reusable housing assembly 6004 is attached, the plug 6008 will be pushed into the exit 6028 and fully seeded. This is beneficial for many reasons, including, but not limited to, preventing or decreasing the incidences of leakage due to a less than fully sealed interface between the connector 6010 and the exit 6028.

The connector body portion 6018 may include gripping features, however, in the some embodiments; the connector 6010 is sized such that a user may grip the connector 6010 for insertion/attachment with the disposable housing assembly 6000. In some embodiments including grip features which, in various embodiments, may include, but are not limited to, one or more of the following: a textured surface, bumps, lumps, protrusions or indentations in any size, shape and/or number.

In various embodiments of the connector 6010, once the connector 6010 is connected to the disposable housing assembly 6000, the reusable housing assembly 6004 may be connected/attached to the disposable housing assembly 6000 by being rotated about the disposable housing assembly 6000. As the reusable housing assembly 6004 is rotatably connected to the disposable housing assembly 6000, the locking ring and/or nub 808, having a spring actuated tab 2980, on the reusable housing assembly 6004 may interact with the connector 6010, such that the rotation of the reusable housing assembly 6004 about the disposable housing assembly 6000 prevents the connector 6010 from being removed from the disposable housing assembly 6000. In some embodiments, once the reusable housing assembly 6004 is attached to the disposable housing assembly 6000, the spring plunger/tab in the nub 808 may be released, making a "click" sound. The "click" may also produce a tactile feedback that may be perceived by the user/patient. This tactile and audio feedback is indicative to the user that the reusable housing assembly 6004 is fully connected to the disposable housing assembly 6000, and, that the connector 6010 is connected such that it will be maintained connected to the disposable housing assembly 6000 until and unless the user wishes to remove the connector 6010. In some embodiments, the nub 808, having a spring actuated tab 2980, presses downward on the connector 6010, maintaining the connector 6010 in an attached position. In some embodiments, features in the locking ring interact with a locking ring feature on the connector 6010 and contribute to maintain the connector 6010 in position with respect to the disposable housing assembly 6000. In some embodiments, the body portion 6018 of the connector 6018 may include an indent portion 6040 which may be configured to interact with the nub 808 and/or spring plunger/tab of the locking ring assembly of the reusable housing assembly 6004. In some embodiments, once the reusable housing assembly 6004 is attached to the disposable housing assembly 6000, the connector 6010 may not be removed from the disposable housing assembly 6000. Rather, in these embodiments, the reusable housing assembly 6004 must first be detached from the disposable housing assembly 6000 before the connector 6010 may be removed from the disposable housing assembly 6000. In some embodiments, once the connector 6010 is attached to the disposable housing assembly 6000, it may not be removed.

In some embodiments, for example, referring to FIG. 36, the tactile and audio feedback from the "click", referenced above, may be sensed using the AVS. In some embodiments, as described above, the locking ring assembly 806 may include a sensing component (e.g., magnet 844) that may interact with a component of reusable housing assembly 802 (e.g., a Hall Effect sensor) to provide an indication of whether reusable housing assembly 802 is properly engaged with the mating component. The Hall Effect sensor may detect when the locking ring has been rotated to a closed position. Thus, the Hall Effect sensor together with magnet 844 may provide a system for determining whether the locking ring has been rotated to a closed position.

In some embodiments, once the system determines that the sensing component has come into proximate contact with the Hall Effect sensor, the system may turn on the AVS microphone to listen for the "click" sounds from the indent. In some embodiments, the AVS microphone may be turned on for a predetermined period of time, for example, 20 seconds, to listen for the "click". Thus, the system detects that a rotation is occurring before the "click" occurs and may turn on the AVS microphone to listen for a predetermined audio fingerprint. In some embodiments, the system may recognize the "click" sounds based on one or more, but not limited to, the following: frequency, amplitude, duration, and/or width. Once the system determines that the "click" sound has been made, the reusable housing assembly/pump and/or the remote control assembly may beep or otherwise indicate to the user that a successful attachment of the disposable housing assembly 6000 to the reusable housing assembly 6004 has been made.

In some embodiments, where the "click" has not been recognized by the system, the reusable housing assembly 6004/pump and/or remote control assembly may alert and/or alarm. In some embodiments, where the "click" is not heard, the reusable housing assembly 6004/pump may not begin basal or other delivery programs.

In some embodiments, once the attachment has been successfully made, the infusion pump system may start a timer from when the reusable housing assembly/pump/system recognizes that the disposable housing assembly 6000 is attached to the reusable house assembly 6004 and could notify the user in a predetermined period of time, for example, 3 days, that the disposable housing assembly 6000 should be changed.

In some embodiments, the connector 6010 could include one or more indents or bumps or other types of texture that, when heard by the AVS microphone, may indicate a code to tell the system various pieces of information, for example, but not limited to, that the connector 6010 is different from the connector 6010 previously used, and or other information about the connector, for example, the lot number, etc. In some embodiments, each connector 6010 may include a unique identification indicator that may be heard by the AVS microphone when the disposable housing assembly 6000 and reusable housing assembly 6004 are attached. This may be beneficial for many reasons, including, but not limited to, the system may be able to differentiate between connectors 6010 and may determine not to pump/deliver if, for example, a new/different connector 6010 is not connected to a disposable housing assembly 6000, e.g., 3 days after a connector 6010 is connected to a disposable housing assembly 6000. In some embodiments, the system may recognize whether a connector 6010 is being reused and inform the user/patient that the connector 6010 was previously used and/or prevent the connector 6010 from being reused by alerting/alarming and not beginning delivery until and unless a new connector 6010 is connected. Also, in some embodiments, this may be beneficial to track the manufacturing lot and/or the expiration date of the connector 6010 to inform the user/patient that a recalled and/or expired connector has been attached to the disposable housing assembly 6000. In some embodiments, the system may prevent a recalled and/or expired and/or previously used connector 6010 from being used for patient/user safety.

In the embodiment shown in FIGS. 236A-236T, the connector 6010 connects to the disposable housing assembly 6000 by the connector 6010 being rotated clockwise with respect to the disposable housing assembly 6000. In other embodiments, the various features described may be configured differently and the connector 6010 may be connected to the disposable housing assembly 6000 by the connector 6010 being rotated counter-clockwise with respect to the disposable housing assembly 6000. In some embodiments, the connector 6010 may include a "core" 6090 on the bottom.

In some embodiments, the disposable housing assembly 6000 may include a plug 6008 and the connector 6010 may include a plug receiver 6068 according to the various embodiment described herein. In some embodiments, the plug 6008 may be located in a different location and/or orientation than is shown herein. In various embodiments, the disposable housing assembly 6000 may include one or more mating features that correspond to one or more mating features on a connector 6010. In some embodiments, these mating features may be located and/or orientated differently than is shown herein.

In various embodiments, the tubing 6002, whether connected to a connector 6010 or directly to the disposable housing assembly 6000, may connect to a cannula assembly 6026 on the opposite end. The cannula assembly 6026 may be any cannula assembly known in the art and may include a cannula, whether plastic or metal, and/or an interface between the tubing 6002 and a cannula which, in some embodiments, may include a septum or a needle interface. In some embodiments, the cannula assembly 6026 includes all of these elements.

Referring now also to FIG. 237, in some embodiments, the connector 6010 may include a "core" 6090 on the bottom. The core 6090 may be an opening in the connector 6010. In some embodiments, an identification tag 6092 may be located in the core 6090, however, in various other embodiments, the identification tag 6092 may be located in another location on the connector 6010 (and in some embodiments, the identification tag 6092 may be located on the disposable housing assembly 6000 and/or on the cannula assembly 6026). In some embodiments it may be desired to include a method of the system identifying the connector 6010 (and/or disposable housing assembly 6000 and/or cannula assembly 6026) and/or a device for the system to identify the connector 6010. In some embodiments, the identification tag 6092 may be an RFID tag. In some embodiments, the identification tag 6092 may be a near-field communication ("NFC") readable RFID tag. In some embodiments, the identification tag 6092 may be a 2D or 3D bar code. In some embodiments, the identification tag 6092 may be a QR code.

In various embodiments, either before the connector 6010 is connected to the disposable housing assembly 6000 or after the reusable housing assembly 6004 has been connected to the disposable housing assembly 6000, the reusable housing assembly 6004 and/or the remote control unit may read the identification tag 6092. The identification tag 6092 may include various information, including, but not limited to, one or more of the following: unique identification number, date of manufacture, date of expiration, part number, lot number, and/or date of sale. Once the system reads the identification tag 6092, the system may recognize the connector 6010 by its unique identification number or other, and thus, be able to recognize that the connector 6010 is either a new connector 6010, i.e., has not been used previously, or is an old connector 6010, i.e., the connector 6010 has been used previously. In some embodiments, once the connector 6010 is attached, the system may start a timer and the infusion pump may alert/alarm and/or turn off after a predetermined period of time where the connector 6010 has been used by the system. In some embodiments, this predetermined time may be the maximum time that the manufacturer recommends using the connector 6010 and/or cannula assembly 6026 attached to the connector 6010. In some embodiments, this predetermined time may be the maximum time that the manufacturer recommends using the disposable housing assembly 6000.

In some embodiments, the information conveyed by the identification tag 6092 may include information to authenticate the connector 6010, i.e., to ensure that the connector 6010 is not a counterfeit part. In some embodiments, the remote control unit and/or reusable housing assembly 6004/pump may include a listing of authentic identification information such that the system may "authenticate" the connector 6010 based on information received from the manufacturer.

In various embodiments, the identification tag 6092 may be a "peel and stick" RFID tag, which may be attached to the connector 6010, for example, in the core 6090 area of the connector 6010. In some embodiments, the identification tag 6092 may be glued and/or potted and/or another part may be pressed over the identification tag 6092 to sandwich the identification tag 6092. In some embodiments, the identification tag 6092 may be taped to the connector 6010. In some embodiments, where the identification tag 6092 is a bar code and/or QR code, the identification tag 6092 may be embossed, printed and/or molded onto the connector 6010.

In some embodiments, the identification tag 6092 may be an RFID tag. In some embodiments, the RFID tag may be a tag that includes an antenna and chip. In some embodiments, the connector 6010 may be manufactured with a conductive ring and a chip could be electrically connected to the conductive ring. In some embodiments, the RFID tag could be on the label which could include additional information, for example, but not limited to, text, for example, part number, label, instructions, expiration date.

In some embodiments, the reusable housing assembly 6004 may include hardware to read the identification tag 6092, which may include an RFID chip and/or a bar code, for example, 2D or 3D, or a QR code. For example, in some embodiments, the hardware may be an antenna which may be a copper trace on a board. In some embodiments the hardware may include a camera and/or a bar code scanner. In some embodiments, the remote control until may include hardware to read the identification tag 6092, for example, in some embodiments, the remote control until may include an RFID transceiver and/or a near-field communication transceiver which may read the identification tag in those embodiments where the identification tag is an RFID tag. In some embodiments, the RFID tag may be one that may be read by an NFC transceiver. In some embodiments the remote control until may include a camera and/or a bar code scanner.

In some embodiments, using NFC may be desirable for many reasons, including, but not limited to, the reusable housing assembly 6004 and the remote control unit could both include NFC transceivers and the reusable housing assembly 6004 and the remote control unit may be paired in this fashion. This provides that the reusable housing assembly 6004 and the remote control unit come into physical contact with one another. This may be beneficial for many reasons including, but not limited to, the devices being paired are both in control of the user/patient and therefore, this may provide additional localized security when pairing the devices, i.e., to ensure that a non-intended device is not paired with either the remote control unit or the reusable housing assembly.

In some embodiments, the cannula assembly 6026, connector 6010 and/or the disposable housing assembly 6000 may include identification tags 6092 and may include one or more of the features discussed above with respect to identification tags 6092 and/or may be used in one or more of the methods discussed above.

In various embodiments, the reusable housing assembly 6004 may begin pumping fluid only after either the reusable housing assembly 6004 or the remote control unit has received the information from the one or more identification tags 6092 in the system (e.g., disposable housing assembly 6000, cannula assembly 6026 and/or connector 6010) and has determined that the information received is acceptable. For example, in some embodiments, if the information received does not convey to the system that a "new" and/or "acceptable" (i.e., is not expired, has not been recalled) connector 6010 and/or disposable housing assembly 6000 and/or cannula assembly 6026 is being connected to the system, then the system may not pump fluid and or may alert/alarm.

Various embodiments of the connector 6010 may be made from any color desired. In some embodiments, the connector 6010 may be made from a different color than the disposable housing assembly 6000. In some embodiments, the connector 6010 may be made from the same color as the disposable housing assembly 6000.

In some embodiments the connector 6010, after being connected/attached to the disposable housing assembly 6000, may not be removed from the disposable housing assembly 6000. In some embodiments, once connected/attached to the disposable housing assembly 6000, it may be difficult for a user to remove the connector 6010 from the disposable housing assembly 6000. In some embodiments, this may be beneficial and/or desirable for once the tubing has been primed; the tubing 6002 is full of fluid, which, in some embodiments, may include a therapeutic fluid. If the connector 6010 were removed from the disposable housing assembly 6000, and a cannula assembly 6026, in fluid communication with the connector 6010, was already inserted into a user, and if the connector 6010 were to be elevated such that it was higher than the cannula assembly 6026, the fluid in the tubing 6002 may be delivered through the cannula assembly 6026 to the user. In some circumstances, this may not be desirable for many reasons, including, but not limited to, unintentional delivery of a volume of fluid. Therefore, prevention of this circumstance may be desirable.

In some embodiments, the disposable housing assembly 6000 may include fluid membranes that are not over molded, but rather molded separately then attached between the two layers of the disposable housing assembly 6000 and the layers may retain the membranes by affecting a seal through laser welding, however, in some embodiments, we may affect the seal through other processes, which may include, but are not limited to, one or more of the following: ultrasonic welding, heat staking, gluing, bonding or other processes.

Referring now also to FIGS. 191, 192, 193A and 193B, in some embodiments, an alternative to having the locking ring on the reusable housing assembly 5010/pump housing, as described herein, is to move the locking ring to the disposable housing assembly. In some embodiments this may be desirable for many reasons, including, but not limited to, preventing potential build up of dirt and debris in the interface; allowing the charger to seat further into the reusable housing assembly, protecting the charger pins; removing significant volume since the ring makes up approximately 10% volume; allows for the housing to be used as a big button by using compliant material around its base and a magnet and sensor to detect its displacement, both angular and y axis (pressing down). For example, as shown in FIG. 191, in some embodiments, the locking ring on the disposable housing assembly 5006 may be a sliding interface 5008. A charger 5012, shown in FIG. 192, may include an interlocking interface with the disposable housing assembly 5006 sliding interface 5008. As shown in FIG. 193A-193B, in some embodiments, the reusable housing assembly 5010 may include a magnet 5012 that may be sensed by a sensor 5014 that may sense proximity and/or angle, on the disposable housing assembly 5006. In some embodiments, the locking ring 5008 may be made from a compliant material and in some embodiments, this allows for twisting and depressing of the reusable housing assembly 5010 with respect to the disposable housing assembly 5006 when being attached.

In some embodiments, rather than a sliding screw style latch, the locking ring may use a spring latch, for example, as shown in FIG. 194. In some embodiments, the spring latch requires that the disposable housing assembly and the reusable housing assembly be aligned and pressed together with a spring, circular in shape, to be compressed while engaging and that snaps to lock in place as shown by the arrows in FIG. 194.

Referring now also to FIG. 195, regarding disposable housing assembly 5018 detection, in some embodiments, a flexible strip 5016 may be used which changes its resistance based on the amount it is bent to determine if the AVS module 5022 has been displaced by an installed/attached disposable housing assembly 5018.

Referring now also to FIG. 196, it is desirable to measure the initial reservoir 5028 volume of the disposable housing assembly 5018 after fill. One method to measure this volume, in some embodiments, includes the use of a flat plate 5026 on the top of the reservoir 5028 with a flexible membrane around the edges. Once filled, the flat plate 5026 distance may be measured at a number of points, for example, in some embodiments; the number of points may be from one to three points, using an optical sensor or, in some embodiments, using a magnetic sensor on a spring loaded protrusion from the pump. To measure 20 units, for example, in some embodiments, may require approximately 0.01 mm to 0.25 mm resolution in height. In some embodiments, standard triangulation may be used to estimate the distance using a linear array and LED, for example. Additionally, a flat plate 5026 may be beneficial for the reservoir 5028 to start with no air.

Referring now also to FIG. 197, in some embodiments, a serpentine reservoir, such as the one shown, may be used. In some embodiments, the serpentine reservoir shown may be a tube-like structure with a hydrophobic filter 5030 on the end. The passages, in some embodiments, may be rounded or square and, in some embodiments, constructed of welded TOPAS or polycarbonate plastic. In some embodiments, the reservoir may be filled from one end through a septum 5032. As fluid is drawn out of the reservoir by the pump, aid is drawn in through the filter 5030. The filter 5030 may be configured to allow the passage of air but inhibit the passage of fluid or water vapor (in some embodiments, the filter may be a polypropylene filter and/or a filter made from PTFE). In various embodiments, it is desirable to prevent water vapor from passing through the filter/membrane 5030 to avoid concentrating the fluid through evaporation. In various embodiments, the fluid in the passage may be kept in place by the reservoir valve on one end and by surface tension on the other end. In various embodiments, the small diameter of the passage and surface tension at one end may prevent the fluid from "sloshing" which may degrade the fluid, for example, where the fluid is insulin or another therapeutic fluid.

In some embodiments of the various embodiments of the infusion pump assembly described herein, the pump chamber inlet valve may be an active valve, for example, actuated using shape-memory allow or other actuated.

Alarm and Alerts

In various embodiments, the remote control assembly and/or the infusion pump assembly and/or both may include at least one speaker and in some embodiments, the remote control assembly and/or the infusion pump assembly and/or both may include at least one graphical user interface and/or indicator lights. In some embodiments, the remote control assembly and/or the infusion pump assembly and/or both may include reminders and/or alarms and/or alerts to signal to the user either a critical or non-critical condition. The critical or non-critical condition may include, but is not limited to, an occlusion, low battery, low reservoir, change cannula reminder, reminder to check blood glucose, reminder to change glucose and/or interstitial sensor. Therefore, some reminders and/or alarms and/or alerts to signal to the user that a critical, i.e., therapeutically critical, situation is occurring that requires immediate action and/or a situation is occurring that requires the user to be immediately informed. In some embodiments, there situations are those that may or have the ability to immediately cause a negative outcome, medically, to the user. However, some reminders and/or alarms and/or alerts to signal to the user that a non-critical, i.e., therapeutically non-critical, situation is occurring that does not require immediate action and/or a situation is occurring that does not require the user to be immediately informed. In some embodiments, these situations are those that may not or may not have the ability to immediately cause a negative outcome, medically, to the user.

Thus, in some embodiments, for reminders and/or alarms and/or alerts that signal to the user that a non-critical situation is occurring, the user may program and/or select the mode of notification. In some embodiments, depending on the non-critical situation, a different mode of notification may be used. In some embodiments, all non-critical situations may include the same mode of notification. Thus, in some embodiments, user may select, but are not limited to, one or more of the following modes for one or more of non-critical situations giving rise to notifications:

1) "turn on mode" where the graphical user interface lights up and displays a message for a predetermined and/or preselected and/or preprogrammed duration or until the user confirms (e.g., user presses a button or other to indicate they confirm); 2) vibration only mode (vibration for a predetermined and/or preselected and/or preprogrammed duration or until the user confirms (e.g., user presses a button or other to indicate they confirm); 3) vibration then alarm mode (vibrate for a duration and if no confirmation (e.g., user presses a button or other to indicate they confirm), then alarm until confirmation by the user and/or alarm for a predetermined and/or preselected and/or preprogrammed duration); 4) alarm only (alarm for a predetermined and/or preselected and/or preprogrammed duration or until user confirms (e.g., user presses a button or other to indicate they confirm) in some embodiments, after confirmation but no further action, the sequence may repeat; 5) silent until turn on (no indication until the user wakes up the device and then the device indicates, for example, on the graphical user interface, the condition/situation); 6) vibrate only (vibrate for a predetermined and/or preselected and/or preprogrammed duration or until user confirms (e.g., user presses a button or other to indicate they confirm), in some embodiments, after confirmation but no further action, the sequence may repeat; 7) wake up/turn on (i.e., graphical interface/screen lights up/turns on and displays the situation/alarm/alert/reminder) until confirmation, then silent/sleep and/or may repeat sequence if anticipated action not taken in predetermined/preprogrammed/preselected duration). In some embodiments, a silent until wake up may refer to where there is a non-critical condition, the system may not remind and/or alarm and/or alert until the user wakes up the graphical user interface and/or device and, in some embodiments, upon first "wake up" the screen displays the reminder and/or alarm and/or alert.

In some embodiments, it may be desirable for the user to have the option to preselect/preprogram/predetermine when a non-critical reminder/alarm/alert is given, regardless of the type of reminder/alarm/alert. For example, in some embodiments, the user may request that no non-critical reminder/alarm/alert be given between 11 pm and 6 am, i.e., while the user is sleeping. In some embodiments, this may be termed a timeout. In some embodiments, the user may request a "temporary" timeout for non-critical reminders/alarms/alerts, for example, between 6 pm-8 pm, while, for example, attending a quiet event. Thus, in some embodiments, for non-critical reminder/alarms/alerts the user may do one or more, but not limited to, the following: preselect/predetermine/preprogram the duration of the reminder/alarm/alert; reselect/predetermine/preprogram the type of the reminder/alarm/alert; reselect/predetermine/preprogram timeout or quiet times where no reminder/alarm/alert is given (and in some embodiments, where this is selected by the user, upon wake up, the device may display the reminder/alarm/alert, and/or in some embodiments, at the end of the preselected/predetermined/preprogrammed time-out, any reminder/alarm/alert may be given).

In some embodiments where, for example, the system may remind the user to change their cannula, for example, 3 days after filling the cannula. The user may request, for these reminders, that for this reminder, a reminder timeout between 10 pm and 6 am. Thus, the user will not be awoken to remind them to change the cannula. In some embodiments, when the user wakes up the device, for example, at 7 am, the reminder, if applicable, may be indicated, which, in some embodiments, may be indicated by the method eselected/preprogrammed/predetermined by the user.

Referring now also to FIGS. 239 and 240, another embodiment of the AVS assembly 7000 is shown. With respect to FIG. 240, the AVS assembly 7000 includes a speaker 7002 and two microphones, one shown as 7008. The AVS assembly 7000 includes a "figure eight" seal 7010. The AVS assembly 7000 includes a top housing 7004 and a bottom housing 7006.

Referring now also to FIG. 239, the AVS membrane 7012, which, in the exemplary embodiment, is located in the disposable housing assembly 6000, and an acoustic seal 7014 is shown. In some embodiments, the acoustic seal is overmolded onto the reusable housing assembly 6004 portion and is therefore located between the disposable housing assembly 6000 and the reusable housing assembly 6004. When the reusable housing assembly 6004 is engaged with the disposable housing assembly 6000, the acoustic seal 7014 comes into contact with surfaces on the disposable housing assembly 6000 and a seal is made.

In this embodiment of the AVS assembly, a spring is not included; however, in various other embodiments of this embodiment of the AVS assembly, a spring may be included. In the embodiments without a spring, the AVS membrane 7012 may be made from SEBS and may include properties that are desirable for the AVS membrane 7012.

The membrane in the disposable housing assembly 6000 may be made from plastic and in some embodiments, more than one type of plastic. For example, in some embodiments, the membrane may be made from SEBS and SANTOPRENE. In some embodiments, the AVS membrane 7012 is made from SEBS and the remainder of the membranes is made from SANTOPRENE. In various embodiments of the membrane, the membrane may be at least partially coated with parylene, and in some embodiments, the entire membrane is coated with parylene.

Referring now also to FIGS. 244A and 244B, another embodiment of the disposable housing assembly 7000 is shown. The disposable housing assembly 7000 includes a tubing 7034 and a cannula assembly 7026, similar to those describe above. With respect to the disposable housing assembly 7000, in some embodiments, the disposable housing assembly 7000 includes a fluid path 7038 that may, in some embodiments, include a chevron path 7040. This may be desirable/beneficial for many reasons, including, but not limited to, minimizing the amount of air that may become trapped in the fluid path 7038.

Referring now also to FIGS. 245A and 245B, in some embodiments of the disposable housing assembly 7000, the pump chamber membrane 7042 may be shaped as a preformed dome like structure. In some embodiments this may be beneficial/desirable for many reasons, including, but not limited to, providing a higher vacuum force on the reservoir to pump greater volumes of fluid per pump stroke and moving more fluid from the reservoir to the pump chamber with less displacement. In some embodiments, and as shown in FIG. 245B, the pump plunger 7044 may be pre-engaged with the pump chamber membrane 7042. Thus, as the pump plunger 7044 is actuated by the actuator assembly, the pump plunger 7044, already engaged with the pump chamber member 7042, may travel less distance to pump fluid from the reservoir 908. This may be beneficial for many reasons, including, but not limited to, exerting less wear and tear on the shape memory alloy and therefore, increasing the longevity of the shape memory alloy. Thus, the pump may move more fluid using less force, i.e., the pump is more efficient.

Referring now also to FIGS. 246A and 246B, in some embodiments, the cover 7046 of the reusable housing assembly, which may include at least some of the features described above with respect to the reusable housing assembly, may include a speaker 7048. The speaker 7048 may be heat staked in the cover 7036. A printed circuit board ("PCB") 7050 may also be located adjacent to the speaker 7048, in some embodiments, which may include, in some embodiments, spring loaded contacts 7052 such that the speaker 7048 may be connected to the PCB through spring loaded electrical contracts. Placement of the speaker 7048 in the cover 7046 of the reusable housing assembly may be desirable/beneficial for many reasons, including, but not limited to, providing louder/better sound quality to the user by placement of the speaker 7048 closer to the "outside" of the infusion pump system.

In various embodiments, these methods may be used with respect to any device and/or medical device and/or any controller and/or remote controller for any device and/or medical device and/or any device used in conjunction with or in association with any device and/or medical device.

A number of embodiments have been described. Nevertheless, it will be understood that various modifications may be made. Accordingly, other embodiments are within the scope of the following claims.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A wearable infusion pump assembly comprising:
a disposable housing portion;
a reusable housing portion comprising:
 a locking ring assembly of the reusable housing portion; and
 a spring actuated tab assembly operably coupled with the locking ring assembly;

a connector, the connector comprising:
- a body portion comprising:
  - an indent configured to interact with the spring actuated tab assembly;
  - a plug portion located on the body portion, the plug portion comprising a fluid path and configured to be inserted into an exit of the disposable housing portion of the wearable infusion pump assembly;
  - a tubing, wherein the plug portion is overmolded onto a first end of the tubing, and wherein the first end of the tubing fluidly connected to the plug fluid path;
  - a catch feature located on a first end of the body portion and configured to interact with the disposable housing portion of the wearable infusion pump assembly; and
  - a latching feature located on a second end of the body portion, the latching feature configured to interact and lock onto the disposable housing portion of the wearable infusion pump assembly.

2. The wearable infusion pump of claim 1 wherein the catch feature comprising a ramp.

3. The wearable infusion pump of claim 1 wherein the second end of the tubing is connected to a cannula assembly.

4. The wearable infusion pump of claim 1 wherein the body portion further comprising a tapered tubing opening, the first end of the tubing connecting to the tapered tubing opening.

5. The wearable infusion pump of claim 1 wherein an underside of the body portion comprising a core.

6. The wearable infusion pump of claim 5 wherein the core comprising an identification tag.

7. The wearable infusion pump of claim 1 wherein the body portion comprising an identification tag.

8. The wearable infusion pump of claim 7 wherein the identification tag is an RFID tag.

9. The wearable infusion pump of claim 8 wherein the identification tag is a near-field communication readable RFID.

10. The wearable infusion pump of claim 1 wherein a first end of the body portion further comprising a locked icon.

* * * * *